US010047105B2

(12) United States Patent  
Creighton et al.

(10) Patent No.: US 10,047,105 B2  
(45) Date of Patent: *Aug. 14, 2018

(54) GYRASE INHIBITORS

(71) Applicant: Merck Sharp & Dohme Corp., Rahway, NJ (US)

(72) Inventors: Christopher J. Creighton, San Diego, CA (US); Leslie William Tari, San Diego, CA (US); Zhiyong Chen, San Diego, CA (US); Mark Hilgers, San Diego, CA (US); Thanh To Lam, San Diego, CA (US); Xiaoming Li, San Diego, CA (US); Michael Trzoss, San Diego, CA (US); Junhu Zhang, San Diego, CA (US); John Finn, San Diego, CA (US); Daniel Bensen, Carlsbad, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/267,978

(22) Filed: Sep. 16, 2016

(65) Prior Publication Data

US 2017/0037059 A1   Feb. 9, 2017

Related U.S. Application Data

(62) Division of application No. 13/394,985, filed as application No. PCT/US2010/048538 on Sep. 10, 2010, now Pat. No. 9,481,675.

(60) Provisional application No. 61/241,833, filed on Sep. 11, 2009.

(51) Int. Cl.
| | |
|---|---|
| C07D 487/04 | (2006.01) |
| C07D 519/00 | (2006.01) |
| C07D 471/04 | (2006.01) |
| C07D 487/16 | (2006.01) |
| C07D 491/048 | (2006.01) |
| C07D 513/04 | (2006.01) |
| C07D 471/16 | (2006.01) |

(52) U.S. Cl.
CPC ......... *C07D 519/00* (2013.01); *C07D 471/04* (2013.01); *C07D 471/16* (2013.01); *C07D 487/04* (2013.01); *C07D 487/16* (2013.01); *C07D 491/048* (2013.01); *C07D 513/04* (2013.01)

(58) Field of Classification Search
CPC .................................................. C07D 487/04
See application file for complete search history.

(56) References Cited

U.S. PATENT DOCUMENTS 6,632,809 B2   10/2003   Grillot  
2006/0093274 A1   5/2006   Kahle et al.

FOREIGN PATENT DOCUMENTS

WO   2009020990   2/2009  
WO   2009087225   7/2009

OTHER PUBLICATIONS

U.S. Appl. No. 13/394,985, filed Jul. 30, 2012.  
Chang et al., 2,6,8-Trisubstituted 1-deazapurines as adenosine receptor antagonists, Journal of Medicinal Chemistry, vol. 50, No. 4, pp. 828-834 (2007).  
Lubbers et al., Design, synthesis, and structure-activity relationship studies of ATP analogues as DNA gyrase inhibitors, Bioorganic & Medicinal Chemistry Letters, vol. 10, No. 8, pp. 821-826 (2000).  
Oblak, Discovery and development of ATPase inhibitors of DNA gyrase as antibacterial agents, Current Medicinal Chemistry, vol. 14, No. 19, p. 2033 (2007).  
Seela et al., 7-Functionalized 7-deazapurine ribonucleosides related to 2-aminoadenosine, guanosine, and xanthosine: glycosylation of pyrrolo[2,3-d]pyrimidine with 1-o-acetyl-2,3,5-tri-O-benzoyl-D-rribofuranose, The Journal of Organic Chemistry, vol. 71, No. 1, pp. 81-90 (2006).  
International Search Report and Written Opinion dated Feb. 17, 2012 for PCT/US2010/048538, filed Sep. 10, 2010.

*Primary Examiner* — Noble E Jarrell  
*Assistant Examiner* — John S Kenyon  
(74) *Attorney, Agent, or Firm* — Richard S. Parr; Catherine D. Fitch

(57) ABSTRACT

Novel gyrase inhibitors and related compositions and methods are useful for impeding bacterial growth. Compounds of Formula (I), are disclosed: Formula (I), wherein Y is N or CH; Z is N or $CR^5$; $R^5$ is H, a substituted or unsubstituted hydrocarbyl residue (1-3C) containing 0-2 heteroatoms selected from O, S and N, or is an inorganic residue; L is O, S, $NR^7$, or $CR^8R^9$; $R^7$ is H or $C_{1-3}$ alkyl; $R^8$ and $R^9$ are each independently H or $C_{1-3}$ alkyl; $R^2$ is H, a hydrocarbyl residue (1-40C) containing 0-10 heteroatoms selected from O, S and N optionally substituted with an inorganic residue; $R^4$ is H, an inorganic residue, or a hydrocarbyl residue (1-30C) containing 0-12 heteroatoms selected from O, S and N and containing 0-10 inorganic residues, wherein $R^5$ and $R^4$ together may join to form a fused ring; and $R^6$ is selected from the group consisting of H, $C_{1-5}$ alkyl, $C_{2-5}$ alkenyl, $C_{2-5}$ alkynyl, halo $C_{1-5}$ alkyl, halo $C_{2-5}$ alkenyl, halo $C_{2-5}$ alkynyl, $C_{1-5}$ hydroxyalkyl, $C_{1-5}$ alkyl chloride, $C_{2-5}$ alkenyl chloride, and $C_{2-5}$ alkynyl chloride; or a pharmaceutically-acceptable salt, ester, or prodrug thereof.

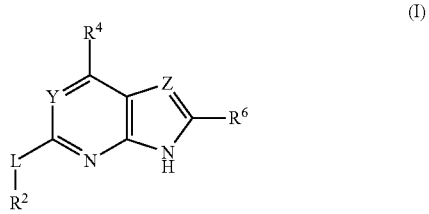

(I)

15 Claims, No Drawings

GYRASE INHIBITORS

CROSS-REFERENCE TO RELATED APPLICATIONS

This application claims priority to U.S. application Ser. No. 13/394,985, which is a national stage entry of PCT/US2010/048538 filed Sep. 10, 2010, which claims priority from U.S. Provisional Application No. 61/241,833, filed Sep. 11, 2009, which is incorporated herein by reference in its entirety.

STATEMENT REGARDING FEDERALLY SPONSORED R&D

This invention was made with government support under HHSN 272200800042C awarded by the National Institute of Allergy and Infectious Diseases. The government has certain rights in the invention.

BACKGROUND OF THE INVENTION

Field of the Invention

The disclosure relates to pharmaceutically-useful compositions, methods of making and using them for treatment and prophylaxis of diseases in mammals.

Description of the Related Art

Bacterial infections pose a continuing medical problem because anti-bacterial drugs eventually engender resistance in the bacteria on which they are used. Consequently, a need exists for new drugs with efficacy against pathogenic bacteria for use in the therapy and prophylaxis of bacterial infections.

One target for development of anti-bacterial drugs has been topoisomerase gyrase B, an enzyme catalyzes interconversion of topomers of DNA between supercoiled and relaxed forms used for storage and cell division, respectively. Gyrase inhibitors have been disclosed in RE40,245 which is hereby incorporated by reference in its entirety.

SUMMARY OF THE EMBODIMENTS

A compound useful in pharmaceutical compositions such as antibacterial drugs may have the structure of Formula I:

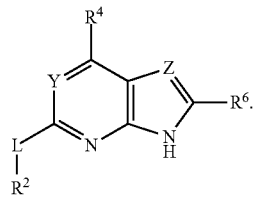

wherein
Y is N or CH
Z is N or $CR^5$;
$R^5$ is H, a substituted or unsubstituted hydrocarbyl residue (1-3C) containing 0-2 heteroatoms selected from O, S and N, or is an inorganic residue;
L is O, S, $NR^7$, or $CR^8R^9$;
$R^7$ is H or $C_{1-3}$ alkyl;
$R^8$ and $R^9$ are each independently H or $C_{1-3}$ alkyl;
$R^2$ is H, a hydrocarbyl residue (1-40C) containing 0-10 heteroatoms selected from O, S and N optionally substituted with an inorganic residue;
$R^4$ is H, an inorganic residue, or a hydrocarbyl residue (1-30C) containing 0-12 heteroatoms selected from O, S and N and containing 0-10 inorganic residues, wherein $R^5$ and $R^4$ together may join to form a fused ring; and
$R^6$ is selected from the group consisting of H, $C_{1-5}$ alkyl, $C_{2-5}$ alkenyl, $C_{2-5}$ alkynyl, halo $C_{1-5}$ alkyl, halo $C_{2-5}$ alkenyl, halo $C_{2-5}$ alkynyl, $C_{1-5}$ hydroxyalkyl, $C_{1-5}$ alkyl chloride, $C_{2-5}$ alkenyl chloride, and $C_{2-5}$ alkynyl chloride;
or a pharmaceutically-acceptable salt, ester, or prodrug thereof.

Some embodiments also include methods of preparing the compound, dosage form or the pharmaceutical composition described herein.

Embodiments also include methods of and uses for treating a bacterial infection comprising administering the compound, dosage form or the pharmaceutical composition described herein to a subject in need thereof.

These and other embodiments are described in greater detail below.

BRIEF DESCRIPTION OF THE DRAWINGS

Table 1 contains a list of compounds that have been prepared and may be used in pharmaceutical compositions and methods described herein.

Table 2 lists MIC data for various compounds described herein.

DETAILED DESCRIPTION OF THE PREFERRED EMBODIMENT

Compounds herein may have the structure of Formula I:

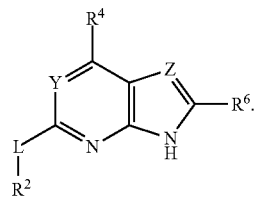

Y may be N or CH. In some aspects, Y is N.
Z may be N or $CR^5$. $R^5$ may be H, a substituted or unsubstituted hydrocarbyl residue (1-3C) containing 0-2 heteroatoms selected from O, S and N, or is an inorganic residue. In some aspects, Z is $CR^5$, wherein $R^5$ is selected from the group consisting of hydrogen, halo, unsubstituted $C_{1-3}$ alkyl, or $C_{1-3}$ alkyl substituted with one or more substituents selected from the group consisting of =O, halo, $NH_2$, $NHCH_3$, and ≡N, or $C_{2-3}$ alkenyl, wherein $R^5$ and $R^4$ together may join to form a fused ring. For instance, $R^5$ may be methyl, $C(O)CH_3$, $C(O)NH_2$, $CH_2OH$, $CF_3$, $CN$, $CHF_2$, CHO, acetyl, Cl or Br.

$R^5$ and $R^4$ together may form

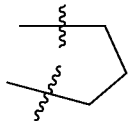

L is a linker and is intended to impart a distance between portions of the molecule. Typical linkers include O, S, $NR^7$, or $CR^8R^9$; wherein $R^7$ may be H or $C_{1-3}$ alkyl and $R^8$ and $R^9$ may be each independently H or $C_{1-3}$ alkyl. In some aspects, at least one of $R^8$ and $R^9$ is H. In some aspects, L may be O, S, NH, or $CH_2$.

$R^2$ may be H, a hydrocarbyl residue (1-40C) containing 0-10 heteroatoms selected from O, S and N optionally substituted with an inorganic residue. $R^2$ may comprise at least one aryl or heteroaryl moiety. In some aspects, the aryl or a heteroaryl moiety of $R^2$ is directly linked to L. The at least one aryl or heteroaryl moiety of $R^2$ may be substituted with 0-4 alkyl, alkenyl, alkynyl, aryl, arylalkyl, acyl, aroyl, heteroaryl, heteroalkyl, heteroalkenyl, heteroalkynyl, haloalkyl, haloalkenyl, haloalkynyl, heteroarylalkyl, NH-aroyl, arylacyl, heteroarylacyl, halo, $O^-$ (if $R^2$ contains N), OR, $NR_2$, SR, SOR, $SO_2R$, OCOR, CONROR, NRCOR, $NRCONR_2$, NRCOOR, $OCONR_2$, COOR, $SO_3R$, $CONR_2$, $CONR_2OR$, $SO_2NR_2$, $NRSO_2NR_2$, CN, $CF_3$, or $NO_2$, wherein each R is independently H, alkyl, alkenyl or aryl or heteroforms thereof, and wherein two of said substituents on adjacent positions can be joined to form a fused, optionally substituted aromatic or nonaromatic, saturated or unsaturated ring which contains 3-14 members. Typically, the substituent may contain 1-15C, such as 1-10C, 1-6C or 1-3C, although it is understood that substituents such as alkenyl and alkynyl have at least two carbon atoms such as 2-15C, 2-10C, 2-6C, and 2-3C. In some aspects, the aryl or heteroaryl moiety of $R^2$ comprises at least one moiety selected from the group consisting of phenyl, pyrido[2,3-b]pyrazine, pyridyl, thiazole, quinoline, pyridazine, pyrimidinedione, pyrido[2,3-d]pyrimidinedione, pyrimidine, [1,2,3]triazolo[4,5-b]pyridine, oxazole, benzotriazine, furo[3,2-b]pyridine, thiazolo[5,4-b]pyridine, pyrazolo[3,4-b]pyridine, imidazo[4,5-b]pyridine, pyrido[3,2-d]pyrimidine, 1,5-naphthyridine, quinolone, quinazoline, and quinoxoline.

In some embodiments, $L-R^2$ may be one of

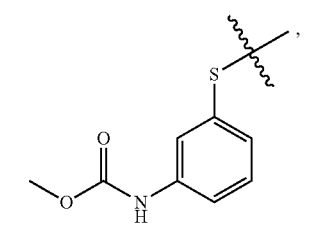

-continued

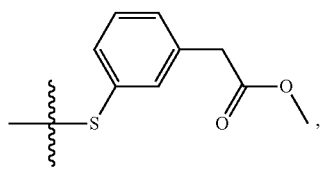

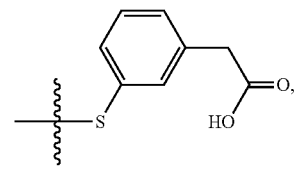

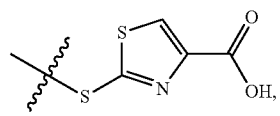

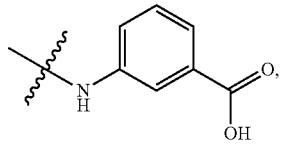

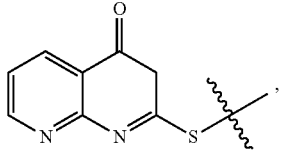


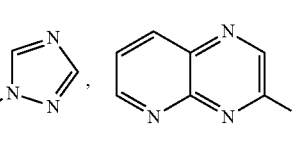

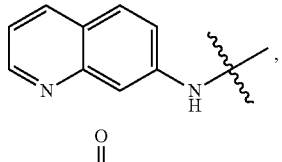

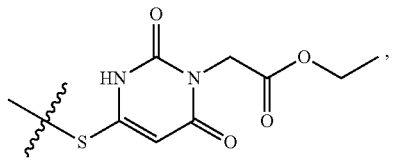

-continued
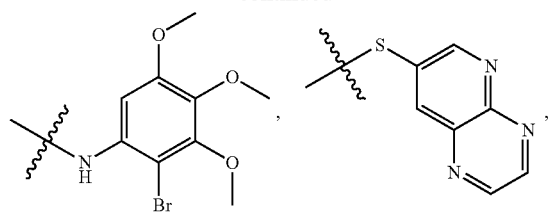
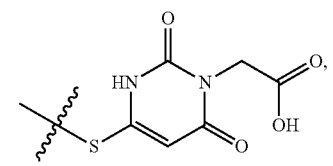
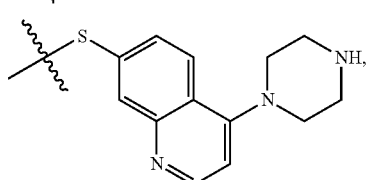
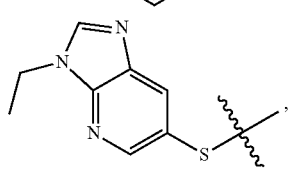
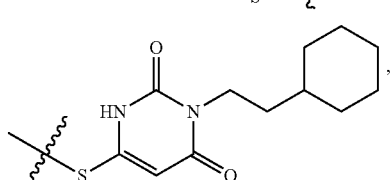
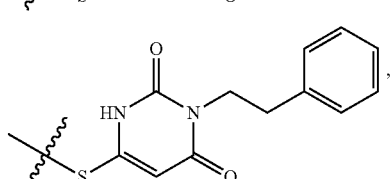
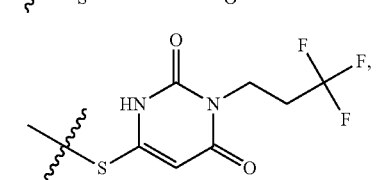
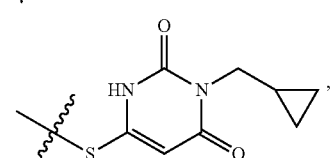
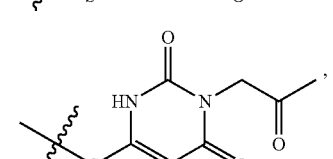
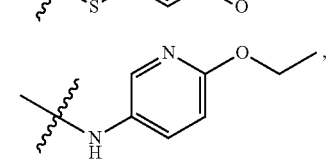
-continued
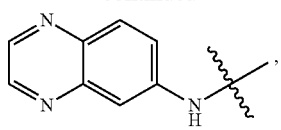
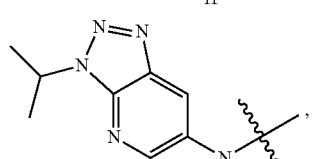
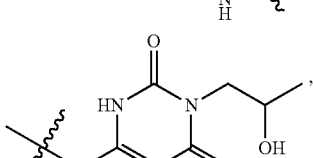
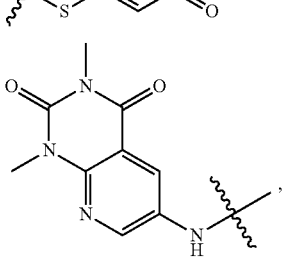
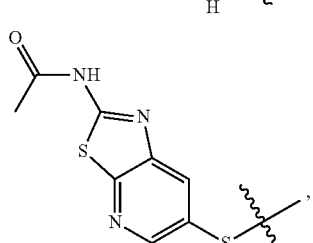
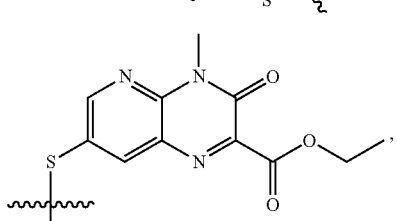
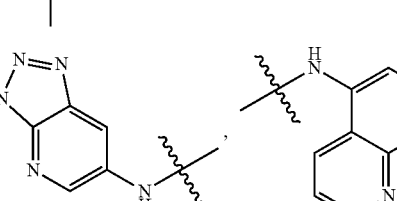
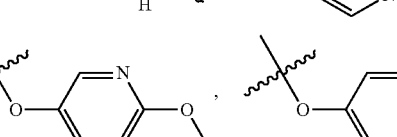
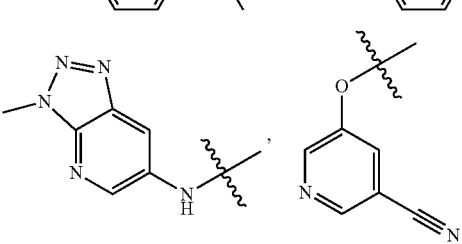

-continued
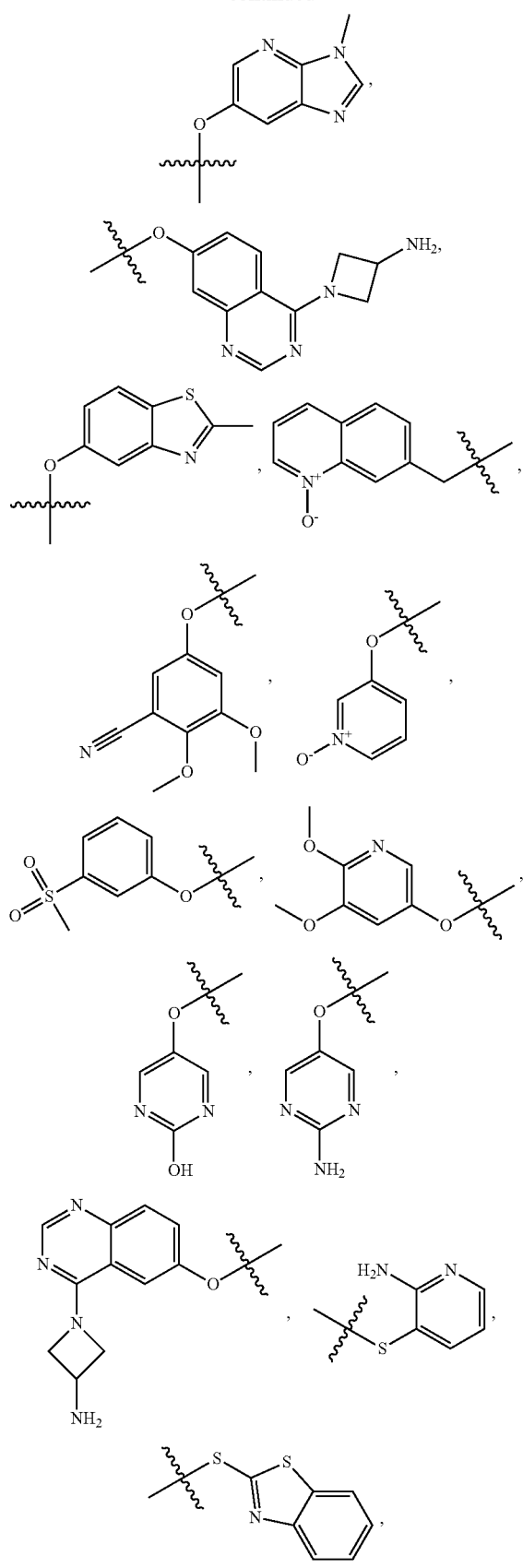
-continued
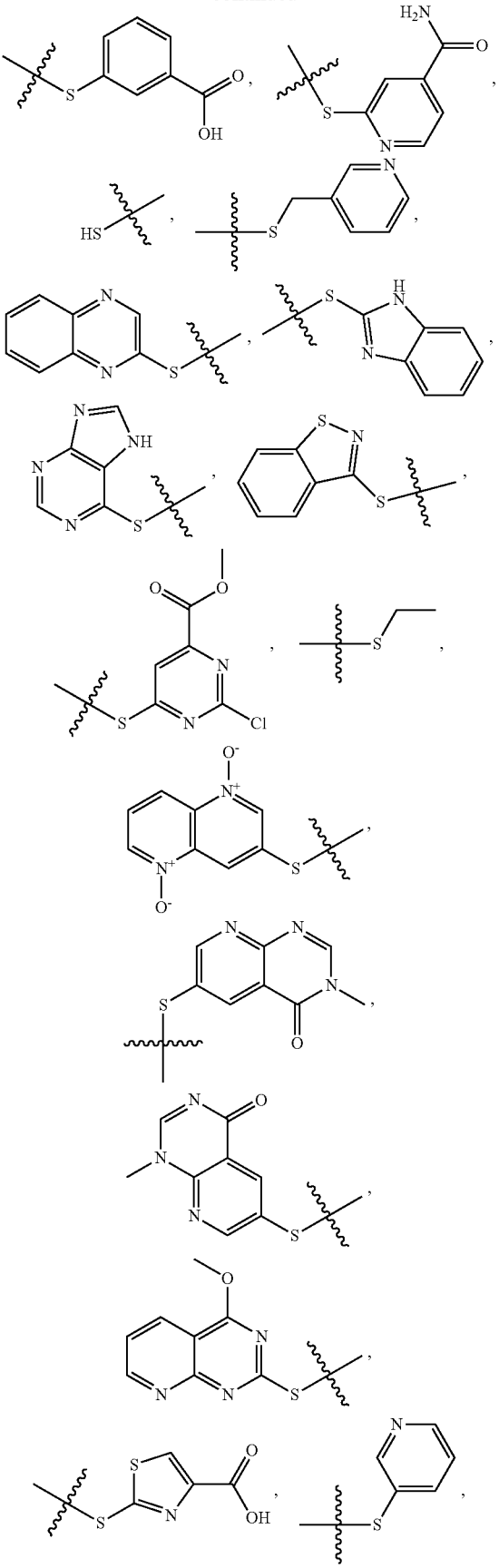

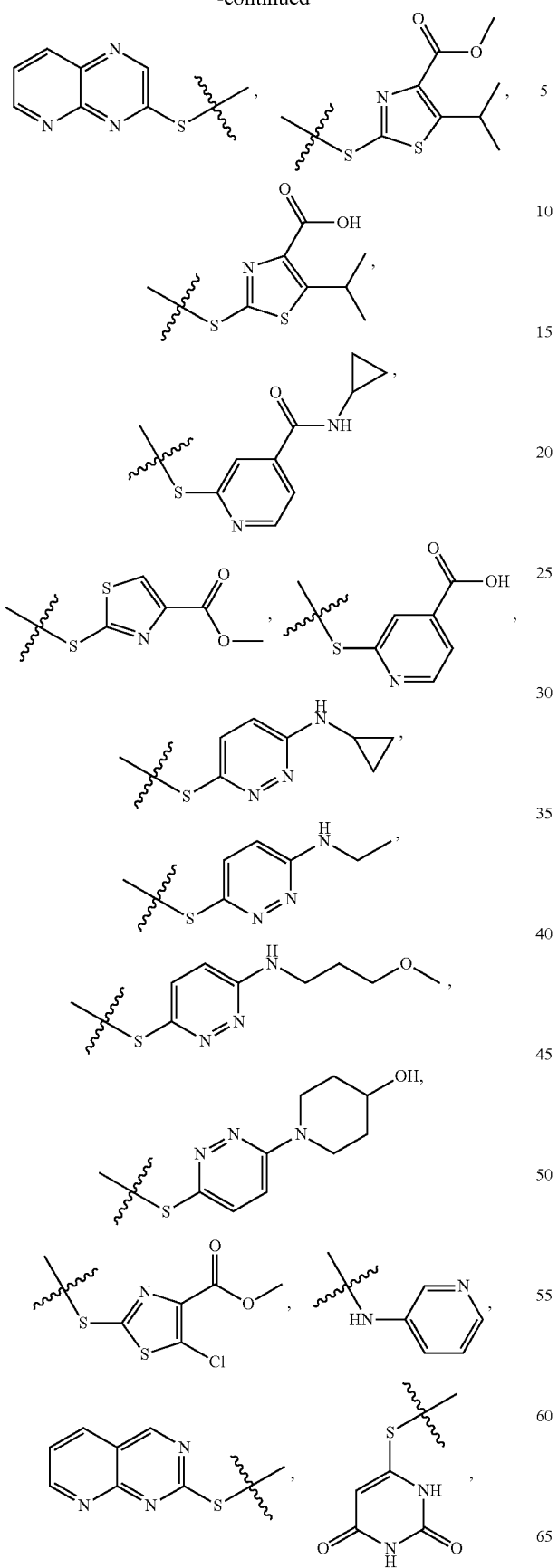
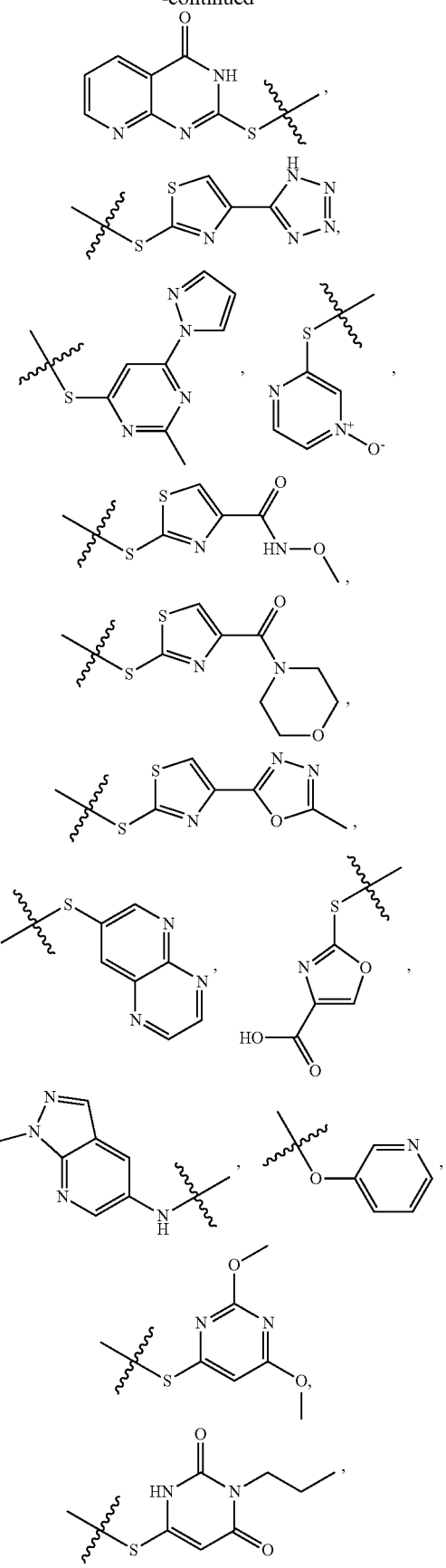

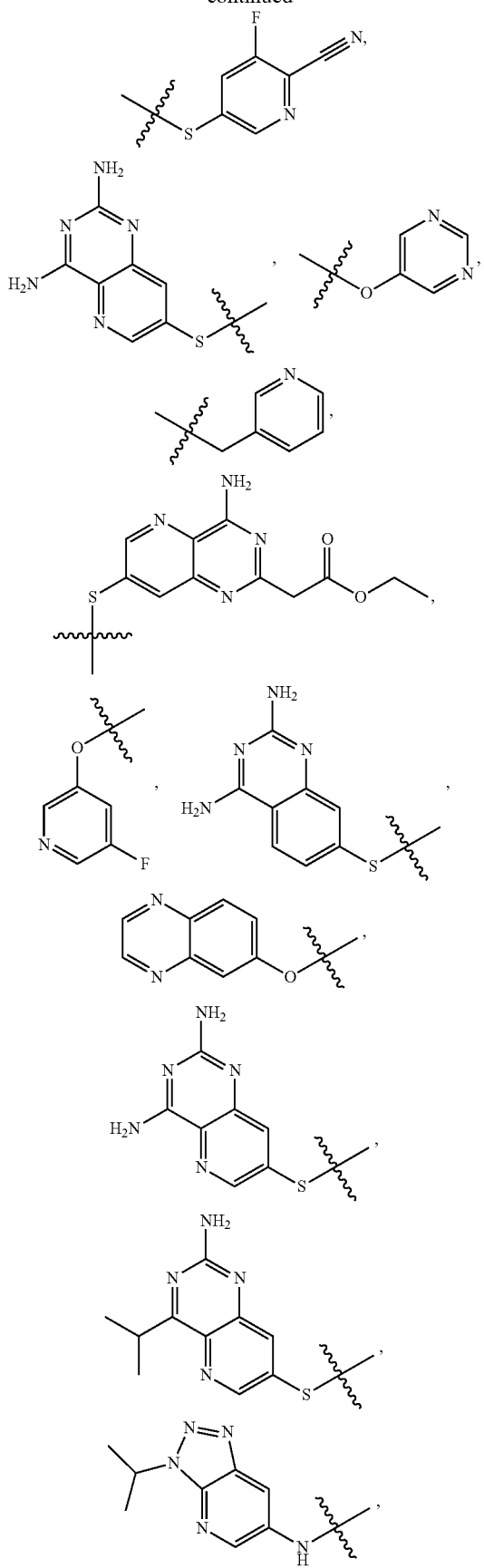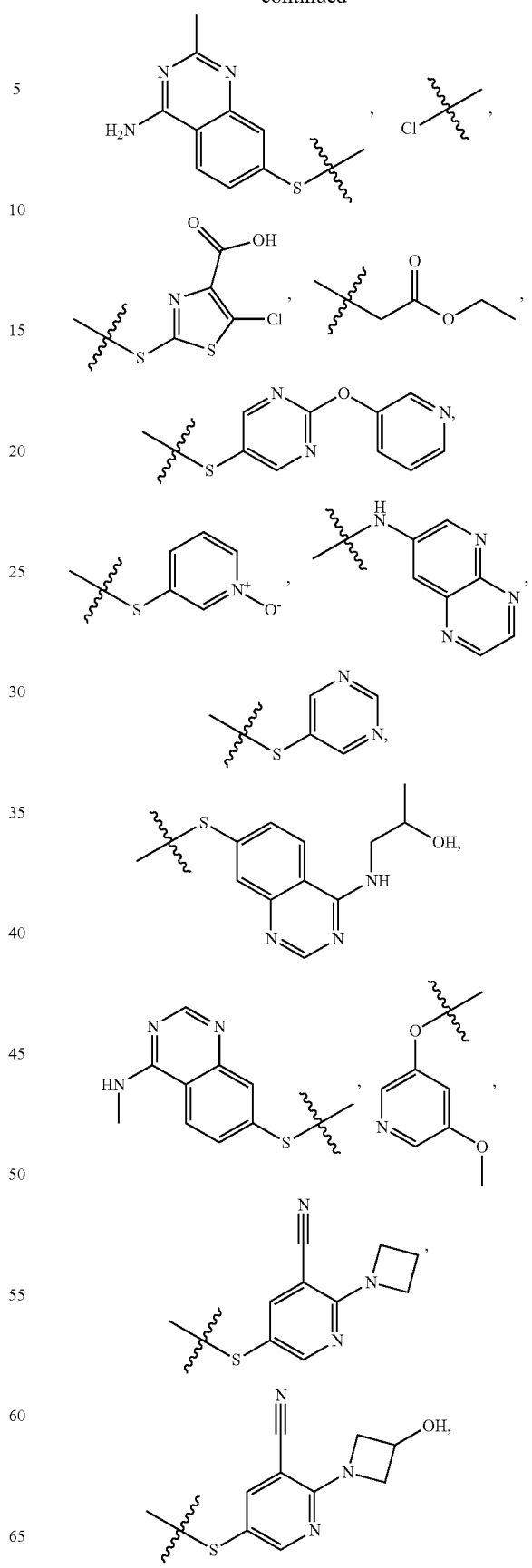

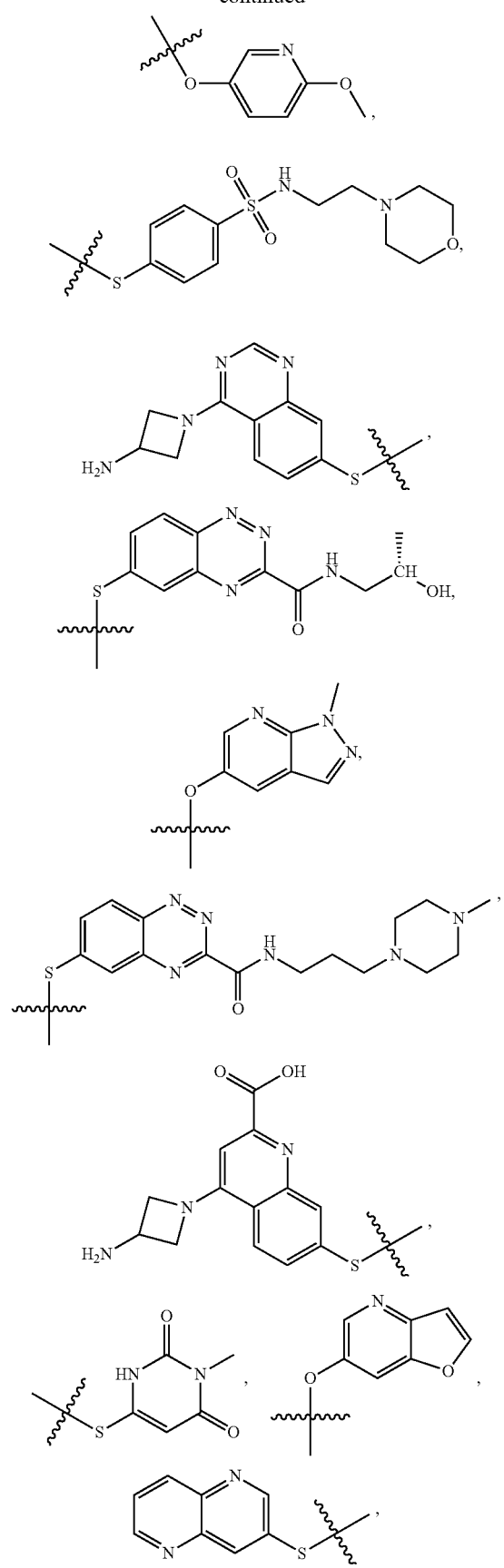
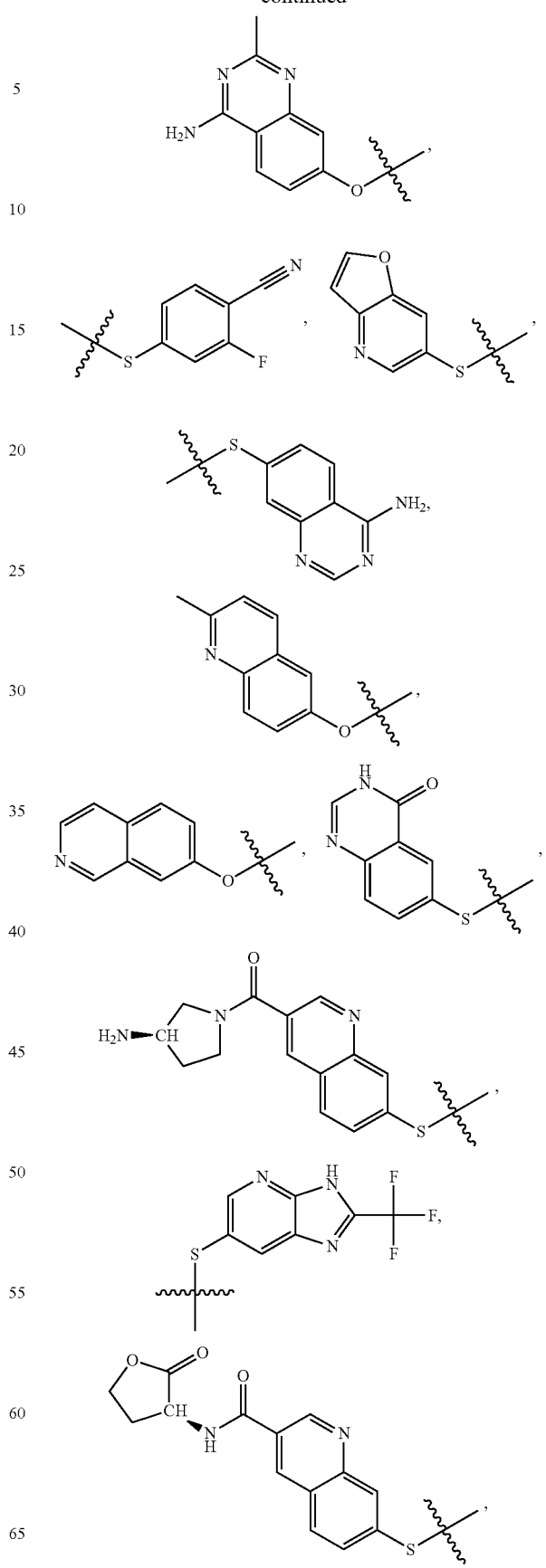

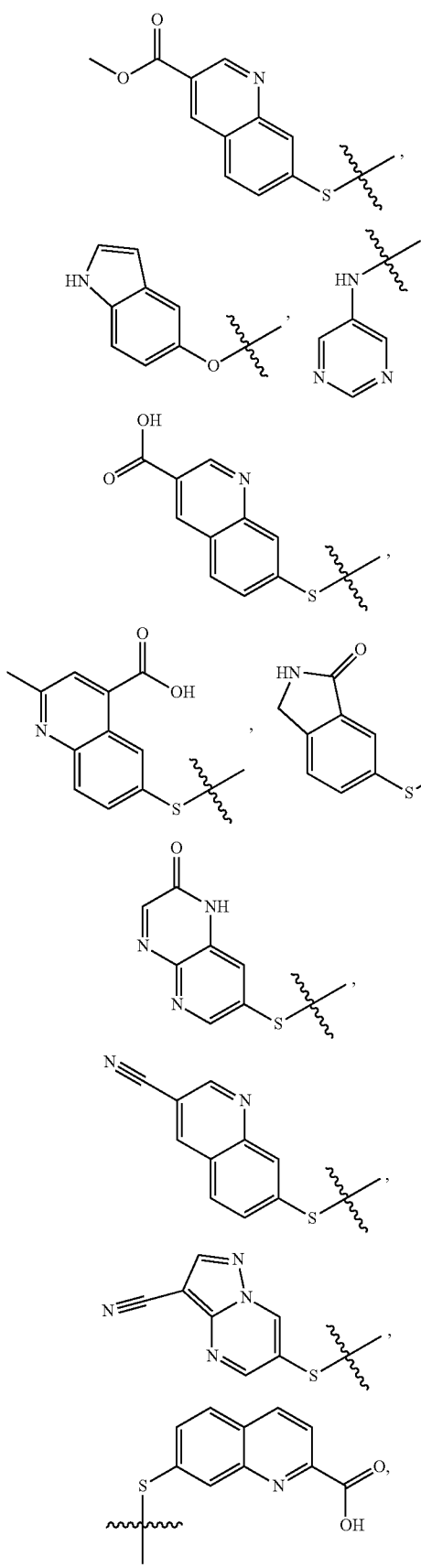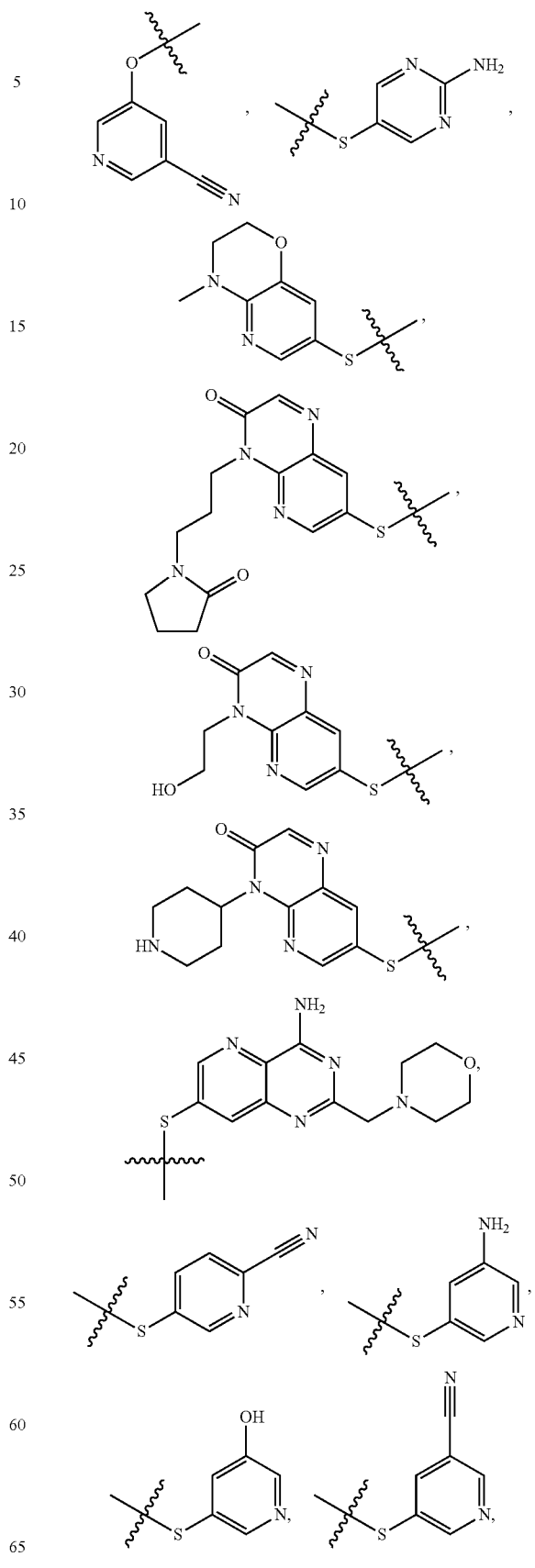

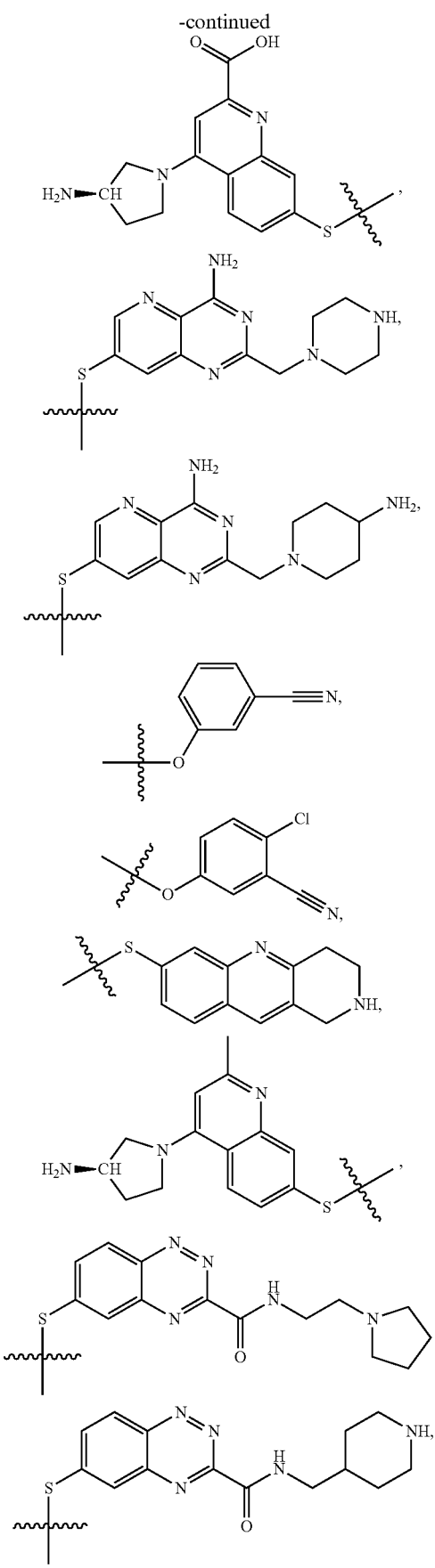
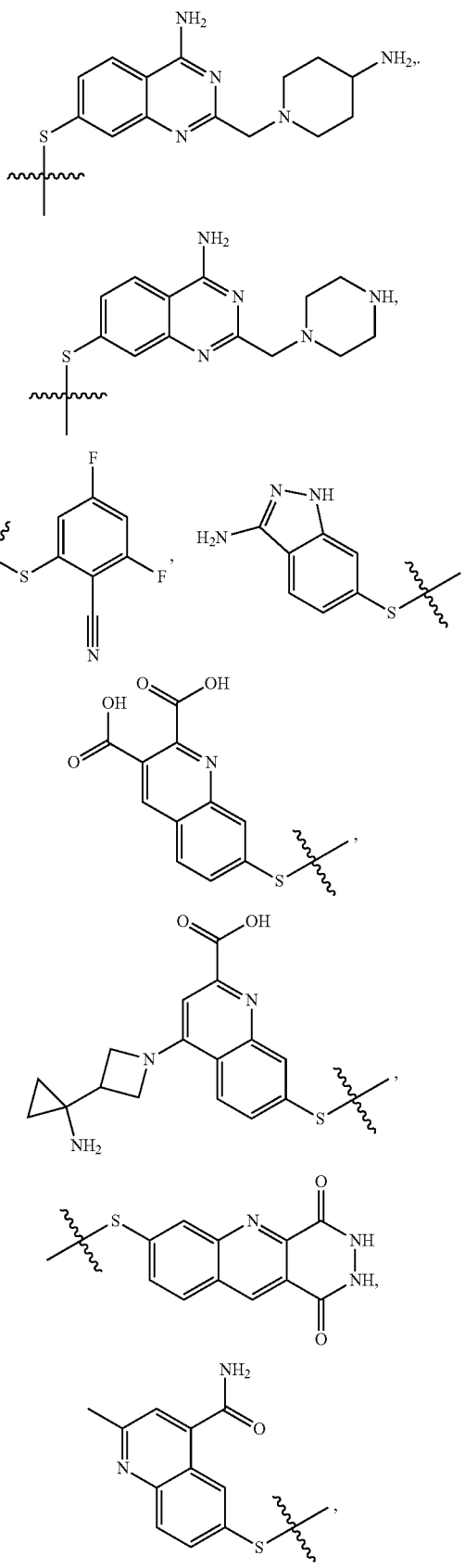

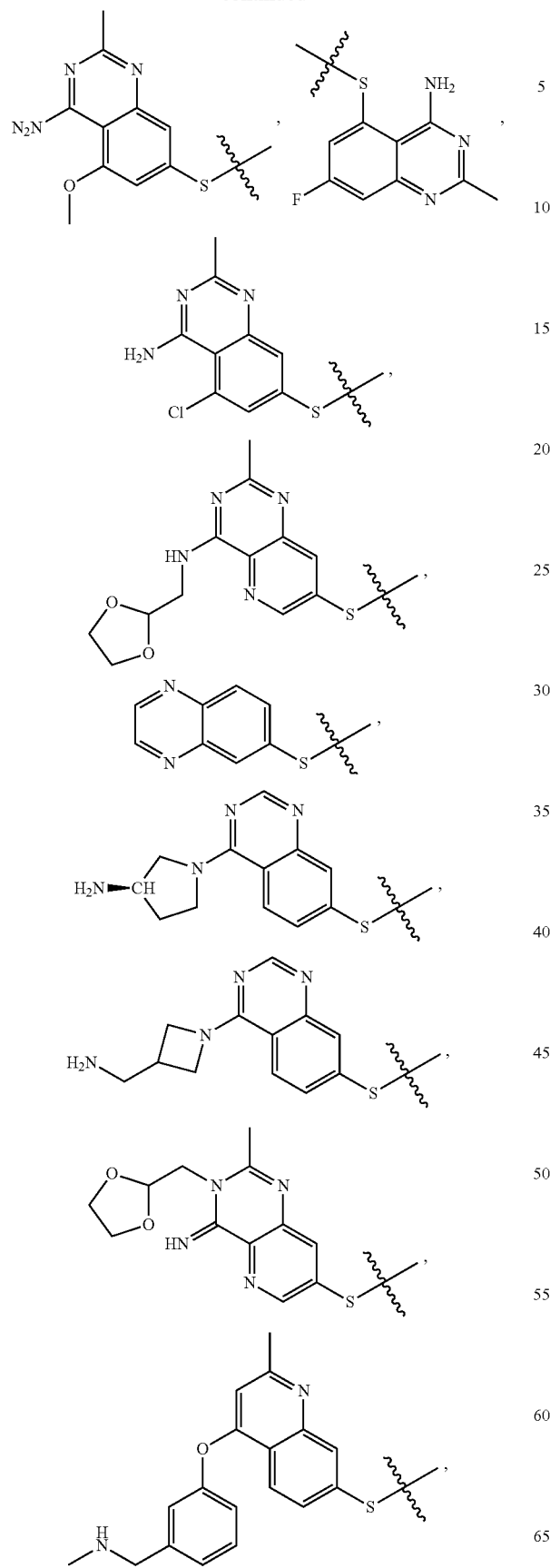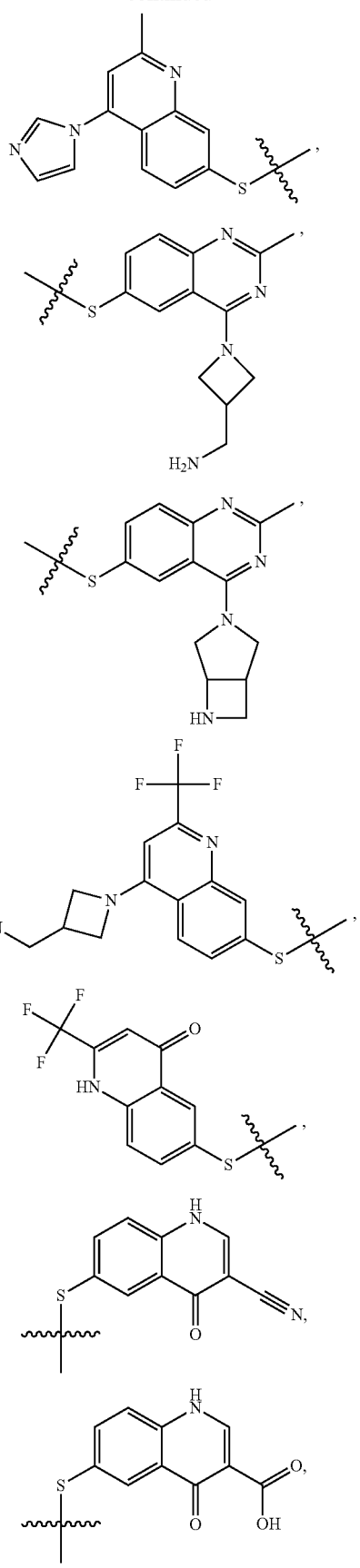

-continued
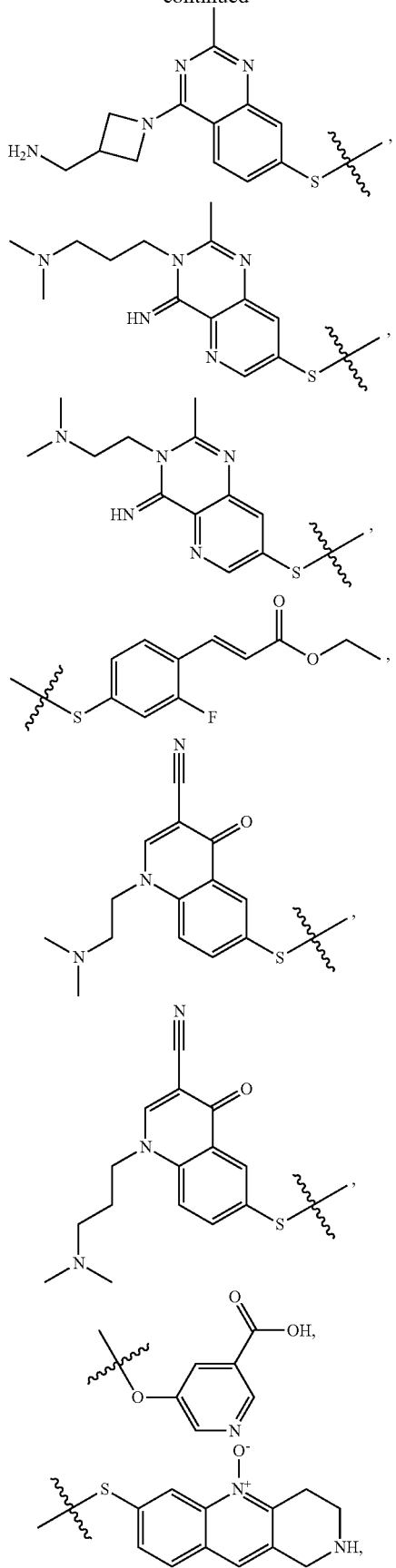
-continued
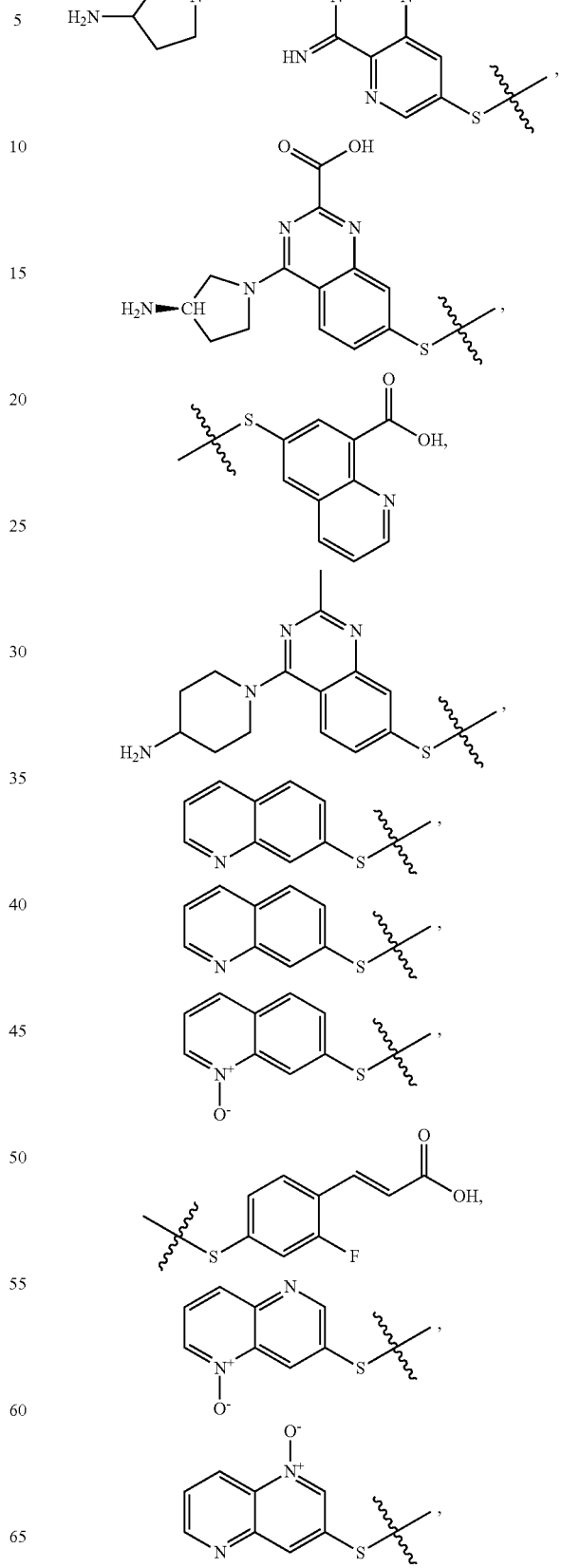

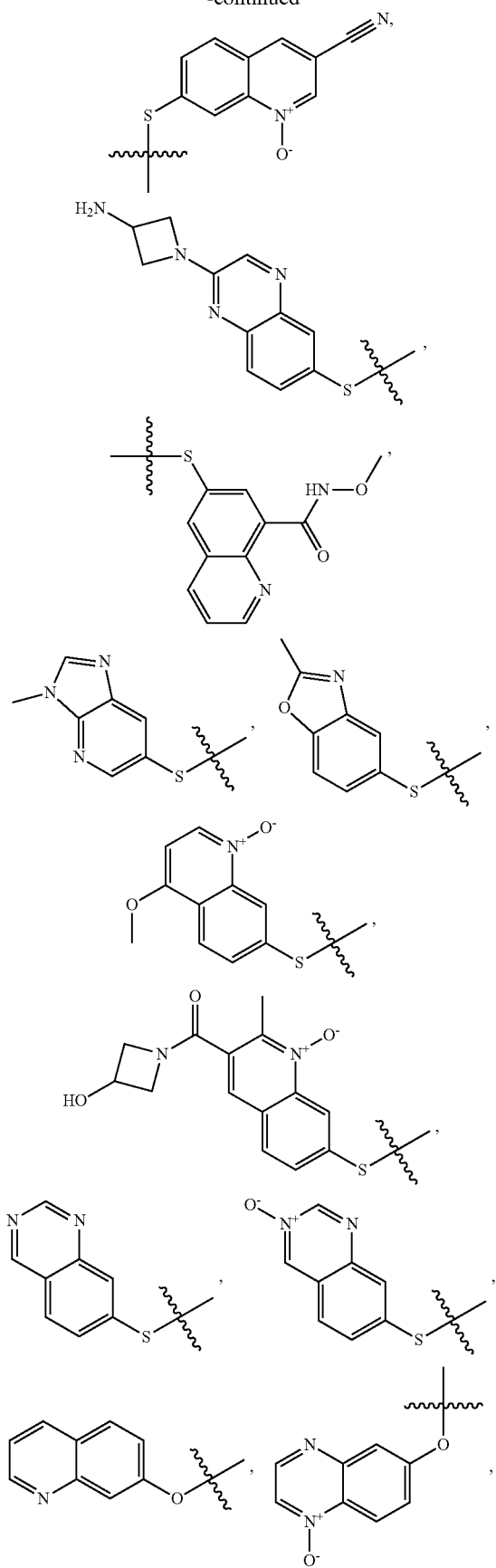
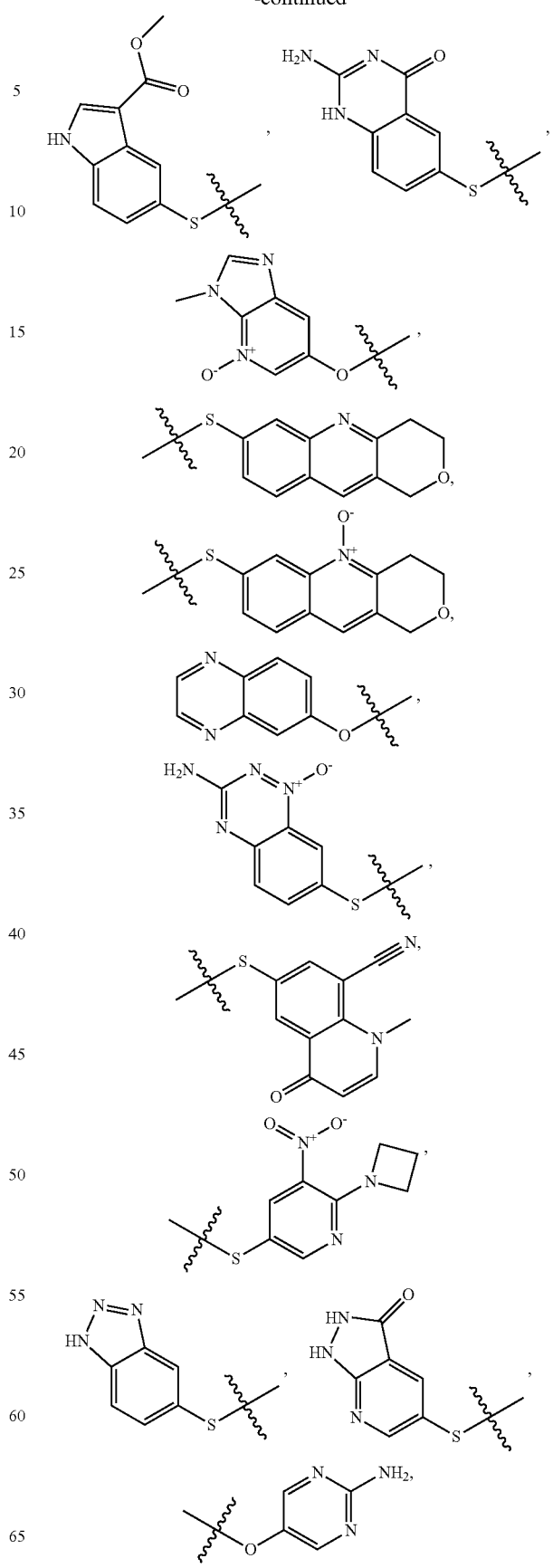

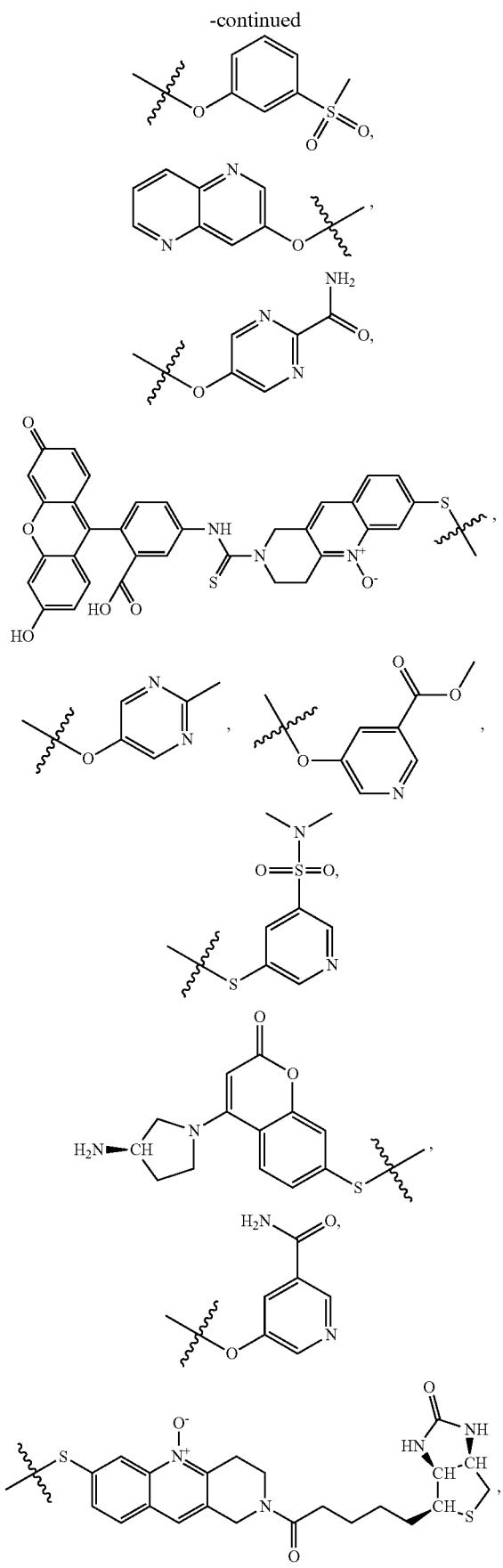

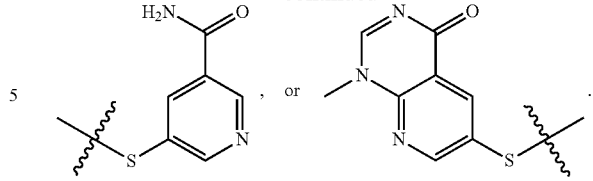

, or

Of course, the linker L in the above embodiments may be interchanged with another linker described herein, such as O, S, NH, or CH$_2$.

$R^4$ may be H, an inorganic residue, or a hydrocarbyl residue (1-30C) containing 0-12 heteroatoms selected from O, S and N and containing 0-10 inorganic residues, wherein $R^5$ and $R^4$ together may join to form a fused ring.

An inorganic residue of $R^4$ may be H, halo, OH, NH$_2$, SH, SO$_2$H, NHOH, SO$_3$H, SO$_2$NH$_2$, or NHSO$_2$NH$_2$.

In some embodiments, a hydrocarbyl residue (1-30C) containing 0-12 heteroatoms selected from O, S and N of $R^4$ may be an aryl C$_{5-14}$ or heteroaryl C$_{1-14}$ moiety that may be substituted with 0-10 substituents selected from alkyl, alkenyl, alkynyl, aryl, arylalkyl, acyl, aroyl, heteroaryl, heteroalkyl, heteroalkenyl, heteroalkynyl, haloalkyl, haloalkenyl, haloalkynyl, heteroarylalkyl, NH-aroyl, arylacyl, heteroarylacyl, halo, —O (if $R^4$ contains N), OR', NR'$_2$, SR', SOR', SO$_2$R', OCOR', N-alkyl-OR', CONR'OR', NR'COR', NR'CONR'$_2$, NR'COOR', OCONR'$_2$, OR', NR'$_2$, COOR', alkyl-OOR', SO$_3$R', CONR'$_2$, CONR'$_2$OH, SO$_2$NR'$_2$, NR'SO$_2$NR'$_2$, CN, CF$_3$, or NO$_2$, wherein each R' is independently H, alkyl, alkenyl or aryl or heteroforms thereof, and wherein two of said substituents on adjacent positions can be joined to form a fused, optionally substituted aromatic or nonaromatic, saturated or unsaturated ring which contains 3-14 members.

In some embodiments, a hydrocarbyl residue (1-30C) containing 0-12 heteroatoms selected from O, S and N of $R^4$ may be an alkyl, alkenyl, alkynyl, heteroalkyl, heteroalkenyl, heteroalkynyl, arylalkyl, arylalkenyl, arylalkynyl, heteroarylalkyl, heteroarylalkenyl, or heteroarylalkynyl moiety substituted with 0-10 substituents selected from the group consisting of. aryl, haloaryl, arylalkyl, arylalkenyl, arylalkynyl, haloaryl, heteroaryl, heteroarylalkyl, heteroarylalkenyl, heteroarylalkynyl, acyl, aroyl, NH-aroyl, arylacyl, heteroarylacyl, halo, —O (if $R^4$ contains N), =O, =NH, OR'', NR''$_2$, SR'', SOR'', SO$_2$R'', OCOR'', CONR''OR'', NR''COR'', NR''CONR''$_2$, NR''COOR'', NR''COCOOR'', OCONR''$_2$, COOR'', SO$_3$R'', CONR''$_2$, CONR''$_2$OH, SO$_2$NR''$_2$, NR''SO$_2$R'', NR''SO$_2$NR''$_2$, CN, CF$_3$, or NO$_2$, wherein each R'' is independently H, optionally substituted alkyl, alkenyl, alkynyl, aryl, heteroalkyl, heteroalkenyl, heteroalkynyl, heteroaryl, or halo forms thereof, and wherein two of said substituents on adjacent positions can be joined to form a fused, optionally substituted aromatic or nonaromatic, saturated or unsaturated ring which contains 3-14 members.

In further embodiments, a hydrocarbyl residue (1-30C) containing 0-12 heteroatoms selected from O, S and N of $R^4$ may be OR''', NR'''$_2$, or OSO$_2$R''', wherein R''' is an aryl C$_{5-14}$ or heteroaryl C$_{1-14}$ moiety substituted with 0-10 substituents selected from alkyl, alkenyl, alkynyl, aryl, arylalkyl, acyl, aroyl, heteroaryl, heteroalkyl, heteroalkenyl, heteroalkynyl, haloalkyl, haloalkenyl, haloalkynyl, heteroarylalkyl, NH-aroyl, arylacyl, heteroarylacyl, halo, —O (if $R^4$ contains N), OR', NR'$_2$, SR', SOR', SO$_2$R', OCOR', N-alkyl-OR', CONR'OR', NR'COR', NR'CONR'$_2$, NR'COOR', OCONR'$_2$, COOR', alkyl-OOR', SO$_3$R', CONR'$_2$, CONR'$_2$OH, SO$_2$NR'$_2$, NR'SO$_2$NR'$_2$, CN, CF$_3$, or NO$_2$, wherein each R' is independently H, alkyl, alkenyl or aryl or heteroforms thereof, and wherein two of said substituents on adjacent positions can be joined to form a fused, optionally substituted aromatic or nonaromatic, saturated or unsaturated ring which contains 3-14 members.

In some aspects, R$^4$ may be selected from the group consisting of a) H, halo, or OH;

b) C3-6 heteroaryl moiety containing 1-4 heteroatoms selected from O, S, and N;

c) an alkyl, alkenyl, arylalkenyl, arylalkyl, heteroalkyl, heteroalkynyl, heteroarylalkyl, moiety substituted with 0-10 substituents selected from the group consisting of: haloaryl, haloheteroaryl, heteroaryl, acyl, aroyl, NH-aroyl, halo, =O, =NH, OR'', NR''$_2$, SO$_2$R'', NR''CONR''$_2$, NR''COOR'', NR''COCOOR'', COOR'', NR''SO$_2$R'', wherein each R'' is independently H, optionally substituted alkyl, aryl, heteroalkyl, heteroaryl, optionally substituted with one or more halo, OH, CN, or =O and wherein two of said substituents on adjacent positions can be joined to form a fused, optionally substituted aromatic or nonaromatic, saturated or unsaturated ring which contains 3-14 members; or d) OR''', NR'''$_2$, or OSO$_2$R''', wherein R''' is aryl C$_{5-14}$ or heteroaryl C$_{1-14}$ containing 1-5 O, S, or N substituted with 0-3 substituents selected from alkyl, acyl, aroyl, heteroalkyl, halo, —O (if R$^4$ contains N), OR', NR'$_2$, NHCOR', NHCO$_2$R', NHCONHR', SO$_2$R', COOR', CN, wherein each R' is independently H, alkyl.

Embodiments of R4 include:

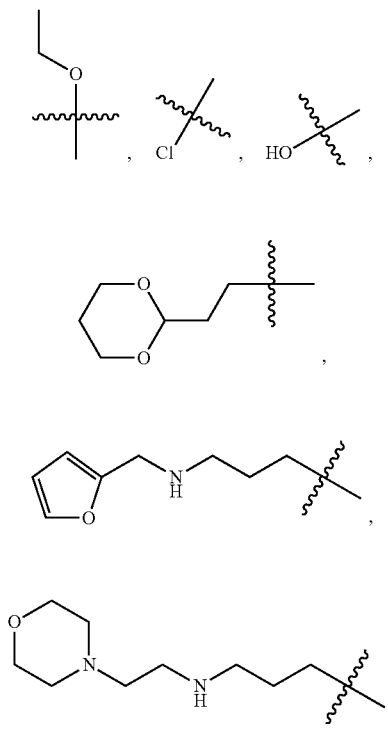

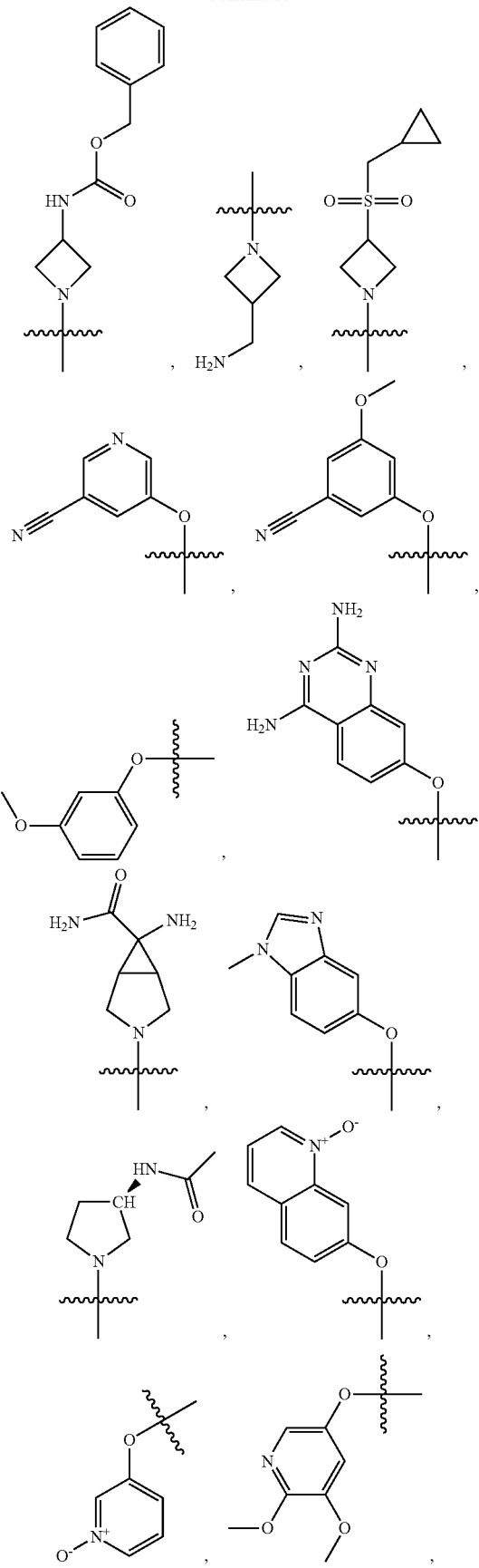

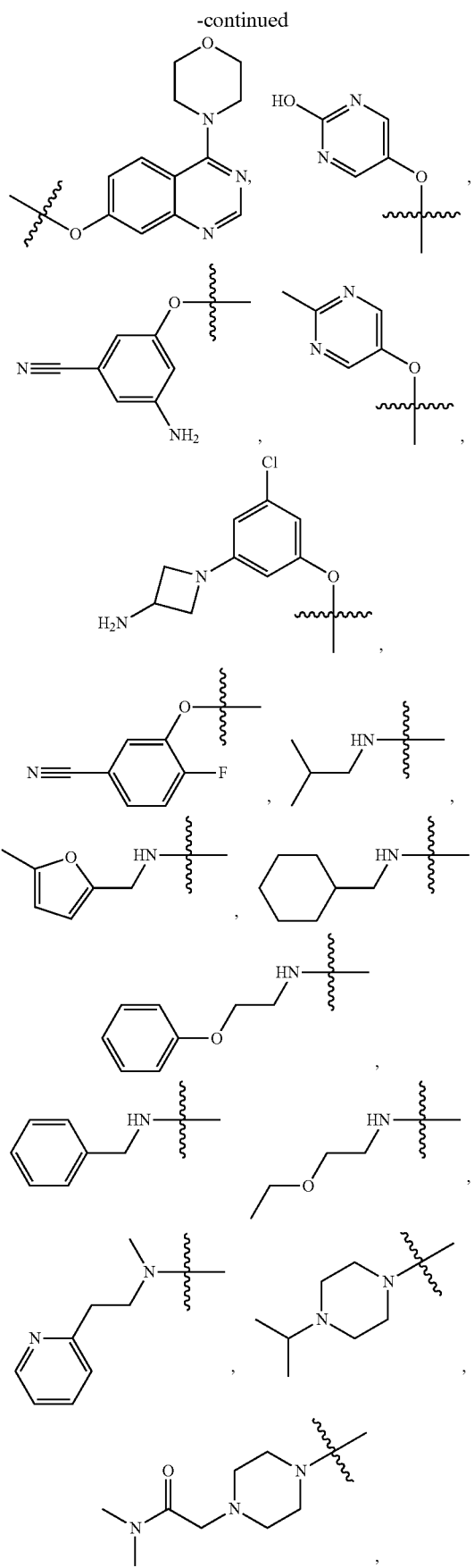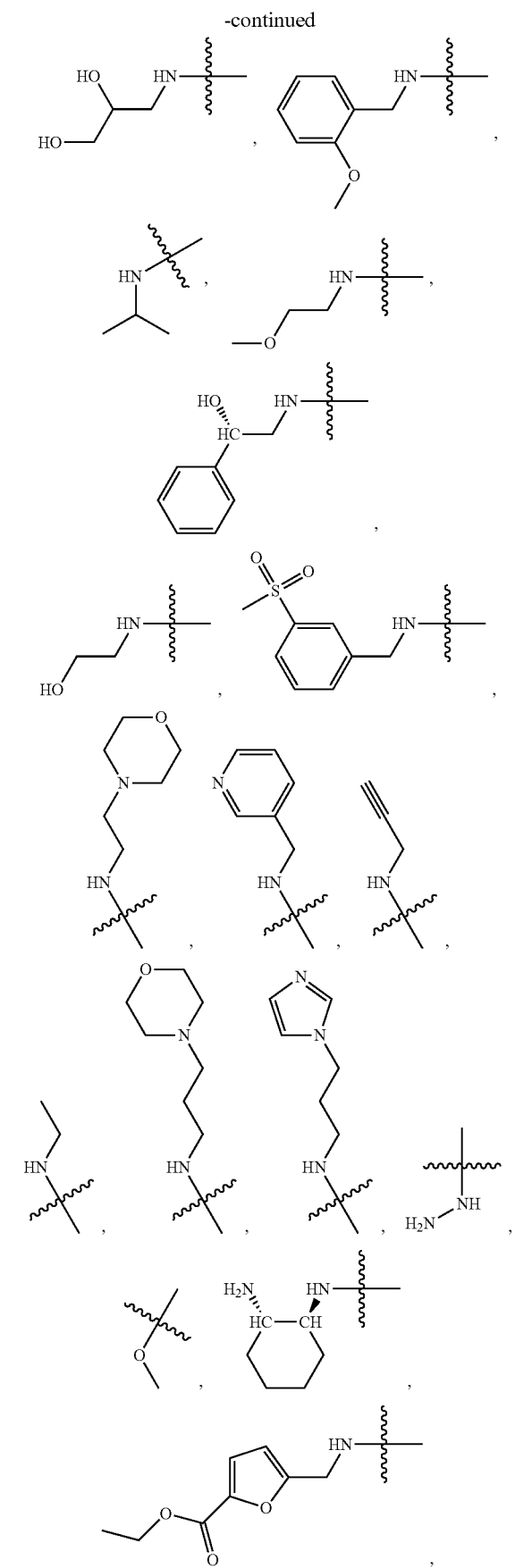

-continued
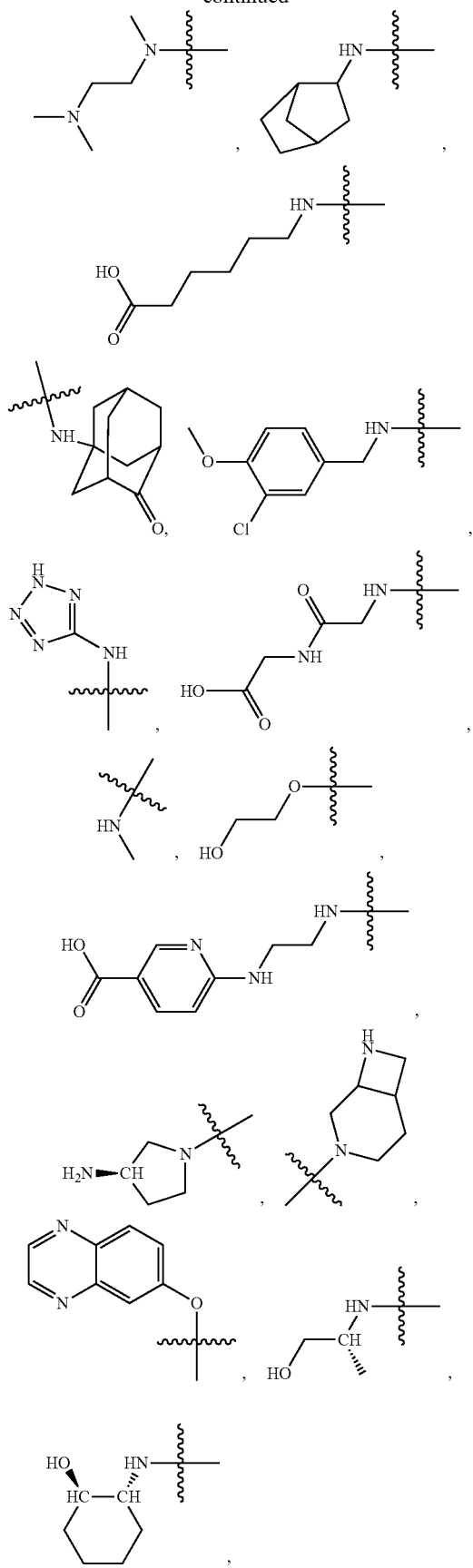
,
-continued
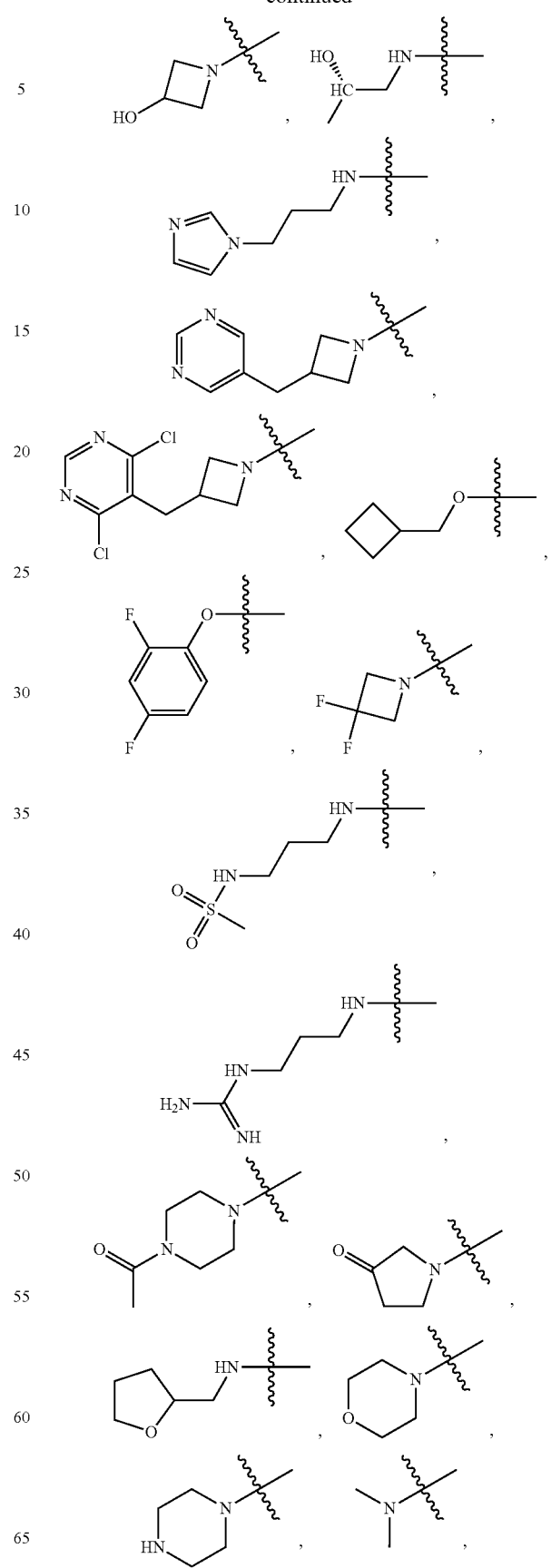
,

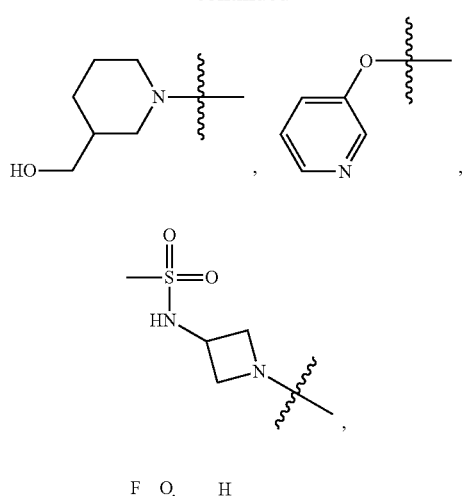
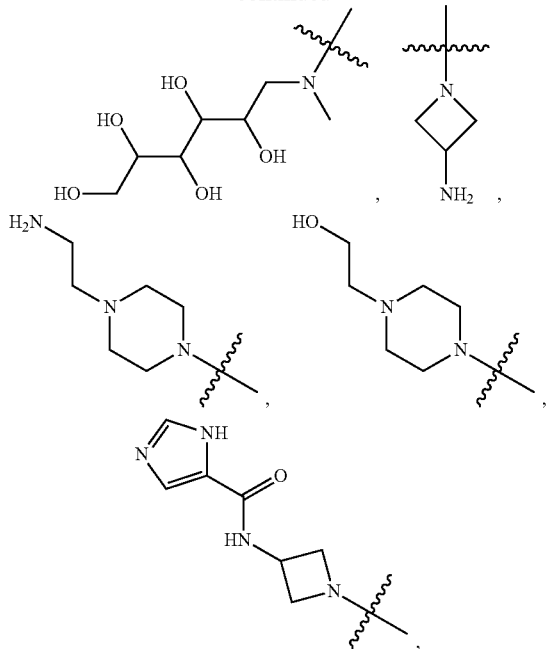
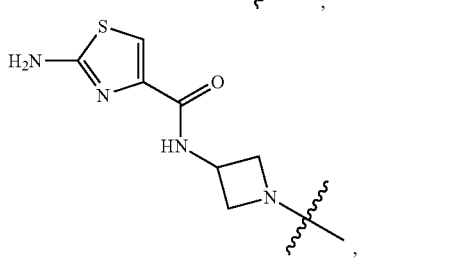
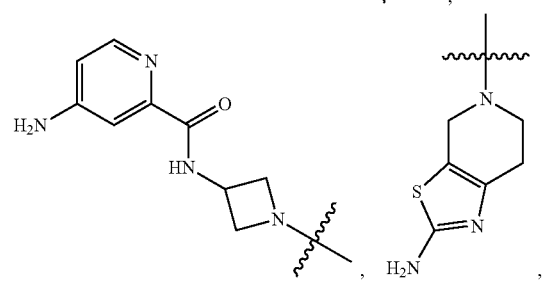
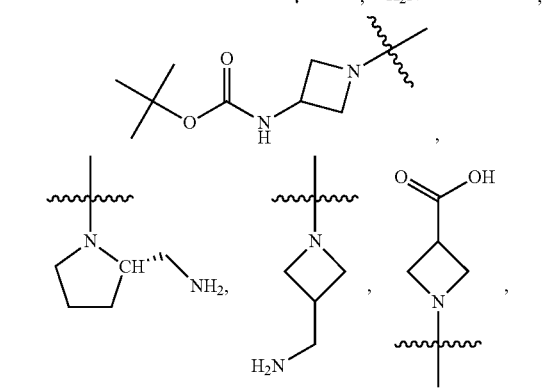
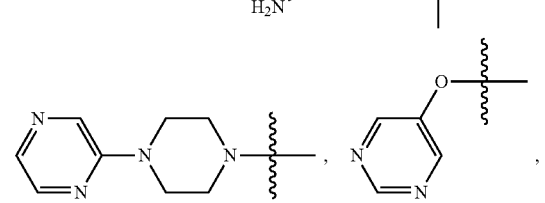

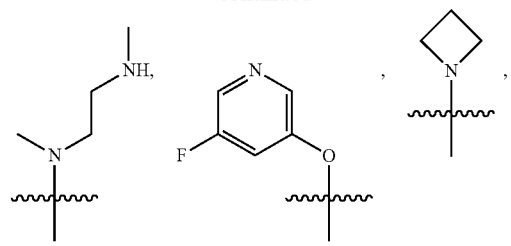
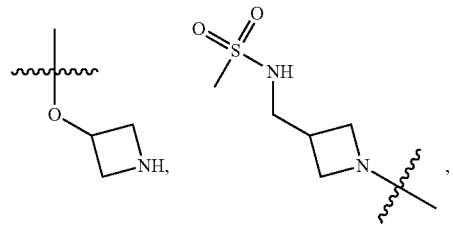
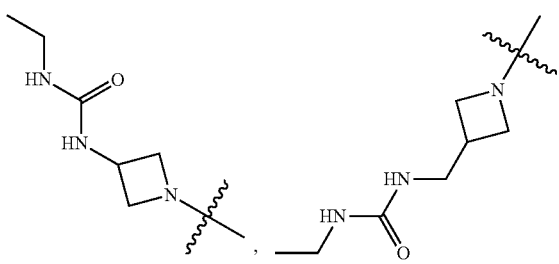
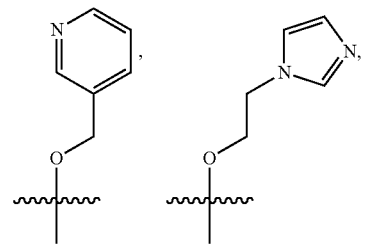
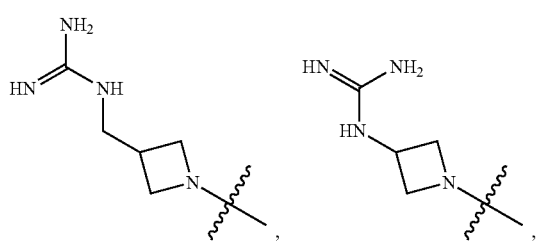
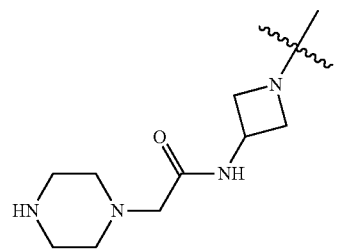
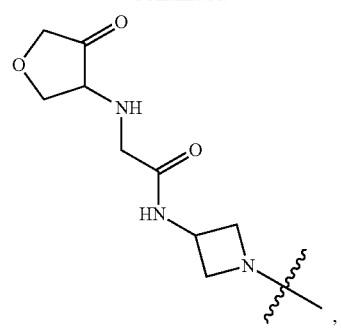
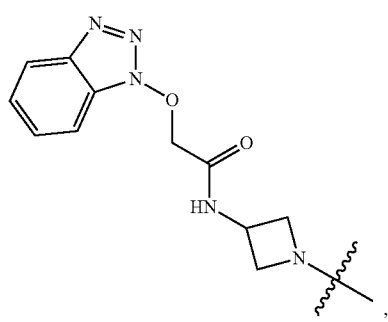
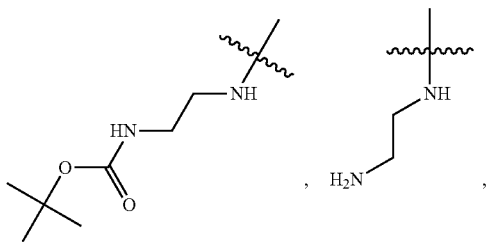
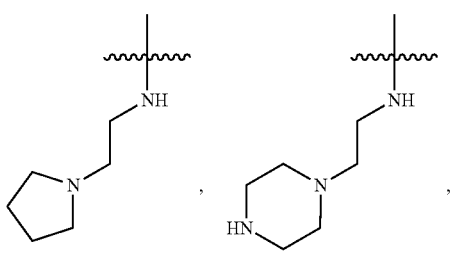
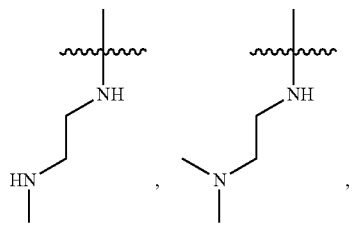
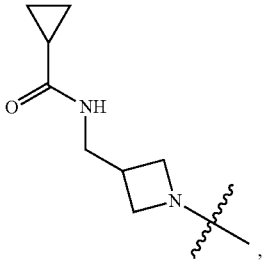

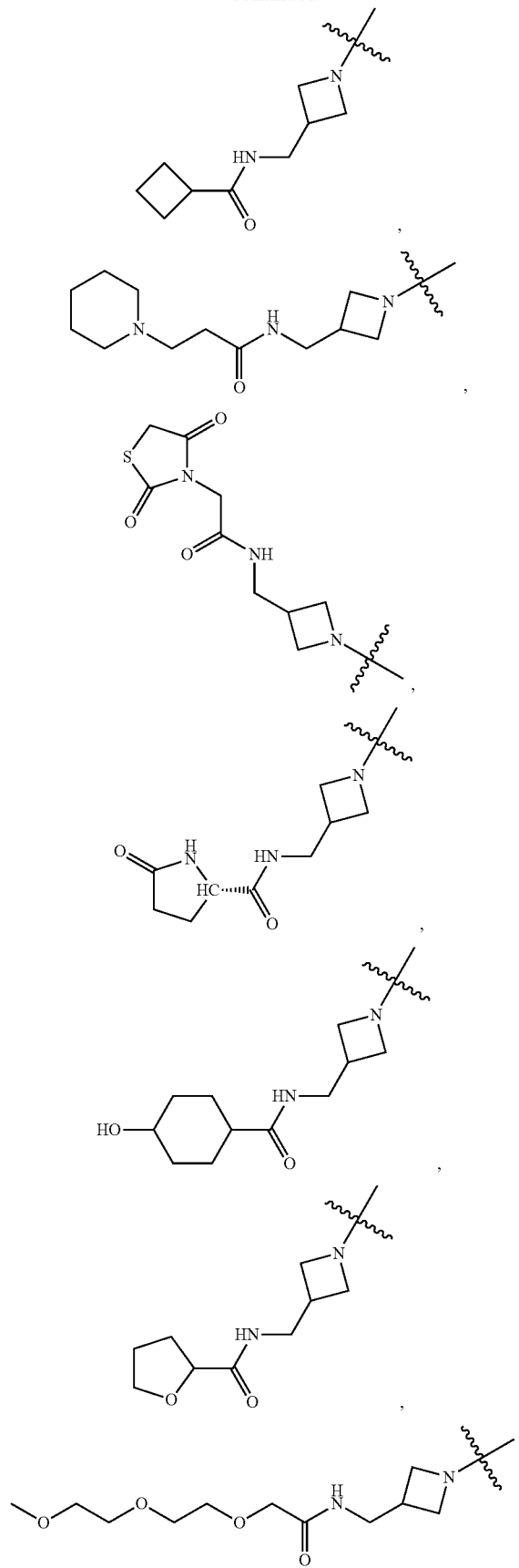
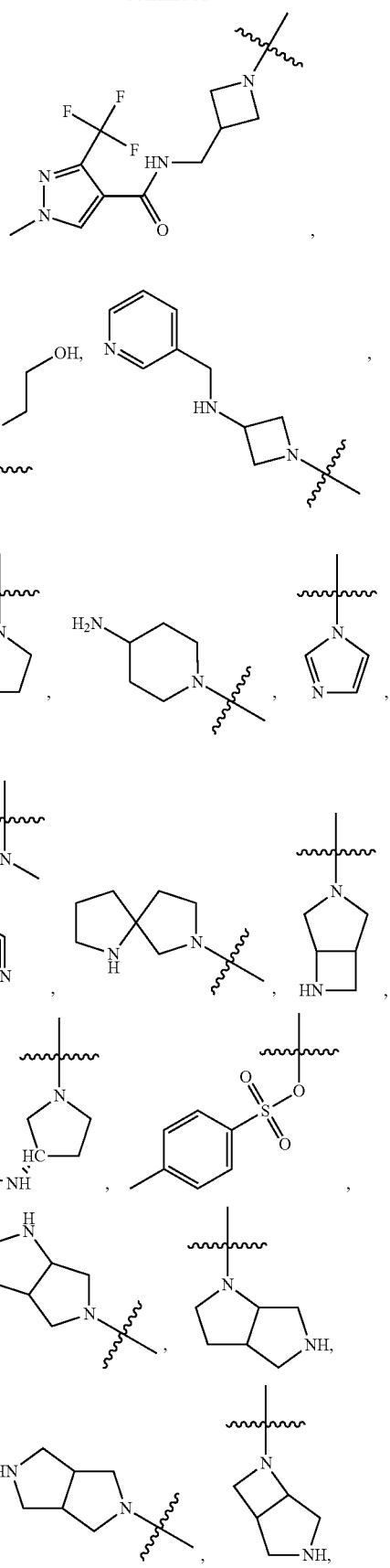

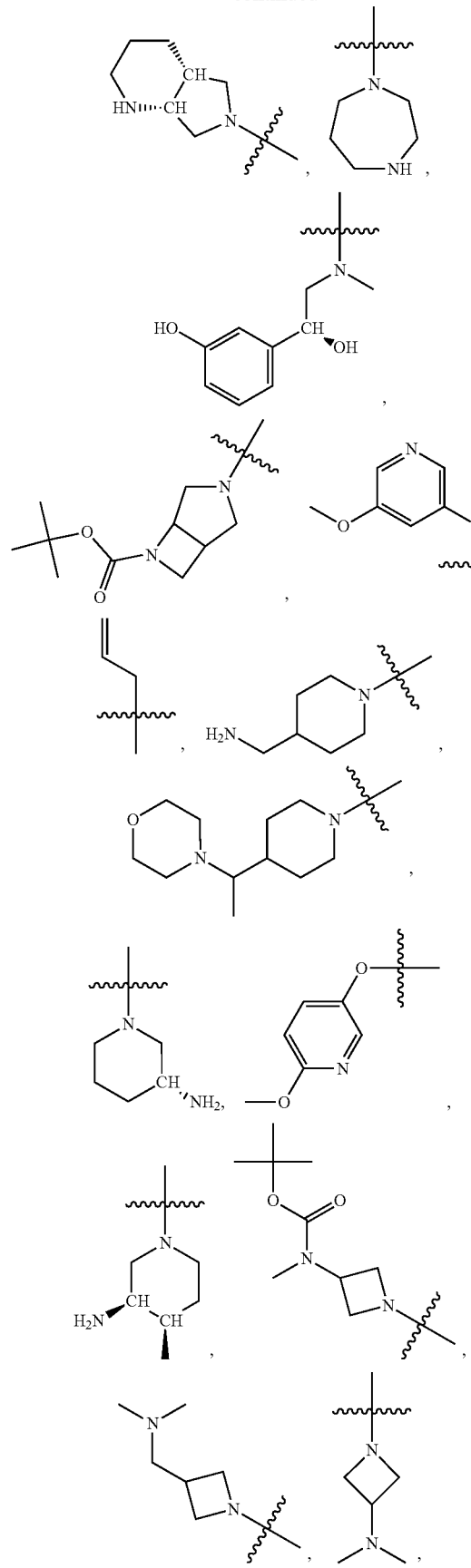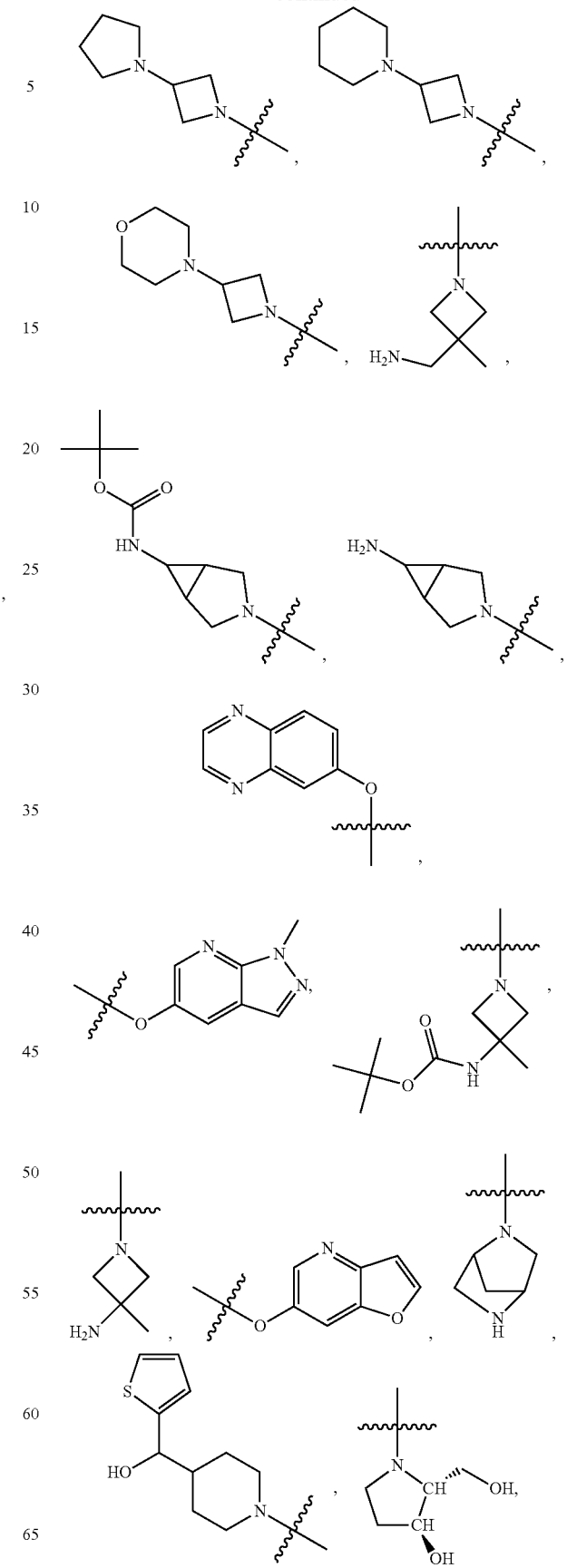

41
-continued
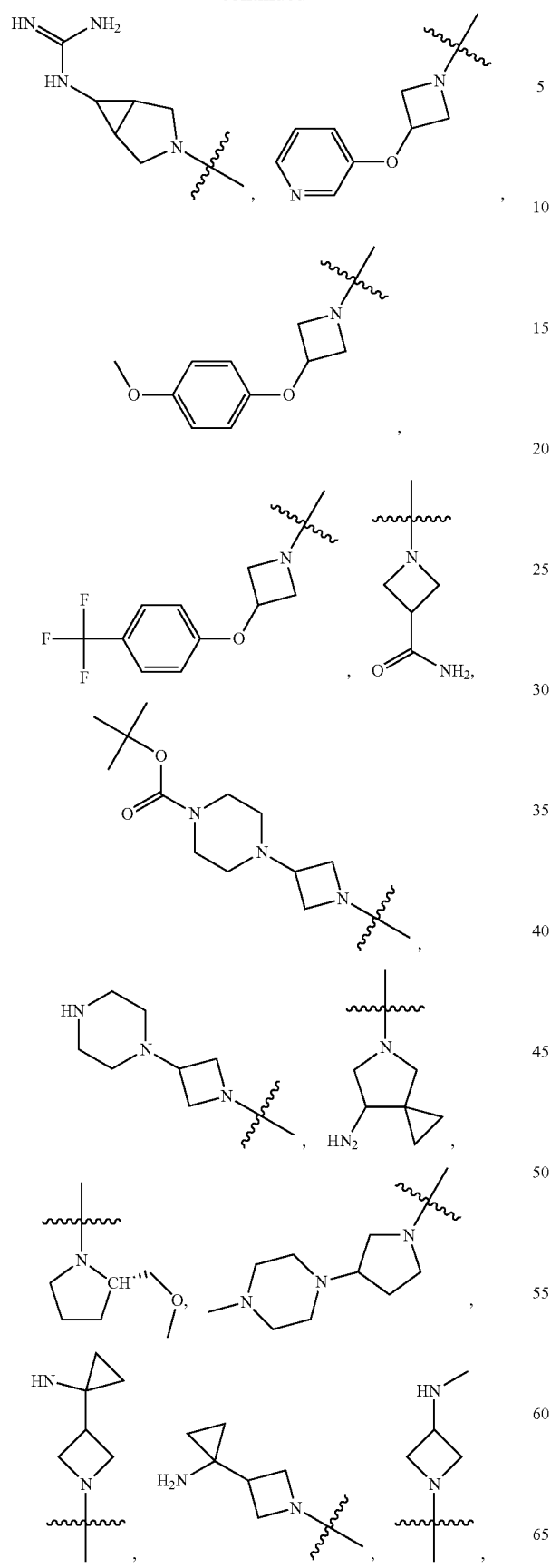
42
-continued
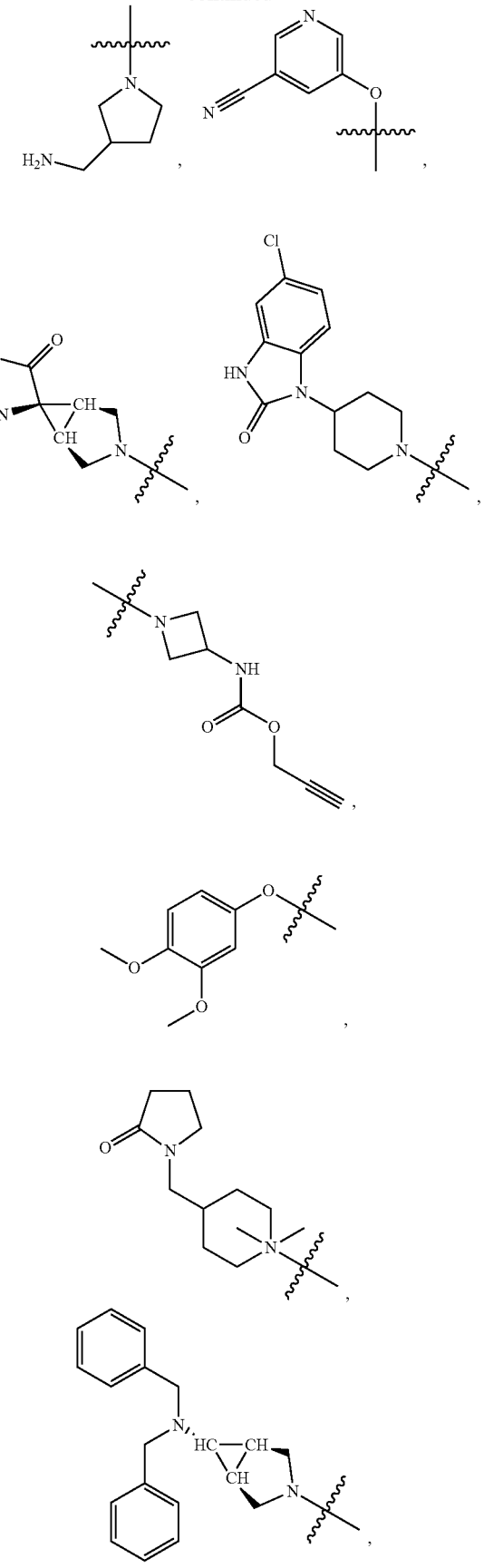

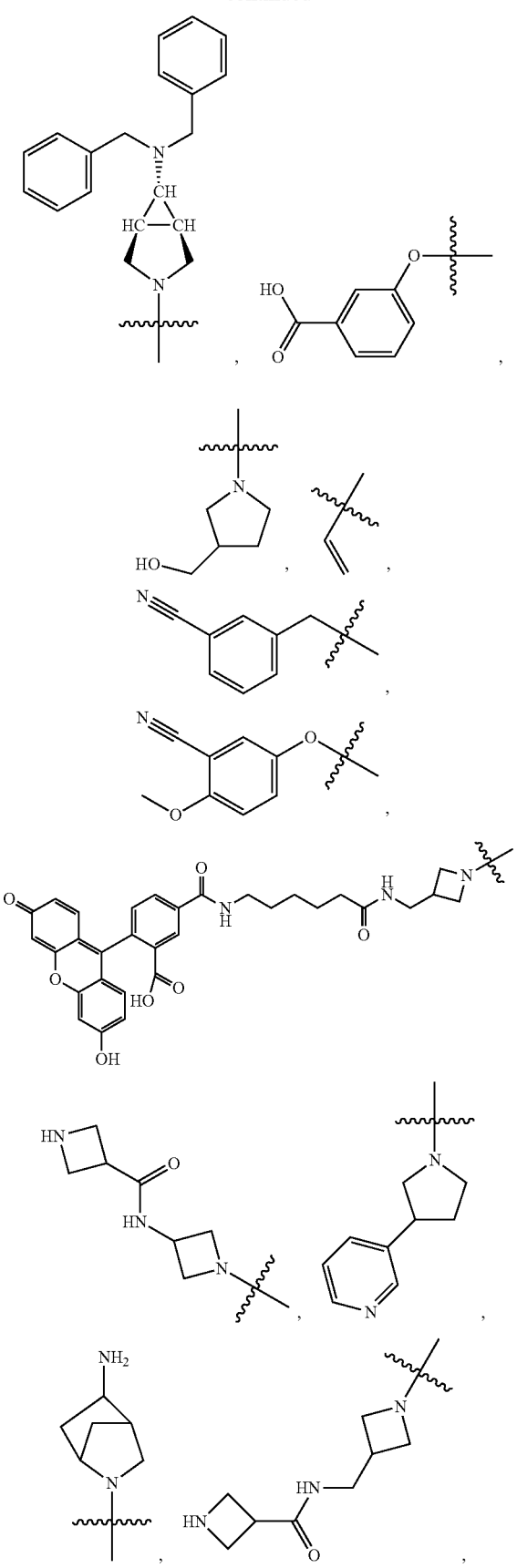
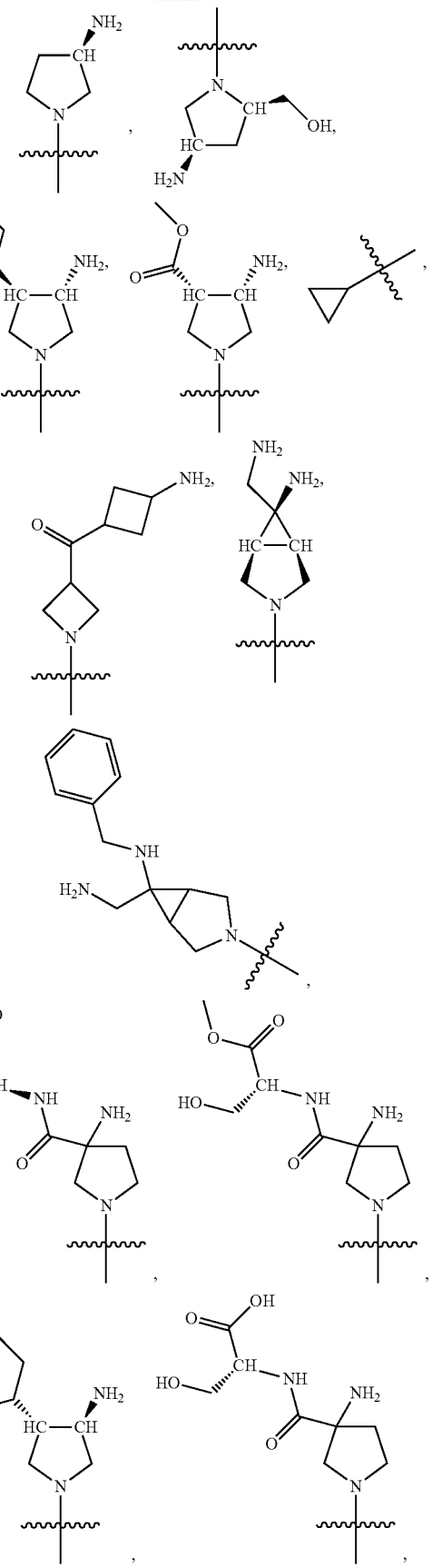

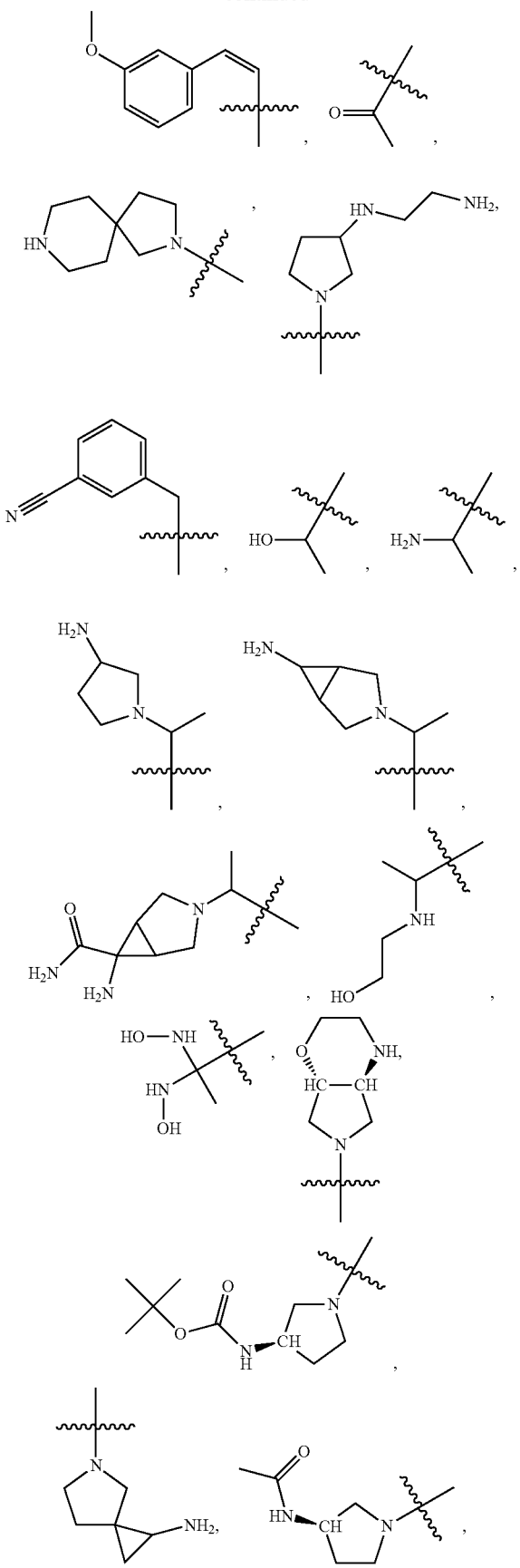
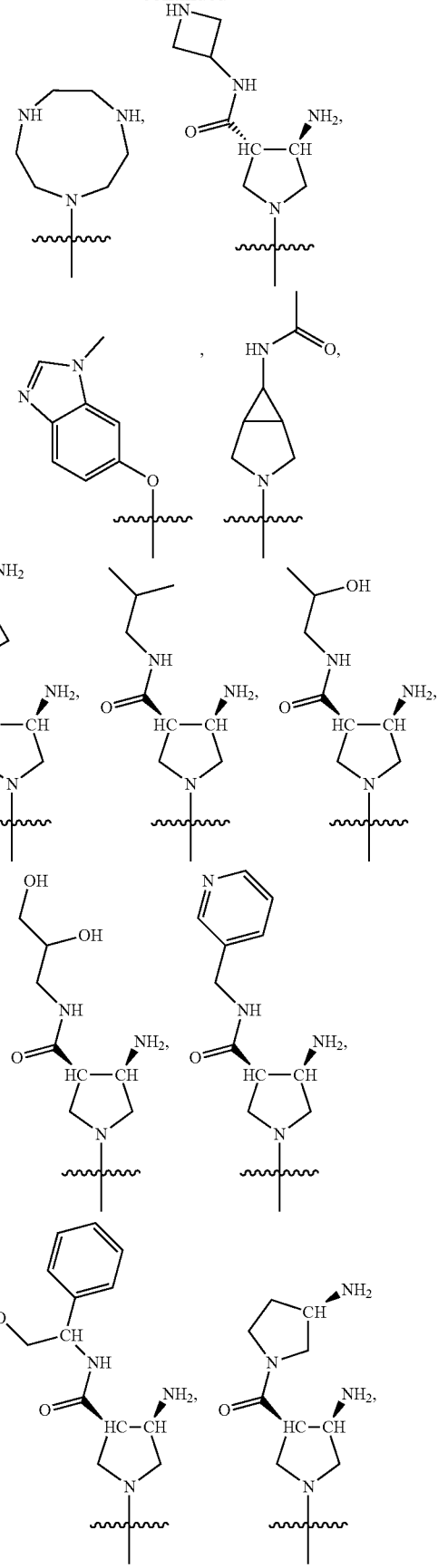

-continued
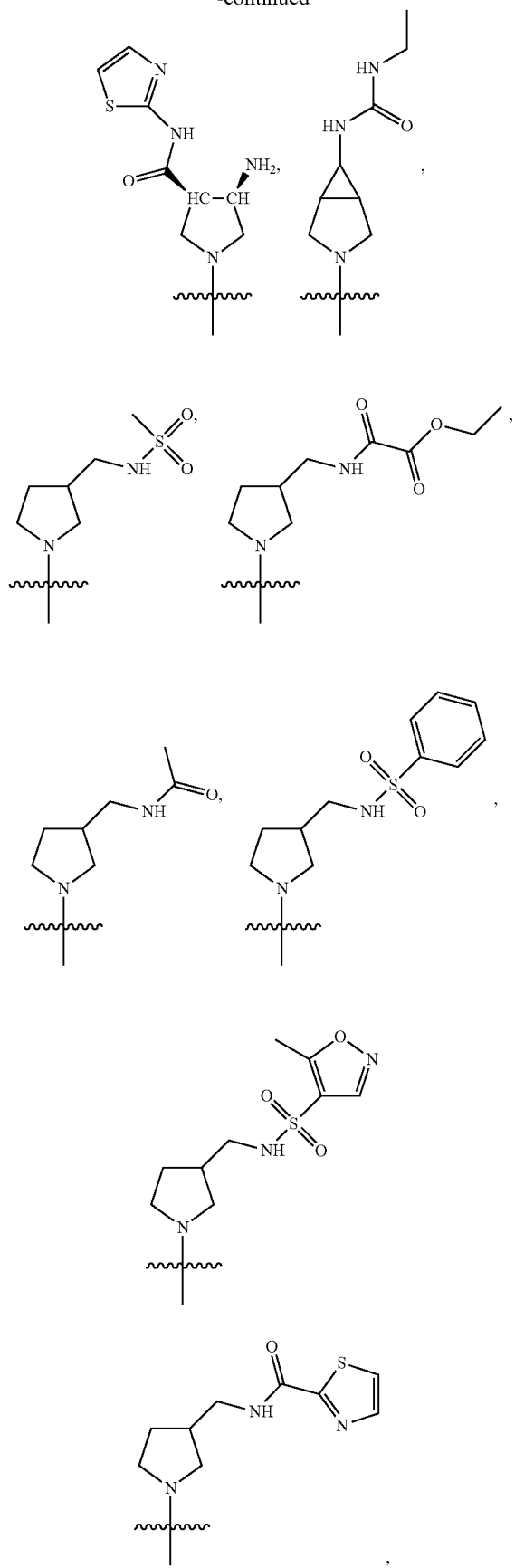
-continued
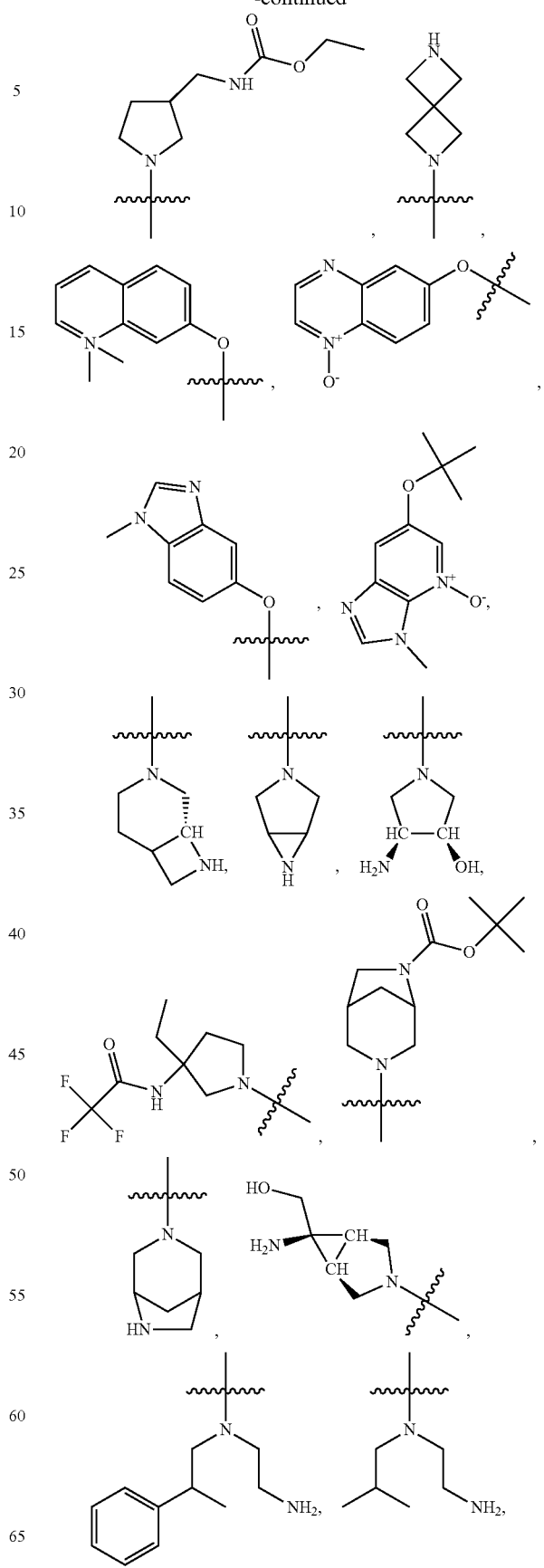

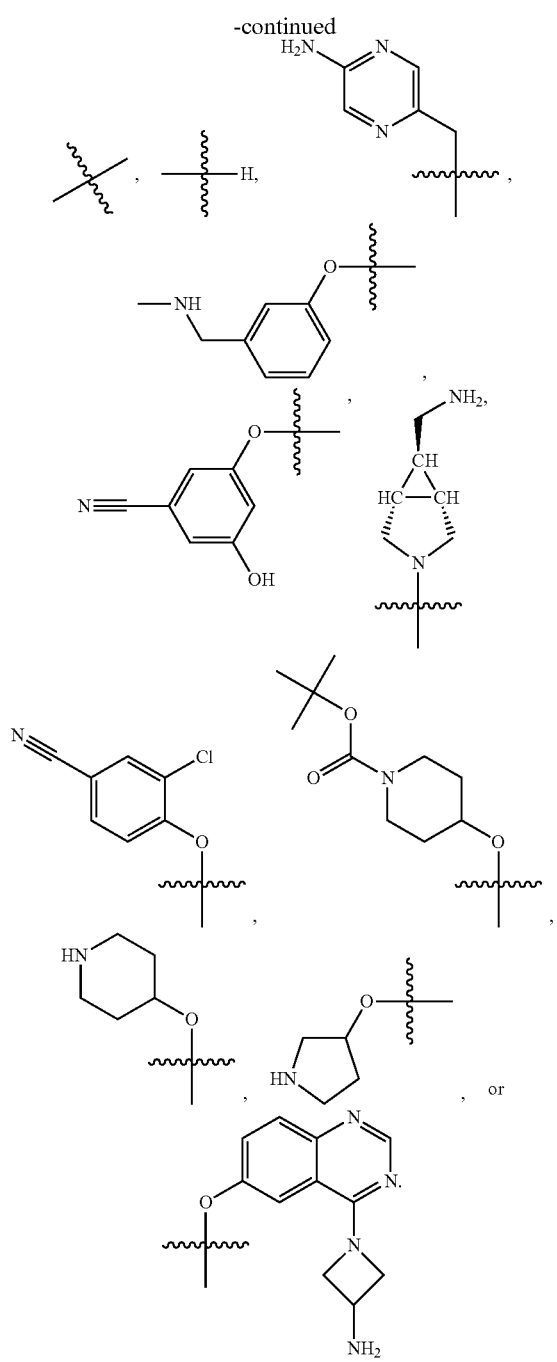

R[4] may also be selected from the group consisting of optionally-substituted azetidine, pyrrolidine, piperidine, piperazine, and morpholine. In addition, R[4] may be selected from the group consisting azetidin-3-amine, pyrrolidin-3-amine, 3,6-diazabicyclo[3.2.0]heptane, 3-azabicyclo[3.1.0]hexan-6-amine, 1H-pyrrolo[3,4-b]pyridine, octahydropyrrolo[3,4-b]pyrrole, and 2-azabicyclo[2.2.1]heptan-5-amine.

R[6] may be H, $C_5$ alkyl, $C_{2-5}$ alkenyl, $C_{2-5}$ alkynyl, halo $C_{1-5}$ alkyl, halo $C_{2-5}$ alkenyl, halo $C_{2-5}$ alkynyl, $C_{1-5}$ hydroxyalkyl, $C_{1-5}$ alkyl chloride, $C_{2-5}$ alkenyl chloride, and $C_{2-5}$ alkynyl chloride. For example, R[6] may be selected from the group consisting of H, Cl, ethyl, vinyl, vinyl chloride, vinyl dichloride, $CH_2CH_2OH$, $CH(OH)CH_3$, cyclopropyl, $CH_2CF_3$, or ethynyl chloride. In some embodiments, R[6] is ethyl.

In some aspects, R[6] may be Cl, Br, I, Me, Et, $CH_2F$, $CHF_2$, $CF_3$, $CH_2OH$, or 2-chlorovinylidene.

As used herein, the term "alkyl," "alkenyl" and "alkynyl" include straight- and branched-chain and cyclic monovalent substituents. Examples include methyl, ethyl, isobutyl, cyclopropyl, cyclohexyl, cyclopentylethyl, 2-propenyl, 3-butynyl, and the like. Typically, the alkyl, alkenyl and alkynyl substituents contain 1-15C (alkyl) or 2-10C (alkenyl or alkynyl). They may contain 1-10 or 1-6C (alkyl), or 2-8 or 2-6C (alkenyl or alkynyl). Heteroalkyl, heteroalkenyl and heteroalkynyl are similarly defined but may contain 1-10, such as 1-6, O, S or N heteroatoms or combinations thereof within the backbone residue. Some heteroalkyl, heteroalkenyl and heteroalkynyl contain, 1, 2, 3, 4, 5, 6, 7, 8, 9, or 10, O, S or N heteroatoms or combinations thereof. The term "alkyl," "alkenyl" or "alkynyl" also includes consecutive ring systems wherein two or more ring systems are spaced by a bond or acyclic alkyl, alkenyl, alkynyl, heteroalkyl, heteroalkenyl and heteroalkynyl. For example, two immediately adjacent cycloalkyl and/or heteroalkyl rings, or two such rings spaced by, for example, alkyl or heteroalkyl. Cyclic substituents encompass fused multiple ring systems including fused bridged rings and spiro systems wherein the cycloalkyl ring or heterocycloalkyl ring has a carbon ring atom in common with another ring.

"Alicyclic" refers to optionally-substituted cycloalkanes comprising 3-14 carbon atoms in either a monocyclic or, where possible, fused bicyclic arrangement. Alicyclic may have C3-10 or C3-6 carbon atoms. "Heterocyclic" (or "heterocycle") refers to optionally-substituted monocyclic and fused bicyclic non-aromatic groups, saturated or unsaturated, having the specified number of members, containing 1-4 heteroatoms selected from N, O and S. Examples include tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, and tetrahydrothiophene.

"Optionally-substituted" refers to the possible presence of one or more pendant substituents. "Substituted" refers to the presence of one or more pendant substituents in which hydrogen is replaced by a group such as but not restricted to halo, alkyl, alkenyl, cycloalkyl, cycloalkenyl, alkoxy, cycloalkoxy, amino, hydroxy, alkylhydroxy, alkylamine, cycloalkylamine, carboxy, carboxamide, sulfonamide, or heterocyclyl nitrile, alkyl sulfoxide, or thioether. Substituents are discussed herein with respect to various R groups. "Optionally substituted substituent" refers to the possible presence of additional pendant substituents on the first-named substituent, which may be similar to the type of first-named substituent. In some embodiments, substituents that are present are "non-interfering" and thus leave the antibiotic activity of the compound of Formula I qualitatively intact. Thus, the substituent may alter the degree of antibiotic activity. However, as long as the compound of Formula I retains some antibiotic activity, the substituent is considered non-interfering.

"Aryl" refers to optionally-substituted monocyclic and fused bicyclic carbocyclic groups having from five to 12 carbon atoms and having at least one aromatic ring. Examples of particular aryl groups include phenyl and naphthyl.

"Heteroaryl" refers to optionally-substituted aromatic monocyclic and fused bicyclic groups having the specified number of members and containing 1-10 heteroatoms selected from N, O and S. Examples of particular heteroaryl groups include furan, furopyridine, thiophene, pyrrole, imidazole, imidazopyridine, pyrazole, triazole, triazolopyridine, tetrazole, thiazole, thiazolopuridine, oxazole, isoxazole, oxadiazole, thiadiazole, isothiazole, purine pyridine, pyridopurazine, pyridopyrimidine, pyrazolopyridine, pyridazine, pyrazine, pyrimidine, quinoline, quinoxaline isoquinoline, benzofuran, benzopyran, benzothiophene, benzotriazine, naphthyridine, indole, and indazole.

Substituents on aryl or heteroaryl may occupy all available positions of the ring, such as 1 or 2 positions, or a single position. The aryl or heteroaryl may be unsubstituted. If substituted, these substituents may be optionally substituted with substituents similar to those listed. Of course some substituents, such as halo, are not further substituted, as known to one skilled in the art. Two substituents may join and form a fused 3-14 member ring As used herein, "hydrocarbyl residue" refers to a residue which contains only carbon and hydrogen. The residue may be aliphatic or aromatic, straight-chain, cyclic, branched, saturated or unsaturated. The hydrocarbyl residue, when so stated however, may contain heteroatoms over and above the carbon and hydrogen members of the substituent residue. Thus, when specifically noted as containing such heteroatoms, the hydrocarbyl residue may also contain carbonyl groups, amino groups, sulfonyl groups, nitrile groups, hydroxyl groups and the like, or may contain heteroatoms or groups containing heteroatoms within the "backbone" of the hydrocarbyl residue.

As used herein, "inorganic residue" refers to a residue that does not contain carbon. Examples include, but are not limited to, halo, hydroxy, $NH_2$, $SO_2$ and the like.

As used herein, "acyl" encompasses the definitions of alkyl, alkenyl, alkynyl and the related hetero-forms which are coupled to an additional residue through a carbonyl group.

Similarly, "arylalkyl" and "heteroarylalkyl" contain both aryl and alkyl components, which may contain heteroatoms in either or both components. For example, aromatic and heteroaromatic systems may be coupled to another residue through a carbon chain, including substituted or unsubstituted, saturated or unsaturated, carbon chains, typically of 1-10C, containing 0-5 heteroatoms. These carbon chains may also include a carbonyl group, thus making them able to provide these substituents as acyl moieties. Arylalkenyl and arylalkynyl and hetero forms thereof are similarly defined.

In some embodiments, the compound of Formula I has the structure of Formula II

Formula II

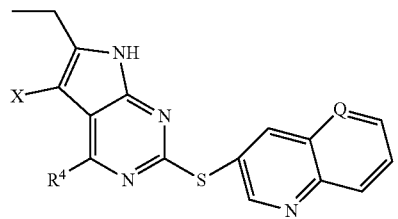

X may be halogen, such as Cl or Br, which in some aspects is Cl.

Q may be N or $N^+$—$O^-$.

$R^4$ may be an amine-substituted heteroalicyclic ring such as a 4-7 or 5-6 membered heteroalicyclic ring containing an N heteroatom, such as in the backbone of the ring. The heteroalicyclic ring may include a single ring, a fused ring, or a bridged ring structure. For example, $R^4$ may be

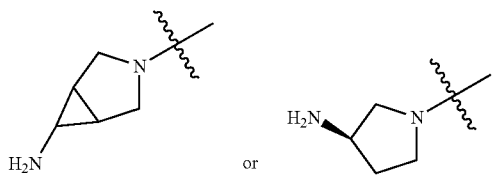

An amine substituent may be a primary amine such as such as $NH_2$, a secondary amine such as NH-alkyl (1-3C) or the tertiary amine such as N-(alkyl (1-3C))$_2$. In some aspects the 5-6 membered heteroalicyclic ring is substituted with one $NH_2$, for example, in a position that is not immediately adjacent to the heteroatom such as the N heteroatom in the heteroalicyclic ring.

A compound of Formula II may have the structure:

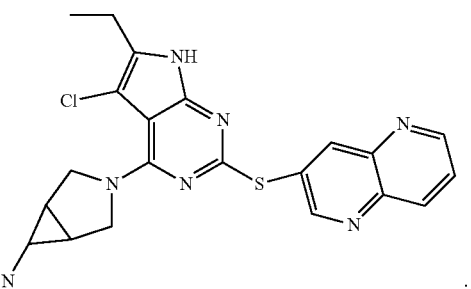

A compound of Formula II may have the structure:

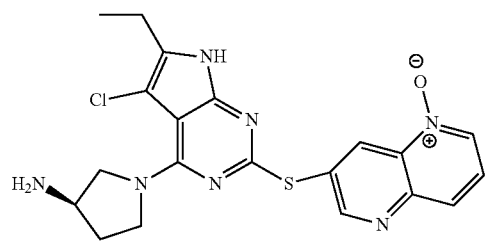

A compound of Formula II also may have the structure:

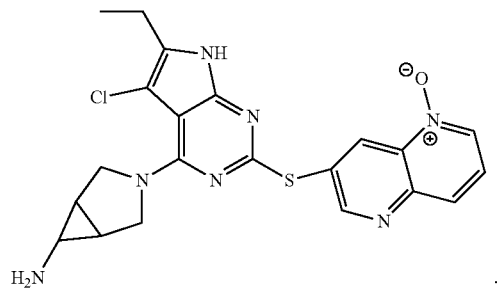 [SMILES: CCc1[nH]c2nc(Sc3cnc4ccc[n+]([O-])c4c3)nc(N3CC4C(N)C4C3)c2c1Cl]

Groups may be defined in one, two or more ways. For example, the group

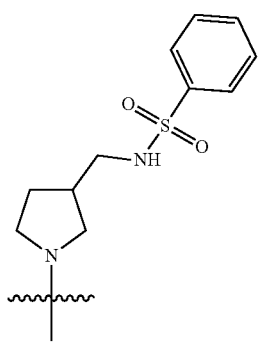 [SMILES: *N1CCC(CNS(=O)(=O)c2ccccc2)C1]

may be defined as both a) a heteroalkyl group substituted with NHSO₂R", wherein R" is a aryl, or b) a heteroalkyl group substituted with two =O (on S) and further substituted with aryl (on S), wherein N and S are in the "backbone" of the heteroalkyl group.

When the compounds of Formula I and II contain one or more chiral centers, the invention includes optically pure forms as well as mixtures of stereoisomers or enantiomers.

The term "members" or "membered" in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

A pharmaceutically-acceptable salt, ester, or prodrug of the compound of Formula I or II is also contemplated. Those skilled in the art will appreciate that a variety of prodrugs, salts, hydrates, solvates, and polymorphs can be produced from the compounds disclosed here, and that various isotopically-substituted variants (through, e.g., substitution of deuterium for hydrogen, $^{13}$C for carbon, $^{15}$N for nitrogen, or $^{32}$P for phosphorus) known as "isotopomers" can also be readily produced. All such derivatives are contemplated within the scope of this disclosure.

Many of the compounds here are disclosed as hydrochloride or other salts, but those skilled in medicinal chemistry will appreciate that the choice of salt is not critical, and other pharmaceutically-acceptable salts can be prepared by well-known methods. Handbook of Pharmaceutical Salts: Properties, Selection and Use. (P. Heinrich Stahl and Camille G. Wermuth, eds.) International Union of Pure and Applied Chemistry, Wiley-VCH 2002 and L. D. Bighley, S. M. Berge, D. C. Monkhouse, in "Encyclopedia of Pharmaceutical Technology". Eds. J. Swarbrick and J. C. Boylan, Vol. 13, Marcel Dekker, Inc., New York, Basel, Hong Kong 1995, pp. 453-499 discuss such salts in detail.

More generally, those skilled in the art will appreciate that a variety of prodrugs, salts, hydrates, solvates, and polymorphs can be produced from the compounds disclosed here, and that various isotopically-substituted variants (through, e.g., substitution of deuterium for hydrogen, $^{13}$C for carbon, $^{15}$N for nitrogen) can also be readily produced. All such derivatives are contemplated within the scope of this disclosure.

Compounds disclosed herein include those structures that are set out in Table 1 appended to the application. In some embodiments, the compound is in a pharmaceutical composition or a dosage form, wherein the pharmaceutical composition or dosage form provides an effective antibiotic-treating or -preventing amount of the compound.

In another aspect, the present disclosure relates to a pharmaceutical composition comprising one or more physiologically acceptable surface active agents, additional carriers, diluents, excipients, smoothing agents, suspension agents, film forming substances, and coating assistants, or a combination thereof; and a composition disclosed herein. Acceptable additional carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. Pharmaceutical compositions can also be obtained by reacting the free acid dihydrogen phosphate with inorganic or organic bases such as sodium hydroxide or magnesium hydroxide. In some embodiments, pharmaceutically acceptable salts of the compounds disclosed herein (e.g., as made in situ during the manufacture of an intravenous formulation) are provided.

The term "carrier" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" refers to a carrier or diluent that does not abrogate the biological activity and properties of the compound.

The pharmaceutical compounds described herein can be administered to a human patient per se, or in pharmaceutical compositions where they are mixed with other active ingredient(s), as in combination therapy, or suitable carriers or excipient(s). In some embodiments, a dosage form includes those forms in which the compound is administered per se. In addition, a dosage form may include a pharmaceutical composition. In any case, the dosage form may comprise a sufficient amount of the dimer compound to treat a bacterial infection as part of a particular administration protocol, as would be understood by those of skill in the art. Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the composition can be formulated readily by combining the compositions of interest with pharmaceutically acceptable carriers well known in the art. Such carriers, which may be used in addition to the cationic polymeric carrier, enable the compositions of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), e.g., Povidone. If desired, disintegrating agents may be added, such as the cross-linked polyvinylpyrrolidone (e.g. Crospovidone), agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

For administration by inhalation, the composition can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Methods for treating bacterial infections may include administering a therapeutically effective amount of the therapeutic compounds as described herein. Treating a bacterial infection may also include prophylactically administering the therapeutic compounds to prevent infection or the spread of an infection in a subject at imminent risk of infection, such as a subject receiving or about to undergo surgery, an immunocompromised subject, or subject otherwise at risk of an infection if the compound was not administered. The compounds show inhibitory activity against a broad spectrum of bacteria including *H. influenzae, E. coli, S. aureus, A. baumannii, S. pneumoniae, P. aeruginosa,* and *B. thailandensis*, for example methicillin resistant *Staphylococcus aureus* (MRSA). See Table 2. The compounds have excellent relative antibiotic activity with a relatively low concentration. Further, the compounds of the present invention may exert potent antibacterial activity versus various human and animal pathogens, including Gram-positive and Gram-negative bacteria. In an embodiment, the bacterial infection that may be treated or ameliorated is MRSA.

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the active compound into contact with living tissue.

Pharmaceutical compositions suitable for administration include compositions where the active ingredients are contained in an amount effective to achieve its intended purpose. In some embodiments, a therapeutically effective amount of a compound is an amount effective to treat a bacterial infection, for example, in a mammalian subject (e.g., a human). The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are about 0.1% to about 500%, more preferably about 25% to about 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively the compositions of the invention may be administered by continuous intravenous infusion, preferably at a dose of up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the infection, the manner of administration and the judgment of the prescribing physician.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

In some embodiments, in the pharmaceutical industry, it standard practice to provide substantially pure material when formulating pharmaceutical compositions. Therefore, in some embodiments, "substantially pure" refers to the amount of purity required for formulating pharmaceuticals, which may include, for example, a small amount of other material that will not affects the suitability for pharmaceutical use. In some embodiments, the substantially pure compound contains at least about 96% of the compound by weight, such as at least about 97%, 98%, 99%, or 100% of the compound.

The terms "approximately, "about," and "substantially" as used herein represent an amount close to the stated amount that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

Methods of Making the Compounds

As shown in the Examples below, similar methods may be used to make various groups of compounds. In many cases, the final step includes deprotecting a protected form of a compound of Formula I or II wherein Z is C-halo. Protecting groups are well known in the art and include, for example, BOC. In some aspects the final or penultimate step includes halogenating a protected form of the compound of Formula I or II wherein Z is CH to form a compound of Formula I or II wherein Z is C-halo Other steps may include before the halogenating step, aminating a compound of Formula I or II wherein Z is CH and $R^4$ is OH, or a protected form thereof, to form a compound of Formula I or II wherein $R^4$ is a group comprising an amine.

Other steps include, such as before the aminating step, adding an aryl or heteroaryl to a compound of Formula I or II wherein $R_2$ is H to form a compound of Formula I or II wherein $R_2$ is a group comprising an aryl or heteroaryl group directly linked to L.

In addition to the compounds discussed herein, the Examples also include methods for making various intermediates useful in making the compounds.

EXAMPLES

Preparation of Compounds

The 2-mercapto-7H-pyrrolo[2,3-d]pyrimidine intermediates can be prepared as shown in the following scheme and illustrated in Examples 1-3, where $R^6$=ethyl.

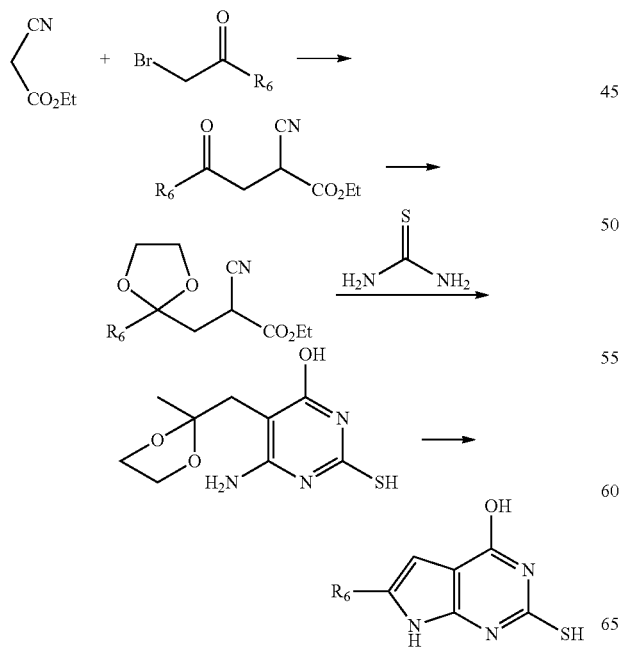

Example 1

6-Amino-5-((2-ethyl-1,3-dioxolan-2-yl)methyl)-2-mercaptopyrimidin-4-ol

Ethyl cyanoacetate (35 mL, 331 mmol) was dissolved in toluene (1.5 L) and DBU (50 mL, 331 mmol) was added via dropping funnel. The reaction was allowed to stir for 30 minutes. The pot was placed in an ice bath and allowed to cool to 0° C. followed by dropwise addition of 1-bromo-2-butanone (50 g, 331 mmol). This reaction was slightly exothermic so it was monitored and the temperature was not allowed to rise over 10° C. Once addition was complete the reaction turned a brown color. It was allowed slowly warm to room temperature and to react overnight. The next morning the reaction was poured into a separatory funnel and washed 2× with 1 M HCl and 1× with brine. The organic layer was dried with sodium sulfate and filtered. The toluene was removed by rotary evaporator to yield 50 grams of a dark brown liquid. The product was pure as determined by NMR and was carried on to the next step.

The product, ethyl 2-cyano-4-oxohexanoate, (50 g, 273 mmol) was dissolved in benzene (550 mL). To this solution was added ethylene glycol (22.8 mL, 409 mmol) and p-toluenesulfonic acid monohydrate (1 g, 5.46 mmol). The reaction was equipped with a Dean-Stark trap, a heating mantle and a reflux condenser and the reaction was heated to reflux until the appropriate amount of water was removed from the reaction, anywhere from 2-12 h. The reaction was cooled and poured into a separatory funnel and washed 2× with 10% sodium carbonate and 1× with brine. The organic layer was dried with sodium sulfate, filtered and the solvent removed by rotary evaporator to yield a dark oil. NMR indicated this product was about >90% pure therefore we used it for the next step without further purification.

Thiourea (20.1 g, 264 mmol) was suspended in dry ethanol (400 mL) and sodium ethoxide (21% solution) (100 mL, 264 mmol) was added. To this reaction was added ethyl 2-cyano-3-(2-ethyl-1,3-dioxolan-2-yl)propanoate (60 g, 264 mmol). The reaction was equipped with a mechanical stirrer, a heating mantle and a reflux condenser and heated to reflux for 6 h during which a precipitate was observed. The next morning the solvent was removed and water (300 mL) was added to the crude product followed by addition of 10% citric acid to pH 7. The solid was collected and the wet cake was washed with cold ethanol to remove most of the brown discoloration. The cake was dried in a vacuum oven overnight to yield the desired amino pyrimidine. The product was used without further purification.

Example 2

6-Ethyl-2-mercapto-7H-pyrrolo[2,3-d]pyrimidin-4-ol

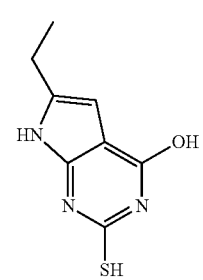

6-Amino-5-((2-ethyl-1,3-dioxolan-2-yl)methyl)-2-mercaptopyrimidin-4-ol (Example 1) (55 g) was added to THF (200 mL) and to this suspension was added 1 M HCl in water (200 mL). The pyrimidine slowly dissolved in this solution over a 1 h period and a new precipitate formed. The reaction was allowed to proceed overnight and the next day the precipitate was collect via filtration. The filter cake was washed with water and dried in a vacuum oven overnight.

2-Mercapto-7H-pyrrolo[2,3-d]pyrimidine intermediates can be readily converted into 2-arylthio-7H-pyrrolo[2,3-d] pyrimidines by copper catalyzed coupling with aryl halides as shown in Example 3.

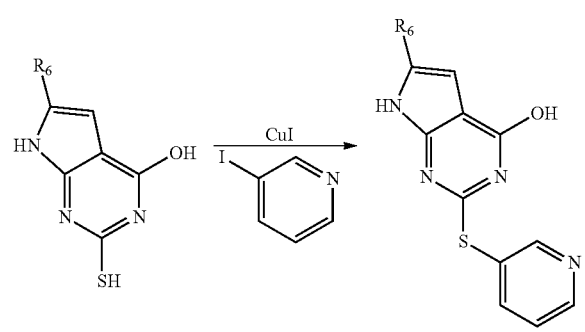

Example 3

6-Ethyl-2-(pyridin-3-ylthio)-7H-pyrrolo[2,3-d]pyrimidin-4-ol

6-Ethyl-2-mercapto-7H-pyrrolo[2,3-d]pyrimidin-4-ol (Example 2) (10 g, 51.2 mmol) was combined with potassium carbonate (21.24 g, 154 mmol), 3-iodopyridine (10.5 g, 51.2 mmol), copper iodide (0.488 g, 2.56 mmol), and NMP (256 mL). The reaction was purged of oxygen with a dry stream of nitrogen followed by the addition of ethylene glycol (5.71 mL, 102 mmol). The reaction was heated to 145° C. and followed by LCMS. After 6 h the NMP was removed by rotary evaporator and water (200 mL) was added followed by adjusting the pH to neutral using 1 M HCl. The solids were collected. Washed 4× with 100 mL water and 2× with 50 mL of ethyl ether. The precipitate was dried in a vacuum oven overnight and used without further purification.

Conversion of 2-arylthio-7H-pyrrolo[2,3-d]pyrimidines into compounds of Formula I where $Z=CR^5$ and $R^5=CHO$ is accomplished using the Vilsmeier-Haack formulation/chlorination followed by the nucleophilic addition of the $R^4$ group (both $R^4$=optionally substituted O and $R^4$=optionally substituted N) as shown in Examples 4-6.

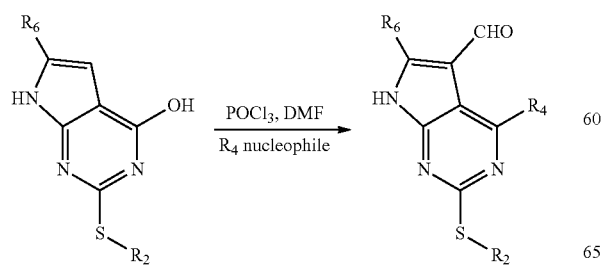

Example 4

4-Chloro-6-ethyl-2-(pyridin-3-ylthio)-7H-pyrrolo[2,3-d]pyrimidine-5-carbaldehyde N,N-dimethylformamide (1 mL) was dissolved in phosphorous oxychloride (120 mL). 6-Ethyl-2-(pyridin-3-ylthio)-7H-pyrrolo[2,3-d]pyrimidin-4-ol (Example 3) was slowly added to the reaction pot and heated to 105° C. for 3 h. The phosphorous oxychloride was removed by rotary evaporator and the remaining syrup was carefully poured syrup on 500 mL of chipped ice. The precipitate was collected and washed with water and dried in a vacuum oven overnight.

Example 5

4-Ethoxy-6-ethyl-2-(pyridin-3-ylthio)-7H-pyrrolo[2,3-d]pyrimidine-5-carbaldehyde 4-Chloro-6-ethyl-2-(pyridin-3-ylthio)-7H-pyrrolo[2,3-d]pyrimidine-5-carbaldehyde (Example 4) (0.020 g) was dissolved in ethanol (2 mL) and sodium hydride (0.020 g) was added to the solution followed by heating in a sealed tube at 150° C. for 10 min. Compound 8 was purified by reverse phase high performance liquid chromatography (HPLC).

Example 6

4-(dimethylamino)-6-ethyl-2-(pyridin-3-ylthio)-7H-pyrrolo[2,3-d]pyrimidine-5-carbaldehyde 4-Chloro-6-ethyl-2-(pyridin-3-ylthio)-7H-pyrrolo[2,3-d] pyrimidine-5-carbaldehyde (Example 4) (0.020 g) was dissolved in NMP (1 mL) and a solution of dimethylamine (2 mL) in THF was added. The reaction was heated to 150° C. for 10 minutes followed by purification of the desired product by RF-HPLC.

In cases where compounds of Formula I where $Z=CR^5$ and $R^5=COCH_3$ can be prepared as shown below in Examples 7-9

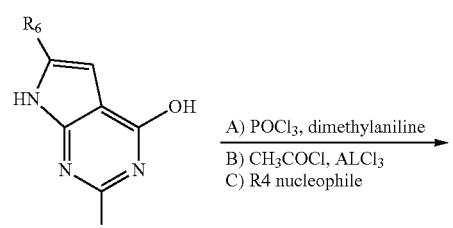

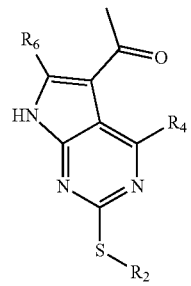

Example 7

4-chloro-6-ethyl-2-(pyridin-3-ylthio)-7H-pyrrolo[2,3-d]pyrimidine 6-ethyl-2-(pyridin-3-ylsulfanyl)-5H-pyrrolo[2,3-d]pyrimidin-4-ol (13 g, 47.7 mmol) (Example 3) was dissolved in phosphorous oxychloride (150 mL) and N, N-dimethylaniline (1 mL, 8 mmol) was added to the solution. The reaction was heated to 105 C for 3 h at which LCMS analysis indicated the reaction was complete. The solvent was removed by rotary evaporator and the syrup was carefully poured on 500 mL chipped ice. After all the ice melted the precipitate was collected by filtration and dried under vacuum overnight.

Example 8

1-(4-chloro-6-ethyl-2-(pyridin-3-ylthio)-7H-pyrrolo[2,3-d]pyrimidin-5-yl)ethanone 4-chloro-6-ethyl-2-(pyridin-3-ylthio)-7H-pyrrolo[2,3-d]pyrimidine (Example 7) (0.2 g, 0.69 mmol), aluminum chloride (0.642 g, 4.8 mmol) was dissolved in dichloromethane (5 mL) and allowed to stir at room temperature for 1 hour. Acetyl chloride (0.050 mL, 0.688 mmol) was added in one aliquot. The reaction was stirred at room temperature for 6 h and poured on ice chips to quench the reaction. Aqueous extraction provided the desired compound which was used without further purification.

Example 9

1-(4-ethoxy-6-ethyl-2-(pyridin-3-ylthio)-7H-pyrrolo[2,3-d]pyrimidin-5-yl)ethanone 1-(4-chloro-6-ethyl-2-(pyridin-3-ylthio)-7H-pyrrolo[2,3-d]pyrimidin-5-yl)ethanone (Example 8) (0.050 g, 0.150 mmol) was dissolved in 2 mL of ethanol. To this reaction mixture was added excess sodium hydride. The reaction was heated to 150° C. for 10 minutes followed by purification of the desired product by RF-HPLC.

In cases where compounds of Formula I where $Z=CR^5$ and $R^5=CH_2OH$ can be prepared as shown below in Example 10.

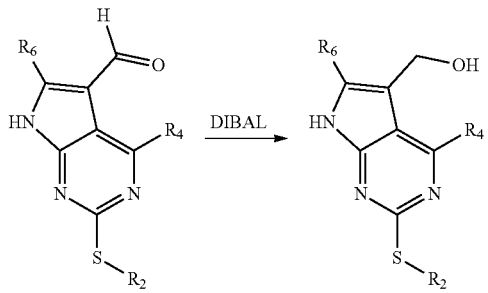

Example 10

(S)-1-(6-ethyl-5-(hydroxymethyl)-2-(pyridin-3-ylthio)-7H-pyrrolo[2,3-d]pyrimidin-4-ylamino)propan-2-ol (compound 700139)

(S)-6-ethyl-4-(2-hydroxypropylamino)-2-(pyridin-3-ylthio)-7H-pyrrolo[2,3-d]pyrimidine-5-carbaldehyde (0.050 g, 0.14 mmol) was dissolved in THF and diisobutylaluminum hydride in THF (2 mL, 2 mmol). The reaction was allowed to proceed for 2 h and quenched with methanol and purified by RP-HPLC. MS: 360 M+H.

A variety of Formula I compounds where $R_2$ is a unsubstituted or substituted uracil can be prepared as shown by Examples 11-17.

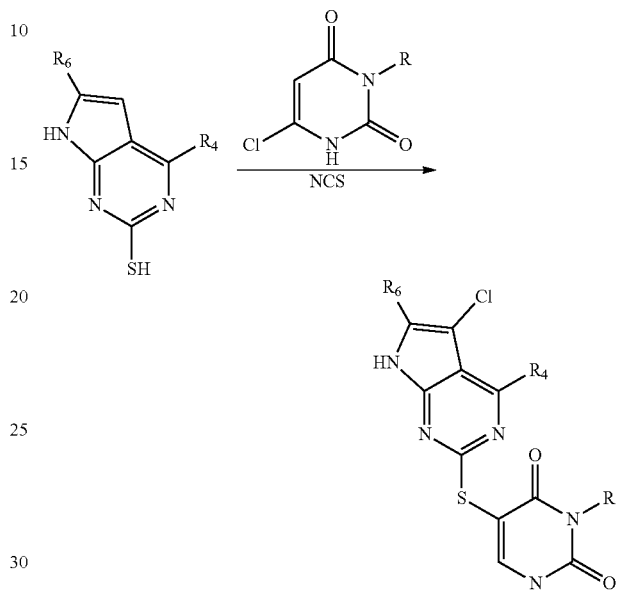

Example 11

6-(4-ethoxy-6-ethyl-7H-pyrrolo[2,3-d]pyrimidin-2-ylthio)pyrimidine-2,4(1H,3H)-dione 4-ethoxy-6-ethyl-7H-pyrrolo[2,3-d]pyrimidine-2-thiol (0.050 g, 0.220 mmol) was dissolved in acetic acid (0.750 mL) followed by addition 6-chlorouracil (0.033 g, 0.220 mmol). The reaction was heated to 100° C. for 0.5 h. The reaction was allowed to cool followed by precipitation with water. The solid was collected and dried on a filter and used for the next step without further purification.

Example 12

6-(5-chloro-4-ethoxy-6-ethyl-7H-pyrrolo[2,3-d]pyrimidin-2-ylthio)pyrimidine-2,4(1H,3H)-dione (compound 700347)

6-(4-ethoxy-6-ethyl-7H-pyrrolo[2,3-d]pyrimidin-2-ylthio)pyrimidine-2,4(1H,3H)-dione (Example 11) 0.045 g, 0.134 mmol) was dissolved in acetic acid followed by addition of N-chlorosuccinimide (0.018 g, 134 mmol). The reaction was allowed to proceed at room temperature for 2 h. Water was added to precipitate the product. The filtrate was collected and dissolved in methanol and this solution was purified by RP-HPLC yielding the desired product. MS: 368 (M+H).

Example 13

6-chloro-1-((2-(trimethylsilyl)ethoxy)methyl)pyrimidine-2,4(1H,3H)-dione 6-chlorouracil (3 g, 20.47 mmol) and lithium bromide monohydrate (2.147 g, 20.47 mmol) was dissolved in NMP (70 mL) followed by addition of sodium hydride (0.8 g, 20.5 mmol). This mixture was allowed to stir at room temperature for 30 minutes followed by addition of SEM-Cl (3.61 mL, 20.47 mmol). The reaction proceeded for 3 h after which it was poured into a separatory funnel charged with ethyl acetate and 10% sodium carbonate solution. The organic layer was washed 3 times with brine, dried with sodium sulfate and the solvent was removed by rotary evaporator. The product was sufficiently pure to use for the next step.

Example 14

Ethyl 2-(4-chloro-2,6-dioxo-3-((2-(trimethylsilyl)ethoxy)methyl)-2,3-dihydropyrimidin-1(6H)-yl)acetate 6-chloro-1-((2-(trimethylsilyl)ethoxy)methyl)pyrimidine-2,4(1H,3H)-dione (Example 13) (1 g, 3.61 mmol), NMP (12 mL) and cesium carbonate (2.4 g, 7.3 mmol) were added to a 50 mL round bottom flask followed by addition of ethyl chloroacetate (0.385 mL, 3.61 mmol). The reaction was allowed to proceed for 6 h after which it was poured into a separatory funnel charged with ethyl acetate and brine. The organic layer was washed 3× with brine and dried with sodium sulfate. The solvent was removed by rotary evaporator and the crude product was purified by flash chromatography.

Example 15

Ethyl 2-(4-chloro-2,6-dioxo-2,3-dihydropyrimidin-1(6H)-yl)acetate

Ethyl 2-(4-chloro-2,6-dioxo-3-((2-(trimethylsilyl)ethoxy)methyl)-2,3-dihydropyrimidin-1(6H)-yl)acetate (Example 14) (1 g, 2.8 mmol) was dissolved in neat TFA. The reaction was allowed to proceed for 2 h after which the solvent was removed and the solids dissolved in ethyl ether. The solution was allowed to stand overnight and the desired compound crystallized. This compound was sufficiently pure to couple to the pyrrolopyrimidine.

Example 16

Ethyl 2-(4-(6-ethyl-4-(3-hydroxyazetidin-1-yl)-7H-pyrrolo[2,3-d]pyrimidin-2-ylthio)-2,6-dioxo-2,3-dihydropyrimidin-1 (6H)-yl)acetate A 10 mL microwave reaction vessel was charged with ethyl 2-(4-chloro-2,6-dioxo-2,3-dihydropyrimidin-1(6H)-yl)acetate (Example 15) (9.3 mg, 0.040 mmol), 1-(6-ethyl-2-mercapto-7H-pyrrolo[2,3-d]pyrimidin-4-yl)azetidin-3-ol (0.010 g, 0.040 mmol) and acetic acid (1 mL). The reaction was heated to 100° C. for 0.5 h followed by addition of water to precipitate the product followed by filtration. The product was dried on a filter overnight and was used without further purification.

Example 17

Ethyl 2-(4-(5-bromo-6-ethyl-4-(3-hydroxyazetidin-1-yl)-7H-pyrrolo[2,3-d]pyrimidin-2-ylthio)-2,6-dioxo-2,3-dihydropyrimidin-1 (6H)-yl)acetate (compound 700386)

Ethyl 2-(4-(6-ethyl-4-(3-hydroxyazetidin-1-yl)-7H-pyrrolo[2,3-d]pyrimidin-2-ylthio)-2,6-dioxo-2,3-dihydropyrimidin-1(6H)-yl)acetate (Example 16) 0.02 g, 0.045 mmol) was dissolved in THF (0.150 mL) and cooled to −78° C. followed by addition of N-bromosuccinimide (8 mg, 0.045 mmol). The reaction was complete within 5 min. The THF was removed by reduced pressure and the reaction was dissolved in methanol and purified by RP-HPLC. MS: 526 M+H.

A wide variety of Formula I compounds where $R^4$ is a disubstituted N can be prepared from 2-arylthio-7H-pyrrolo[2,3-d]pyrimidines as shown by Examples 18-21.

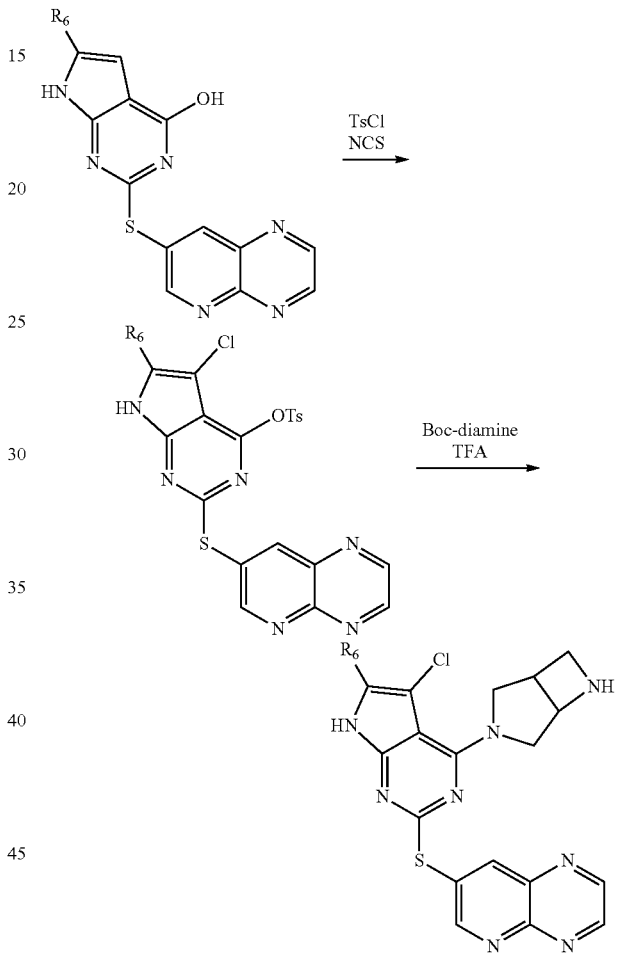

Example 18

6-ethyl-2-(pyrido[3,2-b]pyrazin-7-ylthio)-7H-pyrrolo[2,3-d]pyrimidin-4-yl 4-methylbenzenesulfonate 6-ethyl-2-(pyrido[3,2-b]pyrazin-7-ylthio)-7H-pyrrolo[2,3-d]pyrimidin-4-ol (1 g, 3.08 mmol) was dissolved in NMP followed by addition of sodium hydride (0.142 g, 3.7 mmol) and p-toluenesulfonyl chloride (0.705 g, 3.7 mmol). The mixture was allowed to react for 1 h after which the crude reaction was poured into water (200 mL) to induce precipitation. The precipitate was collected by filtration and dried using a vacuum oven overnight. The product was sufficiently pure to use for the next step.

Example 19

5-chloro-6-ethyl-2-(pyrido[3,2-b]pyrazin-7-ylthio)-7H-pyrrolo[2,3-d]pyrimidin-4-yl 4-methylbenzenesulfonate 6-ethyl-2-(pyrido[3,2-b]pyrazin-7-ylthio)-7H-pyrrolo[2,3-d]pyrimidin-4-yl 4-methylbenzenesulfonate (Example 18) (0.2 g, 0.418 mmol) was dissolved in dichloromethane (2 mL) followed by addition of N-chlorosuccinimide (0.056 g, 0.418 mmol). The reaction was sealed and heated to 60° C. for 0.5 h. The product was purified by flash chromatography on a silica column 60:40 ethyl acetate/hexane. MS: 513 m+H.

Example 20

Tert-butyl 3-(5-chloro-6-ethyl-2-(pyrido[3,2-b]pyrazin-7-ylthio)-7H-pyrrolo[2,3-d]pyrimidin-4-yl)-3,6-diazabicyclo[3.2.0]heptane-6-carboxylate To a 10 mL microwave reaction vessel compound 5-chloro-6-ethyl-2-(pyrido[3,2-b]pyrazin-7-ylthio)-7H-pyrrolo[2,3-d]pyrimidin-4-yl 4-methylbenzenesulfonate (Example 19) (0.02 g, 0.039 mmol) and tert-butyl 3,6-diazabicyclo[3.2.0]heptane-6-carboxylate (7.7 mg, 0.039 mmol) was dissolved in ethanol (0.1 mL). The reaction was sealed and heated to 100° C. for 0.5 h after which the solvent was removed and the crude was used for the next step without further purification

Example 21

7-(4-(3,6-diazabicyclo[3.2.0]heptan-3-yl)-5-chloro-6-ethyl-7H-pyrrolo[2,3-d]pyrimidin-2-ylthio)pyrido[3,2-b]pyrazine (compound 700548)

Crude tert-butyl 3-(5-chloro-6-ethyl-2-(pyrido[3,2-b]pyrazin-7-ylthio)-7H-pyrrolo[2,3-d]pyrimidin-4-yl)-3,6-diazabicyclo[3.2.0]heptane-6-carboxylate (Example 20) was dissolved in trifluoroacetic acid (0.1 mL) and allowed to react for 30 minutes after which the solvent was removed. The crude was dissolved in methanol and injected directly on the preparative RP-HPLC for purification which yielded the desired product. MS: 540 M+H.

A broad range of Formula I compounds can be prepared from various 4-pyrrolidines-2-thio-7H-pyrrolo[2,3-d]pyrimidines that can be generated from disulfides as shown in Examples 22-25.

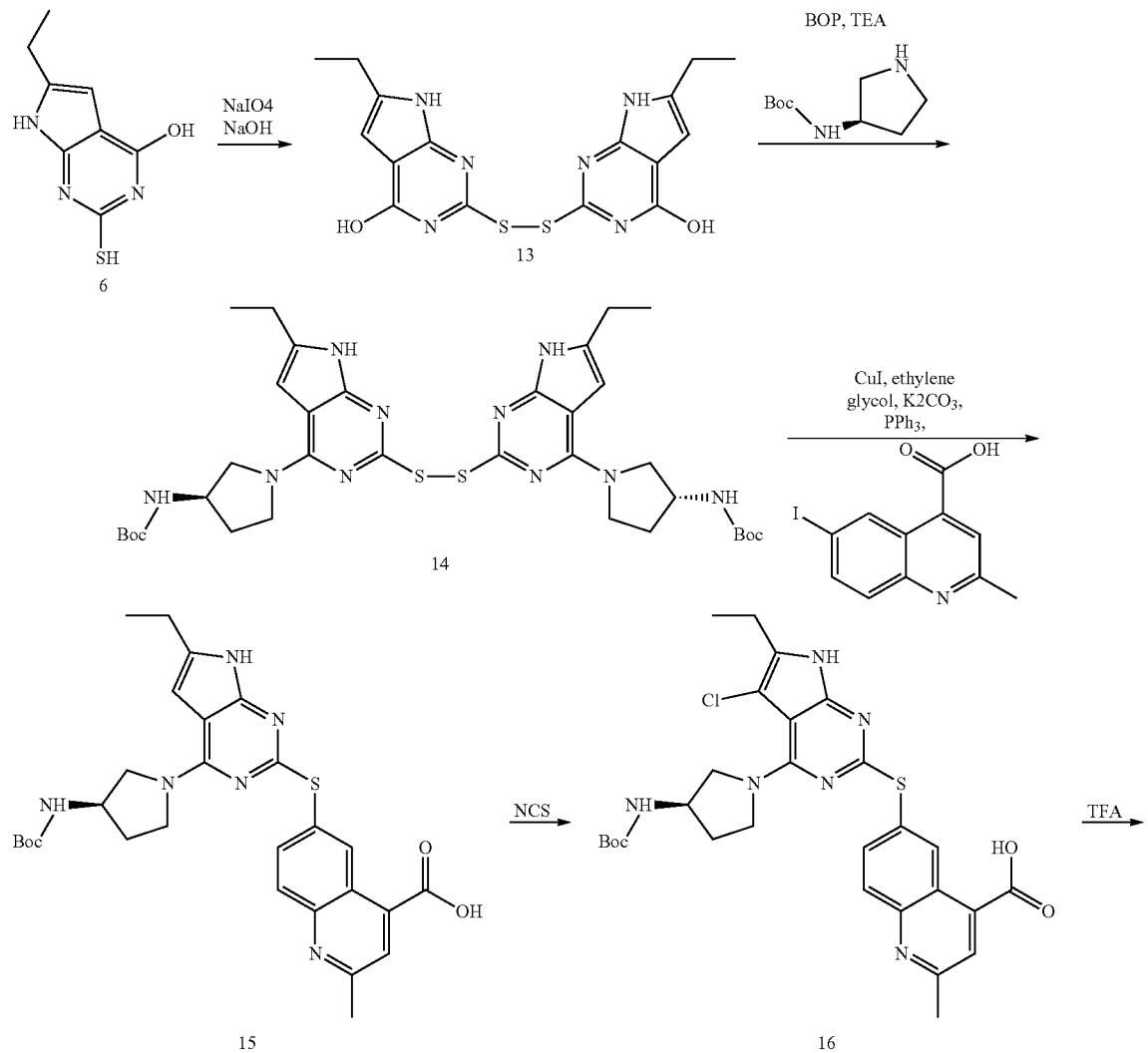

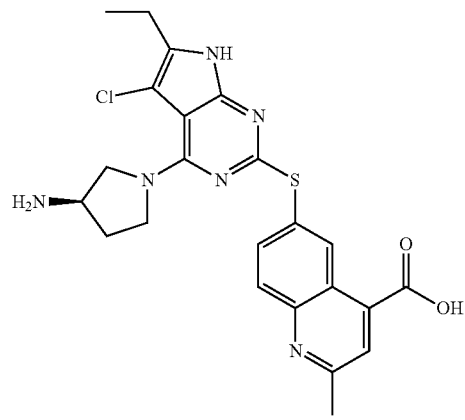

17

Example 22

2,2'-disulfanediylbis(6-ethyl-7H-pyrrolo[2,3-d]pyrimidin-4-ol)

6-ethyl-2-mercapto-7H-pyrrolo[2,3-d]pyrimidin-4-ol (Example 2) (5 g, 25.6 mmol) was suspended in water (250 mL) followed by addition of sodium hydroxide (2 M, 26 mL, 51 mmol). The mixture was allowed to stir at room temperature until all the pyrrolopyrimidine dissolved. Sodium periodate (5.48 g, 25.6 mmol) was dissolved in water (25 mL) and this solution was added to the reaction and allowed to stir for 5 h at room temperature. The reaction was neutralized with 1 M HCl and the resulting solid was collected and dried on a sinter glass funnel. The reaction was quantitative and sufficiently pure to use for the next step.

Example 23 tert-butyl (3R,3'R)-1,1'-(2,2'-disulfanediylbis(6-ethyl-7H-pyrrolo[2,3-d]pyrimidine-4,2-diyl))bis(pyrrolidine-3,1-diyl)dicarbamate 2,2'-disulfanediylbis(6-ethyl-7H-pyrrolo[2,3-d]pyrimidin-4-ol (0.5 g, 1.287 mmol) was suspended in DMF (5 mL) and cooled to 0° C. followed by the addition of BOP reagent (1.42 g, 3.22 mmol) and triethylamine (7.2 mL, 5.1 mmol). The reaction was allowed to proceed to the activated ether after which (R)-tert-butyl pyrrolidin-3-ylcarbamate (0.48 g, 2.6 mmol) was added. The reaction was allowed to proceed for 12 h at room temperature after which the crude was added dropwise to water (200 mL). The precipitate was collected by filtration and allowed to dry. The product was used for the next step without further purification.

Example 24

(R)-6-(4-(3-(tert-butoxycarbonylamino)pyrrolidin-1-yl)-6-ethyl-7H-pyrrolo[2,3-d]pyrimidin-2-ylthio)-2-methylquinoline-4-carboxylic acid tert-butyl (3R,3'R)-1,1'-(2,2'-disulfanediylbis(6-ethyl-7H-pyrrolo[2,3-d]pyrimidine-4,2-diyl))bis(pyrrolidine-3,1-diyl) dicarbamate (Example 23) (0.1 g, 0.138 mmol), 6-iodo-2-methylquinoline-4-carboxylic acid (0.086 g, 0.28 mmol), triphenylphosphine (0.036 g, 0.138 mmol), and potassium carbonate (0.038 g, 0.276 mmol) were dissolved in NMP (0.5 mL). A small test tube was charged with copper iodide (2.6 mg, 0.014 mmol) NMP (0.1 mL) and N,N'-dimethylcyclohexane-1,2-diamine (0.004 g, 0.028 mmol). The copper solution was allowed to react for 10 min and added to the reaction mixture followed by flushing the reaction with nitrogen, sealing the reaction and heating to 130° C. for 1 h. Upon completion of the coupling the reaction was diluted with methanol (1 mL) and injected directly on the HPLC for purification. MS 549 (M+H+).

Example 25

(R)-6-(4-(3-aminopyrrolidin-1-yl)-5-chloro-6-ethyl-7H-pyrrolo[2,3-d]pyrimidin-2-ylthio)-2-methylquinoline-4-carboxylic acid (compound 700708)

(R)-6-(4-(3-(tert-butoxycarbonylamino)pyrrolidin-1-yl)-6-ethyl-7H-pyrrolo[2,3-d]pyrimidin-2-ylthio)-2-methylquinoline-4-carboxylic acid (Example 24) (0.036 g, 0.066 mmol) was suspended in dichloromethane (1 mL). N-chlorosuccinimide (8.8 mg, 0.066 mmol) was added to the suspension and the reaction was sealed and heated to 60° C. for 30 minutes. The reaction was allowed to cool to room temperature followed by the addition of trifluoroacetic acid (1 mL). Boc removal proceeded smoothly and after 15 minutes the solvent was removed and the crude product was dissolved in methanol and purified by reverse phase HPLC. MS 483 (M+H+).

The following compounds were made following a similar procedure as Examples 22-25.

| Rx ID | product | LC-MS |
|---|---|---|
| 700708 |  | |

| Rx ID | product | LC-MS |
|---|---|---|
| 700710 | 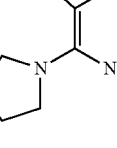 | |
| 700711 | | |
| 700712 | | |
| 700797 | | |
| 700798 | | |
| 700799 | | |
| Rx ID | product | LC-MS |
|---|---|---|
| 700862 | 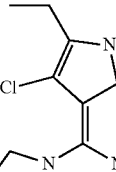 | |
The intermediate from Example 2 can be converted into a 2-(methylsulfonyl)-pyrrolo[2,3-d]pyrimidine intermediate useful in preparing Formula I compounds where L=N as shown in Examples 26-30.
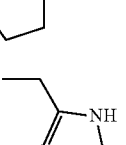

Example 26

6-Ethyl-2-(methylthio)-3H-pyrrolo[2,3-d]pyrimidin-4(7H)-one

To a suspension of 6-ethyl-2-sulfanyl-3,4a,7,7a-tetrahydro-4H-pyrrolo[2,3-d]pyrimidin-4-one (tautomeric form of Example 2) (2.00 g, 10.24 mmol) and NaOH (3.85 g, 96.3 mmol) in EtOH (50 mL) was added CH3I (0.64 mL, 10.3 mmol) dropwise. The resulting mixture was vigorously stirred for one hour at room temperature. Solvents were removed under the reduced pressure. The residue was dissolved the minimum amount of water and then acidified with 6 M HCl to PH about 3. The precipitate was collected by filtration, washed with water and dried to give 6-Ethyl-2-(methylthio)-3H-pyrrolo[2,3-d]pyrimidin-4(7H)-one 1.80 g (84%) as a white powder. MS (ESI) m/z 210 (M+H)+.

Example 27

4-Chloro-6-ethyl-2-(methylthio)-7H-pyrrolo[2,3-d]pyrimidine

Phosphorous oxychloride (17.6 mL, 192.3 mmol) was carefully added to a mixture of 6-ethyl-2-(methylthio)-3H-pyrrolo[2,3-d]pyrimidin-4(7H)-one (Example 26) (4.75 g, 22.7 mmol) and N,N-dimethylaniline (1.5 mL, 11.8 mmol) at room temperature. The reaction mixture was then heated to 95° C. for 12 h, cooled to room temperature. The excess of POCl3 was removed under the reduced pressure. Ice water (50 g) was added and the precipitate was collected by filtration, dried to give a solid 4-chloro-6-ethyl-2-(methylthio)-7H-pyrrolo[2,3-d]pyrimidine 3.87 g (75%). MS (ESI) m/z 228 (M+H)+.

Example 28

4-Ethoxy-6-ethyl-2-(methylthio)-7H-pyrrolo[2,3-d]pyrimidine

A mixture of 4-chloro-6-ethyl-2-(methylthio)-7H-pyrrolo[2,3-d]pyrimidine (Example 27) (1.01 g, 4.44 mmol), 21% wt. sodium ethoxide (10 mL, 25.2 mmol) was heated in a microwave oven at 150° C. for one hour. Water (120 mL) was added to the reaction mixture. The precipitate was collected and dried to give 4-ethoxy-6-ethyl-2-(methylthio)-7H-pyrrolo[2,3-d]pyrimidine 1.04 g (99%) as a grey powder. MS (ESI) m/z 238 (M+H)+.

Example 29

4-Ethoxy-6-ethyl-2-(methylthio)-7-(phenylsulfonyl)-7H-pyrrolo[2,3-d]pyrimidine NaH (60% in mineral oil, 186.4 mg, 4.66 mmol) was added to 10 mL of DMF cooled to 0° C., followed by addition of 4-ethoxy-6-ethyl-2-(methylthio)-7H-pyrrolo[2,3-d]pyrimidine (Example 28) (1.05 g, 4.42 mmol) in DMF (10 mL) over 5 minutes. The stirring was continued for 15 minutes at 0° C., then benzenesulfonyl chloride (0.4 mL, 3.11 mmol) was added dropwise. After addition, the reaction mixture was warmed up to room temperature and stirred for one hour. Water (150 mL) was added. The precipitate was collected by filtration and dried to give 4-ethoxy-6-ethyl-2-(methylthio)-7-(phenylsulfonyl)-7H-pyrrolo[2,3-d]pyrimidine 1.35 g (81%) as a white solid. MS (ESI) m/z 378 (M+H)+.

Example 30

4-Ethoxy-6-ethyl-2-(methylsulfonyl)-7-(phenylsulfonyl)-7H-pyrrolo[2,3-d]pyrimidine m-Chloroperoxybenzoic acid (MCPBA, 1.37 g, 77%, 6.11 mmol) was added to a stirring solution of 4-ethoxy-6-ethyl-2-(methylthio)-7-(phenylsulfonyl)-7H-pyrrolo[2,3-d]pyrimidine (Example 29) (0.884 g, 2.35 mmol) in DMF (33 mL) at room temperature. The stirring was continued for 17 h. Water (80 mL) was added. The precipitate was filtered to give 0.81 g of white solid product which was contaminated with MCPBA. Ether (1 mL) was added to the white solid and the suspension was filtered to give 4-ethoxy-6-ethyl-2-(methylsulfonyl)-7-(phenylsulfonyl)-7H-pyrrolo[2,3-d]0.64 g (67%) as a white powder. MS (ESI) m/z 410 (M+H)+.

The intermediate prepared in Example 30 may be converted into a variety of Formula I compounds where L=N and $R^4$ is a substituted O as shown by Examples 31-33.

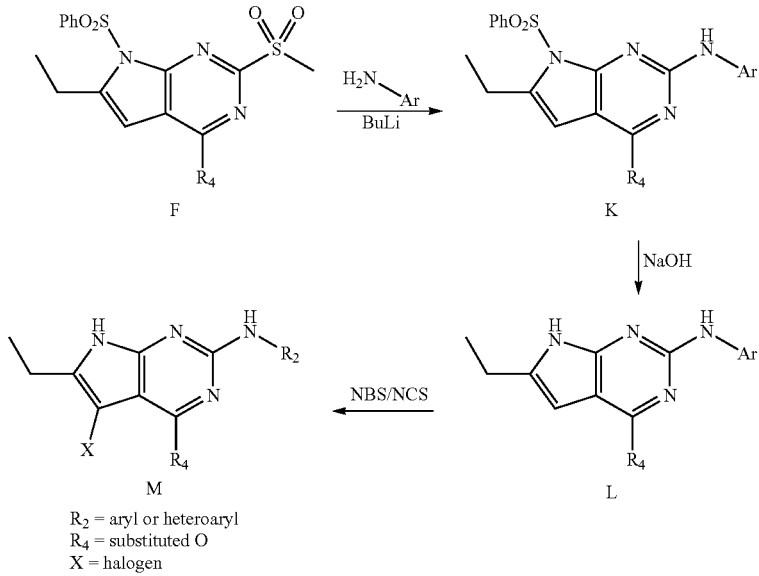

Example 31

Preparation of 4-Ethoxy-6-ethyl-7-(phenylsulfonyl)-N-(pyridin-3-yl)-7H-pyrrolo[2,3-d]pyrimidin-2-amine (Compound K)

n-BuLi (1.6 M in hexanes, 0.62 mL, 1 mmol) was added dropwise to a cooled stirring solution of an amine, 3-aminopyridine ($H_2N$—Ar) (1 mmol) in THF (3 to 5 mL, depending on solubility) at −78° C. The stirring was continued for 20 minutes at −78° C., then the resulting solution was quickly transferred into a stirring solution of compound F (Example 30) (102 mg, 0.25 mmol) in THF (2 mL) at room temperature. After 5 minutes stirring, water (25 mL) was added. The mixture was extracted with EtOAc (3×40 mL). The combined organic layers were washed with brine, dried over $Na_2SO_4$ and concentrated. Flash chromatography of the residue over silica gel (eluent: 20% EtOAc/hexanes) to give 4-Ethoxy-6-ethyl-7-(phenylsulfonyl)-N-(pyridin-3-yl)-7H-pyrrolo[2,3-d]pyrimidin-2-amine (compound K).

Example 32

Preparation of 4-Ethoxy-6-ethyl-N-(pyridin-3-yl)-7H-pyrrolo[2,3-d]pyrimidin-2-amine (Compound L)

4-Ethoxy-6-ethyl-7-(phenylsulfonyl)-N-(pyridin-3-yl)-7H-pyrrolo[2,3-d]pyrimidin-2-amine (Compound K) (0.088 mmol) was added to a stirring solution of NaOH (0.3 g, 7.5 mmol) in THF (2 mL) and MeOH (1 mL). The stirring was continued for 15 minutes. LC-MS indicated the reaction was completed. TFA (3 mL) was added to the reaction mixture. The solvents were removed under the reduced pressure. The resulting residue (L) was used directly for the next step.

Example 33

Preparation of 5-bromo-4-ethoxy-6-ethyl-N-(pyridin-3-yl)-7H-pyrrolo[2,3-d]pyrimidin-2-amine (Compound M)

N-Bromosuccinimide (NBS) or N-chlorosuccinimide (NCS) (0.088 mmol) was added to a stirring solution of 4-Ethoxy-6-ethyl-N-(pyridin-3-yl)-7H-pyrrolo[2,3-d]pyrimidin-2-amine (compound L) (0.088 mmol) in THF (3 mL) at room temperature. In the case of NBS, MeOH (5 mL) was added to the reaction mixture within 5 minutes after addition. For NCS, LC-MS monitoring the reaction, and the reaction usually took several h to complete, occasionally heating needed. After removal of all solvents, the residue was dissolved in DMSO (2 mL) which was separated by prep-HPLC (CH3CN/H2O in 0.1% TFA) to give compound M in above scheme. give 5-bromo-4-ethoxy-6-ethyl-N-(pyridin-3-yl)-7H-pyrrolo[2,3-d]pyrimidin-2-amine.

Additional analogs prepared by the scheme exemplified by Examples 31-33 include:
- N-(5-bromo-4-ethoxy-6-ethyl-7H-pyrrolo[2,3-d]pyrimidin-2-yl)quinolin-3-amine
- N-(5-bromo-4-ethoxy-6-ethyl-7H-pyrrolo[2,3-d]pyrimidin-2-yl)-1-isopropyl-1H-pyrazolo[3,4-b]pyridin-5-amine
- N-(5-chloro-4-ethoxy-6-ethyl-7H-pyrrolo[2,3-d]pyrimidin-2-yl)-1-isopropyl-1H-pyrazolo[3,4-b]pyridin-5-amine
- 5-bromo-4-ethoxy-6-ethyl-N-(pyrimidin-5-yl)-7H-pyrrolo[2,3-d]pyrimidin-2-amine
- 5-chloro-4-ethoxy-6-ethyl-N-(pyrimidin-5-yl)-7H-pyrrolo[2,3-d]pyrimidin-2-amine Compounds of Formula I where L=N and $R^4$ is a substituted N may be prepared as shown by Examples 34-41 using the methyl sulfide intermediate described in Example 26.

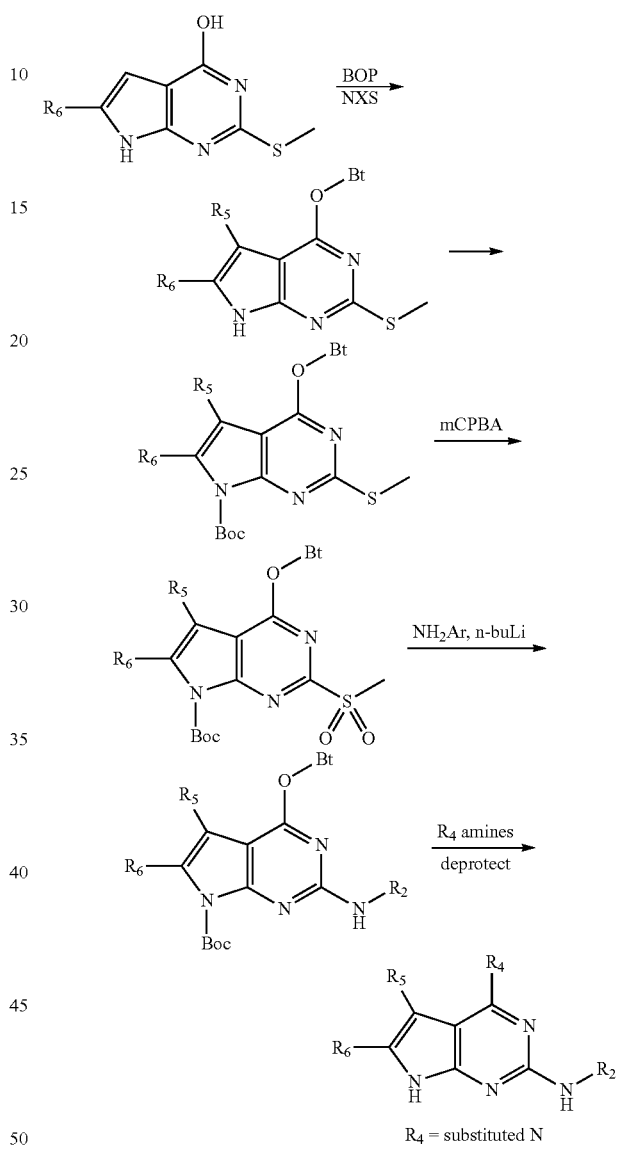

Example 34

1-(6-Ethyl-2-(methylthio)-7H-pyrrolo[2,3-d]pyrimidin-4-yloxy)-1H-benzo[d][1,2,3]triazole Benzotriazole-1-yl-oxy-tris-(dimethylamino)-phosphonium hexafluorophosphate (BOP, 9.52 g, 21.5 mmol) was added slowly to a stirring solution of 6-ethyl-2-(methylthio)-3H-pyrrolo[2,3-d]pyrimidin-4(7H)-one (Example 26) (3.6 g, 17.2 mmol), Et3N (3.0 mL, 21.5 mmol) in NMP (100 mL) at 0° C. The stirring was continued for 30 minutes at 0° C., and then 30 minutes at room temperature. HOBt (2.33 g, 17.2 mmol) and Et3N (2.4 mL, 17.2 mmol) was added. The mixture was heated to 40° C. for 12 h (LC-MS monitoring reaction). Water (300 mL) was added to the reaction mixture. The precipitate was collected by filtration and dried to give 4.4 g (78%) of 1-(6-Ethyl-2-(methylthio)-7H-pyrrolo[2,3-d]pyrimidin-4-yloxy)-1H-benzo[d][1,2,3]triazole. MS (ESI) m/z 327 (M+H)+.

Example 35

1-(5-Bromo-6-ethyl-2-(methylthio)-7H-pyrrolo[2,3-d]pyrimidin-4-yloxy)-1H-benzo[d][1,2,3]triazole N-Bromosuccinimide (0.530 g, 2.98 mmol) was added portion-wise to a stirring solution of 1-(6-ethyl-2-(methylthio)-7H-pyrrolo[2,3-d]pyrimidin-4-yloxy)-1H-benzo[d][1,2,3]triazole (0.97 g, 2.98 mmol) in THF (50 mL). The stirring was continued for 5 minutes after addition, and then half of the THF was removed under the reduced pressure. Water (50 mL) was added. The precipitate was filtered and dried to give 0.88 g (73%) of the grey solid 1-(5-bromo-6-ethyl-2-(methylthio)-7H-pyrrolo[2,3-d]pyrimidin-4-yloxy)-1H-benzo[d][1,2,3]triazole. MS (ESI) m/z 407 (M+H)+.

Example 36

Tert-Butyl 4-(1H-benzo[d][1,2,3]triazol-1-yloxy)-5-bromo-6-ethyl-2-(methylthio)-7H-pyrrolo[2,3-d]pyrimidine-7-carboxylate Di-tert-butyl dicarbonate (327 mg, 1.50 mmol) was added to a stirring solution of 1-(5-bromo-6-ethyl-2-(methylthio)-7H-pyrrolo[2,3-d]pyrimidin-4-yloxy)-1H-benzo[d][1,2,3]triazole (368 mg, 0.910 mmol), Et3N (0.28 mL, 2.0 mmol) and 4-dimethylaminopyridine (25 mg, 0.2 mmol) in THF (25 mL) at room temperature. The stirring was continued for one hour. LC-MS indicated that the reaction was completed. Water (50 mL) was added. The mixture was extracted with EtOAc (3×80 mL). The combined organic layers were washed with brine, dried over Na2SO4 and concentrated. Flash chromatography of the residue over silica gel (eluent: 20% EtOAc/hexane) to give 344 mg (75%) of tert-butyl 4-(1H-benzo[d][1,2,3]triazol-1-yloxy)-5-bromo-6-ethyl-2-(methylthio)-7H-pyrrolo[2,3-d]pyrimidine-7-carboxylate. MS (ESI) m/z 507 (M+H)+.

Example 37

Tert-Butyl 4-(1H-benzo[d][1,2,3]triazol-1-yloxy)-5-bromo-6-ethyl-2-(methylsulfonyl)-7H-pyrrolo[2,3-d]pyrimidine-7-carboxylate)

m-Chloroperoxybenzoic acid (MCPBA, 487 mg, 77%, 2.17 mmol) was added to a stirring solution of tert-butyl 4-(1H-benzo[d][1,2,3]triazol-1-yloxy)-5-bromo-6-ethyl-2-(methylthio)-7H-pyrrolo[2,3-d]pyrimidine-7-carboxylate (0.423 g, 0.836 mmol) in DMF (12 mL) at room temperature. The stirring was continued for 17 h. Water (50 mL) was added. The mixture was extracted with EtOAc (3×80 mL). The combined organic layers were washed with brine, dried over Na2SO4 and concentrated. Flash chromatography of the residue over silica gel (eluent: 30% EtOAc/hexane) to give 330 mg (73%) of Tert-butyl 4-(1H-benzo[d][1,2,3]triazol-1-yloxy)-5-bromo-6-ethyl-2-(methylsulfonyl)-7H-pyrrolo[2,3-d]pyrimidine-7-carboxylate. MS (ESI) m/z 539 (M+H)+.

Example 38

Tert-butyl 4-(1H-benzo[d][1,2,3]triazol-1-yloxy)-5-bromo-6-ethyl-2-(3-isopropyl-3H-[1,2,3]triazolo[4,5-b]pyridin-6-ylamino)-7H-pyrrolo[2,3-d]pyrimidine-7-carboxylate n-BuLi (1.6 M in hexanes, 0.35 mL, 0.56 mmol) was added dropwise to a cooled stirring solution of an amine, 3-isopropyl-3H-[1,2,3]triazolo[4,5-b]pyridin-6-amine (99 mg, 0.56 mmol) in THF (2 mL) at −78° C. The stirring was continued for 20 minutes at −78° C., then the resulting solution was quickly transferred into a stirring solution of J (100 mg, 0.186 mmol) in THF (1 mL) at room temperature. After 5 minutes stirring, water (20 mL) was added. The mixture was extracted with EtOAc (3×30 mL). The combined organic layers were washed with brine, dried over Na2SO4 and concentrated. Flash chromatography of the residue over silica gel (eluent: 20% EtOAc/hexanes) to give the desired product 47 mg (40%). MS (ESI) m/z 634 (M+H)+.

Example 39

1-(5-Bromo-6-ethyl-2-(3-isopropyl-3H-[1,2,3]triazolo[4,5-b]pyridin-6-ylamino)-7H-pyrrolo[2,3-d]pyrimidin-4-yl)azetidin-3-ol Azetidin-3-ol hydrochloride (6.5 mg, 0.06 mmol) was added to a stirring solution of Et3N (20 µL) and tert-butyl 4-(1H-benzo[d][1,2,3]triazol-1-yloxy)-5-bromo-6-ethyl-2-(3-isopropyl-3H-[1,2,3]triazolo[4,5-b]pyridin-6-ylamino)-7H-pyrrolo[2,3-d]pyrimidine-7-carboxylate (Example 38) (19 mg, 0.03 mmol) in NMP (0.7 mL). The stirring was continued for 6 h. LC-MS indicated the reaction was completed. DMSO (0.5 mL) was added to the mixture. The solution was subjected to prep-HPLC (CH3CH—H2O, in 0.1% TFA) to give the desired product. MS (ESI) m/z 472 (M+H)+.

Example 40 tert-butyl 1-(5-bromo-6-ethyl-2-(3-isopropyl-3H-[1,2,3]triazolo[4,5-b]pyridin-6-ylamino)-7H-pyrrolo[2,3-d]pyrimidin-4-yl)azetidin-3-ylcarbamate tert-butyl azetidin-3-ylcarbamate (8.3 mg, 0.048 mmol) was added to a stirring solution of Et3N (20 µL) tert-butyl 4-(1H-benzo[d][1,2,3]triazol-1-yloxy)-5-bromo-6-ethyl-2-(3-isopropyl-3H-[1,2,3]triazolo[4,5-b]pyridin-6-ylamino)-7H-pyrrolo[2,3-d]pyrimidine-7-carboxylate (Example 39) (15 mg, 0.024 mmol) in NMP (0.7 mL). The stirring was continued for 8 h. LC-MS indicated the reaction was completed. DMSO (0.5 mL) was added to the mixture. The solution was subjected to prep-HPLC (CH3CH—H2O, in 0.1% TFA) to give the desired product. MS (ESI) m/z 571 (M+H)+.

Example 41

N-(4-(3-aminoazetidin-1-yl)-5-bromo-6-ethyl-7H-pyrrolo[2,3-d]pyrimidin-2-yl)-3-isopropyl-3H-[1,2,3]triazolo[4,5-b]pyridin-6-amine A solution of tert-butyl 1-(5-bromo-6-ethyl-2-(3-isopropyl-3H-[1,2,3]triazolo[4,5-b]pyridin-6-ylamino)-7H-pyrrolo[2,3-d]pyrimidin-4-yl)azetidin-3-ylcarbamate (Example 40) (2 mg) in TFA (0.5 mL) was stirring for 30 minutes. LC-MS indicated the reaction was completed. Removal of solvents under the reduced pressure gave the pure desired product. MS (ESI) m/z 471 (M+H)+.

Compounds of Formula I where L=C and $R^4$ is a substituted N or a substituted O may be prepared as shown by Examples 42-49.

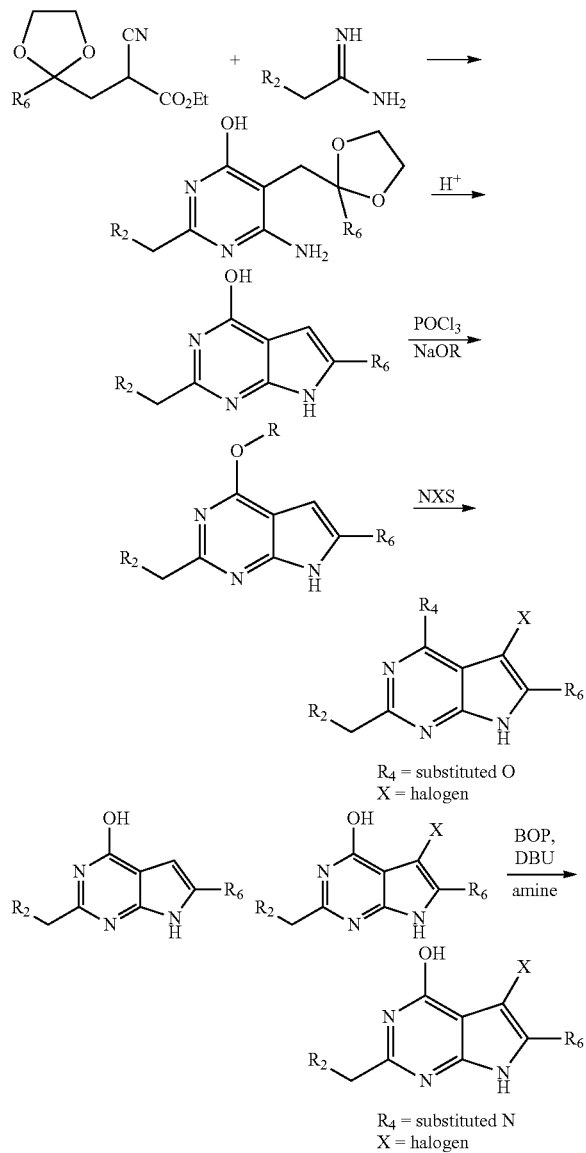

Example 42

6-amino-5-((2-ethyl-1,3-dioxolan-2-yl)methyl)-2-(pyridin-3-ylmethyl)pyrimidin-4-ol Ethyl cyanoacetate (35 mL, 331 mmol) was dissolved in toluene (1.5 L) and DBU (50 mL, 331 mmol) was added via dropping funnel. The reaction was allowed to stir for 30 minutes. The pot was placed in an ice bath and allowed to cool to 0° C. followed by dropwise addition of 1-bromo-2-butanone (50 g, 331 mmol). This reaction was slightly exothermic so it was monitored and the temperature was not allowed to rise over 10° C. Once addition was complete the reaction turned a brown color. It was allowed slowly warm to room temperature and to react overnight. The next morning the reaction was poured into a separatory funnel and washed 2× with 1 M HCl and 1× with brine. The organic layer was dried with sodium sulfate and filtered. The toluene was removed by rotary evaporator to yield 50 grams of a dark brown liquid. The product was pure as determined by NMR and was carried on to the next step.

Ethyl 2-cyano-4-oxohexanoate (50 g, 273 mmol) was dissolved in benzene (550 mL). To this solution was added ethylene glycol (22.8 mL, 409 mmol) and p-toluenesulfonic acid monohydrate (1 g, 5.46 mmol). The reaction was equipped with a Dean-Stark trap, a heating mantle and a reflux condenser and the reaction was heated to reflux until the appropriate amount of water was removed from the reaction, anywhere from 2-12 h. The reaction was cooled and poured into a separatory funnel and washed 2× with 10% sodium carbonate and 1× with brine. The organic layer was dried with sodium sulfate, filtered and the solvent removed by rotary evaporator to yield a dark oil. NMR indicated this product was about >90% pure therefore we used it for the next step without further purification.

2-(pyridin-3-yl)-acetimidamide (1.4 g, 10 mmol) was suspended in dry ethanol (30 mL) and sodium ethoxide (21% solution) (50 mL, 13 mmol) was added. To this reaction was added ethyl 2-cyano-3-(2-ethyl-1,3-dioxolan-2-yl)propanoate (Example 56) (0.3 g, 10 mmol). The reaction was equipped with a mechanical stirrer, a heating mantle and a reflux condenser and heated to reflux for 6 h during which a precipitate was observed. The next morning the solvent was removed and water (30 mL) was added to the crude product followed by addition of 10% citric acid to pH 7. The solid was collected and the wet cake was washed with cold ethanol to remove most of the brown discoloration. The cake was dried in a vacuum oven overnight to yield the desired amino pyrimidine. The product was used without further purification.

Example 43

6-ethyl-2-(pyridin-3-ylmethyl)-7H-pyrrolo[2,3-d]pyrimidin-4-ol 6-amino-5-((2-ethyl-1,3-dioxolan-2-yl)methyl)-2-(pyridin-3-ylmethyl)pyrimidin-4-ol (Example 60) (2 g) was added to THF (10 mL) and to this suspension was added 1 N HCl in water (10 mL). The pyrimidine slowly dissolves in this solution over a 1 h period and a new precipitate forms. The reaction was allowed to proceed overnight and the next day the precipitate was collect via filtration. The filter cake was washed with water and dried in a vacuum oven overnight.

Example 44

4-chloro-6-ethyl-2-(pyridin-3-ylmethyl)-7H-pyrrolo[2,3-d]pyrimidine 6-ethyl-2-(pyridin-3-ylmethyl)-7H-pyrrolo[2,3-d]pyrimidin-4-ol (Example 61) (500 mg) was dissolved in phosphorous oxychloride (5 mL) and 0.1 mL Hunigs base, and heated to reflux for 3 h. Then the phosphorous oxychloride was removed by rotary evaporator and the remaining syrup was carefully quenched with 100 mL of chipped ice. The precipitate was collected and washed with water and dried in a vacuum oven overnight.

Example 45

6-ethyl-2-(pyridin-3-ylmethyl)-4-(pyridin-3-yloxy)-7H-pyrrolo[2,3-d]pyrimidine Sodium hydride (20 mg) was added into 20 mg pyridin-3-ol in 2 mL NMP and stirred for 5 min, then 4-chloro-6-ethyl-2-(pyridin-3-ylmethyl)-7H-pyrrolo[2,3-d]pyrimidine (Example 44) (10 mg) was added into above solution, the mixture was heated to 160° C. for 20 min, and cooled to ambient temperature, and quenched by 0.5 mL 1 M HCl, the reaction solution was injected to reverse phase HPLC and provided the title compounds, LCMS: 332 (M+H).

Example 46

5-chloro-6-ethyl-2-(pyridin-3-ylmethyl)-4-(pyridin-3-yloxy)-7H-pyrrolo[2,3-d]pyrimidine 6-ethyl-2-(pyridin-3-ylmethyl)-4-(pyridin-3-yloxy)-7H-pyrrolo[2,3-d]pyrimidine (Example 63) (5 mg) was dissolved into 1 mL NMP, then 2 mg NCS was added into the solution, the reaction was monitored by LCMS, after 6-ethyl-2-(pyridin-3-ylmethyl)-4-(pyridin-3-yloxy)-7H-pyrrolo[2,3-d]pyrimidine disappeared, the reaction solution was injected to reverse phase HPLC and provided the title compounds, LCMS: 366 (M+H).

Example 47

5-chloro-6-ethyl-2-(pyridin-3-ylmethyl)-7H-pyrrolo[2,3-d]pyrimidin-4-ol 6-ethyl-2-(pyridin-3-ylmethyl)-7H-pyrrolo[2,3-d]pyrimidin-4-ol (Example 43) (30 mg) was dissolved into 2 mL NMP, then 20 mg NCS was added into the solution, the reaction was monitored by LCMS, after the compounds 8 disappeared, the reaction solution was injected to reverse phase HPLC and provided the title compounds, LCMS: 289 (M+H).

Example 48

1-(6-ethyl-5-methyl-2-(pyridin-3-ylmethyl)-7H-pyrrolo[2,3-d]pyrimidin-4-yl)azetidin-3-amine 5-chloro-6-ethyl-2-(pyridin-3-ylmethyl)-7H-pyrrolo[2,3-d]pyrimidin-4-ol (Example 47) (5 mg) was dissolved into 1 mL DMF, then 10 mg BOP and 20 µL DBU was added into the solution at 0~5° C., the solution was stirred for 10 min, then tert-butyl azetidin-3-ylcarbamate 10 mg was added into the previous solution, the reaction solution was stirred for overnight, and then the reaction solution was injected to reverse phase HPLC and purified. The purified compounds was dried and re-dissolved into 1 mL TFA and stirred for 0.5 hour, then removed the excess TFA to give the title compound, LCMS: 343 (M+H).

Example 49

1-(5-chloro-6-ethyl-2-(pyridin-3-ylmethyl)-7H-pyrrolo[2,3-d]pyrimidin-4-yl)azetidin-3-ol 5-chloro-6-ethyl-2-(pyridin-3-ylmethyl)-7H-pyrrolo[2,3-d]pyrimidin-4-ol (Example 48) (5 mg) was dissolved into 1 mL DMF, then 10 mg BOP and 20 µL DBU was added into the solution at 0~5° C., the solution was stirred for 10 min, then tert-butyl azetidin-3-ylcarbamate 10 mg was added into the previous solution, the reaction solution was stirred for overnight, and then the reaction solution was injected to reverse phase HPLC and provided the title compounds, LCMS: 344 (M+H).

Compounds of Formula I where L=O and $R^4$ is a substituted N or a substituted O may be prepared as shown by Examples 50-55.

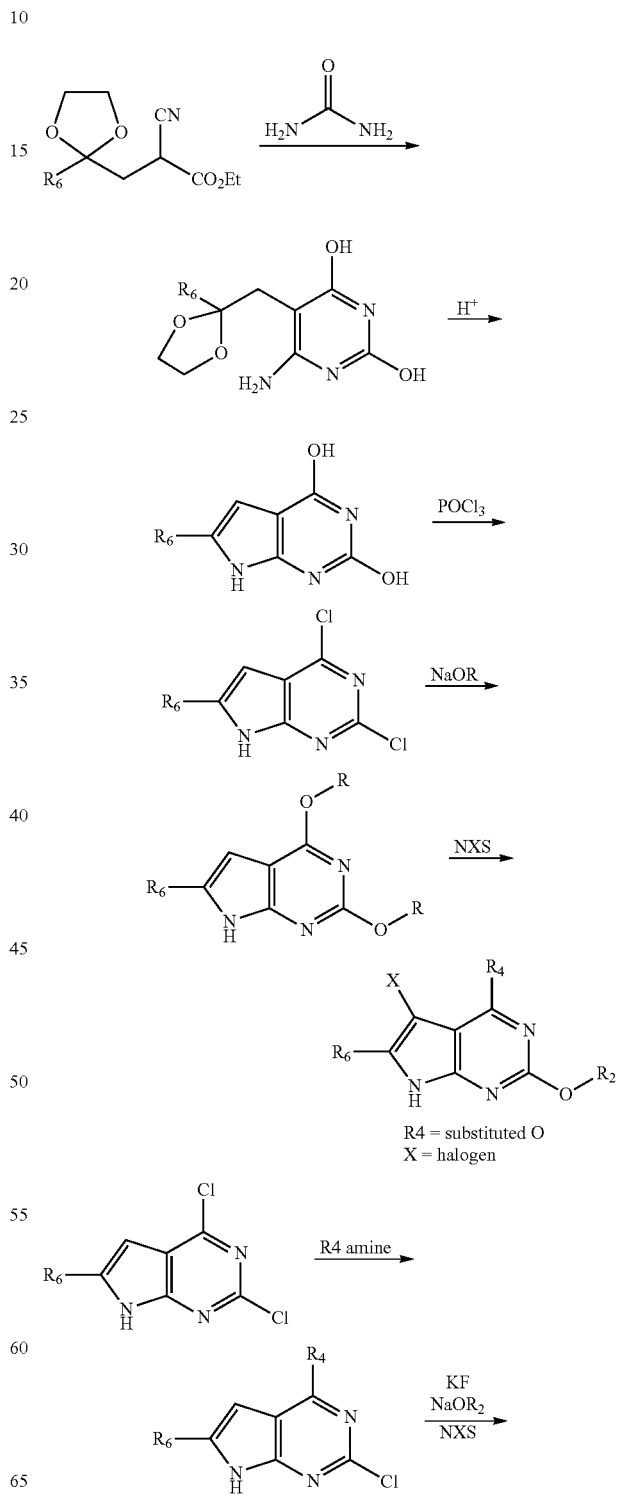

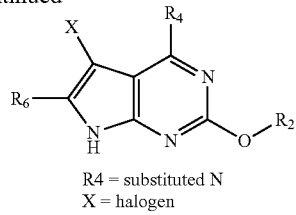

R4 = substituted N
X = halogen

Example 50

6-ethyl-7H-pyrrolo[2,3-d]pyrimidine-2,4-diol

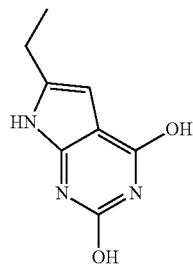

Ethyl cyanoacetate (35 mL, 331 mmol) was dissolved in toluene (1.5 L) and DBU (50 mL, 331 mmol) was added via dropping funnel. The reaction was allowed to stir for 30 minutes. The pot was placed in an ice bath and allowed to cool to 0° C. followed by dropwise addition of 1-bromo-2-butanone (50 g, 331 mmol). This reaction was slightly exothermic so it was monitored and the temperature was not allowed to rise over 10° C. Once addition was complete the reaction turned a brown color. It was allowed slowly warm to room temperature and to react overnight. The next morning the reaction was poured into a separatory funnel and washed 2× with 1 M HCl and 1× with brine. The organic layer was dried with sodium sulfate and filtered. The toluene was removed by rotary evaporator to yield 50 grams of a dark brown liquid. The product was pure as determined by NMR and was carried on to the next step.

Ethyl 2-cyano-4-oxohexanoate (50 g, 273 mmol) from above was dissolved in benzene (550 mL). To this solution was added ethylene glycol (22.8 mL, 409 mmol) and p-toluenesulfonic acid monohydrate (1 g, 5.46 mmol). The reaction was equipped with a Dean-Stark trap, a heating mantle and a reflux condenser and the reaction was heated to reflux until the appropriate amount of water was removed from the reaction, anywhere from 2-12 h. The reaction was cooled and poured into a separatory funnel and washed 2× with 10% sodium carbonate and 1× with brine. The organic layer was dried with sodium sulfate, filtered and the solvent removed by rotary evaporator to yield a dark oil. NMR indicated this product was about >90% pure therefore we used it for the next step without further purification.

Urea (18.0 g, 264 mmol) was suspended in dry ethanol (400 mL) and sodium ethoxide (21% solution) (100 mL, 264 mmol) was added. To this reaction was added ethyl 2-cyano-3-(2-ethyl-1,3-dioxolan-2-yl)propanoate (60 g, 264 mmol). The reaction was equipped with a mechanical stirrer, a heating mantle and a reflux condenser and heated to reflux for 6 h during which a precipitate was observed. The next morning the solvent was removed and water (300 mL) was added to the crude product followed by addition of 10% citric acid to pH 7. The solid was collected and the wet cake was washed with cold ethanol to remove most of the brown discoloration. The cake was dried in a vacuum oven overnight to yield the desired amino pyrimidine. The product was used without further purification.

6-amino-5-((2-ethyl-1,3-dioxolan-2-yl)methyl)pyrimidine-2,4-diol (16 g) was added to THF (50 mL) and to this suspension was added 1 M HCl in water (500 mL). The pyrimidine slowly dissolved in this solution over a 1 h period and a new precipitate formed. The reaction was allowed to proceed overnight and the next day the precipitate was collect via filtration. The filter cake was washed with water and dried in a vacuum oven overnight.

Example 51

2,4-dichloro-6-ethyl-7H-pyrrolo[2,3-d]pyrimidine

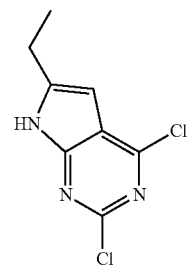

6-amino-5-((2-ethyl-1,3-dioxolan-2-yl)methyl)pyrimidine-2,4-diol (Example 50) (10 g) was dissolved in phosphorous oxychloride (20 mL) and 1 mL Hunigs base, and heated to reflux for 3 h. Then the phosphorous oxychloride was removed by rotary evaporator and the remaining syrup was carefully quenched with 100 mL of chipped ice. The precipitate was collected and washed with water and dried in a vacuum oven overnight.

Example 52

6-Ethyl-2,4-bis(pyridin-3-yloxy)-7H-pyrrolo[2,3-d]pyrimidine 2,4-dichloro-6-ethyl-7H-pyrrolo[2,3-d]pyrimidine (Example 51) (100 mg, 0.46 mmol) was combined with potassium carbonate (80 mg, 0.5 mmol), 3-hydroxypyridine (88 mg, 0.92 mmol), NMP (5 mL). The reaction was purged with dry nitrogen and heated to 120° C. by microwave for 10 min. The NMP was removed by rotary evaporator and the crude product was purified by HPLC. A white solid product was obtained (90 mg), LCMS: 334.21.

Example 53

5-chloro-6-ethyl-2,4-bis(pyridin-3-yloxy)-7H-pyrrolo[2,3-d]pyrimidine

Using the procedure described in Example 25, the title compound was obtained. A white solid product was obtained (20 mg), LCMS: 368.32.

Example 54

5-chloro-6-ethyl-2,4-bis(5-fluoropyridin-3-yloxy)-7H-pyrrolo[2,3-d]pyrimidine Using the procedure described in Examples 52 and 53 the title compound was obtained. LCMS: 368.32.

Example 55

1-(4-(6-Ethyl-2-(pyridin-3-yloxy)-7H-pyrrolo[2,3-d]pyrimidin-4-yl)piperazin-1-yl)ethanone 2,4-dichloro-6-ethyl-7H-pyrrolo[2,3-d]pyrimidine (Example 51) (100 mg, 0.46 mmol) was combined with potassium carbonate (80 mg, 0.5 mmol), 1-acetylpiperazine (59 mg, 0.46 mmol), NMP (5 mL). The reaction was purged of oxygen with a dry stream of nitrogen and microwave heated to 120° C. for 10 min. The NMP was removed by rotary evaporator and the crude product was purified by HPLC. A white solid product was obtained (92 mg), LCMS: 308.11.

The above compound (80 mg, 0.26 mmol) was combined with potassium fluoride (75 mg, 1.3 mmol) and dry acetone (10 mL). The reaction was stirred at RT for 72 hr. The solvent was removed by rotary evaporator. The residues was combined with potassium carbonate (80 mg, 0.5 mmol), 3-hydroxy pyridine (50 mg, 0.52 mmol), NMP (5 mL). The reaction was purged of oxygen with a dry stream of nitrogen and microwave heated to 180° C. for 10 min. The NMP was removed by rotary evaporator and the crude product was purified by HPLC. A white solid product was obtained (40 mg), LCMS: 367.28.

Various $R^4$ groups may contain functionality that can be further elaborated to create additional analogs as demonstrated be Examples 56-62.

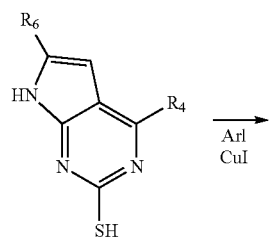

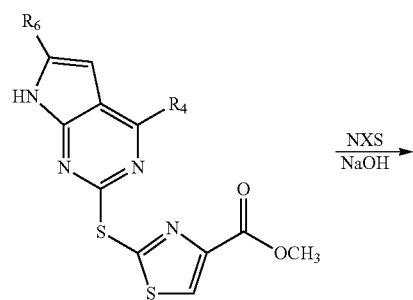

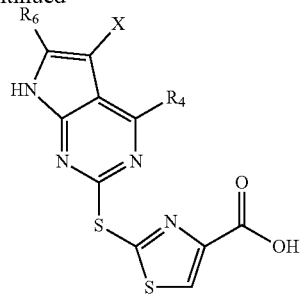

Example 56

Methyl 2-(4-ethoxy-6-ethyl-7H-pyrrolo[2,3-d]pyrimidin-2-ylthio)thiazole-4-carboxylate 4-Ethoxy-6-ethyl-7H-pyrrolo[2,3-d]pyrimidine-2-thiol (100 mg, 0.448 mmol) and methyl 2-bromothiazole-4-carboxylate (104 mg, 0.470 mmol) were added to glacial AcOH (1.5 mL) and the mixture was stirred at 90° C. for 1 h. The mixture was then added to a stirred solution of NaHCO3 and the precipitated methyl 2-(4-ethoxy-6-ethyl-7H-pyrrolo[2,3-d]pyrimidin-2-ylthio)thiazole-4-carboxylate (60 mg, 0.165 mmol, 36.8% yield) was collected by filtration.

Example 57

Methyl 2-(5-bromo-4-ethoxy-6-ethyl-7H-pyrrolo[2,3-d]pyrimidin-2-ylthio)thiazole-4-carboxylate Methyl 2-(4-ethoxy-6-ethyl-7H-pyrrolo[2,3-d]pyrimidin-2-ylthio)thiazole-4-carboxylate (Example 40) (40 mg, 0.110 mmol) was dissolved in NMP (0.5 mL) and NBS (N-bromosuccinimide) (19.53 mg, 0.110 mmol) was added at 0° C. The mixture was stirred at 23° C. for 10 min. Methanol (0.5 mL) was added and the mixture was purified by HPLC to obtain methyl 2-(5-bromo-4-ethoxy-6-ethyl-7H-pyrrolo[2,3-d]pyrimidin-2-ylthio)thiazole-4-carboxylate (15 mg, 0.034 mmol, 30.8% yield). LC-MS 445 (M+H).

Example 58

2-(5-bromo-4-ethoxy-6-ethyl-7H-pyrrolo[2,3-d]pyrimidin-2-ylthio)thiazole-4-carboxylic acid Methyl 2-(5-bromo-4-ethoxy-6-ethyl-7H-pyrrolo[2,3-d]pyrimidin-2-ylthio)thiazole-4-carboxylate (Example 42) (10 mg, 0.023 mmol) and 2 M sodium hydroxide (90 μL, 0.180 mmol) were stirred for 3 min at 90° C. in a mixture of MeOH (0.5 mL) and NMP (0.5 mL) and then stirred for further 30 min at 23° C. The reaction mixture was purified by HPLC to obtain 2-(5-bromo-4-ethoxy-6-ethyl-7H-pyrrolo[2,3-d]pyrimidin-2-ylthio)thiazole-4-carboxylic acid (7 mg, 0.016 mmol, 72.3% yield).

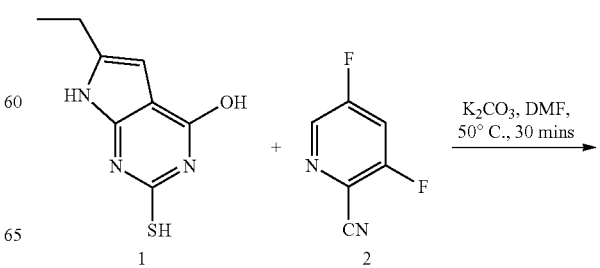

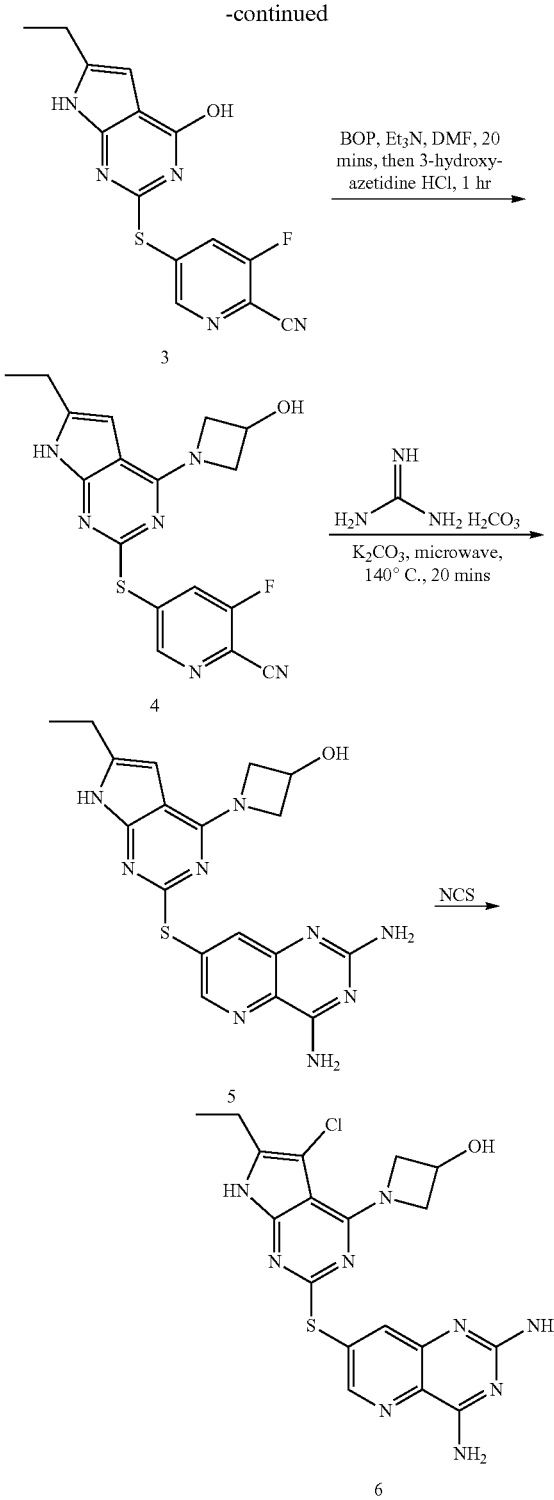

sium carbonate (276.5 mg, 2 mmol) and DMF (2 mL). The reaction was heated at 50° C. for 30 minutes. It was then cooled to room temperature and the solid was filtered off. The product solution was carried on to the next step without purification.

Example 60

5-(6-ethyl-4-(3-hydroxyazetidin-1-yl)-7H-pyrrolo[2,3-d]pyrimidin-2-ylthio)-3-fluoropicolinonitrile To the above solution of 5-(6-ethyl-4-hydroxy-7H-pyrrolo[2,3-d]pyrimidin-2-ylthio)-3-fluoropicolinonitrile was added [benzotriazole-1-yl-oxy-tris-(dimethylamino)phosphonium hexafluorophosphate] (265.4 mg, 0.6 mmol) and triethylamine (0.5 mL). After stirred at room temperature for 20 minutes, the mixture was added with 3-hydroxyazetidine HCl (200 mg, 2 mmol). The reaction was completed in 1 hour at room temperature. The product was purified by column chromatography (100% ethyl acetate).

Example 61

1-(2-(2,4-diaminopyrido[2,3-d]pyrimidin-6-ylthio)-6-ethyl-7H-pyrrolo[2,3-d]pyrimidin-4-yl)azetidin-3-ol 5-(6-ethyl-4-(3-hydroxyazetidin-1-yl)-7H-pyrrolo[2,3-d]pyrimidin-2-ylthio)-3-fluoropicolinonitrile (Example 60) (50 mg, 0.135 mmol) was combined with guanidine carbonate (90.1 mg, 0.5 mmol), potassium carbonate (138.3 mg, 1 mmol), and DMF (2 mL). The reaction was heated at 140° C. under microwave condition for 20 minutes. The mixture was then purified by high performance liquid chromatography to yield the desired product.

Example 62

1-(5-chloro-2-(2,4-diaminopyrido[2,3-d]pyrimidin-6-ylthio)-6-ethyl-7H-pyrrolo[2,3-d]pyrimidin-4-yl)azetidin-3-ol To a solution of 1-(2-(2,4-diaminopyrido[2,3-d]pyrimidin-6-ylthio)-6-ethyl-7H-pyrrolo[2,3-d]pyrimidin-4-yl)azetidin-3-ol (Example 61) (10.24 mg, 0.025 mmol) in THF (1 mL) was added drop-wise a solution of N-chlorosuccinimide (6.8 mg, 0.05 mmol) in DMF (0.5 mL). The reaction was warmed in a 50° C. water bath for 1 minute. The water bath was removed, and the reaction was allowed to stir for another 5 minutes and monitored by LCMS. The warm-up process was repeated if necessary to complete the reaction. The completed reaction was cooled in an iced-water bath and quenched with methanol (0.5 mL). Upon HPLC purification, 1-(5-chloro-2-(2,4-diaminopyrido[2,3-d]pyrimidin-6-ylthio)-6-ethyl-7H-pyrrolo[2,3-d]pyrimidin-4-yl)azetidin-3-ol was obtained as the white solid TFA salt.

Various $R^2$ groups may contain functionality that can be further elaborated to create additional analogs as demonstrated be Examples 63-65.

Example 59

5-(6-ethyl-4-hydroxy-7H-pyrrolo[2,3-d]pyrimidin-2-ylthio)-3-fluoropicolinonitrile 6-ethyl-2-mercapto-7H-pyrrolo[2,3-d]pyrimidin-4-ol (Example 2) (98 mg, 0.5 mmol) and 2-cyano-3,5-difluoropyridine (70.1 mg, 0.5 mmol) were combined with potas-

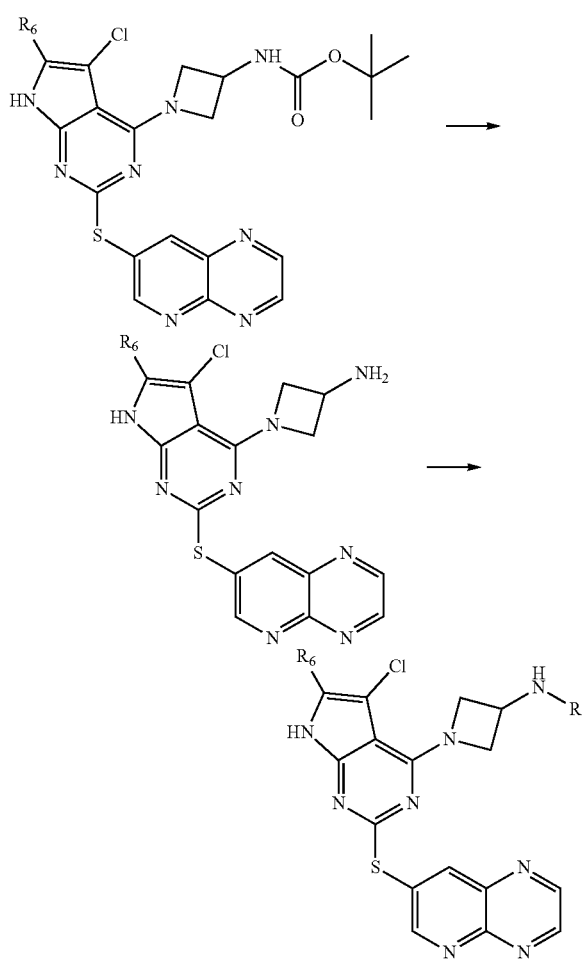

Example 63

1-(5-chloro-6-ethyl-2-(pyrido[3,2-b]pyrazin-7-yl-thio)-7H-pyrrolo[2,3-d]pyrimidin-4-yl)azetidin-3-amine Tert-butyl 1-(5-chloro-6-ethyl-2-(pyrido[3,2-b]pyrazin-7-ylthio)-7H-pyrrolo[2,3-d]pyrimidin-4-yl)azetidin-3-ylcarbamate (800 mg, 1.559 mmol) was added to DCM (20 mL) and the mixture was cooled to 0° C. TFA (5 mL) was added and the mixture was stirred at 40° C. for 1 h. The mixture was then added to rapidly stirring diethyl ether and the precipitated TFA salt of 1-(5-chloro-6-ethyl-2-(pyrido[3,2-b]pyrazin-7-ylthio)-7H-pyrrolo[2,3-d]pyrimidin-4-yl)azetidin-3-amine (650 mg, 1.234 mmol, 79% yield) was collected by filtration under nitrogen.

Example 64

N-(1-(5-chloro-6-ethyl-2-(pyrido[3,2-b]pyrazin-7-ylthio)-7H-pyrrolo[2,3-d]pyrimidin-4-yl)azetidin-3-yl)methane sulfonamide To a stirred solution of 1-(5-chloro-6-ethyl-2-(pyrido[3,2-b]pyrazin-7-ylthio)-7H-pyrrolo[2,3-d]pyrimidin-4-yl)azetidin-3-amine (Example 63) (20 mg, 0.048 mmol) and triethylamine (20.25 µl, 0.145 mmol) in NMP (0.7 mL) was added methanesulfonyl chloride (5.55 mg, 0.048 mmol) at 0° C. and the mixture was stirred at 23° C. for 2 h. MeOH (0.5 mL) was added and the mixture was purified by HPLC to obtain N-(1-(5-chloro-6-ethyl-2-(pyrido[3,2-b]pyrazin-7-ylthio)-7H-pyrrolo[2,3-d]pyrimidin-4-yl)azetidin-3-yl) methanesulfonamide (11 mg, 0.022 mmol, 46.3% yield).

Example 65

N-(1-(5-chloro-6-ethyl-2-(pyrido[3,2-b]pyrazin-7-ylthio)-7H-pyrrolo[2,3-d]pyrimidin-4-yl)azetidin-3-yl)-1H-imidazole-5-carboxamide To a mixture of 1-(5-chloro-6-ethyl-2-(pyrido[3,2-b]pyrazin-7-ylthio)-7H-pyrrolo[2,3-d]pyrimidin-4-yl)azetidin-3-amine (Example 63) (20 mg, 0.048 mmol), 1H-imidazole-5-carboxylic acid (6.52 mg, 0.058 mmol) and BOP (25.7 mg, 0.058 mmol) in NMP (0.7 mL) was added triethylamine (20.25 µl, 0.145 mmol) at 0° C. and the mixture was stirred at 23° C. for 2 h. MeOH (0.5 mL) was added and the mixture was purified by HPLC to obtain N-(1-(5-chloro-6-ethyl-2-(pyrido[3,2-b]pyrazin-7-ylthio)-7H-pyrrolo[2,3-d]pyrimidin-4-yl)azetidin-3-yl)-1H-imidazole-5-carboxamide (9 mg, 0.018 mmol, 36.6% yield).

The $R^6$ ethyl group can be converted to a chlorovinyl group by using multiple equivalents of NCS as shown in Example 66.

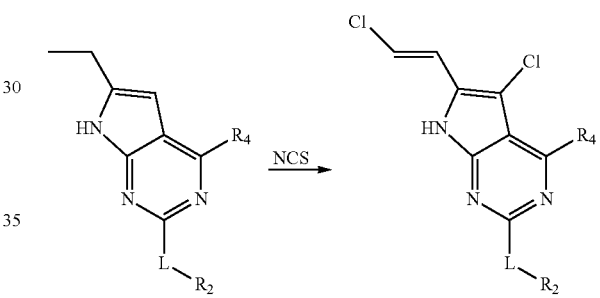

Example 66

(E)-methyl 2-(5-chloro-6-(2-chlorovinyl)-4-(3-(pyrimidin-2-ylmethyl)azetidin-1-yl)-7H-pyrrolo[2,3-d]pyrimidin-2-ylthio)thiazole-4-carboxylate Methyl 2-(6-ethyl-4-(3-(pyrimidin-2-ylmethyl)azetidin-1-yl)-7H-pyrrolo[2,3-d] pyrimidin-2-ylthio)thiazole-4-carboxylate (50 mg, 0.1 mmol) was combined with NCS (21 mg, 0.15 mmol), NMP (5 mL). The reaction was stirred at room temperature overnight. The NMP was removed by rotary evaporator and the crude product was purified by HPLC. A white solid product (3) was obtained (18 mg), LCMS: 468.05. product (4) (15 mg), LCMS: 522.00.

Example 67 General Synthesis Method of S-Linked Compounds

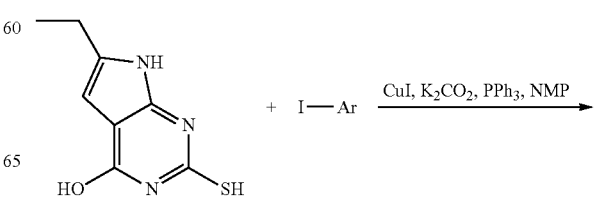

93
-continued

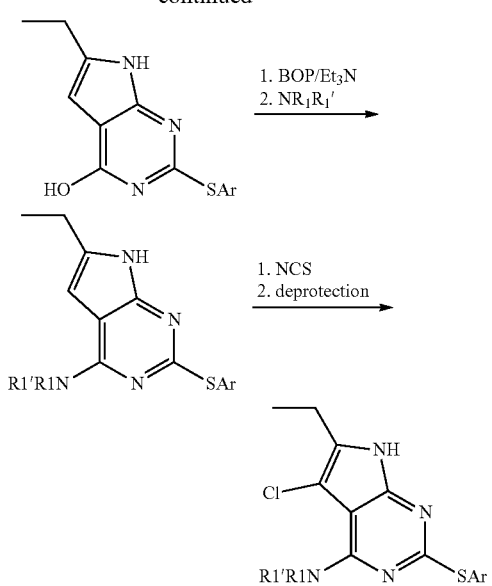

The solution of CuI (67 mg, 0.35 mmol), N,N'-dimethylcyclohexane-1,2-diamine (100 mg, 0.70 mmol) in 9 mL of NMP was added to a stirring suspension of him and (Example 2) (229 mg, 1.17 mmol), a proper I—Ar (1.17 mmol), $K_2CO_3$ (324 mg, 2.35 mmol) and $PPh_3$ (400 mg, 1.53 mmol) in NMP (9 mL). The mixture was heated to 130° C. for 2 to 12 hrs monitored by LC-MS for the completion of the reaction. When the reaction completed, the mixture was cooled to 0° C., BOP (621 mg, 1.40 mmol) and $Et_3N$ (0.41 mL, 2.93 mmol) was added, stirred for 30 minutes at 0° C., then warmed up to room temperature, a suitable Boc-protected diamine (2.34 mmol) was added. The reaction mixture was heated to 50° C. for 30 minutes. LC-MS indicated the completed reaction. At room temperature, N-chlorosuccinimide (NCS, 156 mg, 1.17 mmol) was added in several portions. The mixture was stirred for 2 to 12 hrs for the completion of the reaction, heated to 40° C. if the reaction failed to proceed. TFA was finally added to the mixture to remove the Boc protection group. After removal of solvents, Prep HPLC of the resulting residue (eluent: $CH_3CN/H_2O/0.1\%$ TFA) to give the desired S-linked compounds, such as those identified below. R1 and R1' in the above scheme together refer to the remainder of an amine-containing moiety, such as the heteroalicyclic groups shown in the compounds below.

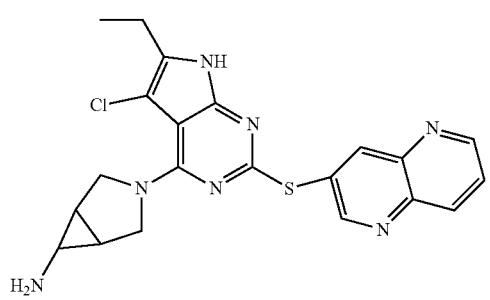

700800

94
3-(2-(1,5-naphthyridin-3-ylthio)-5-chloro-6-ethyl-7H-pyrrolo[2,3-d]pyrimidin-4-yl)-3-azabicyclo[3.1.0]hexan-6-amine

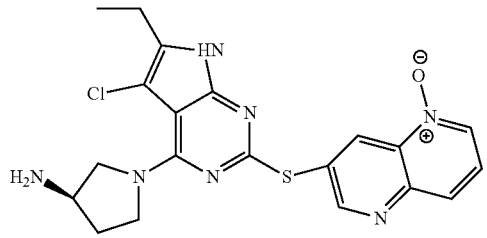

701008

(R)-7-(4-(3-aminopyrrolidin-1-yl)-5-chloro-6-ethyl-7H-pyrrolo[2,3-d]pyrimidin-2-ylthio)-1,5-naphthyridine 1-oxide

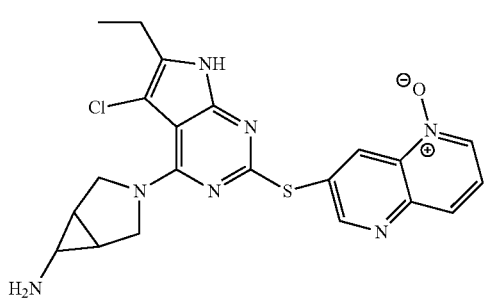

701009

7-(4-(6-amino-3-azabicyclo[3.1.0]hexan-3-yl)-5-chloro-6-ethyl-7H-pyrrolo[2,3-d]pyrimidin-2-ylthio)-1,5-naphthyridine 1-oxide Determination of Anti-Bacterial Efficacy Colonies of *H. influenzae, E. coli, S. aureus, A. baumannii, S. pneumoniae, P. aeruginosa*, and *B. thailandensis* were picked from o/n plates and resuspended in 3 ml DPBS solution. Absorbance was read at 600 nM and solutions were diluted to an OD of 0.1. Inoculums were added to appropriate growth media, and 98 ul of the mixture was plated into columns 1-11 of a 96 well flat-bottomed cell-culture plate. Column 12 was plated with media only. 2 uL of compound dilution series in 100% DMSO were added to columns 1-10. Plates were agitated in plate-shaker for 1 min. Mixtures of cells and media were diluted 1000× in DPBS and 100 uL was plated onto appropriate media and incubated o/n in order to count CFUs. Plates were incubated o/n at 35 C. *H. influenzae* and *S. pneumoniae* plates were incubated with 5% CO2. 10 uL of Alamar Blue (Invitrogen) was added to plates, and plates were agitated for 1 min in plate-shaker. Plates were incubated at 35 C for 1 h. Plates were read by eye, with any change in color from blue read as alive.

Table of Bacterial Strains and Media Used

| | | Resuspended Cells | Media |
|---|---|---|---|
| S. aureus | ATCC 13709 | 50 uL | 20 mL MHCA |
| SA + serum | ATCC 13709 | 50 uL | 16 mL MHCA + 4 mL mouse serum |
| S. pneumoniae | ATCC 51916 | 200 uL | 20 mL MHCA + 3% Laked Horse Blood |
| H. influenzae | ATCC 49247 | 50 uL | 20 mL haemophilus test media |
| E. coli 8 | ATCC 25922 | 100 uL | 20 mL MHCA |
| EC8 + serum | ATCC 25922 | 100 uL | 16 mL MHCA + 4 mL mouse serum |
| E. coli 9 | ATCC 35218 | 100 uL | 20 mL Mueller Hinton cationic adjusted |
| E. coli imp | Benson BAS849 | 100 uL | 20 mL MHCA |
| E. coli Δtolc | BW25113 Δtolc | 100 uL | 20 mL MHCA |
| B. thailandensis | ATCC E264 | 100 uL | 20 mL MHCA |
| P. aeruginosa | ATCC 15692 | 100 uL | 20 mL MHCA |
| A. baumannii | ATCC 19606 | 50 uL | 20 mL MHCA |

Antibacterial Potency MIC (μg/mL)

| compound | 701800 | 701008 | 701009 |
|---|---|---|---|
| S. aureus | ≤0.5 | ≤0.5 | ≤0.5 |
| S. aureus + serum* | 1 | ≤0.5 | ≤0.5 |
| S. pneumoniae | ≤0.5 | 1 | ≤0.5 |
| H. influenzae | 4 | 2 | 2 |
| E. coli (wt) | 4 | 4 | 2 |
| E. coli + serum* | 8 | 2 | 4 |
| E. coli (tolC)** | ≤0.5 | ≤0.5 | ≤0.5 |
| E. coli (Imp)*** | 1 | 1 | ≤0.5 |
| K. pneumoniae 11 | >64 | 32 | 32 |
| K. pneumoniae 101 | ≤0.5 | ≤0.5 | ≤0.5 |
| A. baumannii | 8 | 8 | 4 |
| P. aeruginosa (wt) | 8 | 16 | 4 |

Serum* = 20% mouse serum
tolC** = pump knock-out
Imp*** = permeability mutant

Table 2 illustrates various compounds' bacterial efficacy against S. aureus, S. pneumoniae and E. coli 8 by listing MIC (Minimum Inhibitory Concentration) data.

ATPase Enzymatic Assay

DNA gyrase B activities were determined by following the gyrase B-dependent release of inorganic phosphate from ATP hydrolysis and subsequent detection through use of a 7-methyl-6-thioguanosine/phosphorylase spectrophotometric assay. Assays were performed in 25 mM Tris-HCl buffer (pH 7.9), 5 mM $MgCl_2$, and 200 mM NaCl, 0.2 mM 7-methyl-6-thioguanosine, purine nucleoside phosphorylase (1 unit/mL), 0.4 mM ATP and various concentrations of the inhibitor compounds prepared in $Me_2SO$. The final $Me_2SO$ concentration in each reaction was 2%. The compounds were assayed against full length protein from Enterococcus faecalis and Acinetobacter baumannii. The concentration of enzyme in the assay ranged from 60 nM for E. faecalis full-length gyrase B to 200 nM for A. baumannii full-length Gyrase B. Reactions were initiated with the addition of ATP, and monitored at 360 nm at room temperature for 30 min.

ATPase Assay:

ATPase activities of all DNA Gyrase B and Topoisomerase IV parE were determined through use of a coupled spectrophotometric assay in which the enzyme-dependent release of inorganic phosphate from ATP hydrolysis is measured. The assay comprises between 20-100 nM GyrB or parE (active site concentrations) in 50 mM Tris-HCl buffer (pH 7.6), 2 mM $MgCl_2$, 125 mM NaCl, 0.2 mM 7-methyl-6-thioguanosine, 1 U/ml purine nucleoside phosphorylase. The reaction is initiated by addition of ATP between 0.5 and 4 mM ATP and monitored at 360 nm for 30 min at 27° C. Inhibitor potency is determined by incubating the target enzyme in the presence of various concentrations of inhibitor for 10 minutes prior to addition of substrate. The final concentration of DMSO is kept constant at 2.5% (v/v).

A wide range of wild-type and specific point-mutant full-length GyrB and parE enzyme were assayed, including, but not limited to, E. faecalis, S. aureus, E. coli, F. tularencis, A. baumanii, H. influenzae.

All enzymes were characterized for key kinetic parameter including $K_m$, $k_{cat}$ and active site concentrations using standard methodologies.

Kinetic analysis was carried out using GraphPad Prism version 4.00 for Windows, GraphPad Software, San Diego Calif. USA, on the world wide web at graphpad.com. $K_i$ values were determined through use of the tight-binding kinetic analysis described in Morrison et al, *Biochem. Biophys. Acta*, 1969, 185, 269-286.

| Rx ID | CHEMISTRY | |
|---|---|---|
| 700,075 | | Chemistry 0 |
| 700,076 | | Chemistry 1 |

| Rx ID | CHEMISTRY | |
|---|---|---|
| 700,077 | 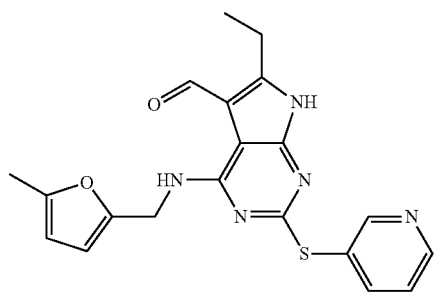 [SMILES: CCc1[nH]c2nc(Sc3cccnc3)nc(NCc3ccc(C)o3)c2c1C=O] | Chemistry 2 |
| 700,078 | 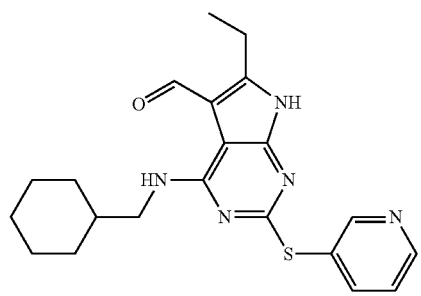 [SMILES: CCc1[nH]c2nc(Sc3cccnc3)nc(NCC3CCCCC3)c2c1C=O] | Chemistry 3 |
| 700,079 | 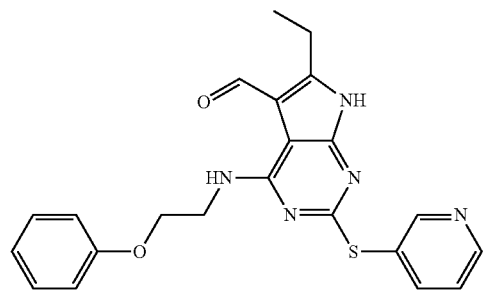 [SMILES: CCc1[nH]c2nc(Sc3cccnc3)nc(NCCOc3ccccc3)c2c1C=O] | Chemistry 4 |
| 700,080 | 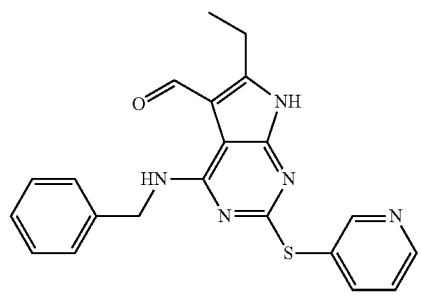 [SMILES: CCc1[nH]c2nc(Sc3cccnc3)nc(NCc3ccccc3)c2c1C=O] | Chemistry 5 |
| 700,081 | 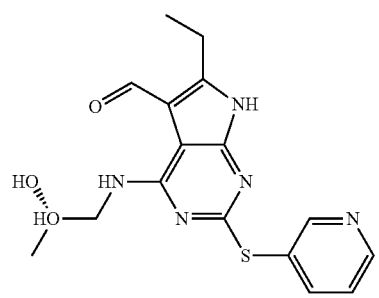 | Chemistry 6 |

-continued
| Rx ID | CHEMISTRY | |
|---|---|---|
| 700,082 | 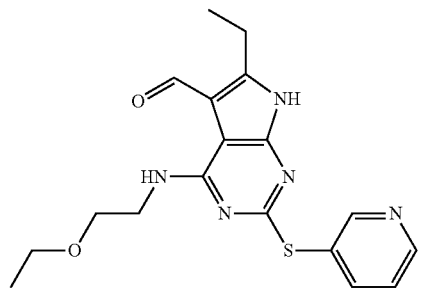 [SMILES: CCOCCNc1nc(Sc2cccnc2)nc2[nH]c(CC)c(C=O)c12] | Chemistry 7 |
| 700,083 | 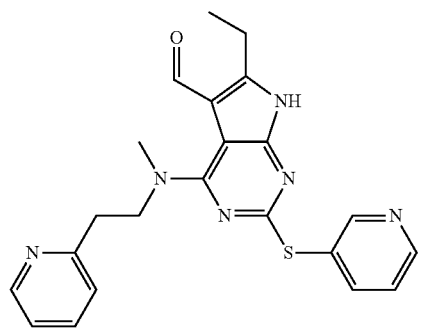 [SMILES: CCc1[nH]c2nc(Sc3cccnc3)nc(N(C)CCc3ccccn3)c2c1C=O] | Chemistry 8 |
| 700,084 | 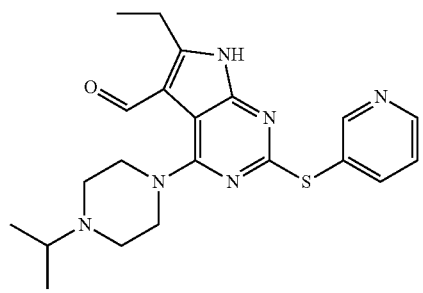 [SMILES: CCc1[nH]c2nc(Sc3cccnc3)nc(N3CCN(C(C)C)CC3)c2c1C=O] | Chemistry 9 |
| 700,085 | 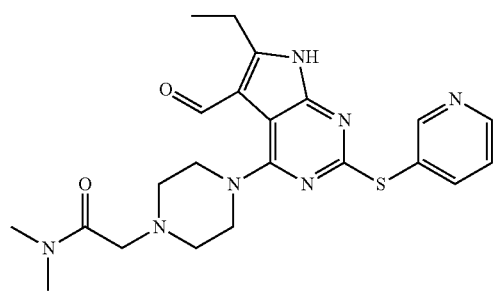 [SMILES: CCc1[nH]c2nc(Sc3cccnc3)nc(N3CCN(CC(=O)N(C)C)CC3)c2c1C=O] | Chemistry 10 |
| 700,088 | 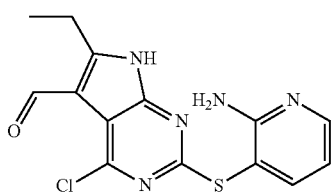 [SMILES: CCc1[nH]c2nc(Sc3cccnc3N)nc(Cl)c2c1C=O] | Chemistry 11 |

-continued
| Rx ID | CHEMISTRY | |
|---|---|---|
| 700,089 | 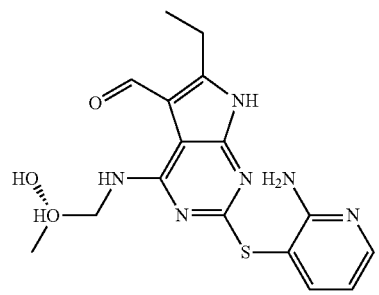 | Chemistry 12 |
| 700,090 | 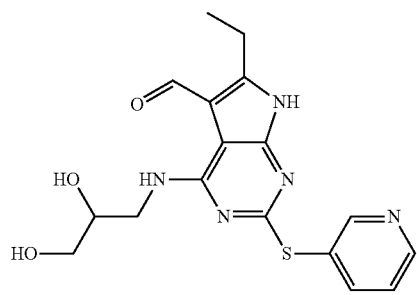 [SMILES: CCc1[nH]c2nc(Sc3cccnc3)nc(NCC(O)CO)c2c1C=O] | Chemistry 13 |
| 700,091 | 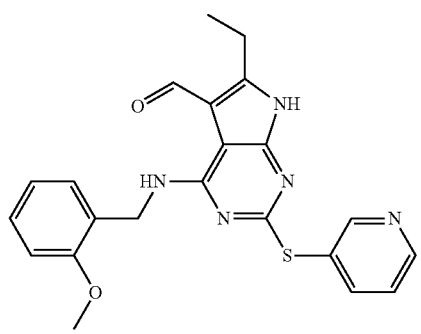 [SMILES: CCc1[nH]c2nc(Sc3cccnc3)nc(NCc3ccccc3OC)c2c1C=O] | Chemistry 14 |
| 700,092 | 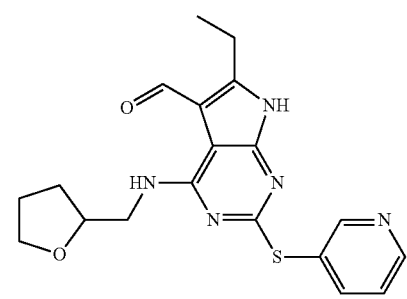 [SMILES: CCc1[nH]c2nc(Sc3cccnc3)nc(NCC3CCCO3)c2c1C=O] | Chemistry 15 |
| 700,093 | 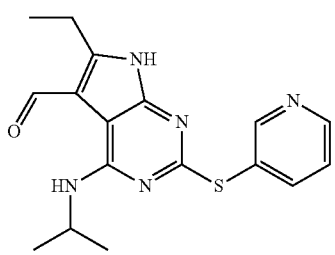 [SMILES: CCc1[nH]c2nc(Sc3cccnc3)nc(NC(C)C)c2c1C=O] | Chemistry 16 |

-continued
| Rx ID | CHEMISTRY | |
|---|---|---|
| 700,094 | 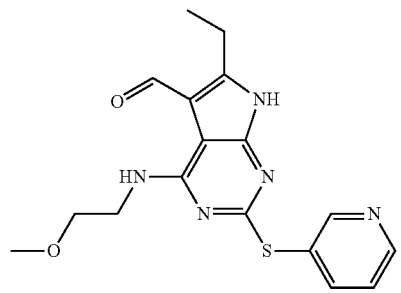 [SMILES: CCc1[nH]c2nc(Sc3cccnc3)nc(NCCOC)c2c1C=O] | Chemistry 17 |
| 700,095 | 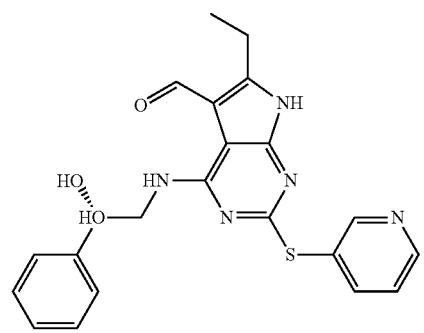 | Chemistry 18 |
| 700,096 | 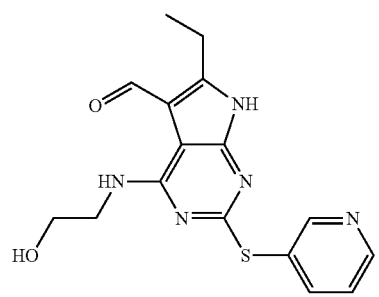 [SMILES: CCc1[nH]c2nc(Sc3cccnc3)nc(NCCO)c2c1C=O] | Chemistry 19 |
| 700,098 | 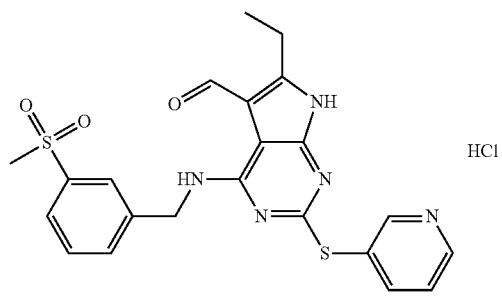 [SMILES: CCc1[nH]c2nc(Sc3cccnc3)nc(NCc3cccc(S(C)(=O)=O)c3)c2c1C=O ; Cl] HCl | Chemistry 20 |
| 700,099 | 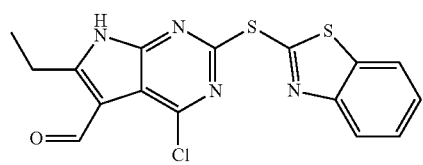 [SMILES: CCc1[nH]c2nc(Sc3nc4ccccc4s3)nc(Cl)c2c1C=O] | Chemistry 21 |

| Rx ID | CHEMISTRY | |
|---|---|---|
| 700,100 | 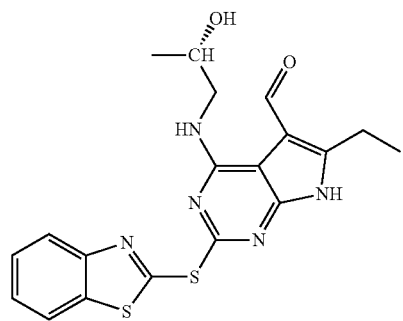 [SMILES: CCc1[nH]c2nc(Sc3nc4ccccc4s3)nc(NC[C@H](C)O)c2c1C=O] | Chemistry 22 |
| 700,101 | 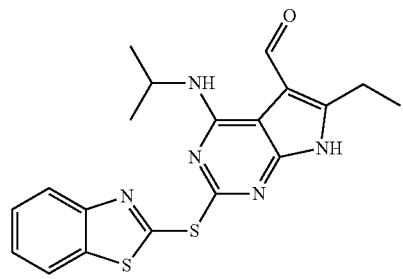 [SMILES: CCc1[nH]c2nc(Sc3nc4ccccc4s3)nc(NC(C)C)c2c1C=O] | Chemistry 23 |
| 700,102 | 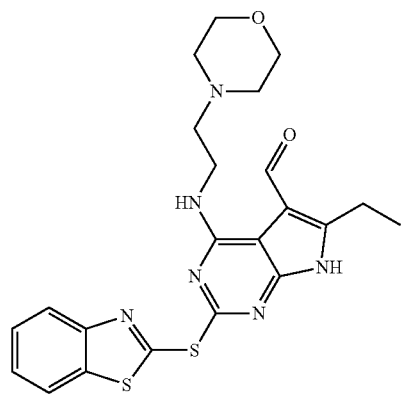 [SMILES: CCc1[nH]c2nc(Sc3nc4ccccc4s3)nc(NCCN3CCOCC3)c2c1C=O] | Chemistry 24 |
| 700,103 | 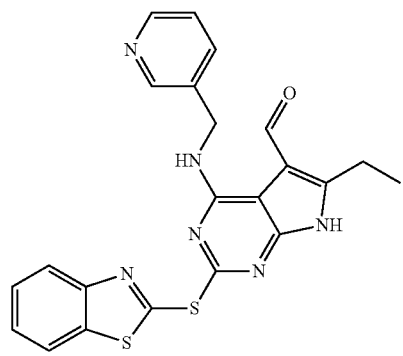 [SMILES: CCc1[nH]c2nc(Sc3nc4ccccc4s3)nc(NCc3cccnc3)c2c1C=O] | Chemistry 25 |

| Rx ID | CHEMISTRY | |
|---|---|---|
| 700,104 | 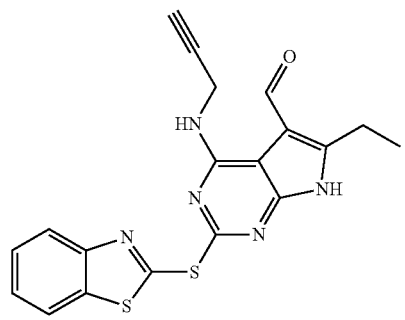 [SMILES: C#CCNc1nc(Sc2nc3ccccc3s2)nc2[nH]c(CC)c(C=O)c12] | Chemistry 26 |
| 700,105 | 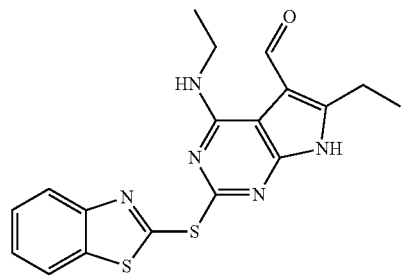 [SMILES: CCNc1nc(Sc2nc3ccccc3s2)nc2[nH]c(CC)c(C=O)c12] | Chemistry 27 |
| 700,106 | 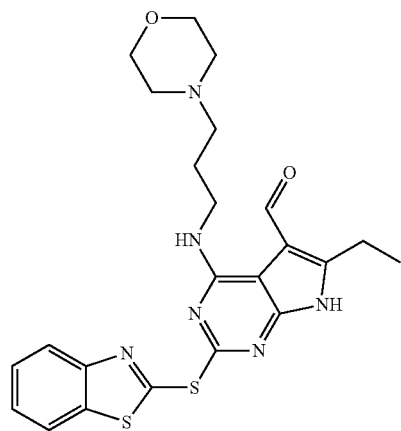 [SMILES: CCc1[nH]c2nc(Sc3nc4ccccc4s3)nc(NCCCN3CCOCC3)c2c1C=O] | Chemistry 28 |
| 700,107 | 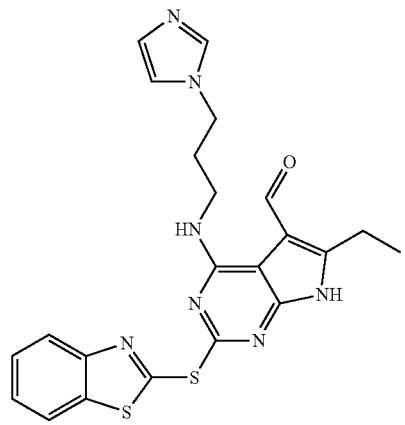 [SMILES: CCc1[nH]c2nc(Sc3nc4ccccc4s3)nc(NCCCn3ccnc3)c2c1C=O] | Chemistry 29 |

-continued
| Rx ID | CHEMISTRY | |
|---|---|---|
| 700,108 | 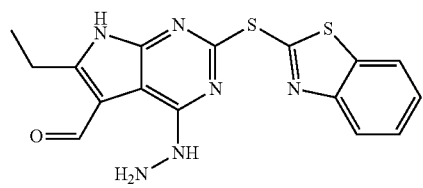 [SMILES: CCc1[nH]c2nc(Sc3nc4ccccc4s3)nc(NN)c2c1C=O] | Chemistry 30 |
| 700,109 | 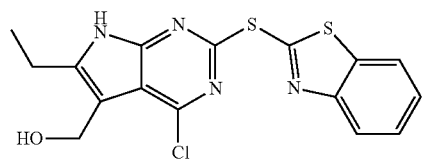 [SMILES: CCc1[nH]c2nc(Sc3nc4ccccc4s3)nc(Cl)c2c1CO] | Chemistry 31 |
| 700,118 | 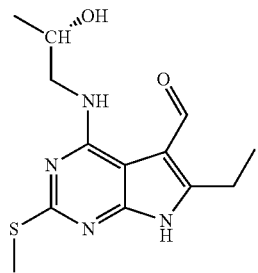 [SMILES: CCc1[nH]c2nc(SC)nc(NC[C@H](C)O)c2c1C=O] | Chemistry 32 |
| 700,119 | 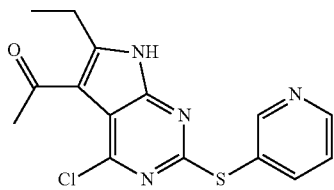 [SMILES: CCc1[nH]c2nc(Sc3cccnc3)nc(Cl)c2c1C(C)=O] | Chemistry 33 |
| 700,120 | 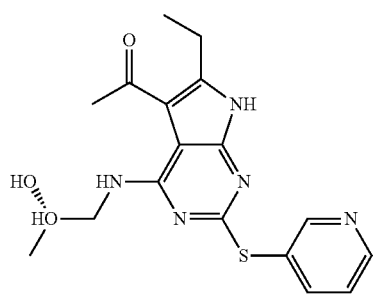 | Chemistry 34 |
| 700,121 | 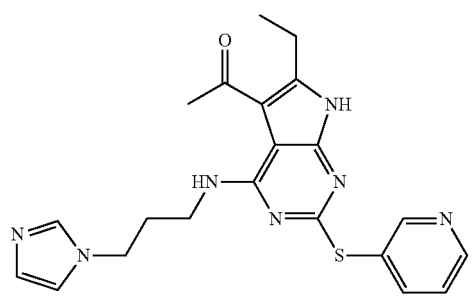 [SMILES: CCc1[nH]c2nc(Sc3cccnc3)nc(NCCCn3ccnc3)c2c1C(C)=O] | Chemistry 35 |

| Rx ID | CHEMISTRY | |
|---|---|---|
| 700,122 | 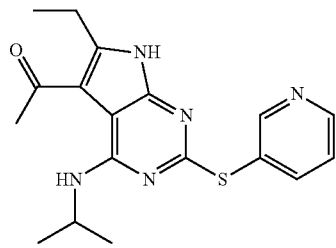 [SMILES: CCc1[nH]c2nc(Sc3cccnc3)nc(NC(C)C)c2c1C(C)=O] | Chemistry 36 |
| 700,127 | 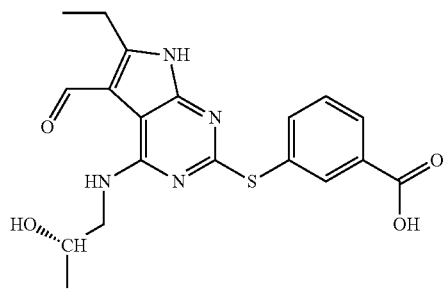 [SMILES: CCc1[nH]c2nc(Sc3cccc(C(=O)O)c3)nc(NC[C@H](C)O)c2c1C=O] | Chemistry 37 |
| 700,128 | 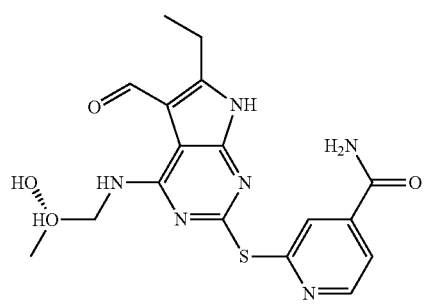 | Chemistry 38 |
| 700,129 | 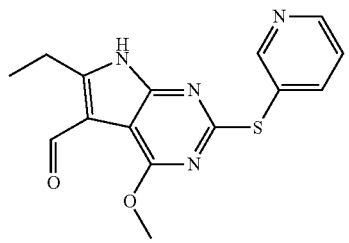 [SMILES: CCc1[nH]c2nc(Sc3cccnc3)nc(OC)c2c1C=O] | Chemistry 39 |
| 700,130 | 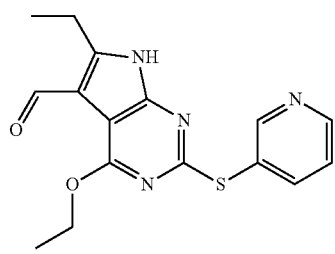 [SMILES: CCOc1nc(Sc2cccnc2)nc2[nH]c(CC)c(C=O)c12] | Chemistry 40 |

| Rx ID | CHEMISTRY | |
|---|---|---|
| 700,133 | 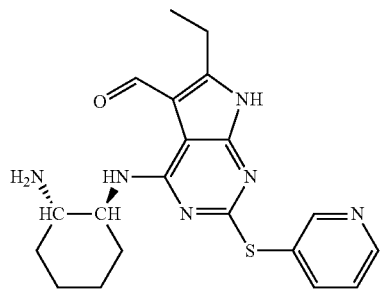 [SMILES: CCc1[nH]c2nc(Sc3cccnc3)nc(N[C@H]3CCCC[C@@H]3N)c2c1C=O] | Chemistry 41 |
| 700,135 | 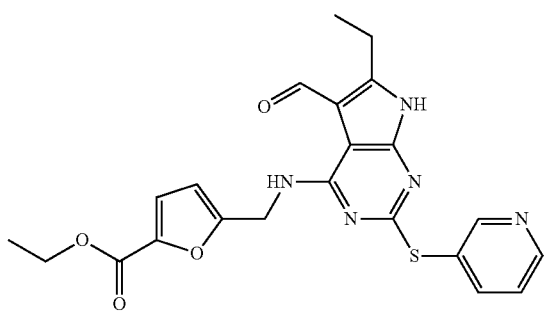 [SMILES: CCOC(=O)c1ccc(CNc2nc(Sc3cccnc3)nc3[nH]c(CC)c(C=O)c23)o1] | Chemistry 42 |
| 700,136 | 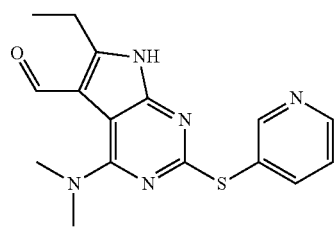 [SMILES: CCc1[nH]c2nc(Sc3cccnc3)nc(N(C)C)c2c1C=O] | Chemistry 43 |
| 700,137 | 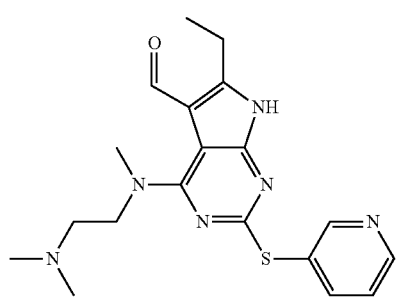 [SMILES: CCc1[nH]c2nc(Sc3cccnc3)nc(N(C)CCN(C)C)c2c1C=O] | Chemistry 44 |
| 700,138 | 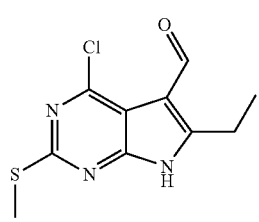 [SMILES: CCc1[nH]c2nc(SC)nc(Cl)c2c1C=O] | Chemistry 45 |

-continued
| Rx ID | CHEMISTRY | |
|---|---|---|
| 700,139 | 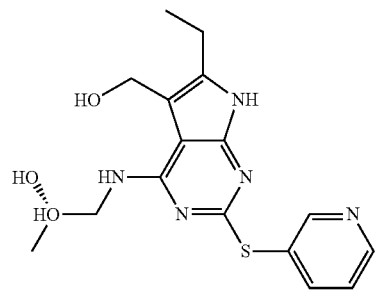 | Chemistry 46 |
| 700,140 | 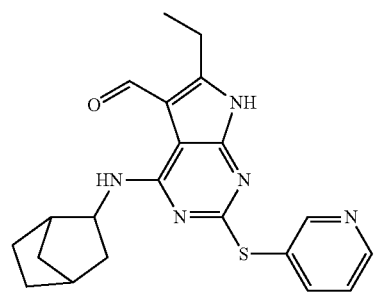 [SMILES: CCc1[nH]c2nc(Sc3cccnc3)nc(NC3CC4CCC3C4)c2c1C=O] | Chemistry 47 |
| 700,141 | 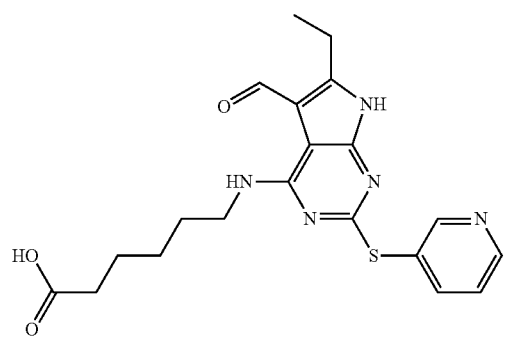 [SMILES: CCc1[nH]c2nc(Sc3cccnc3)nc(NCCCCCC(=O)O)c2c1C=O] | Chemistry 48 |
| 700,142 | 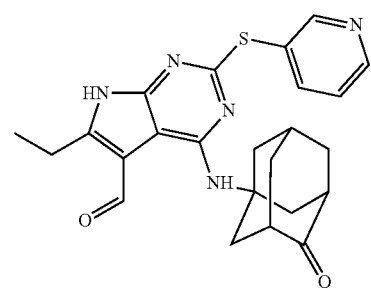 [SMILES: CCc1[nH]c2nc(Sc3cccnc3)nc(NC34CC5CC(C3)C(=O)C(C5)C4)c2c1C=O] | Chemistry 49 |
| 700,143 | 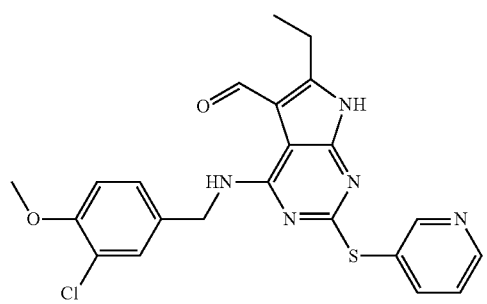 [SMILES: CCc1[nH]c2nc(Sc3cccnc3)nc(NCc3ccc(OC)c(Cl)c3)c2c1C=O] | Chemistry 50 |

| Rx ID | CHEMISTRY | |
|---|---|---|
| 700,144 | 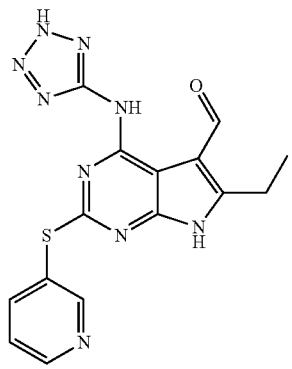 [SMILES: CCc1[nH]c2nc(Sc3cccnc3)nc(Nc3nn[nH]n3)c2c1C=O] | Chemistry 53 |
| 700,145 | 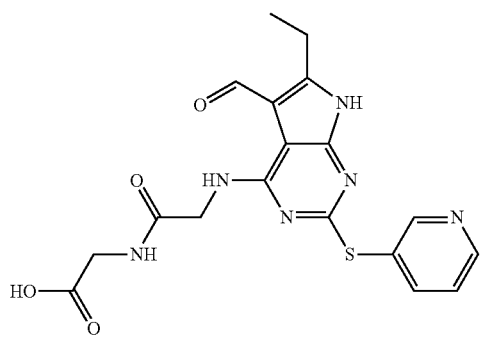 [SMILES: CCc1[nH]c2nc(Sc3cccnc3)nc(NCC(=O)NCC(=O)O)c2c1C=O] | Chemistry 52 |
| 700,146 | 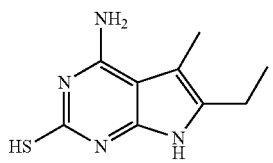 | Chemistry 53 |
| 700,147 | 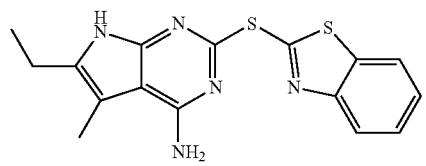 [SMILES: CCc1[nH]c2nc(Sc3nc4ccccc4s3)nc(N)c2c1C] | Chemistry 54 |
| 700,148 | 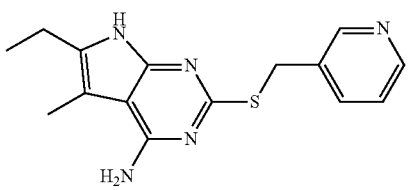 [SMILES: CCc1[nH]c2nc(SCc3cccnc3)nc(N)c2c1C] | Chemistry 55 |
| 700,149 | 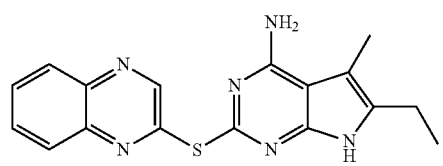 [SMILES: CCc1[nH]c2nc(Sc3cnc4ccccc4n3)nc(N)c2c1C] | Chemistry 56 |
| 700,150 | 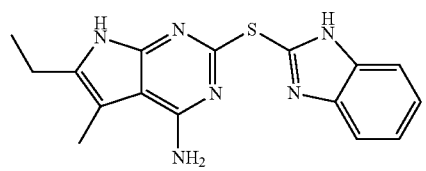 [SMILES: CCc1[nH]c2nc(Sc3nc4ccccc4[nH]3)nc(N)c2c1C] | Chemistry 57 |

-continued

| Rx ID | CHEMISTRY | |
|---|---|---|
| 700,151 | | Chemistry 58 |
| 700,152 | | Chemistry 59 |
| 700,153 | | Chemistry 60 |
| 700,154 | | Chemistry 61 |
| 700,155 | | Chemistry 62 |
| 700,156 | | Chemistry 63 |
| 700,157 | | Chemistry 64 |

| Rx ID | CHEMISTRY | |
|---|---|---|
| 700,158 | 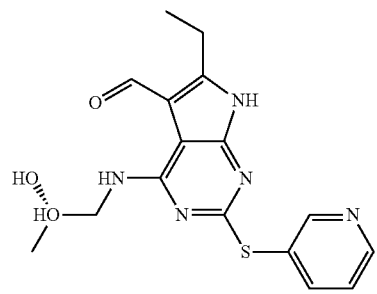 | Chemistry 65 |
| 700,159 | 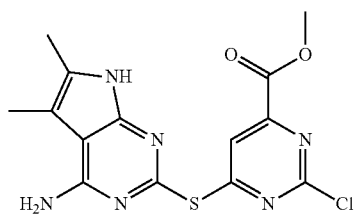 [SMILES: COC(=O)c1cc(Sc2nc(N)c3c(C)c(C)[nH]c3n2)nc(Cl)n1] | Chemistry 66 |
| 700,160 | 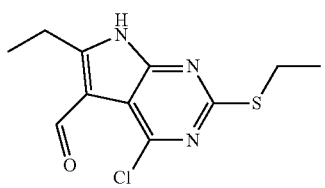 [SMILES: CCSc1nc(Cl)c2c(C=O)c(CC)[nH]c2n1] | Chemistry 67 |
| 700,244 | 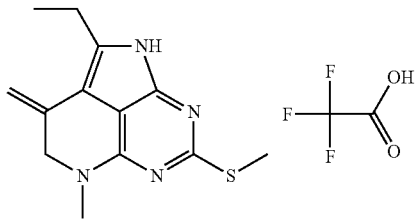 | Chemistry 68 |
| 700,246 | 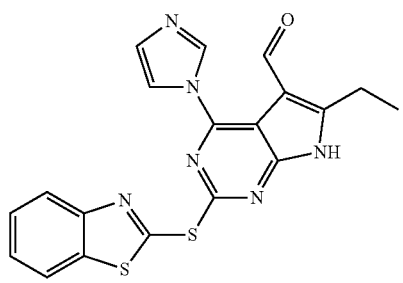 [SMILES: CCc1[nH]c2nc(Sc3nc4ccccc4s3)nc(-n3ccnc3)c2c1C=O] | Chemistry 69 |
| 700,261 | 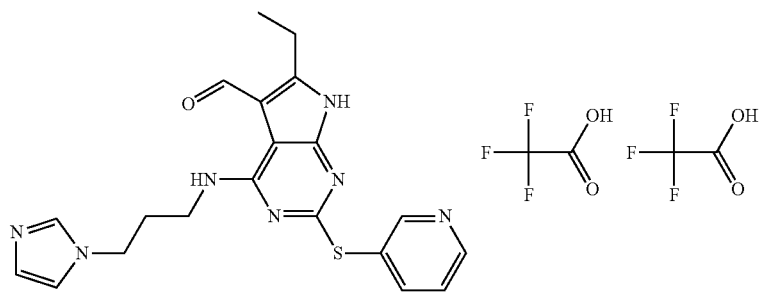 | Chemistry 70 |

| Rx ID | CHEMISTRY | |
|---|---|---|
| 700,287 | 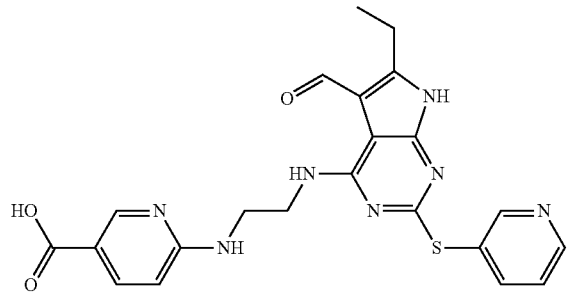 [SMILES: CCc1[nH]c2nc(Sc3cccnc3)nc(NCCNc3ccc(C(=O)O)cn3)c2c1C=O] | Chemistry 71 |
| 700,351 | 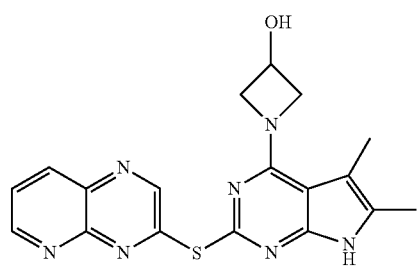 [SMILES: Cc1[nH]c2nc(Sc3cnc4cccnc4n3)nc(N3CC(O)C3)c2c1C] | Chemistry 72 |
| 700,654 | 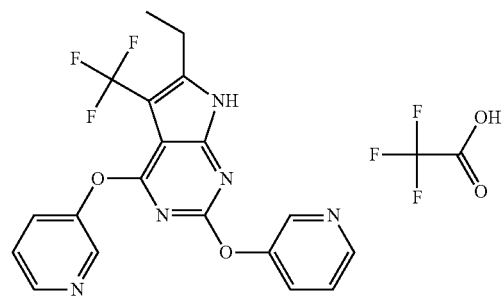 [SMILES: CCc1[nH]c2nc(Oc3cccnc3)nc(Oc3cccnc3)c2c1C(F)(F)F ; O=C(O)C(F)(F)F] | Chemistry 73 |
| 701,077 | 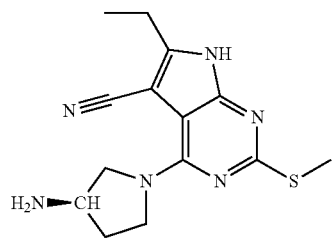 [SMILES: CCc1[nH]c2nc(SC)nc(N3CC[C@@H](N)C3)c2c1C#N] | Chemistry 74 |
| 7,011,092 | 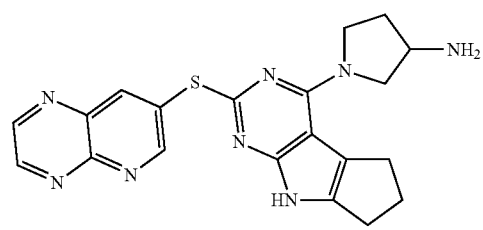 [SMILES: NC1CCN(c2nc(Sc3cnc4nccnc4c3)nc3[nH]c4c(c23)CCC4)C1] | Chemistry 77 |

-continued
| Rx ID | CHEMISTRY | |
|---|---|---|
| 701,117 | 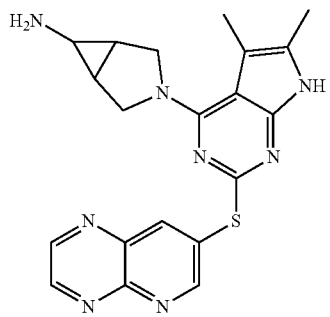 [SMILES: Cc1[nH]c2nc(Sc3cnc4nccnc4c3)nc(N3CC4C(N)C4C3)c2c1C] | Chemistry 79 |
| 701,143 | 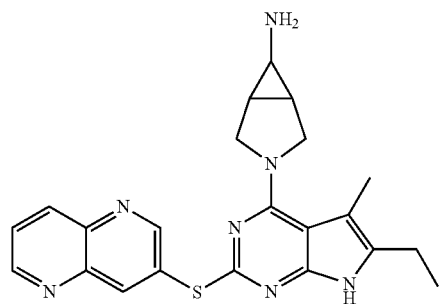 [SMILES: CCc1[nH]c2nc(Sc3cnc4cccnc4c3)nc(N3CC4C(N)C4C3)c2c1C] | Chemistry 80 |
| 701,153 | 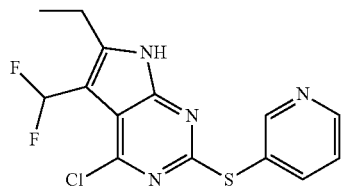 [SMILES: CCc1[nH]c2nc(Sc3cccnc3)nc(Cl)c2c1C(F)F] | Chemistry 81 |
| 701,156 | 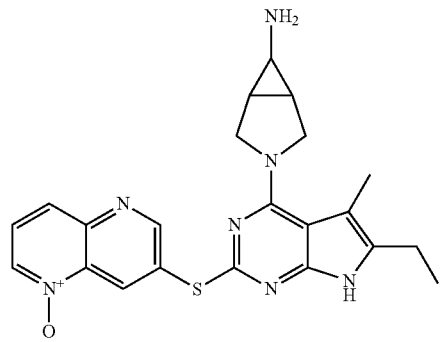 [SMILES: CCc1[nH]c2nc(Sc3cnc4ccc[n+](O)c4c3)nc(N3CC4C(N)C4C3)c2c1C] | Chemistry 82 |
| 701,157 | 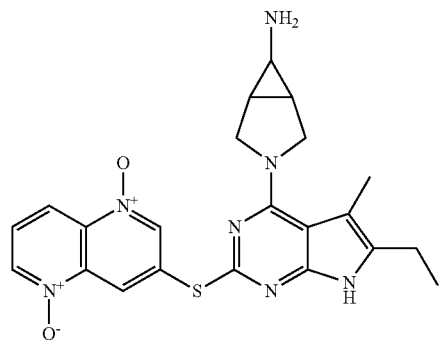 [SMILES: CCc1[nH]c2nc(Sc3cc4c(ccc[n+]4[O-])[n+](O)c3)nc(N3CC4C(N)C4C3)c2c1C] | Chemistry 83 |

| Rx ID | CHEMISTRY | |
|---|---|---|
| 701,162 | 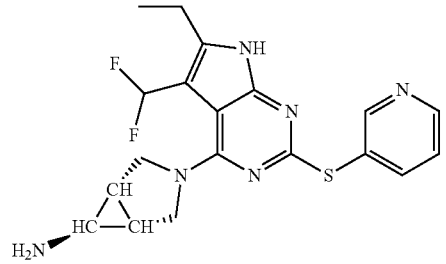 [SMILES: CCc1[nH]c2nc(Sc3cccnc3)nc(N3C[C@@H]4[C@@H](N)[C@@H]4C3)c2c1C(F)F] | Chemistry 84 |
| 701,161 | 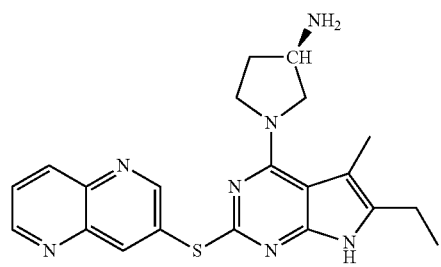 [SMILES: CCc1[nH]c2nc(Sc3cnc4cccnc4c3)nc(N3CC[C@@H](N)C3)c2c1C] | Chemistry 85 |
| 701,182 | 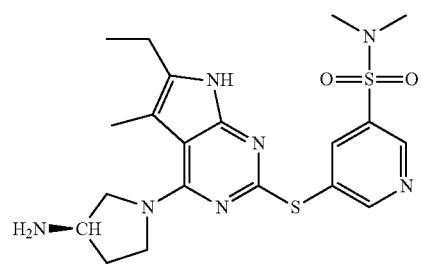 [SMILES: CCc1[nH]c2nc(Sc3cncc(S(=O)(=O)N(C)C)c3)nc(N3CC[C@@H](N)C3)c2c1C] | Chemistry 86 |
| 701,183 | 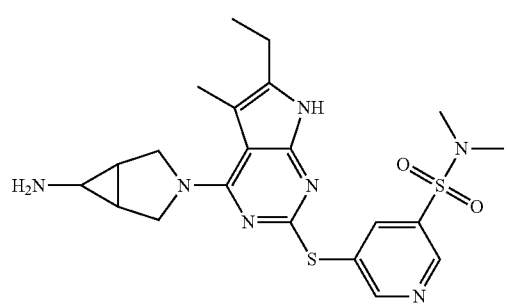 | Chemistry 87 |
| 701,193 | 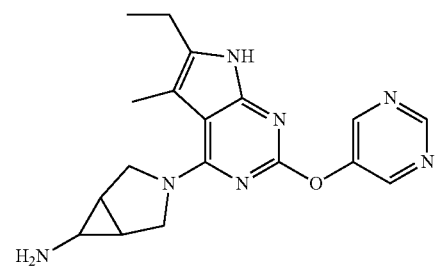 [SMILES: CCc1[nH]c2nc(Oc3cncnc3)nc(N3CC4C(N)C4C3)c2c1C] | Chemistry 88 |

-continued
| Rx ID | CHEMISTRY | |
|---|---|---|
| 701,233 | 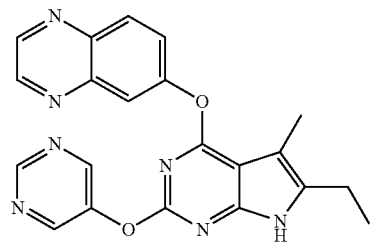 [SMILES: CCc1[nH]c2nc(Oc3cncnc3)nc(Oc3ccc4nccnc4c3)c2c1C] | Chemistry 89 |
| 701,239 | 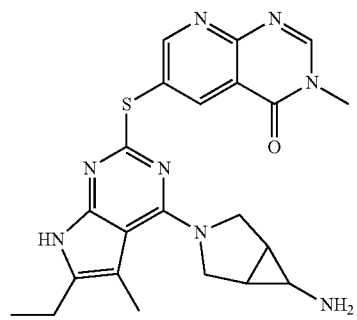 [SMILES: CCc1[nH]c2nc(Sc3cnc4ncn(C)c(=O)c4c3)nc(N3CC4C(N)C4C3)c2c1C] | Chemistry 90 |
| 701,292 | 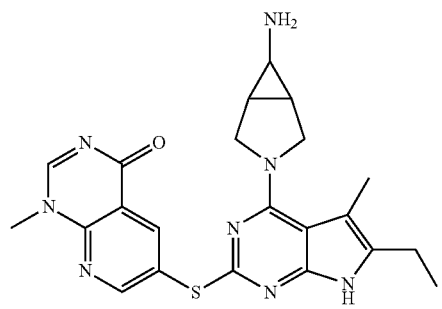 | Chemistry 91 |
| 700,131 | 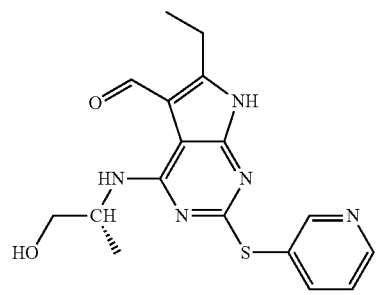 [SMILES: CCc1[nH]c2nc(Sc3cccnc3)nc(N[C@H](C)CO)c2c1C=O] | Chemistry 92 |
| 700,132 | 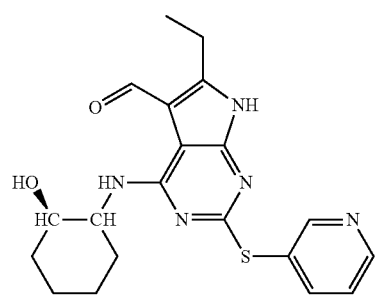 [SMILES: CCc1[nH]c2nc(Sc3cccnc3)nc(NC3CCCC[C@H]3O)c2c1C=O] | Chemistry 93 |

| Rx ID | CHEMISTRY | |
|---|---|---|
| 700,220 | 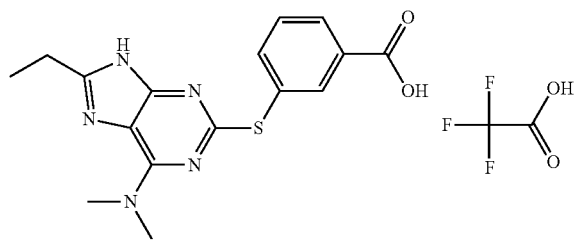 | |
| 700,538 | 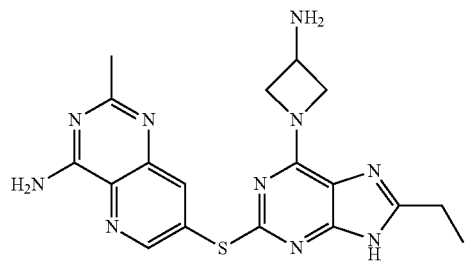 [SMILES: CCc1nc2c(N3CC(N)C3)nc(Sc3cnc4c(N)nc(C)nc4c3)nc2[nH]1] | |
| 700,280 | 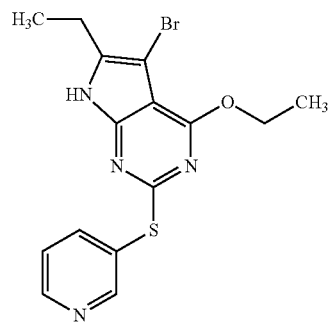 [SMILES: CCOc1nc(Sc2cccnc2)nc2[nH]c(CC)c(Br)c12] | |
| 700,241 | 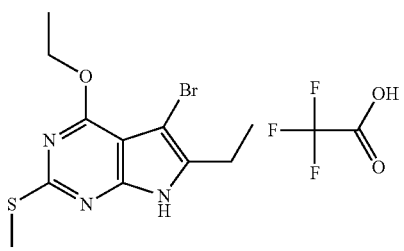 | Chemistry 0 |
| 700,267 | 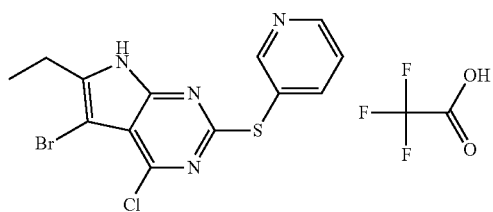 | Chemistry 1 |
| 700,269 | 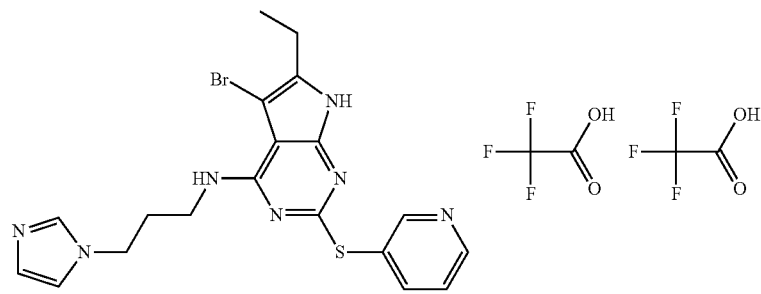 | Chemistry 2 |

| Rx ID | CHEMISTRY | |
|---|---|---|
| 700,270 | 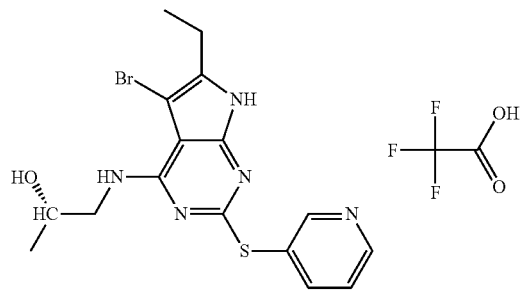 [SMILES: CCc1[nH]c2nc(Sc3cccnc3)nc(NC[C@H](C)O)c2c1Br ; O=C(O)C(F)(F)F] | Chemistry 3 |
| 700,271 | 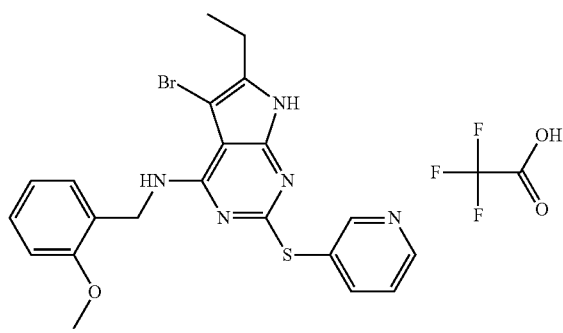 [SMILES: CCc1[nH]c2nc(Sc3cccnc3)nc(NCc3ccccc3OC)c2c1Br ; O=C(O)C(F)(F)F] | Chemistry 4 |
| 700,275 | 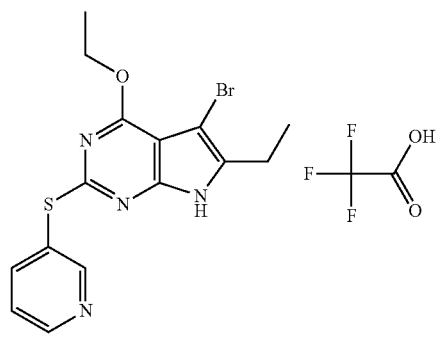 | Chemistry 5 |
| 700,281 | 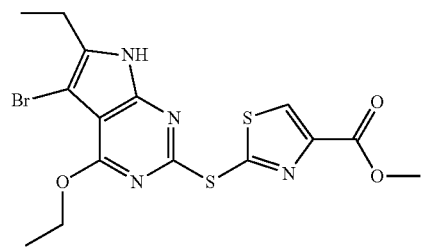 [SMILES: CCOc1nc(Sc2nc(C(=O)OC)cs2)nc2[nH]c(CC)c(Br)c12] | Chemistry 6 |
| 700,282 | 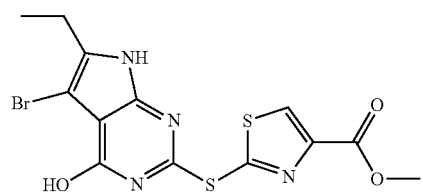 | Chemistry 7 |

| Rx ID | CHEMISTRY | |
|---|---|---|
| 700,286 | 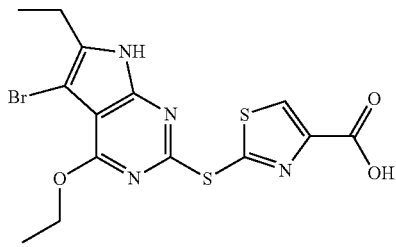 | Chemistry 8 |
| 700,288 | 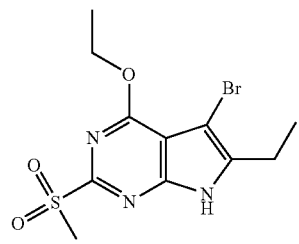 [SMILES: CCOc1nc(S(C)(=O)=O)nc2[nH]c(CC)c(Br)c12] | Chemistry 9 |
| 700,290 | 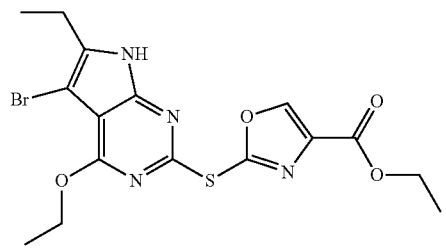 [SMILES: CCOC(=O)c1coc(Sc2nc(OCC)c3c(Br)c(CC)[nH]c3n2)n1] | Chemistry 10 |
| 700,291 | 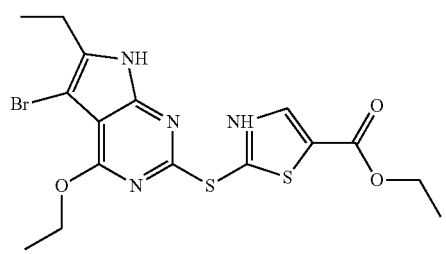 [SMILES: CCOC(=O)c1cnc(Sc2nc(OCC)c3c(Br)c(CC)[nH]c3n2)s1] | Chemistry 11 |
| 700,292 | 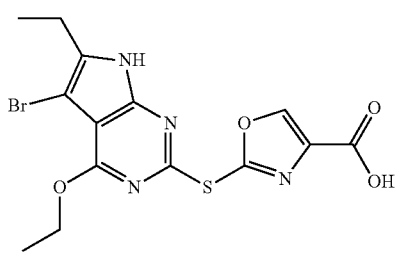 [SMILES: CCOc1nc(Sc2nc(C(=O)O)co2)nc2[nH]c(CC)c(Br)c12] | Chemistry 12 |
| 700,293 | 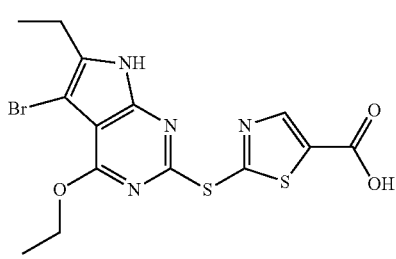 [SMILES: CCOc1nc(Sc2ncc(C(=O)O)s2)nc2[nH]c(CC)c(Br)c12] | Chemistry 13 |

| Rx ID | CHEMISTRY | |
|---|---|---|
| 700,294 | 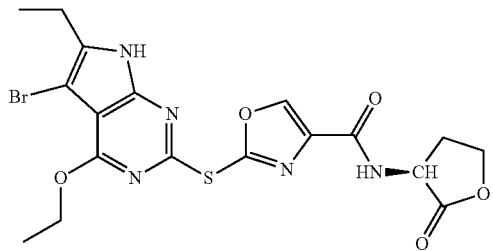 [SMILES: CCOc1nc(Sc2nc(C(=O)N[C@H]3CCOC3=O)co2)nc2[nH]c(CC)c(Br)c12] | Chemistry 14 |
| 700,295 | 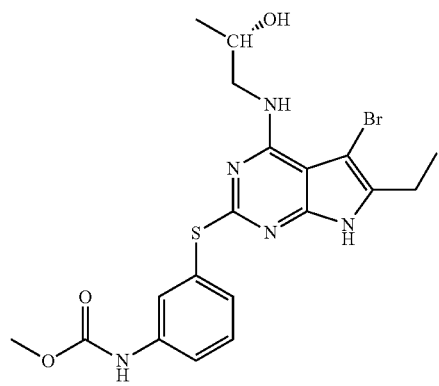 [SMILES: CCc1[nH]c2nc(Sc3cccc(NC(=O)OC)c3)nc(NC[C@H](C)O)c2c1Br] | Chemistry 15 |
| 700,296 | 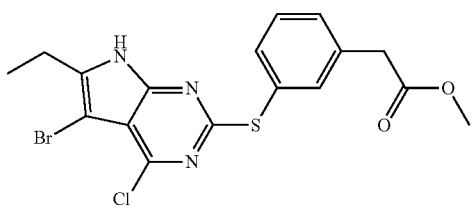 [SMILES: CCc1[nH]c2nc(Sc3cccc(CC(=O)OC)c3)nc(Cl)c2c1Br] | Chemistry 16 |
| 700,297 | 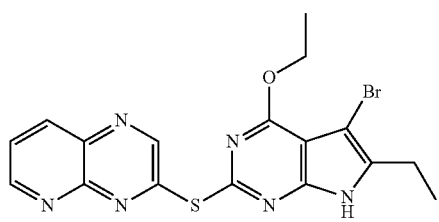 | Chemistry 17 |
| 700,301 | 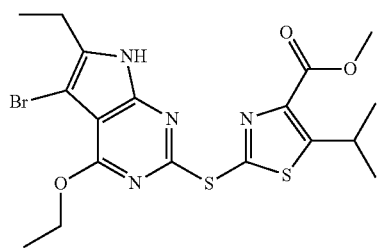 | Chemistry 18 |
| 700,303 | 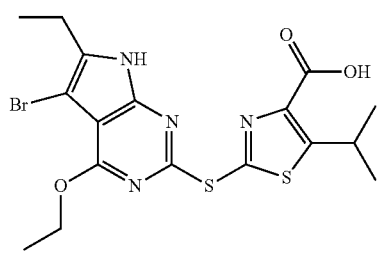 [SMILES: CCOc1nc(Sc2nc(C(=O)O)c(C(C)C)s2)nc2[nH]c(CC)c(Br)c12] | Chemistry 19 |

| Rx ID | CHEMISTRY | |
|---|---|---|
| 700,305 | 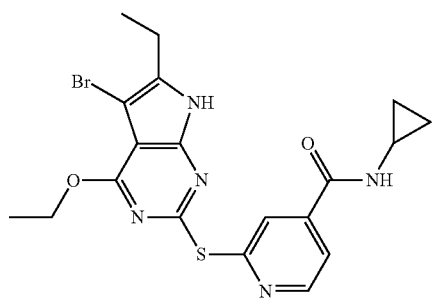 | Chemistry 20 |
| 700,307 | 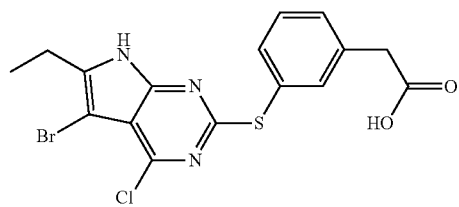 [SMILES: CCc1[nH]c2nc(Sc3cccc(CC(=O)O)c3)nc(Cl)c2c1Br] | Chemistry 21 |
| 700,315 | 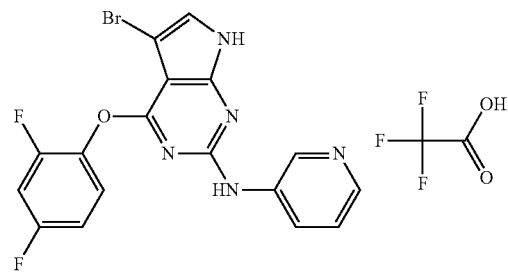 | Chemistry 22 |
| 700,331 | 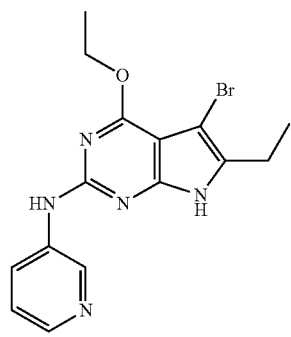 [SMILES: CCOc1nc(Nc2cccnc2)nc2[nH]c(CC)c(Br)c12] | Chemistry 23 |
| 700,332 | 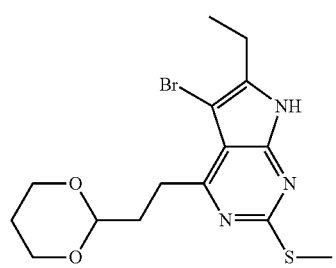 [SMILES: CCc1[nH]c2nc(SC)nc(CCC3OCCCO3)c2c1Br] | Chemistry 24 |

-continued
| Rx ID | CHEMISTRY | |
|---|---|---|
| 700,333 | 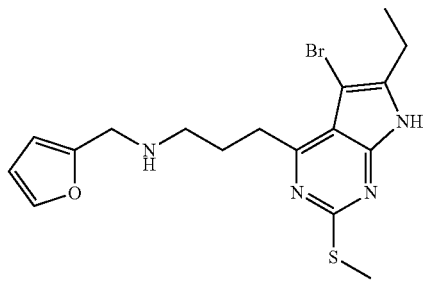 [SMILES: CCc1[nH]c2nc(SC)nc(CCCNCc3ccco3)c2c1Br] | Chemistry 25 |
| 700,334 | 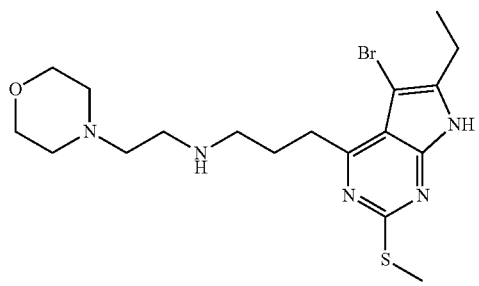 [SMILES: CCc1[nH]c2nc(SC)nc(CCCNCCN3CCOCC3)c2c1Br] | Chemistry 26 |
| 700,346 | 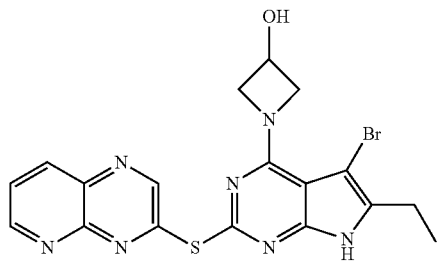 | Chemistry 27 |
| 700,350 | 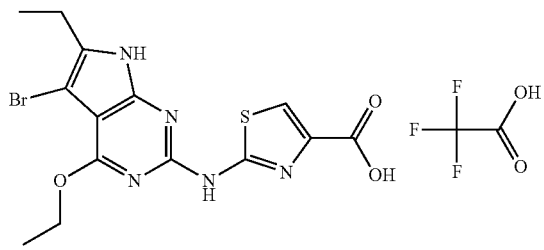 | Chemistry 28 |
| 700,354 | 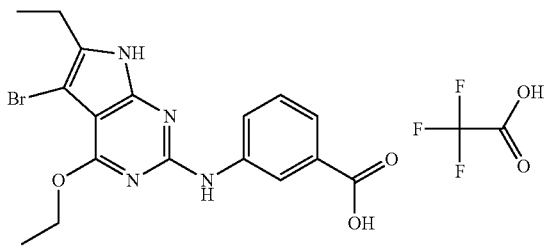 | Chemistry 29 |
| 700,358 | 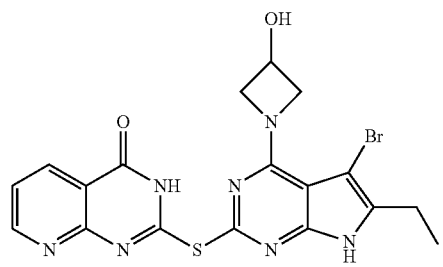 [SMILES: CCc1[nH]c2nc(Sc3nc4ncccc4c(=O)[nH]3)nc(N3CC(O)C3)c2c1Br] | Chemistry 30 |

-continued
| Rx ID | CHEMISTRY | |
|---|---|---|
| 700,360 | 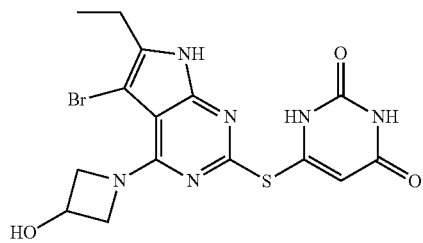 [SMILES: CCc1[nH]c2nc(Sc3cc(=O)[nH]c(=O)[nH]3)nc(N3CC(O)C3)c2c1Br] | Chemistry 31 |
| 700,362 | 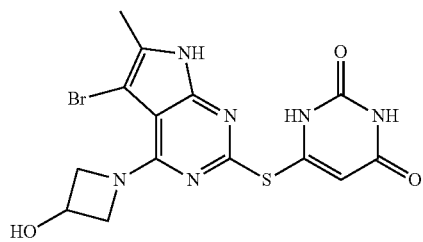 [SMILES: Cc1[nH]c2nc(Sc3cc(=O)[nH]c(=O)[nH]3)nc(N3CC(O)C3)c2c1Br] | Chemistry 32 |
| 700,363 | 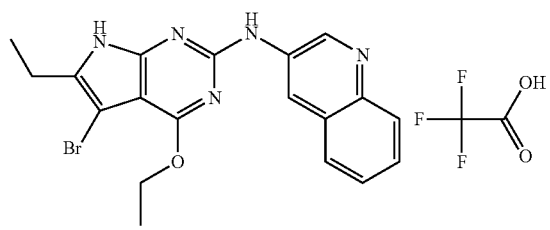 | Chemistry 33 |
| 700,374 | 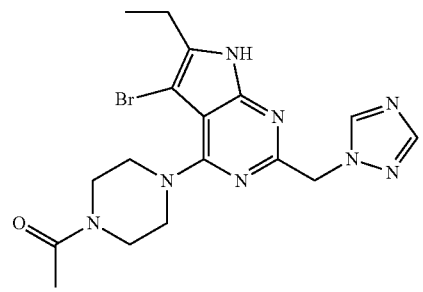 [SMILES: CCc1[nH]c2nc(Cn3cncn3)nc(N3CCN(C(C)=O)CC3)c2c1Br] | Chemistry 34 |
| 700,378 | 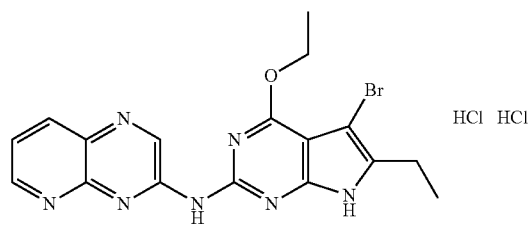 [SMILES: CCOc1nc(Nc2cnc3cccnc3n2)nc2[nH]c(CC)c(Br)c12 ; Cl ; Cl] | Chemistry 35 |
| 700,388 | 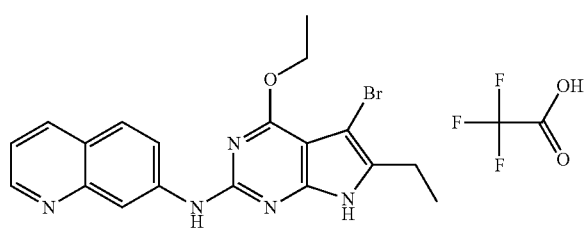 | Chemistry 36 |

-continued
| Rx ID | CHEMISTRY | |
|---|---|---|
| 700,381 | 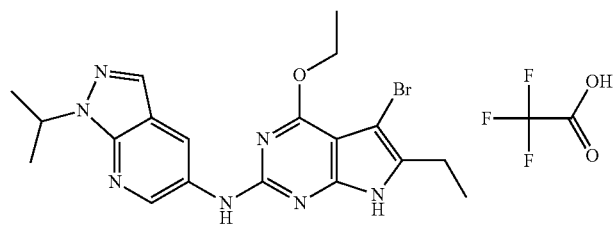 | Chemistry 37 |
| 700,385 | 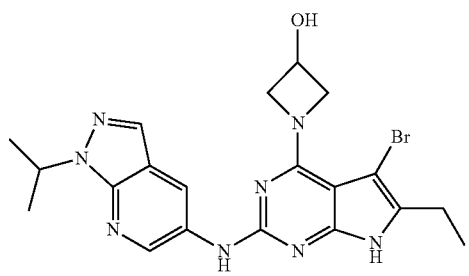 [SMILES: CCc1[nH]c2nc(Nc3cnc4c(cnn4C(C)C)c3)nc(N3CC(O)C3)c2c1Br] | Chemistry 38 |
| 700,386 | 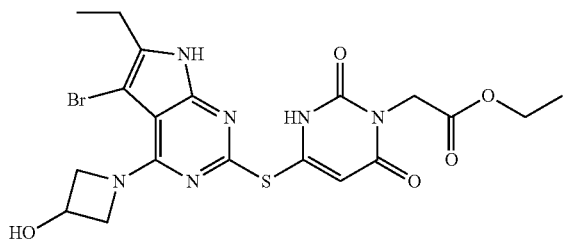 [SMILES: CCOC(=O)Cn1c(=O)cc(Sc2nc(N3CC(O)C3)c3c(Br)c(CC)[nH]c3n2)[nH]c1=O] | Chemistry 39 |
| 700,389 | 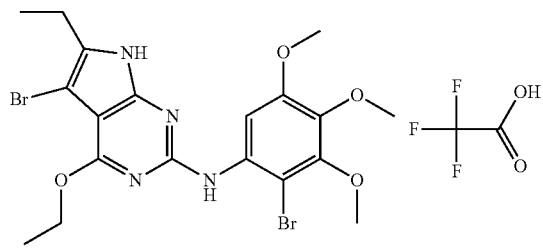 | Chemistry 40 |
| 700,390 | 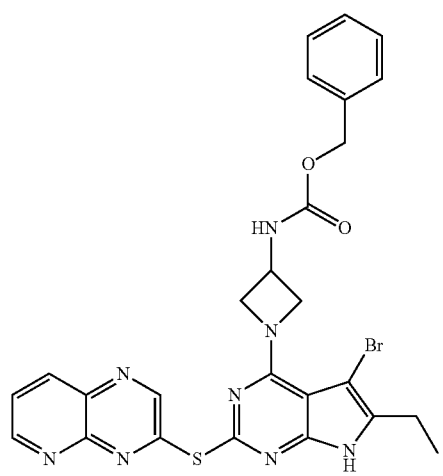 [SMILES: CCc1[nH]c2nc(Sc3cnc4cccnc4n3)nc(N3CC(NC(=O)OCc4ccccc4)C3)c2c1Br] | Chemistry 41 |

| Rx ID | CHEMISTRY | |
|---|---|---|
| 700,391 | 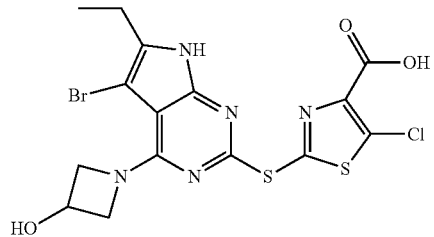 [SMILES: CCc1[nH]c2nc(Sc3nc(C(=O)O)c(Cl)s3)nc(N3CC(O)C3)c2c1Br] | Chemistry 42 |
| 700,392 | 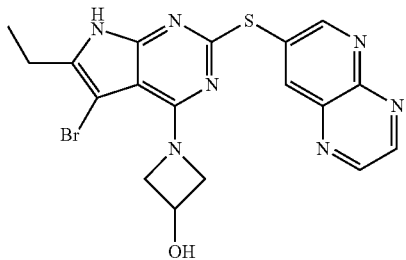 [SMILES: CCc1[nH]c2nc(Sc3cnc4nccnc4c3)nc(N3CC(O)C3)c2c1Br] | Chemistry 43 |
| 700,402 | 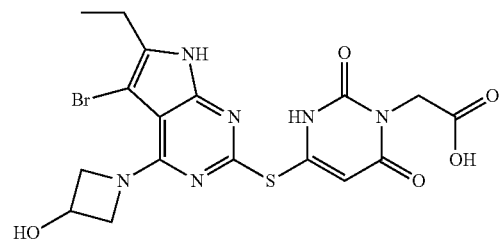 [SMILES: CCc1[nH]c2nc(Sc3cc(=O)n(CC(=O)O)c(=O)[nH]3)nc(N3CC(O)C3)c2c1Br] | Chemistry 44 |
| 700,403 | 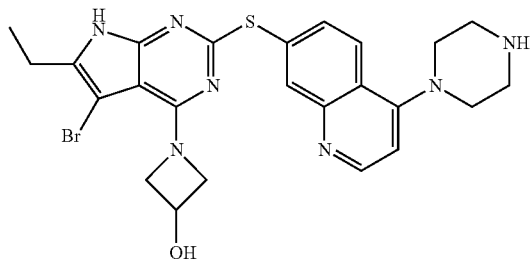 [SMILES: CCc1[nH]c2nc(Sc3ccc4c(N5CCNCC5)ccnc4c3)nc(N3CC(O)C3)c2c1Br] | Chemistry 45 |
| 700,404 | 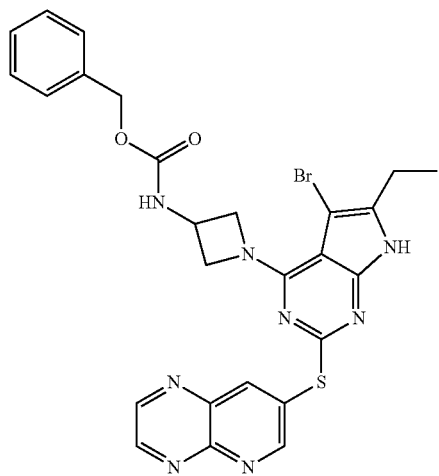 [SMILES: CCc1[nH]c2nc(Sc3cnc4nccnc4c3)nc(N3CC(NC(=O)OCc4ccccc4)C3)c2c1Br] | Chemistry 46 |

| Rx ID | CHEMISTRY | |
|---|---|---|
| 700,405 | 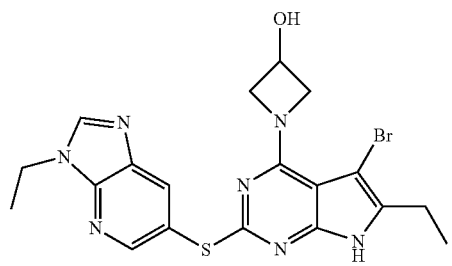 [SMILES: CCc1[nH]c2nc(Sc3cnc4c(c3)ncn4CC)nc(N3CC(O)C3)c2c1Br] | Chemistry 47 |
| 700,412 | 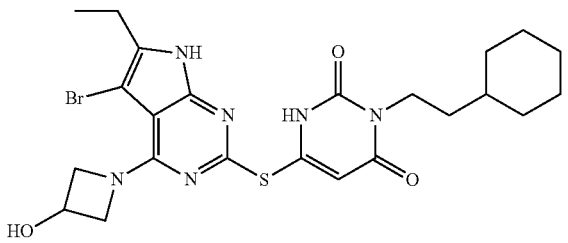 [SMILES: CCc1[nH]c2nc(Sc3cc(=O)n(CCC4CCCCC4)c(=O)[nH]3)nc(N3CC(O)C3)c2c1Br] | Chemistry 48 |
| 700,413 | 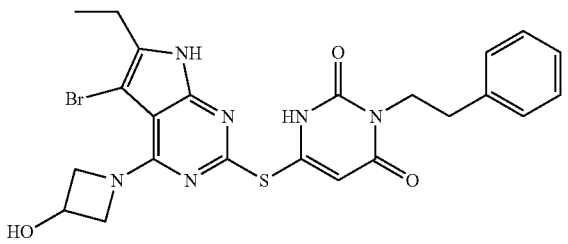 [SMILES: CCc1[nH]c2nc(Sc3cc(=O)n(CCc4ccccc4)c(=O)[nH]3)nc(N3CC(O)C3)c2c1Br] | Chemistry 49 |
| 700,414 | 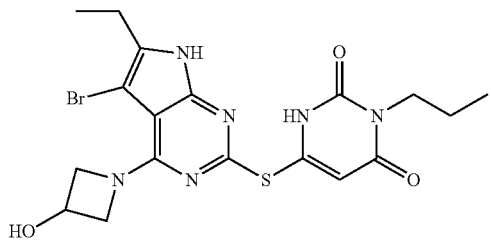 [SMILES: CCCn1c(=O)cc(Sc2nc(N3CC(O)C3)c3c(Br)c(CC)[nH]c3n2)[nH]c1=O] | Chemistry 50 |
| 700,415 | 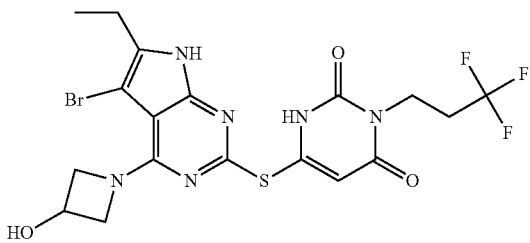 [SMILES: CCc1[nH]c2nc(Sc3cc(=O)n(CCC(F)(F)F)c(=O)[nH]3)nc(N3CC(O)C3)c2c1Br] | Chemistry 51 |
| 700,416 | 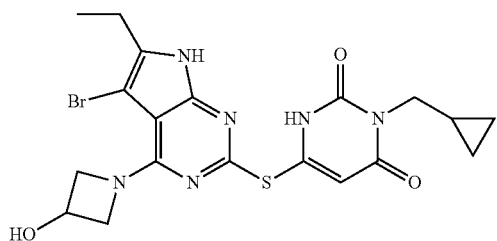 [SMILES: CCc1[nH]c2nc(Sc3cc(=O)n(CC4CC4)c(=O)[nH]3)nc(N3CC(O)C3)c2c1Br] | Chemistry 52 |

-continued
| Rx ID | CHEMISTRY | |
|---|---|---|
| 700,442 | 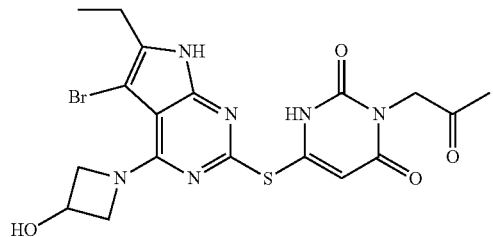 [SMILES: CCc1[nH]c2nc(Sc3cc(=O)n(CC(C)=O)c(=O)[nH]3)nc(N3CC(O)C3)c2c1Br] | Chemistry 53 |
| 700,417 | 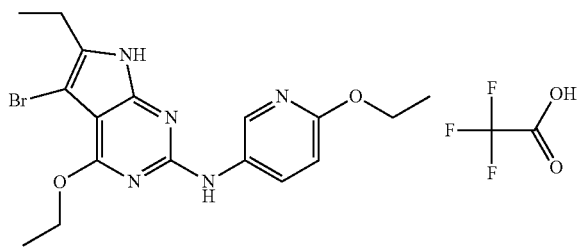 | Chemistry 54 |
| 700,423 | 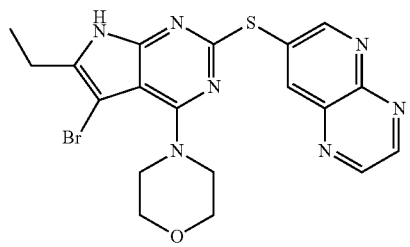 | Chemistry 55 |
| 700,433 | 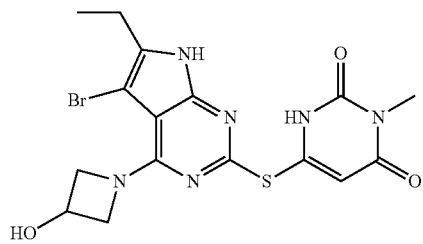 [SMILES: CCc1[nH]c2nc(Sc3cc(=O)n(C)c(=O)[nH]3)nc(N3CC(O)C3)c2c1Br] | Chemistry 56 |
| 700,443 | 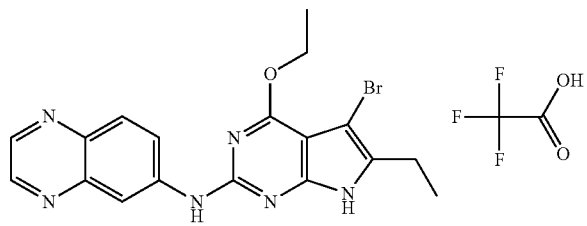 | Chemistry 57 |
| 700,450 | 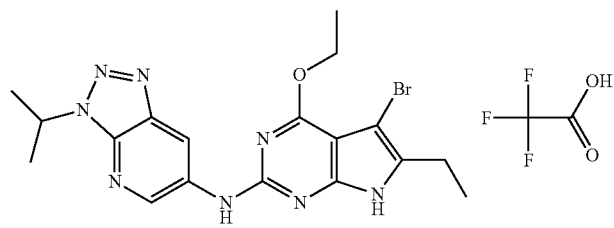 | Chemistry 58 |

| Rx ID | CHEMISTRY | |
|---|---|---|
| 700,451 | 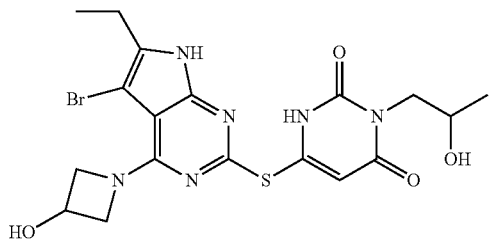 [SMILES: CCc1[nH]c2nc(Sc3cc(=O)n(CC(C)O)c(=O)[nH]3)nc(N3CC(O)C3)c2c1Br] | Chemistry 59 |
| 700,452 | 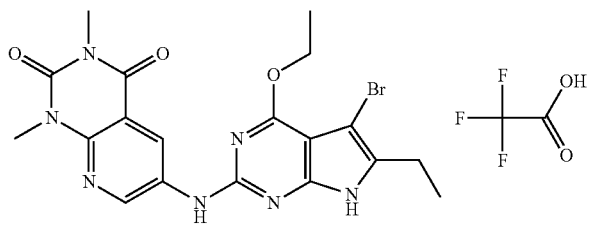 | Chemistry 60 |
| 700,467 | 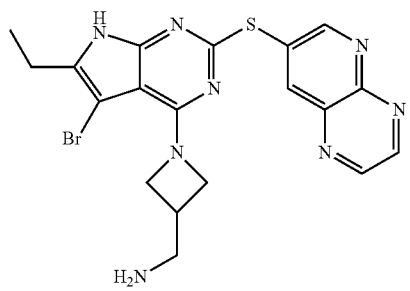 [SMILES: CCc1[nH]c2nc(Sc3cnc4nccnc4c3)nc(N3CC(CN)C3)c2c1Br] | Chemistry 61 |
| 700,468 | 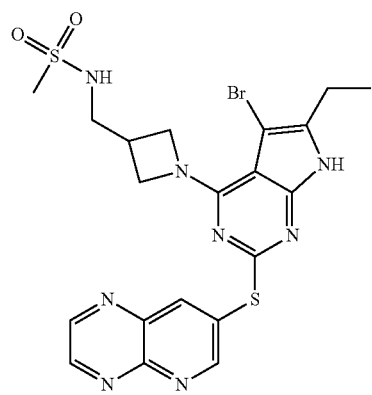 [SMILES: CCc1[nH]c2nc(Sc3cnc4nccnc4c3)nc(N3CC(CNS(C)(=O)=O)C3)c2c1Br] | Chemistry 62 |
| 700,469 | 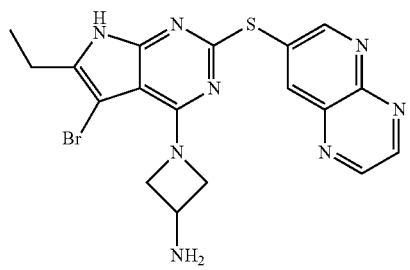 | Chemistry 63 |

US 10,047,105 B2
155	156
-continued
| Rx ID | CHEMISTRY | |
|---|---|---|
| 700,470 | 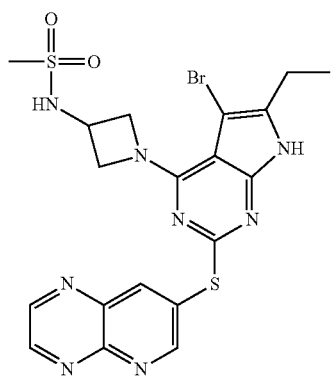 [SMILES: CCc1[nH]c2nc(Sc3cnc4nccnc4c3)nc(N3CC(NS(C)(=O)=O)C3)c2c1Br] | Chemistry 64 |
| 700,471 | 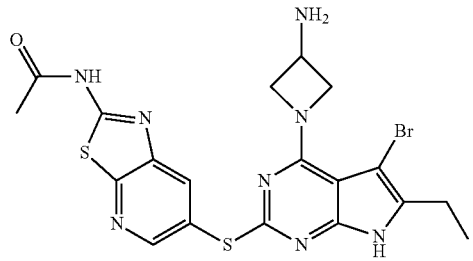 [SMILES: CCc1[nH]c2nc(Sc3cnc4sc(NC(C)=O)nc4c3)nc(N3CC(N)C3)c2c1Br] | Chemistry 65 |
| 700,475 | 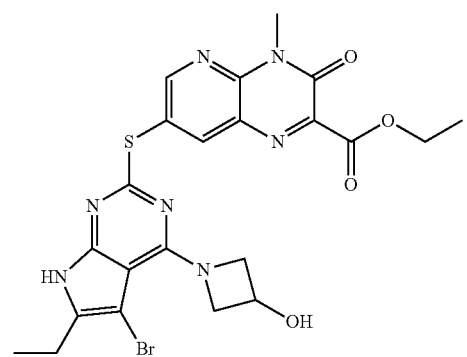 [SMILES: CCOC(=O)c1nc2cc(Sc3nc(N4CC(O)C4)c4c(Br)c(CC)[nH]c4n3)cnc2n(C)c1=O] | Chemistry 66 |
| 700,476 | 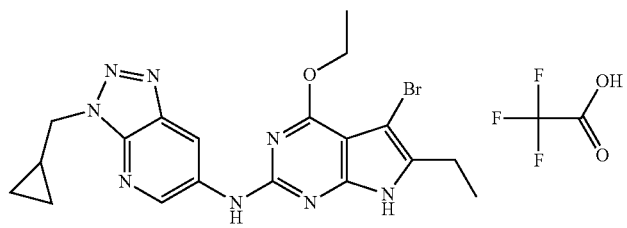 | Chemistry 67 |
| 700,481 | 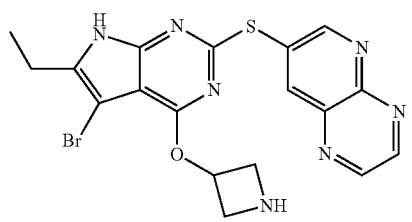 [SMILES: CCc1[nH]c2nc(Sc3cnc4nccnc4c3)nc(OC3CNC3)c2c1Br] | Chemistry 68 |

| Rx ID | CHEMISTRY | |
|---|---|---|
| 700,482 | 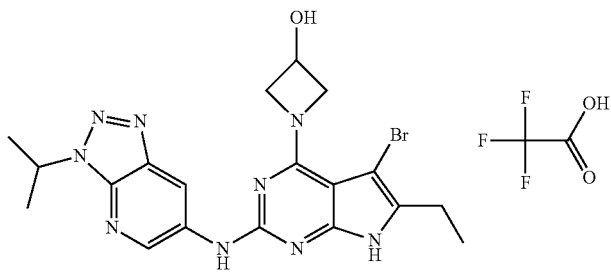 [SMILES: CCc1[nH]c2nc(Nc3cnc4c(c3)nnn4C(C)C)nc(N3CC(O)C3)c2c1Br ; O=C(O)C(F)(F)F] | Chemistry 69 |
| 700,483 | 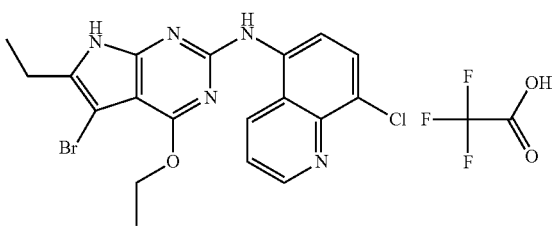 | Chemistry 70 |
| 700,484 | 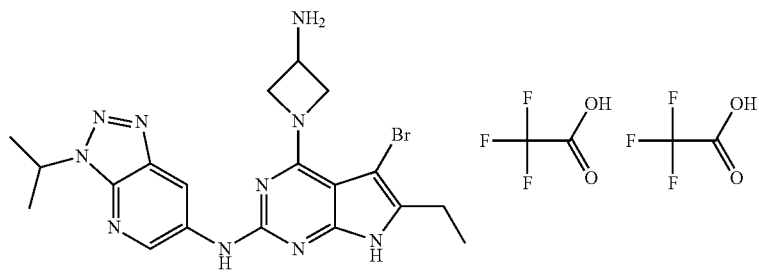 | Chemistry 71 |
| 700,485 | 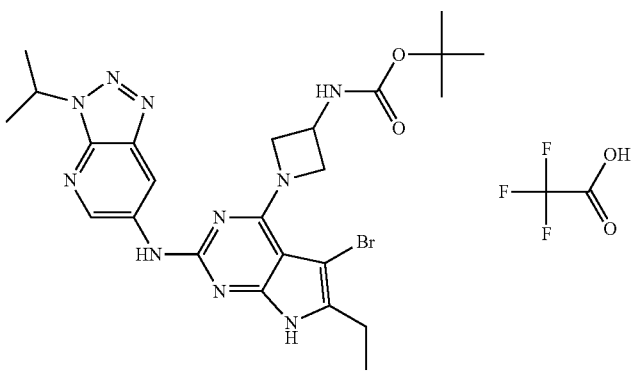 [SMILES: CCc1[nH]c2nc(Nc3cnc4c(c3)nnn4C(C)C)nc(N3CC(NC(=O)OC(C)(C)C)C3)c2c1Br ; O=C(O)C(F)(F)F] | Chemistry 72 |
| 700,498 | 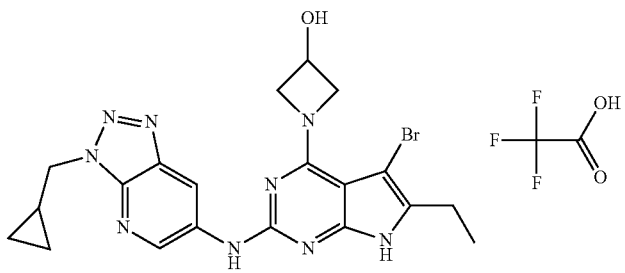 [SMILES: CCc1[nH]c2nc(Nc3cnc4c(c3)nnn4CC3CC3)nc(N3CC(O)C3)c2c1Br ; O=C(O)C(F)(F)F] | Chemistry 73 |

| Rx ID | CHEMISTRY | |
|---|---|---|
| 700,496 | 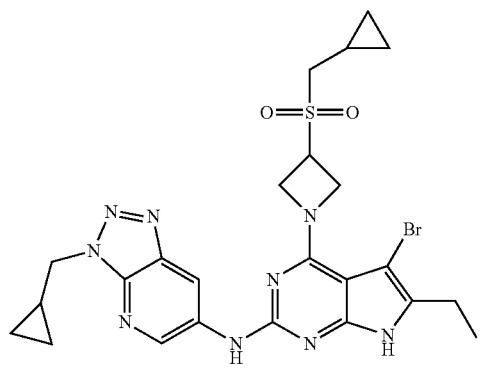 | Chemistry 74 |
| 700,535 | 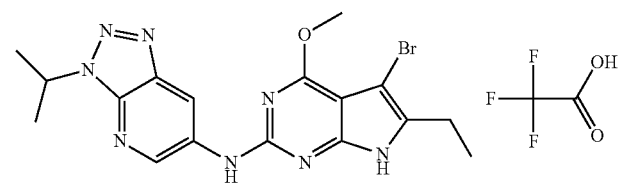 | Chemistry 75 |
| 700,545 | 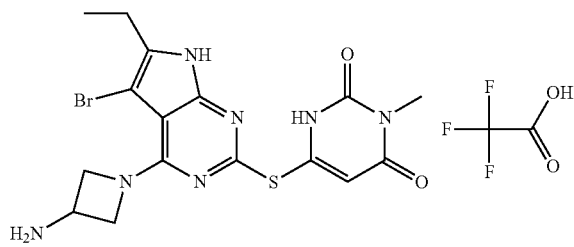 | Chemistry 76 |
| 700,552 | 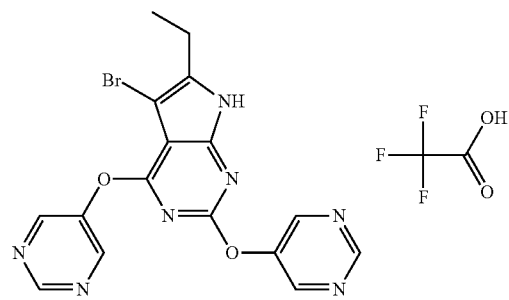 | Chemistry 77 |
| 700,572 | 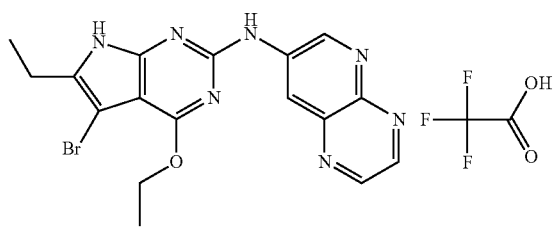 | Chemistry 78 |

| Rx ID | CHEMISTRY | |
|---|---|---|
| 700,591 | 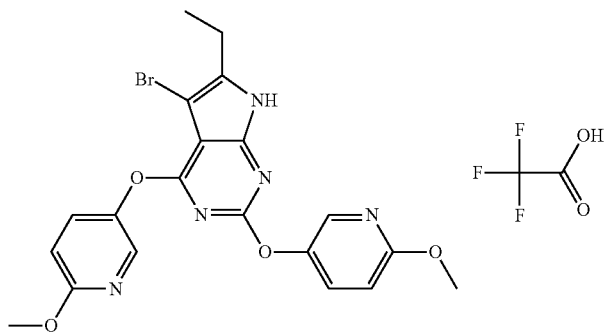 | Chemistry 79 |
| 700,598 | 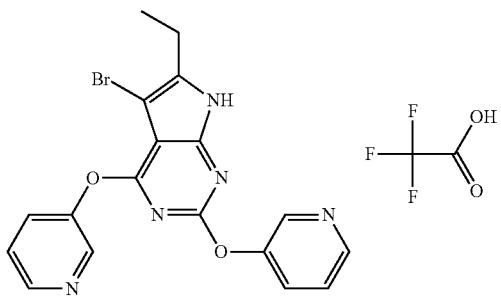 [SMILES: CCc1[nH]c2nc(Oc3cccnc3)nc(Oc3cccnc3)c2c1Br ; O=C(O)C(F)(F)F] | Chemistry 80 |
| 700,599 | 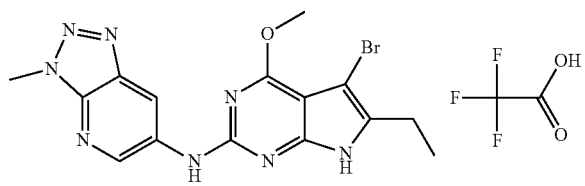 | Chemistry 81 |
| 700,600 | 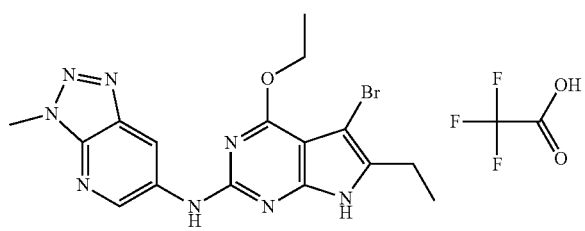 | Chemistry 82 |
| 700,621 | 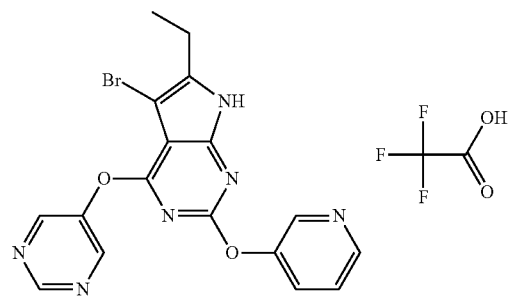 [SMILES: CCc1[nH]c2nc(Oc3cccnc3)nc(Oc3cncnc3)c2c1Br ; O=C(O)C(F)(F)F] | Chemistry 83 |

| Rx ID | CHEMISTRY | |
|---|---|---|
| 700,673 | 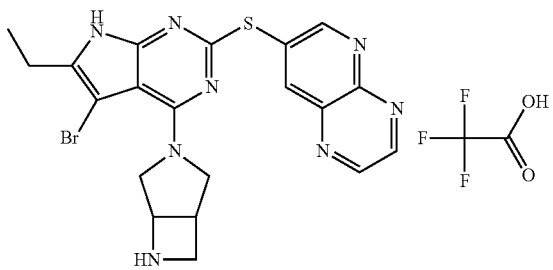 | Chemistry 84 |
| 700,679 | 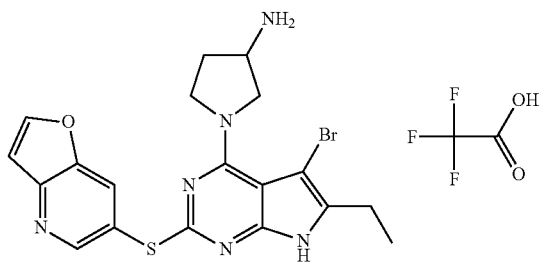 | Chemistry 85 |
| 700,680 | 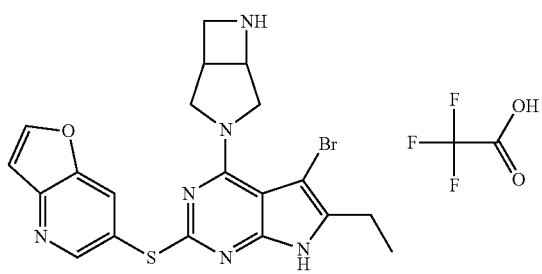 [SMILES: CCc1[nH]c2nc(Sc3cnc4ccoc4c3)nc(N3CC4CNC4C3)c2c1Br ; O=C(O)C(F)(F)F] | Chemistry 86 |
| 700,701 | 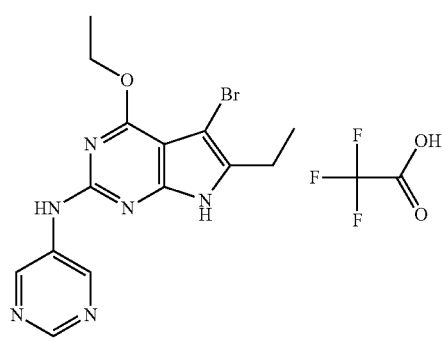 | Chemistry 87 |
| 700,724 | 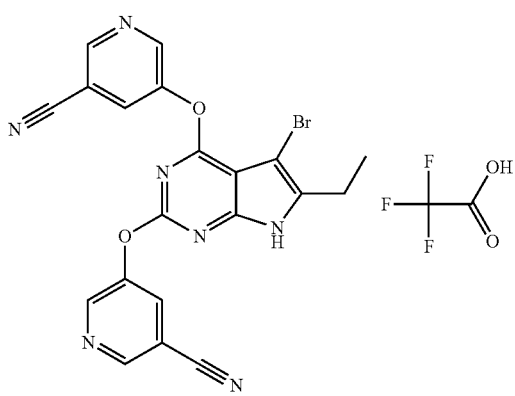 | Chemistry 88 |

| Rx ID | CHEMISTRY | |
|---|---|---|
| 700,793 | 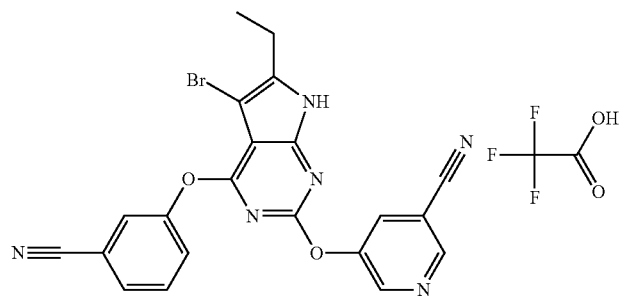 | Chemistry 89 |
| 700,866 | 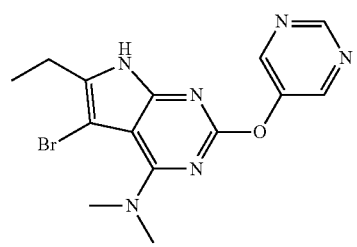 [SMILES: CCc1[nH]c2nc(Oc3cncnc3)nc(N(C)C)c2c1Br] | Chemistry 90 |
| 700,877 | 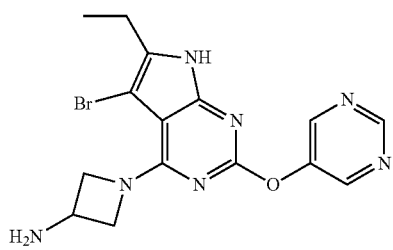 | Chemistry 91 |
| 700,878 | 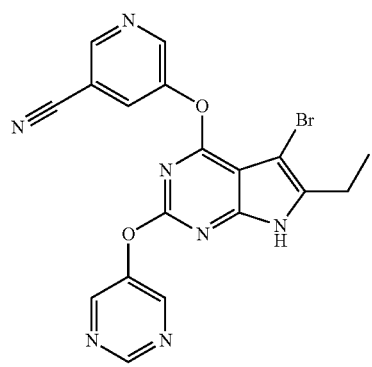 | Chemistry 92 |
| 700,883 | 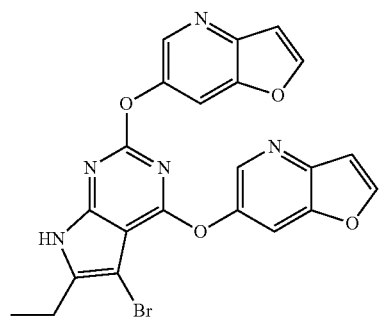 [SMILES: CCc1[nH]c2nc(Oc3cnc4ccoc4c3)nc(Oc3cnc4ccoc4c3)c2c1Br] | Chemistry 93 |

| Rx ID | CHEMISTRY | |
|---|---|---|
| 700,899 | 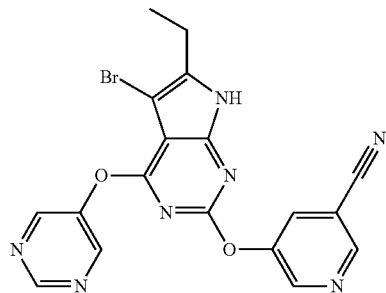 | Chemistry 94 |
| 700,933 | 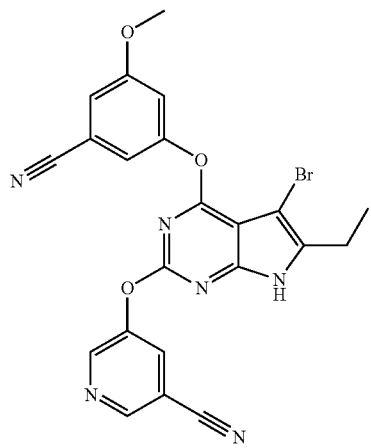 [SMILES: CCc1[nH]c2nc(Oc3cncc(C#N)c3)nc(Oc3cc(C#N)cc(OC)c3)c2c1Br] | Chemistry 95 |
| 700,935 | 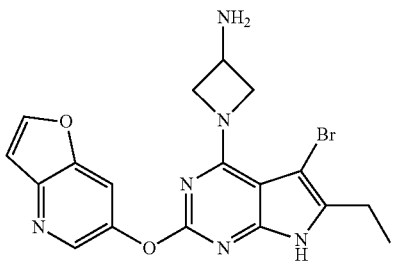 [SMILES: CCc1[nH]c2nc(Oc3cnc4ccoc4c3)nc(N3CC(N)C3)c2c1Br] | Chemistry 96 |
| 700,937 | 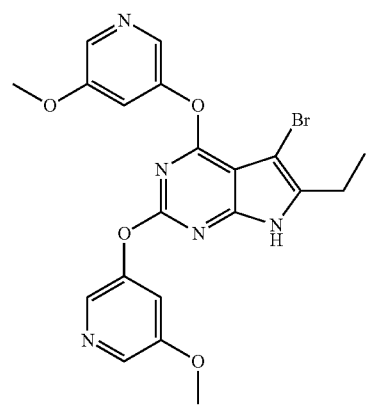 [SMILES: CCc1[nH]c2nc(Oc3cncc(OC)c3)nc(Oc3cncc(OC)c3)c2c1Br] | Chemistry 97 |

| Rx ID | CHEMISTRY | |
|---|---|---|
| 700,938 | 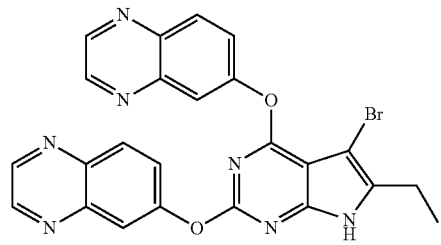 [SMILES: CCc1[nH]c2nc(Oc3ccc4nccnc4c3)nc(Oc3ccc4nccnc4c3)c2c1Br] | Chemistry 98 |
| 700,939 | 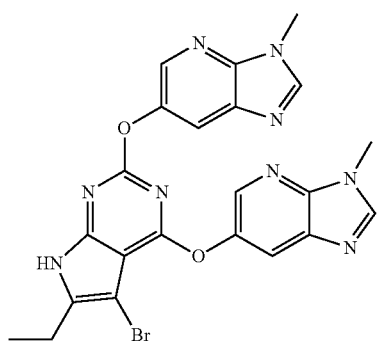 [SMILES: CCc1[nH]c2nc(Oc3cnc4c(c3)ncn4C)nc(Oc3cnc4c(c3)ncn4C)c2c1Br] | Chemistry 99 |
| 700,944 | 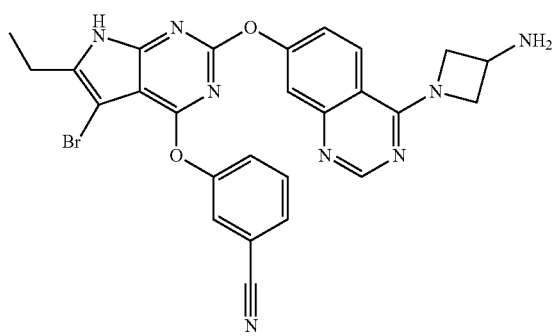 [SMILES: CCc1[nH]c2nc(Oc3ccc4c(N5CC(N)C5)ncnc4c3)nc(Oc3cccc(C#N)c3)c2c1Br] | Chemistry 100 |
| 700,945 | 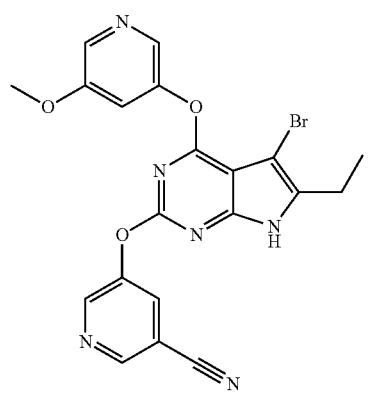 [SMILES: CCc1[nH]c2nc(Oc3cncc(C#N)c3)nc(Oc3cncc(OC)c3)c2c1Br] | Chemistry 101 |

| Rx ID | CHEMISTRY | |
|---|---|---|
| 700,949 | 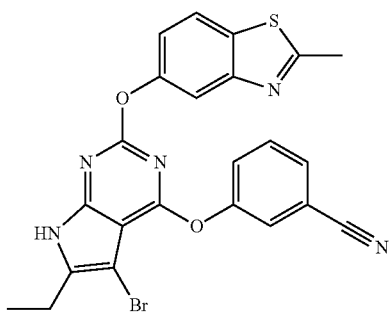 [SMILES: CCc1[nH]c2nc(Oc3ccc4sc(C)nc4c3)nc(Oc3cccc(C#N)c3)c2c1Br] | Chemistry 102 |
| 700,964 | 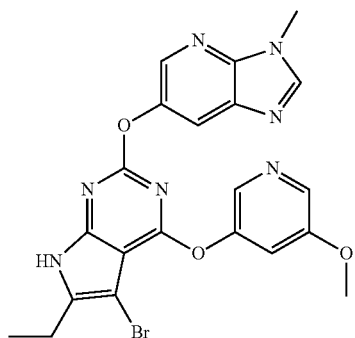 [SMILES: CCc1[nH]c2nc(Oc3cnc4c(c3)ncn4C)nc(Oc3cncc(OC)c3)c2c1Br] | Chemistry 103 |
| 700,965 | 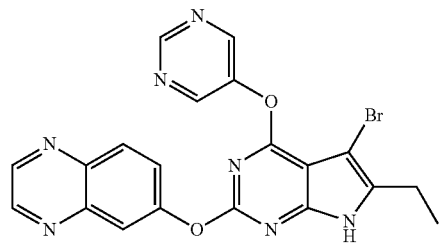 [SMILES: CCc1[nH]c2nc(Oc3ccc4nccnc4c3)nc(Oc3cncnc3)c2c1Br] | Chemistry 104 |
| 700,966 | 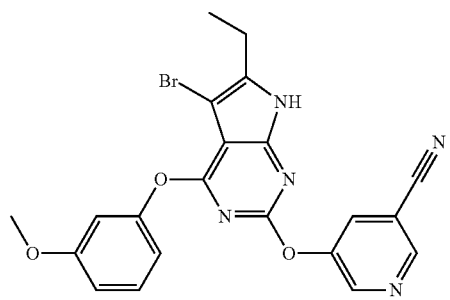 [SMILES: CCc1[nH]c2nc(Oc3cncc(C#N)c3)nc(Oc3cccc(OC)c3)c2c1Br] | Chemistry 105 |
| 700,979 | 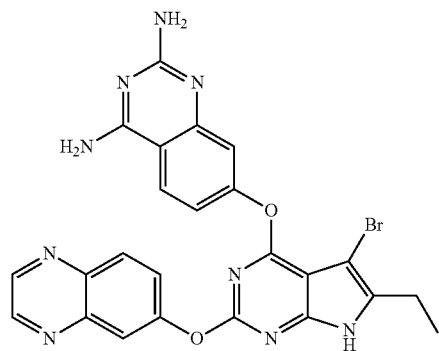 [SMILES: CCc1[nH]c2nc(Oc3ccc4nccnc4c3)nc(Oc3ccc4c(N)nc(N)nc4c3)c2c1Br] | Chemistry 106 |

| Rx ID | CHEMISTRY | |
|---|---|---|
| 700,980 | 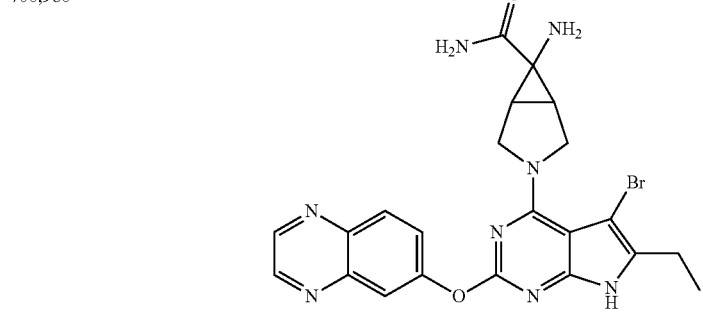 | Chemistry 107 |
| 700,982 | 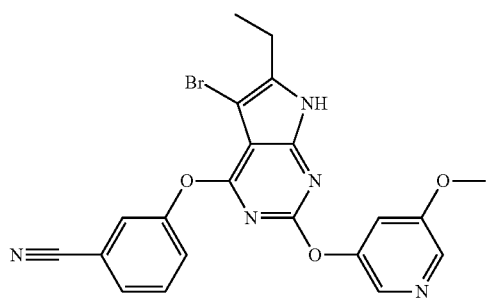 [SMILES: CCc1[nH]c2nc(Oc3cncc(OC)c3)nc(Oc3cccc(C#N)c3)c2c1Br] | Chemistry 108 |
| 700,987 | 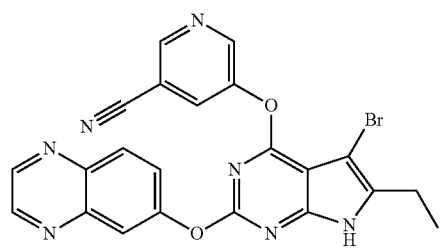 [SMILES: CCc1[nH]c2nc(Oc3ccc4nccnc4c3)nc(Oc3cncc(C#N)c3)c2c1Br] | Chemistry 109 |
| 700,988 | 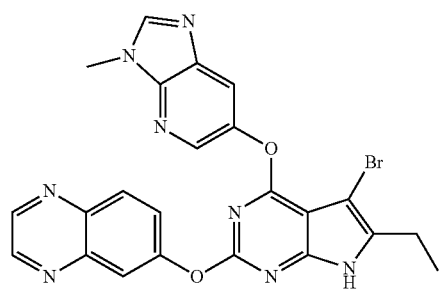 | Chemistry 110 |
| 700,996 | 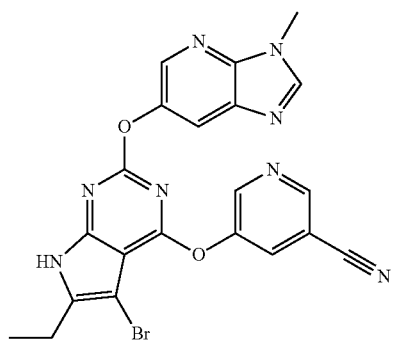 [SMILES: CCc1[nH]c2nc(Oc3cnc4c(c3)ncn4C)nc(Oc3cncc(C#N)c3)c2c1Br] | Chemistry 111 |

| Rx ID | CHEMISTRY | |
|---|---|---|
| 700,997 | 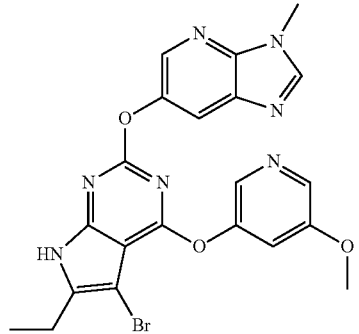 [SMILES: CCc1[nH]c2nc(Oc3cnc4c(c3)ncn4C)nc(Oc3cncc(OC)c3)c2c1Br] | Chemistry 112 |
| 700,998 | 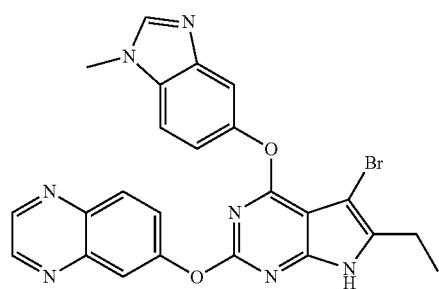 [SMILES: CCc1[nH]c2nc(Oc3ccc4nccnc4c3)nc(Oc3ccc4c(c3)ncn4C)c2c1Br] | Chemistry 113 |
| 701,030 | 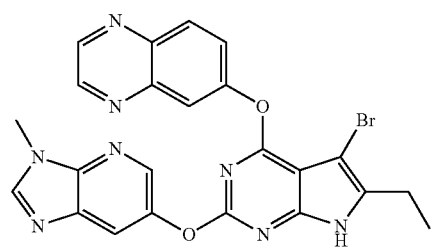 [SMILES: CCc1[nH]c2nc(Oc3cnc4c(c3)ncn4C)nc(Oc3ccc4nccnc4c3)c2c1Br] | Chemistry 114 |
| 701,032 | 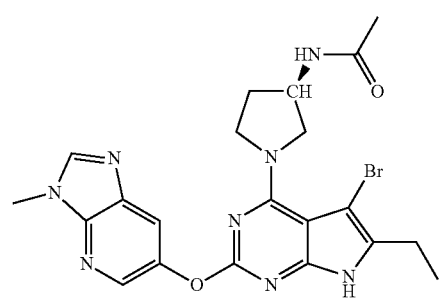 [SMILES: CCc1[nH]c2nc(Oc3cnc4c(c3)ncn4C)nc(N3CC[C@@H](NC(C)=O)C3)c2c1Br] | Chemistry 115 |
| 701,052 | 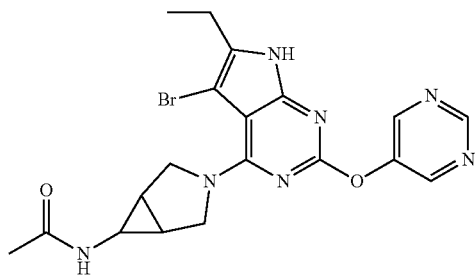 [SMILES: CCc1[nH]c2nc(Oc3cncnc3)nc(N3CC4C(C3)C4NC(C)=O)c2c1Br] | Chemistry 116 |

| Rx ID | CHEMISTRY | |
|---|---|---|
| 701,054 | 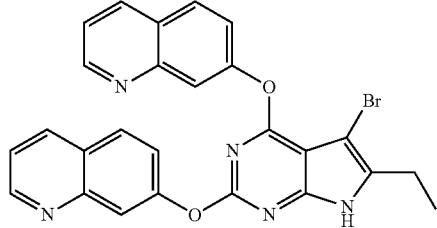 [SMILES: CCc1[nH]c2nc(Oc3ccc4cccnc4c3)nc(Oc3ccc4cccnc4c3)c2c1Br] | Chemistry 117 |
| 701,056 | 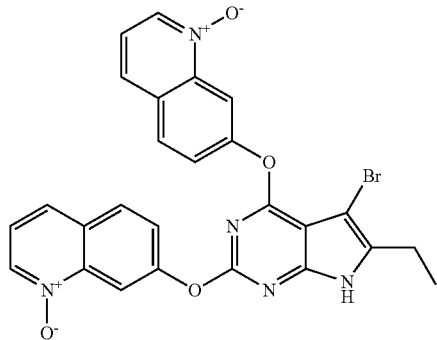 [SMILES: CCc1[nH]c2nc(Oc3ccc4ccc[n+]([O-])c4c3)nc(Oc3ccc4ccc[n+]([O-])c4c3)c2c1Br] | Chemistry 118 |
| 701,058 | 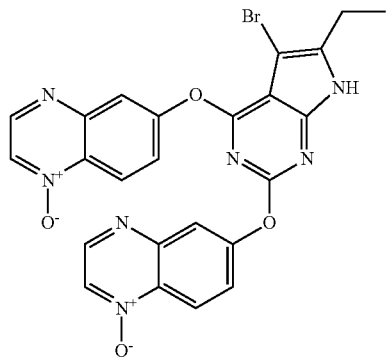 | Chemistry 119 |
| 701,059 | 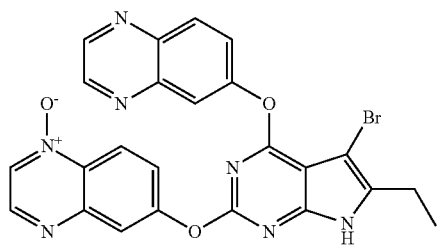 [SMILES: CCc1[nH]c2nc(Oc3ccc4c(c3)ncc[n+]4[O-])nc(Oc3ccc4nccnc4c3)c2c1Br] | Chemistry 120 |
| 701,060 | 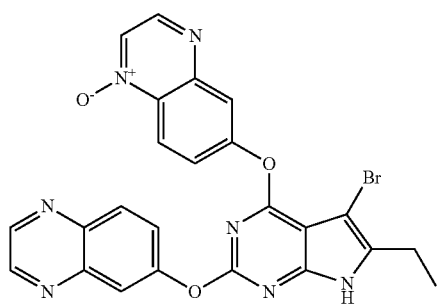 [SMILES: CCc1[nH]c2nc(Oc3ccc4nccnc4c3)nc(Oc3ccc4c(c3)ncc[n+]4[O-])c2c1Br] | Chemistry 121 |

| Rx ID | CHEMISTRY | |
|---|---|---|
| 701,081 | 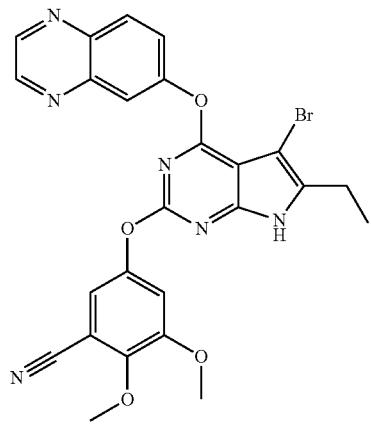 [SMILES: CCc1[nH]c2nc(Oc3cc(C#N)c(OC)c(OC)c3)nc(Oc3ccc4nccnc4c3)c2c1Br] | Chemistry 122 |
| 701,091 | 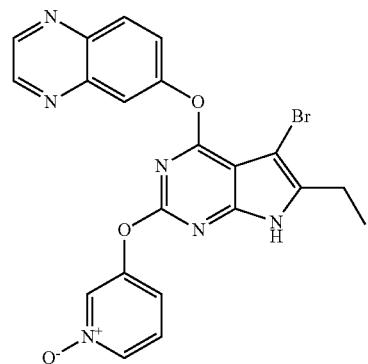 [SMILES: CCc1[nH]c2nc(Oc3ccc[n+]([O-])c3)nc(Oc3ccc4nccnc4c3)c2c1Br] | Chemistry 123 |
| 701,092 | 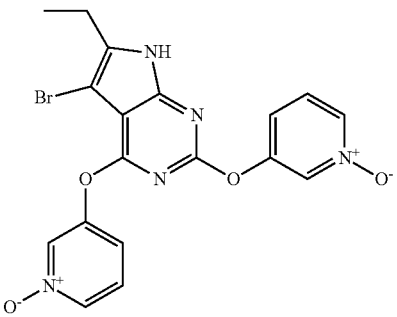 [SMILES: CCc1[nH]c2nc(Oc3ccc[n+]([O-])c3)nc(Oc3ccc[n+]([O-])c3)c2c1Br] | Chemistry 124 |
| 701,093 | 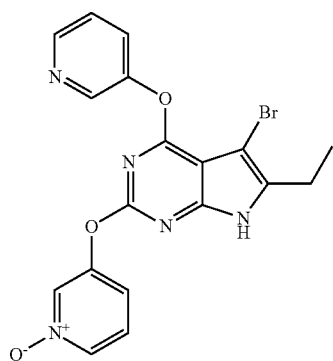 [SMILES: CCc1[nH]c2nc(Oc3ccc[n+]([O-])c3)nc(Oc3cccnc3)c2c1Br] | Chemistry 125 |

| Rx ID | CHEMISTRY | |
|---|---|---|
| 701,095 | 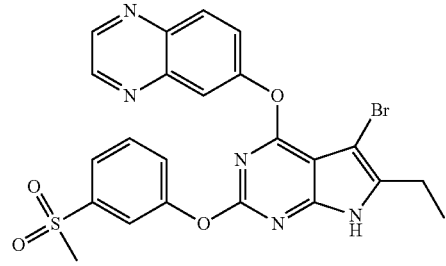 [SMILES: CCc1[nH]c2nc(Oc3cccc(S(C)(=O)=O)c3)nc(Oc3ccc4nccnc4c3)c2c1Br] | Chemistry 126 |
| 701,096 | 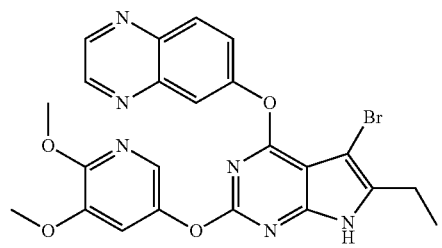 [SMILES: CCc1[nH]c2nc(Oc3cnc(OC)c(OC)c3)nc(Oc3ccc4nccnc4c3)c2c1Br] | Chemistry 127 |
| 701,097 | 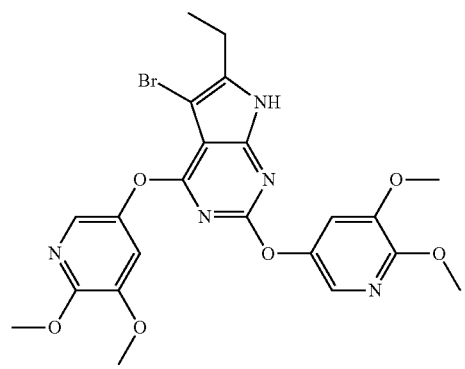 | Chemistry 128 |
| 701,104 | 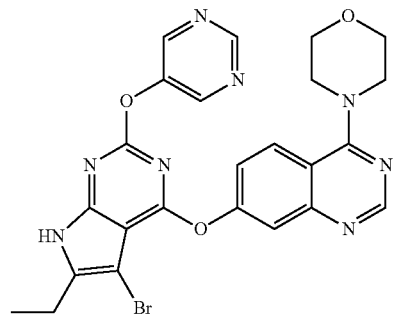 [SMILES: CCc1[nH]c2nc(Oc3cncnc3)nc(Oc3ccc4c(N5CCOCC5)ncnc4c3)c2c1Br] | Chemistry 129 |

-continued
| Rx ID | CHEMISTRY | |
|---|---|---|
| 701,105 | 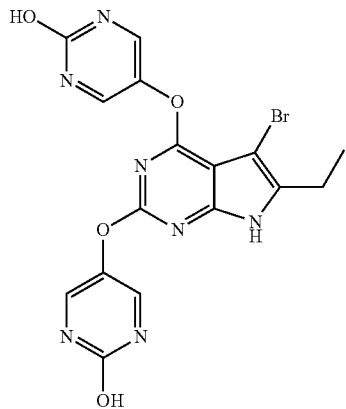 [SMILES: CCc1[nH]c2nc(Oc3cnc(O)nc3)nc(Oc3cnc(O)nc3)c2c1Br] | Chemistry 130 |
| 701,106 | 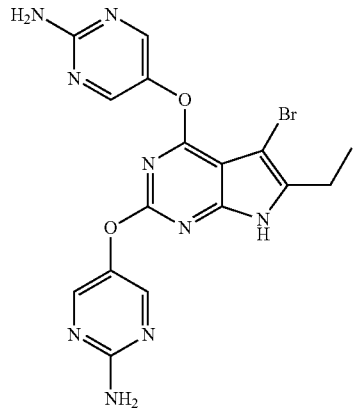 [SMILES: CCc1[nH]c2nc(Oc3cnc(N)nc3)nc(Oc3cnc(N)nc3)c2c1Br] | Chemistry 131 |
| 701,114 | 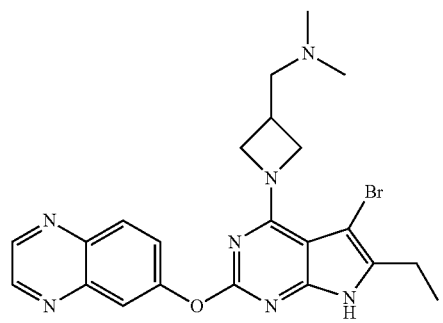 | Chemistry 132 |
| 701,249 | 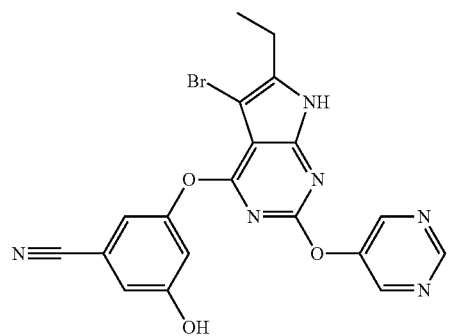 | Chemistry 133 |

| Rx ID | CHEMISTRY | |
|---|---|---|
| 701,250 | 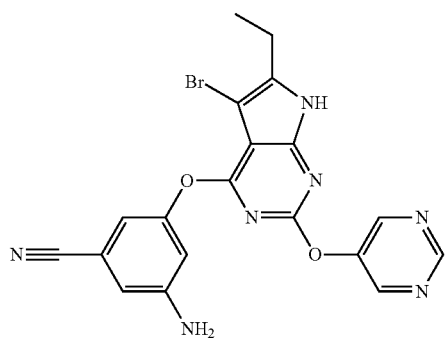 [SMILES: CCc1[nH]c2nc(Oc3cncnc3)nc(Oc3cc(N)cc(C#N)c3)c2c1Br] | Chemistry 134 |
| 701,252 | 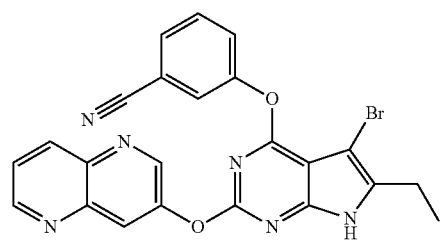 [SMILES: CCc1[nH]c2nc(Oc3cnc4cccnc4c3)nc(Oc3cccc(C#N)c3)c2c1Br] | Chemistry 135 |
| 701,253 | 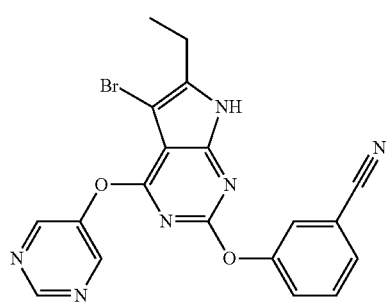 | Chemistry 136 |
| 701,254 | 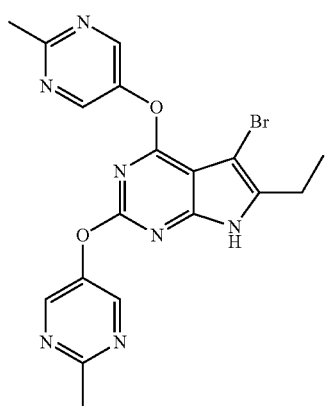 [SMILES: CCc1[nH]c2nc(Oc3cnc(C)nc3)nc(Oc3cnc(C)nc3)c2c1Br] | Chemistry 137 |

| Rx ID | CHEMISTRY | |
|---|---|---|
| 701,255 | 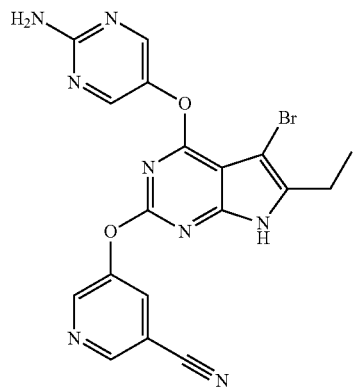 [SMILES: CCc1[nH]c2nc(Oc3cncc(C#N)c3)nc(Oc3cnc(N)nc3)c2c1Br] | Chemistry 138 |
| 701249-2 | 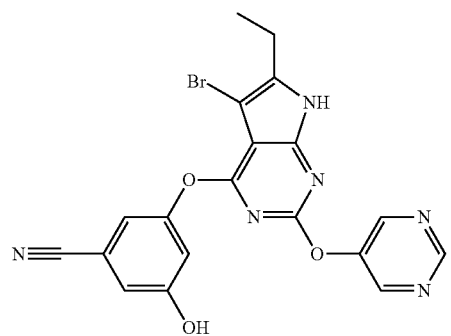 | Chemistry 139 |
| 701,267 |  | Chemistry 140 |
| 701,268 | 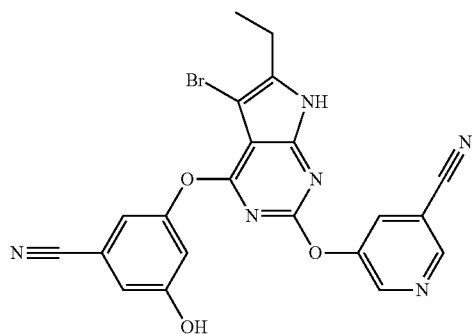 [SMILES: CCc1[nH]c2nc(Oc3cncc(C#N)c3)nc(Oc3cc(O)cc(C#N)c3)c2c1Br] | Chemistry 141 |

| Rx ID | CHEMISTRY | |
|---|---|---|
| 701,273 | 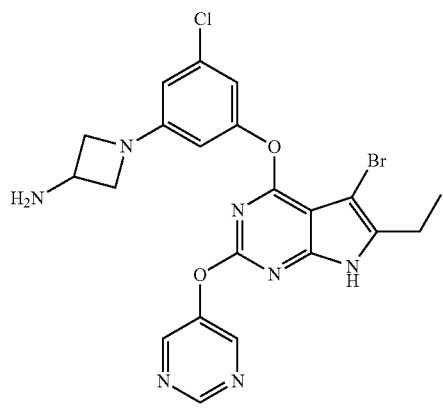 [SMILES: CCc1[nH]c2nc(Oc3cncnc3)nc(Oc3cc(Cl)cc(N4CC(N)C4)c3)c2c1Br] | Chemistry 142 |
| 701,287 | 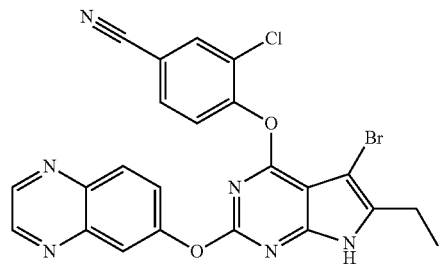 [SMILES: CCc1[nH]c2nc(Oc3ccc4nccnc4c3)nc(Oc3ccc(C#N)cc3Cl)c2c1Br] | Chemistry 143 |
| 701,288 | 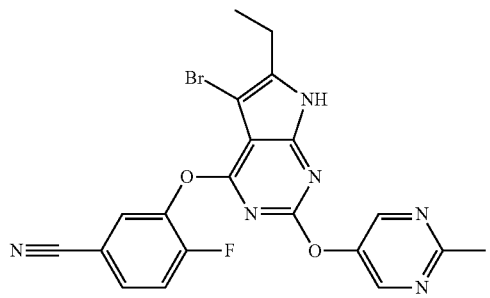 [SMILES: CCc1[nH]c2nc(Oc3cnc(C)nc3)nc(Oc3cc(C#N)ccc3F)c2c1Br] | Chemistry 144 |
| 701,297 | 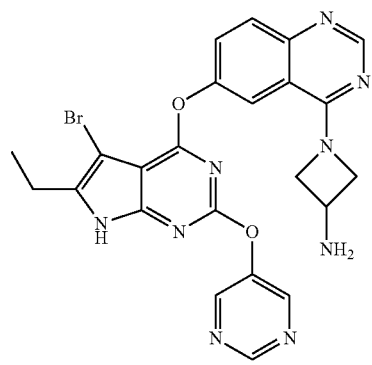 | Chemistry 145 |

| Rx ID | CHEMISTRY | |
|---|---|---|
| 701,298 | 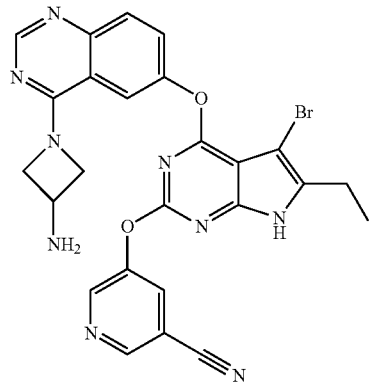 [SMILES: CCc1[nH]c2nc(Oc3cncc(C#N)c3)nc(Oc3ccc4ncnc(N5CC(N)C5)c4c3)c2c1Br] | Chemistry 146 |
| 701,299 | 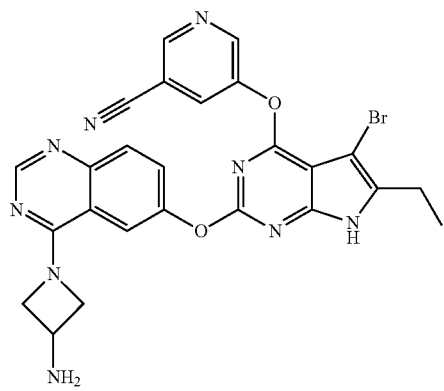 [SMILES: CCc1[nH]c2nc(Oc3ccc4ncnc(N5CC(N)C5)c4c3)nc(Oc3cncc(C#N)c3)c2c1Br] | Chemistry 147 |
| 700,339 | 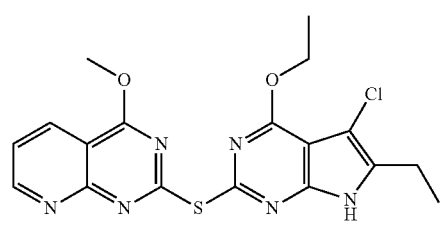 [SMILES: CCOc1nc(Sc2nc(OC)c3cccnc3n2)nc2[nH]c(CC)c(Cl)c12] | Chemistry 0 |
| 700,340 | 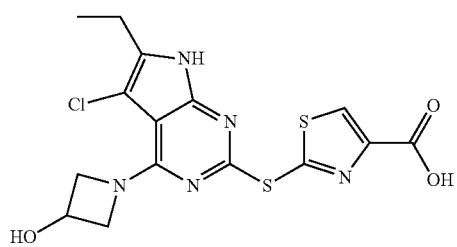 [SMILES: CCc1[nH]c2nc(Sc3nc(C(=O)O)cs3)nc(N3CC(O)C3)c2c1Cl] | Chemistry 1 |
| 700,268 | 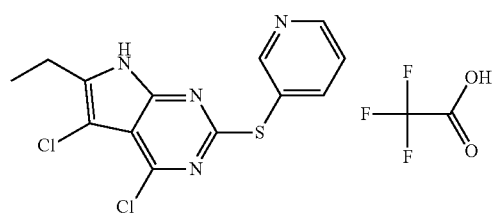 | Chemistry 2 |

| Rx ID | CHEMISTRY | |
|---|---|---|
| 700,273 | 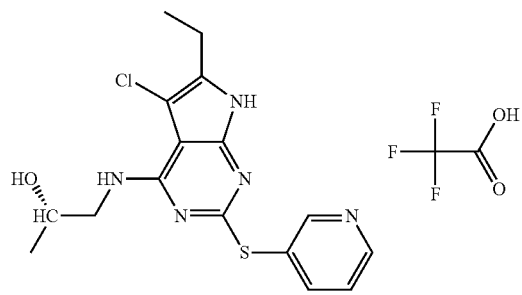 [SMILES: CCc1[nH]c2nc(Sc3cccnc3)nc(NC[C@H](C)O)c2c1Cl ; O=C(O)C(F)(F)F] | Chemistry 3 |
| 700,274 | 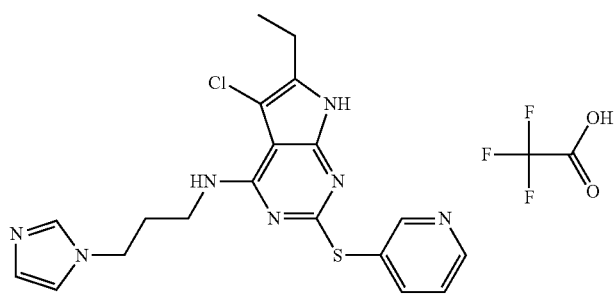 [SMILES: CCc1[nH]c2nc(Sc3cccnc3)nc(NCCCn3ccnc3)c2c1Cl ; O=C(O)C(F)(F)F] | Chemistry 4 |
| 700,298 | 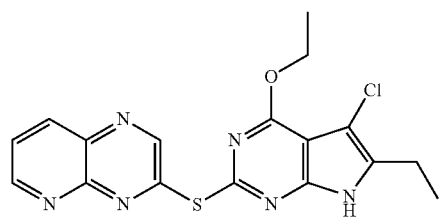 [SMILES: CCOc1nc(Sc2cnc3cccnc3n2)nc2[nH]c(CC)c(Cl)c12] | Chemistry 5 |
| 700,302 | 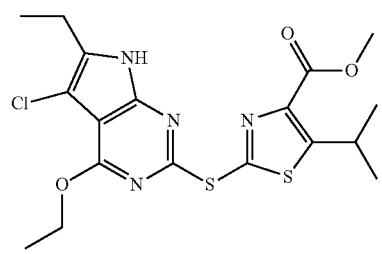 [SMILES: CCOc1nc(Sc2nc(C(=O)OC)c(C(C)C)s2)nc2[nH]c(CC)c(Cl)c12] | Chemistry 6 |
| 700,304 | 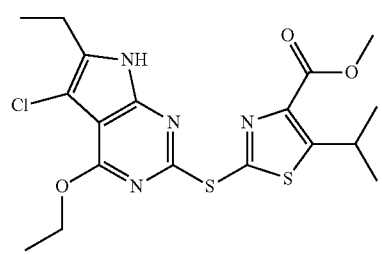 [SMILES: CCOc1nc(Sc2nc(C(=O)OC)c(C(C)C)s2)nc2[nH]c(CC)c(Cl)c12] | Chemistry 7 |

-continued
| Rx ID | CHEMISTRY | |
|---|---|---|
| 700,306 | 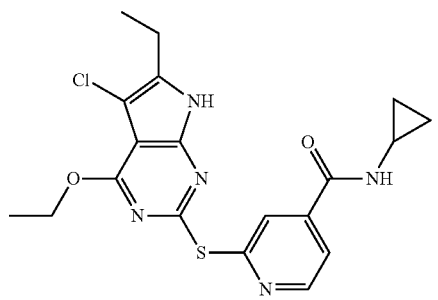 [SMILES: CCOc1nc(Sc2cc(C(=O)NC3CC3)ccn2)nc2[nH]c(CC)c(Cl)c12] | Chemistry 8 |
| 700,316 | 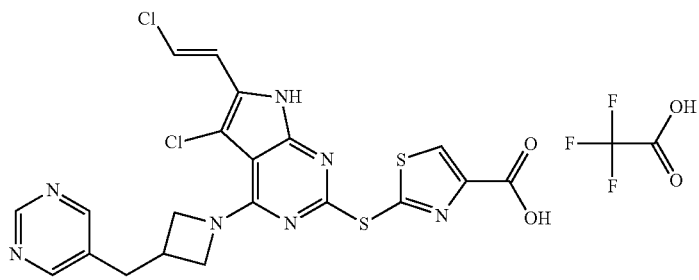 | Chemistry 9 |
| 700,317 | 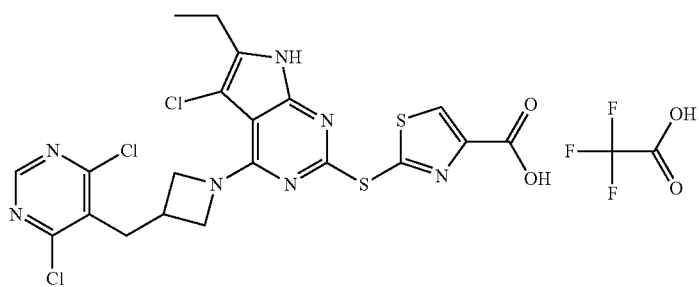 | Chemistry 10 |
| 700,318 | 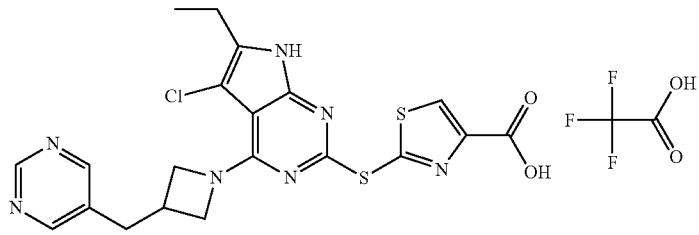 | Chemistry 11 |
| 700,320 | 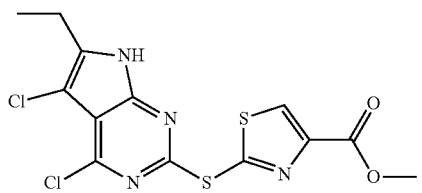 [SMILES: CCc1[nH]c2nc(Sc3nc(C(=O)OC)cs3)nc(Cl)c2c1Cl] | Chemistry 12 |
| 700,321 | 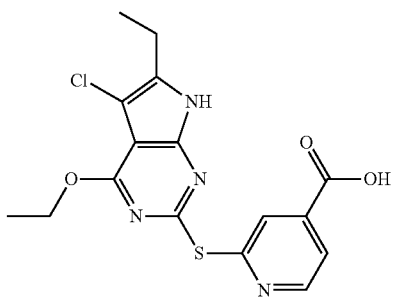 [SMILES: CCOc1nc(Sc2cc(C(=O)O)ccn2)nc2[nH]c(CC)c(Cl)c12] | Chemistry 13 |

| Rx ID | CHEMISTRY | |
|---|---|---|
| 700,322 | 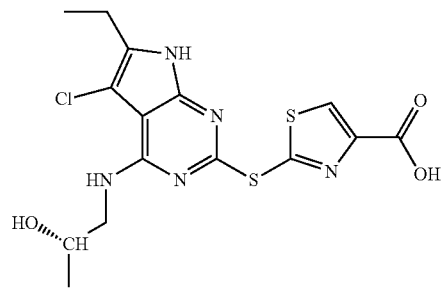 [SMILES: CCc1[nH]c2nc(Sc3nc(C(=O)O)cs3)nc(NC[C@H](C)O)c2c1Cl] | Chemistry 14 |
| 700,323 | 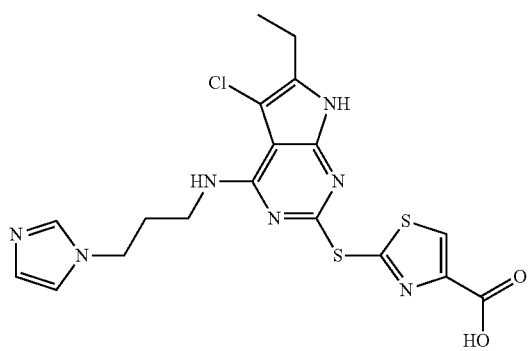 [SMILES: CCc1[nH]c2nc(Sc3nc(C(=O)O)cs3)nc(NCCCn3ccnc3)c2c1Cl] | Chemistry 15 |
| 700,324 | 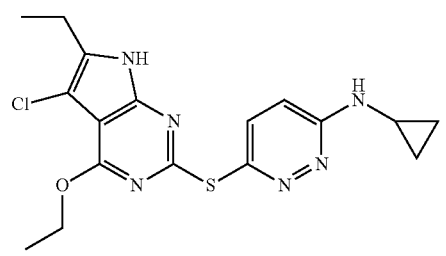 [SMILES: CCOc1nc(Sc2ccc(NC3CC3)nn2)nc2[nH]c(CC)c(Cl)c12] | Chemistry 16 |
| 700,325 | 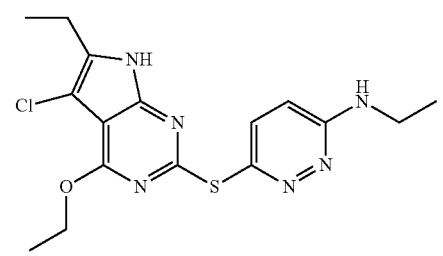 [SMILES: CCNc1ccc(Sc2nc(OCC)c3c(Cl)c(CC)[nH]c3n2)nn1] | Chemistry 17 |
| 700,326 | 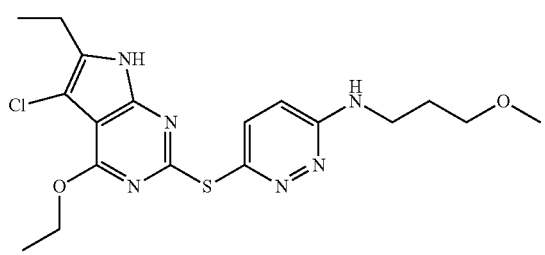 [SMILES: CCOc1nc(Sc2ccc(NCCCOC)nn2)nc2[nH]c(CC)c(Cl)c12] | Chemistry 18 |

-continued
| Rx ID | CHEMISTRY | |
|---|---|---|
| 700,327 | 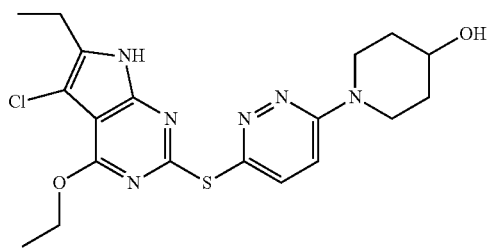 [SMILES: CCOc1nc(Sc2ccc(N3CCC(O)CC3)nn2)nc2[nH]c(CC)c(Cl)c12] | Chemistry 19 |
| 700,328 | 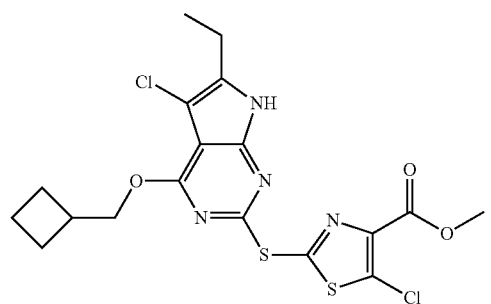 [SMILES: CCc1[nH]c2nc(Sc3nc(C(=O)OC)c(Cl)s3)nc(OCC3CCC3)c2c1Cl] | Chemistry 20 |
| 700,330 | 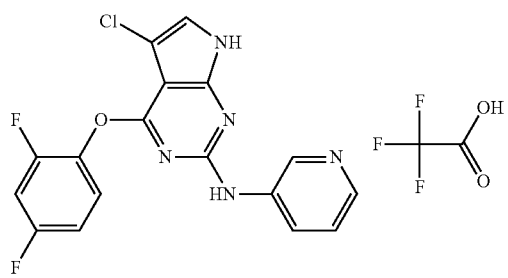 | Chemistry 21 |
| 700,341 | 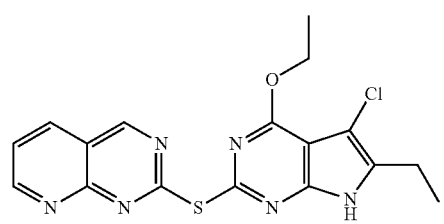 [SMILES: CCOc1nc(Sc2ncc3cccnc3n2)nc2[nH]c(CC)c(Cl)c12] | Chemistry 22 |
| 700,338 | 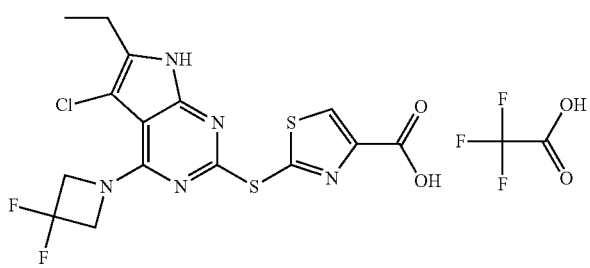 | Chemistry 23 |

| Rx ID | CHEMISTRY | |
|---|---|---|
| 700,342 | 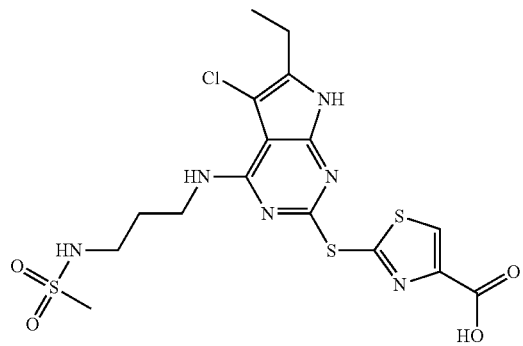 [SMILES: CCc1[nH]c2nc(Sc3nc(C(=O)O)cs3)nc(NCCCNS(C)(=O)=O)c2c1Cl] | Chemistry 24 |
| 700,343 | 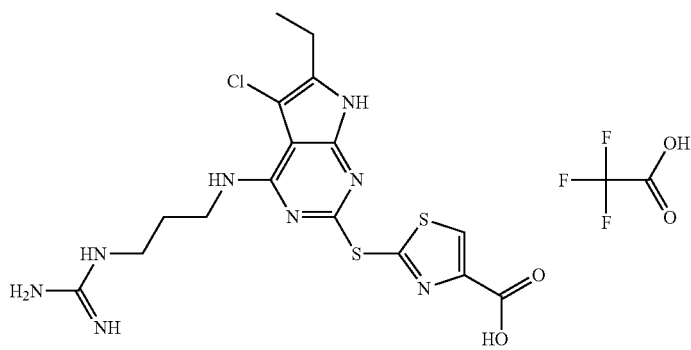 [SMILES: CCc1[nH]c2nc(Sc3nc(C(=O)O)cs3)nc(NCCCNC(=N)N)c2c1Cl ; O=C(O)C(F)(F)F] | Chemistry 25 |
| 700,345 | 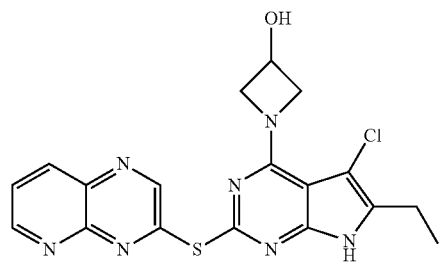 | Chemistry 26 |
| 700,347 | 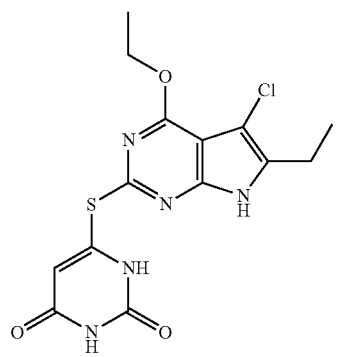 [SMILES: CCOc1nc(Sc2cc(=O)[nH]c(=O)[nH]2)nc2[nH]c(CC)c(Cl)c12] | Chemistry 27 |
| 700,353 | 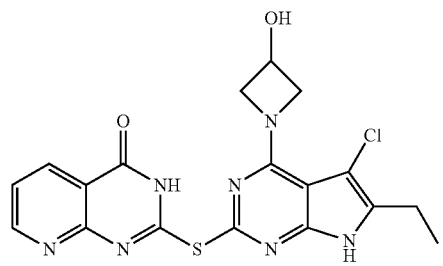 | Chemistry 28 |

| Rx ID | CHEMISTRY | |
|---|---|---|
| 700,355 | 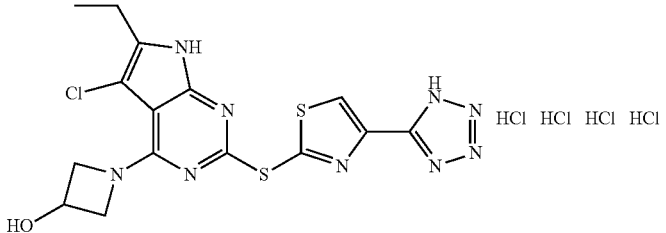 [SMILES: CCc1[nH]c2nc(Sc3nc(-c4nnn[nH]4)cs3)nc(N3CC(O)C3)c2c1Cl ; Cl ; Cl ; Cl ; Cl] | Chemistry 29 |
| 700,356 | 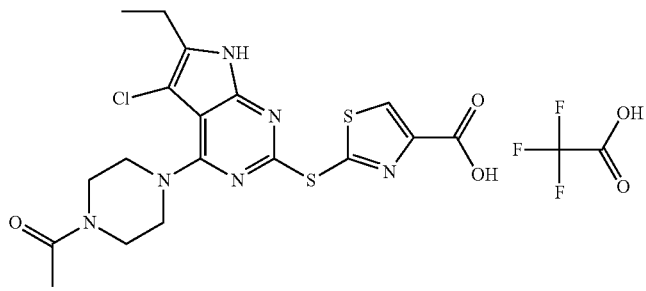 | Chemistry 30 |
| 700,357 | 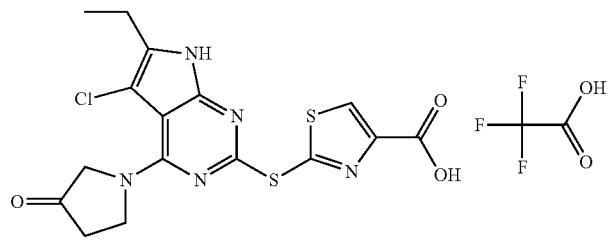 | Chemistry 31 |
| 700,359 | 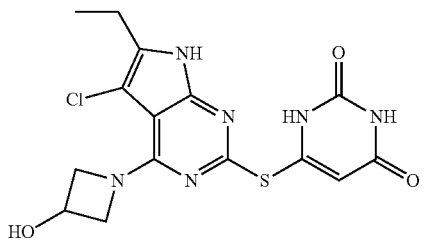 [SMILES: CCc1[nH]c2nc(Sc3cc(=O)[nH]c(=O)[nH]3)nc(N3CC(O)C3)c2c1Cl] | Chemistry 32 |
| 700,373 | 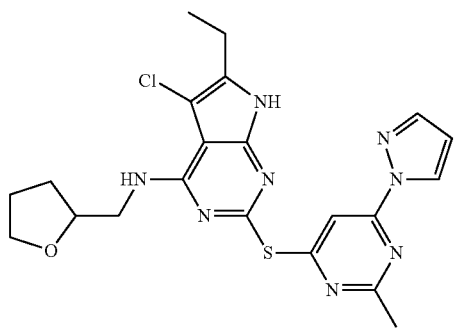 [SMILES: CCc1[nH]c2nc(Sc3cc(-n4cccn4)nc(C)n3)nc(NCC3CCCO3)c2c1Cl] | Chemistry 33 |

| Rx ID | CHEMISTRY | |
|---|---|---|
| 700,361 | 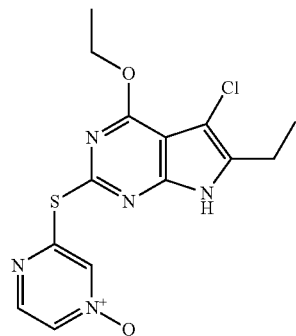 [SMILES: CCOc1nc(Sc2c[n+](O)ccn2)nc2[nH]c(CC)c(Cl)c12] | Chemistry 34 |
| 700,364 | 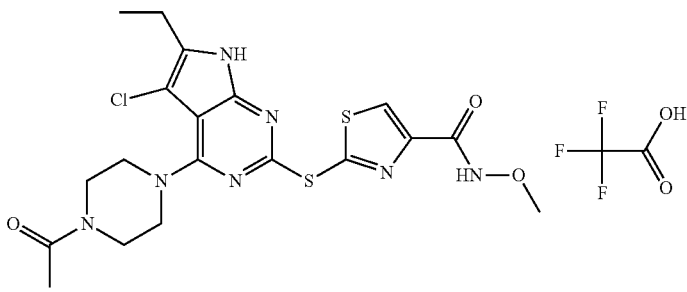 | Chemistry 35 |
| 700,365 | 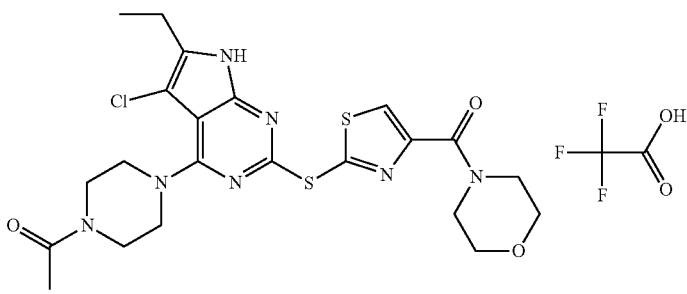 | Chemistry 36 |
| 700,387 | 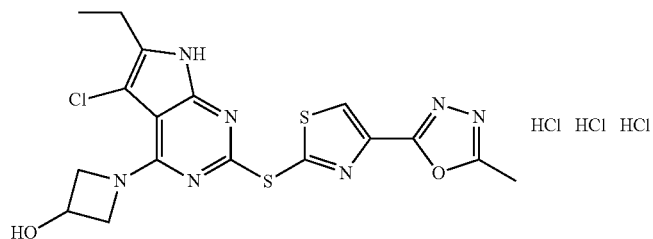 [SMILES: CCc1[nH]c2nc(Sc3nc(-c4nnc(C)o4)cs3)nc(N3CC(O)C3)c2c1Cl ; Cl ; Cl ; Cl] | Chemistry 37 |
| 700,393 | 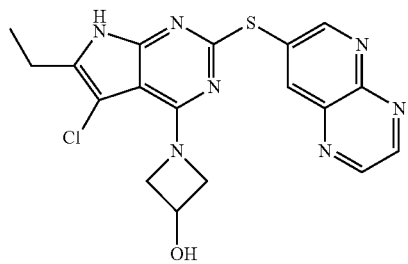 | Chemistry 38 |

-continued
| Rx ID | CHEMISTRY | |
|---|---|---|
| 700,394 | 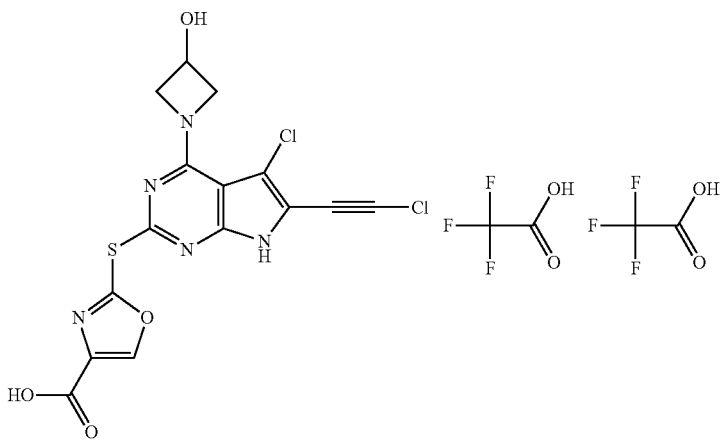 | Chemistry 29 |
| 700,395 | 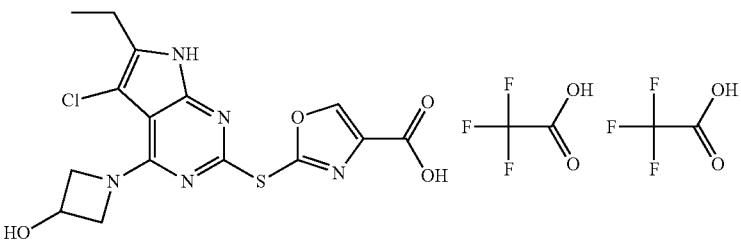 | Chemistry 40 |
| 700,396 | 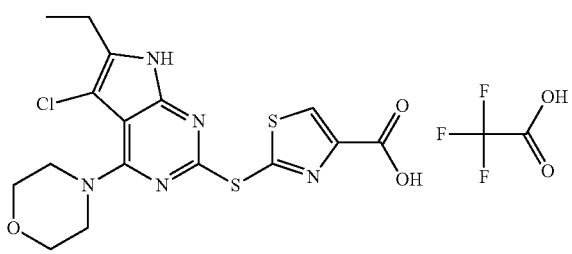 | Chemistry 41 |
| 700,397 | 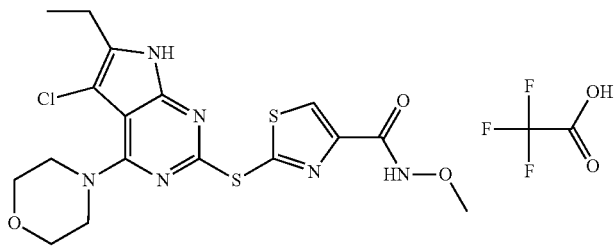 [SMILES: CCc1[nH]c2nc(Sc3nc(C(=O)NOC)cs3)nc(N3CCOCC3)c2c1Cl ; O=C(O)C(F)(F)F] | Chemistry 42 |
| 700,398 | 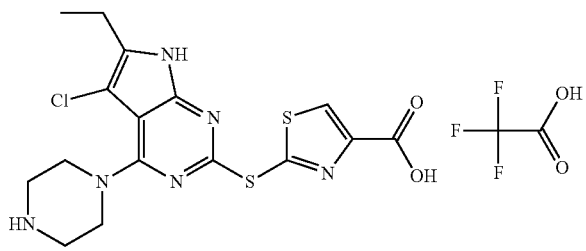 | Chemistry 43 |

-continued
| Rx ID | CHEMISTRY | |
|---|---|---|
| 700,406 | 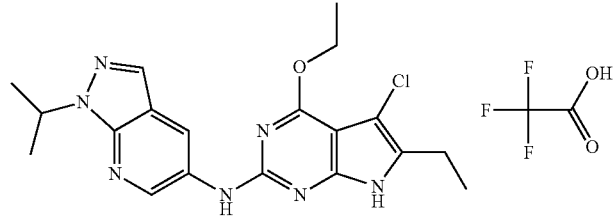 | Chemistry 44 |
| 700,407 | 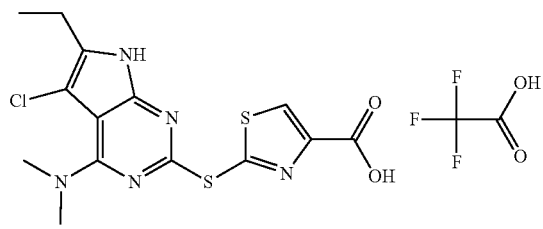 | Chemistry 45 |
| 700,408 | 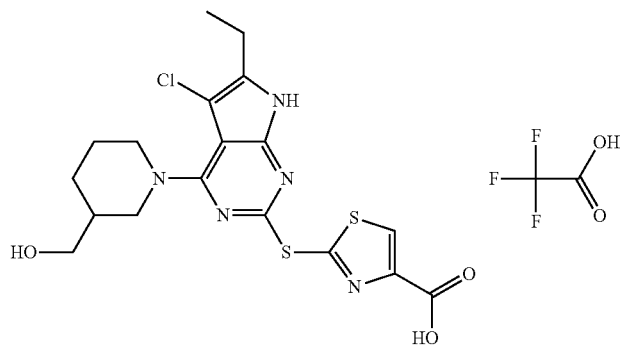 [SMILES: CCc1[nH]c2nc(Sc3nc(C(=O)O)cs3)nc(N3CCCC(CO)C3)c2c1Cl ; O=C(O)C(F)(F)F] | Chemistry 46 |
| 700,410 | 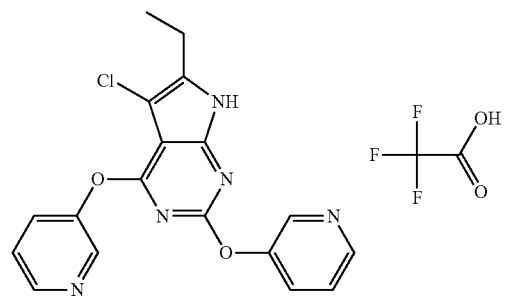 [SMILES: CCc1[nH]c2nc(Oc3cccnc3)nc(Oc3cccnc3)c2c1Cl ; O=C(O)C(F)(F)F] | Chemistry 47 |
| 700,411 | 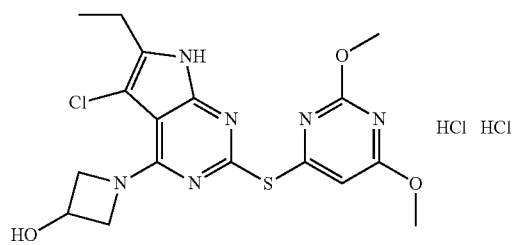 [SMILES: CCc1[nH]c2nc(Sc3cc(OC)nc(OC)n3)nc(N3CC(O)C3)c2c1Cl ; Cl ; Cl] | Chemistry 48 |

| Rx ID | CHEMISTRY | |
|---|---|---|
| 700,435 | 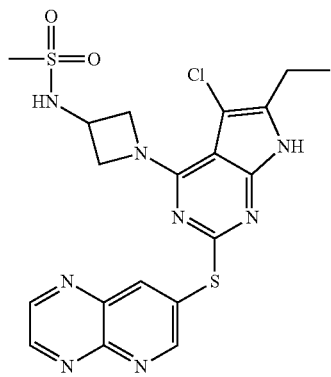 | Chemistry 49 |
| 700,436 | 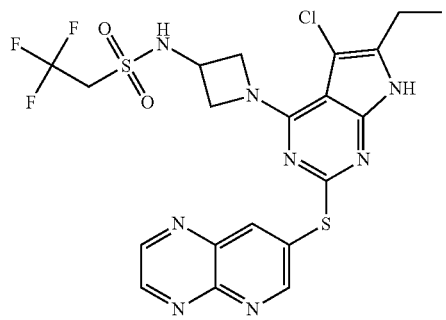 [SMILES: CCc1[nH]c2nc(Sc3cnc4nccnc4c3)nc(N3CC(NS(=O)(=O)CC(F)(F)F)C3)c2c1Cl] | Chemistry 50 |
| 700,437 | 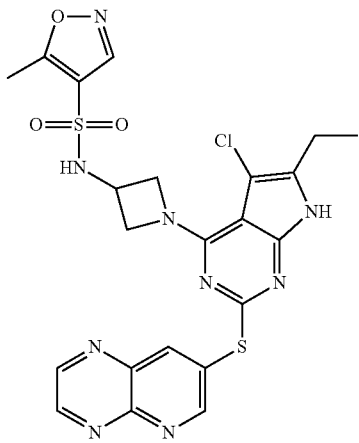 [SMILES: CCc1[nH]c2nc(Sc3cnc4nccnc4c3)nc(N3CC(NS(=O)(=O)c4cnoc4C)C3)c2c1Cl] | Chemistry 51 |
| 700,438 | 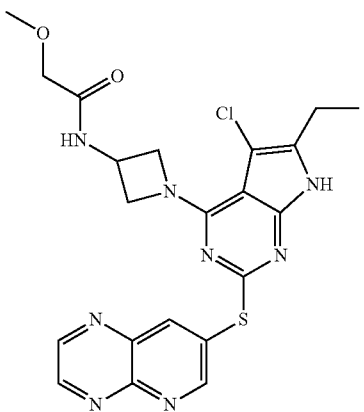 [SMILES: CCc1[nH]c2nc(Sc3cnc4nccnc4c3)nc(N3CC(NC(=O)COC)C3)c2c1Cl] | Chemistry 52 |

| Rx ID | CHEMISTRY | |
|---|---|---|
| 700,439 | 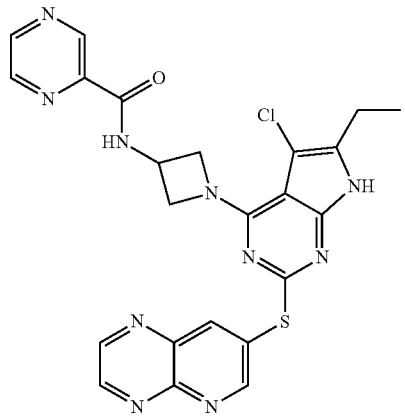 [SMILES: CCc1[nH]c2nc(Sc3cnc4nccnc4c3)nc(N3CC(NC(=O)c4cnccn4)C3)c2c1Cl] | Chemistry 53 |
| 700,440 | 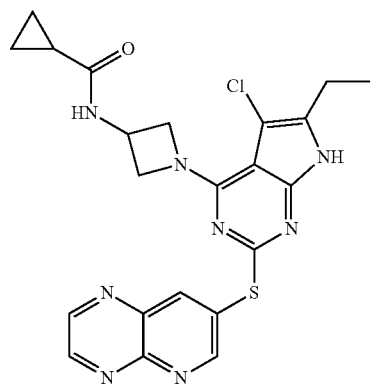 [SMILES: CCc1[nH]c2nc(Sc3cnc4nccnc4c3)nc(N3CC(NC(=O)C4CC4)C3)c2c1Cl] | Chemistry 54 |
| 700,441 | 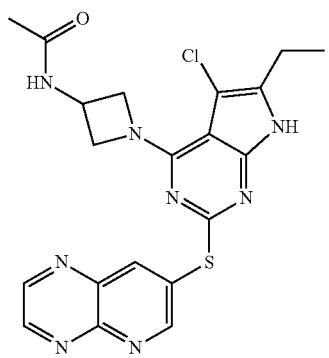 [SMILES: CCc1[nH]c2nc(Sc3cnc4nccnc4c3)nc(N3CC(NC(C)=O)C3)c2c1Cl] | Chemistry 55 |
| 700,418 | 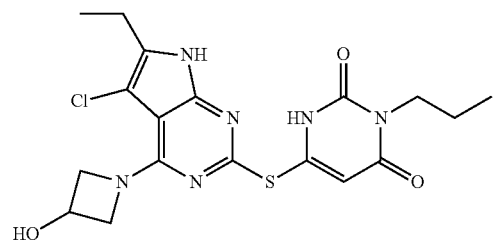 [SMILES: CCCn1c(=O)cc(Sc2nc(N3CC(O)C3)c3c(Cl)c(CC)[nH]c3n2)[nH]c1=O] | Chemistry 56 |

| Rx ID | CHEMISTRY | |
|---|---|---|
| 700,422 | 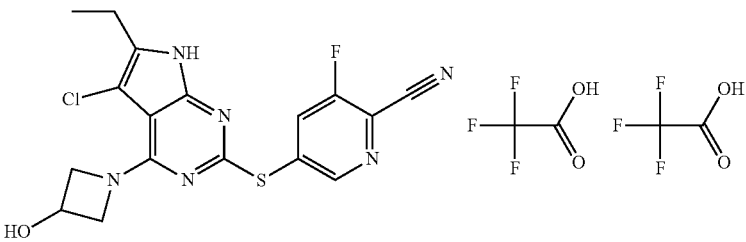 | Chemistry 57 |
| 700,424 | 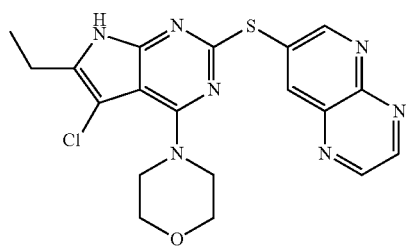 [SMILES: CCc1[nH]c2nc(Sc3cnc4nccnc4c3)nc(N3CCOCC3)c2c1Cl] | Chemistry 58 |
| 700,425 | 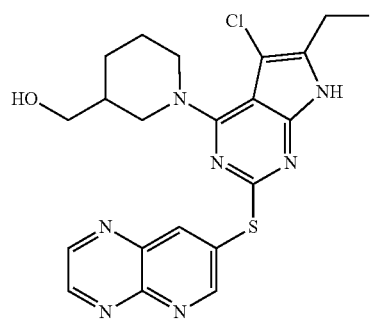 [SMILES: CCc1[nH]c2nc(Sc3cnc4nccnc4c3)nc(N3CCCC(CO)C3)c2c1Cl] | Chemistry 59 |
| 700,426 | 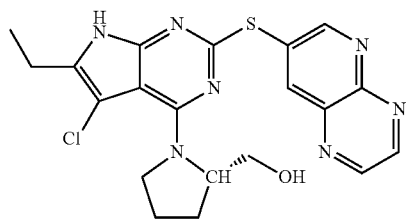 [SMILES: CCc1[nH]c2nc(Sc3cnc4nccnc4c3)nc(N3CCC[C@H]3CO)c2c1Cl] | Chemistry 60 |
| 700,427 | 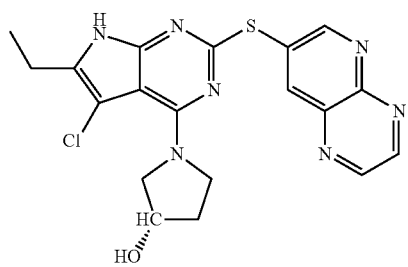 [SMILES: CCc1[nH]c2nc(Sc3cnc4nccnc4c3)nc(N3CC[C@H](O)C3)c2c1Cl] | Chemistry 61 |
| 700,428 | 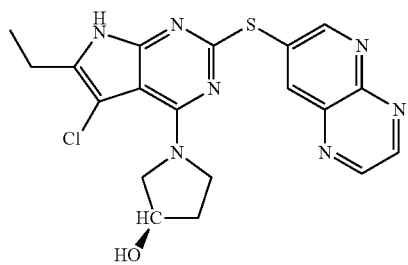 [SMILES: CCc1[nH]c2nc(Sc3cnc4nccnc4c3)nc(N3CC[C@@H](O)C3)c2c1Cl] | Chemistry 62 |

| Rx ID | CHEMISTRY | |
|---|---|---|
| 700,429 | 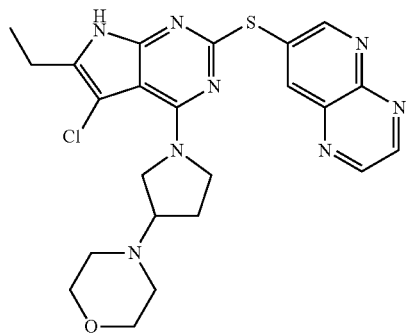 [SMILES: CCc1[nH]c2nc(Sc3cnc4nccnc4c3)nc(N3CCC(N4CCOCC4)C3)c2c1Cl] | Chemistry 63 |
| 700,430 | 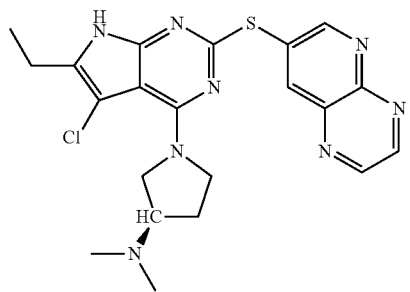 [SMILES: CCc1[nH]c2nc(Sc3cnc4nccnc4c3)nc(N3CC[C@@H](N(C)C)C3)c2c1Cl] | Chemistry 64 |
| 700,431 | 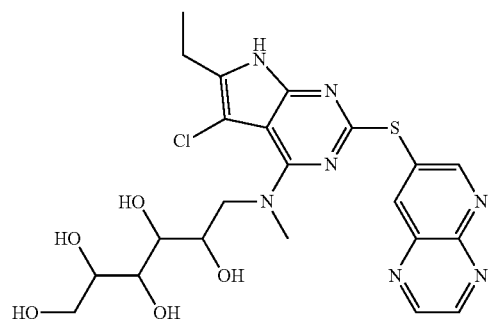 [SMILES: CCc1[nH]c2nc(Sc3cnc4nccnc4c3)nc(N(C)CC(O)C(O)C(O)C(O)CO)c2c1Cl] | Chemistry 65 |
| 700,432 | 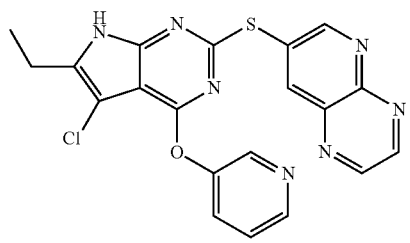 [SMILES: CCc1[nH]c2nc(Sc3cnc4nccnc4c3)nc(Oc3cccnc3)c2c1Cl] | Chemistry 66 |
| 700,434 | 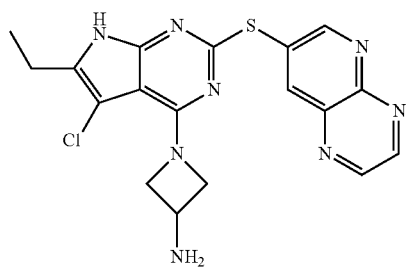 [SMILES: CCc1[nH]c2nc(Sc3cnc4nccnc4c3)nc(N3CC(N)C3)c2c1Cl] | Chemistry 67 |

| Rx ID | CHEMISTRY | |
|---|---|---|
| 700,444 | 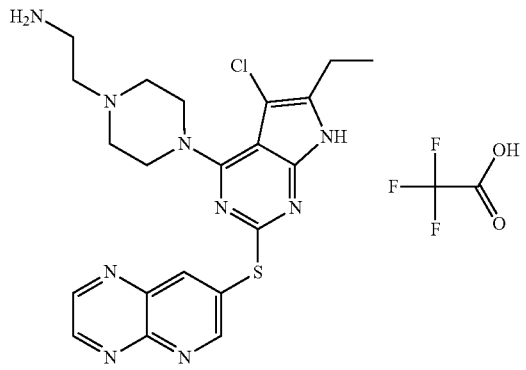 [SMILES: CCc1[nH]c2nc(Sc3cnc4nccnc4c3)nc(N3CCN(CCN)CC3)c2c1Cl ; O=C(O)C(F)(F)F] | Chemistry 68 |
| 700,445 | 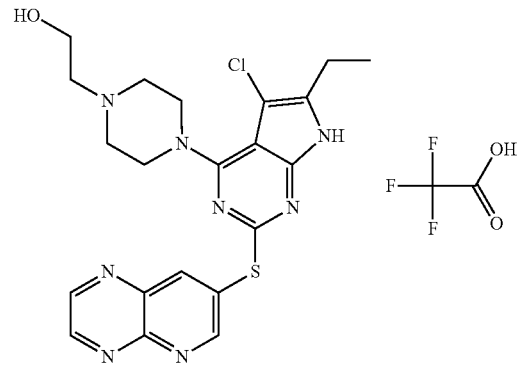 [SMILES: CCc1[nH]c2nc(Sc3cnc4nccnc4c3)nc(N3CCN(CCO)CC3)c2c1Cl ; O=C(O)C(F)(F)F] | Chemistry 69 |
| 101,566 | 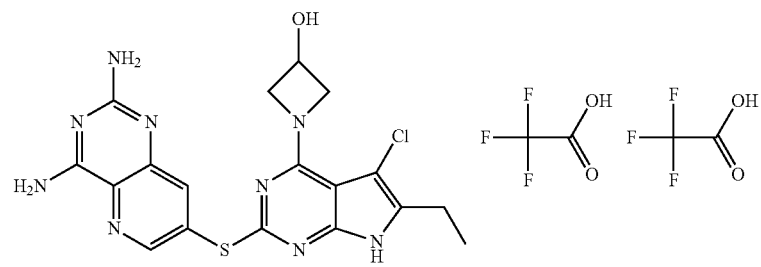 | Chemistry 70 |
| 700,448 | 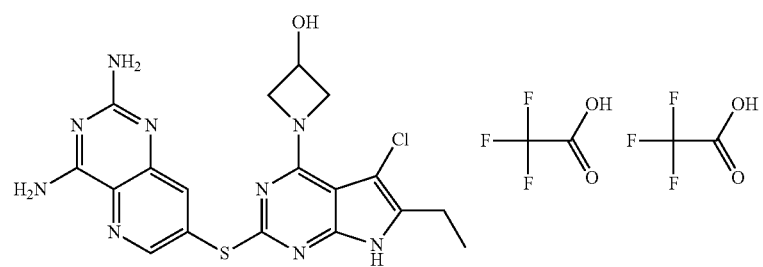 | Chemistry 71 |

| Rx ID | CHEMISTRY | |
|---|---|---|
| 700,449 | 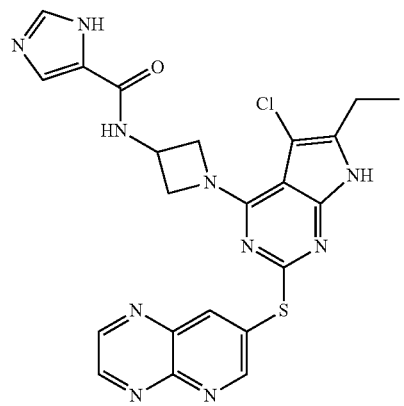 [SMILES: CCc1[nH]c2nc(Sc3cnc4nccnc4c3)nc(N3CC(NC(=O)c4cnc[nH]4)C3)c2c1Cl] | Chemistry 72 |
| 700,453 | 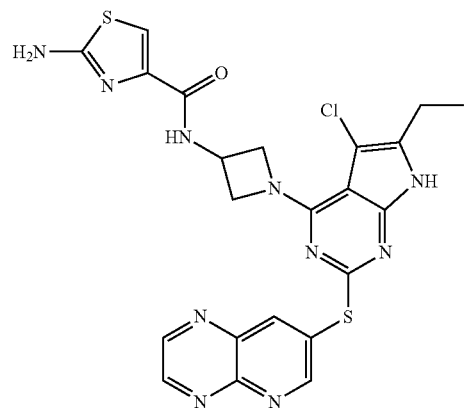 [SMILES: CCc1[nH]c2nc(Sc3cnc4nccnc4c3)nc(N3CC(NC(=O)c4csc(N)n4)C3)c2c1Cl] | Chemistry 73 |
| 700,454 | 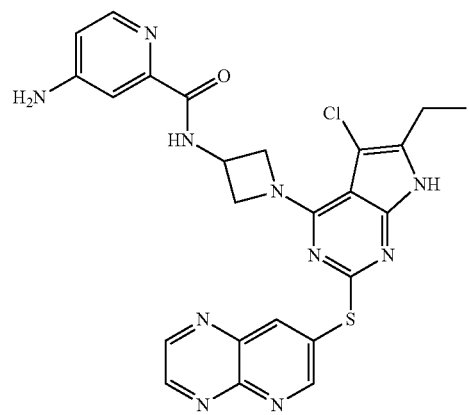 [SMILES: CCc1[nH]c2nc(Sc3cnc4nccnc4c3)nc(N3CC(NC(=O)c4cc(N)ccn4)C3)c2c1Cl] | Chemistry 74 |

| Rx ID | CHEMISTRY | |
|---|---|---|
| 700,455 | 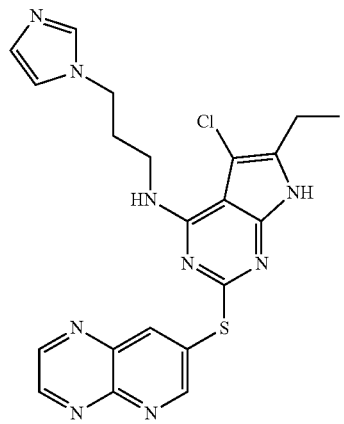 [SMILES: CCc1[nH]c2nc(Sc3cnc4nccnc4c3)nc(NCCCn3ccnc3)c2c1Cl] | Chemistry 75 |
| 700,456 | 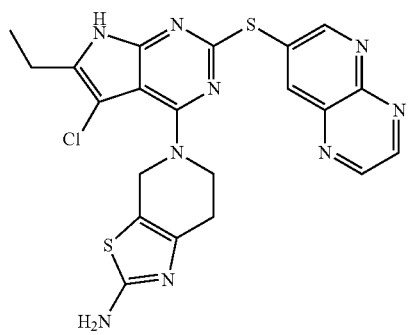 [SMILES: CCc1[nH]c2nc(Sc3cnc4nccnc4c3)nc(N3CCc4nc(N)sc4C3)c2c1Cl] | Chemistry 76 |
| 700,457 | 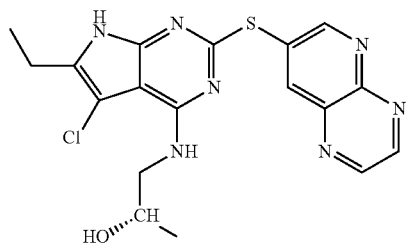 [SMILES: CCc1[nH]c2nc(Sc3cnc4nccnc4c3)nc(NC[C@H](C)O)c2c1Cl] | Chemistry 77 |
| 700,458 | 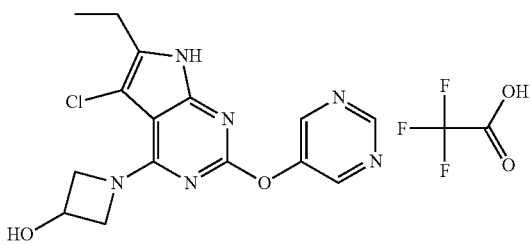 | Chemistry 78 |
| 700,459 | 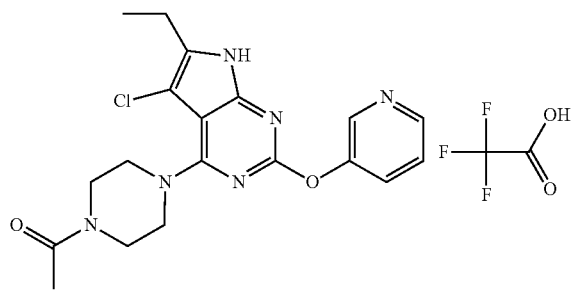 | Chemistry 79 |

| Rx ID | CHEMISTRY | |
|---|---|---|
| 700,460 | 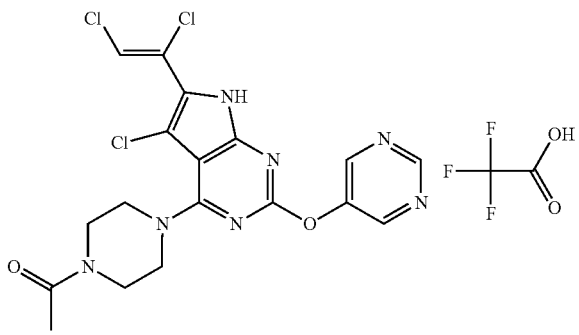 | Chemistry 80 |
| 700,461 | 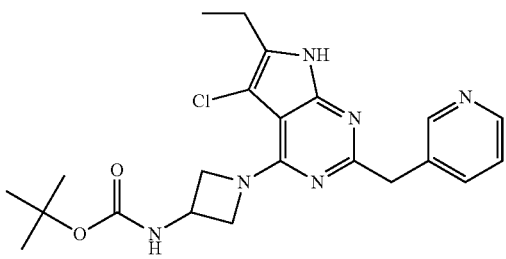 [SMILES: CCc1[nH]c2nc(Cc3cccnc3)nc(N3CC(NC(=O)OC(C)(C)C)C3)c2c1Cl] | Chemistry 81 |
| 700,462 | 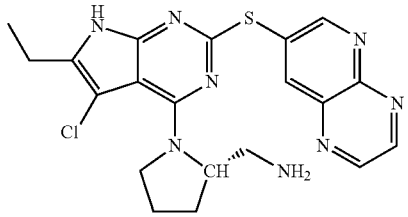 | Chemistry 82 |
| 700,463 | 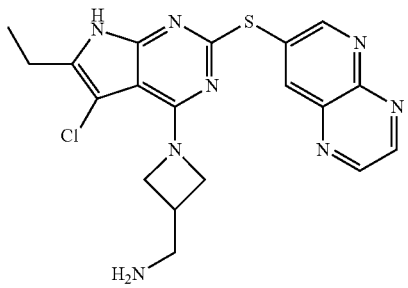 | Chemistry 83 |
| 700,464 | 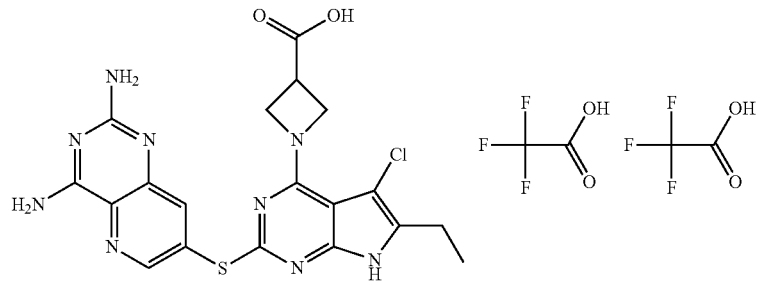 | Chemistry 84 |

| Rx ID | CHEMISTRY | |
|---|---|---|
| 700,465 | 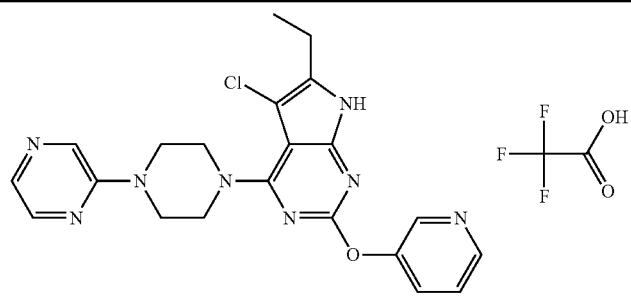 | Chemistry 85 |
| 700,466 | 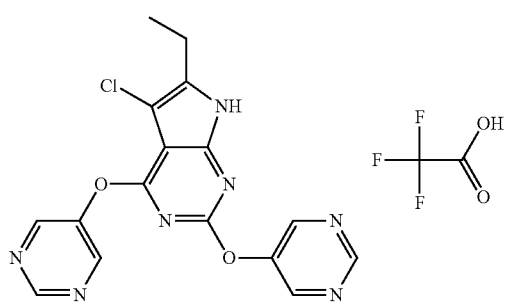 | Chemistry 86 |
| 700,472 | 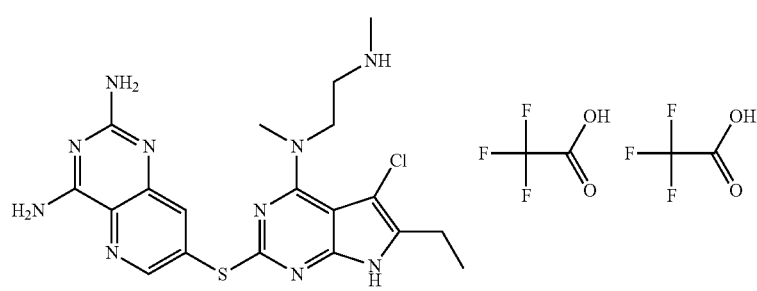 | Chemistry 87 |
| 700,473 | 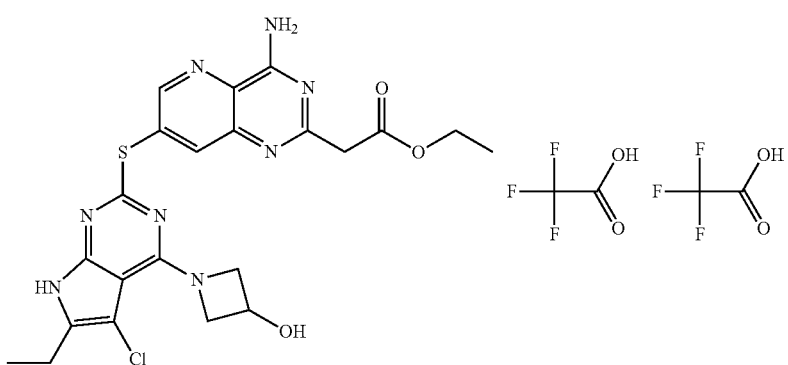 | Chemistry 88 |
| 700,474 | 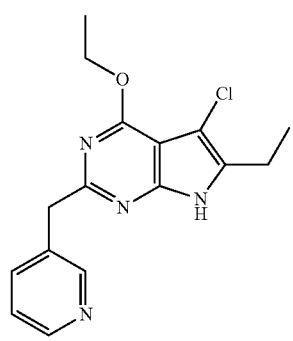 [SMILES: CCOc1nc(Cc2cccnc2)nc2[nH]c(CC)c(Cl)c12] | Chemistry 89 |

| Rx ID | CHEMISTRY | |
|---|---|---|
| 700,477 | 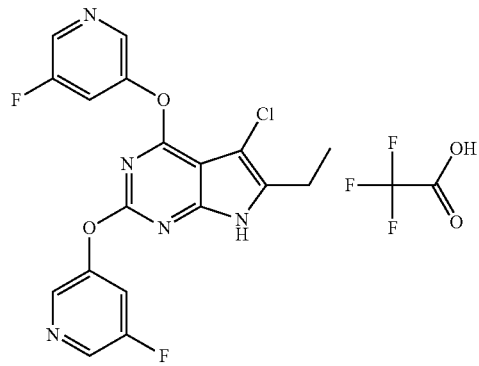 | Chemistry 90 |
| 700,478 | 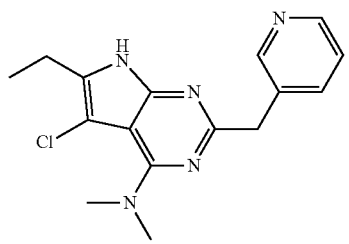 [SMILES: CCc1[nH]c2nc(Cc3cccnc3)nc(N(C)C)c2c1Cl] | Chemistry 91 |
| 700,479 | 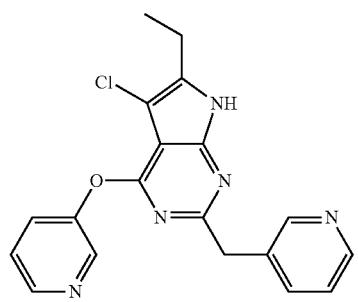 [SMILES: CCc1[nH]c2nc(Cc3cccnc3)nc(Oc3cccnc3)c2c1Cl] | Chemistry 92 |
| 700,480 | 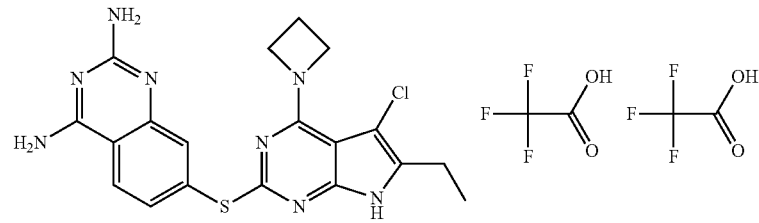 | Chemistry 93 |
| 700,486 | 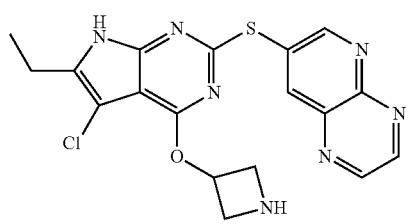 | Chemistry 94 |

| Rx ID | CHEMISTRY | |
|---|---|---|
| 700,487 | 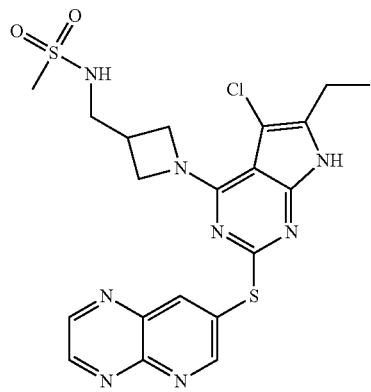 [SMILES: CCc1[nH]c2nc(Sc3cnc4nccnc4c3)nc(N3CC(CNS(C)(=O)=O)C3)c2c1Cl] | Chemistry 95 |
| 700,499 | 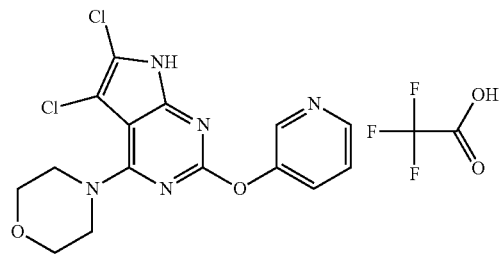 | Chemistry 96 |
| 700,500 | 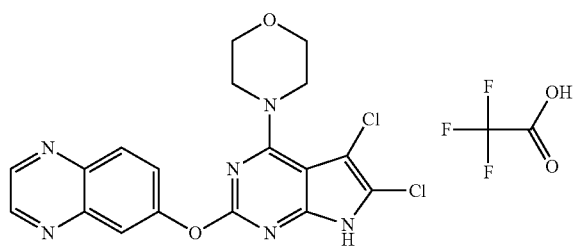 [SMILES: Clc1[nH]c2nc(Oc3ccc4nccnc4c3)nc(N3CCOCC3)c2c1Cl ; O=C(O)C(F)(F)F] | Chemistry 97 |
| 700,501 | 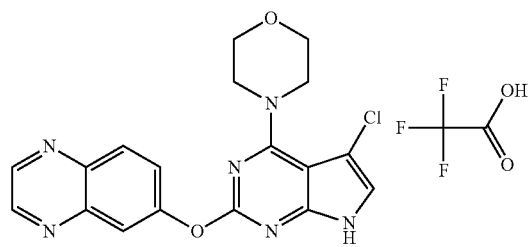 | Chemistry 98 |
| 700,490 | 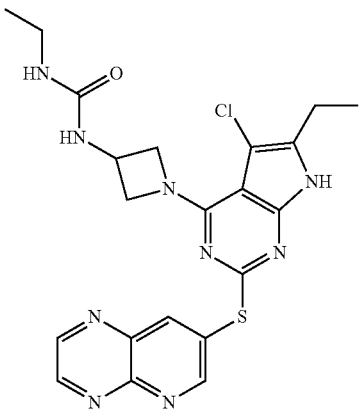 [SMILES: CCNC(=O)NC1CN(c2nc(Sc3cnc4nccnc4c3)nc3[nH]c(CC)c(Cl)c23)C1] | Chemistry 99 |

| Rx ID | CHEMISTRY | |
|---|---|---|
| 700,491 | 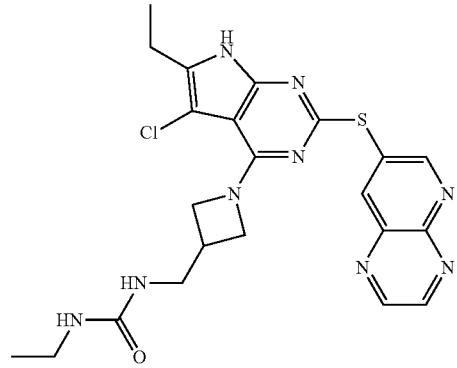 [SMILES: CCNC(=O)NCC1CN(c2nc(Sc3cnc4nccnc4c3)nc3[nH]c(CC)c(Cl)c23)C1] | Chemistry 100 |
| 700,492 | 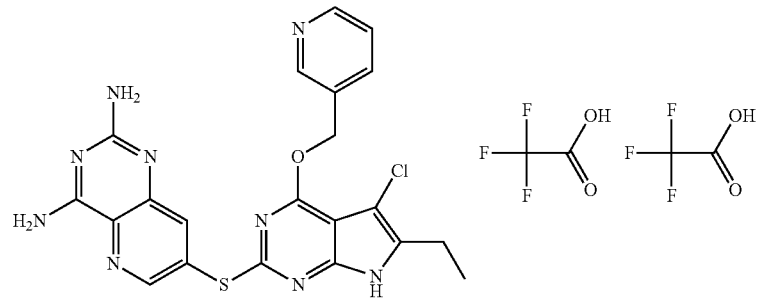 | Chemistry 101 |
| 700,493 | 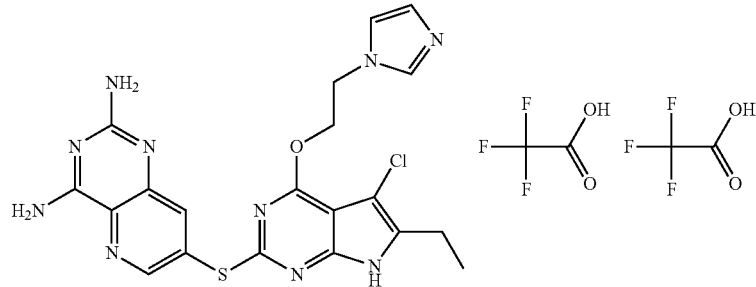 | Chemistry 102 |
| 700,494 | 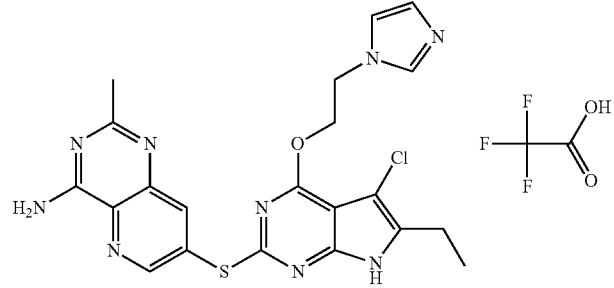 [SMILES: CCc1[nH]c2nc(Sc3cnc4c(N)nc(C)nc4c3)nc(OCCn3ccnc3)c2c1Cl ; O=C(O)C(F)(F)F] | Chemistry 103 |
| 700,495 | 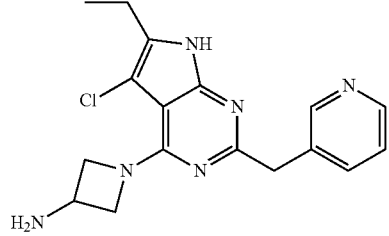 [SMILES: CCc1[nH]c2nc(Cc3cccnc3)nc(N3CC(N)C3)c2c1Cl] | Chemistry 104 |

| Rx ID | CHEMISTRY | |
|---|---|---|
| 700,497 | 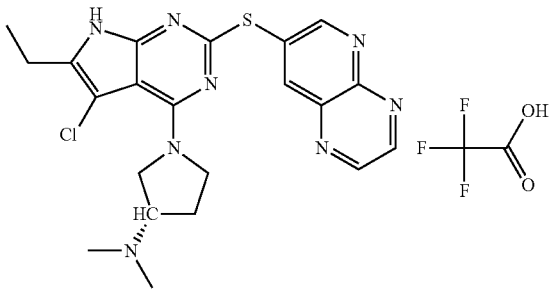 | Chemistry 105 |
| 700,502 | 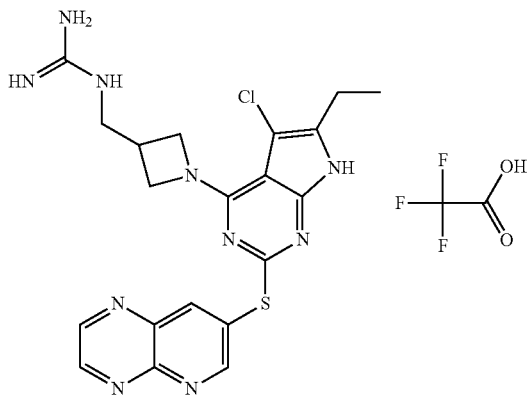 [SMILES: CCc1[nH]c2nc(Sc3cnc4nccnc4c3)nc(N3CC(CNC(=N)N)C3)c2c1Cl ; O=C(O)C(F)(F)F] | Chemistry 106 |
| 700,503 | 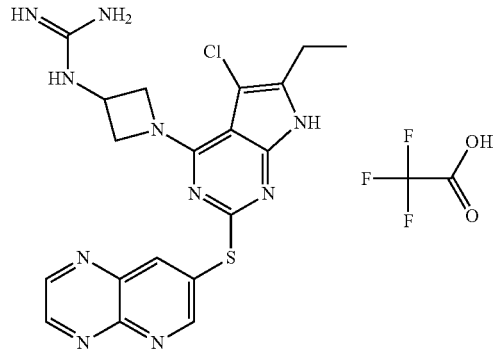 [SMILES: CCc1[nH]c2nc(Sc3cnc4nccnc4c3)nc(N3CC(NC(=N)N)C3)c2c1Cl ; O=C(O)C(F)(F)F] | Chemistry 107 |
| 700,504 | 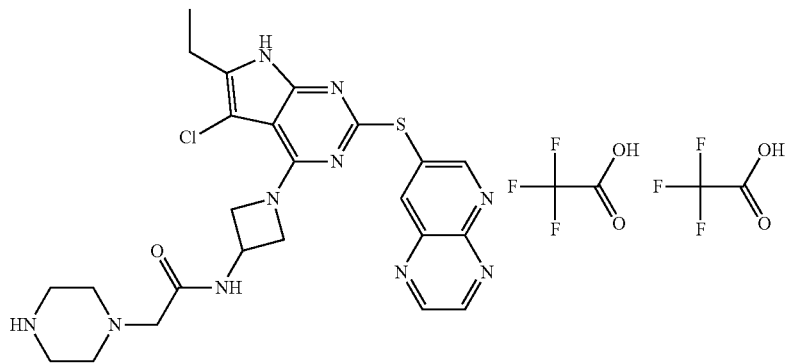 | Chemistry 108 |

| Rx ID | CHEMISTRY | |
|---|---|---|
| 700,505 | 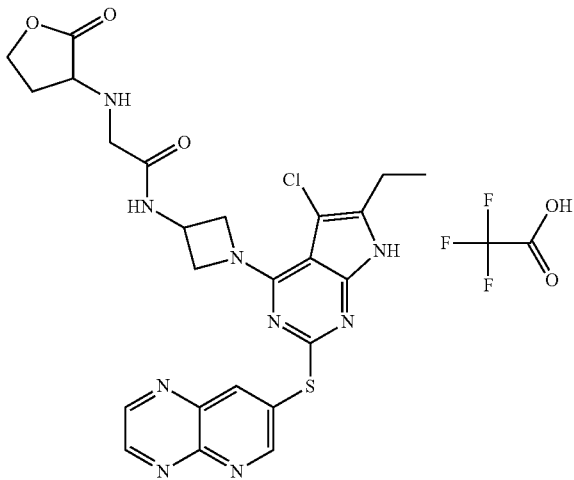 [SMILES: CCc1[nH]c2nc(Sc3cnc4nccnc4c3)nc(N3CC(NC(=O)CNC4CCOC4=O)C3)c2c1Cl ; O=C(O)C(F)(F)F] | Chemistry 109 |
| 700,506 | 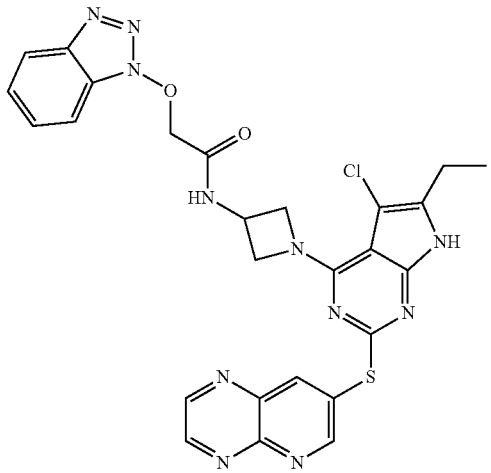 [SMILES: CCc1[nH]c2nc(Sc3cnc4nccnc4c3)nc(N3CC(NC(=O)COn4nnc5ccccc54)C3)c2c1Cl] | Chemistry 110 |
| 700,507 | 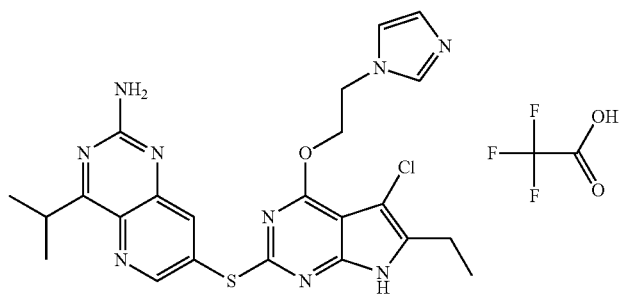 [SMILES: CCc1[nH]c2nc(Sc3cnc4c(C(C)C)nc(N)nc4c3)nc(OCCn3ccnc3)c2c1Cl ; O=C(O)C(F)(F)F] | Chemistry 111 |
| 700,508 | 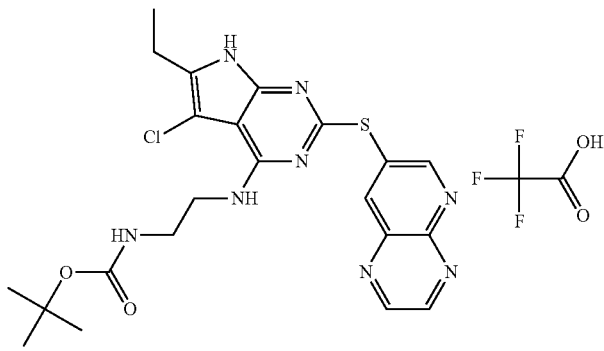 | Chemistry 112 |

| Rx ID | CHEMISTRY | |
|---|---|---|
| 700,509 | 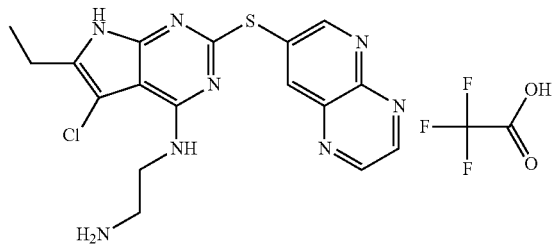 | Chemistry 113 |
| 700,510 | 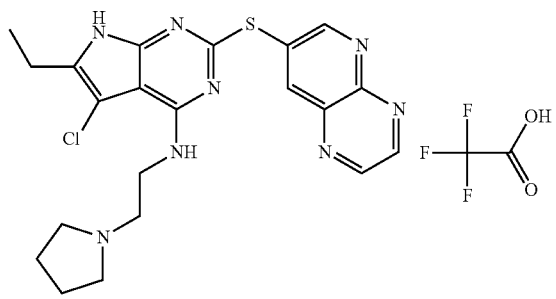 | Chemistry 114 |
| 700,511 | 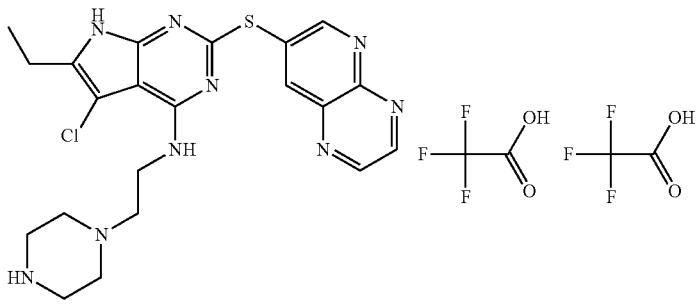 | Chemistry 115 |
| 700,512 | 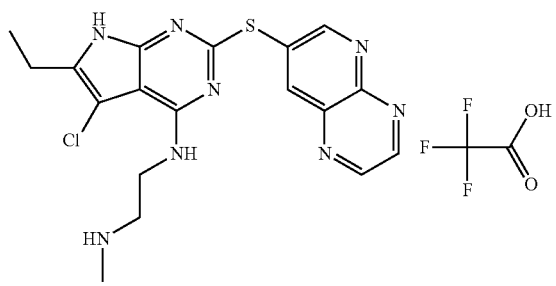 | Chemistry 116 |
| 700,513 | 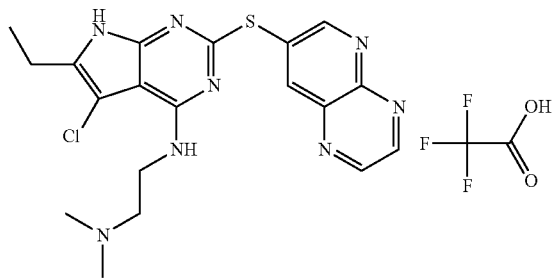 | Chemistry 117 |

| Rx ID | CHEMISTRY | |
|---|---|---|
| 700,514 | 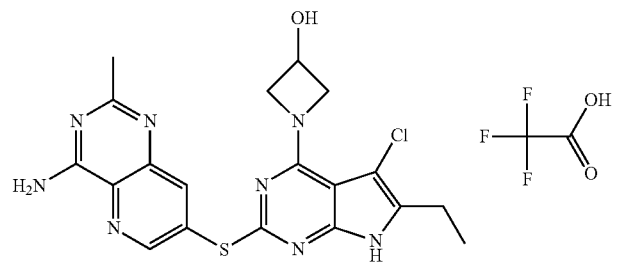 [SMILES: CCc1[nH]c2nc(Sc3cnc4c(N)nc(C)nc4c3)nc(N3CC(O)C3)c2c1Cl ; O=C(O)C(F)(F)F] | Chemistry 118 |
| 700,515 | 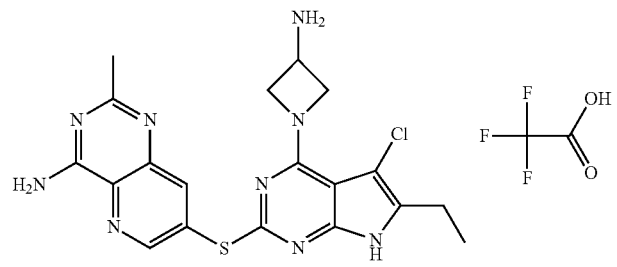 [SMILES: CCc1[nH]c2nc(Sc3cnc4c(N)nc(C)nc4c3)nc(N3CC(N)C3)c2c1Cl ; O=C(O)C(F)(F)F] | Chemistry 119 |
| 700,516 | 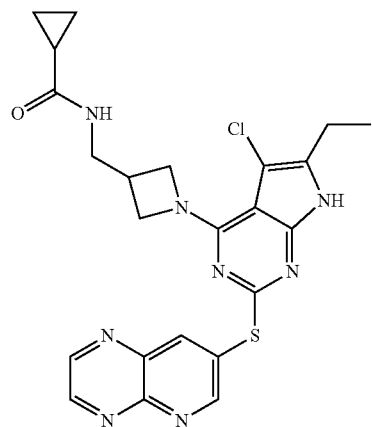 [SMILES: CCc1[nH]c2nc(Sc3cnc4nccnc4c3)nc(N3CC(CNC(=O)C4CC4)C3)c2c1Cl] | Chemistry 120 |
| 700,517 | 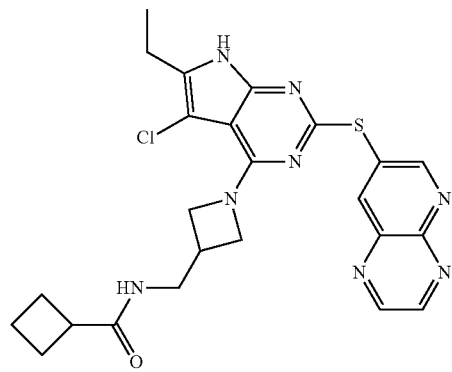 [SMILES: CCc1[nH]c2nc(Sc3cnc4nccnc4c3)nc(N3CC(CNC(=O)C4CCC4)C3)c2c1Cl] | Chemistry 121 |

| Rx ID | CHEMISTRY | |
|---|---|---|
| 700,518 | 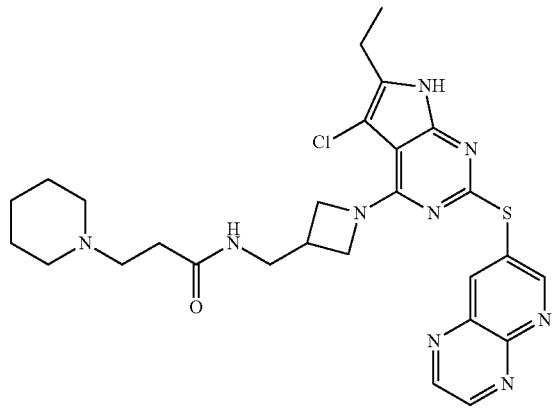 [SMILES: CCc1[nH]c2nc(Sc3cnc4nccnc4c3)nc(N3CC(CNC(=O)CCN4CCCCC4)C3)c2c1Cl] | Chemistry 122 |
| 700,519 | 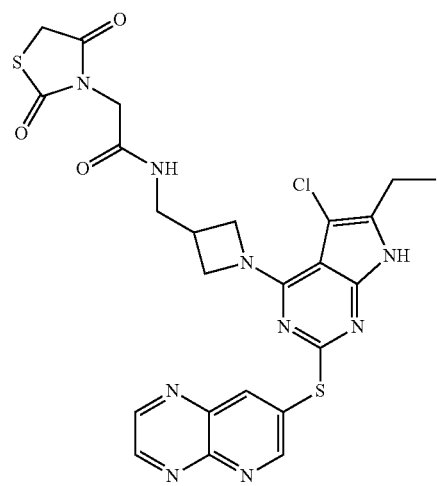 [SMILES: CCc1[nH]c2nc(Sc3cnc4nccnc4c3)nc(N3CC(CNC(=O)CN4C(=O)CSC4=O)C3)c2c1Cl] | Chemistry 123 |
| 700,520 | 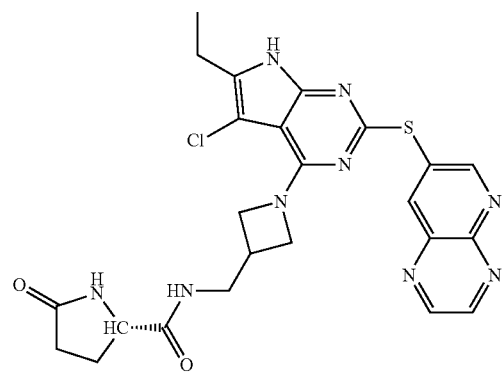 [SMILES: CCc1[nH]c2nc(Sc3cnc4nccnc4c3)nc(N3CC(CNC(=O)[C@@H]4CCC(=O)N4)C3)c2c1Cl] | Chemistry 124 |

| Rx ID | CHEMISTRY | |
|---|---|---|
| 700,521 | 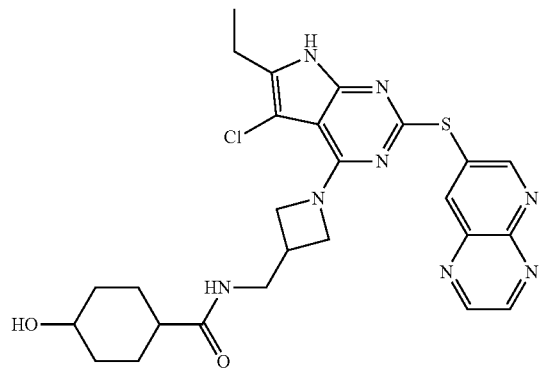 [SMILES: CCc1[nH]c2nc(Sc3cnc4nccnc4c3)nc(N3CC(CNC(=O)C4CCC(O)CC4)C3)c2c1Cl] | Chemistry 125 |
| 700,522 | 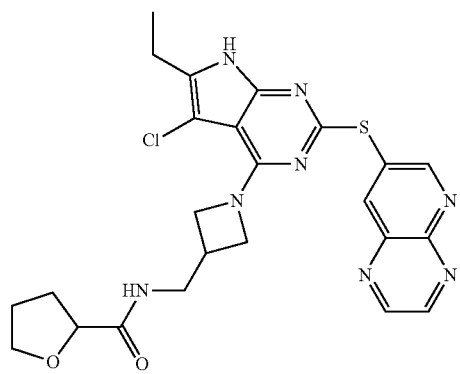 [SMILES: CCc1[nH]c2nc(Sc3cnc4nccnc4c3)nc(N3CC(CNC(=O)C4CCCO4)C3)c2c1Cl] | Chemistry 126 |
| 700,523 | 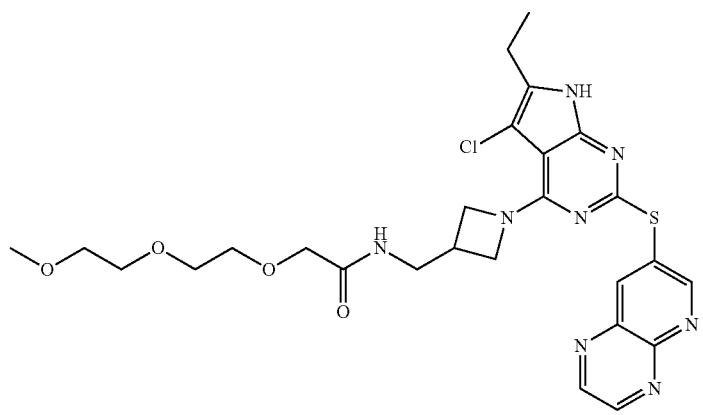 [SMILES: CCc1[nH]c2nc(Sc3cnc4nccnc4c3)nc(N3CC(CNC(=O)COCCOCCOC)C3)c2c1Cl] | Chemistry 127 |
| 700,524 | 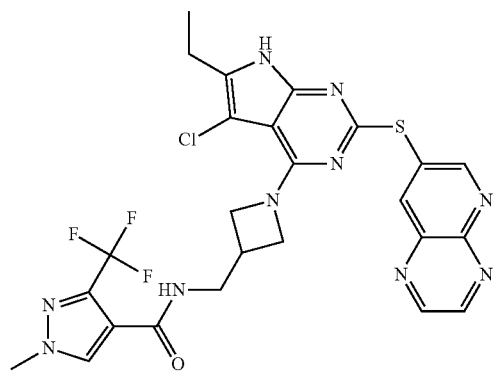 [SMILES: CCc1[nH]c2nc(Sc3cnc4nccnc4c3)nc(N3CC(CNC(=O)c4cn(C)nc4C(F)(F)F)C3)c2c1Cl] | Chemistry 128 |

| Rx ID | CHEMISTRY | |
|---|---|---|
| 700,525 | 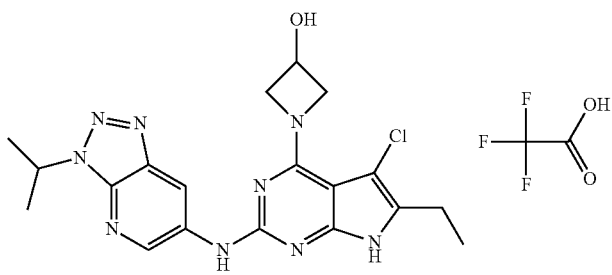 [SMILES: CCc1[nH]c2nc(Nc3cnc4c(c3)nnn4C(C)C)nc(N3CC(O)C3)c2c1Cl ; O=C(O)C(F)(F)F] | Chemistry 129 |
| 700,526 | 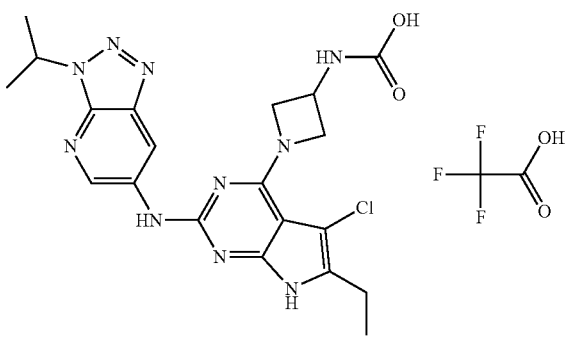 [SMILES: CCc1[nH]c2nc(Nc3cnc4c(c3)nnn4C(C)C)nc(N3CC(NC(=O)O)C3)c2c1Cl ; O=C(O)C(F)(F)F] | Chemistry 130 |
| 700,527 | 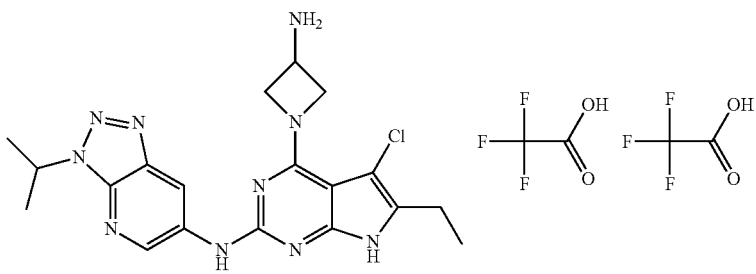 | Chemistry 131 |
| 700,528 | 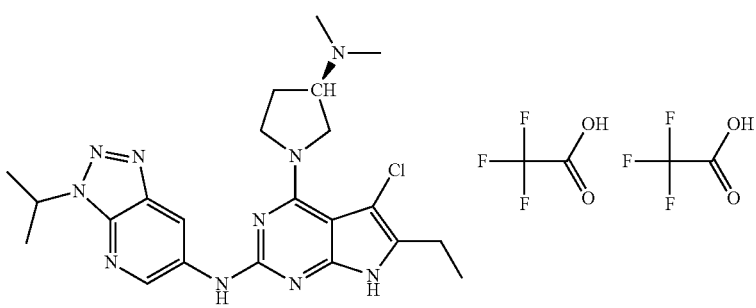 | Chemistry 132 |
| 700,529 | 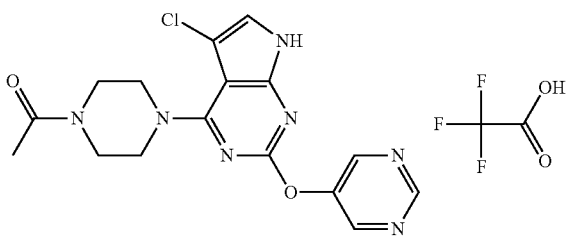 | Chemistry 133 |

| Rx ID | CHEMISTRY | |
|---|---|---|
| 700,530 | 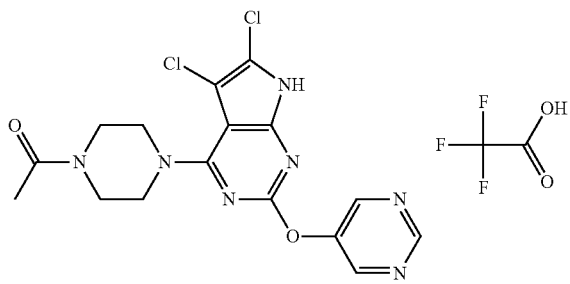 [SMILES: CC(=O)N1CCN(c2nc(Oc3cncnc3)nc3[nH]c(Cl)c(Cl)c23)CC1 ; O=C(O)C(F)(F)F] | Chemistry 134 |
| 700,531 | 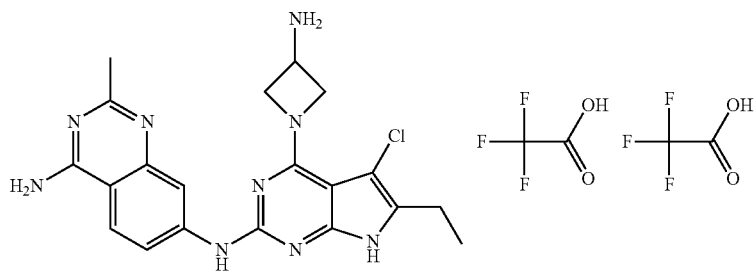 | Chemistry 135 |
| 700,534 | 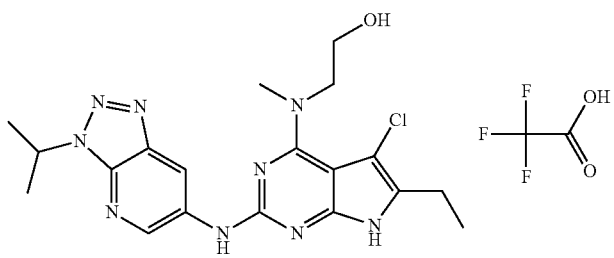 [SMILES: CCc1[nH]c2nc(Nc3cnc4c(c3)nnn4C(C)C)nc(N(C)CCO)c2c1Cl ; O=C(O)C(F)(F)F] | Chemistry 137 |
| 700,539 | 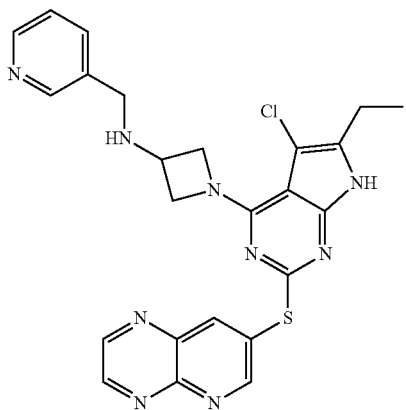 [SMILES: CCc1[nH]c2nc(Sc3cnc4nccnc4c3)nc(N3CC(NCc4cccnc4)C3)c2c1Cl] | Chemistry 138 |
| 700,540 | 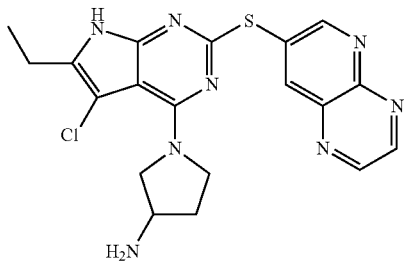 [SMILES: CCc1[nH]c2nc(Sc3cnc4nccnc4c3)nc(N3CCC(N)C3)c2c1Cl] | Chemistry 139 |

| Rx ID | CHEMISTRY | |
|---|---|---|
| 700,541 | 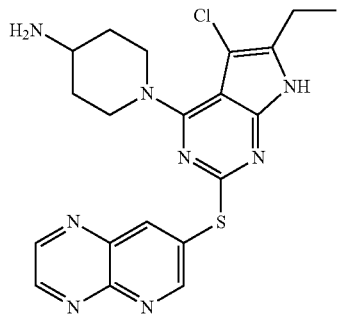 [SMILES: CCc1[nH]c2nc(Sc3cnc4nccnc4c3)nc(N3CCC(N)CC3)c2c1Cl] | Chemistry 140 |
| 700,542 | 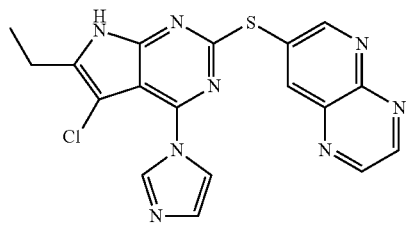 [SMILES: CCc1[nH]c2nc(Sc3cnc4nccnc4c3)nc(-n3ccnc3)c2c1Cl] | Chemistry 141 |
| 700,543 | 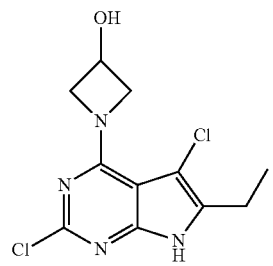 [SMILES: CCc1[nH]c2nc(Cl)nc(N3CC(O)C3)c2c1Cl] | Chemistry 142 |
| 700,546 | 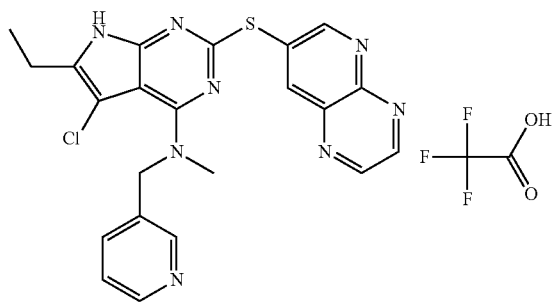 | Chemistry 143 |
| 700,559 | 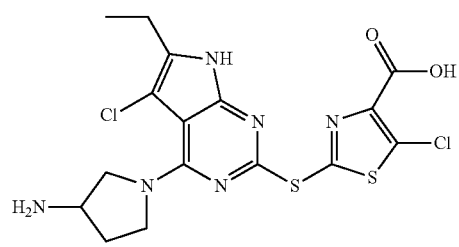 [SMILES: CCc1[nH]c2nc(Sc3nc(C(=O)O)c(Cl)s3)nc(N3CCC(N)C3)c2c1Cl] | Chemistry 144 |

| Rx ID | CHEMISTRY | |
|---|---|---|
| 700,547 | 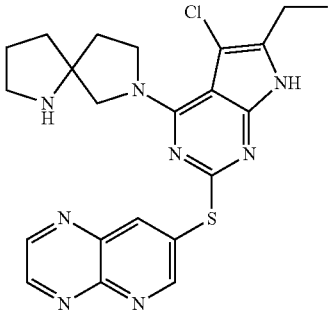 [SMILES: CCc1[nH]c2nc(Sc3cnc4nccnc4c3)nc(N3CCC4(CCCN4)C3)c2c1Cl] | Chemistry 145 |
| 700,548 | 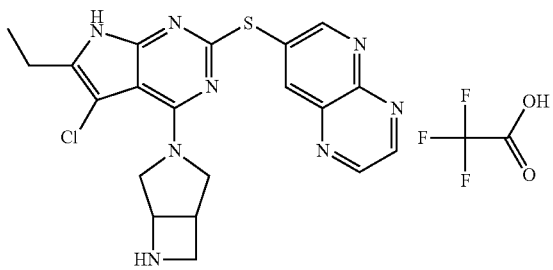 | Chemistry 146 |
| 700,549 |  | Chemistry 147 |
| 700,550 | 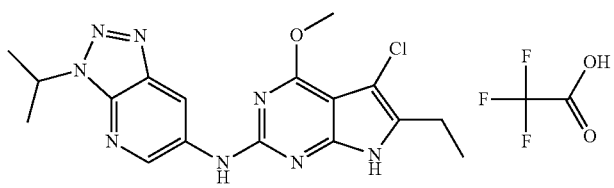 | Chemistry 148 |
| 700,551 | 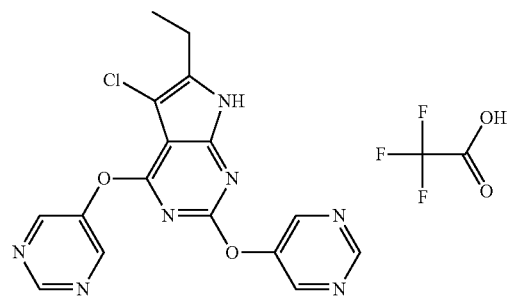 [SMILES: CCc1[nH]c2nc(Oc3cncnc3)nc(Oc3cncnc3)c2c1Cl ; O=C(O)C(F)(F)F] | Chemistry 149 |
| 700,544 | 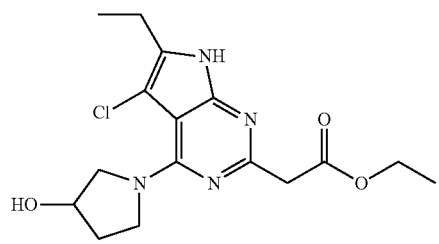 [SMILES: CCOC(=O)Cc1nc(N2CCC(O)C2)c2c(Cl)c(CC)[nH]c2n1] | Chemistry 150 |

-continued
| Rx ID | CHEMISTRY | |
|---|---|---|
| 700,558 | 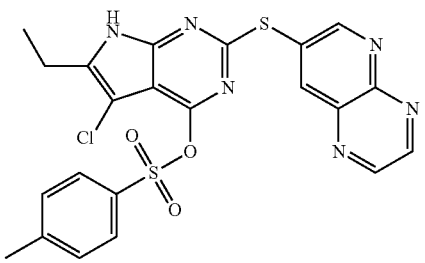 [SMILES: CCc1[nH]c2nc(Sc3cnc4nccnc4c3)nc(OS(=O)(=O)c3ccc(C)cc3)c2c1Cl] | Chemistry 151 |
| 700,560 | 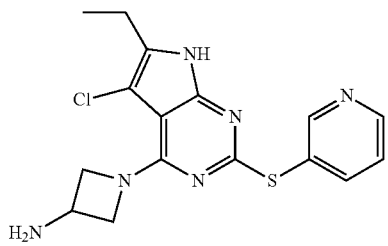 [SMILES: CCc1[nH]c2nc(Sc3cccnc3)nc(N3CC(N)C3)c2c1Cl] | Chemistry 152 |
| 700,561 | 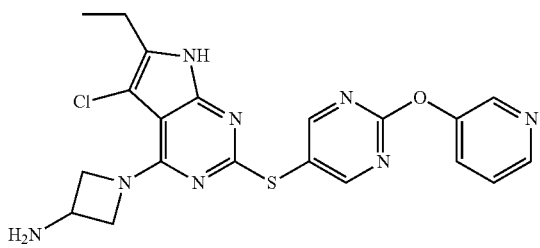 [SMILES: CCc1[nH]c2nc(Sc3cnc(Oc4cccnc4)nc3)nc(N3CC(N)C3)c2c1Cl] | Chemistry 153 |
| 700,562 | 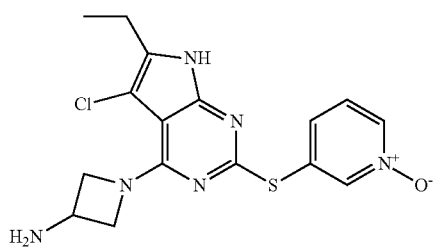 [SMILES: CCc1[nH]c2nc(Sc3ccc[n+]([O-])c3)nc(N3CC(N)C3)c2c1Cl] | Chemistry 154 |
| 700,563 | 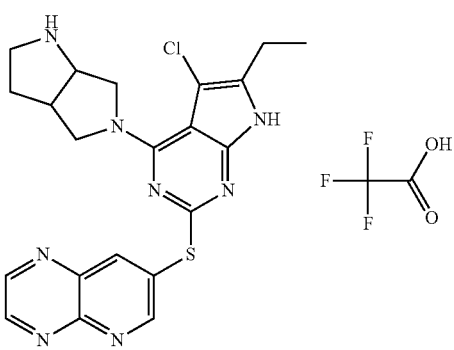 [SMILES: CCc1[nH]c2nc(Sc3cnc4nccnc4c3)nc(N3CC4CCNC4C3)c2c1Cl ; O=C(O)C(F)(F)F] | Chemistry 155 |
| 700,564 | 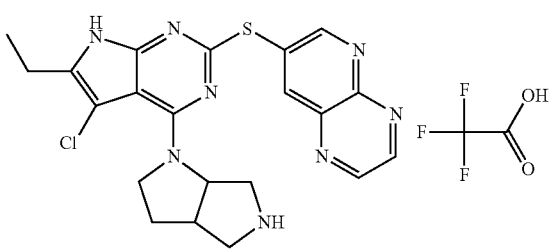 | Chemistry 156 |

| Rx ID | CHEMISTRY | |
|---|---|---|
| 700,565 | 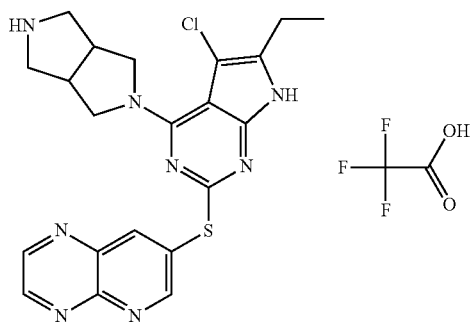 [SMILES: CCc1[nH]c2nc(Sc3cnc4nccnc4c3)nc(N3CC4CNCC4C3)c2c1Cl ; O=C(O)C(F)(F)F] | Chemistry 157 |
| 700,566 | 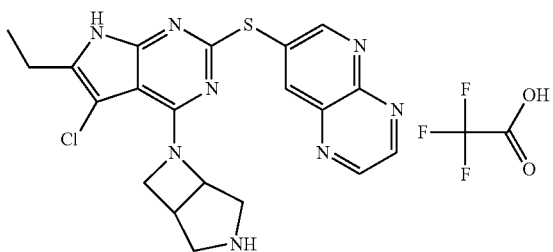 | Chemistry 158 |
| 700,567 | 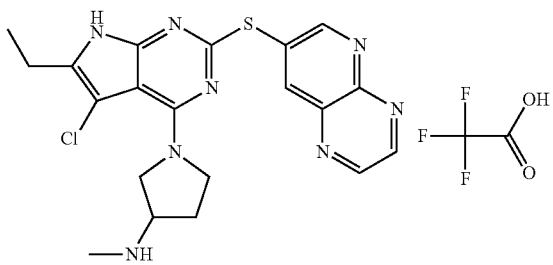 | Chemistry 159 |
| 700,568 | 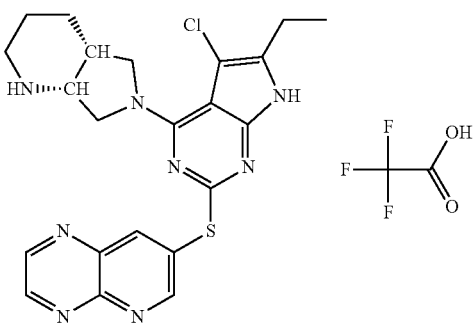 [SMILES: CCc1[nH]c2nc(Sc3cnc4nccnc4c3)nc(N3C[C@H]4CCCN[C@H]4C3)c2c1Cl ; O=C(O)C(F)(F)F] | Chemistry 160 |
| 700,569 | 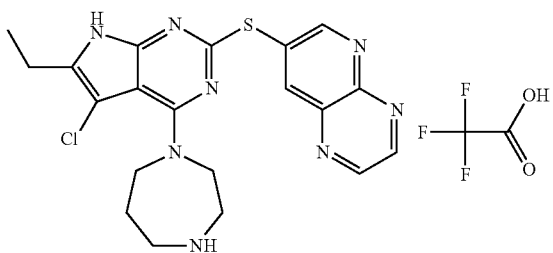 | Chemistry 161 |

-continued
| Rx ID | CHEMISTRY | |
|---|---|---|
| 700,570 | 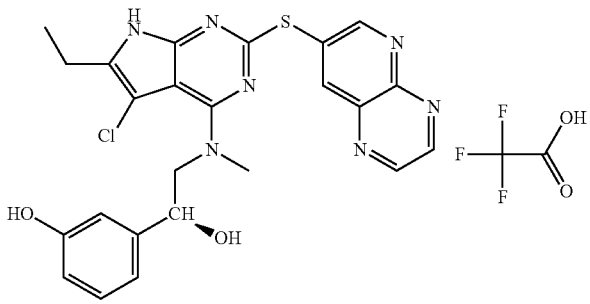 | Chemistry 162 |
| 700,571 | 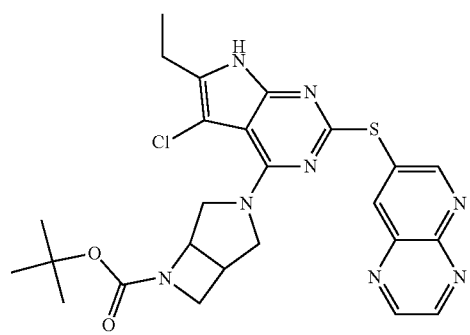 [SMILES: CCc1[nH]c2nc(Sc3cnc4nccnc4c3)nc(N3CC4CN(C(=O)OC(C)(C)C)C4C3)c2c1Cl] | Chemistry 163 |
| 700,573 | 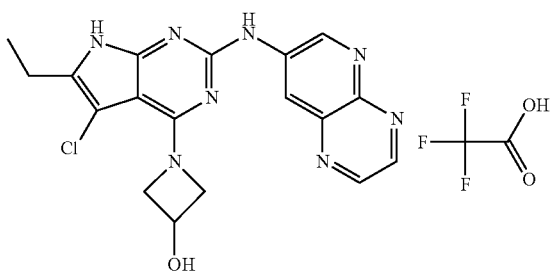 | Chemistry 164 |
| 700,574 | 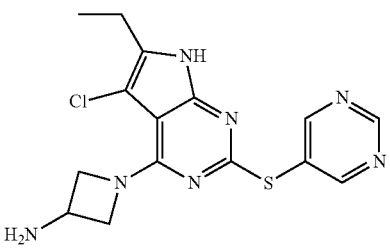 | Chemistry 165 |
| 700,575 | 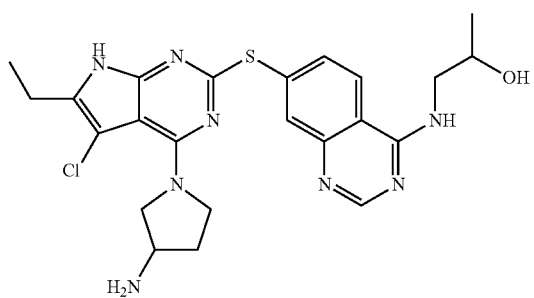 [SMILES: CCc1[nH]c2nc(Sc3ccc4c(NCC(C)O)ncnc4c3)nc(N3CCC(N)C3)c2c1Cl] | Chemistry 166 |

-continued
| Rx ID | CHEMISTRY | |
|---|---|---|
| 700,576 | 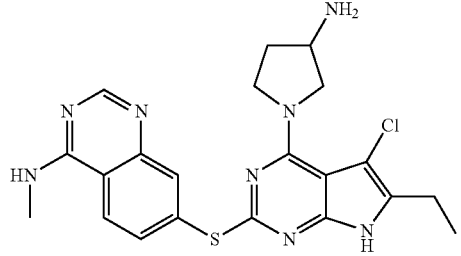 [SMILES: CCc1[nH]c2nc(Sc3ccc4c(NC)ncnc4c3)nc(N3CCC(N)C3)c2c1Cl] | Chemistry 167 |
| 700,577 | 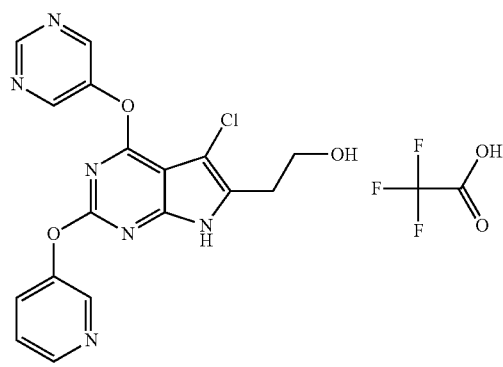 | Chemistry 168 |
| 700,578 | 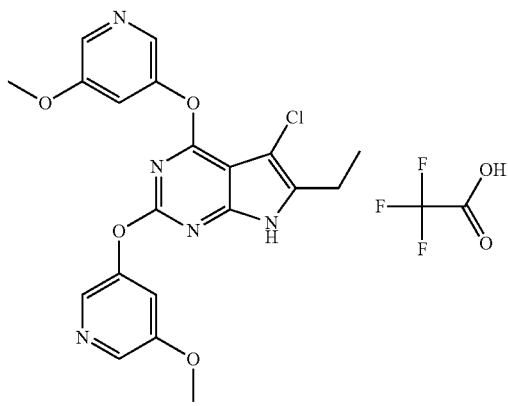 | Chemistry 169 |
| 700,584 | 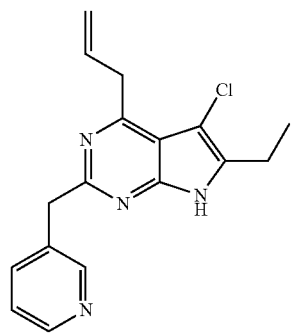 [SMILES: C=CCc1nc(Cc2cccnc2)nc2[nH]c(CC)c(Cl)c12] | Chemistry 170 |

US 10,047,105 B2
263 264
-continued
| Rx ID | CHEMISTRY | |
|---|---|---|
| 700,585 | 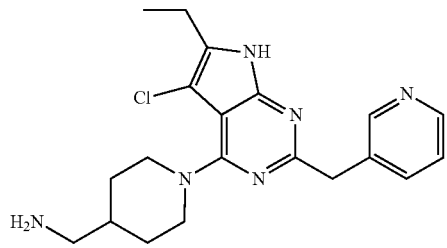 [SMILES: CCc1[nH]c2nc(Cc3cccnc3)nc(N3CCC(CN)CC3)c2c1Cl] | Chemistry 171 |
| 700,586 | 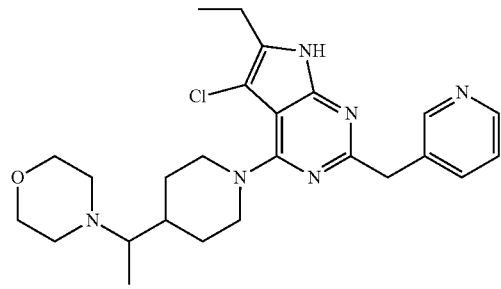 [SMILES: CCc1[nH]c2nc(Cc3cccnc3)nc(N3CCC(C(C)N4CCOCC4)CC3)c2c1Cl] | Chemistry 172 |
| 700,587 | 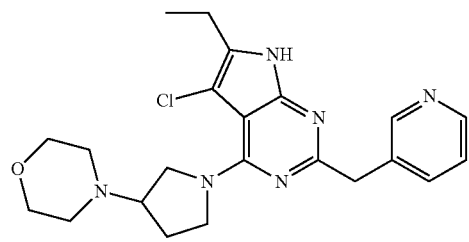 [SMILES: CCc1[nH]c2nc(Cc3cccnc3)nc(N3CCC(N4CCOCC4)C3)c2c1Cl] | Chemistry 173 |
| 700,588 | 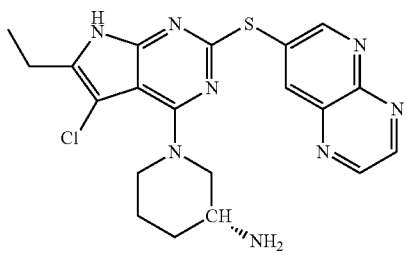 [SMILES: CCc1[nH]c2nc(Sc3cnc4nccnc4c3)nc(N3CCC[C@@H](N)C3)c2c1Cl] | Chemistry 174 |
| 700,589 | 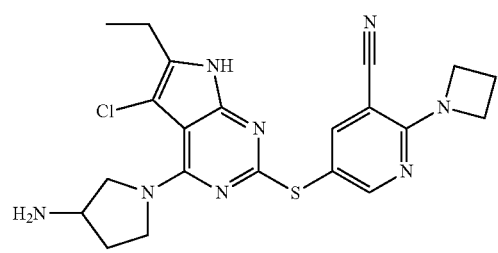 [SMILES: CCc1[nH]c2nc(Sc3cnc(N4CCC4)c(C#N)c3)nc(N3CCC(N)C3)c2c1Cl] | Chemistry 175 |
| 700,590 | 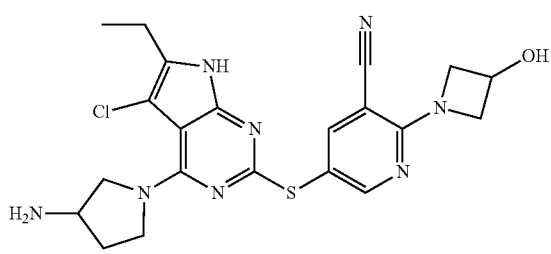 [SMILES: CCc1[nH]c2nc(Sc3cnc(N4CC(O)C4)c(C#N)c3)nc(N3CCC(N)C3)c2c1Cl] | Chemistry 176 |

| Rx ID | CHEMISTRY | |
|---|---|---|
| 700,592 | 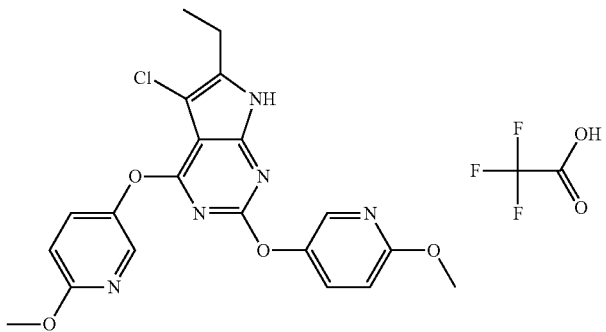 | Chemistry 177 |
| 700,595 | 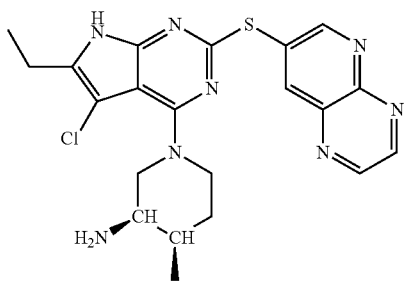 [SMILES: CCc1[nH]c2nc(Sc3cnc4nccnc4c3)nc(N3CC[C@@H](C)[C@@H](N)C3)c2c1Cl] | Chemistry 178 |
| 700,596 | 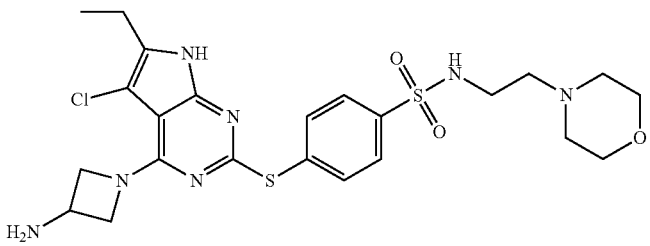 [SMILES: CCc1[nH]c2nc(Sc3ccc(S(=O)(=O)NCCN4CCOCC4)cc3)nc(N3CC(N)C3)c2c1Cl] | Chemistry 179 |
| 700,597 | 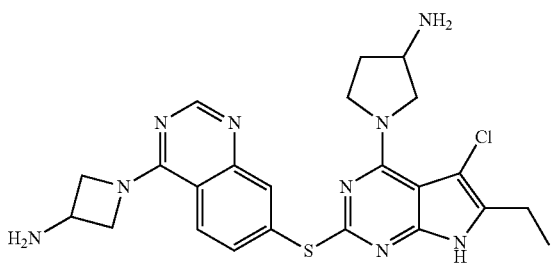 [SMILES: CCc1[nH]c2nc(Sc3ccc4c(N5CC(N)C5)ncnc4c3)nc(N3CCC(N)C3)c2c1Cl] | Chemistry 180 |
| 700,601 | 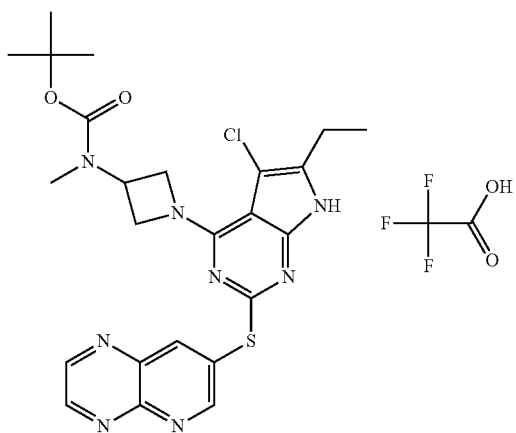 [SMILES: CCc1[nH]c2nc(Sc3cnc4nccnc4c3)nc(N3CC(N(C)C(=O)OC(C)(C)C)C3)c2c1Cl ; O=C(O)C(F)(F)F] | Chemistry 181 |

| Rx ID | CHEMISTRY | |
|---|---|---|
| 700,602 | 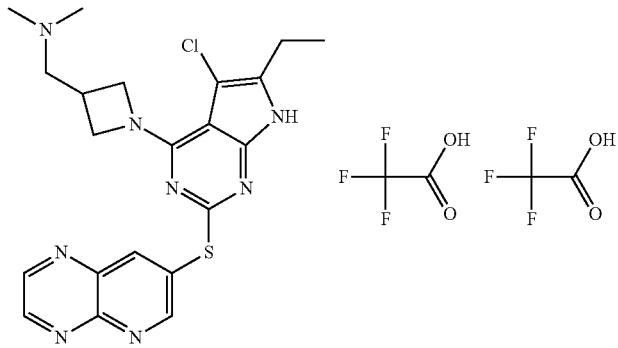 | Chemistry 182 |
| 700,603 | 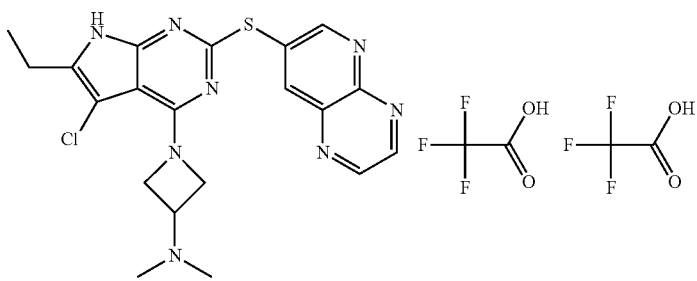 | Chemistry 183 |
| 700,604 | 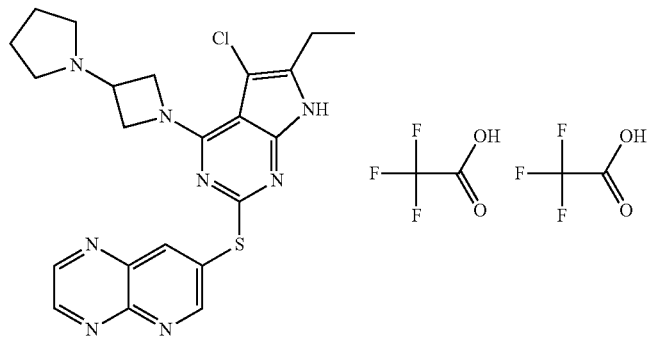 | Chemistry 184 |
| 700,605 | 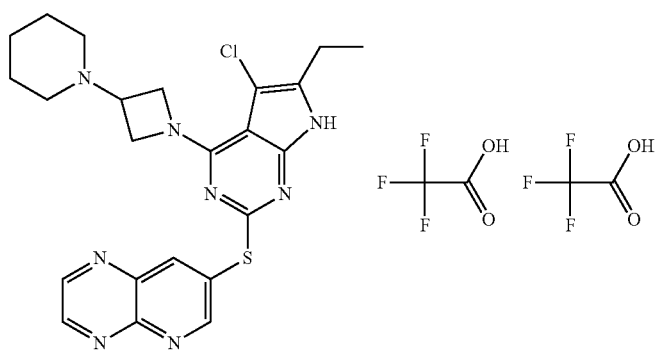 | Chemistry 185 |

| Rx ID | CHEMISTRY | |
|---|---|---|
| 700,606 | 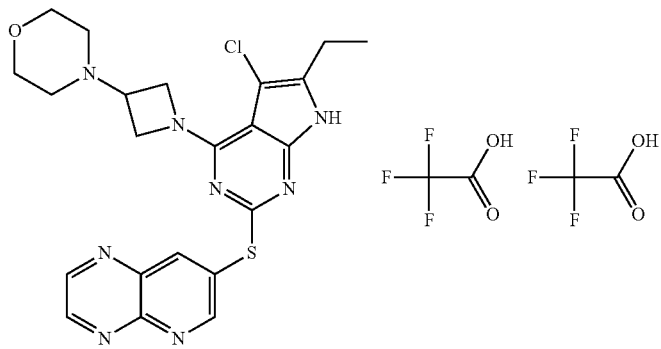 | Chemistry 186 |
| 700,607 | 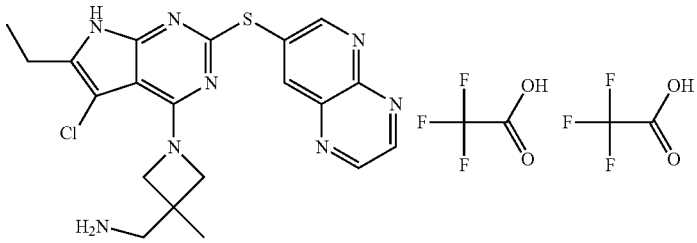 | Chemistry 187 |
| 700,608 | 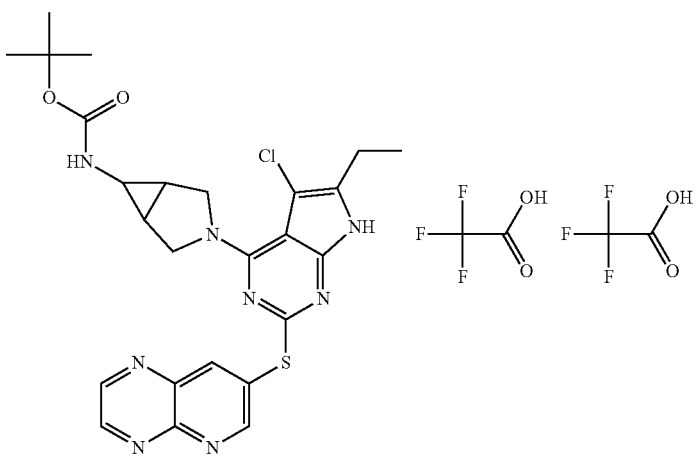 | Chemistry 188 |
| 700,609 | 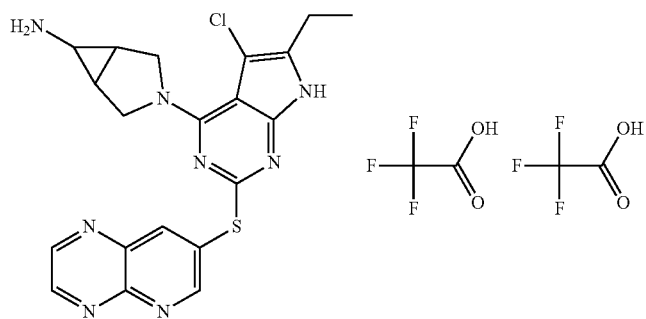 | Chemistry 189 |

US 10,047,105 B2
271                                                                                           272
-continued
| Rx ID | CHEMISTRY | |
|---|---|---|
| 700,611 | 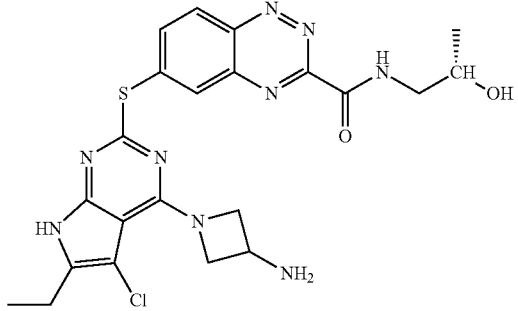 [SMILES: CCc1[nH]c2nc(Sc3ccc4nnc(C(=O)NC[C@H](C)O)nc4c3)nc(N3CC(N)C3)c2c1Cl] | Chemistry 190 |
| 700,612 | 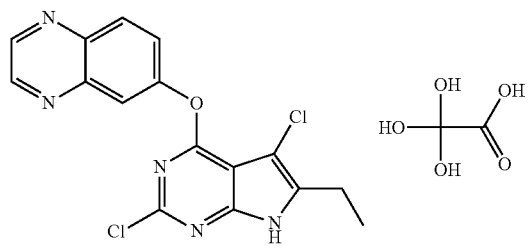 [SMILES: CCc1[nH]c2nc(Cl)nc(Oc3ccc4nccnc4c3)c2c1Cl ; O=C(O)C(O)(O)O] | Chemistry 191 |
| 700,613 | 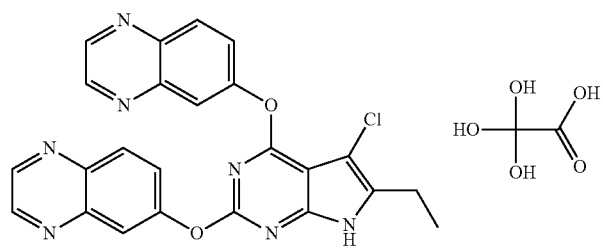 [SMILES: CCc1[nH]c2nc(Oc3ccc4nccnc4c3)nc(Oc3ccc4nccnc4c3)c2c1Cl ; O=C(O)C(O)(O)O] | Chemistry 192 |
| 700,614 | 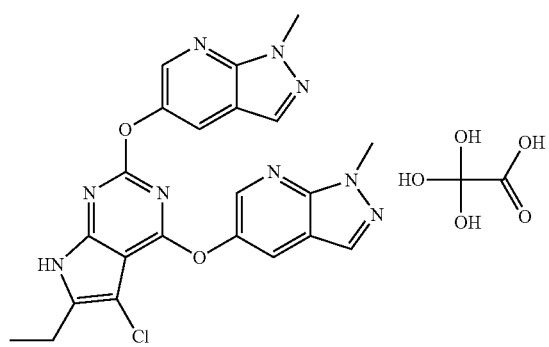 | Chemistry 193 |
| 700,615 | 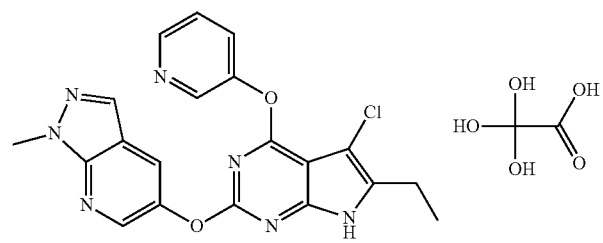 [SMILES: CCc1[nH]c2nc(Oc3cnc4c(cnn4C)c3)nc(Oc3cccnc3)c2c1Cl ; O=C(O)C(O)(O)O] | Chemistry 194 |

| Rx ID | CHEMISTRY | |
|---|---|---|
| 700,617 | 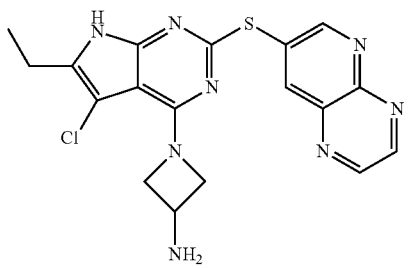 [SMILES: CCc1[nH]c2nc(Sc3cnc4nccnc4c3)nc(N3CC(N)C3)c2c1Cl] | Chemistry 195 |
| 700,618 | 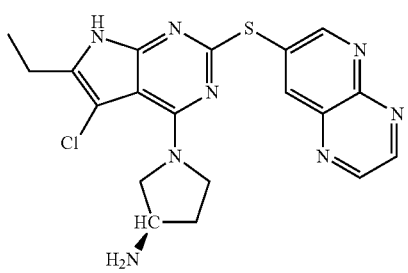 [SMILES: CCc1[nH]c2nc(Sc3cnc4nccnc4c3)nc(N3CC[C@@H](N)C3)c2c1Cl] | Chemistry 196 |
| 700,619 | 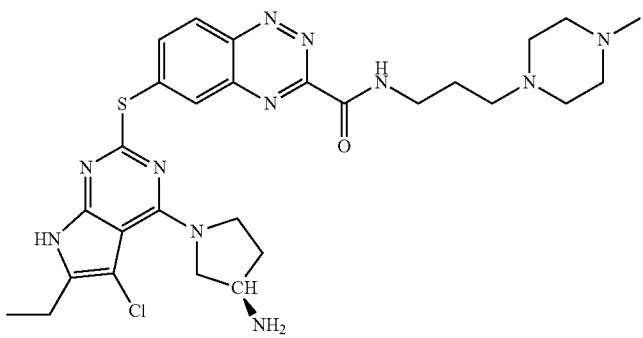 [SMILES: CCc1[nH]c2nc(Sc3ccc4nnc(C(=O)NCCCN5CCN(C)CC5)nc4c3)nc(N3CC[C@@H](N)C3)c2c1Cl] | Chemistry 197 |
| 700,620 | 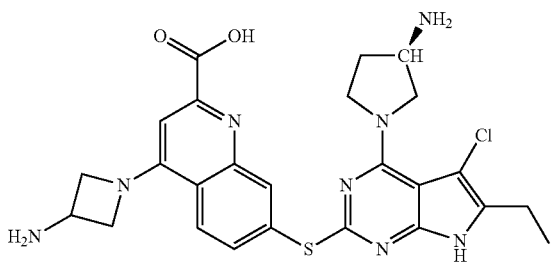 [SMILES: CCc1[nH]c2nc(Sc3ccc4c(N5CC(N)C5)cc(C(=O)O)nc4c3)nc(N3CC[C@@H](N)C3)c2c1Cl] | Chemistry 198 |
| 700,627 | 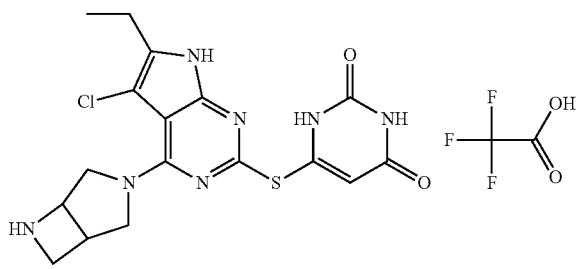 | Chemistry 199 |

| Rx ID | CHEMISTRY | |
|---|---|---|
| 700,628 | 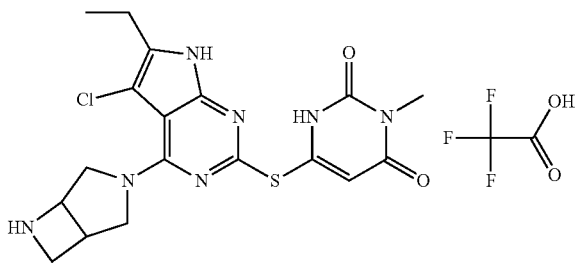 | Chemistry 200 |
| 700,629 | 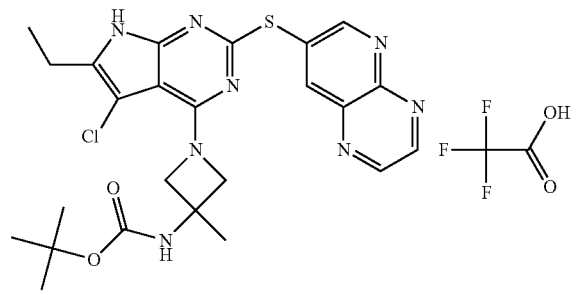 | Chemistry 201 |
| 700,630 | 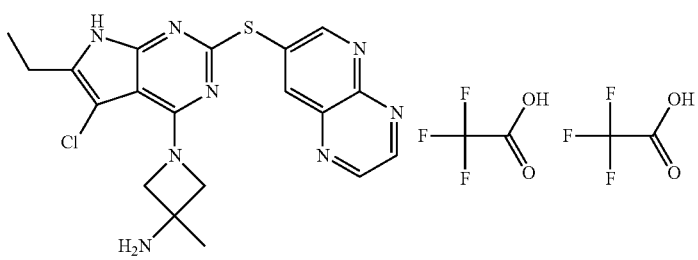 | Chemistry 202 |
| 700,648 | 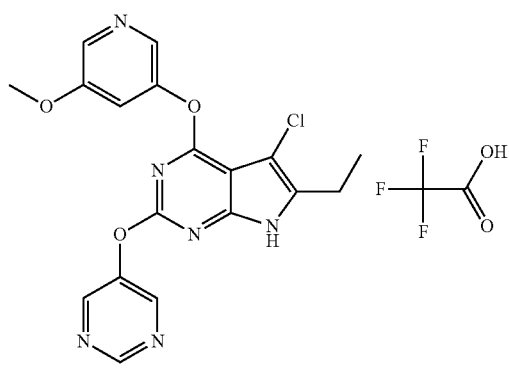 | Chemistry 203 |
| 700,649 | 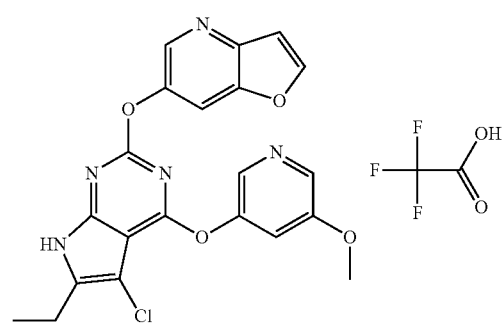 [SMILES: CCc1[nH]c2nc(Oc3cnc4ccoc4c3)nc(Oc3cncc(OC)c3)c2c1Cl ; O=C(O)C(F)(F)F] | Chemistry 204 |

| Rx ID | CHEMISTRY | |
|---|---|---|
| 700,650 | 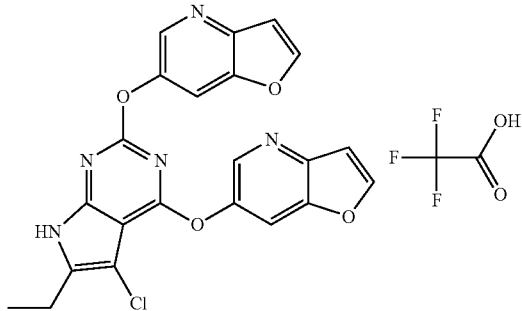 | Chemistry 205 |
| 700,655 | 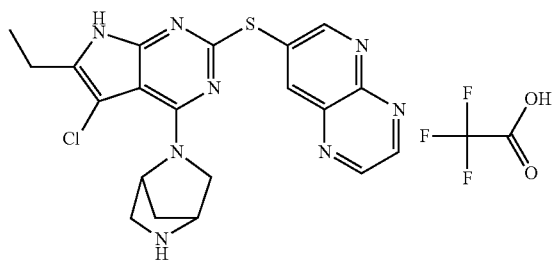 | Chemistry 206 |
| 700,656 | 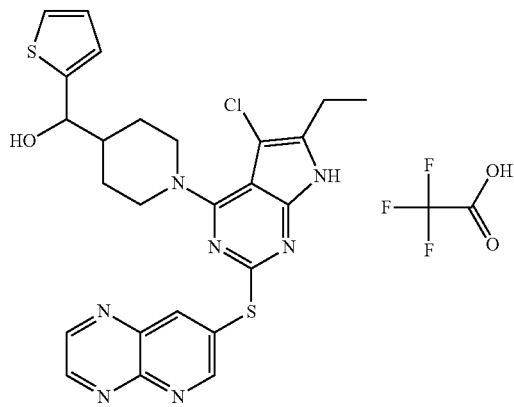 [SMILES: CCc1[nH]c2nc(Sc3cnc4nccnc4c3)nc(N3CCC(C(O)c4cccs4)CC3)c2c1Cl ; O=C(O)C(F)(F)F] | Chemistry 207 |
| 700,657 | 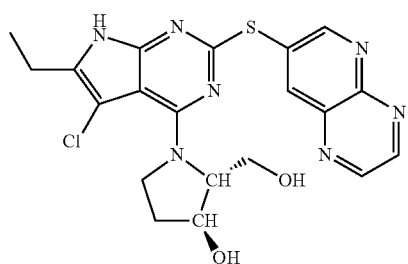 [SMILES: CCc1[nH]c2nc(Sc3cnc4nccnc4c3)nc(N3CC[C@H](O)[C@H]3CO)c2c1Cl] | Chemistry 208 |

| Rx ID | CHEMISTRY | |
|---|---|---|
| 700,658 | 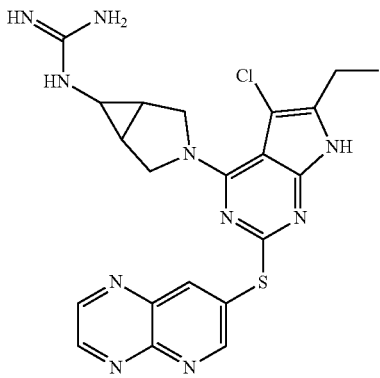 [SMILES: CCc1[nH]c2nc(Sc3cnc4nccnc4c3)nc(N3CC4C(C3)C4NC(=N)N)c2c1Cl] | Chemistry 209 |
| 700,659 | 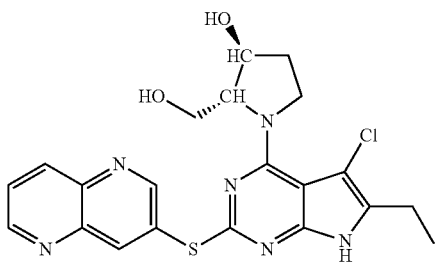 [SMILES: CCc1[nH]c2nc(Sc3cnc4cccnc4c3)nc(N3CC[C@H](O)[C@H]3CO)c2c1Cl] | Chemistry 210 |
| 700,660 | 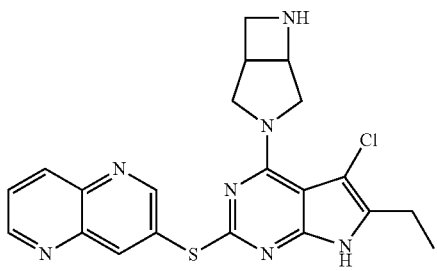 [SMILES: CCc1[nH]c2nc(Sc3cnc4cccnc4c3)nc(N3CC4CNC4C3)c2c1Cl] | Chemistry 211 |
| 700,661 | 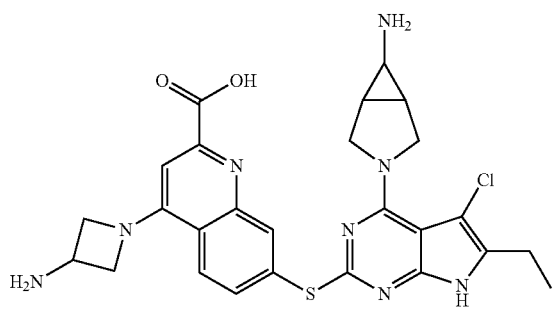 [SMILES: CCc1[nH]c2nc(Sc3ccc4c(N5CC(N)C5)cc(C(=O)O)nc4c3)nc(N3CC4C(N)C4C3)c2c1Cl] | Chemistry 212 |
| 700,664 | 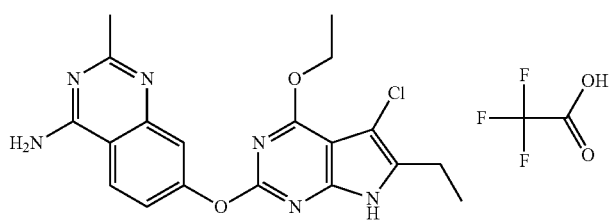 [SMILES: CCOc1nc(Oc2ccc3c(N)nc(C)nc3c2)nc2[nH]c(CC)c(Cl)c12 ; O=C(O)C(F)(F)F] | Chemistry 213 |

| Rx ID | CHEMISTRY | |
|---|---|---|
| 700,665 | 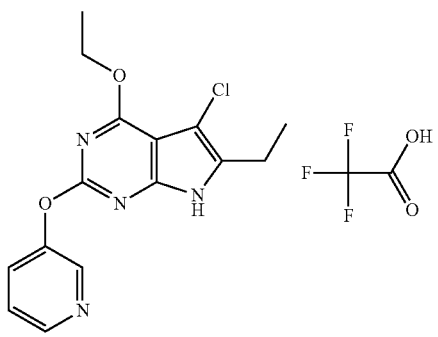 | Chemistry 214 |
| 700,666 | 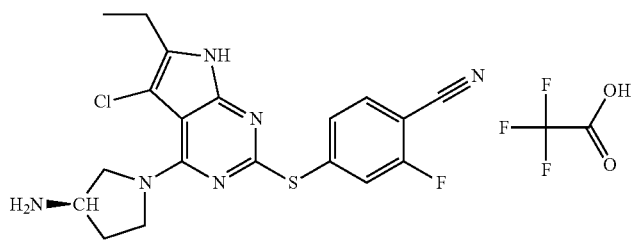 | Chemistry 215 |
| 700,667 | 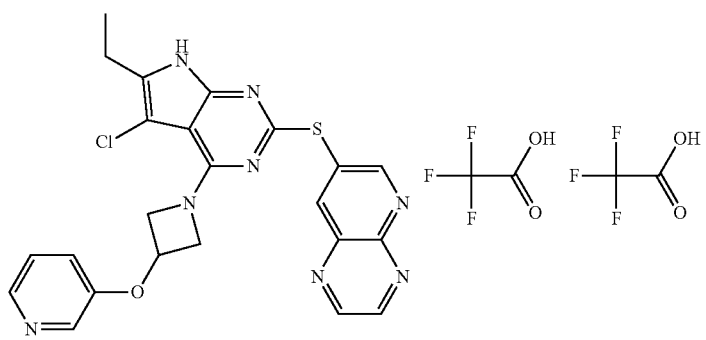 | Chemistry 216 |
| 700,668 | 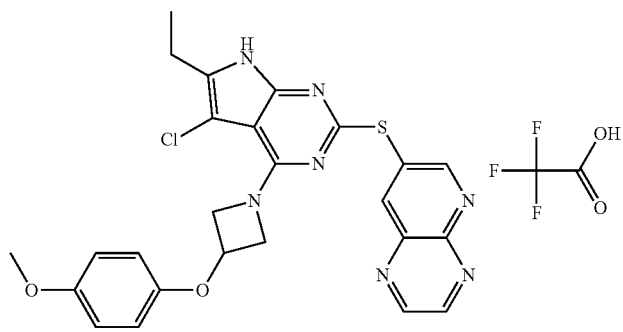 | Chemistry 217 |
| 700,669 | 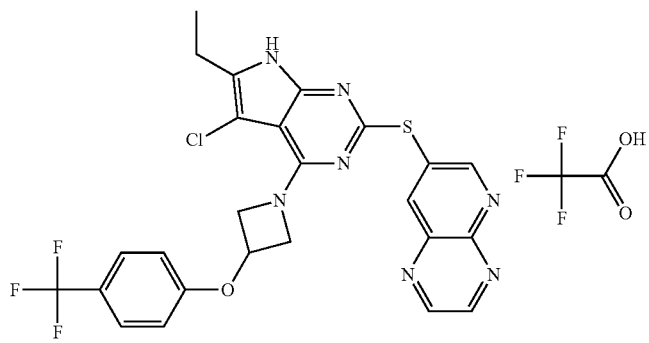 | Chemistry 218 |

| Rx ID | CHEMISTRY | |
|---|---|---|
| 700,670 | 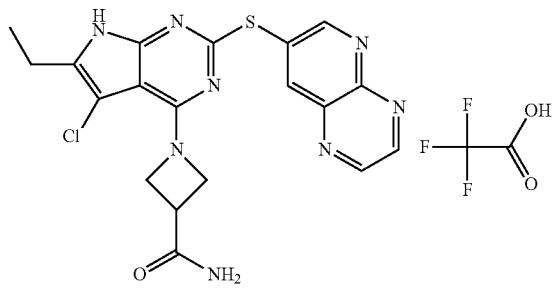 | Chemistry 219 |
| 700,671 | 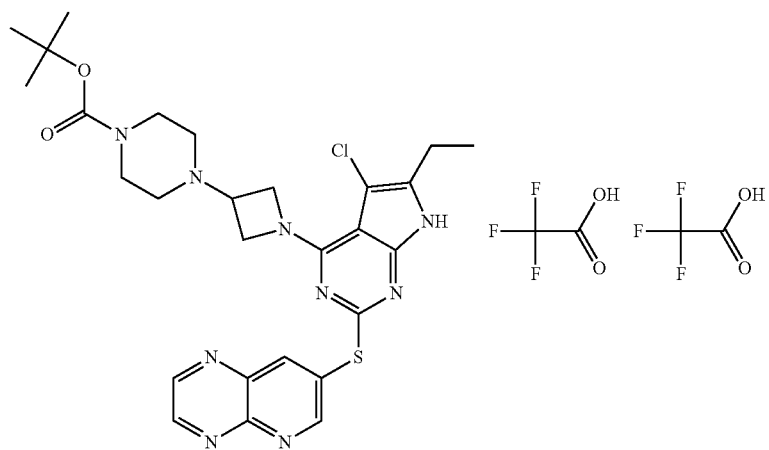 | Chemistry 220 |
| 700,672 | 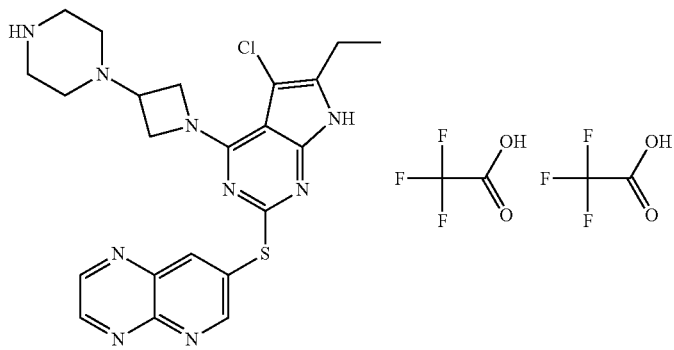 | Chemistry 221 |
| 700,676 | 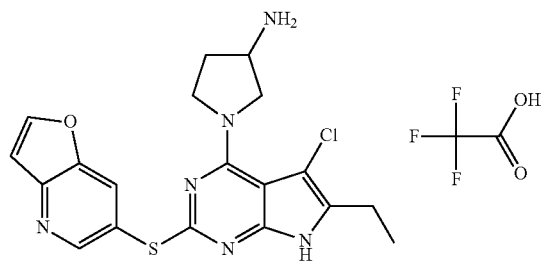 [SMILES: CCc1[nH]c2nc(Sc3cnc4ccoc4c3)nc(N3CCC(N)C3)c2c1Cl ; O=C(O)C(F)(F)F] | Chemistry 222 |

| Rx ID | CHEMISTRY | |
|---|---|---|
| 700,677 | 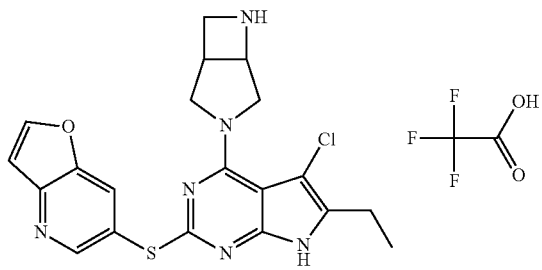 [SMILES: CCc1[nH]c2nc(Sc3cnc4ccoc4c3)nc(N3CC4CNC4C3)c2c1Cl ; O=C(O)C(F)(F)F] | Chemistry 223 |
| 700,678 | 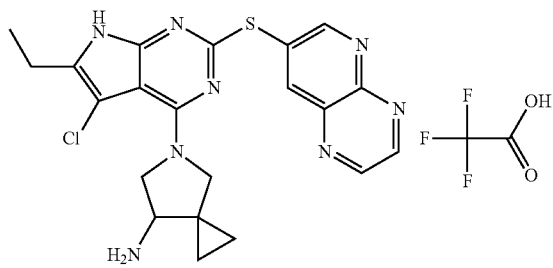 | Chemistry 224 |
| 700,686 | 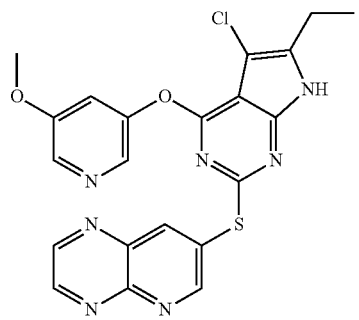 [SMILES: CCc1[nH]c2nc(Sc3cnc4nccnc4c3)nc(Oc3cncc(OC)c3)c2c1Cl] | Chemistry 225 |
| 700,687 | 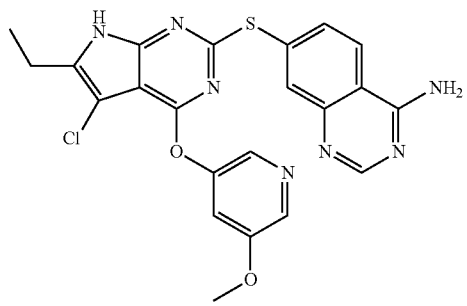 [SMILES: CCc1[nH]c2nc(Sc3ccc4c(N)ncnc4c3)nc(Oc3cncc(OC)c3)c2c1Cl] | Chemistry 226 |
| 700,688 | 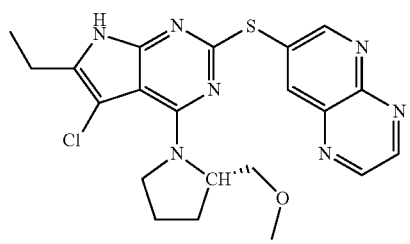 [SMILES: CCc1[nH]c2nc(Sc3cnc4nccnc4c3)nc(N3CCC[C@H]3COC)c2c1Cl] | Chemistry 227 |

-continued
| Rx ID | CHEMISTRY | |
|---|---|---|
| 700,689 | 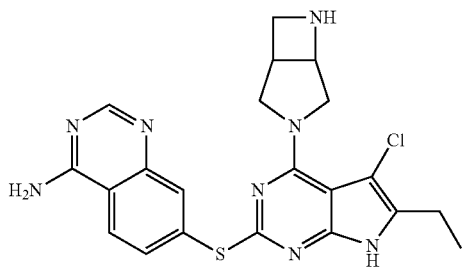 [SMILES: CCc1[nH]c2nc(Sc3ccc4c(N)ncnc4c3)nc(N3CC4CNC4C3)c2c1Cl] | Chemistry 228 |
| 700,690 | 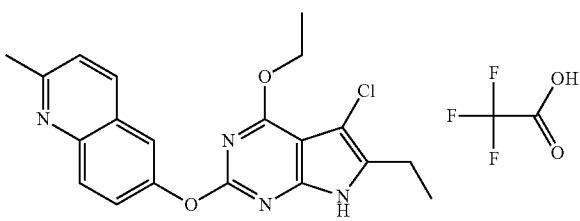 [SMILES: CCOc1nc(Oc2ccc3nc(C)ccc3c2)nc2[nH]c(CC)c(Cl)c12 ; O=C(O)C(F)(F)F] | Chemistry 229 |
| 700,691 | 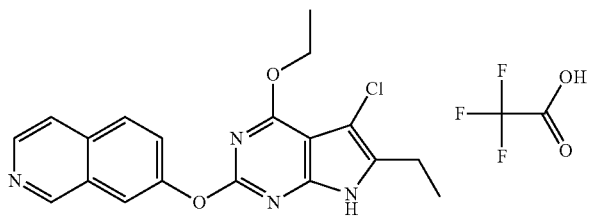 [SMILES: CCOc1nc(Oc2ccc3ccncc3c2)nc2[nH]c(CC)c(Cl)c12 ; O=C(O)C(F)(F)F] | Chemistry 230 |
| 700,694 | 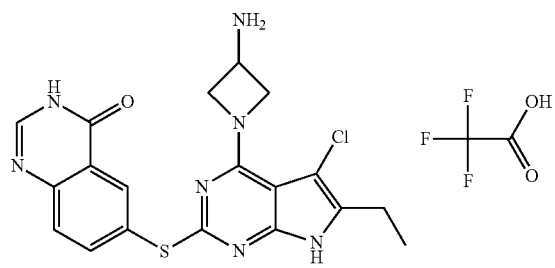 [SMILES: CCc1[nH]c2nc(Sc3ccc4nc[nH]c(=O)c4c3)nc(N3CC(N)C3)c2c1Cl ; O=C(O)C(F)(F)F] | Chemistry 231 |
| 700,695 | 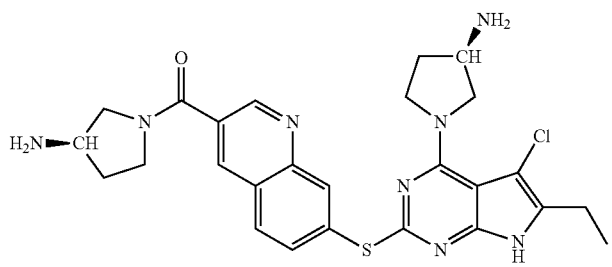 [SMILES: CCc1[nH]c2nc(Sc3ccc4cc(C(=O)N5CC[C@@H](N)C5)cnc4c3)nc(N3CC[C@@H](N)C3)c2c1Cl] | Chemistry 232 |
| 700,696 | 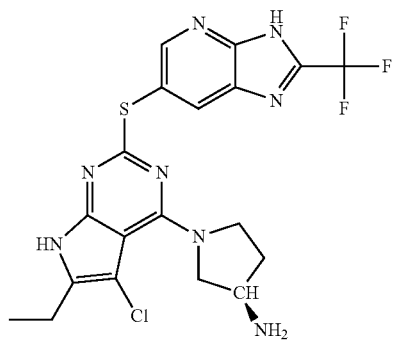 [SMILES: CCc1[nH]c2nc(Sc3cnc4[nH]c(C(F)(F)F)nc4c3)nc(N3CC[C@@H](N)C3)c2c1Cl] | Chemistry 233 |

| Rx ID | CHEMISTRY | |
|---|---|---|
| 700,697 | 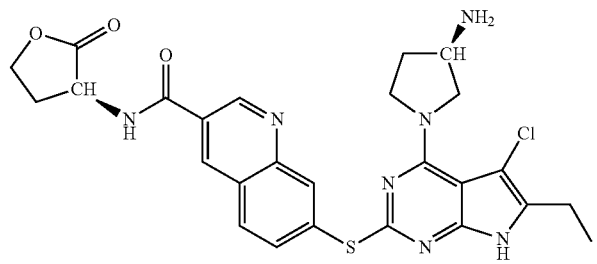 [SMILES: CCc1[nH]c2nc(Sc3ccc4cc(C(=O)N[C@H]5CCOC5=O)cnc4c3)nc(N3CC[C@@H](N)C3)c2c1Cl] | Chemistry 234 |
| 700,698 | 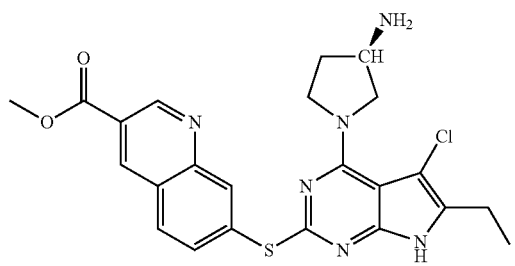 [SMILES: CCc1[nH]c2nc(Sc3ccc4cc(C(=O)OC)cnc4c3)nc(N3CC[C@@H](N)C3)c2c1Cl] | Chemistry 235 |
| 700,699 | 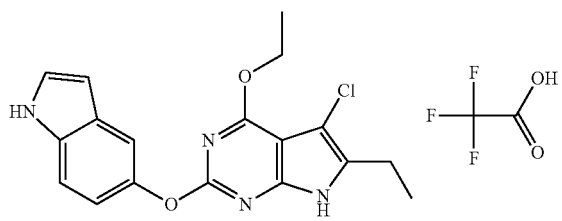 [SMILES: CCOc1nc(Oc2ccc3[nH]ccc3c2)nc2[nH]c(CC)c(Cl)c12 ; O=C(O)C(F)(F)F] | Chemistry 236 |
| 700,700 | 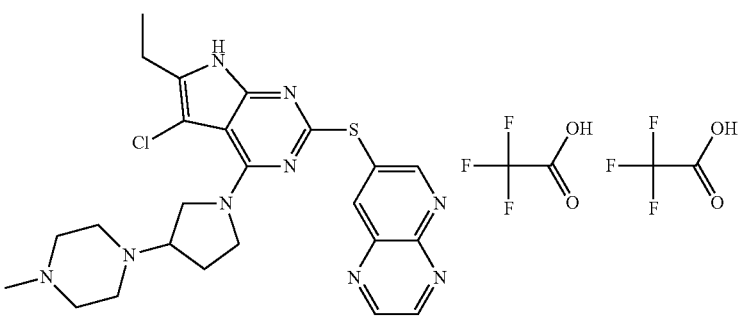 | Chemistry 237 |
| 700,702 | 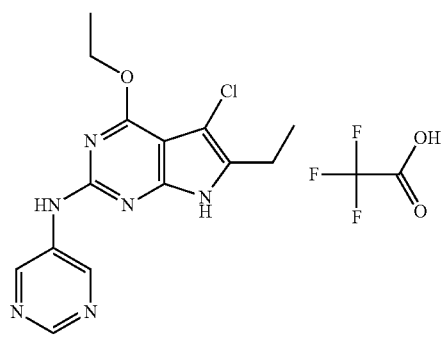 | Chemistry 238 |

| Rx ID | CHEMISTRY | |
|---|---|---|
| 700,705 | 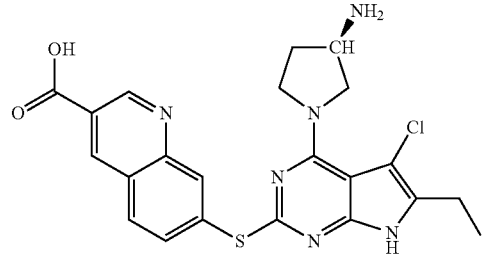 [SMILES: CCc1[nH]c2nc(Sc3ccc4cc(C(=O)O)cnc4c3)nc(N3CC[C@@H](N)C3)c2c1Cl] | Chemistry 239 |
| 700,706 | 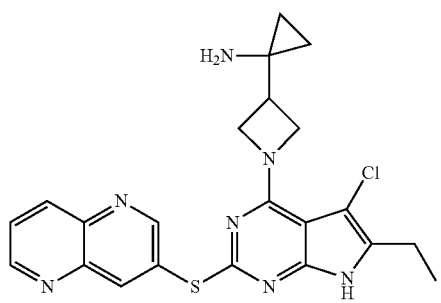 [SMILES: CCc1[nH]c2nc(Sc3cnc4cccnc4c3)nc(N3CC(C4(N)CC4)C3)c2c1Cl] | Chemistry 240 |
| 700,707 | 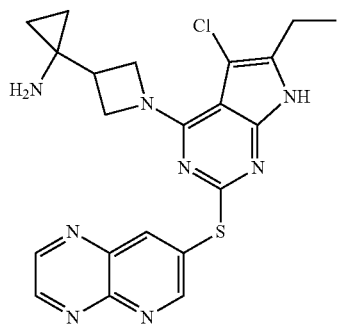 [SMILES: CCc1[nH]c2nc(Sc3cnc4nccnc4c3)nc(N3CC(C4(N)CC4)C3)c2c1Cl] | Chemistry 241 |
| 700,708 | 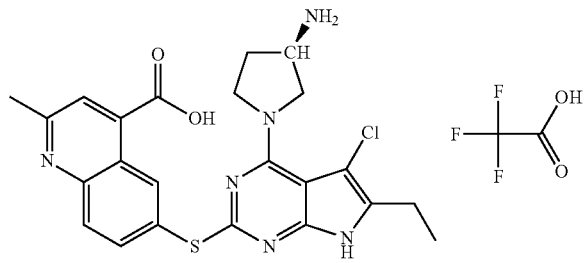 [SMILES: CCc1[nH]c2nc(Sc3ccc4nc(C)cc(C(=O)O)c4c3)nc(N3CC[C@@H](N)C3)c2c1Cl ; O=C(O)C(F)(F)F] | Chemistry 242 |
| 700,710 | 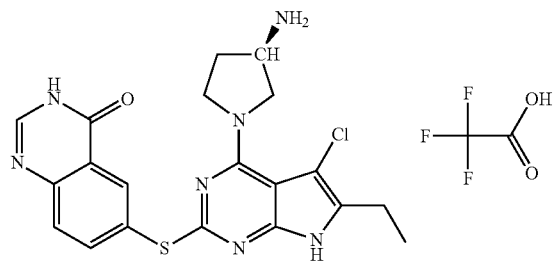 [SMILES: CCc1[nH]c2nc(Sc3ccc4nc[nH]c(=O)c4c3)nc(N3CC[C@@H](N)C3)c2c1Cl ; O=C(O)C(F)(F)F] | Chemistry 243 |

| Rx ID | CHEMISTRY | |
|---|---|---|
| 700,711 | 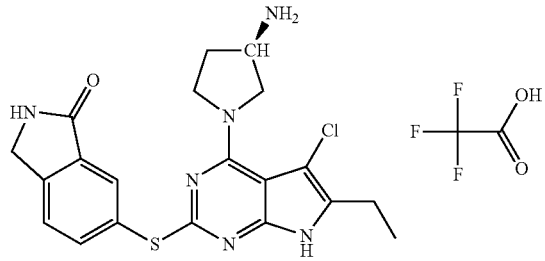 [SMILES: CCc1[nH]c2nc(Sc3ccc4c(c3)C(=O)NC4)nc(N3CC[C@@H](N)C3)c2c1Cl ; O=C(O)C(F)(F)F] | Chemistry 244 |
| 700,712 | 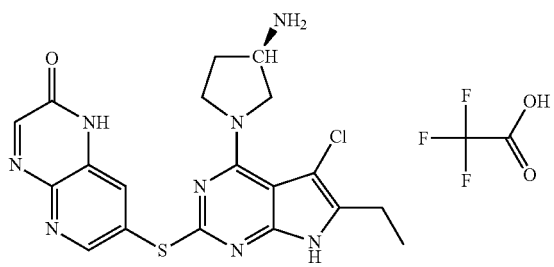 [SMILES: CCc1[nH]c2nc(Sc3cnc4ncc(=O)[nH]c4c3)nc(N3CC[C@@H](N)C3)c2c1Cl ; O=C(O)C(F)(F)F] | Chemistry 245 |
| 700,713 | 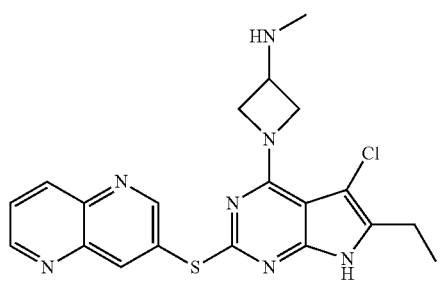 [SMILES: CCc1[nH]c2nc(Sc3cnc4cccnc4c3)nc(N3CC(NC)C3)c2c1Cl] | Chemistry 246 |
| 700,714 | 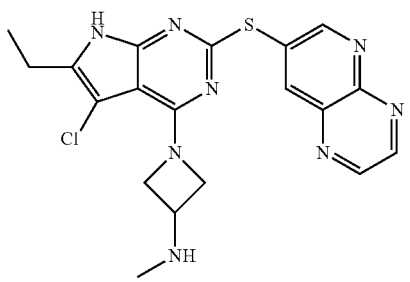 [SMILES: CCc1[nH]c2nc(Sc3cnc4nccnc4c3)nc(N3CC(NC)C3)c2c1Cl] | Chemistry 247 |
| 700,715 | 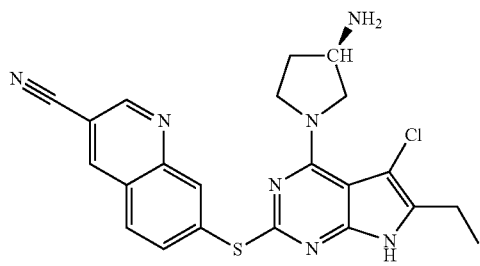 [SMILES: CCc1[nH]c2nc(Sc3ccc4cc(C#N)cnc4c3)nc(N3CC[C@@H](N)C3)c2c1Cl] | Chemistry 248 |

| Rx ID | CHEMISTRY | |
|---|---|---|
| 700,716 | 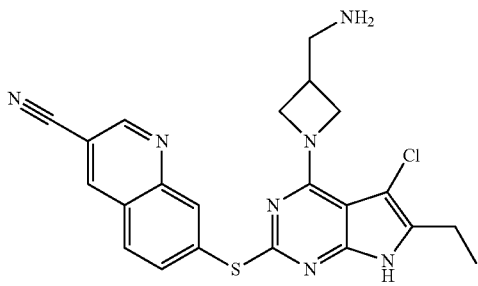 [SMILES: CCc1[nH]c2nc(Sc3ccc4cc(C#N)cnc4c3)nc(N3CC(CN)C3)c2c1Cl] | Chemistry 249 |
| 700,717 | 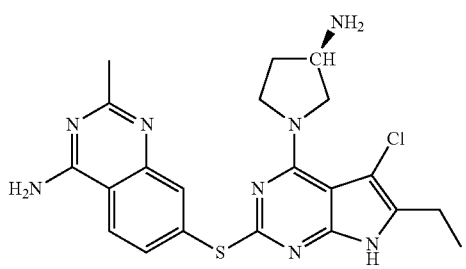 [SMILES: CCc1[nH]c2nc(Sc3ccc4c(N)nc(C)nc4c3)nc(N3CC[C@@H](N)C3)c2c1Cl] | Chemistry 250 |
| 700,718 | 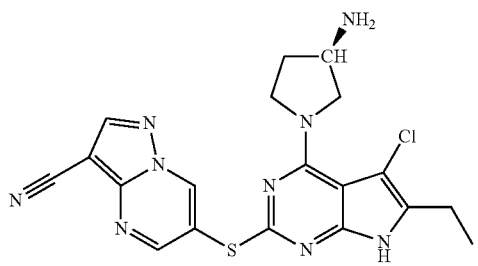 [SMILES: CCc1[nH]c2nc(Sc3cnc4c(C#N)cnn4c3)nc(N3CC[C@@H](N)C3)c2c1Cl] | Chemistry 251 |
| 700,719 | 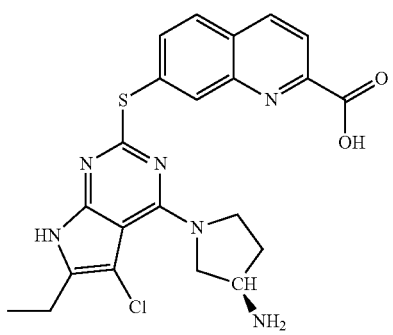 [SMILES: CCc1[nH]c2nc(Sc3ccc4ccc(C(=O)O)nc4c3)nc(N3CC[C@@H](N)C3)c2c1Cl] | Chemistry 252 |
| 700,720 | 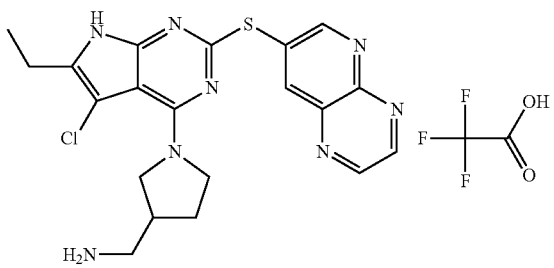 | Chemistry 253 |

| Rx ID | CHEMISTRY | |
|---|---|---|
| 700,721 | 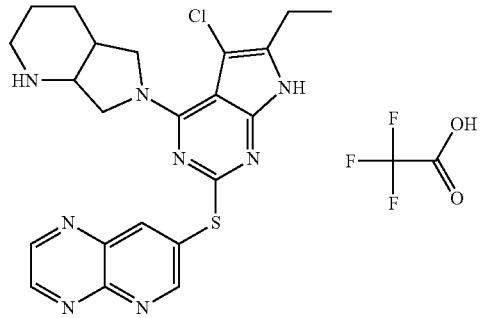 [SMILES: CCc1[nH]c2nc(Sc3cnc4nccnc4c3)nc(N3CC4CCCNC4C3)c2c1Cl ; O=C(O)C(F)(F)F] | Chemistry 254 |
| 700,722 | 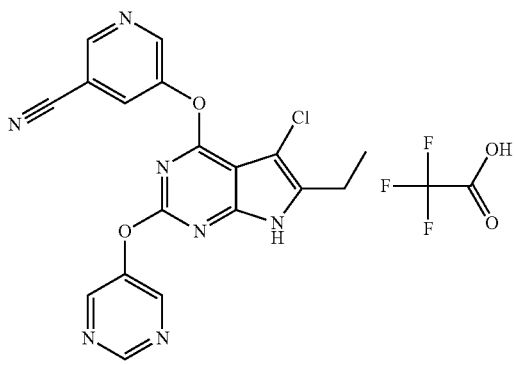 | Chemistry 255 |
| 700,723 | 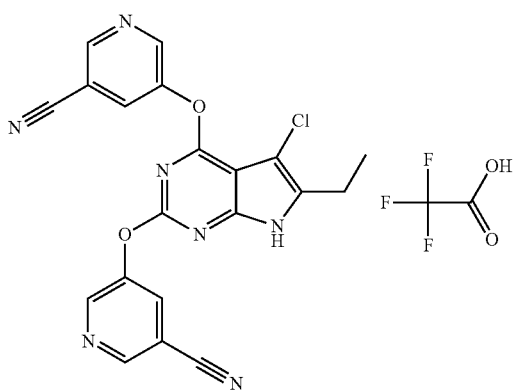 | Chemistry 256 |
| 700,781 | 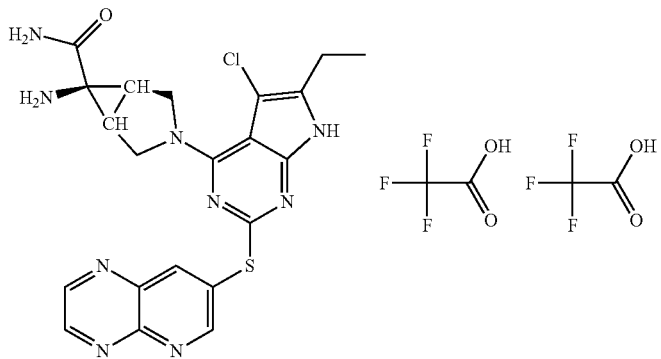 | Chemistry 257 |

-continued
| Rx ID | CHEMISTRY | |
|---|---|---|
| 700,782 | 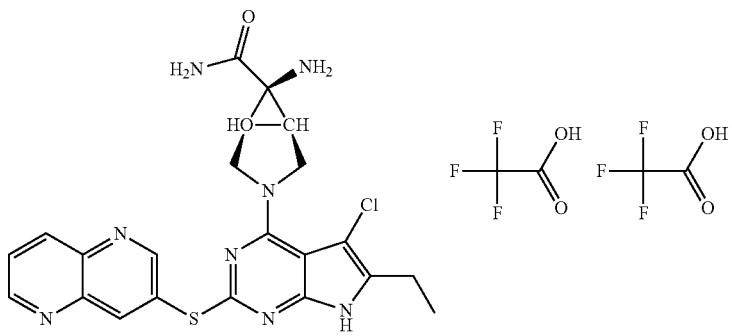 | Chemistry 258 |
| 700,783 | 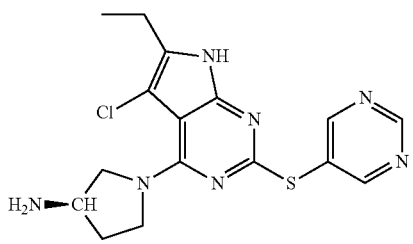 [SMILES: CCc1[nH]c2nc(Sc3cncnc3)nc(N3CC[C@@H](N)C3)c2c1Cl] | Chemistry 259 |
| 700,784 | 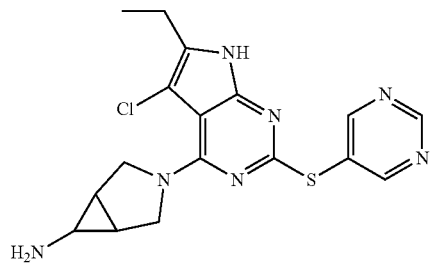 [SMILES: CCc1[nH]c2nc(Sc3cncnc3)nc(N3CC4C(N)C4C3)c2c1Cl] | Chemistry 260 |
| 700,785 | 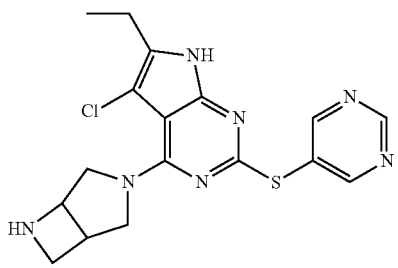 [SMILES: CCc1[nH]c2nc(Sc3cncnc3)nc(N3CC4CNC4C3)c2c1Cl] | Chemistry 261 |
| 700,786 | 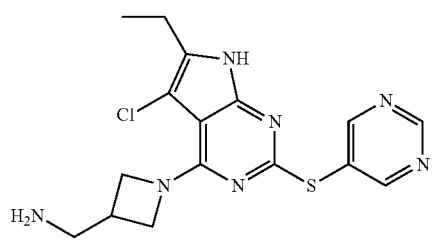 [SMILES: CCc1[nH]c2nc(Sc3cncnc3)nc(N3CC(CN)C3)c2c1Cl] | Chemistry 262 |
| 700,787 | 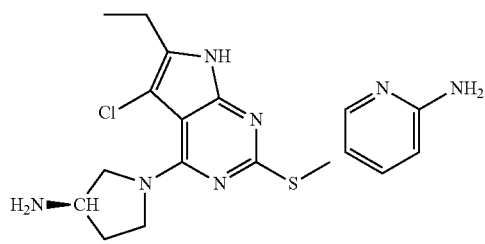 | Chemistry 263 |

US 10,047,105 B2
-continued
| Rx ID | CHEMISTRY | |
|---|---|---|
| 700,788 | 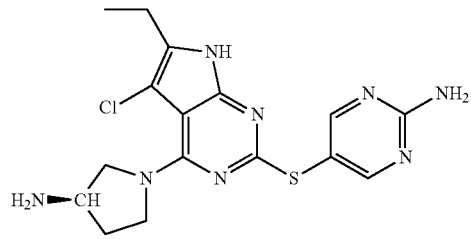 [SMILES: CCc1[nH]c2nc(Sc3cnc(N)nc3)nc(N3CC[C@@H](N)C3)c2c1Cl] | Chemistry 264 |
| 700,789 | 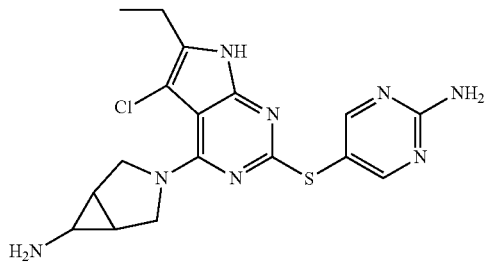 [SMILES: CCc1[nH]c2nc(Sc3cnc(N)nc3)nc(N3CC4C(N)C4C3)c2c1Cl] | Chemistry 265 |
| 700,790 | 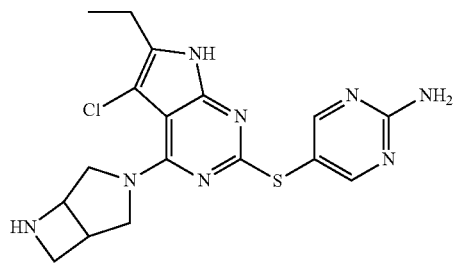 [SMILES: CCc1[nH]c2nc(Sc3cnc(N)nc3)nc(N3CC4CNC4C3)c2c1Cl] | Chemistry 266 |
| 700,791 | 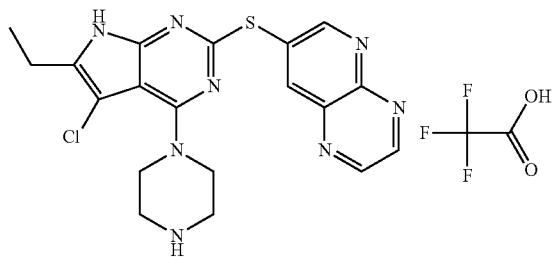 | Chemistry 267 |
| 700,792 | 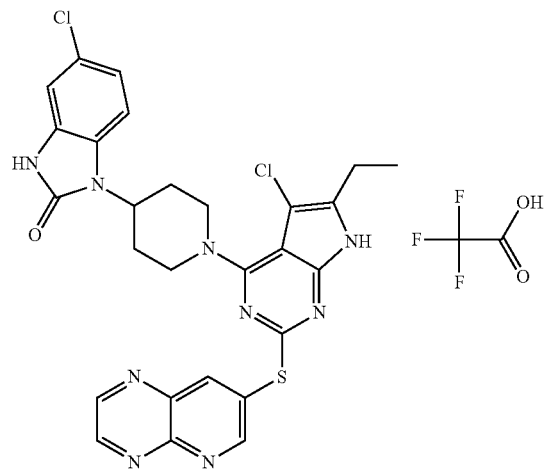 [SMILES: CCc1[nH]c2nc(Sc3cnc4nccnc4c3)nc(N3CCC(n4c(=O)[nH]c5cc(Cl)ccc54)CC3)c2c1Cl ; O=C(O)C(F)(F)F] | Chemistry 268 |

| Rx ID | CHEMISTRY | |
|---|---|---|
| 700,794 | 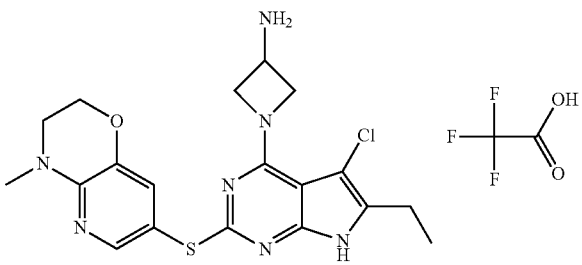 [SMILES: CCc1[nH]c2nc(Sc3cnc4c(c3)OCCN4C)nc(N3CC(N)C3)c2c1Cl ; O=C(O)C(F)(F)F] | Chemistry 269 |
| 700,795 | 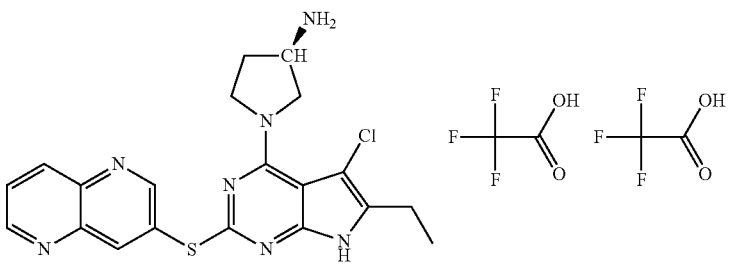 | Chemistry 270 |
| 700,796 | 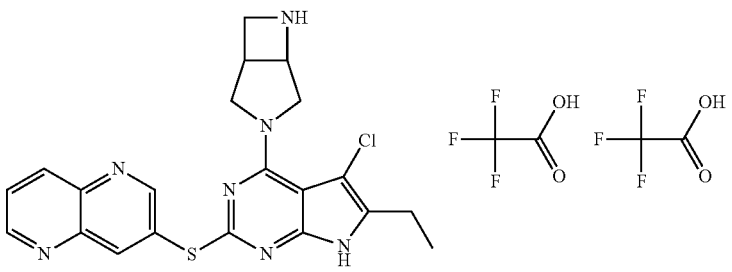 | Chemistry 271 |
| 700,797 | 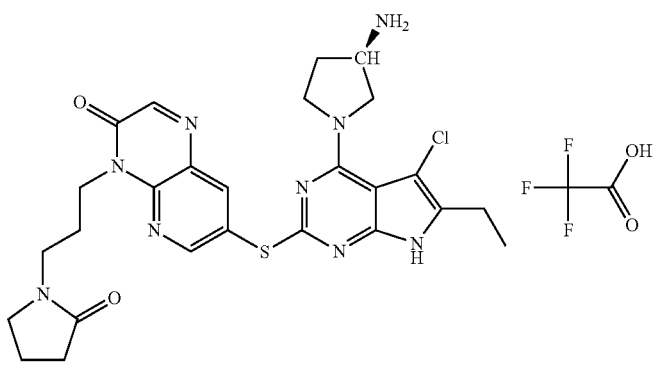 | Chemistry 272 |
| 700,798 | 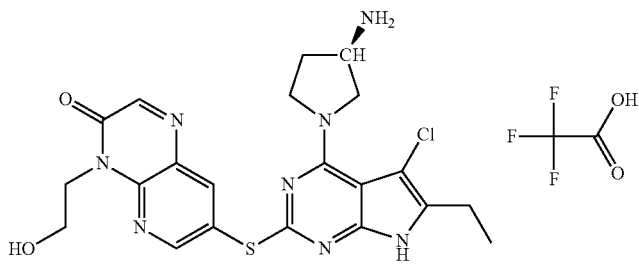 [SMILES: CCc1[nH]c2nc(Sc3cnc4c(c3)ncc(=O)n4CCO)nc(N3CC[C@@H](N)C3)c2c1Cl ; O=C(O)C(F)(F)F] | Chemistry 273 |

| Rx ID | CHEMISTRY | |
|---|---|---|
| 700,799 | 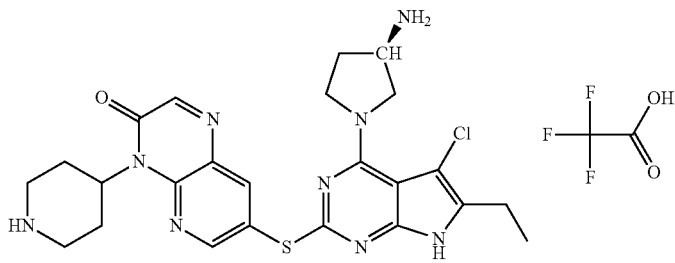 [SMILES: CCc1[nH]c2nc(Sc3cnc4c(c3)ncc(=O)n4C3CCNCC3)nc(N3CC[C@@H](N)C3)c2c1Cl ; O=C(O)C(F)(F)F] | Chemistry 274 |
| 700,800 | 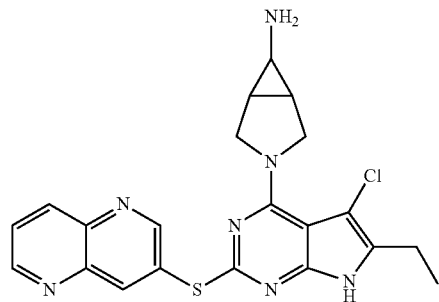 | Chemistry 275 |
| 700,801 | 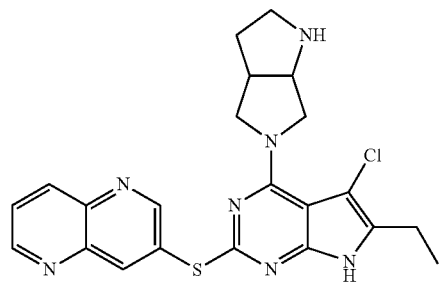 [SMILES: CCc1[nH]c2nc(Sc3cnc4cccnc4c3)nc(N3CC4CCNC4C3)c2c1Cl] | Chemistry 276 |
| 700,802 | 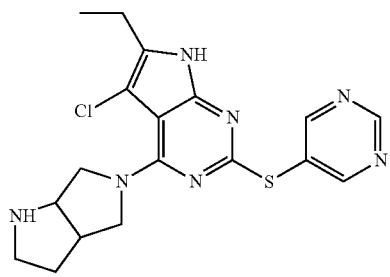 [SMILES: CCc1[nH]c2nc(Sc3cncnc3)nc(N3CC4CCNC4C3)c2c1Cl] | Chemistry 277 |
| 700,803 | 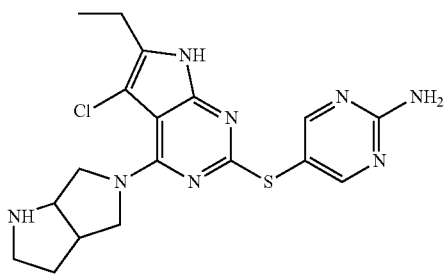 [SMILES: CCc1[nH]c2nc(Sc3cnc(N)nc3)nc(N3CC4CCNC4C3)c2c1Cl] | Chemistry 278 |

US 10,047,105 B2
307 308
-continued
| Rx ID | CHEMISTRY | |
|---|---|---|
| 700,804 | 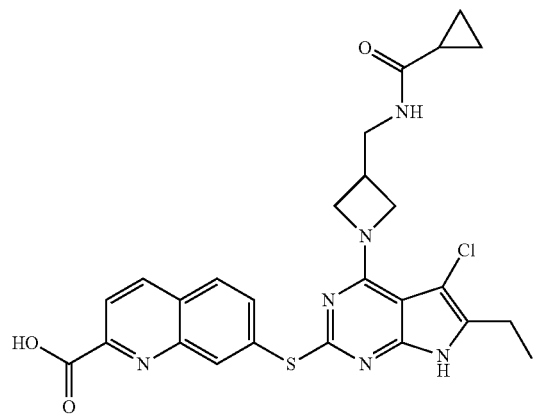 [SMILES: CCc1[nH]c2nc(Sc3ccc4ccc(C(=O)O)nc4c3)nc(N3CC(CNC(=O)C4CC4)C3)c2c1Cl] | Chemistry 279 |
| 700,805 | 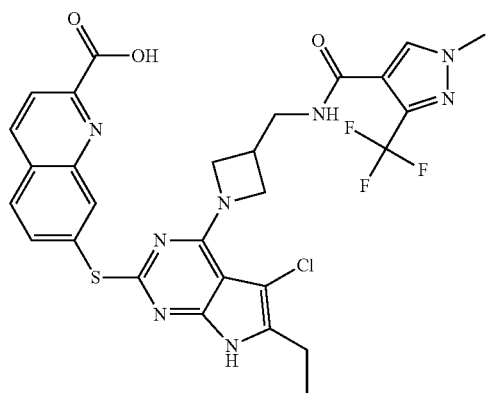 [SMILES: CCc1[nH]c2nc(Sc3ccc4ccc(C(=O)O)nc4c3)nc(N3CC(CNC(=O)c4cn(C)nc4C(F)(F)F)C3)c2c1Cl] | Chemistry 280 |
| 700,806 | 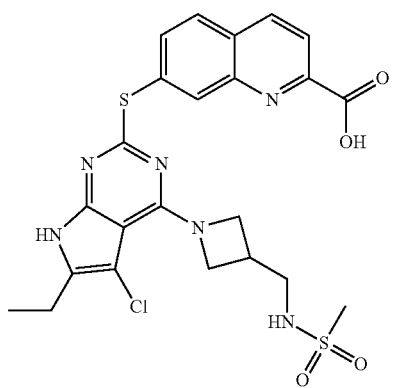 [SMILES: CCc1[nH]c2nc(Sc3ccc4ccc(C(=O)O)nc4c3)nc(N3CC(CNS(C)(=O)=O)C3)c2c1Cl] | Chemistry 281 |
| 700,807 | 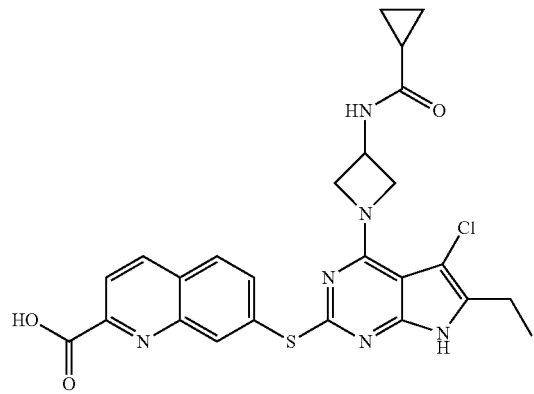 [SMILES: CCc1[nH]c2nc(Sc3ccc4ccc(C(=O)O)nc4c3)nc(N3CC(NC(=O)C4CC4)C3)c2c1Cl] | Chemistry 282 |

-continued
| Rx ID | CHEMISTRY | |
|---|---|---|
| 700,808 | 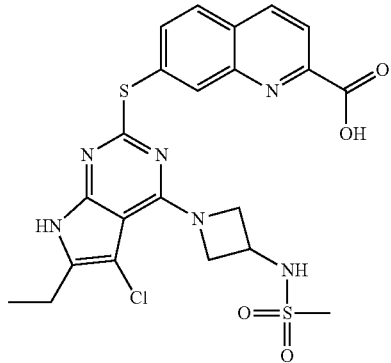 [SMILES: CCc1[nH]c2nc(Sc3ccc4ccc(C(=O)O)nc4c3)nc(N3CC(NS(C)(=O)=O)C3)c2c1Cl] | Chemistry 283 |
| 700,809 | 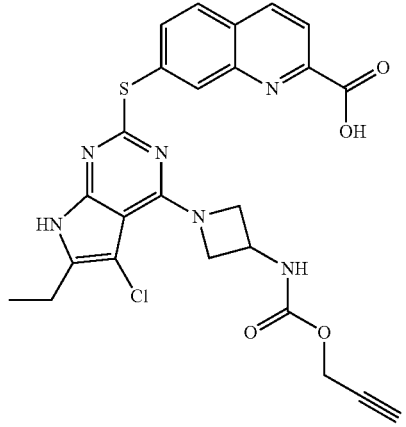 [SMILES: C#CCOC(=O)NC1CN(c2nc(Sc3ccc4ccc(C(=O)O)nc4c3)nc3[nH]c(CC)c(Cl)c23)C1] | Chemistry 284 |
| 700,812 | 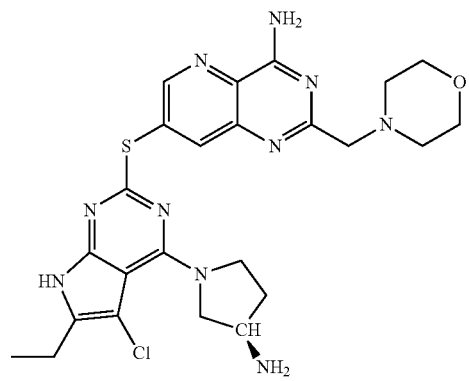 [SMILES: CCc1[nH]c2nc(Sc3cnc4c(N)nc(CN5CCOCC5)nc4c3)nc(N3CC[C@@H](N)C3)c2c1Cl] | Chemistry 285 |
| 700,813 | 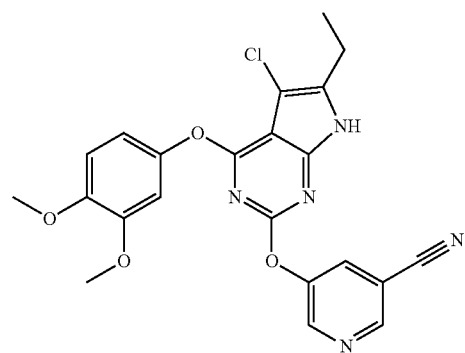 [SMILES: CCc1[nH]c2nc(Oc3cncc(C#N)c3)nc(Oc3ccc(OC)c(OC)c3)c2c1Cl] | Chemistry 286 |

US 10,047,105 B2
311 312
-continued
| Rx ID | CHEMISTRY | |
|---|---|---|
| 700,814 | 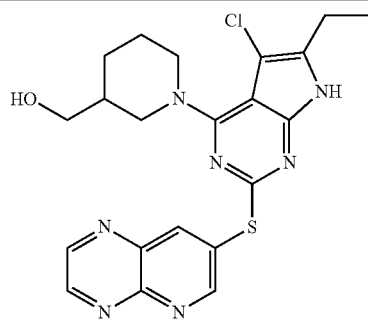 [SMILES: CCc1[nH]c2nc(Sc3cnc4nccnc4c3)nc(N3CCCC(CO)C3)c2c1Cl] | Chemistry 287 |
| 700,815 | 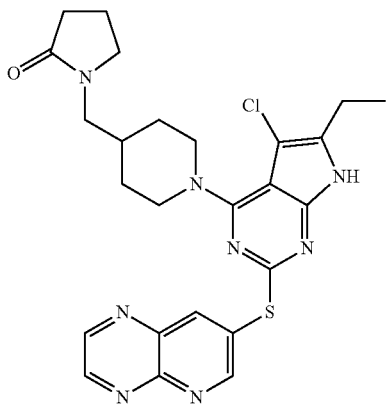 [SMILES: CCc1[nH]c2nc(Sc3cnc4nccnc4c3)nc(N3CCC(CN4CCCC4=O)CC3)c2c1Cl] | Chemistry 288 |
| 700,816 | 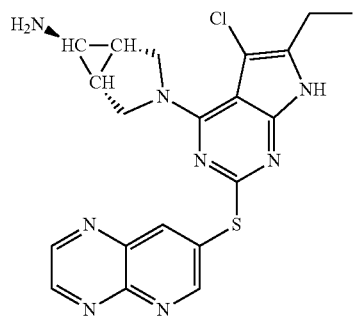 [SMILES: CCc1[nH]c2nc(Sc3cnc4nccnc4c3)nc(N3C[C@@H]4[C@@H](N)[C@@H]4C3)c2c1Cl] | Chemistry 289 |
| 700,817 | 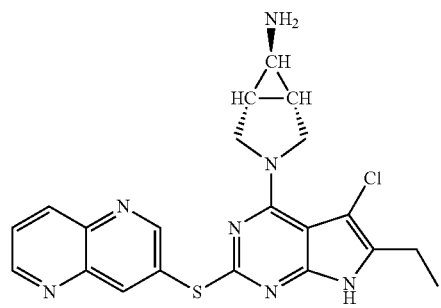 [SMILES: CCc1[nH]c2nc(Sc3cnc4cccnc4c3)nc(N3C[C@@H]4[C@@H](N)[C@@H]4C3)c2c1Cl] | Chemistry 290 |
| 700,818 | 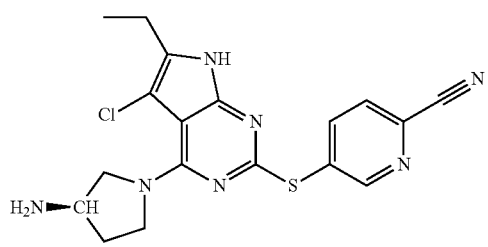 [SMILES: CCc1[nH]c2nc(Sc3ccc(C#N)nc3)nc(N3CC[C@@H](N)C3)c2c1Cl] | Chemistry 291 |

-continued
| Rx ID | CHEMISTRY | |
|---|---|---|
| 700,820 | 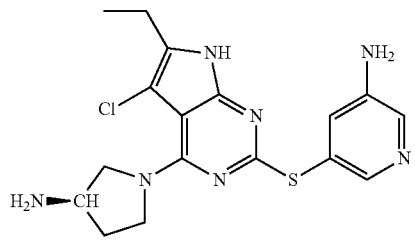 [SMILES: CCc1[nH]c2nc(Sc3cncc(N)c3)nc(N3CC[C@@H](N)C3)c2c1Cl] | Chemistry 292 |
| 700,821 | 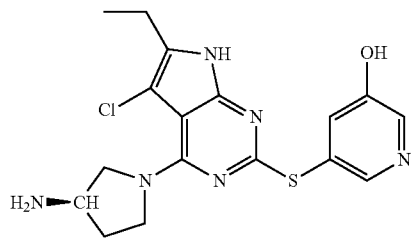 [SMILES: CCc1[nH]c2nc(Sc3cncc(O)c3)nc(N3CC[C@@H](N)C3)c2c1Cl] | Chemistry 293 |
| 700,822 | 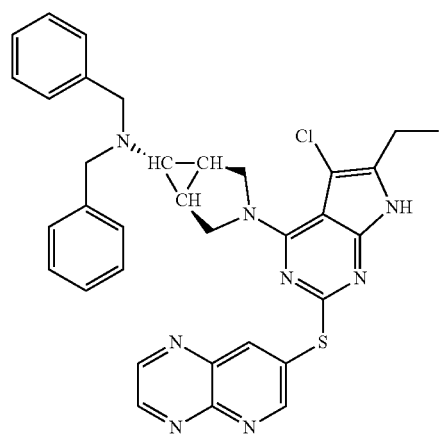 [SMILES: CCc1[nH]c2nc(Sc3cnc4nccnc4c3)nc(N3C[C@@H]4[C@H](C3)[C@H]4N(Cc3ccccc3)Cc3ccccc3)c2c1Cl] | Chemistry 294 |
| 700,823 | 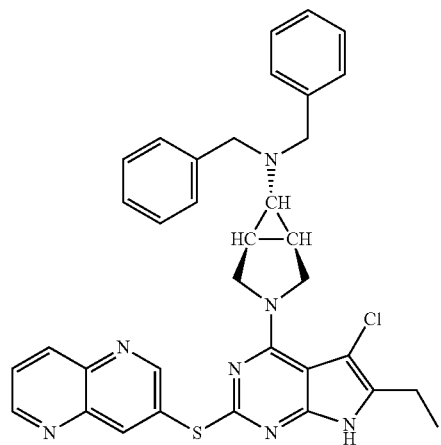 [SMILES: CCc1[nH]c2nc(Sc3cnc4cccnc4c3)nc(N3C[C@@H]4[C@H](C3)[C@H]4N(Cc3ccccc3)Cc3ccccc3)c2c1Cl] | Chemistry 295 |

| Rx ID | CHEMISTRY | |
|---|---|---|
| 700618-2 | 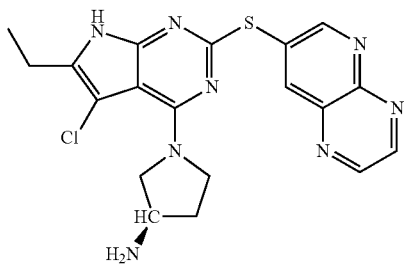 [SMILES: CCc1[nH]c2nc(Sc3cnc4nccnc4c3)nc(N3CC[C@@H](N)C3)c2c1Cl] | Chemistry 296 |
| 700,824 | 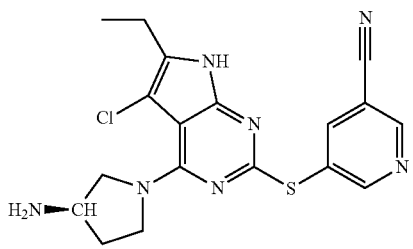 [SMILES: CCc1[nH]c2nc(Sc3cncc(C#N)c3)nc(N3CC[C@@H](N)C3)c2c1Cl] | Chemistry 297 |
| 700,825 | 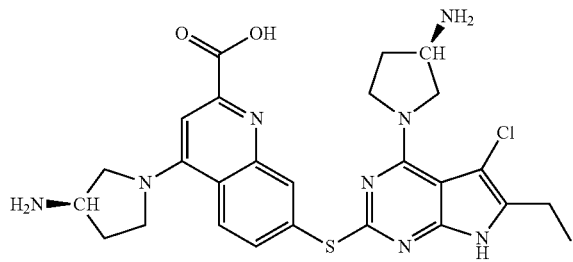 | Chemistry 298 |
| 700,826 | 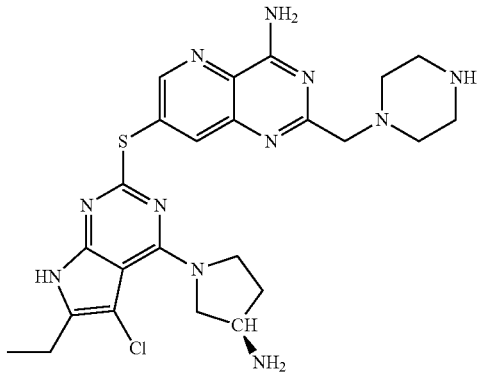 [SMILES: CCc1[nH]c2nc(Sc3cnc4c(N)nc(CN5CCNCC5)nc4c3)nc(N3CC[C@@H](N)C3)c2c1Cl] | Chemistry 299 |
| 700,827 | 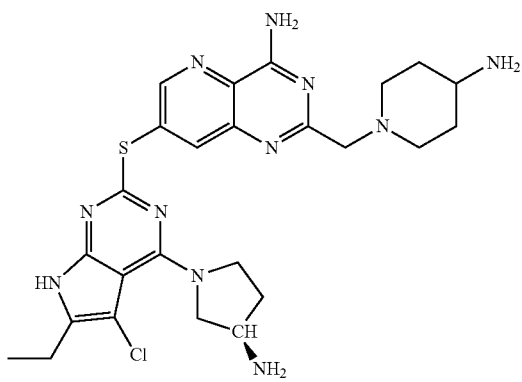 [SMILES: CCc1[nH]c2nc(Sc3cnc4c(N)nc(CN5CCC(N)CC5)nc4c3)nc(N3CC[C@@H](N)C3)c2c1Cl] | Chemistry 300 |

US 10,047,105 B2
317                                                                      318
-continued
| Rx ID | CHEMISTRY | |
|---|---|---|
| 700,828 | 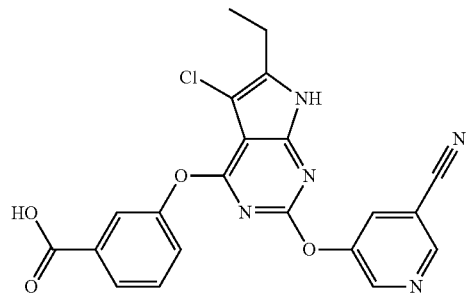 [SMILES: CCc1[nH]c2nc(Oc3cncc(C#N)c3)nc(Oc3cccc(C(=O)O)c3)c2c1Cl] | Chemistry 301 |
| 700,829 | 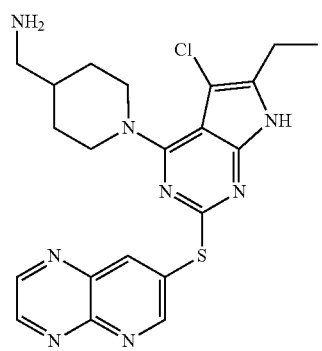 [SMILES: CCc1[nH]c2nc(Sc3cnc4nccnc4c3)nc(N3CCC(CN)CC3)c2c1Cl] | Chemistry 302 |
| 700,830 | 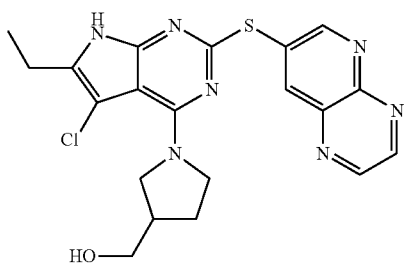 [SMILES: CCc1[nH]c2nc(Sc3cnc4nccnc4c3)nc(N3CCC(CO)C3)c2c1Cl] | Chemistry 303 |
| 700,831 | 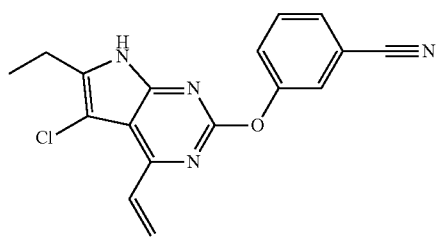 [SMILES: C=Cc1nc(Oc2cccc(C#N)c2)nc2[nH]c(CC)c(Cl)c12] | Chemistry 304 |
| 700,832 | 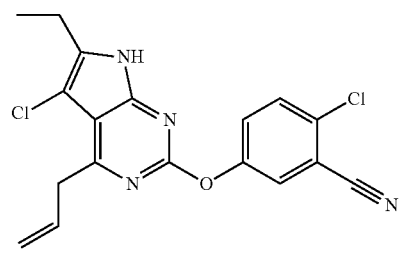 [SMILES: C=CCc1nc(Oc2ccc(Cl)c(C#N)c2)nc2[nH]c(CC)c(Cl)c12] | Chemistry 305 |

| Rx ID | CHEMISTRY | |
|---|---|---|
| 700,833 | 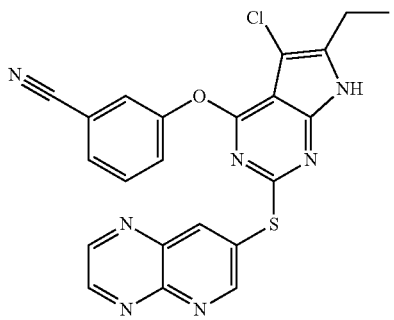 [SMILES: CCc1[nH]c2nc(Sc3cnc4nccnc4c3)nc(Oc3cccc(C#N)c3)c2c1Cl] | Chemistry 306 |
| 700,834 | 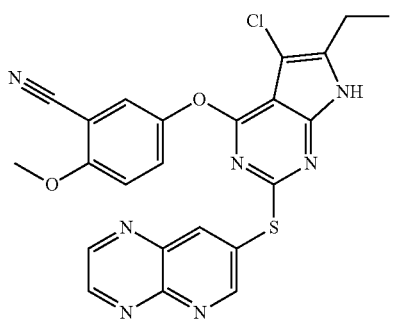 [SMILES: CCc1[nH]c2nc(Sc3cnc4nccnc4c3)nc(Oc3ccc(OC)c(C#N)c3)c2c1Cl] | Chemistry 307 |
| 700,835 | 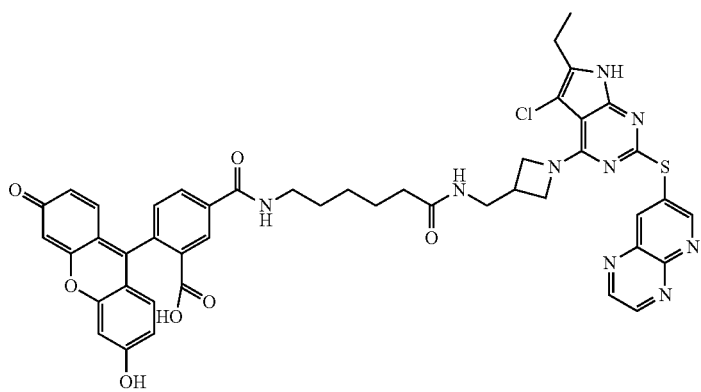 [SMILES: CCc1[nH]c2nc(Sc3cnc4nccnc4c3)nc(N3CC(CNC(=O)CCCCCNC(=O)c4ccc(-c5c6ccc(=O)cc-6oc6cc(O)ccc56)c(C(=O)O)c4)C3)c2c1Cl] | Chemistry 308 |
| 700,841 | 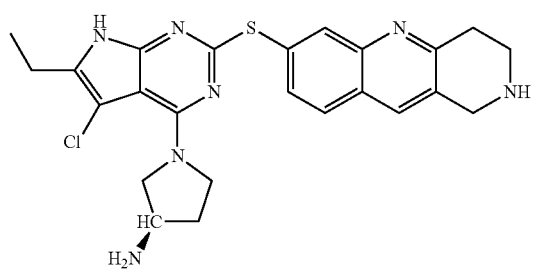 [SMILES: CCc1[nH]c2nc(Sc3ccc4cc5c(nc4c3)CCNC5)nc(N3CC[C@@H](N)C3)c2c1Cl] | Chemistry 309 |

| Rx ID | CHEMISTRY | |
|---|---|---|
| 700,842 | 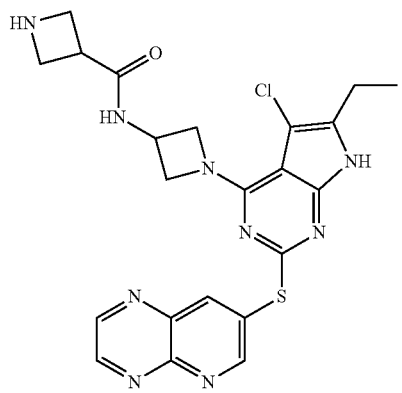 [SMILES: CCc1[nH]c2nc(Sc3cnc4nccnc4c3)nc(N3CC(NC(=O)C4CNC4)C3)c2c1Cl] | Chemistry 310 |
| 700,843 | 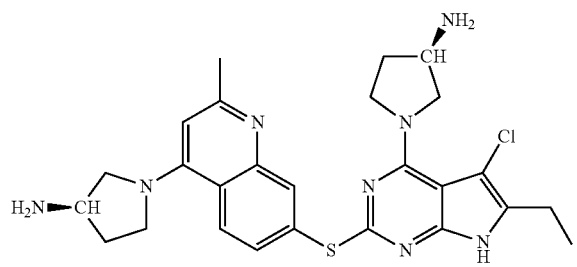 [SMILES: CCc1[nH]c2nc(Sc3ccc4c(N5CC[C@@H](N)C5)cc(C)nc4c3)nc(N3CC[C@@H](N)C3)c2c1Cl] | Chemistry 311 |
| 700,844 | 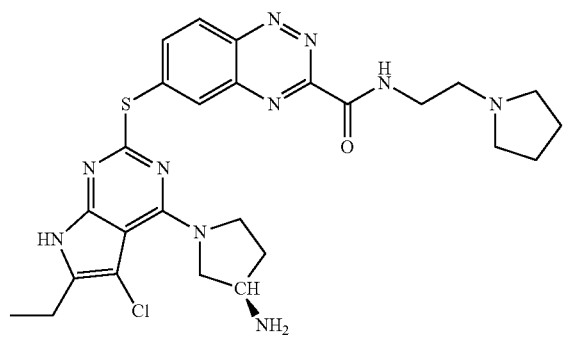 [SMILES: CCc1[nH]c2nc(Sc3ccc4nnc(C(=O)NCCN5CCCC5)nc4c3)nc(N3CC[C@@H](N)C3)c2c1Cl] | Chemistry 312 |
| 700,845 | 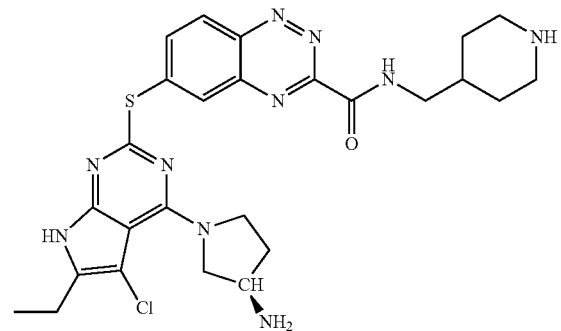 [SMILES: CCc1[nH]c2nc(Sc3ccc4nnc(C(=O)NCC5CCNCC5)nc4c3)nc(N3CC[C@@H](N)C3)c2c1Cl] | Chemistry 313 |

| Rx ID | CHEMISTRY | |
|---|---|---|
| 700,846 | 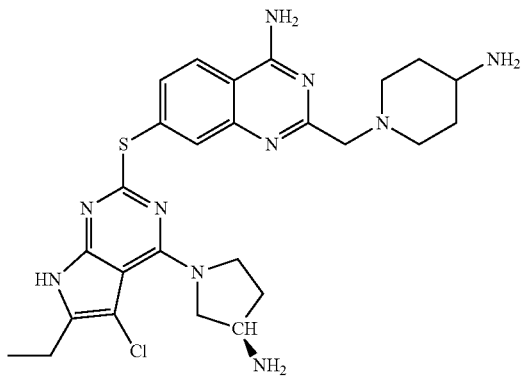 [SMILES: CCc1[nH]c2nc(Sc3ccc4c(N)nc(CN5CCC(N)CC5)nc4c3)nc(N3CC[C@@H](N)C3)c2c1Cl] | Chemistry 314 |
| 700,847 | 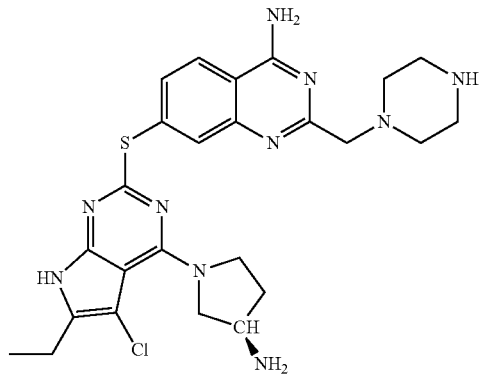 [SMILES: CCc1[nH]c2nc(Sc3ccc4c(N)nc(CN5CCNCC5)nc4c3)nc(N3CC[C@@H](N)C3)c2c1Cl] | Chemistry 315 |
| 700,848 | 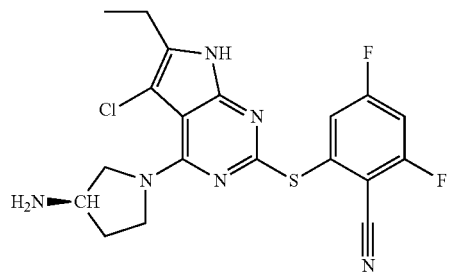 [SMILES: CCc1[nH]c2nc(Sc3cc(F)cc(F)c3C#N)nc(N3CC[C@@H](N)C3)c2c1Cl] | Chemistry 316 |
| 700,850 | 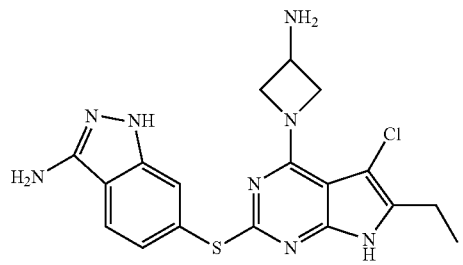 [SMILES: CCc1[nH]c2nc(Sc3ccc4c(N)n[nH]c4c3)nc(N3CC(N)C3)c2c1Cl] | Chemistry 317 |

| Rx ID | CHEMISTRY | |
|---|---|---|
| 700,851 | 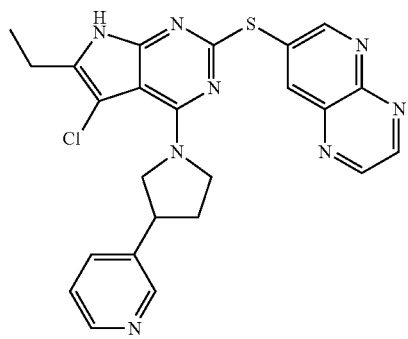 [SMILES: CCc1[nH]c2nc(Sc3cnc4nccnc4c3)nc(N3CCC(c4cccnc4)C3)c2c1Cl] | Chemistry 318 |
| 700,857 | 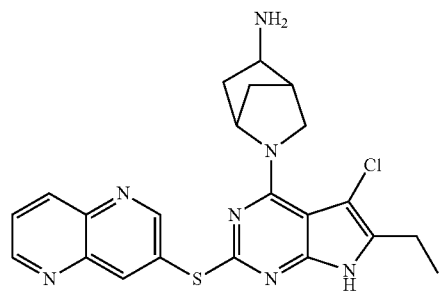 [SMILES: CCc1[nH]c2nc(Sc3cnc4cccnc4c3)nc(N3CC4CC3CC4N)c2c1Cl] | Chemistry 319 |
| 700,858 | 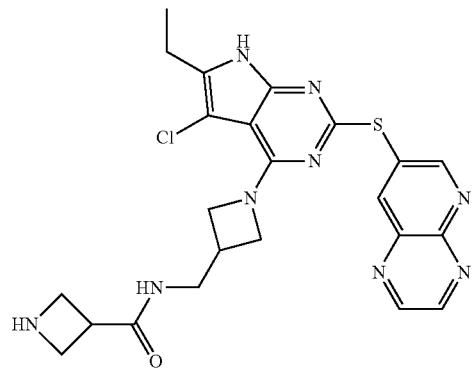 [SMILES: CCc1[nH]c2nc(Sc3cnc4nccnc4c3)nc(N3CC(CNC(=O)C4CNC4)C3)c2c1Cl] | Chemistry 320 |
| 700,859 | 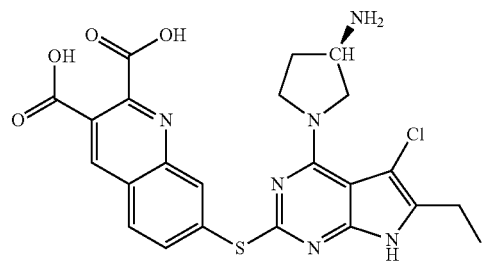 [SMILES: CCc1[nH]c2nc(Sc3ccc4cc(C(=O)O)c(C(=O)O)nc4c3)nc(N3CC[C@@H](N)C3)c2c1Cl] | Chemistry 321 |
| 700,860 | 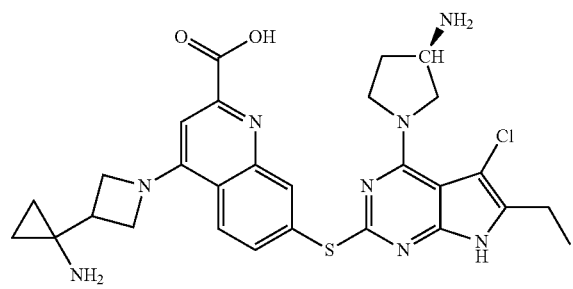 [SMILES: CCc1[nH]c2nc(Sc3ccc4c(N5CC(C6(N)CC6)C5)cc(C(=O)O)nc4c3)nc(N3CC[C@@H](N)C3)c2c1Cl] | Chemistry 322 |

| Rx ID | CHEMISTRY | |
|---|---|---|
| 700,861 | 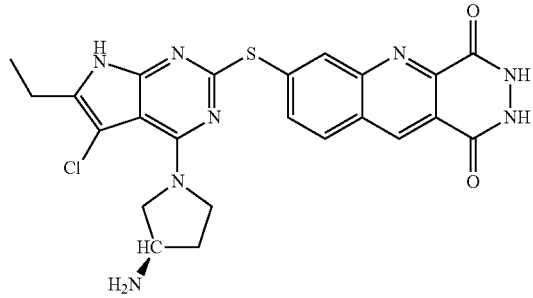 [SMILES: CCc1[nH]c2nc(Sc3ccc4cc5c(=O)[nH][nH]c(=O)c5nc4c3)nc(N3CC[C@@H](N)C3)c2c1Cl] | Chemistry 323 |
| 700,862 | 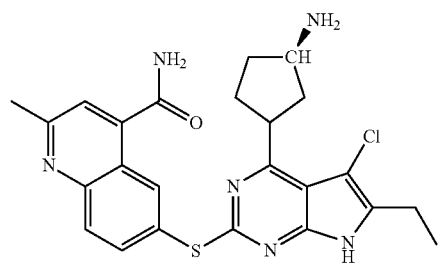 [SMILES: CCc1[nH]c2nc(Sc3ccc4nc(C)cc(C(N)=O)c4c3)nc(C3CC[C@@H](N)C3)c2c1Cl] | Chemistry 324 |
| 700,863 | 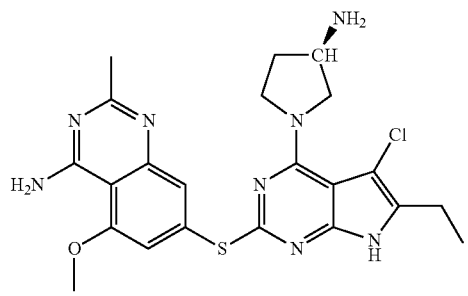 [SMILES: CCc1[nH]c2nc(Sc3cc(OC)c4c(N)nc(C)nc4c3)nc(N3CC[C@@H](N)C3)c2c1Cl] | Chemistry 325 |
| 700,864 | 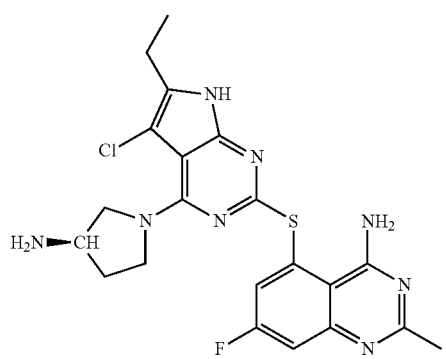 [SMILES: CCc1[nH]c2nc(Sc3cc(F)cc4nc(C)nc(N)c34)nc(N3CC[C@@H](N)C3)c2c1Cl] | Chemistry 326 |
| 700,865 | 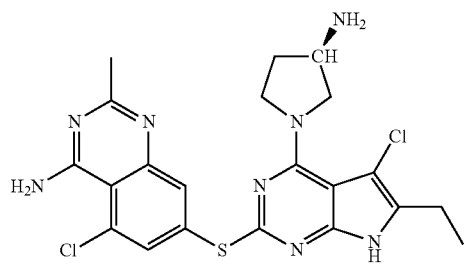 [SMILES: CCc1[nH]c2nc(Sc3cc(Cl)c4c(N)nc(C)nc4c3)nc(N3CC[C@@H](N)C3)c2c1Cl] | Chemistry 327 |

| Rx ID | CHEMISTRY | |
|---|---|---|
| 700,867 | 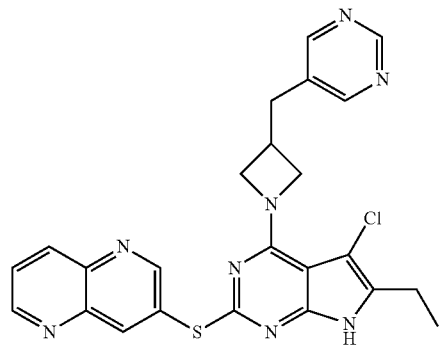 [SMILES: CCc1[nH]c2nc(Sc3cnc4cccnc4c3)nc(N3CC(Cc4cncnc4)C3)c2c1Cl] | Chemistry 328 |
| 700,868 | 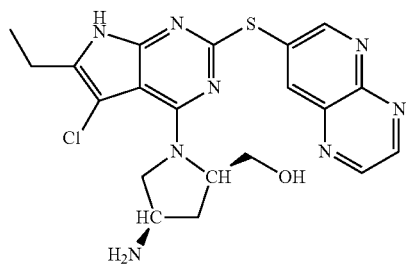 [SMILES: CCc1[nH]c2nc(Sc3cnc4nccnc4c3)nc(N3C[C@H](N)C[C@@H]3CO)c2c1Cl] | Chemistry 329 |
| 700,869 | 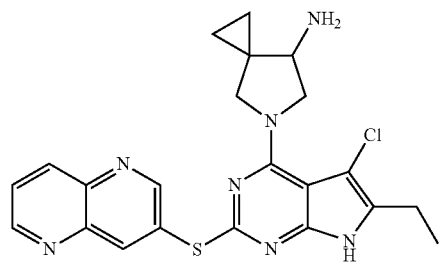 [SMILES: CCc1[nH]c2nc(Sc3cnc4cccnc4c3)nc(N3CC(N)C4(CC4)C3)c2c1Cl] | Chemistry 330 |
| 700,870 | 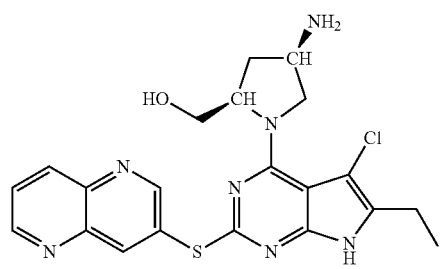 [SMILES: CCc1[nH]c2nc(Sc3cnc4cccnc4c3)nc(N3C[C@H](N)C[C@@H]3CO)c2c1Cl] | Chemistry 331 |
| 700,871 | 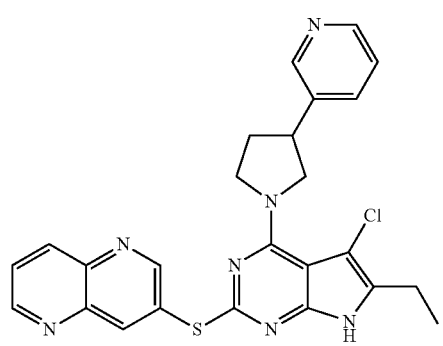 [SMILES: CCc1[nH]c2nc(Sc3cnc4cccnc4c3)nc(N3CCC(c4cccnc4)C3)c2c1Cl] | Chemistry 332 |

| Rx ID | CHEMISTRY | |
|---|---|---|
| 700,872 | 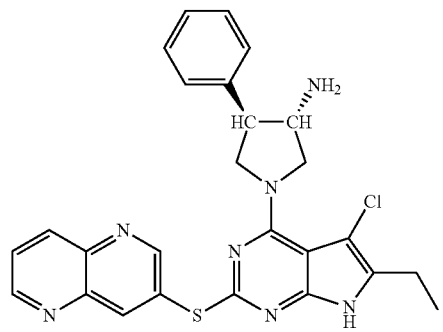 [SMILES: CCc1[nH]c2nc(Sc3cnc4cccnc4c3)nc(N3C[C@@H](N)[C@H](c4ccccc4)C3)c2c1Cl] | Chemistry 333 |
| 700,873 | 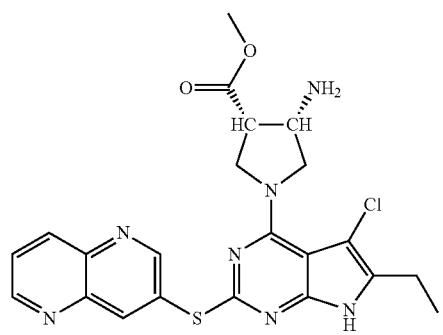 [SMILES: CCc1[nH]c2nc(Sc3cnc4cccnc4c3)nc(N3C[C@@H](N)[C@@H](C(=O)OC)C3)c2c1Cl] | Chemistry 334 |
| 700,874 | 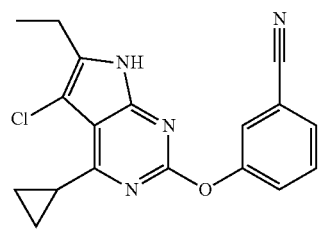 [SMILES: CCc1[nH]c2nc(Oc3cccc(C#N)c3)nc(C3CC3)c2c1Cl] | Chemistry 335 |
| 700,875 | 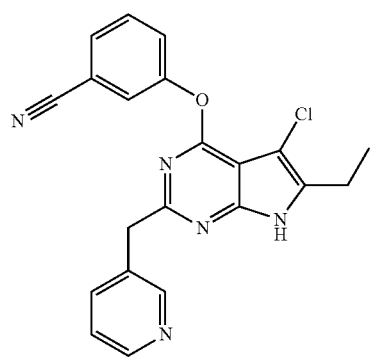 [SMILES: CCc1[nH]c2nc(Cc3cccnc3)nc(Oc3cccc(C#N)c3)c2c1Cl] | Chemistry 336 |
| 700,876 | 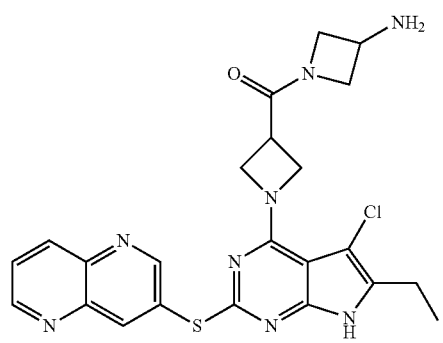 [SMILES: CCc1[nH]c2nc(Sc3cnc4cccnc4c3)nc(N3CC(C(=O)N4CC(N)C4)C3)c2c1Cl] | Chemistry 337 |

| Rx ID | CHEMISTRY | |
|---|---|---|
| 700781-2 | 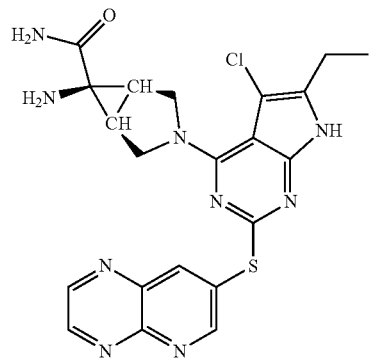 [SMILES: CCc1[nH]c2nc(Sc3cnc4nccnc4c3)nc(N3C[C@@H]4[C@H](C3)[C@@]4(N)C(N)=O)c2c1Cl] | Chemistry 338 |
| 700,884 | 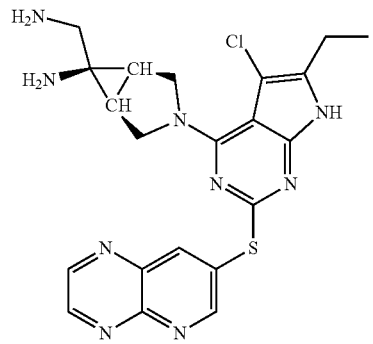 [SMILES: CCc1[nH]c2nc(Sc3cnc4nccnc4c3)nc(N3C[C@@H]4[C@H](C3)[C@@]4(N)CN)c2c1Cl] | Chemistry 339 |
| 700,885 | 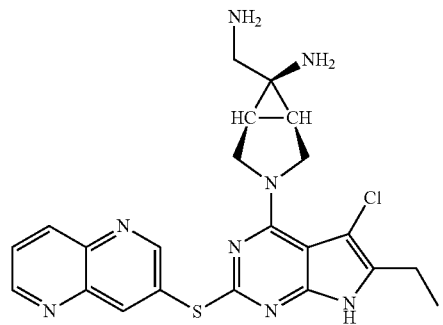 [SMILES: CCc1[nH]c2nc(Sc3cnc4cccnc4c3)nc(N3C[C@@H]4[C@H](C3)[C@@]4(N)CN)c2c1Cl] | Chemistry 340 |
| 700,886 | 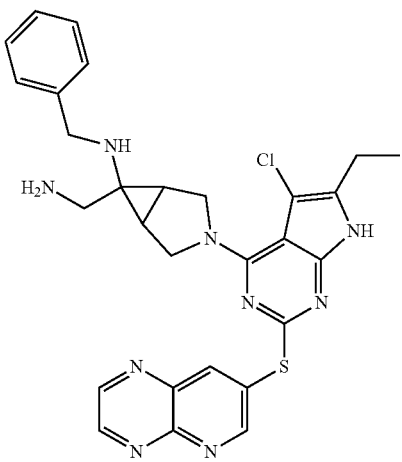 [SMILES: CCc1[nH]c2nc(Sc3cnc4nccnc4c3)nc(N3CC4C(C3)C4(CN)NCc3ccccc3)c2c1Cl] | Chemistry 341 |

| Rx ID | CHEMISTRY | |
|---|---|---|
| 700,887 | 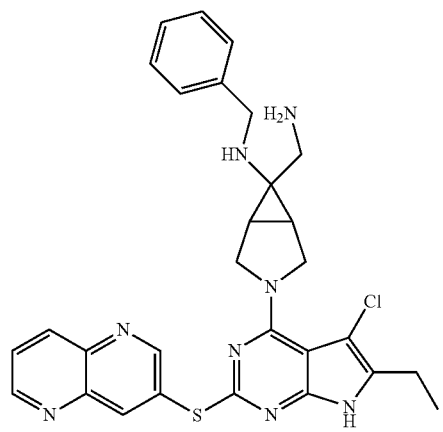 [SMILES: CCc1[nH]c2nc(Sc3cnc4cccnc4c3)nc(N3CC4C(C3)C4(CN)NCc3ccccc3)c2c1Cl] | Chemistry 342 |
| 700,888 | 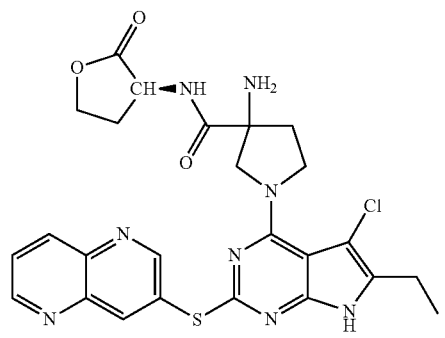 [SMILES: CCc1[nH]c2nc(Sc3cnc4cccnc4c3)nc(N3CCC(N)(C(=O)N[C@H]4CCOC4=O)C3)c2c1Cl] | Chemistry 343 |
| 700,889 | 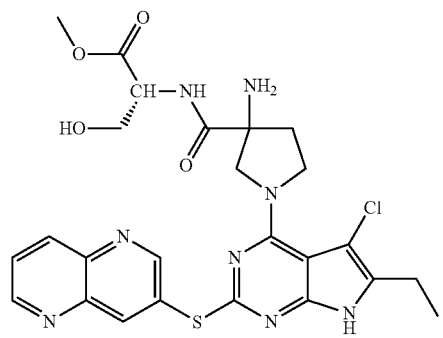 [SMILES: CCc1[nH]c2nc(Sc3cnc4cccnc4c3)nc(N3CCC(N)(C(=O)N[C@H](CO)C(=O)OC)C3)c2c1Cl] | Chemistry 344 |
| 700,890 | 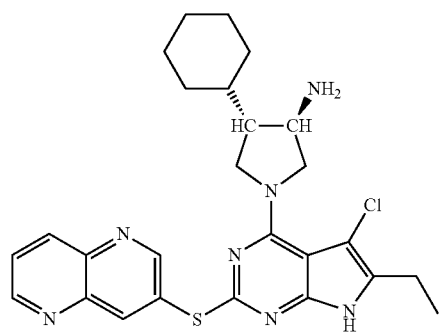 [SMILES: CCc1[nH]c2nc(Sc3cnc4cccnc4c3)nc(N3C[C@H](C4CCCCC4)[C@@H](N)C3)c2c1Cl] | Chemistry 345 |

| Rx ID | CHEMISTRY | |
|---|---|---|
| 700,891 | 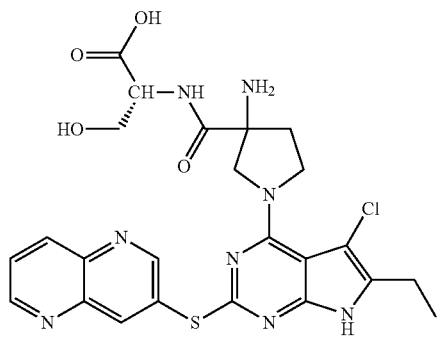 [SMILES: CCc1[nH]c2nc(Sc3cnc4cccnc4c3)nc(N3CCC(N)(C(=O)N[C@H](CO)C(=O)O)C3)c2c1Cl] | Chemistry 346 |
| 700,892 | 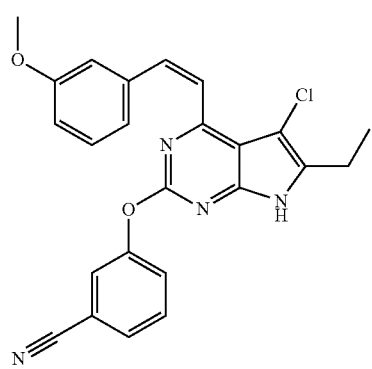 [SMILES: CCc1[nH]c2nc(Oc3cccc(C#N)c3)nc(/C=C\c3cccc(OC)c3)c2c1Cl] | Chemistry 347 |
| 700,893 | 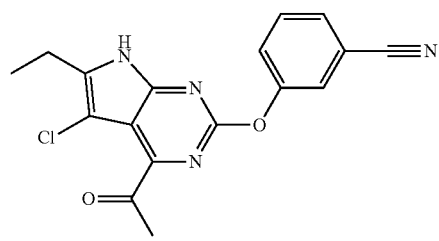 [SMILES: CCc1[nH]c2nc(Oc3cccc(C#N)c3)nc(C(C)=O)c2c1Cl] | Chemistry 348 |
| 700,894 | 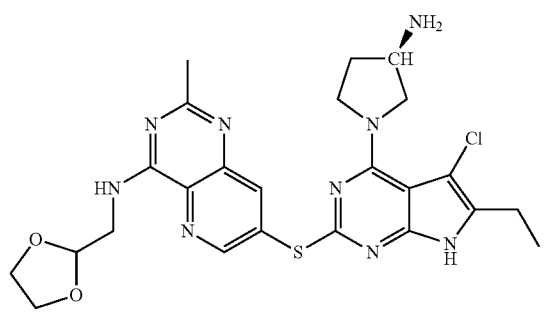 [SMILES: CCc1[nH]c2nc(Sc3cnc4c(NCC5OCCO5)nc(C)nc4c3)nc(N3CC[C@@H](N)C3)c2c1Cl] | Chemistry 349 |
| 700,898 | 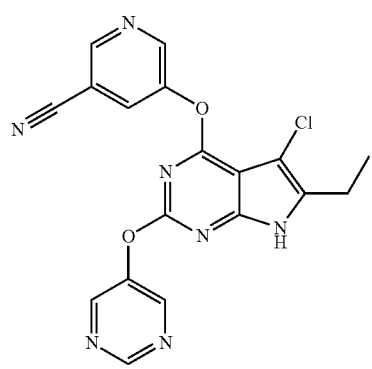 [SMILES: CCc1[nH]c2nc(Oc3cncnc3)nc(Oc3cncc(C#N)c3)c2c1Cl] | Chemistry 350 |

| Rx ID | CHEMISTRY | |
|---|---|---|
| 700,900 | 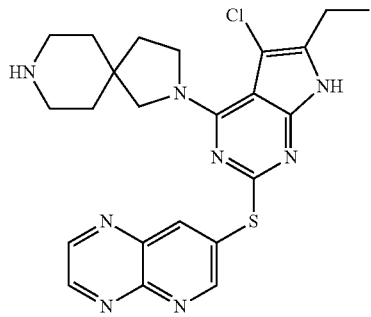 [SMILES: CCc1[nH]c2nc(Sc3cnc4nccnc4c3)nc(N3CCC4(CCNCC4)C3)c2c1Cl] | Chemistry 351 |
| 700,901 | 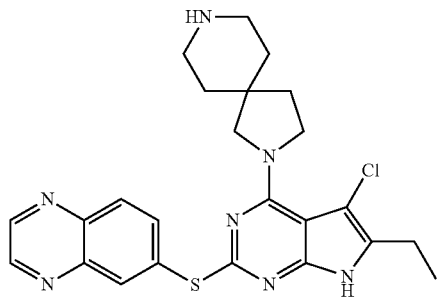 [SMILES: CCc1[nH]c2nc(Sc3ccc4nccnc4c3)nc(N3CCC4(CCNCC4)C3)c2c1Cl] | Chemistry 352 |
| 700,903 | 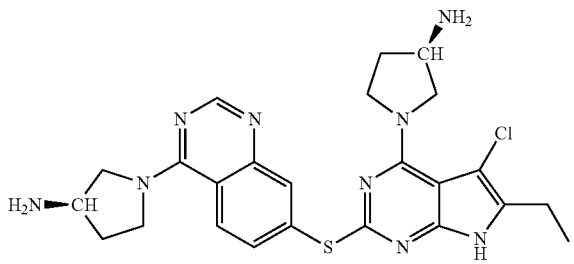 [SMILES: CCc1[nH]c2nc(Sc3ccc4c(N5CC[C@@H](N)C5)ncnc4c3)nc(N3CC[C@@H](N)C3)c2c1Cl] | Chemistry 353 |
| 700,904 | 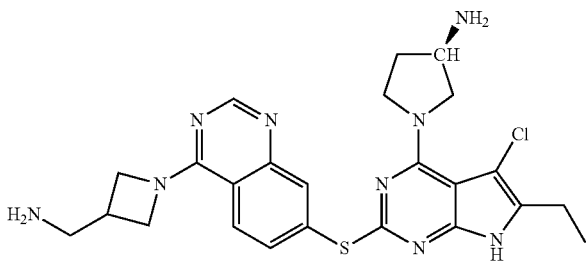 [SMILES: CCc1[nH]c2nc(Sc3ccc4c(N5CC(CN)C5)ncnc4c3)nc(N3CC[C@@H](N)C3)c2c1Cl] | Chemistry 354 |
| 700,906 | 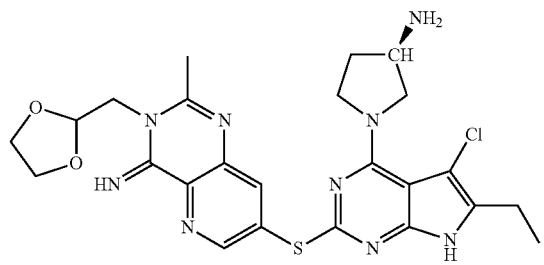 [SMILES: CCc1[nH]c2nc(Sc3cnc4c(=N)n(CC5OCCO5)c(C)nc4c3)nc(N3CC[C@@H](N)C3)c2c1Cl] | Chemistry 355 |

| Rx ID | CHEMISTRY | |
|---|---|---|
| 700,907 | 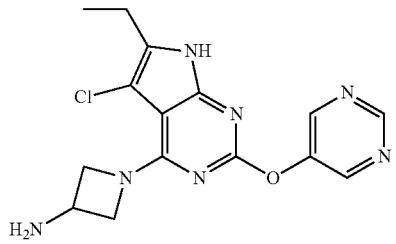 [SMILES: CCc1[nH]c2nc(Oc3cncnc3)nc(N3CC(N)C3)c2c1Cl] | Chemistry 356 |
| 700,908 | 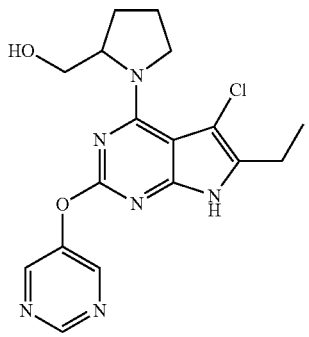 [SMILES: CCc1[nH]c2nc(Oc3cncnc3)nc(N3CCCC3CO)c2c1Cl] | Chemistry 357 |
| 700,909 | 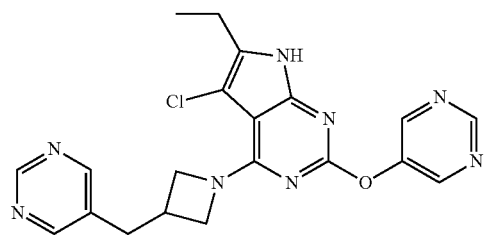 [SMILES: CCc1[nH]c2nc(Oc3cncnc3)nc(N3CC(Cc4cncnc4)C3)c2c1Cl] | Chemistry 358 |
| 700,910 | 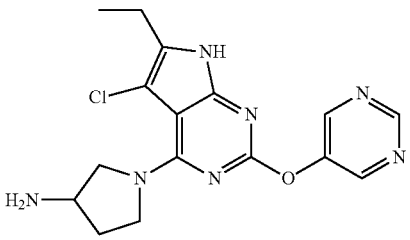 [SMILES: CCc1[nH]c2nc(Oc3cncnc3)nc(N3CCC(N)C3)c2c1Cl] | Chemistry 359 |
| 700,911 | 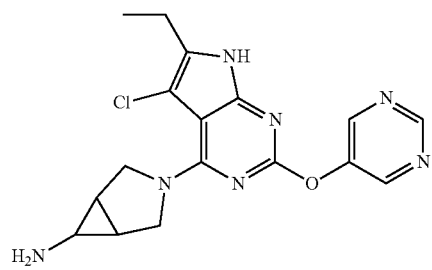 | Chemistry 360 |

| Rx ID | CHEMISTRY | |
|---|---|---|
| 700,912 | 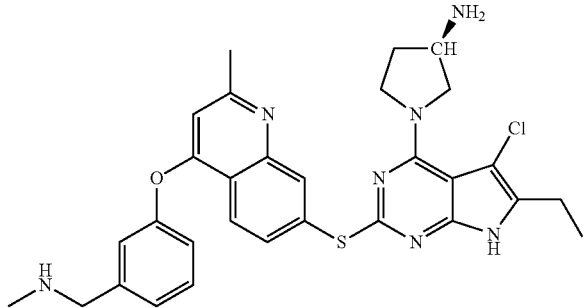 [SMILES: CCc1[nH]c2nc(Sc3ccc4c(Oc5cccc(CNC)c5)cc(C)nc4c3)nc(N3CC[C@@H](N)C3)c2c1Cl] | Chemistry 361 |
| 700,913 | 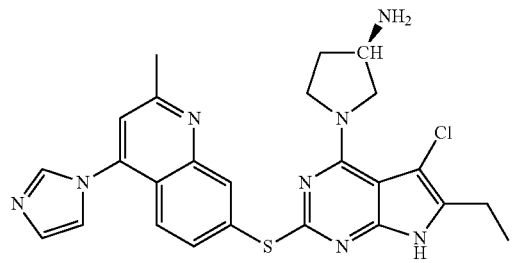 [SMILES: CCc1[nH]c2nc(Sc3ccc4c(-n5ccnc5)cc(C)nc4c3)nc(N3CC[C@@H](N)C3)c2c1Cl] | Chemistry 362 |
| 700,914 | 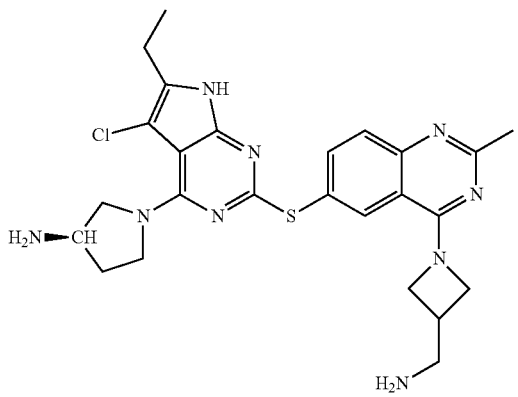 [SMILES: CCc1[nH]c2nc(Sc3ccc4nc(C)nc(N5CC(CN)C5)c4c3)nc(N3CC[C@@H](N)C3)c2c1Cl] | Chemistry 363 |
| 700,915 | 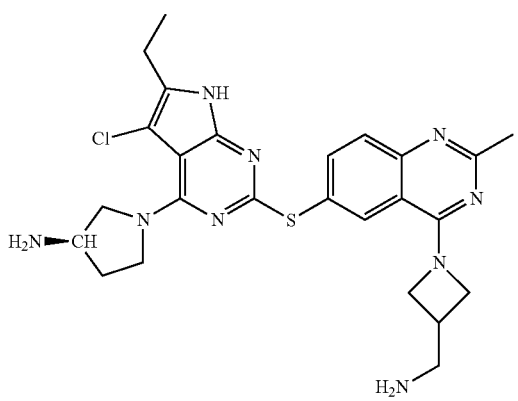 [SMILES: CCc1[nH]c2nc(Sc3ccc4nc(C)nc(N5CC(CN)C5)c4c3)nc(N3CC[C@@H](N)C3)c2c1Cl] | Chemistry 364 |

| Rx ID | CHEMISTRY | |
|---|---|---|
| 700,916 | 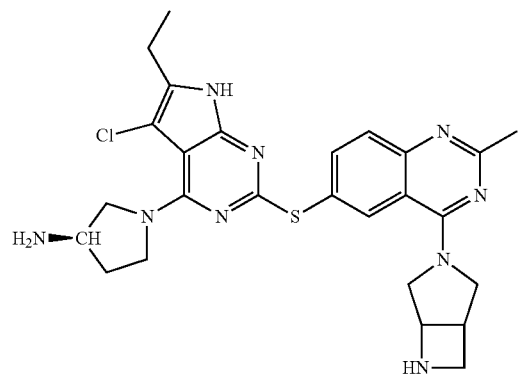 [SMILES: CCc1[nH]c2nc(Sc3ccc4nc(C)nc(N5CC6CNC6C5)c4c3)nc(N3CC[C@@H](N)C3)c2c1Cl] | Chemistry 365 |
| 700,917 | 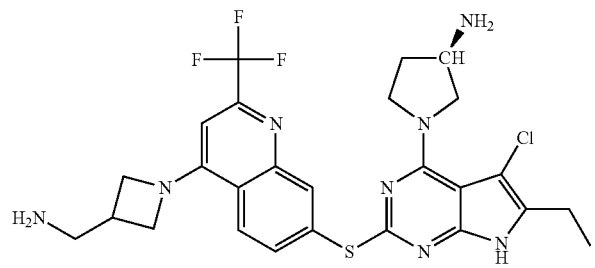 [SMILES: CCc1[nH]c2nc(Sc3ccc4c(N5CC(CN)C5)cc(C(F)(F)F)nc4c3)nc(N3CC[C@@H](N)C3)c2c1Cl] | Chemistry 366 |
| 700,918 | 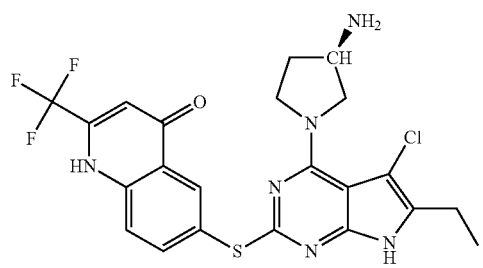 [SMILES: CCc1[nH]c2nc(Sc3ccc4[nH]c(C(F)(F)F)cc(=O)c4c3)nc(N3CC[C@@H](N)C3)c2c1Cl] | Chemistry 367 |
| 700,919 | 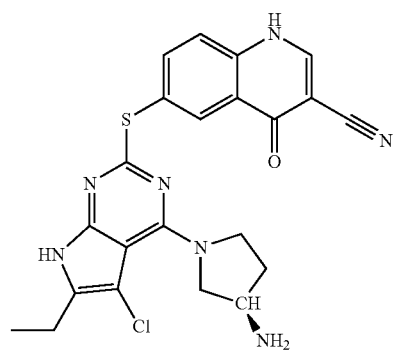 [SMILES: CCc1[nH]c2nc(Sc3ccc4[nH]cc(C#N)c(=O)c4c3)nc(N3CC[C@@H](N)C3)c2c1Cl] | Chemistry 368 |

| Rx ID | CHEMISTRY | |
|---|---|---|
| 700,920 | 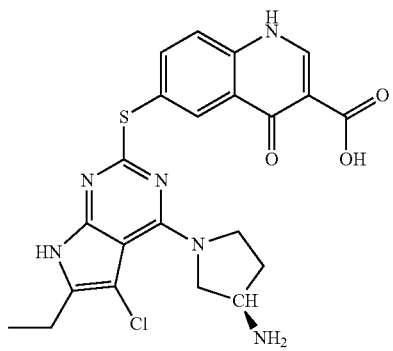 [SMILES: CCc1[nH]c2nc(Sc3ccc4[nH]cc(C(=O)O)c(=O)c4c3)nc(N3CC[C@@H](N)C3)c2c1Cl] | Chemistry 369 |
| 700,921 | 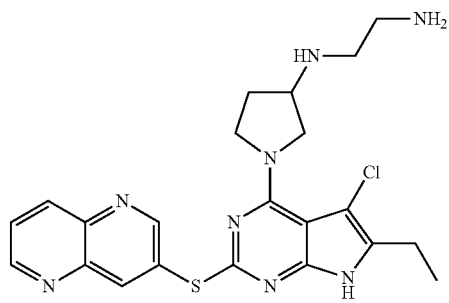 [SMILES: CCc1[nH]c2nc(Sc3cnc4cccnc4c3)nc(N3CCC(NCCN)C3)c2c1Cl] | Chemistry 370 |
| 700,922 | 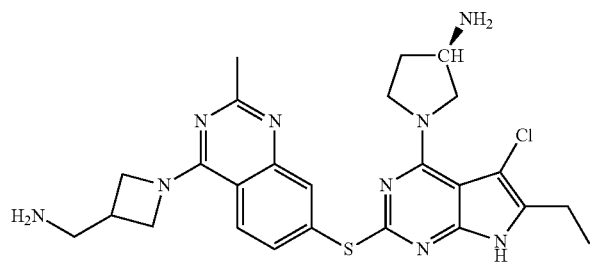 [SMILES: CCc1[nH]c2nc(Sc3ccc4c(N5CC(CN)C5)nc(C)nc4c3)nc(N3CC[C@@H](N)C3)c2c1Cl] | Chemistry 371 |
| 700,923 | 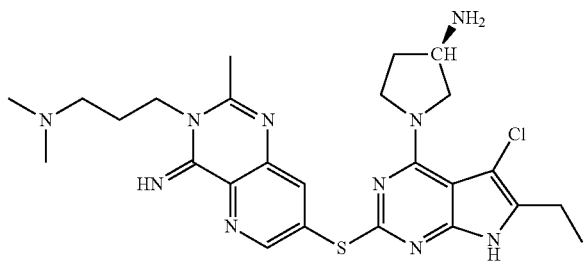 [SMILES: CCc1[nH]c2nc(Sc3cnc4c(=N)n(CCCN(C)C)c(C)nc4c3)nc(N3CC[C@@H](N)C3)c2c1Cl] | Chemistry 372 |
| 700,924 | 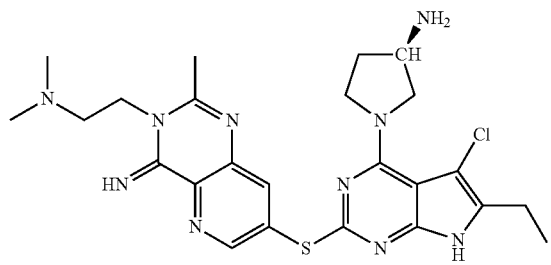 [SMILES: CCc1[nH]c2nc(Sc3cnc4c(=N)n(CCN(C)C)c(C)nc4c3)nc(N3CC[C@@H](N)C3)c2c1Cl] | Chemistry 373 |

| Rx ID | CHEMISTRY | |
|---|---|---|
| 700,925 | 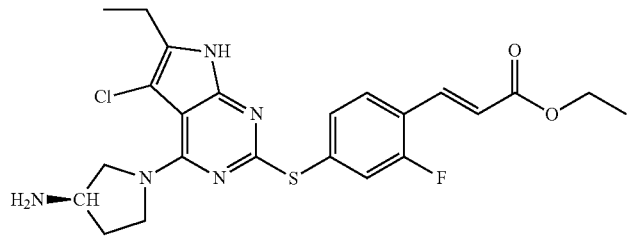 [SMILES: CCOC(=O)/C=C/c1ccc(Sc2nc(N3CC[C@@H](N)C3)c3c(Cl)c(CC)[nH]c3n2)cc1F] | Chemistry 374 |
| 700,926 | 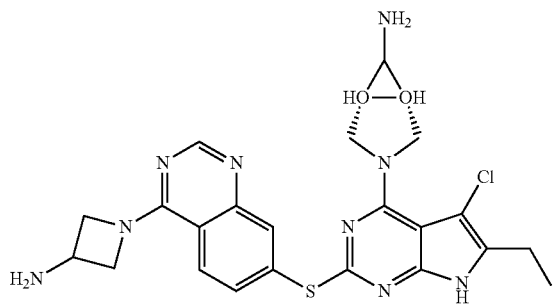 | Chemistry 375 |
| 700,927 | 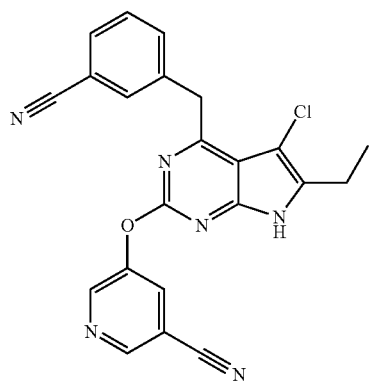 [SMILES: CCc1[nH]c2nc(Oc3cncc(C#N)c3)nc(Cc3cccc(C#N)c3)c2c1Cl] | Chemistry 376 |
| 700,928 | 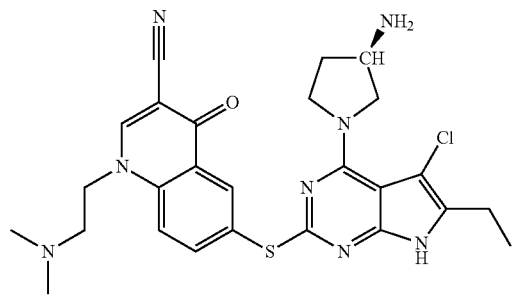 [SMILES: CCc1[nH]c2nc(Sc3ccc4c(c3)c(=O)c(C#N)cn4CCN(C)C)nc(N3CC[C@@H](N)C3)c2c1Cl] | Chemistry 377 |
| 700,929 | 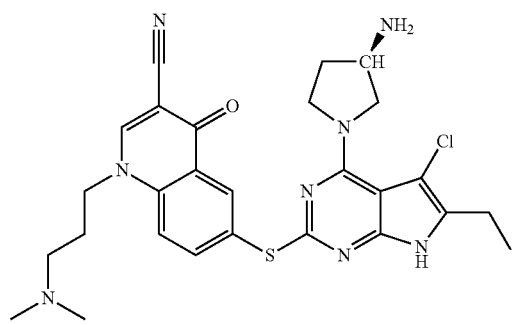 [SMILES: CCc1[nH]c2nc(Sc3ccc4c(c3)c(=O)c(C#N)cn4CCCN(C)C)nc(N3CC[C@@H](N)C3)c2c1Cl] | Chemistry 378 |

| Rx ID | CHEMISTRY | |
|---|---|---|
| 700,930 | 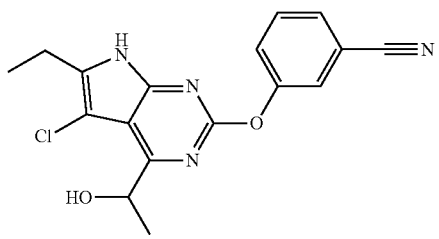 | Chemistry 379 |
| 700,931 | 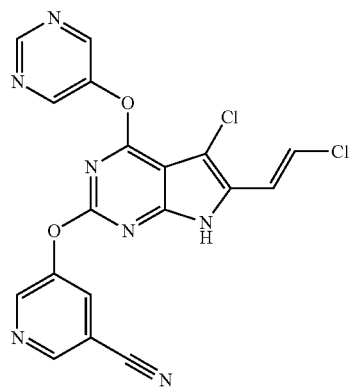 [SMILES: N#Cc1cncc(Oc2nc(Oc3cncnc3)c3c(Cl)c(/C=C/Cl)[nH]c3n2)c1] | Chemistry 380 |
| 700,932 | 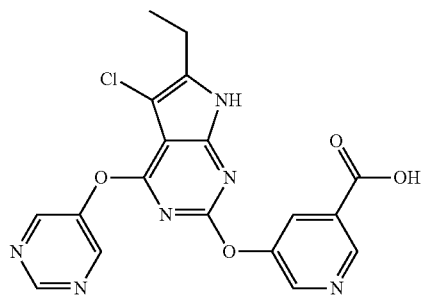 [SMILES: CCc1[nH]c2nc(Oc3cncc(C(=O)O)c3)nc(Oc3cncnc3)c2c1Cl] | Chemistry 381 |
| 700,934 | 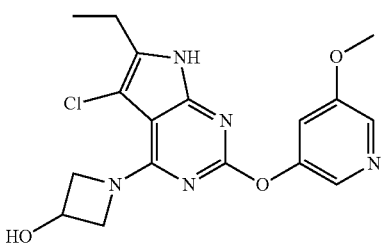 [SMILES: CCc1[nH]c2nc(Oc3cncc(OC)c3)nc(N3CC(O)C3)c2c1Cl] | Chemistry 382 |
| 700,936 | 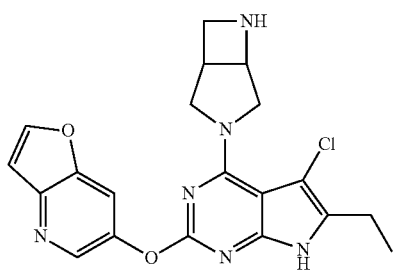 [SMILES: CCc1[nH]c2nc(Oc3cnc4ccoc4c3)nc(N3CC4CNC4C3)c2c1Cl] | Chemistry 383 |

| Rx ID | CHEMISTRY | |
|---|---|---|
| 700,940 | 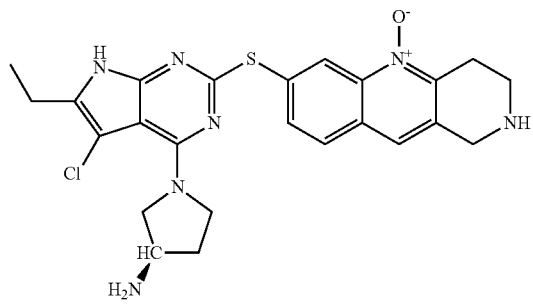 [SMILES: CCc1[nH]c2nc(Sc3ccc4cc5c([n+]([O-])c4c3)CCNC5)nc(N3CC[C@@H](N)C3)c2c1Cl] | Chemistry 384 |
| 700,941 | 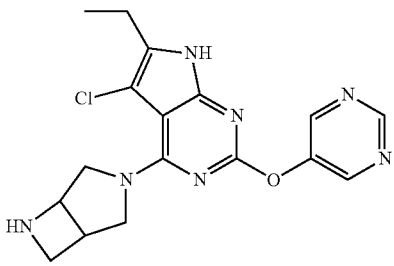 [SMILES: CCc1[nH]c2nc(Oc3cncnc3)nc(N3CC4CNC4C3)c2c1Cl] | Chemistry 385 |
| 700,942 | 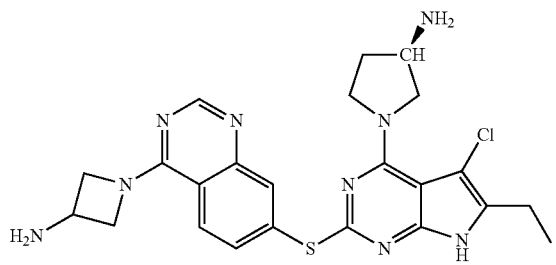 [SMILES: CCc1[nH]c2nc(Sc3ccc4c(N5CC(N)C5)ncnc4c3)nc(N3CC[C@@H](N)C3)c2c1Cl] | Chemistry 386 |
| 700,943 | 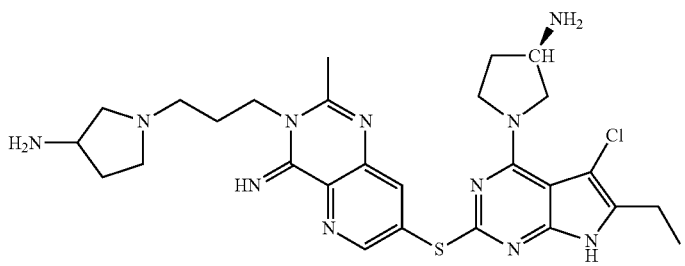 [SMILES: CCc1[nH]c2nc(Sc3cnc4c(=N)n(CCCN5CCC(N)C5)c(C)nc4c3)nc(N3CC[C@@H](N)C3)c2c1Cl] | Chemistry 387 |
| 700,946 | 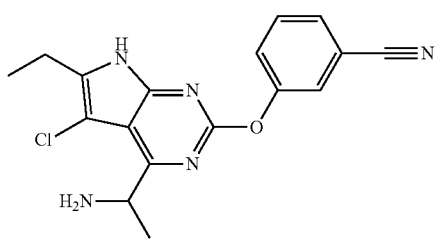 [SMILES: CCc1[nH]c2nc(Oc3cccc(C#N)c3)nc(C(C)N)c2c1Cl] | Chemistry 388 |
| 700,947 | 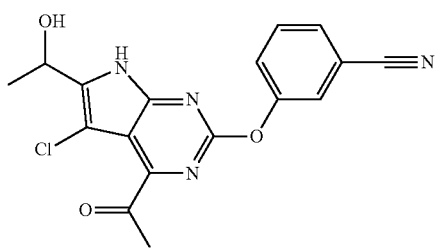 [SMILES: CC(=O)c1nc(Oc2cccc(C#N)c2)nc2[nH]c(C(C)O)c(Cl)c12] | Chemistry 389 |

| Rx ID | CHEMISTRY | |
|---|---|---|
| 700,948 | 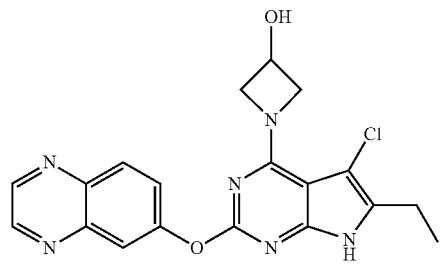 [SMILES: CCc1[nH]c2nc(Oc3ccc4nccnc4c3)nc(N3CC(O)C3)c2c1Cl] | Chemistry 390 |
| 700,950 | 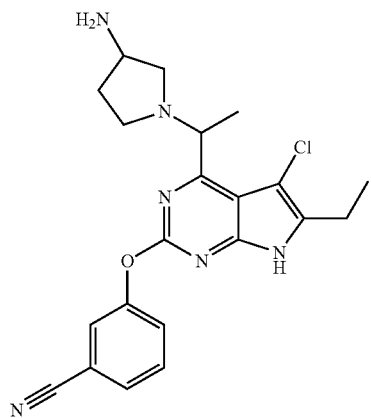 [SMILES: CCc1[nH]c2nc(Oc3cccc(C#N)c3)nc(C(C)N3CCC(N)C3)c2c1Cl] | Chemistry 391 |
| 700,951 | 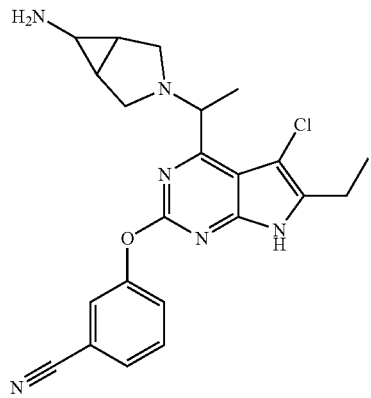 [SMILES: CCc1[nH]c2nc(Oc3cccc(C#N)c3)nc(C(C)N3CC4C(N)C4C3)c2c1Cl] | Chemistry 392 |
| 700,952 | 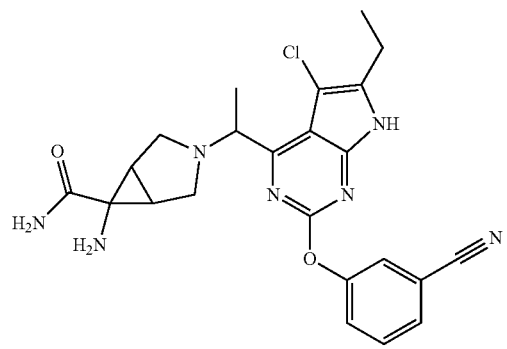 [SMILES: CCc1[nH]c2nc(Oc3cccc(C#N)c3)nc(C(C)N3CC4C(C3)C4(N)C(N)=O)c2c1Cl] | Chemistry 393 |

| Rx ID | CHEMISTRY | |
|---|---|---|
| 700,953 | 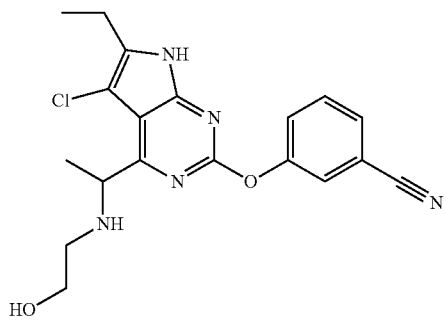 [SMILES: CCc1[nH]c2nc(Oc3cccc(C#N)c3)nc(C(C)NCCO)c2c1Cl] | Chemistry 394 |
| 700,954 | 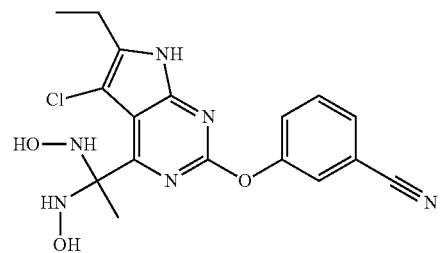 [SMILES: CCc1[nH]c2nc(Oc3cccc(C#N)c3)nc(C(C)(NO)NO)c2c1Cl] | Chemistry 395 |
| 700,955 | 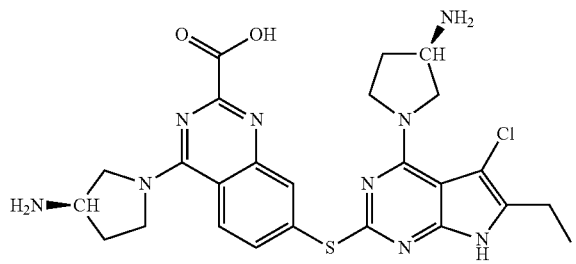 [SMILES: CCc1[nH]c2nc(Sc3ccc4c(N5CC[C@@H](N)C5)nc(C(=O)O)nc4c3)nc(N3CC[C@@H](N)C3)c2c1Cl] | Chemistry 396 |
| 700,956 | 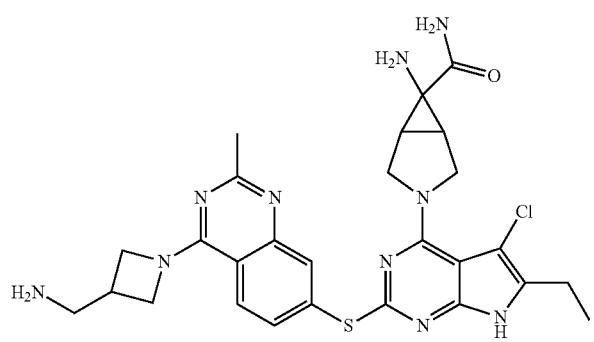 [SMILES: CCc1[nH]c2nc(Sc3ccc4c(N5CC(CN)C5)nc(C)nc4c3)nc(N3CC4C(C3)C4(N)C(N)=O)c2c1Cl] | Chemistry 397 |
| 700,957 | 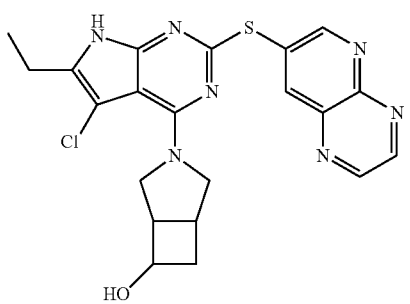 [SMILES: CCc1[nH]c2nc(Sc3cnc4nccnc4c3)nc(N3CC4CC(O)C4C3)c2c1Cl] | Chemistry 398 |

| Rx ID | CHEMISTRY | |
|---|---|---|
| 700,958 | 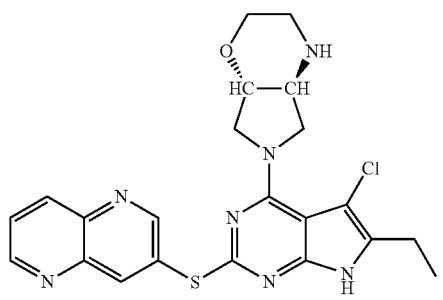 [SMILES: CCc1[nH]c2nc(Sc3cnc4cccnc4c3)nc(N3C[C@@H]4NCCO[C@H]4C3)c2c1Cl] | Chemistry 399 |
| 700,959 | 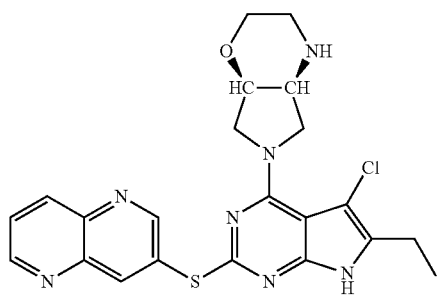 [SMILES: CCc1[nH]c2nc(Sc3cnc4cccnc4c3)nc(N3C[C@@H]4NCCO[C@@H]4C3)c2c1Cl] | Chemistry 400 |
| 700,960 | 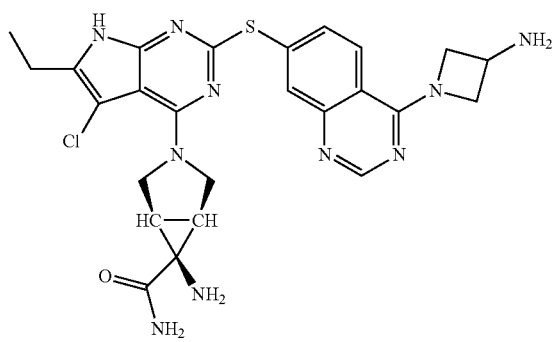 [SMILES: CCc1[nH]c2nc(Sc3ccc4c(N5CC(N)C5)ncnc4c3)nc(N3C[C@@H]4[C@H](C3)[C@@]4(N)C(N)=O)c2c1Cl] | Chemistry 401 |
| 700,961 | 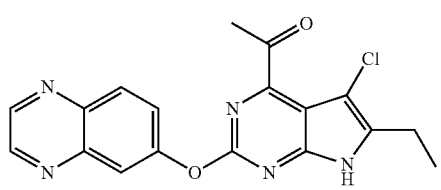 [SMILES: CCc1[nH]c2nc(Oc3ccc4nccnc4c3)nc(C(C)=O)c2c1Cl] | Chemistry 402 |
| 700,962 | 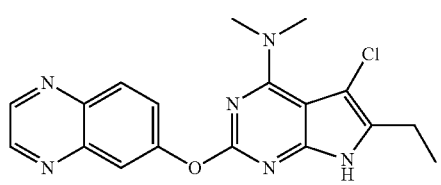 [SMILES: CCc1[nH]c2nc(Oc3ccc4nccnc4c3)nc(N(C)C)c2c1Cl] | Chemistry 403 |
| 700,963 | 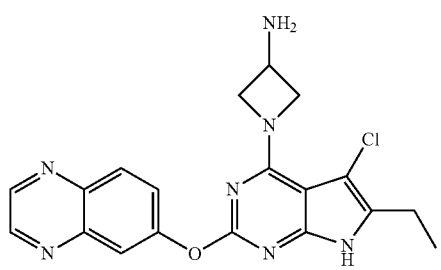 [SMILES: CCc1[nH]c2nc(Oc3ccc4nccnc4c3)nc(N3CC(N)C3)c2c1Cl] | Chemistry 404 |

| Rx ID | CHEMISTRY | |
|---|---|---|
| 700,967 | 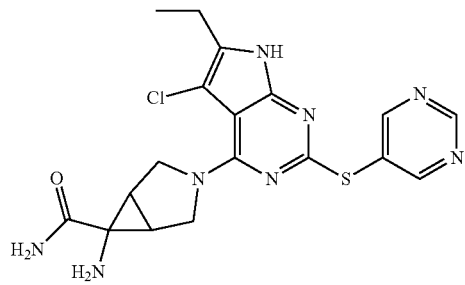 [SMILES: CCc1[nH]c2nc(Sc3cncnc3)nc(N3CC4C(C3)C4(N)C(N)=O)c2c1Cl] | Chemistry 405 |
| 700,968 | 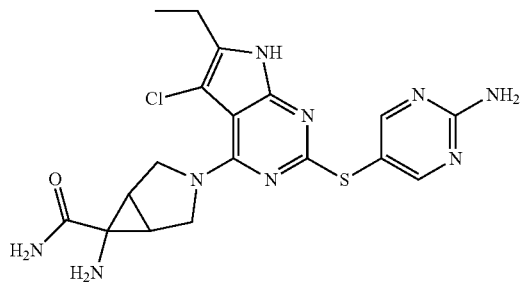 [SMILES: CCc1[nH]c2nc(Sc3cnc(N)nc3)nc(N3CC4C(C3)C4(N)C(N)=O)c2c1Cl] | Chemistry 406 |
| 700,969 | 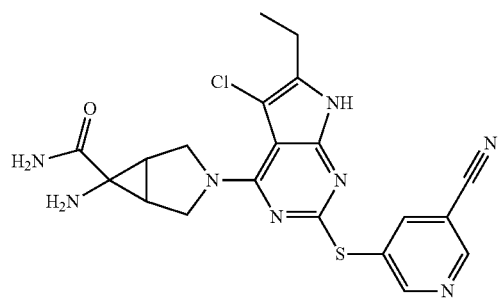 [SMILES: CCc1[nH]c2nc(Sc3cncc(C#N)c3)nc(N3CC4C(C3)C4(N)C(N)=O)c2c1Cl] | Chemistry 407 |
| 700,970 | 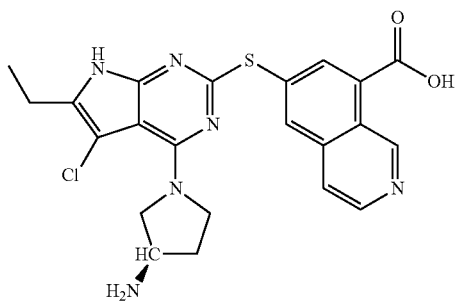 [SMILES: CCc1[nH]c2nc(Sc3cc(C(=O)O)c4cnccc4c3)nc(N3CC[C@@H](N)C3)c2c1Cl] | Chemistry 408 |
| 700,971 | 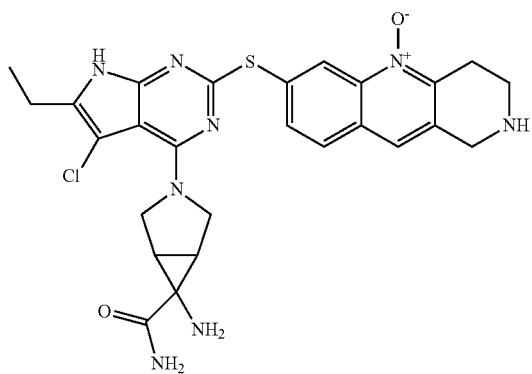 [SMILES: CCc1[nH]c2nc(Sc3ccc4cc5c([n+]([O-])c4c3)CCNC5)nc(N3CC4C(C3)C4(N)C(N)=O)c2c1Cl] | Chemistry 409 |

| Rx ID | CHEMISTRY | |
|---|---|---|
| 700,972 | 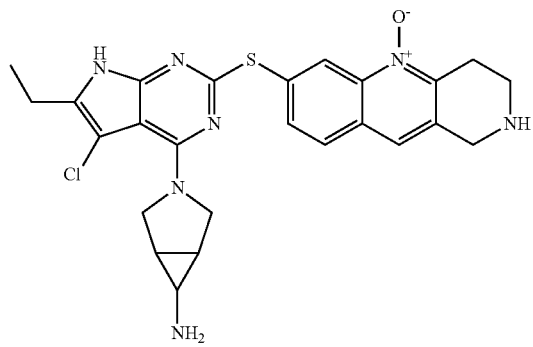 [SMILES: CCc1[nH]c2nc(Sc3ccc4cc5c([n+]([O-])c4c3)CCNC5)nc(N3CC4C(N)C4C3)c2c1Cl] | Chemistry 410 |
| 700,973 | 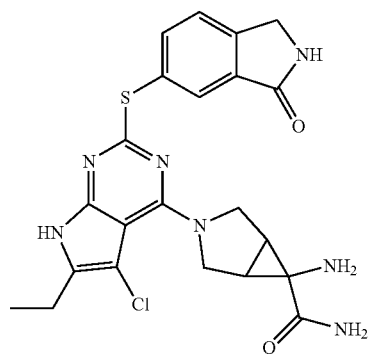 [SMILES: CCc1[nH]c2nc(Sc3ccc4c(c3)C(=O)NC4)nc(N3CC4C(C3)C4(N)C(N)=O)c2c1Cl] | Chemistry 411 |
| 700,974 | 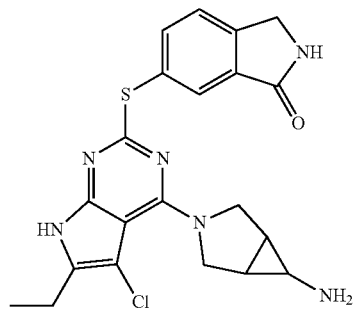 [SMILES: CCc1[nH]c2nc(Sc3ccc4c(c3)C(=O)NC4)nc(N3CC4C(N)C4C3)c2c1Cl] | Chemistry 412 |
| 700,975 | 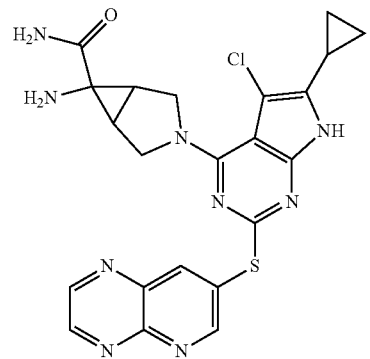 [SMILES: NC(=O)C1(N)C2CN(c3nc(Sc4cnc5nccnc5c4)nc4[nH]c(C5CC5)c(Cl)c34)CC21] | Chemistry 413 |

| Rx ID | CHEMISTRY | |
|---|---|---|
| 700,976 | 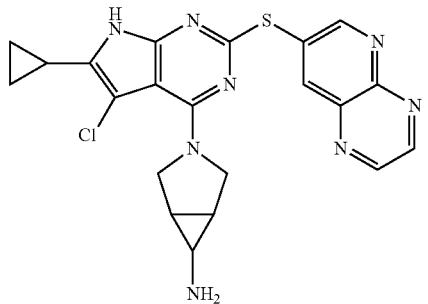 [SMILES: NC1C2CN(c3nc(Sc4cnc5nccnc5c4)nc4[nH]c(C5CC5)c(Cl)c34)CC12] | Chemistry 414 |
| 700,977 | 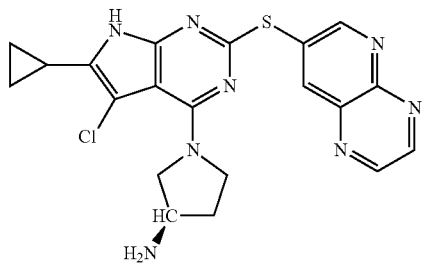 [SMILES: N[C@@H]1CCN(c2nc(Sc3cnc4nccnc4c3)nc3[nH]c(C4CC4)c(Cl)c23)C1] | Chemistry 415 |
| 700,978 | 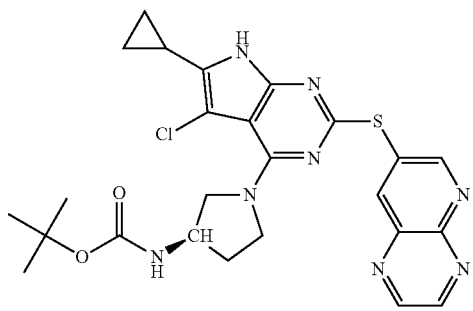 [SMILES: CC(C)(C)OC(=O)N[C@@H]1CCN(c2nc(Sc3cnc4nccnc4c3)nc3[nH]c(C4CC4)c(Cl)c23)C1] | Chemistry 416 |
| 700,981 | 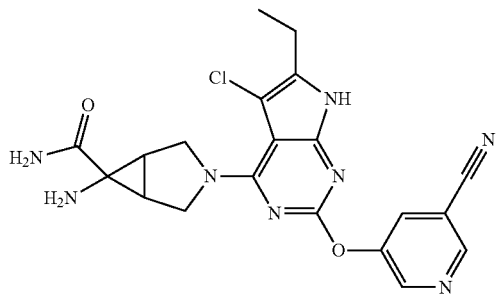 | Chemistry 417 |
| 700,983 | 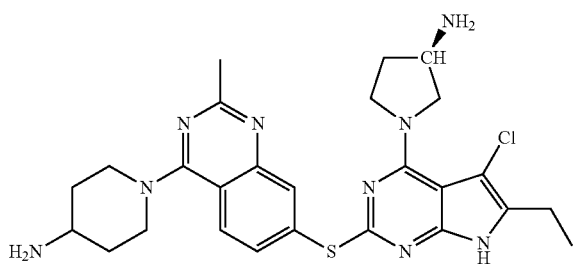 [SMILES: CCc1[nH]c2nc(Sc3ccc4c(N5CCC(N)CC5)nc(C)nc4c3)nc(N3CC[C@@H](N)C3)c2c1Cl] | Chemistry 418 |

| Rx ID | CHEMISTRY | |
|---|---|---|
| 700,984 | 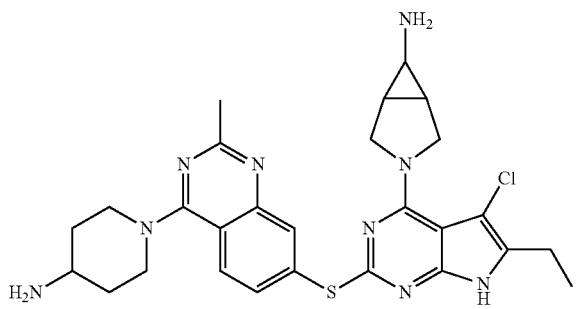 [SMILES: CCc1[nH]c2nc(Sc3ccc4c(N5CCC(N)CC5)nc(C)nc4c3)nc(N3CC4C(N)C4C3)c2c1Cl] | Chemistry 419 |
| 700,986 | 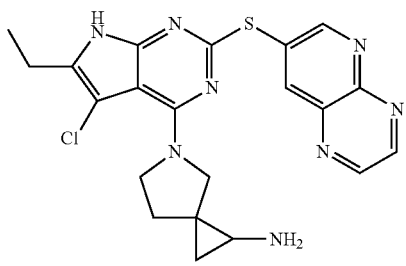 [SMILES: CCc1[nH]c2nc(Sc3cnc4nccnc4c3)nc(N3CCC4(CC4N)C3)c2c1Cl] | Chemistry 420 |
| 700,989 | 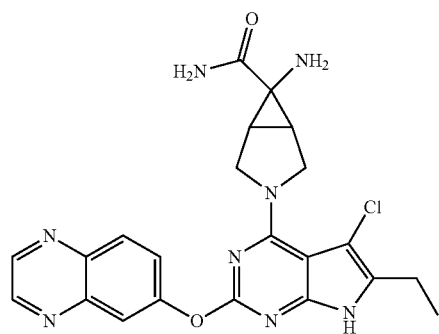 [SMILES: CCc1[nH]c2nc(Oc3ccc4nccnc4c3)nc(N3CC4C(C3)C4(N)C(N)=O)c2c1Cl] | Chemistry 421 |
| 700,990 | 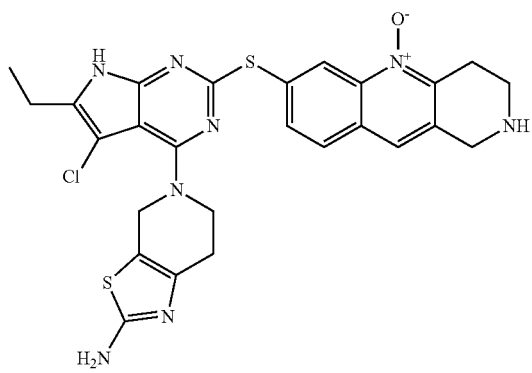 [SMILES: CCc1[nH]c2nc(Sc3ccc4cc5c([n+]([O-])c4c3)CCNC5)nc(N3CCc4nc(N)sc4C3)c2c1Cl] | Chemistry 422 |
| 700,991 | 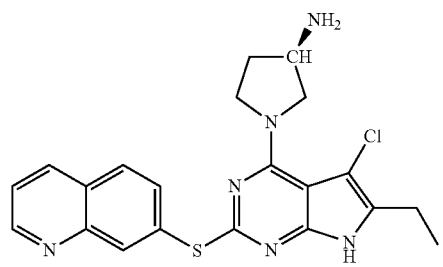 [SMILES: CCc1[nH]c2nc(Sc3ccc4cccnc4c3)nc(N3CC[C@@H](N)C3)c2c1Cl] | Chemistry 423 |

-continued
| Rx ID | CHEMISTRY | |
|---|---|---|
| 700,992 | 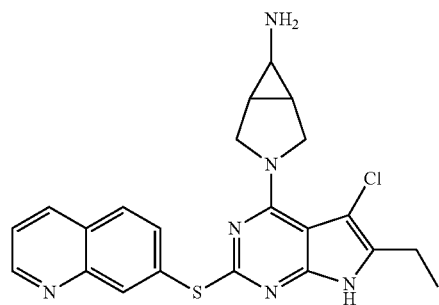 [SMILES: CCc1[nH]c2nc(Sc3ccc4cccnc4c3)nc(N3CC4C(N)C4C3)c2c1Cl] | Chemistry 424 |
| 700,993 | 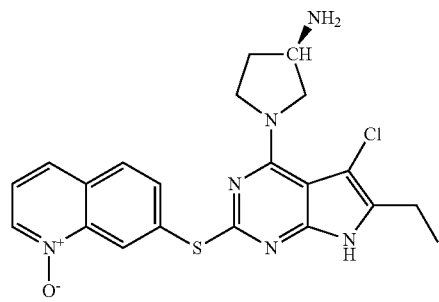 [SMILES: CCc1[nH]c2nc(Sc3ccc4ccc[n+]([O-])c4c3)nc(N3CC[C@@H](N)C3)c2c1Cl] | Chemistry 425 |
| 700,994 | 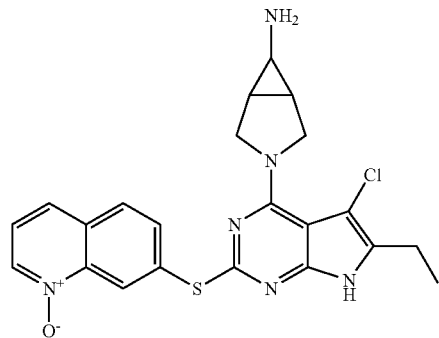 [SMILES: CCc1[nH]c2nc(Sc3ccc4ccc[n+]([O-])c4c3)nc(N3CC4C(N)C4C3)c2c1Cl] | Chemistry 426 |
| 700,995 | 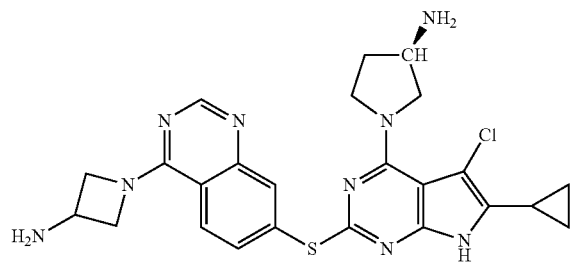 [SMILES: NC1CN(c2ncnc3cc(Sc4nc(N5CC[C@@H](N)C5)c5c(Cl)c(C6CC6)[nH]c5n4)ccc23)C1] | Chemistry 427 |
| 700,999 | 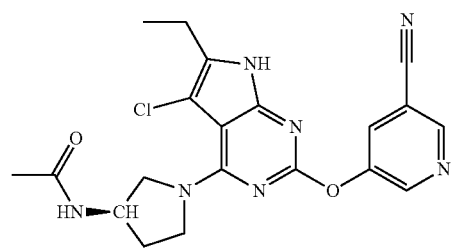 [SMILES: CCc1[nH]c2nc(Oc3cncc(C#N)c3)nc(N3CC[C@@H](NC(C)=O)C3)c2c1Cl] | Chemistry 428 |

-continued
| Rx ID | CHEMISTRY | |
|---|---|---|
| 701,000 | 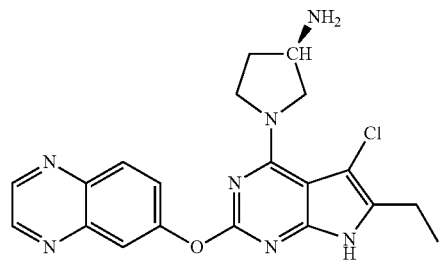 | Chemistry 429 |
| 701,001 | 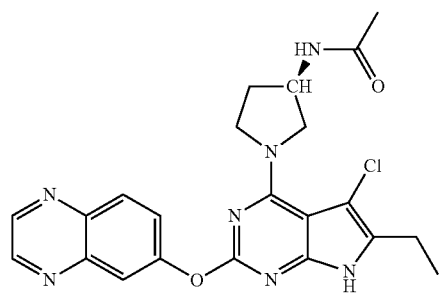 [SMILES: CCc1[nH]c2nc(Oc3ccc4nccnc4c3)nc(N3CC[C@@H](NC(C)=O)C3)c2c1Cl] | Chemistry 430 |
| 701,002 | 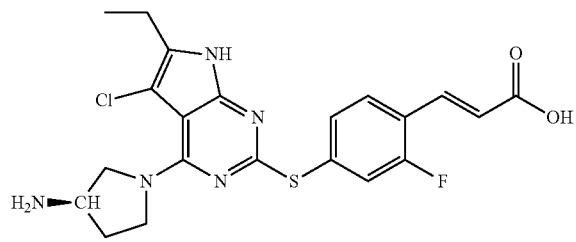 [SMILES: CCc1[nH]c2nc(Sc3ccc(/C=C/C(=O)O)c(F)c3)nc(N3CC[C@@H](N)C3)c2c1Cl] | Chemistry 431 |
| 701,003 | 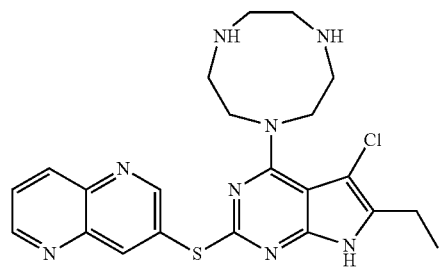 [SMILES: CCc1[nH]c2nc(Sc3cnc4cccnc4c3)nc(N3CCNCCNCC3)c2c1Cl] | Chemistry 432 |
| 701,004 | 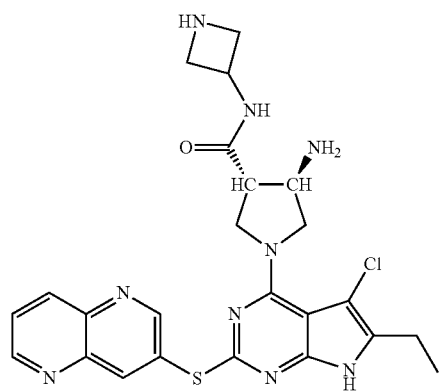 [SMILES: CCc1[nH]c2nc(Sc3cnc4cccnc4c3)nc(N3C[C@H](C(=O)NC4CNC4)[C@@H](N)C3)c2c1Cl] | Chemistry 433 |

-continued
| Rx ID | CHEMISTRY | |
|---|---|---|
| 701,005 | 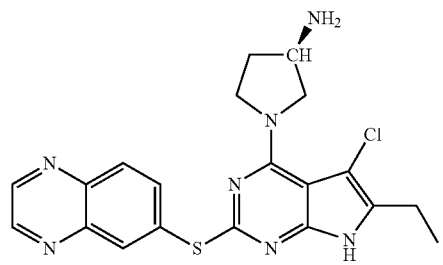 [SMILES: CCc1[nH]c2nc(Sc3ccc4nccnc4c3)nc(N3CC[C@@H](N)C3)c2c1Cl] | Chemistry 434 |
| 701,006 | 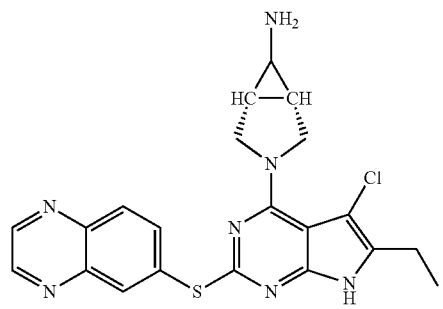 [SMILES: CCc1[nH]c2nc(Sc3ccc4nccnc4c3)nc(N3C[C@@H]4C(N)[C@@H]4C3)c2c1Cl] | Chemistry 435 |
| 701,007 | 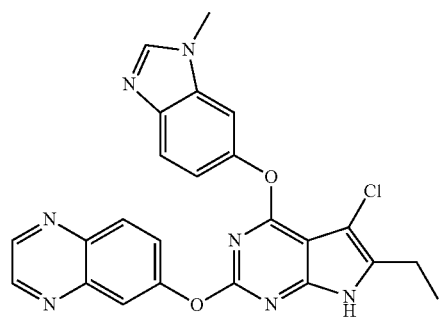 [SMILES: CCc1[nH]c2nc(Oc3ccc4nccnc4c3)nc(Oc3ccc4ncn(C)c4c3)c2c1Cl] | Chemistry 436 |
| 701,008 | 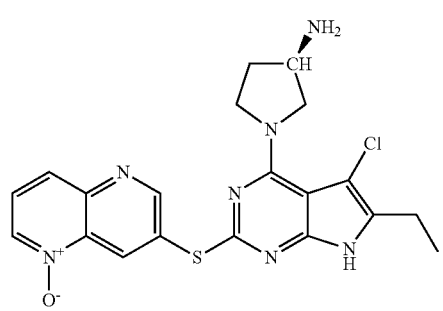 [SMILES: CCc1[nH]c2nc(Sc3cnc4ccc[n+]([O-])c4c3)nc(N3CC[C@@H](N)C3)c2c1Cl] | Chemistry 437 |
| 701,009 | 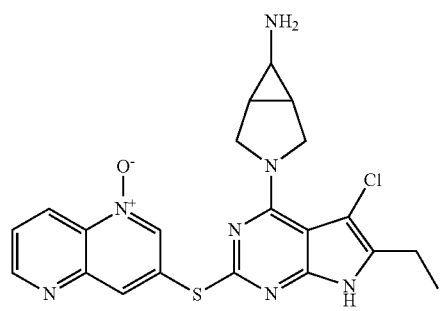 [SMILES: CCc1[nH]c2nc(Sc3cc4ncccc4[n+]([O-])c3)nc(N3CC4C(N)C4C3)c2c1Cl] | Chemistry 438 |

US 10,047,105 B2
375                                                                                 376
-continued
| Rx ID | CHEMISTRY | |
|---|---|---|
| 701,010 | 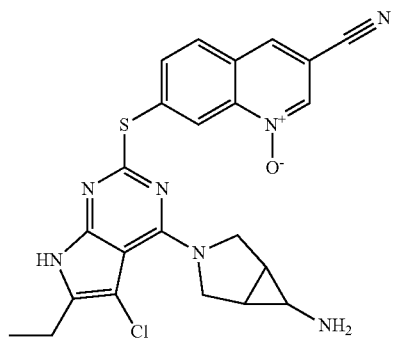 [SMILES: CCc1[nH]c2nc(Sc3ccc4cc(C#N)c[n+]([O-])c4c3)nc(N3CC4C(N)C4C3)c2c1Cl] | Chemistry 439 |
| 701,011 | 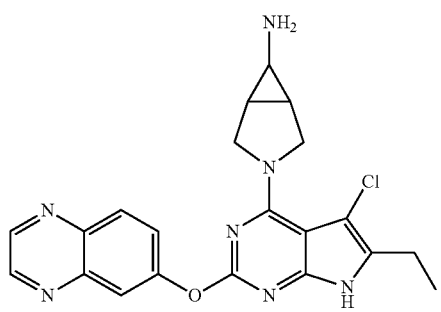 [SMILES: CCc1[nH]c2nc(Oc3ccc4nccnc4c3)nc(N3CC4C(N)C4C3)c2c1Cl] | Chemistry 440 |
| 701,012 | 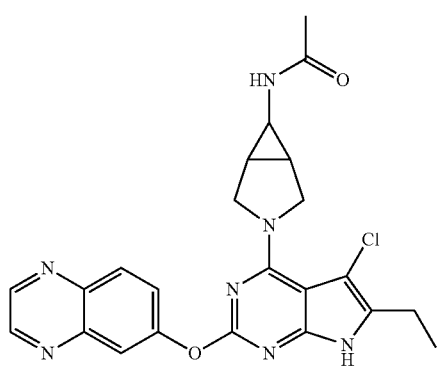 [SMILES: CCc1[nH]c2nc(Oc3ccc4nccnc4c3)nc(N3CC4C(C3)C4NC(C)=O)c2c1Cl] | Chemistry 441 |
| 701,013 | 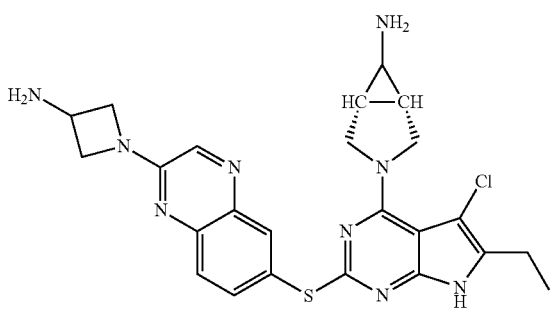 [SMILES: CCc1[nH]c2nc(Sc3ccc4nc(N5CC(N)C5)cnc4c3)nc(N3C[C@@H]4C(N)[C@@H]4C3)c2c1Cl] | Chemistry 442 |
| 701,014 | 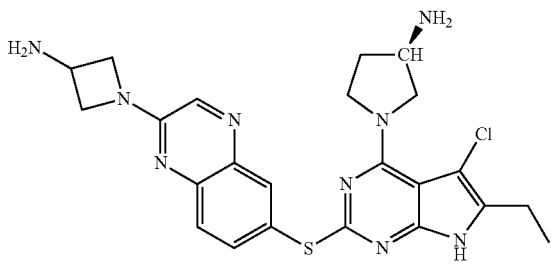 [SMILES: CCc1[nH]c2nc(Sc3ccc4nc(N5CC(N)C5)cnc4c3)nc(N3CC[C@@H](N)C3)c2c1Cl] | Chemistry 443 |

-continued
| Rx ID | CHEMISTRY | |
|---|---|---|
| 701008-2 | 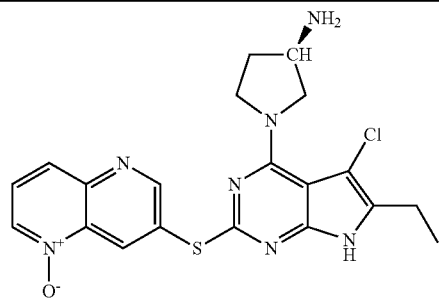 | Chemistry 444 |
| 701009-2 | 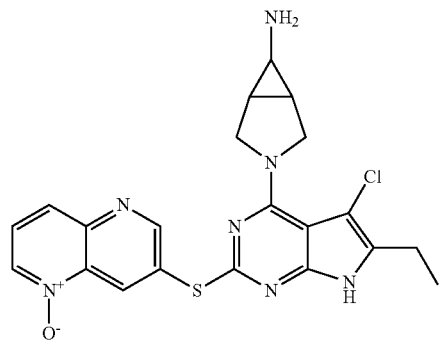 | Chemistry 445 |
| 700795-2 | 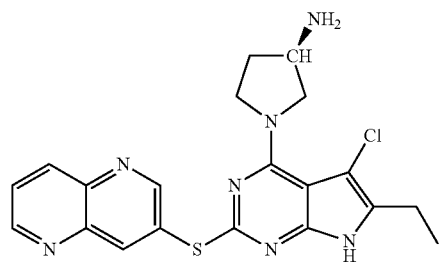 [SMILES: CCc1[nH]c2nc(Sc3cnc4cccnc4c3)nc(N3CC[C@@H](N)C3)c2c1Cl] | Chemistry 446 |
| 701,015 | 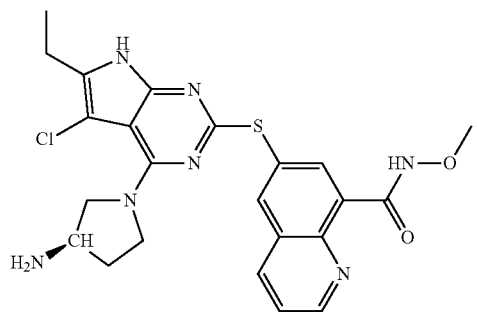 [SMILES: CCc1[nH]c2nc(Sc3cc(C(=O)NOC)c4ncccc4c3)nc(N3CC[C@@H](N)C3)c2c1Cl] | Chemistry 447 |
| 701,016 | 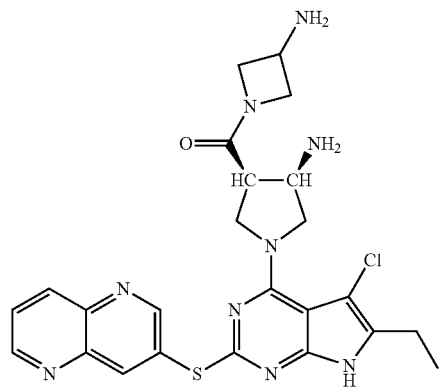 [SMILES: CCc1[nH]c2nc(Sc3cnc4cccnc4c3)nc(N3C[C@H](N)[C@H](C(=O)N4CC(N)C4)C3)c2c1Cl] | Chemistry 448 |

| Rx ID | CHEMISTRY | |
|---|---|---|
| 701,017 | 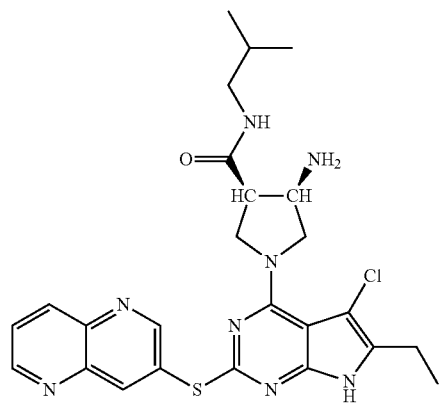 [SMILES: CCc1[nH]c2nc(Sc3cnc4cccnc4c3)nc(N3C[C@H](N)[C@H](C(=O)NCC(C)C)C3)c2c1Cl] | Chemistry 449 |
| 701,018 | 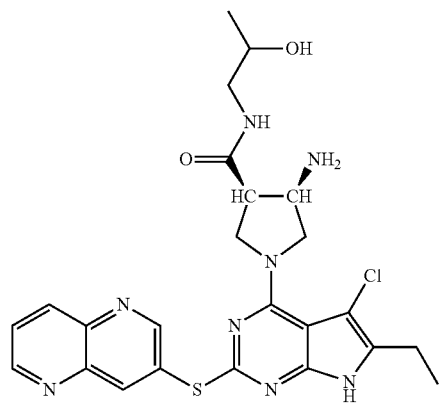 [SMILES: CCc1[nH]c2nc(Sc3cnc4cccnc4c3)nc(N3C[C@H](N)[C@H](C(=O)NCC(C)O)C3)c2c1Cl] | Chemistry 450 |
| 701,019 | 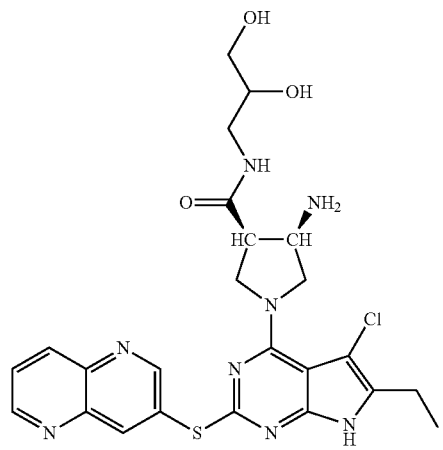 [SMILES: CCc1[nH]c2nc(Sc3cnc4cccnc4c3)nc(N3C[C@H](N)[C@H](C(=O)NCC(O)CO)C3)c2c1Cl] | Chemistry 451 |

| Rx ID | CHEMISTRY | |
|---|---|---|
| 701,020 | 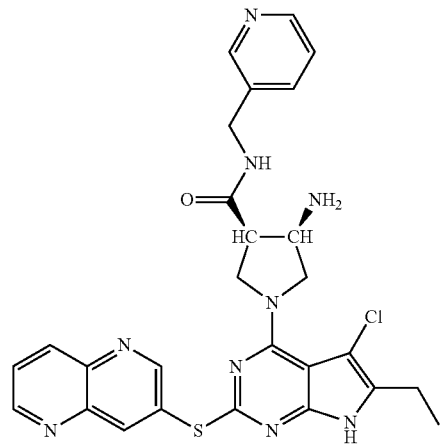 [SMILES: CCc1[nH]c2nc(Sc3cnc4cccnc4c3)nc(N3C[C@H](N)[C@H](C(=O)NCc4cccnc4)C3)c2c1Cl] | Chemistry 452 |
| 701,021 | 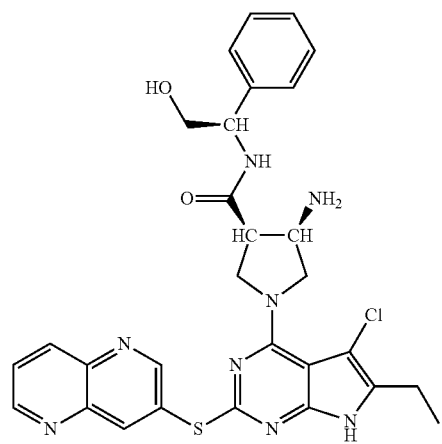 [SMILES: CCc1[nH]c2nc(Sc3cnc4cccnc4c3)nc(N3C[C@H](N)[C@H](C(=O)N[C@@H](CO)c4ccccc4)C3)c2c1Cl] | Chemistry 453 |
| 701,022 | 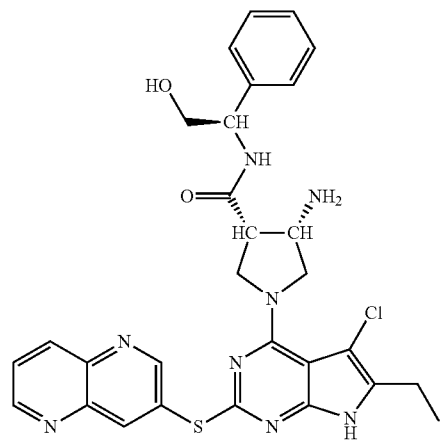 [SMILES: CCc1[nH]c2nc(Sc3cnc4cccnc4c3)nc(N3C[C@@H](N)[C@@H](C(=O)N[C@@H](CO)c4ccccc4)C3)c2c1Cl] | Chemistry 454 |

-continued
| Rx ID | CHEMISTRY | |
|---|---|---|
| 701,023 | 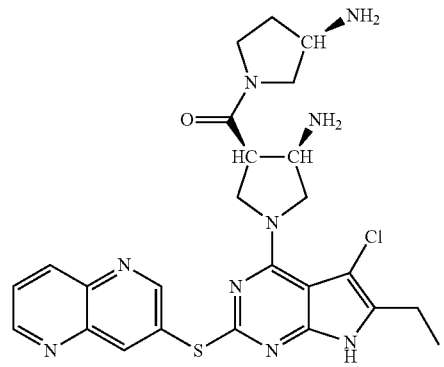 [SMILES: CCc1[nH]c2nc(Sc3cnc4cccnc4c3)nc(N3C[C@H](N)[C@H](C(=O)N4CC[C@@H](N)C4)C3)c2c1Cl] | Chemistry 455 |
| 701,024 | 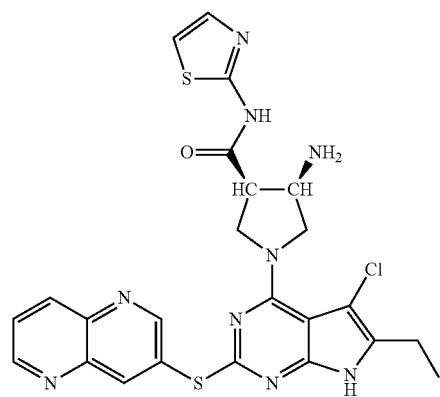 [SMILES: CCc1[nH]c2nc(Sc3cnc4cccnc4c3)nc(N3C[C@H](N)[C@H](C(=O)Nc4nccs4)C3)c2c1Cl] | Chemistry 456 |
| 701,025 | 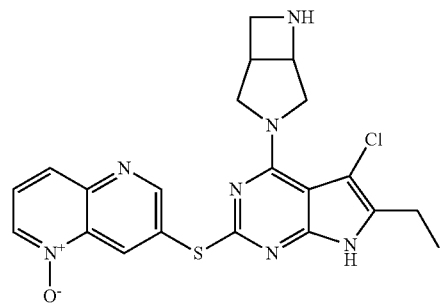 [SMILES: CCc1[nH]c2nc(Sc3cnc4ccc[n+]([O-])c4c3)nc(N3CC4CNC4C3)c2c1Cl] | Chemistry 457 |
| 701,026 | 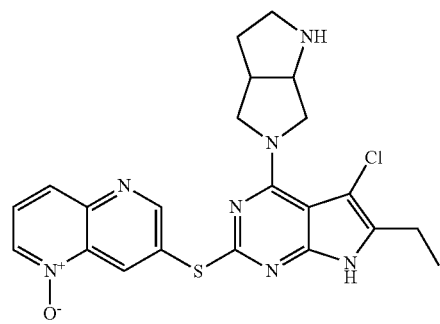 [SMILES: CCc1[nH]c2nc(Sc3cnc4ccc[n+]([O-])c4c3)nc(N3CC4CCNC4C3)c2c1Cl] | Chemistry 458 |

| Rx ID | CHEMISTRY | |
|---|---|---|
| 701,027 | 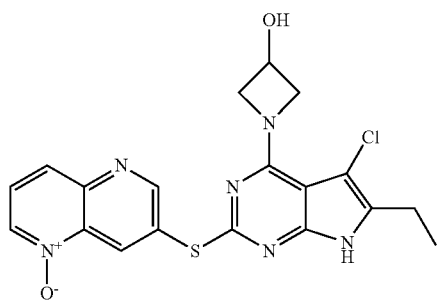 [SMILES: CCc1[nH]c2nc(Sc3cnc4ccc[n+]([O-])c4c3)nc(N3CC(O)C3)c2c1Cl] | Chemistry 459 |
| 701,028 | 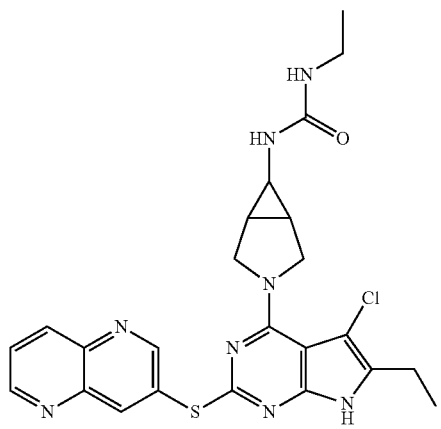 [SMILES: CCNC(=O)NC1C2CN(c3nc(Sc4cnc5cccnc5c4)nc4[nH]c(CC)c(Cl)c34)CC21] | Chemistry 460 |
| 701,029 | 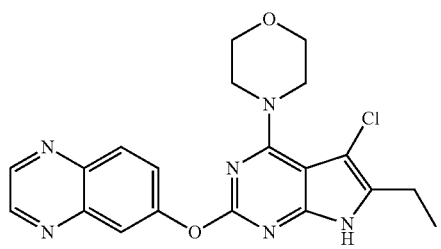 [SMILES: CCc1[nH]c2nc(Oc3ccc4nccnc4c3)nc(N3CCOCC3)c2c1Cl] | Chemistry 461 |
| 701,031 | 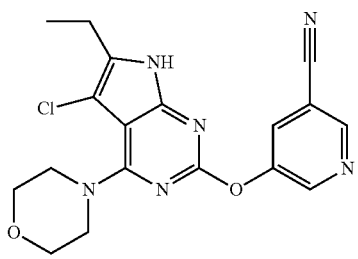 [SMILES: CCc1[nH]c2nc(Oc3cncc(C#N)c3)nc(N3CCOCC3)c2c1Cl] | Chemistry 462 |
| 701,033 | 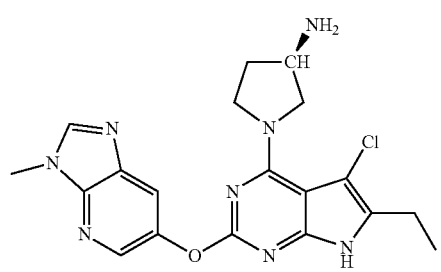 [SMILES: CCc1[nH]c2nc(Oc3cnc4c(c3)ncn4C)nc(N3CC[C@@H](N)C3)c2c1Cl] | Chemistry 463 |

| Rx ID | CHEMISTRY | |
|---|---|---|
| 701,034 | 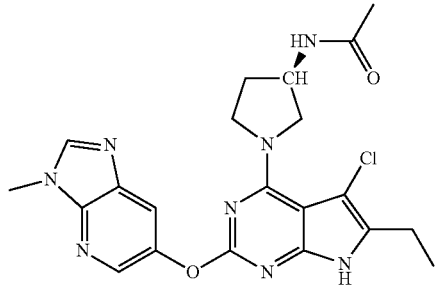 [SMILES: CCc1[nH]c2nc(Oc3cnc4c(c3)ncn4C)nc(N3CC[C@@H](NC(C)=O)C3)c2c1Cl] | Chemistry 464 |
| 701,042 | 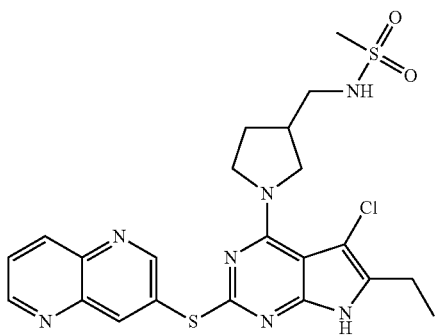 [SMILES: CCc1[nH]c2nc(Sc3cnc4cccnc4c3)nc(N3CCC(CNS(C)(=O)=O)C3)c2c1Cl] | Chemistry 465 |
| 701,043 |  | Chemistry 466 |
| 701,044 | 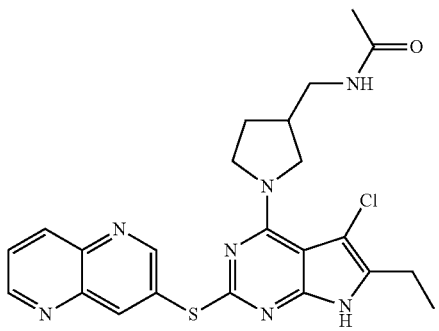 [SMILES: CCc1[nH]c2nc(Sc3cnc4cccnc4c3)nc(N3CCC(CNC(C)=O)C3)c2c1Cl] | Chemistry 467 |

-continued
| Rx ID | CHEMISTRY | |
|---|---|---|
| 701,045 | 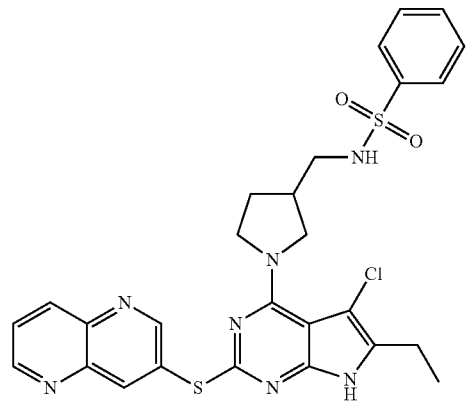 [SMILES: CCc1[nH]c2nc(Sc3cnc4cccnc4c3)nc(N3CCC(CNS(=O)(=O)c4ccccc4)C3)c2c1Cl] | Chemistry 468 |
| 701,046 | 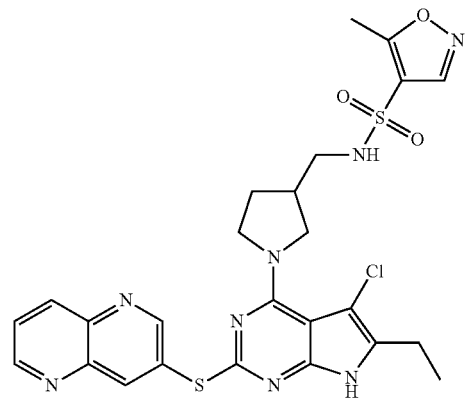 [SMILES: CCc1[nH]c2nc(Sc3cnc4cccnc4c3)nc(N3CCC(CNS(=O)(=O)c4cnoc4C)C3)c2c1Cl] | Chemistry 469 |
| 701,047 | 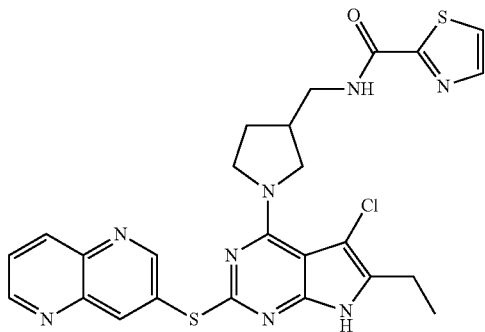 [SMILES: CCc1[nH]c2nc(Sc3cnc4cccnc4c3)nc(N3CCC(CNC(=O)c4nccs4)C3)c2c1Cl] | Chemistry 470 |
| 701,035 | 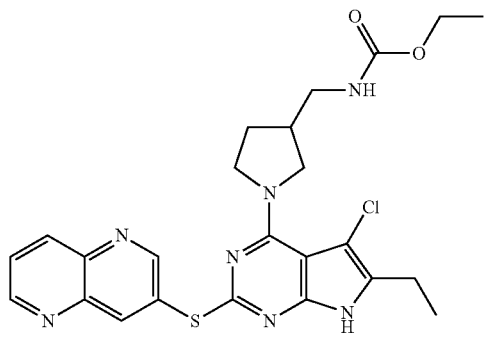 [SMILES: CCOC(=O)NCC1CCN(c2nc(Sc3cnc4cccnc4c3)nc3[nH]c(CC)c(Cl)c23)C1] | Chemistry 471 |

-continued
| Rx ID | CHEMISTRY | |
|---|---|---|
| 701,036 | 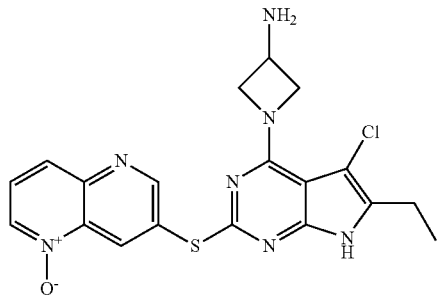 | Chemistry 472 |
| 701,037 | 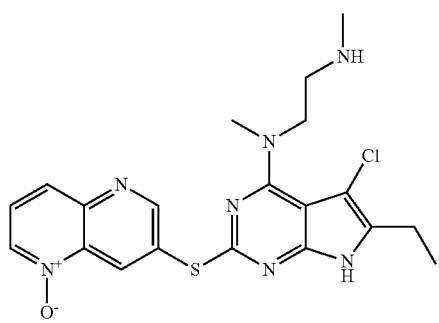 [SMILES: CCc1[nH]c2nc(Sc3cnc4ccc[n+]([O-])c4c3)nc(N(C)CCNC)c2c1Cl] | Chemistry 473 |
| 701,038 | 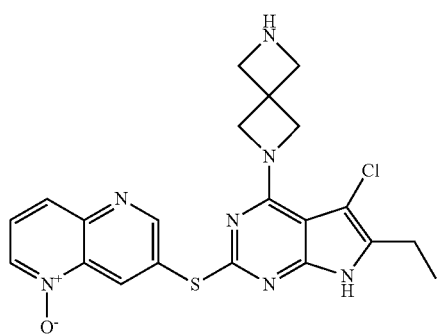 [SMILES: CCc1[nH]c2nc(Sc3cnc4ccc[n+]([O-])c4c3)nc(N3CC4(CNC4)C3)c2c1Cl] | Chemistry 474 |
| 701,039 | 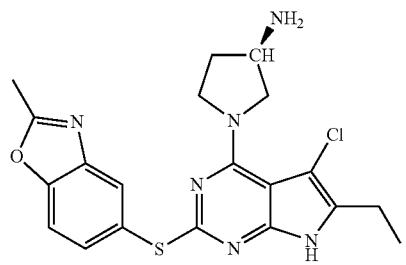 [SMILES: CCc1[nH]c2nc(Sc3ccc4oc(C)nc4c3)nc(N3CC[C@@H](N)C3)c2c1Cl] | Chemistry 475 |
| 701,040 | 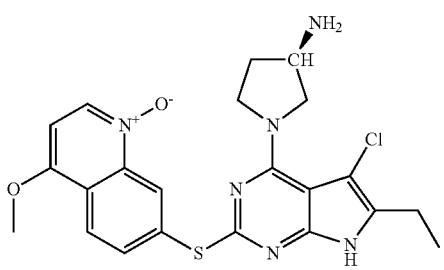 [SMILES: CCc1[nH]c2nc(Sc3ccc4c(OC)cc[n+]([O-])c4c3)nc(N3CC[C@@H](N)C3)c2c1Cl] | Chemistry 476 |

| Rx ID | CHEMISTRY | |
|---|---|---|
| 701,041 | 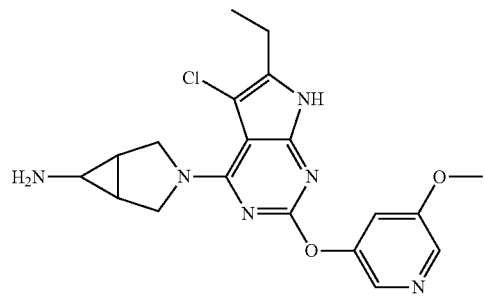 [SMILES: CCc1[nH]c2nc(Oc3cncc(OC)c3)nc(N3CC4C(N)C4C3)c2c1Cl] | Chemistry 477 |
| 701,048 | 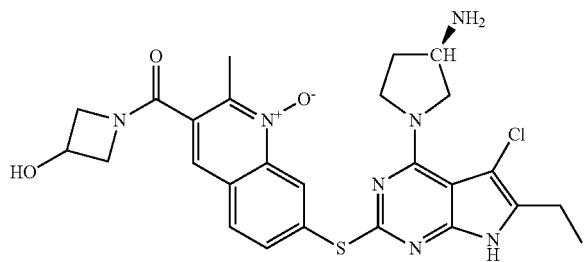 [SMILES: CCc1[nH]c2nc(Sc3ccc4cc(C(=O)N5CC(O)C5)c(C)[n+]([O-])c4c3)nc(N3CC[C@@H](N)C3)c2c1Cl] | Chemistry 478 |
| 701,049 | 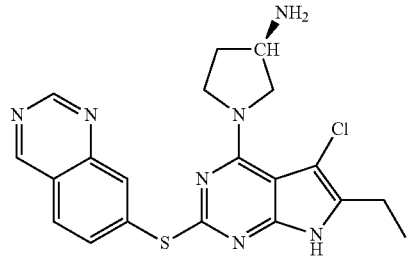 [SMILES: CCc1[nH]c2nc(Sc3ccc4cncnc4c3)nc(N3CC[C@@H](N)C3)c2c1Cl] | Chemistry 479 |
| 701,050 | 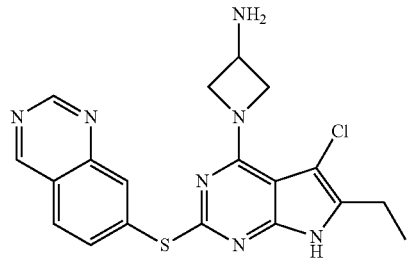 [SMILES: CCc1[nH]c2nc(Sc3ccc4cncnc4c3)nc(N3CC(N)C3)c2c1Cl] | Chemistry 480 |
| 701,051 | 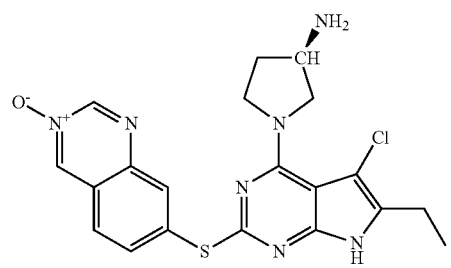 [SMILES: CCc1[nH]c2nc(Sc3ccc4c[n+]([O-])cnc4c3)nc(N3CC[C@@H](N)C3)c2c1Cl] | Chemistry 481 |

| Rx ID | CHEMISTRY | |
|---|---|---|
| 701,053 | 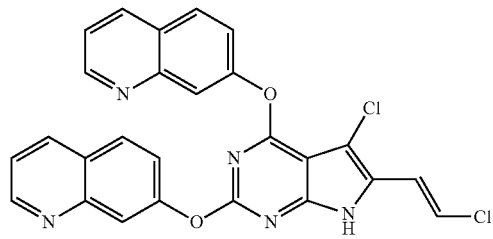 [SMILES: Cl/C=C/c1[nH]c2nc(Oc3ccc4cccnc4c3)nc(Oc3ccc4cccnc4c3)c2c1Cl] | Chemistry 482 |
| 701,055 | 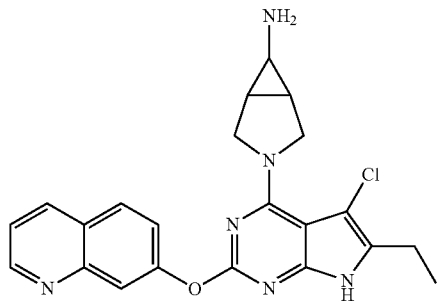 | Chemistry 483 |
| 701,057 | 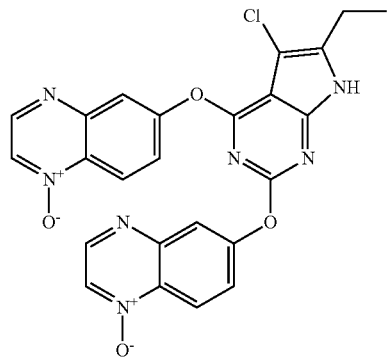 [SMILES: CCc1[nH]c2nc(Oc3ccc4c(c3)ncc[n+]4[O-])nc(Oc3ccc4c(c3)ncc[n+]4[O-])c2c1Cl] | Chemistry 484 |
| 701,061 | 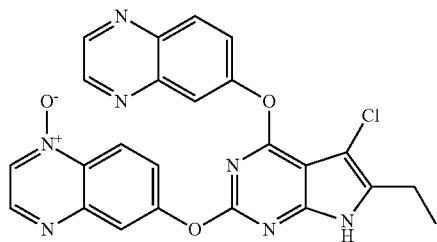 [SMILES: CCc1[nH]c2nc(Oc3ccc4c(c3)ncc[n+]4[O-])nc(Oc3ccc4nccnc4c3)c2c1Cl] | Chemistry 485 |
| 701008-3 | 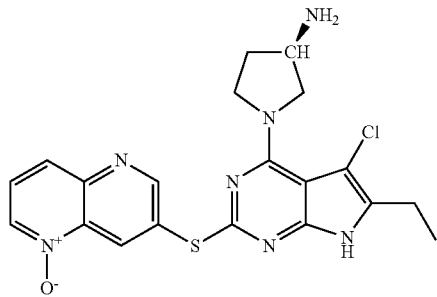 | Chemistry 486 |

| Rx ID | CHEMISTRY | |
|---|---|---|
| 701,062 | 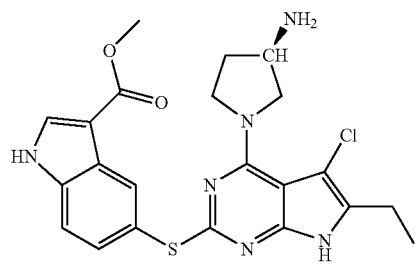 [SMILES: CCc1[nH]c2nc(Sc3ccc4[nH]cc(C(=O)OC)c4c3)nc(N3CC[C@@H](N)C3)c2c1Cl] | Chemistry 487 |
| 701,063 | 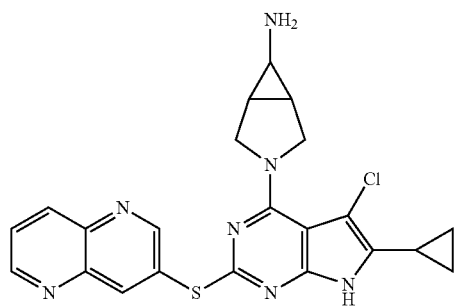 [SMILES: NC1C2CN(c3nc(Sc4cnc5cccnc5c4)nc4[nH]c(C5CC5)c(Cl)c34)CC12] | Chemistry 488 |
| 701,064 | 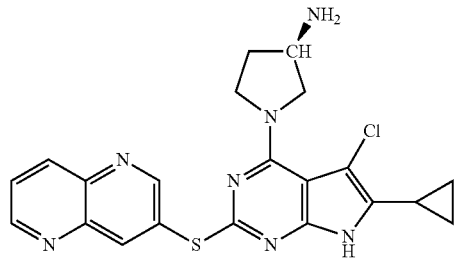 [SMILES: N[C@@H]1CCN(c2nc(Sc3cnc4cccnc4c3)nc3[nH]c(C4CC4)c(Cl)c23)C1] | Chemistry 489 |
| 701,065 | 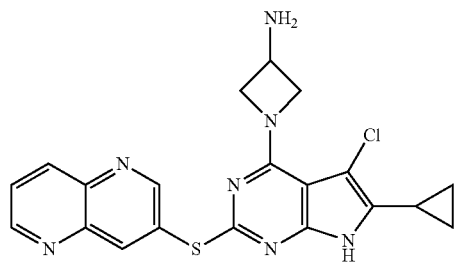 [SMILES: NC1CN(c2nc(Sc3cnc4cccnc4c3)nc3[nH]c(C4CC4)c(Cl)c23)C1] | Chemistry 490 |
| 701,066 | 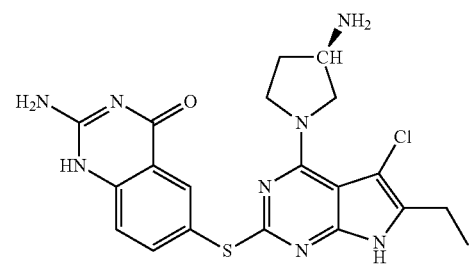 [SMILES: CCc1[nH]c2nc(Sc3ccc4[nH]c(N)nc(=O)c4c3)nc(N3CC[C@@H](N)C3)c2c1Cl] | Chemistry 491 |

| Rx ID | CHEMISTRY | |
|---|---|---|
| 701,067 | 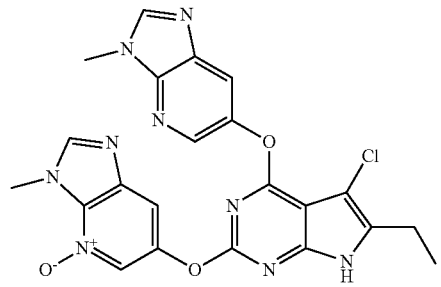 [SMILES: CCc1[nH]c2nc(Oc3cc4ncn(C)c4[n+]([O-])c3)nc(Oc3cnc4c(c3)ncn4C)c2c1Cl] | Chemistry 492 |
| 701,068 | 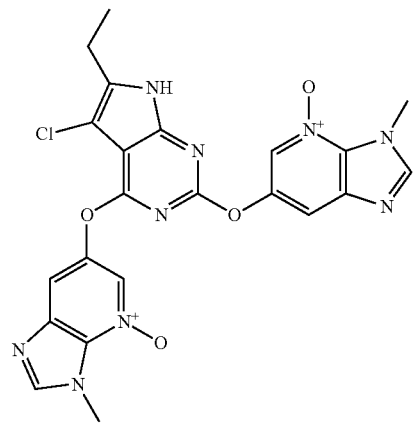 [SMILES: CCc1[nH]c2nc(Oc3cc4ncn(C)c4[n+](O)c3)nc(Oc3cc4ncn(C)c4[n+](O)c3)c2c1Cl] | Chemistry 493 |
| 701,069 | 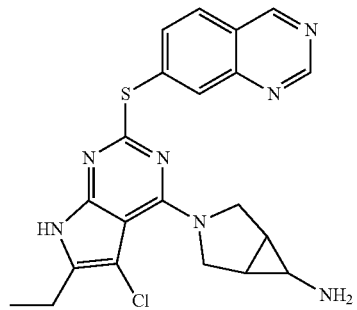 [SMILES: CCc1[nH]c2nc(Sc3ccc4cncnc4c3)nc(N3CC4C(N)C4C3)c2c1Cl] | Chemistry 494 |
| 701008-3 | 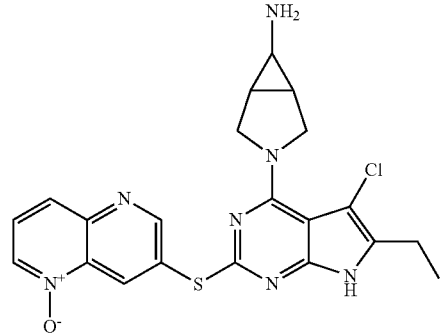 [SMILES: CCc1[nH]c2nc(Sc3cnc4ccc[n+]([O-])c4c3)nc(N3CC4C(N)C4C3)c2c1Cl] | Chemistry 495 |

-continued
| Rx ID | CHEMISTRY | |
|---|---|---|
| 701,070 | 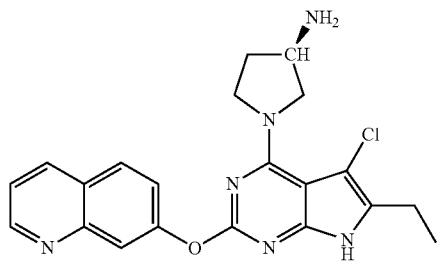 [SMILES: CCc1[nH]c2nc(Oc3ccc4cccnc4c3)nc(N3CC[C@@H](N)C3)c2c1Cl] | Chemistry 496 |
| 701,071 | 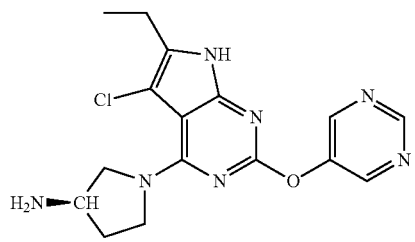 [SMILES: CCc1[nH]c2nc(Oc3cncnc3)nc(N3CC[C@@H](N)C3)c2c1Cl] | Chemistry 497 |
| 701,074 | 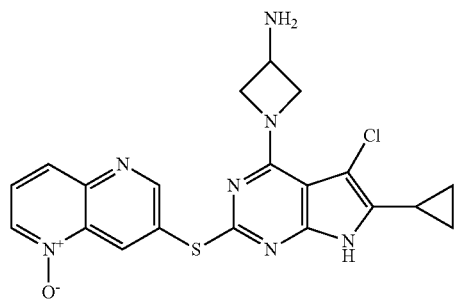 [SMILES: NC1CN(c2nc(Sc3cnc4ccc[n+]([O-])c4c3)nc3[nH]c(C4CC4)c(Cl)c23)C1] | Chemistry 498 |
| 701,075 | 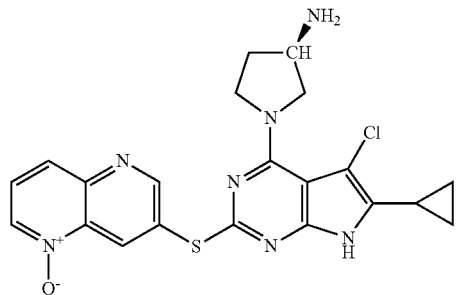 [SMILES: N[C@@H]1CCN(c2nc(Sc3cnc4ccc[n+]([O-])c4c3)nc3[nH]c(C4CC4)c(Cl)c23)C1] | Chemistry 499 |
| 701,076 | 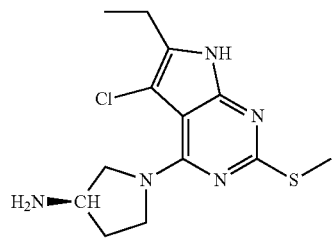 [SMILES: CCc1[nH]c2nc(SC)nc(N3CC[C@@H](N)C3)c2c1Cl] | Chemistry 500 |

-continued
| Rx ID | CHEMISTRY | |
|---|---|---|
| 701,080 | 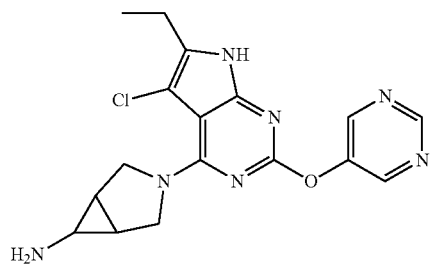 [SMILES: CCc1[nH]c2nc(Oc3cncnc3)nc(N3CC4C(N)C4C3)c2c1Cl] | Chemistry 501 |
| 701,082 | 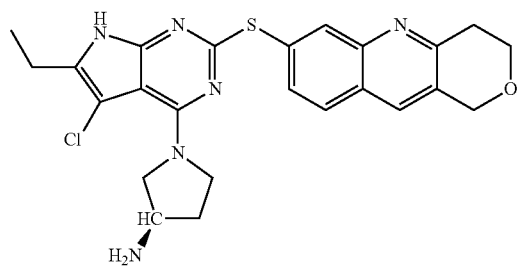 [SMILES: CCc1[nH]c2nc(Sc3ccc4cc5c(nc4c3)CCOC5)nc(N3CC[C@@H](N)C3)c2c1Cl] | Chemistry 502 |
| 701,083 | 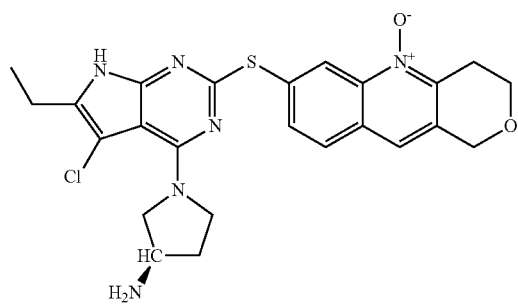 [SMILES: CCc1[nH]c2nc(Sc3ccc4cc5c([n+]([O-])c4c3)CCOC5)nc(N3CC[C@@H](N)C3)c2c1Cl] | Chemistry 503 |
| 701,084 | 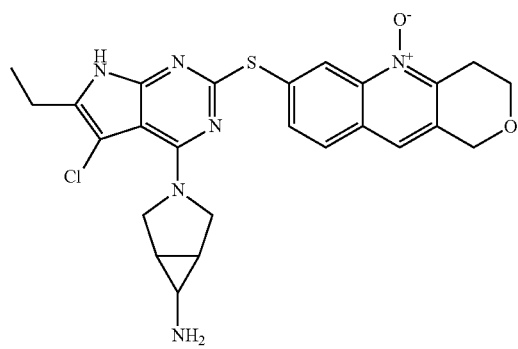 [SMILES: CCc1[nH]c2nc(Sc3ccc4cc5c([n+]([O-])c4c3)CCOC5)nc(N3CC4C(N)C4C3)c2c1Cl] | Chemistry 504 |
| 701,011 | 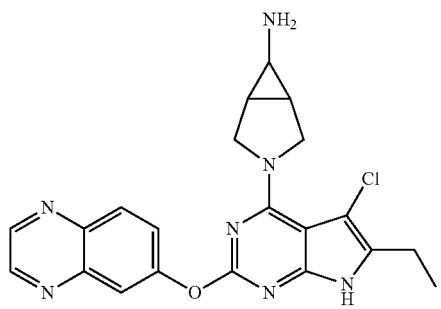 [SMILES: CCc1[nH]c2nc(Oc3ccc4nccnc4c3)nc(N3CC4C(N)C4C3)c2c1Cl] | Chemistry 505 |

-continued
| Rx ID | CHEMISTRY | |
|---|---|---|
| 701,011 | 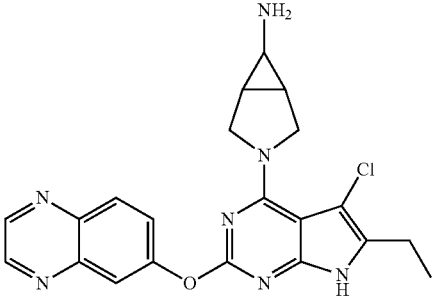 | Chemistry 506 |
| 701,071 | 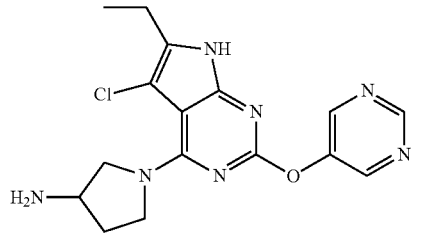 [SMILES: CCc1[nH]c2nc(Oc3cncnc3)nc(N3CCC(N)C3)c2c1Cl] | Chemistry 507 |
| 701,087 | 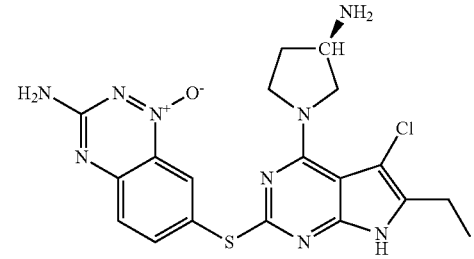 [SMILES: CCc1[nH]c2nc(Sc3ccc4nc(N)n[n+]([O-])c4c3)nc(N3CC[C@@H](N)C3)c2c1Cl] | Chemistry 508 |
| 701,088 | 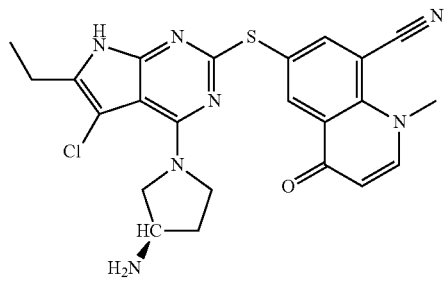 [SMILES: CCc1[nH]c2nc(Sc3cc(C#N)c4c(c3)c(=O)ccn4C)nc(N3CC[C@@H](N)C3)c2c1Cl] | Chemistry 509 |
| 701,089 | 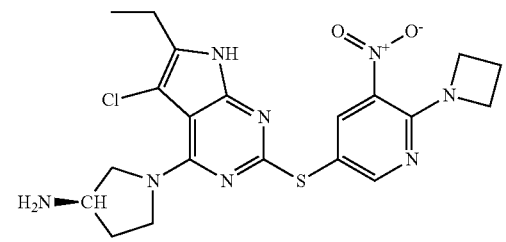 [SMILES: CCc1[nH]c2nc(Sc3cnc(N4CCC4)c([N+](=O)[O-])c3)nc(N3CC[C@@H](N)C3)c2c1Cl] | Chemistry 510 |
| 701,090 | 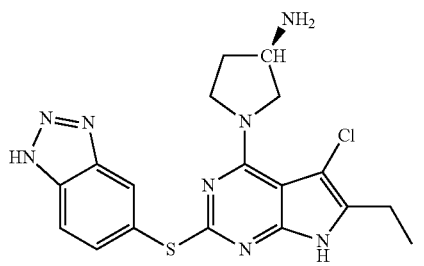 [SMILES: CCc1[nH]c2nc(Sc3ccc4[nH]nnc4c3)nc(N3CC[C@@H](N)C3)c2c1Cl] | Chemistry 511 |

US 10,047,105 B2
407                                                                 408
-continued
| Rx ID | CHEMISTRY | |
|---|---|---|
| 701,094 | 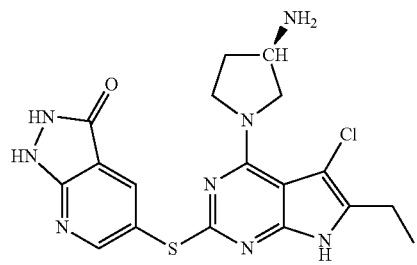 [SMILES: CCc1[nH]c2nc(Sc3cnc4[nH][nH]c(=O)c4c3)nc(N3CC[C@@H](N)C3)c2c1Cl] | Chemistry 512 |
| 701,098 | 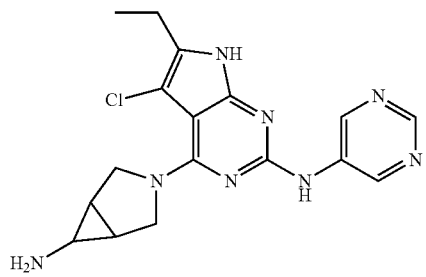 [SMILES: CCc1[nH]c2nc(Nc3cncnc3)nc(N3CC4C(N)C4C3)c2c1Cl] | Chemistry 513 |
| 701,102 | 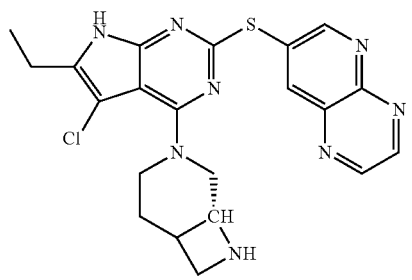 | Chemistry 514 |
| 701,103 | 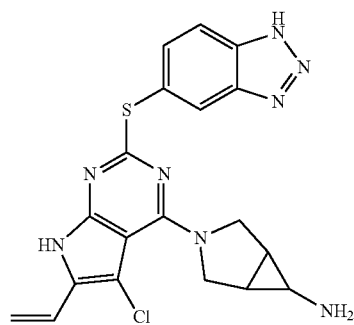 [SMILES: C=Cc1[nH]c2nc(Sc3ccc4[nH]nnc4c3)nc(N3CC4C(N)C4C3)c2c1Cl] | Chemistry 515 |
| 701,080 | 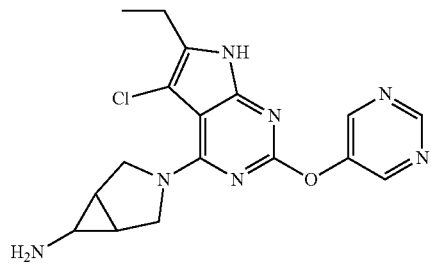 [SMILES: CCc1[nH]c2nc(Oc3cncnc3)nc(N3CC4C(N)C4C3)c2c1Cl] | Chemistry 516 |

| Rx ID | CHEMISTRY | |
|---|---|---|
| 701,112 | 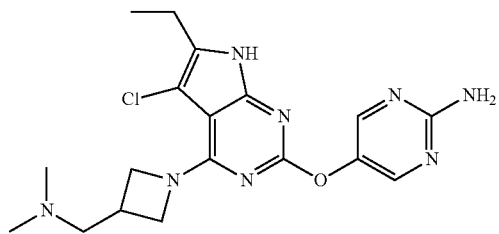 [SMILES: CCc1[nH]c2nc(Oc3cnc(N)nc3)nc(N3CC(CN(C)C)C3)c2c1Cl] | Chemistry 517 |
| 701,113 | 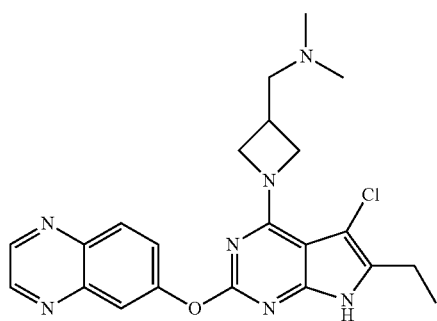 [SMILES: CCc1[nH]c2nc(Oc3ccc4nccnc4c3)nc(N3CC(CN(C)C)C3)c2c1Cl] | Chemistry 518 |
| 701,115 | 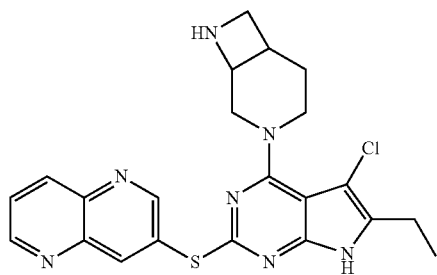 [SMILES: CCc1[nH]c2nc(Sc3cnc4cccnc4c3)nc(N3CCC4CNC4C3)c2c1Cl] | Chemistry 519 |
| 701,116 | 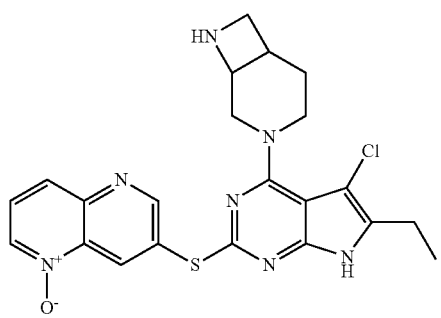 [SMILES: CCc1[nH]c2nc(Sc3cnc4ccc[n+]([O-])c4c3)nc(N3CCC4CNC4C3)c2c1Cl] | Chemistry 520 |
| 701,118 | 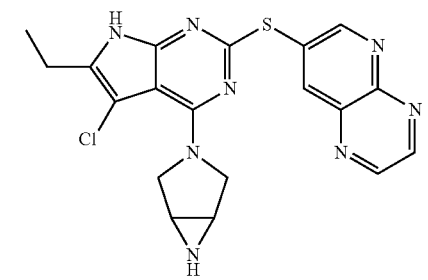 [SMILES: CCc1[nH]c2nc(Sc3cnc4nccnc4c3)nc(N3CC4NC4C3)c2c1Cl] | Chemistry 521 |

| Rx ID | CHEMISTRY | |
|---|---|---|
| 701,119 | 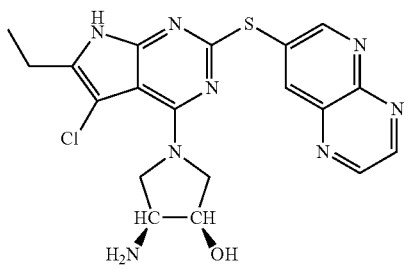 [SMILES: CCc1[nH]c2nc(Sc3cnc4nccnc4c3)nc(N3C[C@@H](O)[C@@H](N)C3)c2c1Cl] | Chemistry 522 |
| 701,120 | 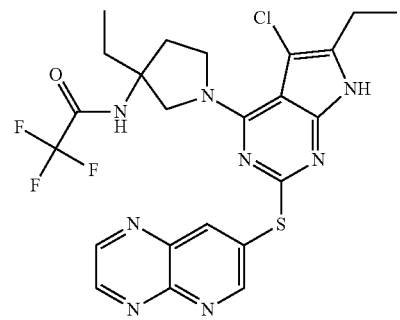 [SMILES: CCc1[nH]c2nc(Sc3cnc4nccnc4c3)nc(N3CCC(CC)(NC(=O)C(F)(F)F)C3)c2c1Cl] | Chemistry 523 |
| 701,121 | 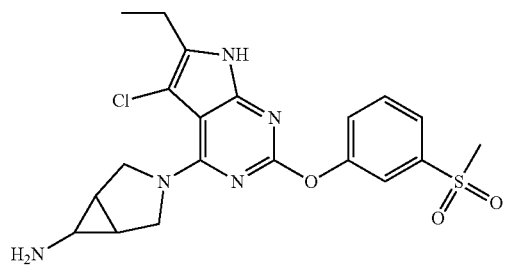 [SMILES: CCc1[nH]c2nc(Oc3cccc(S(C)(=O)=O)c3)nc(N3CC4C(N)C4C3)c2c1Cl] | Chemistry 524 |
| 701,121 | 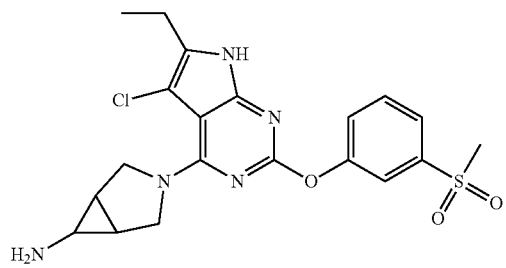 [SMILES: CCc1[nH]c2nc(Oc3cccc(S(C)(=O)=O)c3)nc(N3CC4C(N)C4C3)c2c1Cl] | Chemistry 525 |
| 701,122 | 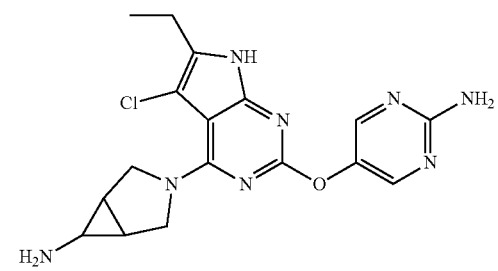 [SMILES: CCc1[nH]c2nc(Oc3cnc(N)nc3)nc(N3CC4C(N)C4C3)c2c1Cl] | Chemistry 526 |

| Rx ID | CHEMISTRY | |
|---|---|---|
| 701,121 | 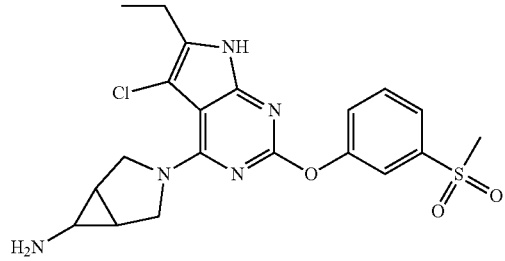 [SMILES: CCc1[nH]c2nc(Oc3cccc(S(C)(=O)=O)c3)nc(N3CC4C(N)C4C3)c2c1Cl] | Chemistry 527 |
| 701,126 | 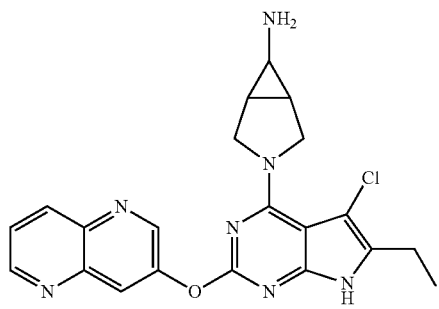 [SMILES: CCc1[nH]c2nc(Oc3cnc4cccnc4c3)nc(N3CC4C(N)C4C3)c2c1Cl] | Chemistry 528 |
| 700,800 | 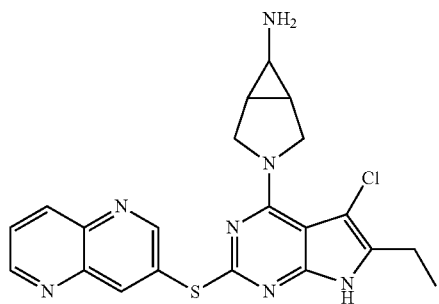 | Chemistry 579 |
| 701,098 | 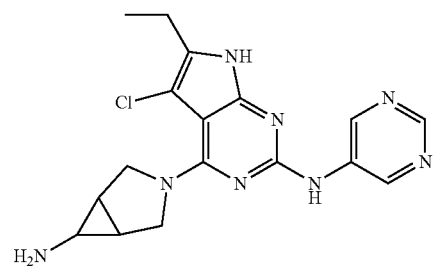 [SMILES: CCc1[nH]c2nc(Nc3cncnc3)nc(N3CC4C(N)C4C3)c2c1Cl] | Chemistry 530 |
| 701,132 | 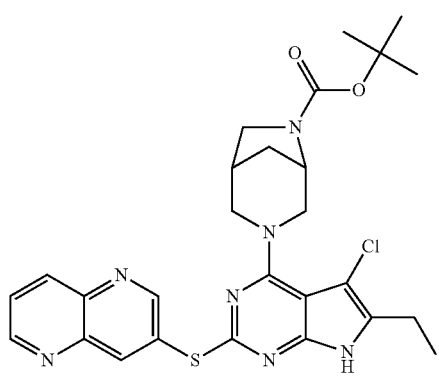 [SMILES: CCc1[nH]c2nc(Sc3cnc4cccnc4c3)nc(N3CC4CC(C3)N(C(=O)OC(C)(C)C)C4)c2c1Cl] | Chemistry 531 |

| Rx ID | CHEMISTRY | |
|---|---|---|
| 701,133 | 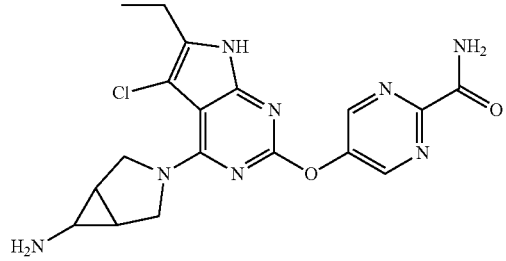 [SMILES: CCc1[nH]c2nc(Oc3cnc(C(N)=O)nc3)nc(N3CC4C(N)C4C3)c2c1Cl] | Chemistry 532 |
| 701,080 | 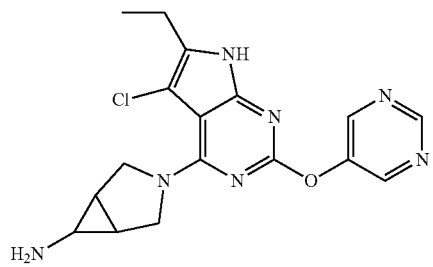 [SMILES: CCc1[nH]c2nc(Oc3cncnc3)nc(N3CC4C(N)C4C3)c2c1Cl] | Chemistry 533 |
| 700,434 | 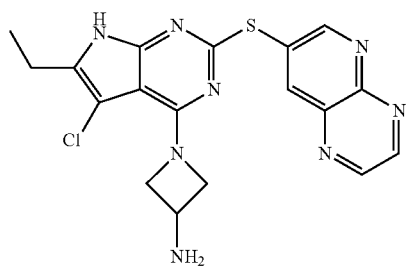 | Chemistry 534 |
| 701,137 | 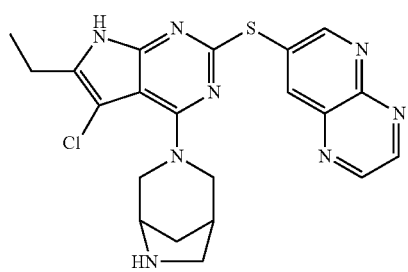 [SMILES: CCc1[nH]c2nc(Sc3cnc4nccnc4c3)nc(N3CC4CNC(C4)C3)c2c1Cl] | Chemistry 535 |
| 700,609 | 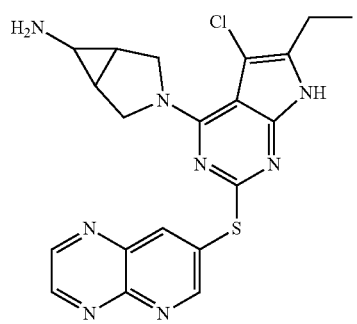 [SMILES: CCc1[nH]c2nc(Sc3cnc4nccnc4c3)nc(N3CC4C(N)C4C3)c2c1Cl] | Chemistry 536 |

| Rx ID | CHEMISTRY | |
|---|---|---|
| 701,140 | 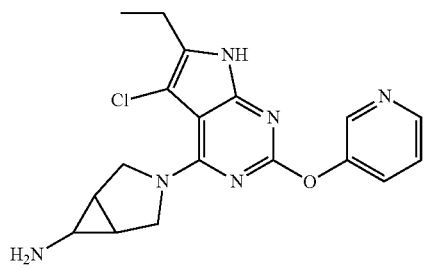 [SMILES: CCc1[nH]c2nc(Oc3cccnc3)nc(N3CC4C(N)C4C3)c2c1Cl] | Chemistry 537 |
| 701,080 | 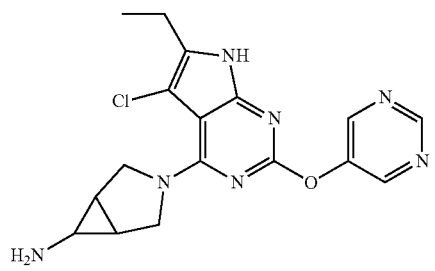 [SMILES: CCc1[nH]c2nc(Oc3cncnc3)nc(N3CC4C(N)C4C3)c2c1Cl] | Chemistry 538 |
| 701,080 | 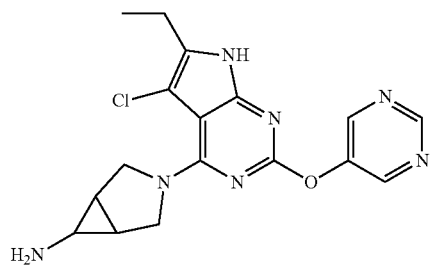 [SMILES: CCc1[nH]c2nc(Oc3cncnc3)nc(N3CC4C(N)C4C3)c2c1Cl] | Chemistry 539 |
| 701,141 | 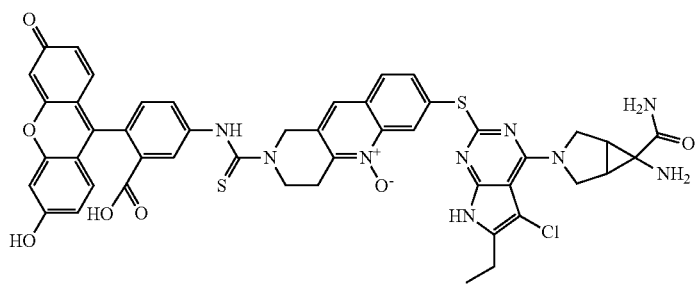 [SMILES: CCc1[nH]c2nc(Sc3ccc4cc5c([n+]([O-])c4c3)CCN(C(=S)Nc3ccc(-c4c6ccc(=O)cc-6oc6cc(O)ccc46)c(C(=O)O)c3)C5)nc(N3CC4C(C3)C4(N)C(N)=O)c2c1Cl] | Chemistry 540 |
| 701,144 | 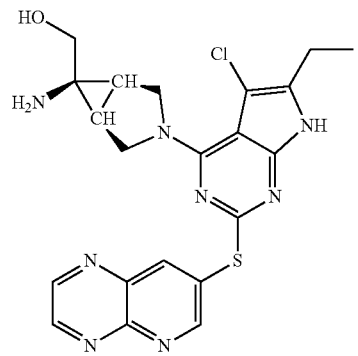 [SMILES: CCc1[nH]c2nc(Sc3cnc4nccnc4c3)nc(N3C[C@@H]4[C@H](C3)[C@@]4(N)CO)c2c1Cl] | Chemistry 541 |

| Rx ID | CHEMISTRY | |
|---|---|---|
| 701,107 | 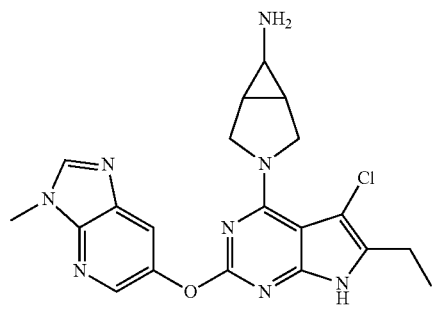 [SMILES: CCc1[nH]c2nc(Oc3cnc4c(c3)ncn4C)nc(N3CC4C(N)C4C3)c2c1Cl] | Chemistry 542 |
| 701,107 | 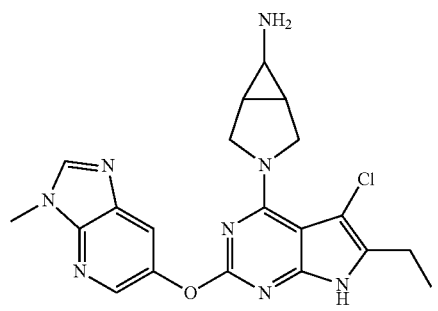 [SMILES: CCc1[nH]c2nc(Oc3cnc4c(c3)ncn4C)nc(N3CC4C(N)C4C3)c2c1Cl] | Chemistry 543 |
| 701,147 | 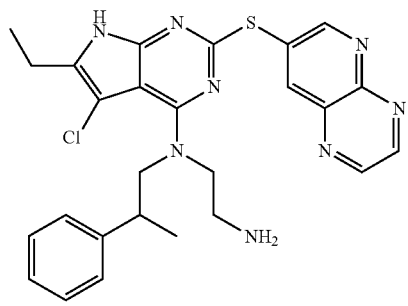 [SMILES: CCc1[nH]c2nc(Sc3cnc4nccnc4c3)nc(N(CCN)CC(C)c3ccccc3)c2c1Cl] | Chemistry 544 |
| 701,148 | 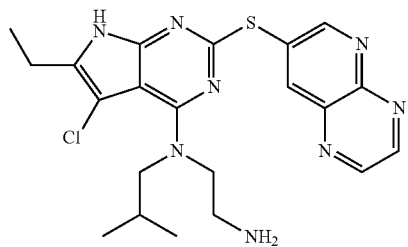 [SMILES: CCc1[nH]c2nc(Sc3cnc4nccnc4c3)nc(N(CCN)CC(C)C)c2c1Cl] | Chemistry 545 |
| 701,151 | 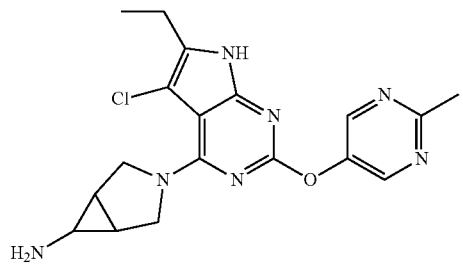 [SMILES: CCc1[nH]c2nc(Oc3cnc(C)nc3)nc(N3CC4C(N)C4C3)c2c1Cl] | Chemistry 546 |

-continued
| Rx ID | CHEMISTRY | |
|---|---|---|
| 701,163 | 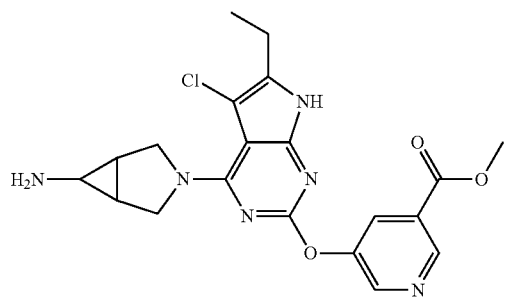 [SMILES: CCc1[nH]c2nc(Oc3cncc(C(=O)OC)c3)nc(N3CC4C(N)C4C3)c2c1Cl] | Chemistry 547 |
| 701,164 | 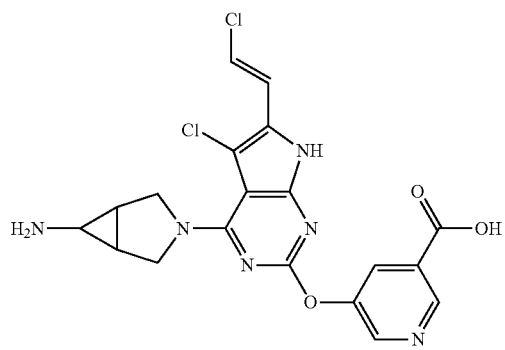 [SMILES: NC1C2CN(c3nc(Oc4cncc(C(=O)O)c4)nc4[nH]c(/C=C/Cl)c(Cl)c34)CC12] | Chemistry 548 |
| 701,165 | 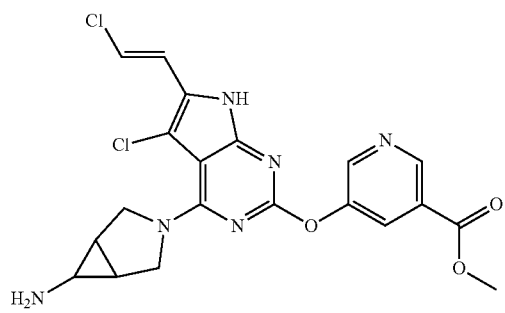 [SMILES: COC(=O)c1cncc(Oc2nc(N3CC4C(N)C4C3)c3c(Cl)c(/C=C/Cl)[nH]c3n2)c1] | Chemistry 549 |
| 701,009 | 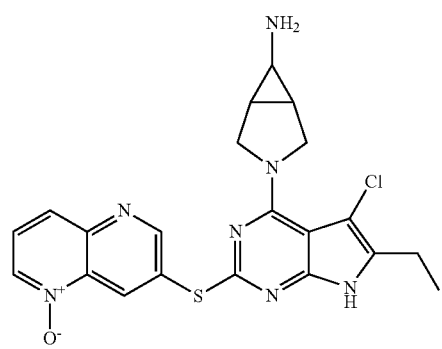 | Chemistry 550 |
| 701,180 | 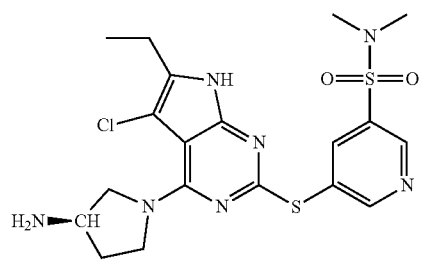 [SMILES: CCc1[nH]c2nc(Sc3cncc(S(=O)(=O)N(C)C)c3)nc(N3CC[C@@H](N)C3)c2c1Cl] | Chemistry 551 |

-continued
| Rx ID | CHEMISTRY | |
|---|---|---|
| 701,181 | 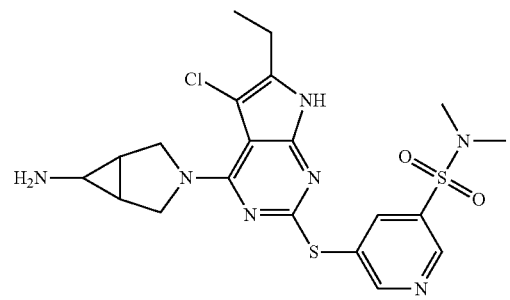 [SMILES: CCc1[nH]c2nc(Sc3cncc(S(=O)(=O)N(C)C)c3)nc(N3CC4C(N)C4C3)c2c1Cl] | Chemistry 552 |
| 701,184 | 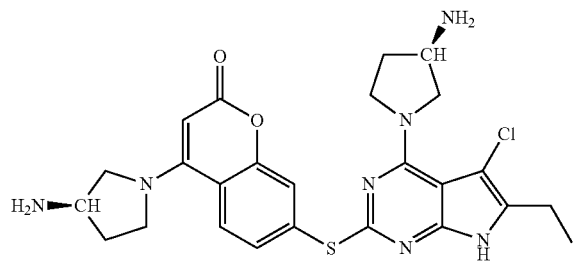 | Chemistry 553 |
| 701,209 | 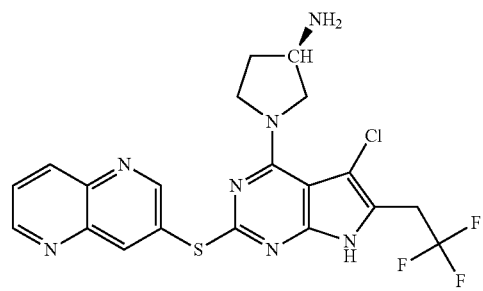 [SMILES: N[C@@H]1CCN(c2nc(Sc3cnc4cccnc4c3)nc3[nH]c(CC(F)(F)F)c(Cl)c23)C1] | Chemistry 554 |
| 701,231 | 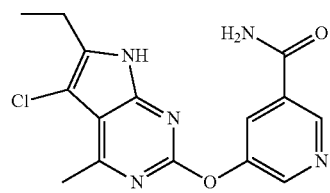 [SMILES: CCc1[nH]c2nc(Oc3cncc(C(N)=O)c3)nc(C)c2c1Cl] | Chemistry 555 |
| 701,232 | 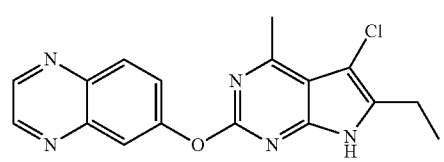 [SMILES: CCc1[nH]c2nc(Oc3ccc4nccnc4c3)nc(C)c2c1Cl] | Chemistry 556 |

| Rx ID | CHEMISTRY | |
|---|---|---|
| 701,229 | 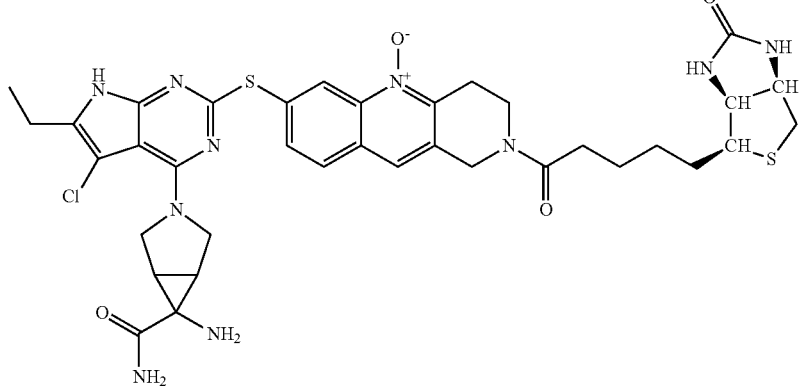 | Chemistry 557 |
| 701,236 | 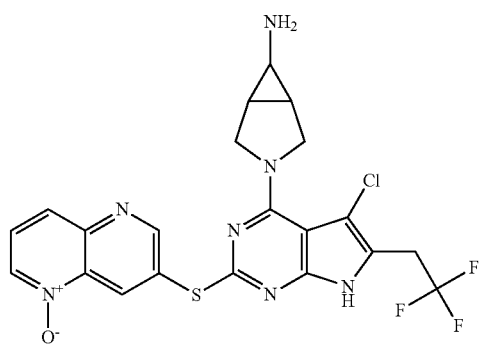 [SMILES: NC1C2CN(c3nc(Sc4cnc5ccc[n+]([O-])c5c4)nc4[nH]c(CC(F)(F)F)c(Cl)c34)CC12] | Chemistry 558 |
| 701,237 | 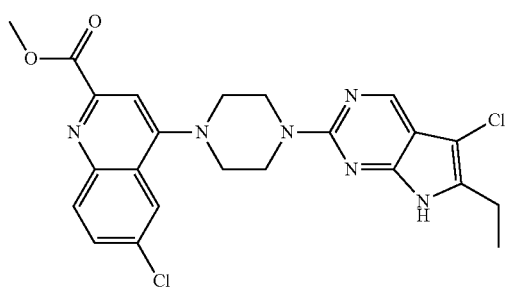 [SMILES: CCc1[nH]c2nc(N3CCN(c4cc(C(=O)OC)nc5ccc(Cl)cc45)CC3)ncc2c1Cl] | Chemistry 559 |
| 701,238 | 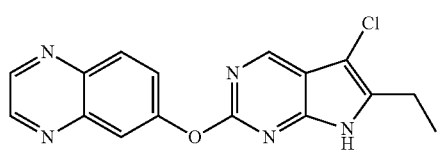 [SMILES: CCc1[nH]c2nc(Oc3ccc4nccnc4c3)ncc2c1Cl] | Chemistry 560 |
| 701,240 | 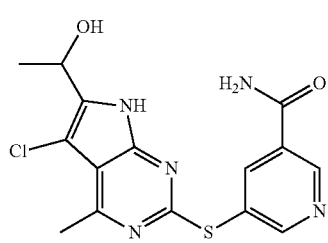 [SMILES: Cc1nc(Sc2cncc(C(N)=O)c2)nc2[nH]c(C(C)O)c(Cl)c12] | Chemistry 561 |

| Rx ID | CHEMISTRY | |
|---|---|---|
| 701,241 | 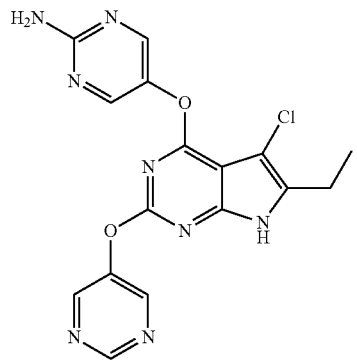 [SMILES: CCc1[nH]c2nc(Oc3cncnc3)nc(Oc3cnc(N)nc3)c2c1Cl] | Chemistry 562 |
| 701,251 | 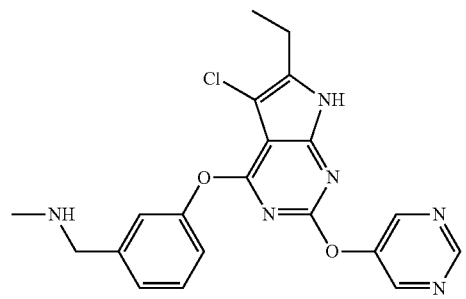 [SMILES: CCc1[nH]c2nc(Oc3cncnc3)nc(Oc3cccc(CNC)c3)c2c1Cl] | Chemistry 563 |
| 701,260 | 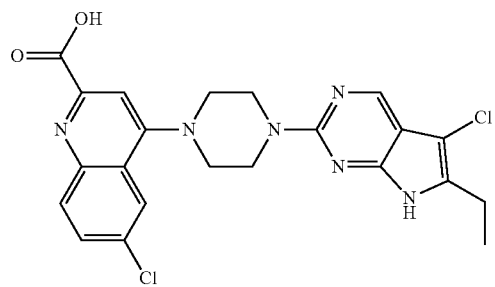 [SMILES: CCc1[nH]c2nc(N3CCN(c4cc(C(=O)O)nc5ccc(Cl)cc45)CC3)ncc2c1Cl] | Chemistry 564 |
| 701,261 | 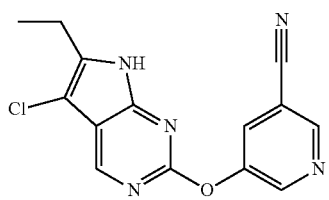 [SMILES: CCc1[nH]c2nc(Oc3cncc(C#N)c3)ncc2c1Cl] | Chemistry 565 |
| 701,263 | 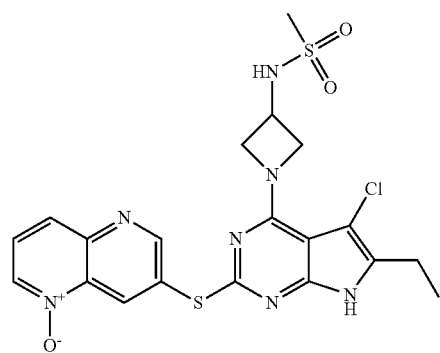 [SMILES: CCc1[nH]c2nc(Sc3cnc4ccc[n+]([O-])c4c3)nc(N3CC(NS(C)(=O)=O)C3)c2c1Cl] | Chemistry 566 |

-continued
| Rx ID | CHEMISTRY | |
|---|---|---|
| 701,265 | 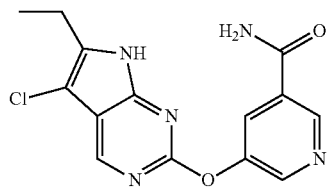 [SMILES: CCc1[nH]c2nc(Oc3cncc(C(N)=O)c3)ncc2c1Cl] | Chemistry 567 |
| 701,266 | 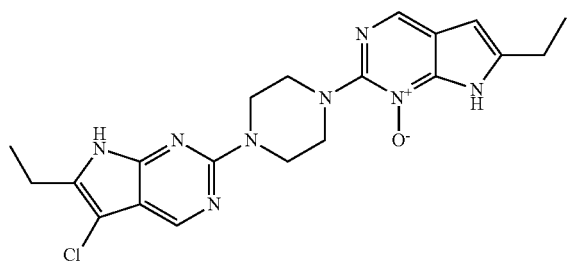 [SMILES: CCc1cc2cnc(N3CCN(c4ncc5c(Cl)c(CC)[nH]c5n4)CC3)[n+]([O-])c2[nH]1] | Chemistry 568 |
| 701,264 | 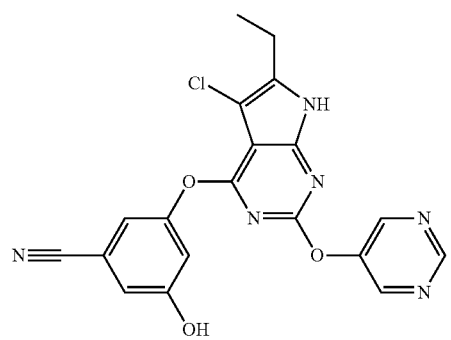 [SMILES: CCc1[nH]c2nc(Oc3cncnc3)nc(Oc3cc(O)cc(C#N)c3)c2c1Cl] | Chemistry 569 |
| 701,270 | 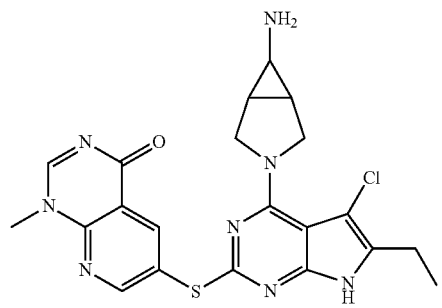 | Chemistry 570 |
| 701,269 | 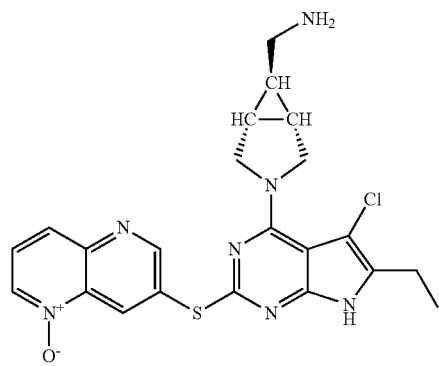 [SMILES: CCc1[nH]c2nc(Sc3cnc4ccc[n+]([O-])c4c3)nc(N3C[C@@H]4[C@@H](CN)[C@@H]4C3)c2c1Cl] | Chemistry 572 |

| Rx ID | CHEMISTRY | |
|---|---|---|
| 701,278 | 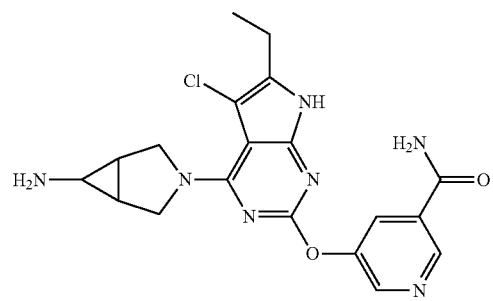 [SMILES: CCc1[nH]c2nc(Oc3cncc(C(N)=O)c3)nc(N3CC4C(N)C4C3)c2c1Cl] | Chemistry 573 |
| 701,279 | 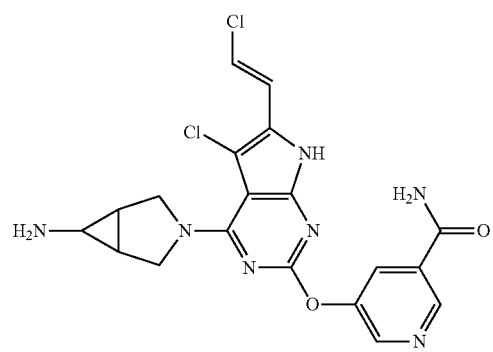 [SMILES: NC(=O)c1cncc(Oc2nc(N3CC4C(N)C4C3)c3c(Cl)c(/C=C/Cl)[nH]c3n2)c1] | Chemistry 574 |
| 701,286 | 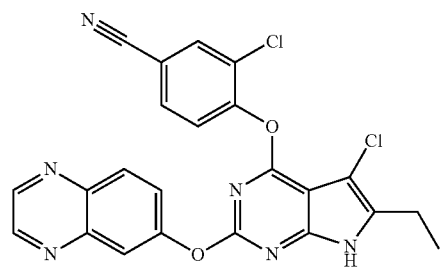 | Chemistry 575 |
| 701,289 | 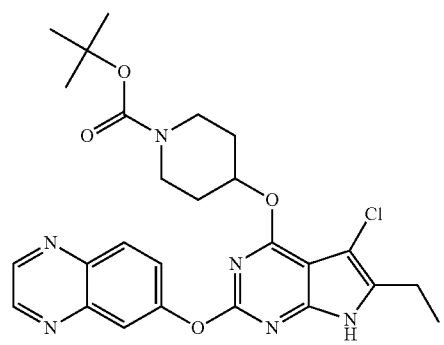 [SMILES: CCc1[nH]c2nc(Oc3ccc4nccnc4c3)nc(OC3CCN(C(=O)OC(C)(C)C)CC3)c2c1Cl] | Chemistry 576 |
| 701,290 | 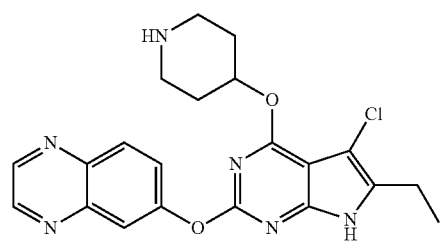 [SMILES: CCc1[nH]c2nc(Oc3ccc4nccnc4c3)nc(OC3CCNCC3)c2c1Cl] | Chemistry 577 |

| Rx ID | CHEMISTRY | |
|---|---|---|
| 701,291 | (structure) | Chemistry 578 |
| 701,296 | (structure) | Chemistry 579 |

TABLE 2

| Rx_ID | SA | Spn52 | EC8 |
|---|---|---|---|
| 700,075 | 64 | | |
| 700,076 | >64 | | |
| 700,077 | >64 | | |
| 700,078 | >64 | | |
| 700,079 | >64 | | |
| 700,080 | >64 | | |
| 700,081 | 16 | | |
| 700,082 | >64 | | |
| 700,084 | >64 | | |
| 700,085 | >64 | | |
| 700,088 | >64 | | |
| 700,089 | >64 | | |
| 700,090 | >64 | | |
| 700,091 | >64 | | |
| 700,092 | 64 | | |
| 700,093 | >64 | | |
| 700,094 | 64 | | |
| 700,095 | >64 | | |
| 700,096 | >64 | | |
| 700,098 | >64 | | |
| 700,099 | >64 | | |
| 700,100 | >64 | | |
| 700,101 | >64 | | |
| 700,102 | >64 | | |
| 700,103 | >64 | | |
| 700,104 | >64 | | |
| 700,105 | >64 | | |
| 700,106 | >64 | | |
| 700,107 | >64 | | |
| 700,108 | >64 | | |
| 700,109 | >64 | | |
| 700,119 | 64 | | |
| 700,120 | 4 | | |
| 700,121 | 32 | | |
| 700,122 | >64 | | |
| 700,127 | >64 | | |
| 700,128 | >64 | | |
| 700,129 | 16 | | |
| 700,130 | 8 | | |
| 700,131 | 64 | | |
| 700,132 | 32 | | |
| 700,133 | >64 | | |
| 700,135 | >64 | | |
| 700,136 | 16 | | |
| 700,137 | 64 | | |
| 700,141 | 64 | | |
| 700,142 | 32 | | |
| 700,147 | >64 | | |
| 700,148 | >64 | | |
| 700,149 | >64 | | |
| 700,150 | | | |
| 700,220 | >64 | 64 | |
| 700,261 | 16 | 32 | |
| 700,267 | 2 | 16 | |
| 700,268 | 4 | 16 | |
| 700,269 | 4 | 16 | |
| 700,270 | 2 | 8 | |
| 700,271 | >64 | >64 | |
| 700,273 | 4 | 16 | |
| 700,274 | 4 | 16 | |
| 700,275 | 1 | 8 | |
| 700,281 | 32 | 64 | |
| 700,282 | <=0.5 | 4 | |
| 700,286 | 4 | 32 | |
| 700,287 | >64 | >64 | |
| 700,288 | >64 | 64 | |
| 700,290 | >64 | >64 | |
| 700,291 | >64 | >64 | |
| 700,292 | >64 | >64 | |
| 700,293 | 32 | 32 | |
| 700,294 | >64 | >64 | |
| 700,295 | >64 | 32 | |
| 700,296 | >64 | 64 | |
| 700,297 | <=0.5 | 2 | |
| 700,298 | 2 | 8 | |
| 700,301 | 64 | >64 | |
| 700,302 | 32 | >64 | |
| 700,303 | 4 | 32 | |

TABLE 2-continued

| Rx_ID | SA | Spn52 | EC8 |
|---|---|---|---|
| 700,304 | 8 | 32 | |
| 700,305 | >64 | >64 | |
| 700,306 | >64 | >64 | |
| 700,307 | 4 | 64 | |
| 700,315 | 16 | 64 | |
| 700,317 | >64 | >64 | |
| 700,318 | >64 | >64 | |
| 700,320 | >64 | >64 | |
| 700,321 | 64 | 64 | |
| 700,322 | >64 | >64 | |
| 700,323 | >64 | >64 | |
| 700,324 | >64 | 64 | |
| 700,325 | >64 | >64 | |
| 700,326 | >64 | 32 | |
| 700,327 | 32 | 64 | |
| 700,328 | >64 | 64 | |
| 700,331 | 8 | >64 | |
| 700,332 | >64 | >64 | |
| 700,334 | >64 | >64 | |
| 700,338 | 8 | 64 | |
| 700,339 | >64 | >64 | |
| 700,340 | >64 | >64 | |
| 700,341 | >64 | >64 | |
| 700,342 | >64 | >64 | |
| 700,343 | >64 | >64 | |
| 700,345 | <=0.5 | 2 | |
| 700,346 | <=0.5 | <=0.5 | |
| 700,347 | 1 | 8 | |
| 700,350 | 32 | 64 | |
| 700,351 | >64 | >64 | |
| 700,353 | >64 | >64 | |
| 700,354 | 2 | >64 | |
| 700,355 | >64 | >64 | |
| 700,356 | >64 | >64 | |
| 700,357 | >64 | >64 | |
| 700,358 | >64 | >64 | |
| 700,359 | 2 | 8 | |
| 700,360 | <=0.5 | 2 | |
| 700,361 | >64 | >64 | |
| 700,362 | >64 | >64 | |
| 700,363 | >64 | >64 | |
| 700,364 | 32 | >64 | |
| 700,365 | >64 | >64 | |
| 700,373 | >64 | >64 | |
| 700,374 | >64 | >64 | |
| 700,378 | >64 | >64 | |
| 700,381 | 1 | 8 | |
| 700,385 | 8 | >64 | |
| 700,386 | <=0.5 | 8 | |
| 700,387 | 16 | >64 | |
| 700,388 | 4 | 16 | |
| 700,389 | >64 | >64 | |
| 700,390 | <=0.5 | <=0.5 | |
| 700,391 | >64 | >64 | |
| 700,392 | <=0.5 | <=0.5 | |
| 700,393 | <=0.5 | 1 | |
| 700,395 | >64 | >64 | |
| 700,396 | >64 | >64 | |
| 700,397 | >64 | >64 | |
| 700,398 | >64 | >64 | |
| 700,402 | >64 | >64 | |
| 700,403 | 4 | 8 | |
| 700,404 | <=0.5 | <=0.5 | |
| 700,405 | <=0.5 | 2 | |
| 700,406 | 2 | 16 | |
| 700,407 | >64 | >64 | |
| 700,408 | >64 | >64 | |
| 700,410 | 1 | 4 | |
| 700,411 | >64 | >64 | |
| 700,412 | >64 | >64 | |
| 700,413 | 8, 1 | 8 | |
| 700,414 | <=0.5 | 1 | |
| 700,415 | <=0.5 | 1 | |
| 700,416 | <=0.5 | 2 | |
| 700,417 | 1 | 16 | |
| 700,418 | 1 | 8 | |
| 700,422 | >64 | >64 | |
| 700,423 | 1 | 2 | |
| 700,424 | <=0.5 | 1 | |
| 700,425 | <=0.5 | 2 | |
| 700,426 | 1 | 1 | |
| 700,427 | <=0.5 | 1 | |
| 700,428 | <=0.5 | 1 | |
| 700,429 | <=0.5 | 2 | |
| 700,430 | 32 | 32 | |
| 700,431 | >64 | >64 | |
| 700,432 | 1 | 4 | |
| 700,433 | <=0.5 | 1 | |
| 700,434 | 1 | 2 | |
| 700,434 | 1 | 2 | |
| 700,435 | <=0.5 | 1 | |
| 700,436 | <=0.5 | 1 | |
| 700,437 | <=0.5 | 2 | |
| 700,438 | <=0.5 | 1 | |
| 700,439 | <=0.5 | 1 | |
| 700,440 | <=0.5 | <=0.5 | |
| 700,441 | <=0.5 | 2 | |
| 700,442 | <=0.5 | 2 | |
| 700,443 | >64 | >64 | |
| 700,444 | 4 | 8 | |
| 700,445 | 16 | 16 | |
| 700,448 | 1 | 2 | |
| 700,449 | 1 | 1 | |
| 700,450 | <=0.5 | 4 | |
| 700,451 | 1 | 4 | |
| 700,452 | >64 | >64 | |
| 700,453 | <=0.5 | <=0.5 | |
| 700,454 | <=0.5 | 1 | |
| 700,455 | 2 | 2 | |
| 700,456 | <=0.5 | 4 | |
| 700,457 | 1 | 2 | |
| 700,458 | 2 | 8 | |
| 700,459 | 16 | 32 | |
| 700,461 | 1 | >64 | |
| 700,462 | >64 | 32 | |
| 700,463 | 2 | 4 | |
| 700,464 | >64 | >64 | |
| 700,465 | 8 | 32 | |
| 700,466 | 4 | 16 | |
| 700,467 | 4 | 16 | |
| 700,468 | <=0.5 | 1 | |
| 700,469 | 1 | 2 | |
| 700,470 | <=0.5 | 1 | |
| 700,471 | 2 | 8 | |
| 700,472 | 64 | 64 | |
| 700,473 | 32 | 64 | |
| 700,474 | 8 | 8 | |
| 700,475 | >64 | >64 | |
| 700,476 | >64 | >64 | |
| 700,477 | 1 | 16 | |
| 700,478 | 64 | >64 | |
| 700,479 | 4 | 32 | |
| 700,480 | 16 | >64 | |
| 700,481 | 8 | 2 | |
| 700,482 | >64 | >64 | |
| 700,483 | 32 | 32 | |
| 700,484 | 4 | 8 | |
| 700,485 | 4 | >64 | |
| 700,486 | 16 | 8 | |
| 700,487 | <=0.5 | <=0.5 | |
| 700,490 | >64 | 1 | |
| 700,491 | <=0.5 | 1 | |
| 700,492 | 8 | >64 | |
| 700,493 | >64 | >64 | |
| 700,494 | >64 | >64 | |
| 700,495 | 64 | >64 | |
| 700,496 | >64 | >64 | |
| 700,497 | 1 | 4 | |
| 700,498 | 16 | >64 | |
| 700,502 | 16 | >64 | |
| 700,503 | 16 | >64 | |
| 700,504 | 4 | 32 | |
| 700,505 | 4 | 32 | |
| 700,506 | <=0.5 | 1 | |
| 700,507 | >64 | >64 | |
| 700,508 | 2 | 4 | |

TABLE 2-continued

| Rx_ID | SA | Spn52 | EC8 |
|---|---|---|---|
| 700,509 | 16 | 16 | |
| 700,510 | >64 | >64 | |
| 700,511 | >64 | >64 | |
| 700,512 | >64 | >64 | |
| 700,513 | >64 | 32 | |
| 700,514 | <=0.5 | <=0.5 | |
| 700,515 | 1 | 1 | |
| 700,516 | <=0.5 | 1 | |
| 700,517 | <=0.5 | 2 | |
| 700,518 | 4 | 4 | |
| 700,519 | 1 | 1 | |
| 700,520 | 8 | 16 | |
| 700,521 | 1 | 2 | |
| 700,522 | <=0.5 | 2 | |
| 700,523 | 2 | 4 | |
| 700,524 | <=0.5 | <=0.5 | |
| 700,525 | >64 | >64 | |
| 700,526 | 8 | >64 | |
| 700,527 | 16 | 8 | |
| 700,528 | 8 | 8 | |
| 700,531 | 8 | 4 | |
| 700,534 | 2 | >32 | |
| 700,535 | <=0.5 | 4 | |
| 700,538 | >16 | >16 | |
| 700,539 | <=0.5 | 1 | |
| 700,540 | 1 | 2 | |
| 700,541 | 4 | 4 | |
| 700,542 | 2 | 8 | |
| 700,544 | >64 | >64 | |
| 700,545 | 2 | 4 | |
| 700,546 | 4 | 16 | |
| 700,547 | 4 | 4 | |
| 700,548 | <=0.5 | 2 | |
| 700,549 | 4 | 4 | |
| 700,550 | 1 | 8 | |
| 700,551 | 2 | 4 | |
| 700,552 | <=0.5 | 2 | |
| 700,558 | 8 | >64 | |
| 700,559 | >64 | >64 | |
| 700,560 | 8 | 32 | |
| 700,561 | 16 | 32 | |
| 700,562 | 16 | 64 | |
| 700,563 | 1 | 2 | |
| 700,564 | 8 | 16 | |
| 700,565 | 2 | 4 | |
| 700,566 | >64 | 64 | |
| 700,567 | 7 | 4 | |
| 700,568 | <=0.5 | 2 | |
| 700,569 | 8 | 4 | |
| 700,570 | 1 | 8 | |
| 700,571 | 8 | 8 | |
| 700,572 | 4 | >8 | |
| 700,573 | >64 | >64 | |
| 700,574 | 4 | 16 | |
| 700,575 | 8 | 16 | |
| 700,576 | 8 | 16 | |
| 700,577 | >64 | >64 | |
| 700,578 | <=0.5 | 1 | |
| 700,584 | 8 | 32 | |
| 700,585 | >64 | >64 | |
| 700,586 | >64 | >64 | |
| 700,587 | 64 | >64 | |
| 700,588 | 8 | 8 | |
| 700,589 | 2 | 8 | |
| 700,590 | 4 | 16 | |
| 700,591 | 2 | >64 | |
| 700,592 | >64 | 4 | |
| 700,595 | 8 | 8 | |
| 700,596 | 32 | 32 | |
| 700,597 | 16 | 16 | |
| 700,598 | 1 | 2 | |
| 700,599 | <=0.5 | 2 | |
| 700,600 | >8 | >8 | |
| 700,601 | <=0.5 | 2 | |
| 700,602 | 4 | 4 | |
| 700,603 | 4 | 8 | |
| 700,604 | 4 | 8 | |
| 700,605 | 4 | 8 | |
| 700,606 | 2 | 4 | |
| 700,607 | 8 | 16 | |
| 700,608 | 1 | 2 | |
| 700,609 | <=0.5 | <=0.5 | |
| 700,609 | | | |
| 700,609 | <=0.5 | <=0.5 | |
| 700,611 | 2 | 8 | |
| 700,612 | >64 | >64 | |
| 700,613 | <=0.5 | 4 | |
| 700,614 | 2 | 16 | |
| 700,615 | <=0.5 | 4 | |
| 700,618 | <=0.5 | 2 | |
| 700,619 | 32 | 32 | |
| 700,620 | 32 | >64 | |
| 700,621 | 4 | 8 | |
| 700,627 | 4 | 16 | |
| 700,628 | 2 | 8 | |
| 700,629 | <=0.5 | 2 | |
| 700,630 | 4 | 8 | |
| 700,648 | <=0.5 | 2 | |
| 700,649 | <=0.5 | 2 | |
| 700,650 | <=0.5 | 1 | |
| 700,654 | >64 | >64 | |
| 700,655 | >64 | 2 | |
| 700,656 | <=0.5 | 2 | |
| 700,657 | 8 | 2 | |
| 700,658 | <=0.5 | 8 | |
| 700,659 | 4 | 2 | |
| 700,660 | <=0.5 | 1 | |
| 700,661 | >64 | >64 | |
| 700,664 | 2 | 4 | |
| 700,665 | 2 | 8 | |
| 700,666 | 2 | 4 | |
| 700,667 | <=0.5 | 1 | |
| 700,668 | 8 | >64 | |
| 700,669 | >64 | >64 | |
| 700,670 | 16 | 16 | |
| 700,671 | 8 | 32 | |
| 700,672 | 8 | 8 | |
| 700,673 | 2 | 4 | |
| 700,676 | 4 | 8 | |
| 700,677 | 2 | 8 | |
| 700,678 | 1 | 2 | |
| 700,679 | >64 | >64 | |
| 700,680 | 16 | 64 | |
| 700,686 | >64 | >64 | |
| 700,687 | >64 | >64 | |
| 700,688 | <=0.5 | <=0.5 | |
| 700,689 | 2 | 8 | |
| 700,690 | >64 | 8 | |
| 700,691 | >64 | >64 | |
| 700,694 | 2 | 8 | |
| 700,695 | 16 | 32 | |
| 700,696 | >64 | 16 | |
| 700,697 | 4 | 8 | |
| 700,698 | <=0.5 | 8 | |
| 700,699 | 2 | 64 | |
| 700,700 | 4 | 8 | |
| 700,701 | 1 | 8 | |
| 700,702 | 2 | 16 | |
| 700,705 | >64 | >64 | |
| 700,706 | 1 | 2 | |
| 700,707 | 2 | 4 | |
| 700,708 | 32 | >64 | |
| 700,710 | 1 | 8 | |
| 700,711 | 1 | 8 | |
| 700,712 | 8 | >64 | |
| 700,713 | 1 | 2 | |
| 700,714 | 2 | 4 | |
| 700,715 | <=0.5 | 1 | |
| 700,716 | 1 | 2 | |
| 700,717 | 2 | 4 | |
| 700,718 | 4 | 8 | |
| 700,719 | 2 | >64 | |
| 700,720 | 8 | 16 | |
| 700,721 | 32 | 32 | |
| 700,722 | 4 | 8 | |
| 700,723 | <=0.5 | 2 | |

TABLE 2-continued

| Rx_ID | SA | Spn52 | EC8 |
|---|---|---|---|
| 700,724 | <=0.5 | <=0.5 | |
| 700,781 | <=0.5 | 1 | |
| 700,782 | <=0.5 | <=0.5 | |
| 700,783 | 8 | 16 | |
| 700,784 | 2 | 8 | |
| 700,785 | 16 | 64 | |
| 700,786 | 16 | 32 | |
| 700,787 | 8 | 32 | |
| 700,788 | 8 | 16 | |
| 700,789 | 2 | 8 | |
| 700,790 | 16 | 64 | |
| 700,791 | 64 | 16 | |
| 700,792 | >64 | >64 | |
| 700,793 | <=0.5 | <=0.5 | |
| 700,794 | 16 | 32 | |
| 700,795 | <=0.5 | <=0.5 | 8 |
| 700,796 | <=0.5 | 1 | |
| 700,797 | >32 | >32 | |
| 700,798 | 16 | 32 | |
| 700,799 | >64 | >64 | |
| 700,800 | <=0.5 | <=0.5 | |
| 700,800 | <=0.5 | <=0.5 | |
| 700,801 | <=0.5 | <=0.5 | |
| 700,802 | 4 | 16 | |
| 700,803 | 8 | 16 | |
| 700,804 | 4 | 16 | |
| 700,805 | <=0.5 | 2 | |
| 700,806 | 4 | 16 | |
| 700,807 | 2 | 8 | |
| 700,808 | 8 | 64 | |
| 700,809 | <=0.5 | 4 | |
| 700,812 | 4 | 4 | |
| 700,813 | >64 | >64 | |
| 700,814 | 2 | 4 | |
| 700,815 | 2 | 2 | |
| 700,816 | <=0.5 | <=0.5 | |
| 700,817 | <=0.5 | <=0.5 | |
| 700,818 | 2 | 8 | |
| 700,820 | 16 | 32 | |
| 700,821 | >64 | >64 | |
| 700,822 | >64 | >64 | |
| 700,823 | 64 | 64 | |
| 700,824 | 2 | 8 | |
| 700,825 | 64 | >64 | |
| 700,826 | 8 | 32 | |
| 700,827 | 4 | 32 | |
| 700,828 | >64 | >64 | |
| 700,829 | 16 | 32 | |
| 700,830 | <=0.5 | 2 | |
| 700,831 | 2 | 4 | |
| 700,832 | 4 | >8 | |
| 700,833 | <=0.5 | 2 | |
| 700,834 | 1 | 8 | |
| 700,841 | 4 | 8 | |
| 700,842 | 4 | >64 | |
| 700,843 | 64 | >64 | |
| 700,844 | 64 | 32 | |
| 700,845 | >64 | >64 | |
| 700,846 | >64 | >64 | |
| 700,847 | >64 | >64 | |
| 700,848 | 64 | 64 | |
| 700,850 | 64 | >64 | |
| 700,851 | <=0.5 | 4 | |
| 700,857 | 1 | 1 | |
| 700,858 | 8 | >64 | |
| 700,859 | 32 | >64 | |
| 700,860 | >64 | >64 | |
| 700,861 | 16 | >64 | |
| 700,862 | >64 | 32 | |
| 700,863 | 8 | 8 | |
| 700,864 | 4 | 4 | |
| 700,865 | 1 | <=0.5 | |
| 700,866 | 1 | 8 | |
| 700,867 | <=0.5 | 1 | |
| 700,868 | >64 | >64 | |
| 700,869 | 2 | 4 | |
| 700,870 | 64 | 64 | |
| 700,871 | <=0.5 | 2 | |
| 700,872 | 1 | 2 | |
| 700,873 | 2 | 32 | |
| 700,874 | 2 | 8 | |
| 700,875 | 32 | >32 | |
| 700,876 | 8 | 8 | |
| 700,877 | 4 | 8 | |
| 700,878 | <=0.5 | <=0.5 | |
| 700,883 | <=0.5 | <=0.5 | |
| 700,884 | 4 | 16 | |
| 700,885 | 2 | 4 | |
| 700,886 | >8 | 8 | |
| 700,887 | 8 | 4 | |
| 700,888 | >64 | >64 | |
| 700,889 | 32 | 32 | |
| 700,890 | 2 | 4 | |
| 700,891 | >64 | >64 | |
| 700,892 | >64 | >64 | |
| 700,893 | 4 | 8 | |
| 700,894 | 32 | 8 | |
| 700,898 | <=0.5 | 2 | |
| 700,899 | <=0.5 | <=0.5 | |
| 700,900 | 8 | 8 | |
| 700,901 | 8 | 4 | |
| 700,903 | 32 | 64 | |
| 700,904 | 32 | >64 | |
| 700,906 | 2 | 4 | >64 |
| 700,907 | 8 | 16 | 64 |
| 700,908 | 8 | 16 | >64 |
| 700,909 | 1 | 4 | >64 |
| 700,910 | >64 | >64 | >64 |
| 700,911 | 1 | 2 | >32 |
| 700,912 | 8 | >64 | 32 |
| 700,913 | 2 | 2 | >64 |
| 700,914 | 64 | >64 | 32 |
| 700,915 | 64 | >64 | 32 |
| 700,916 | 64 | >64 | >64 |
| 700,917 | 4 | 4 | 8 |
| 700,918 | 2 | 8 | >64 |
| 700,919 | >64 | >64 | >64 |
| 700,920 | >64 | >64 | >64 |
| 700,921 | 2 | 4 | >64 |
| 700,922 | 32 | 64 | 4 |
| 700,923 | 16 | 8 | 64 |
| 700,924 | 16 | 4 | 64 |
| 700,925 | 4 | 32 | >64 |
| 700,926 | 1 | 2 | 8 |
| 700,927 | <=0.5 | 1 | >64 |
| 700,928 | 2 | 8 | 16 |
| 700,929 | 16 | 64 | 32 |
| 700,930 | 8 | 16 | >64 |
| 700,932 | >64 | >64 | >64 |
| 700,933 | 2 | 4 | >64 |
| 700,934 | 4 | 16 | >64 |
| 700,935 | 2 | 32 | >64 |
| 700,936 | 64 | 32 | >64 |
| 700,937 | <=0.5 | 1 | >64 |
| 700,938 | <=0.5 | <=0.5 | >64 |
| 700,939 | <=0.5 | 1 | >64 |
| 700,940 | 2 | 8 | 8 |
| 700,941 | 4 | 8 | >64 |
| 700,942 | 16 | 16 | 8 |
| 700,943 | 32 | 32 | 64 |
| 700,944 | 8 | 8 | >64 |
| 700,945 | <=0.5 | <=0.5 | >64 |
| 700,946 | >64 | >64 | >64 |
| 700,947 | >64 | 64 | >64 |
| 700,948 | <=0.5 | 4 | >16 |
| 700,949 | <=0.5 | 4 | >64 |
| 700,950 | >64 | >64 | >64 |
| 700,951 | >16 | >16 | >16 |
| 700,952 | 64 | 64 | >64 |
| 700,953 | >32 | >32 | >32 |
| 700,954 | >32 | >32 | >32 |
| 700,955 | 8 | >64 | 16 |
| 700,956 | 8 | 32 | >64 |
| 700,957 | <=0.5 | 1 | >32 |
| 700,958 | 2 | 4 | >32 |
| 700,959 | 2 | 2 | >64 |

TABLE 2-continued

| Rx_ID | SA | Spn52 | EC8 |
|---|---|---|---|
| 700,960 | 2 | 2 | >32 |
| 700,961 | 1 | 1 | >64 |
| 700,962 | <=0.5 | 2 | >8 |
| 700,963 | 1 | 4 | >64 |
| 700,964 | <=0.5 | <=0.5 | >64 |
| 700,965 | <=0.5 | <=0.5 | 64 |
| 700,966 | <=0.5 | <=0.5 | >64 |
| 700,967 | <=0.5 | 4 | >64 |
| 700,968 | 2 | >64 | >64 |
| 700,969 | <=0.5 | 2 | >64 |
| 700,970 | 8 | 32 | >64 |
| 700,971 | <=0.5 | 2 | >64 |
| 700,972 | <=0.5 | 1 | 4 |
| 700,973 | <=0.5 | 2 | >64 |
| 700,974 | <=0.5 | 2 | 32 |
| 700,975 | 8 | 8 | >64 |
| 700,976 | 4 | 2 | 8 |
| 700,977 | 16 | 4 | 8 |
| 700,978 | >64 | >64 | >64 |
| 700,979 | <=0.5 | 4 | >64 |
| 700,980 | <=0.5 | 2 | >32 |
| 700,981 | 16 | 16 | >32 |
| 700,982 | <=0.5 | <=0.5 | >64 |
| 700,983 | 32 | 32 | 32 |
| 700,984 | 4 | 8 | 8 |
| 700,986 | 1 | 2 | 64 |
| 700,987 | <=0.5 | <=0.5 | >64 |
| 700,988 | <=0.5 | <=0.5 | >64 |
| 700,989 | <=0.5 | <=0.5 | >64 |
| 700,990 | 1 | 16 | >64 |
| 700,991 | 1 | 2 | 32 |
| 700,992 | <=0.5 | <=0.5 | >64 |
| 700,993 | <=0.5 | 2 | 16 |
| 700,994 | <=0.5 | <=0.5 | 8 |
| 700,995 | >64 | >64 | 64 |
| 700,996 | <=0.5 | <=0.5 | >64 |
| 700,997 | <=0.5 | <=0.5 | >64 |
| 700,998 | <=0.5 | 1 | >64 |
| 700,999 | 2 | 2 | >64 |
| 701,000 | 4 | 8 | 64 |
| 701,000 | | | |
| 701,001 | 4 | 8 | >64 |
| 701,002 | 4 | >64 | >64 |
| 701,003 | >64 | 32 | >64 |
| 701,004 | 32 | >64 | >64 |
| 701,005 | <=0.5 | <=0.5 | 16 |
| 701,006 | <=0.5 | <=0.5 | >64 |
| 701,007 | <=0.5 | 2 | >64 |
| 701,010 | <=0.5 | 1 | >16 |
| 701,011 | <=0.5 | <=0.5 | 8 |
| 701,011 | <=0.5 | <=0.5 | 8 |
| 701,011 | <=0.5 | <=0.5 | 8 |
| 701,012 | 1 | 2 | >64 |
| 701,013 | 1 | 2 | 16 |
| 701,014 | 4 | 8 | 32 |
| 701,015 | <=0.5 | 2 | >64 |
| 701,016 | >64 | >64 | >64 |
| 701,017 | 2 | 1 | >64 |
| 701,018 | >64 | 16 | >64 |
| 701,019 | >32 | >32 | >32 |
| 701,020 | 4 | 2 | >64 |
| 701,021 | 4 | 4 | >64 |
| 701,022 | 4 | 2 | >64 |
| 701,023 | >64 | >64 | >64 |
| 701,024 | 2 | 2 | >64 |
| 701,025 | <=0.5 | 2 | 16 |
| 701,026 | <=0.5 | 1 | 8 |
| 701,027 | <=0.5 | 1 | >64 |
| 701,028 | <=0.5 | <=0.5 | >64 |
| 701,029 | 2 | 4 | >64 |
| 701,030 | <=0.5 | <=0.5 | >64 |
| 701,031 | <=0.5 | 2 | >64 |
| 701,032 | 8 | 8 | >64 |
| 701,033 | >64 | >64 | >64 |
| 701,034 | 4 | 4 | >64 |
| 701,035 | <=0.5 | <=0.5 | >64 |
| 701,036 | <=0.5 | 2 | 16 |
| 701,037 | 8 | 16 | >64 |

TABLE 2-continued

| Rx_ID | SA | Spn52 | EC8 |
|---|---|---|---|
| 701,038 | 8 | 32 | 16 |
| 701,039 | 8 | 8 | >64 |
| 701,040 | <=0.5 | 4 | 32 |
| 701,041 | 8 | 16 | >32 |
| 701,042 | <=0.5 | 1 | >64 |
| 701,043 | 1 | >64 | >64 |
| 701,044 | <=0.5 | 1 | >64 |
| 701,045 | <=0.5 | 1 | >64 |
| 701,046 | 2 | 4 | >64 |
| 701,047 | <=0.5 | <=0.5 | >64 |
| 701,048 | 16 | >64 | >64 |
| 701,049 | <=0.5 | <=0.5 | 8 |
| 701,050 | <=0.5 | <=0.5 | 32 |
| 701,051 | 2 | 4 | >32 |
| 701,052 | 4 | 8 | >16 |
| 701,054 | <=0.5 | 1 | >64 |
| 701,055 | >64 | >64 | >64 |
| 701,056 | 4 | 8 | >64 |
| 701,057 | 8 | 32 | >64 |
| 701,058 | <=0.5 | <=0.5 | >32 |
| 701,059 | <=0.5 | <=0.5 | >64 |
| 701,060 | <=0.5 | <=0.5 | >64 |
| 701,061 | <=0.5 | <=0.5 | >32 |
| 701,062 | 16 | 16 | >64 |
| 701,063 | 2 | 2 | 4 |
| 701,064 | 8 | 4 | 4 |
| 701,065 | 8 | 4 | 16 |
| 701,066 | 4 | >64 | >64 |
| 701,067 | >64 | >64 | >64 |
| 701,068 | 64 | >64 | >64 |
| 701,069 | <=0.5 | <=0.5 | 8 |
| 701,070 | 4 | 8 | 64 |
| 701,071 | 8 | 16 | 16 |
| 701,071 | 8 | 16 | 16 |
| 701,074 | 8 | 4 | 8 |
| 701,075 | 8 | 8 | 8 |
| 701,076 | >64 | 64 | >64 |
| 701,077 | >64 | >64 | >64 |
| 701,080 | 1 | 2 | 4 |
| 701,080 | 1 | 2 | 4 |
| 701,080 | 1 | 2 | 4 |
| 701,080 | 1 | 2 | 4 |
| 701,081 | <=0.5 | <=0.5 | >32 |
| 701,082 | <=0.5 | 16 | 4 |
| 701,083 | <=0.5 | 1 | 16 |
| 701,084 | <=0.5 | <=0.5 | 8 |
| 701,087 | <=0.5 | <=0.5 | >64 |
| 701,088 | 1 | 1 | 32 |
| 701,089 | 2 | 4 | >64 |
| 701,090 | 8 | 8 | >64 |
| 701,091 | <=0.5 | <=0.5 | >64 |
| 701,092 | <=0.5 | 2 | >64 |
| 701,093 | <=0.5 | 4 | >32 |
| 701,094 | >64 | >64 | >64 |
| 701,095 | <=0.5 | <=0.5 | >64 |
| 701,096 | <=0.5 | <=0.5 | >64 |
| 701,097 | <=0.5 | 1 | >64 |
| 701,098 | 4 | 4 | 32 |
| 701,098 | 4 | 4 | 32 |
| 701,102 | <=0.5 | 1. | 16 |
| 701,104 | <=0.5 | <=0.5 | >32 |
| 701,105 | 1 | 2 | >64 |
| 701,106 | 2 | 4 | >64 |
| 701,111 | >64 | 16 | >64 |
| 701,112 | 16 | 32 | >64 |
| 701,113 | 32 | 32 | >64 |
| 701,114 | 8 | 16 | >64 |
| 701,115 | <=0.5 | <=0.5 | 16 |
| 701,116 | <=0.5 | 2 | 16 |
| 701,117 | 8 | 8 | >64 |
| 701,118 | 4 | 2 | 64 |
| 701,119 | 32 | 16 | >64 |
| 701,120 | 4 | 32 | >64 |
| 701,121 | 8 | 4 | >64 |
| 701,121 | 8 | 4 | >64 |
| 701,121 | 8 | 4 | >64 |
| 701,122 | 2 | 2 | 32 |

TABLE 2-continued

| Rx_ID | SA | Spn52 | EC8 |
|---|---|---|---|
| 701,126 | <=0.5 | <=0.5 | 4 |
| 701,132 | >64 | >64 | >64 |
| 701,133 | 8 | 8 | >64 |
| 701,137 | 2 | 4 | 64 |
| 701,140 | 4 | 8 | >64 |
| 701,143 | <=0.5 | 2 | 64 |
| 701,144 | <=0.5 | 2 | 32 |
| 701,147 | 32 | 64 | >64 |
| 701,148 | 64 | 64 | >64 |
| 701,151 | <=0.5 | 2 | 8 |
| 701,153 | 64 | >64 | >64 |
| 701,156 | <=0.5 | 2 | 16 |
| 701,157 | 1 | 8 | 64 |
| 701,161 | 4 | 16 | 64 |
| 701,162 | 16 | 32 | >32 |
| 701,163 | >64 | >64 | >64 |
| 701,180 | 16 | 32 | >64 |
| 701,181 | 2 | 8 | >64 |
| 701,182 | >64 | >64 | >64 |
| 701,183 | 16 | 64 | >64 |
| 701,184 | >64 | >64 | >64 |
| 701,193 | 8 | 32 | 64 |
| 701,209 | 2 | 4 | >64 |
| 701,229 | 4 | 32 | >64 |
| 701,231 | 2 | 4 | >64 |
| 701,232 | 1 | 4 | >64 |
| 701,233 | 1. | 8 | >64 |
| 701,236 | >64 | >64 | >64 |
| 701,237 | >64 | >64 | >64 |
| 701,238 | 4 | 32 | >64 |
| 701,239 | 2 | 16 | 64 |
| 701,240 | >64 | >64 | >64 |
| 701,241 | 1 | 2 | >64 |
| 701,249 | <=0.5 | <=0.5 | 8 |
| 701,250 | <=0.5 | <=0.5 | >64 |
| 701,251 | 1 | 2 | >64 |
| 701,252 | <=0.5 | <=0.5 | >64 |
| 701,253 | 1 | 4 | >64 |
| 701,254 | <=0.5 | <=0.5 | >64 |
| 701,255 | <=0.5 | <=0.5 | >64 |
| 701,260 | 8 | 64 | >64 |
| 701,261 | 4 | 16 | >64 |
| 701,263 | <=0.5 | 1 | >64 |
| 701,264 | <=0.5 | <=0.5 | >64 |
| 701,265 | 4 | 16 | >64 |
| 701,267 | <=0.5 | <=0.5 | 32 |
| 701,268 | <=0.5 | <=0.5 | 4 |
| 701,269 | <=0.5 | <=0.5 | 8 |
| 701,270 | <=0.5 | 4 | 32 |
| 701,273 | <=0.5 | <=0.5 | 16 |
| 701,278 | >64 | >64 | >64 |
| 701,286 | >64 | >64 | >64 |
| 701,287 | >64 | >64 | >64 |
| 701,288 | <=0.5 | 1 | >64 |
| 701,289 | 16 | >64 | >64 |
| 701,290 | >64 | 64 | >64 |
| 701,291 | 32 | 16 | 64 |
| 701,292 | 32 | >32 | >32 |
| 701,296 | 8 | 32 | >64 |
| 701,297 | 4 | 16 | >64 |
| 701,298 | 2 | 4 | >64 |
| 701,299 | 2 | 4 | >64 |
| 701008-2 | <=0.5 | 1 | 4 |
| 701009-2 | <=0.5 | <=0.5 | 2 |
| 701249-2 | <=0.5 | <=0.5 | 4 |

What is claimed is:
1. A compound having the structure of Formula I

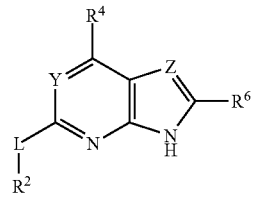

wherein
Y is N;
Z is $CR^5$;
$R^5$ is methyl, $C(O)CH_3$, $C(O)NH_2$, $CH_2OH$, $CF_3$, CN, $CHF_2$, CHO, Cl or Br;
L is O, S, $NR^7$, $SO_2$, or $CR^8R^9$;
$R^7$ is H or $C_{1-3}$ alkyl;
$R^8$ and $R^9$ are each independently H or $C_{1-3}$ alkyl;
$R^2$ is H, $COOCH_2CH_3$, $CH_3$, $CH_2CH_3$ or a hydrocarbyl residue (1-40C) containing 0-10 heteroatoms selected from O, S and N optionally substituted with an inorganic residue wherein the hydrocarbyl residue comprises at least one aryl or heteroaryl moiety;
$R^4$ is
  a) an inorganic residue selected from the group consisting of H, halo, $NH_2$, SH, $SO_2H$, NHOH, $SO_3H$, $SO_2NH_2$, and $NHSO_2NH_2$,
  b) an aryl C5-14 or heteroaryl C1-14 moiety substituted with 0-10 substituents selected from alkyl, alkenyl, alkynyl, aryl, arylalkyl, acyl, aroyl, heteroaryl, heteroalkyl, heteroalkenyl, heteroalkynyl, haloalkyl, haloalkenyl, haloalkynyl, heteroalkylaryl, NH-aroyl, arylacyl, heteroarylacyl, halo, —O, OR', $NR'_2$, SR', SOR', $SO_2R'$, OCOR', N-alkyl-OR', CONR'OR', NR'COR', $NR'CONR'_2$, NR'COOR', $OCONR'_2$, OR', $NR'_2$, COOR', alkyl-OOR', $SO_3R'$, $CONR'_2$, $CONR'_2OH$, $SO_2NR'_2$, $NR'SO_2NR'_2$, CN, $CF_3$, or $NO_2$, wherein each R' is independently H, alkyl, alkenyl or aryl or heteroforms thereof, and wherein two of said substituents on adjacent positions can be joined to form a fused, optionally substituted aromatic or nonaromatic, saturated or unsaturated ring which contains 3-14 members, and said substituents can only be —O if $R^4$ contains N,
  c) alkyl, alkenyl, alkynyl, heteroalkyl, heteroalkenyl, heteroalkynyl, alkylaryl, alkenylaryl, alkynylaryl, heteroalkylaryl, heteroalkenylaryl, or heteroalkynylaryl moiety substituted with 0-10 substituents selected from the group consisting of aryl, haloaryl, arylalkyl, arylalkenyl, arylalkynyl, haloaryl, heteroaryl, heteroarylalkyl, heteroarylalkenyl, heteroarylalkynyl, acyl, aroyl, NH-aroyl, arylacyl, heteroarylacyl, halo, —O, =O, =NH, OR", $NR''_2$, SR", SOR", $SO_2R''$, OCOR", CONR"OR", NR"COR", $NR''CONR''_2$, NR"COOR", NR"CO-COOR", $OCONR''_2$, COOR", $SO_3R''$, $CONR''_2$, $CONR''_2OH$, $SO_2NR''_2$, $NR''SO_2R''$, $NR''SO_2NR''_2$, CN, $CF_3$, or $NO_2$, wherein each R" is independently H, optionally substituted alkyl, alkenyl, alkynyl, aryl, heteroalkyl, heteroalkenyl, heteroalkynyl, heteroaryl, or halo forms thereof, and wherein two of said substituents on adjacent positions can be joined to form a fused, optionally substituted aromatic or nonaromatic, saturated or unsaturated ring which contains 3-14 members, and said substituents can only be —O if $R^4$ contains N, or d) OR''', NR'''$_2$, or OSO$_2$R''', wherein R''' is an aryl C5-14 or heteroaryl C1-14, moiety substituted with 0-10 substituents selected from alkyl, alkenyl, alkynyl, aryl, arylalkyl, acyl, aroyl, heteroaryl, heteroalkyl, heteroalkenyl, heteroalkynyl, haloalkyl, haloalkenyl, haloalkynyl, heteroalkylaryl, NH-aroyl, arylacyl, heteroarylacyl, halo, —O, OR', NR'$_2$, SR', SOR', SO$_2$R', OCOR', N-alkyl-OR', CONR'OR', NR'COR', NR'CONR'$_2$, NR'COOR', OCONR'$_2$, COOR', alkyl-OOR', SO$_3$R', CONR'$_2$, CONR'$_2$OH, SO$_2$NR'$_2$, NR'SO$_2$NR'$_2$, CN, CF$_3$, or NO$_2$, wherein each R' is independently H, alkyl, alkenyl or aryl or heteroforms thereof, and wherein two of said substituents on adjacent positions can be joined to form a fused, optionally substituted aromatic or nonaromatic, saturated or unsaturated ring which contains 3-14 members, and said substituents can only be —O if $R^4$ contains N, optionally wherein $R^5$ and $R^4$ together join to form a fused ring; and $R^6$ is ethyl;

or a pharmaceutically-acceptable salt thereof.

2. The compound of claim 1, or a pharmaceutically acceptable salt thereof, wherein Y is N; and L is O, S, NH, SO$_2$ or CH$_2$.

3. The compound of claim 1, or a pharmaceutically acceptable salt thereof, wherein Z is CR$^5$, wherein $R^5$ is selected from the group consisting of Cl, Br, and methyl.

4. The compound of claim 1, or a pharmaceutically acceptable salt thereof, wherein $R^2$ comprises at least one aryl or heteroaryl moiety.

5. The compound of claim 1, or a pharmaceutically acceptable salt thereof, wherein the at least one aryl or a heteroaryl moiety of $R^2$ is directly linked to L.

6. The compound of claim 1, or a pharmaceutically acceptable salt thereof, wherein the aryl or heteroaryl moiety of $R^2$ comprises at least one moiety selected from the group consisting of phenyl, pyrido[2,3-b]pyrazine, pyridyl, thiazole, quinoline, pyridazine, pyrimidinedione, pyrido[2,3-d]pyrimidinedione, pyrimidine, [1,2,3]triazolo[4,5-b]pyridine, oxazole, benzotriazine, furo[3,2-b]pyridine, thiazolo[5,4-b]pyridine, pyrazolo[3,4-b]pyridine, imidazo[4,5-b]pyridine, pyrido[3,2-d]pyrimidine, 1,5-naphthyridine, quinolone, quinazoline, and quinoxoline.

7. The compound of claim 1, or a pharmaceutically acceptable salt thereof, wherein L-R$^2$ is selected from the group consisting of

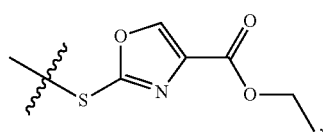

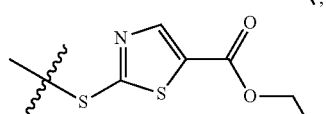

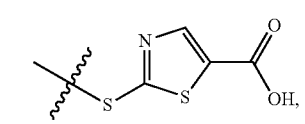

-continued

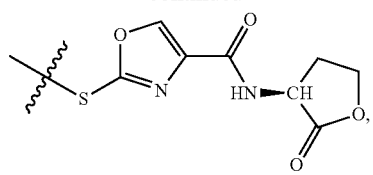

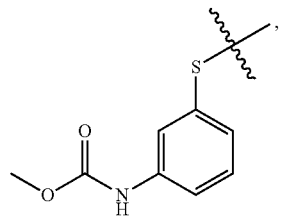

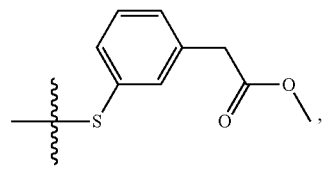

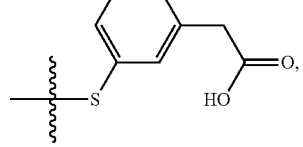

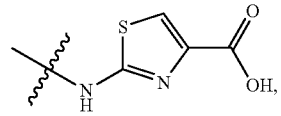

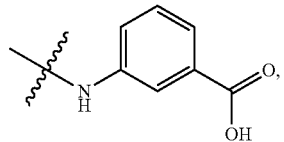

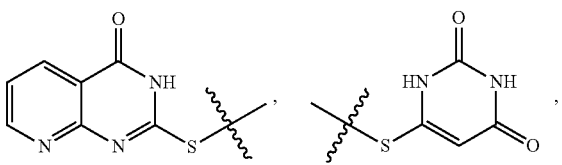

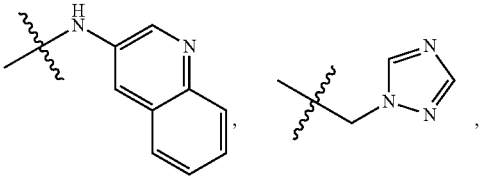

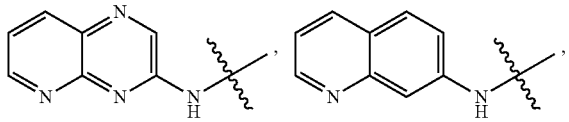

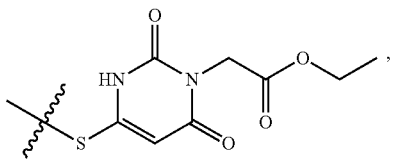

447
-continued
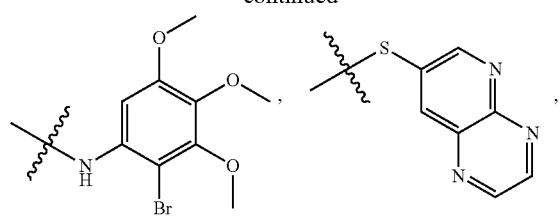
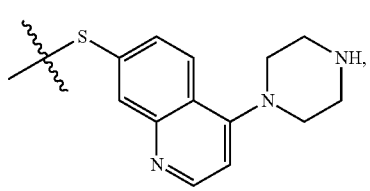
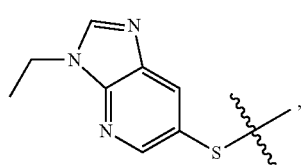
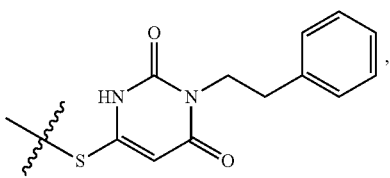
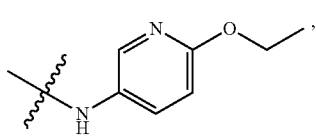
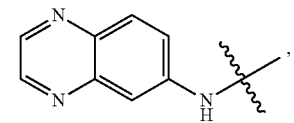
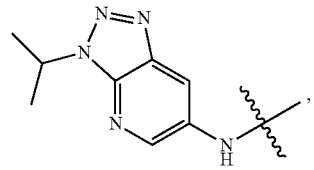
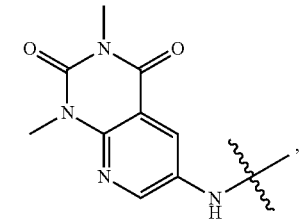
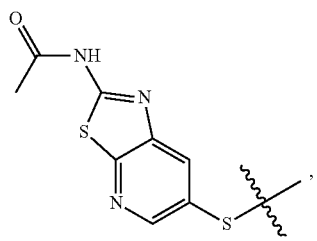
448
-continued
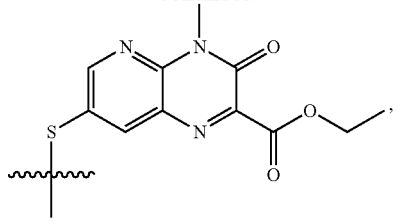
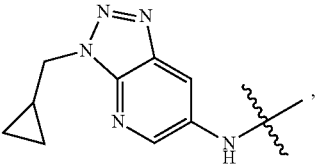
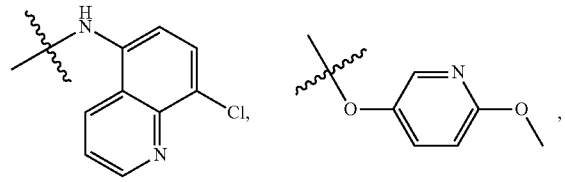
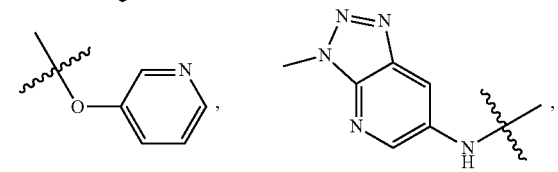
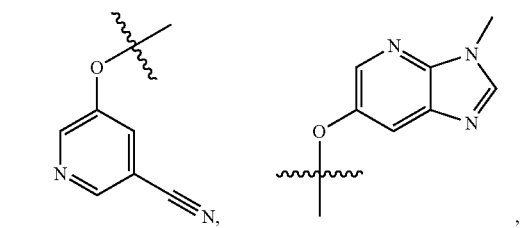
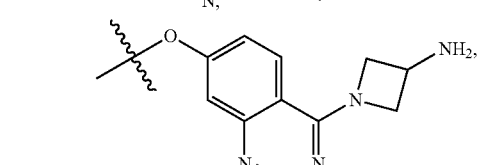
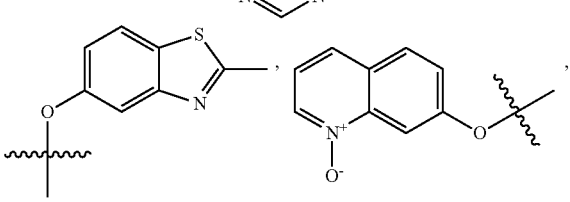
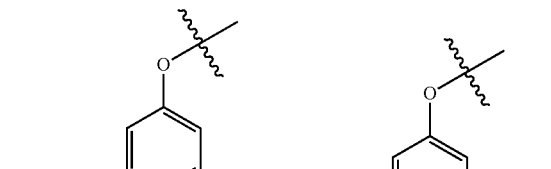
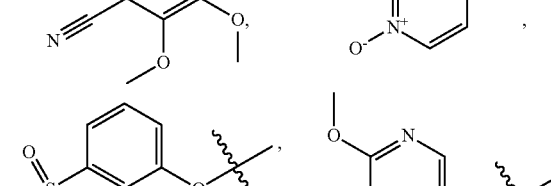

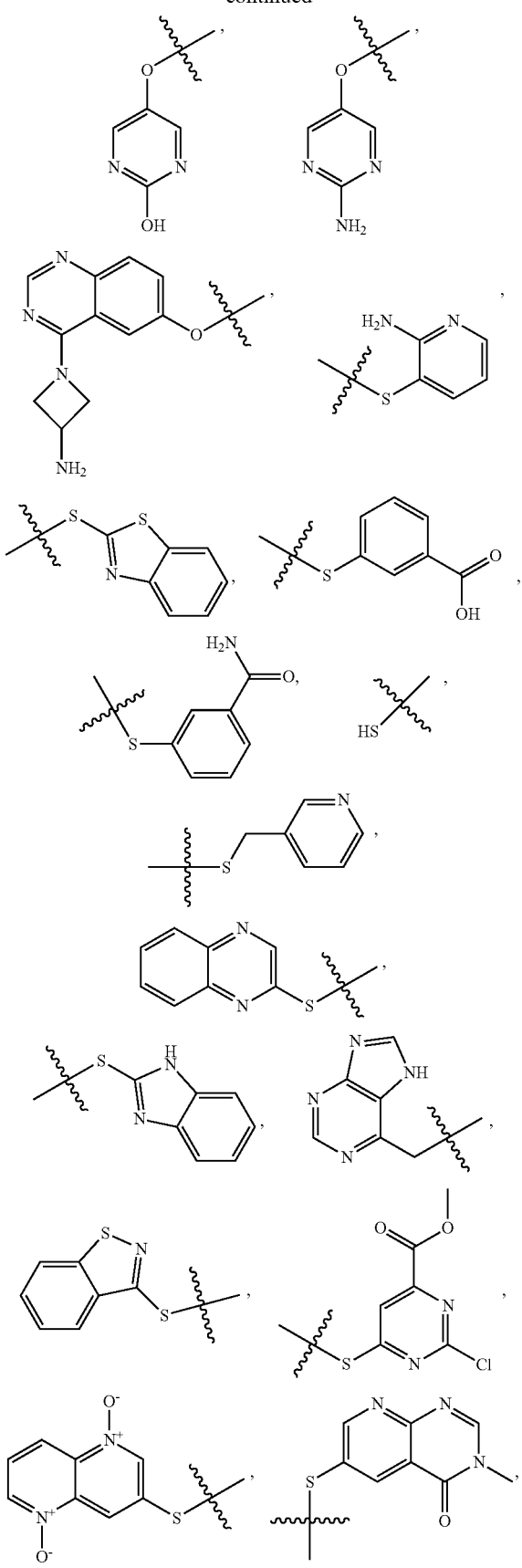
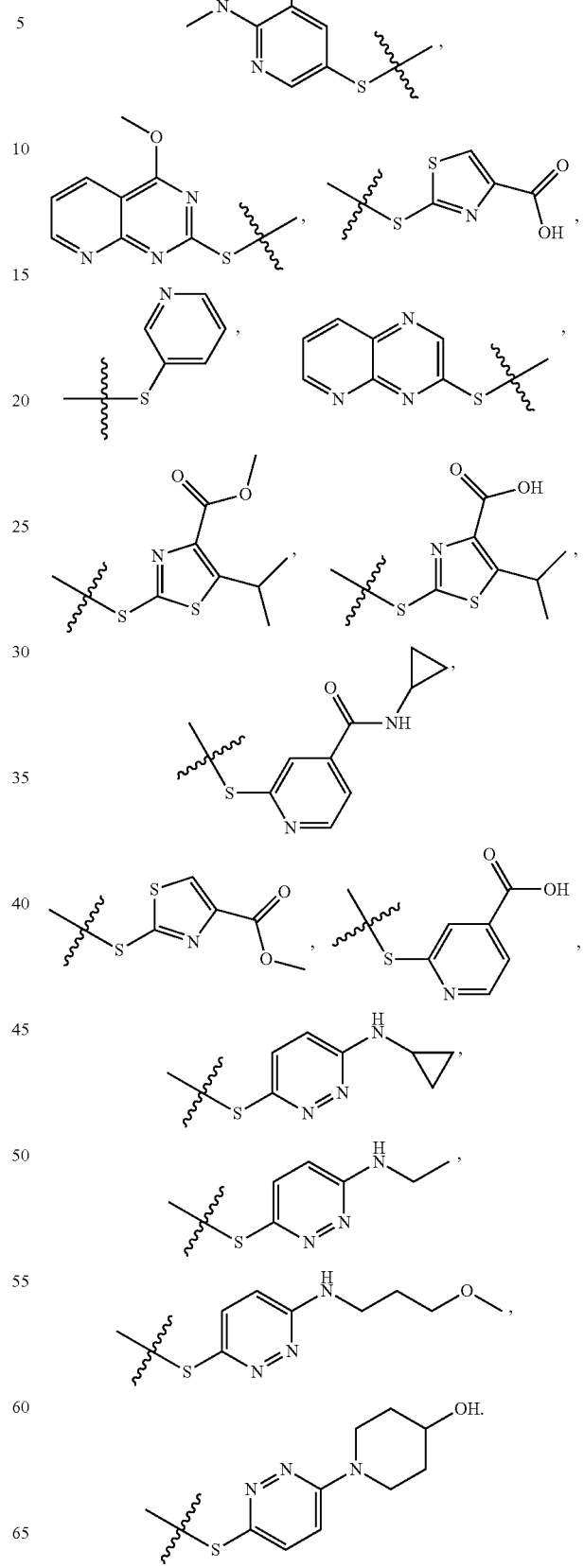

451
-continued
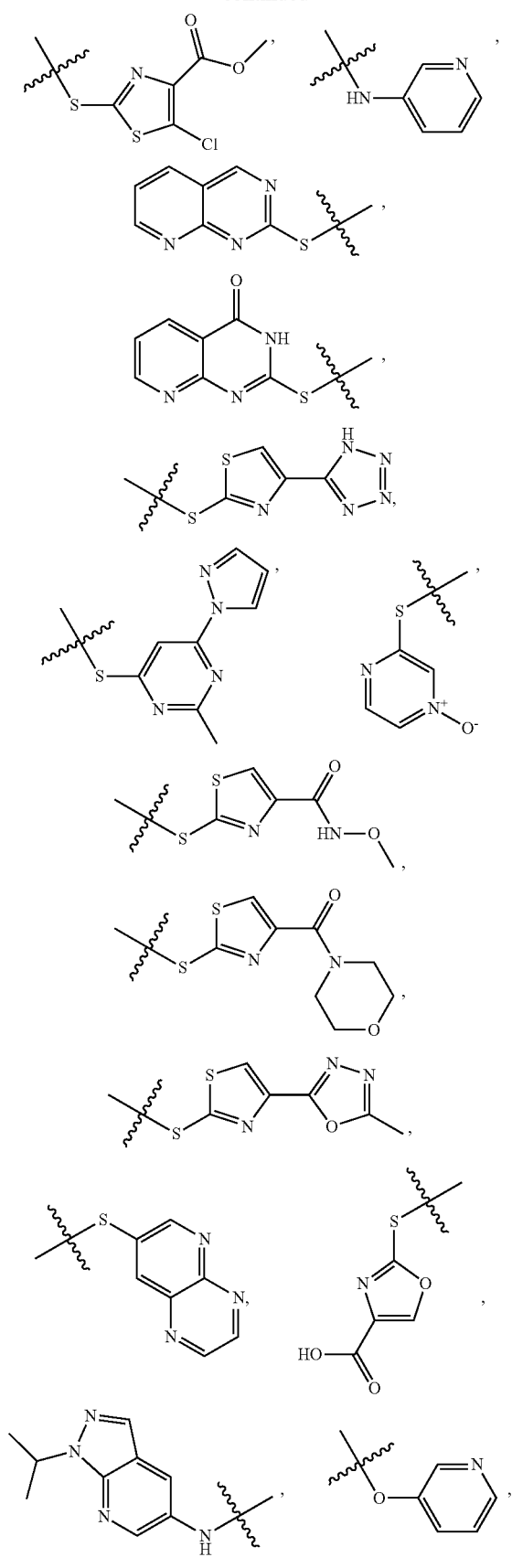
452
-continued
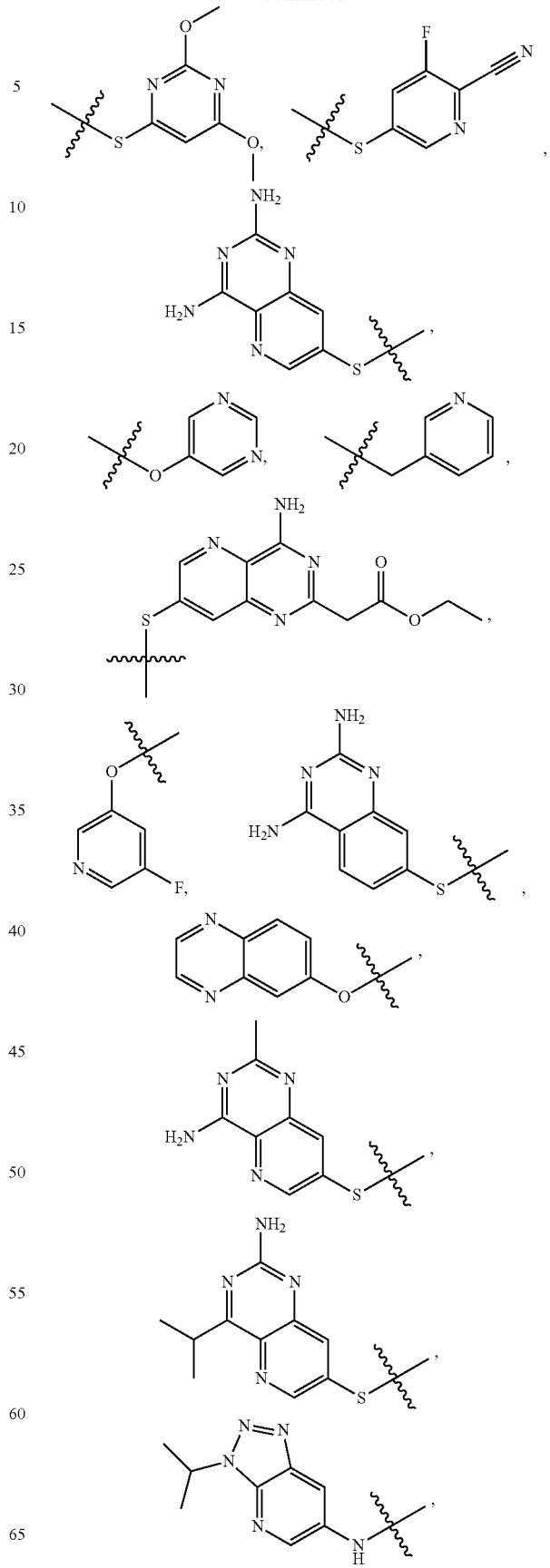

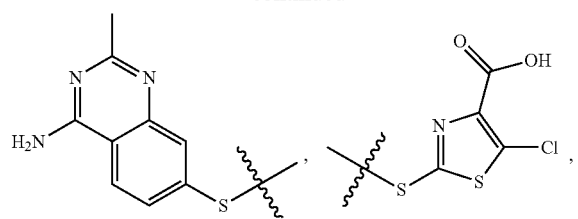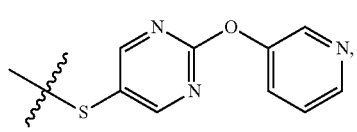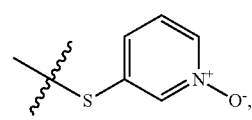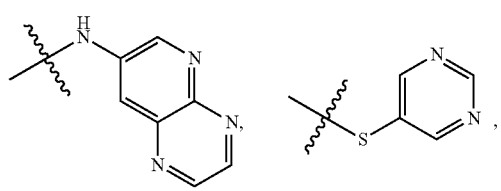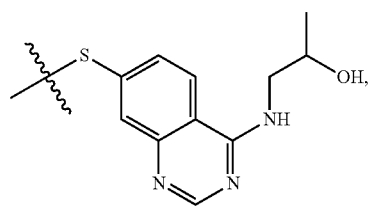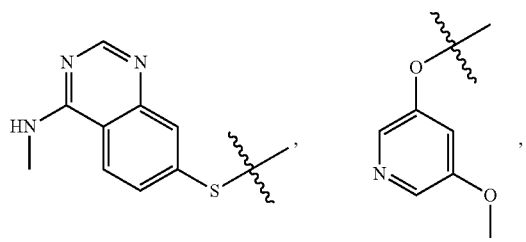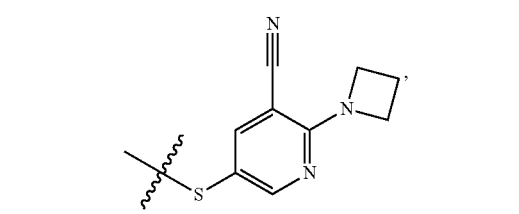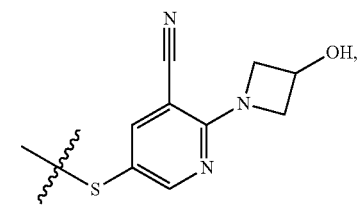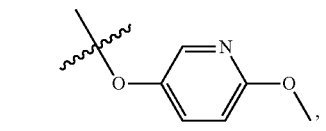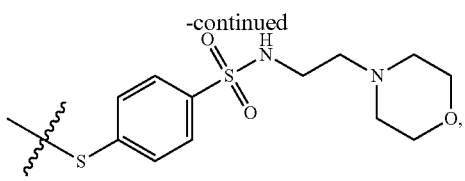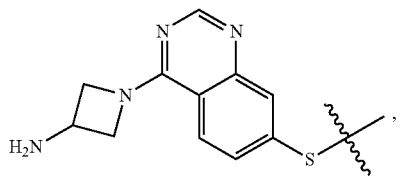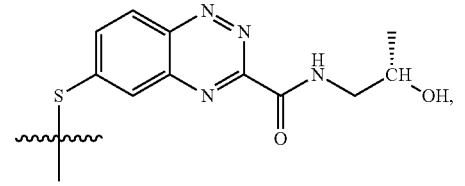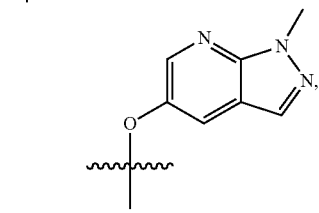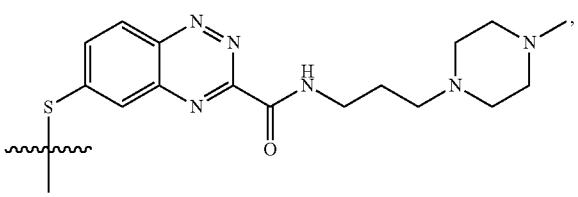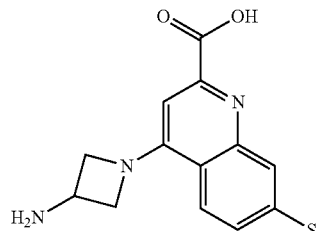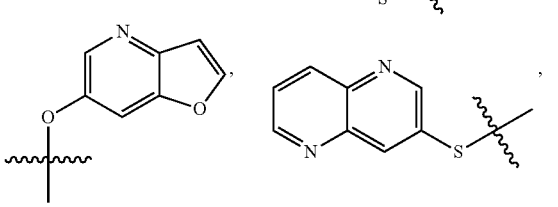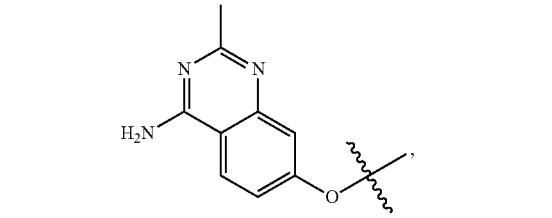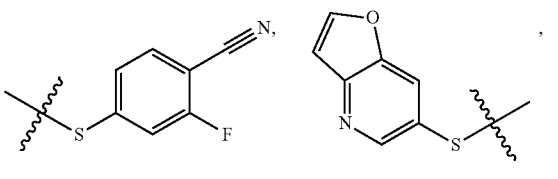

455
-continued
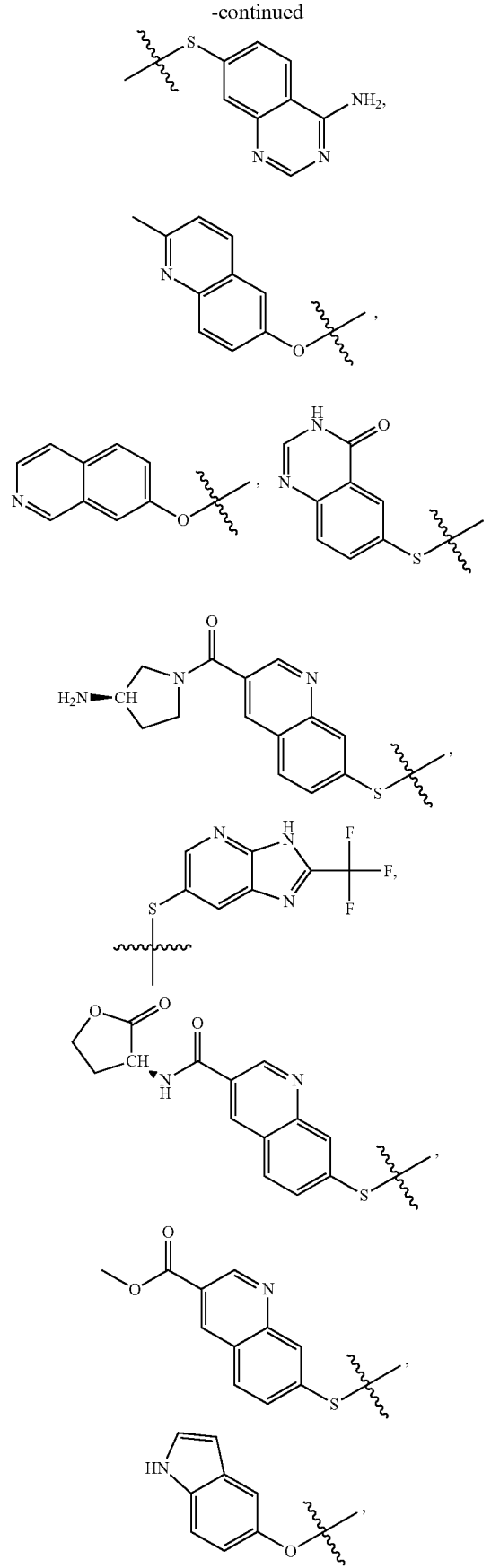
456
-continued
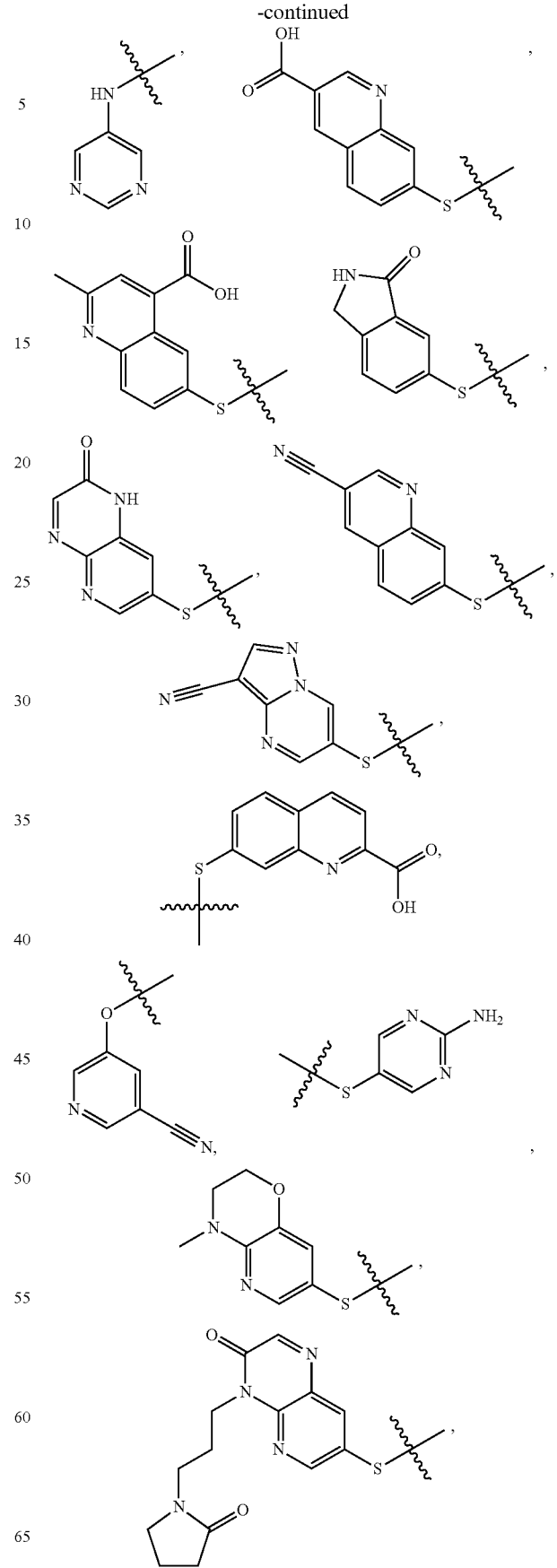

457
-continued
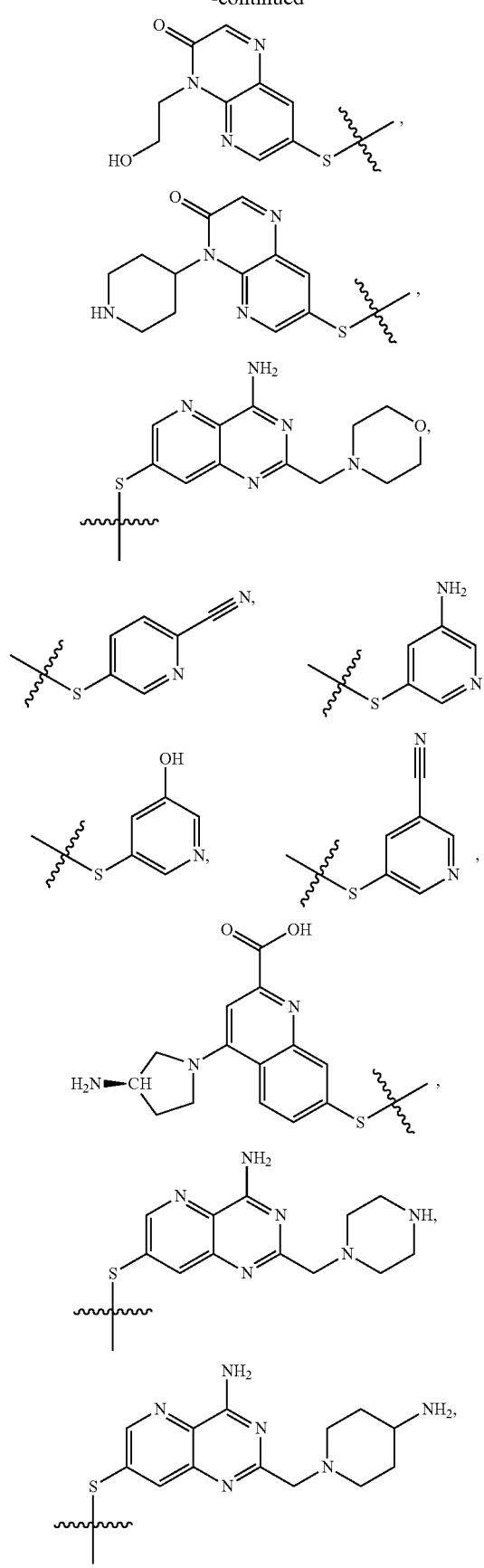
458
-continued
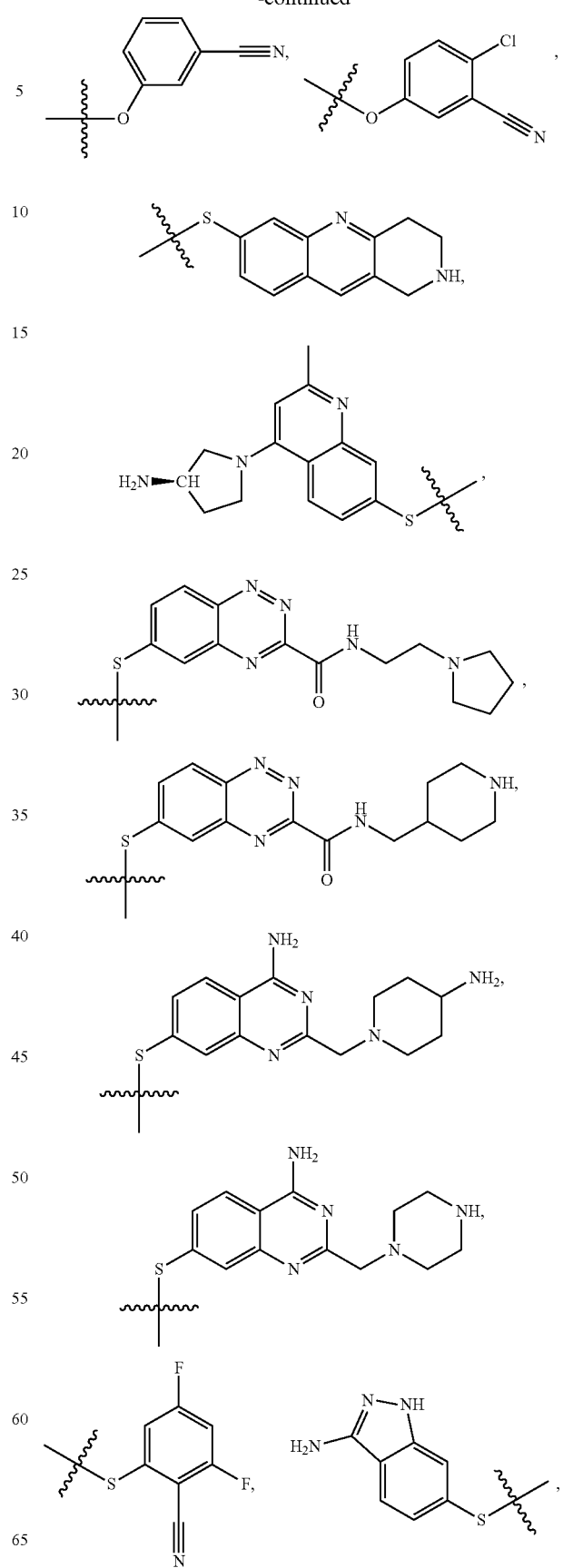

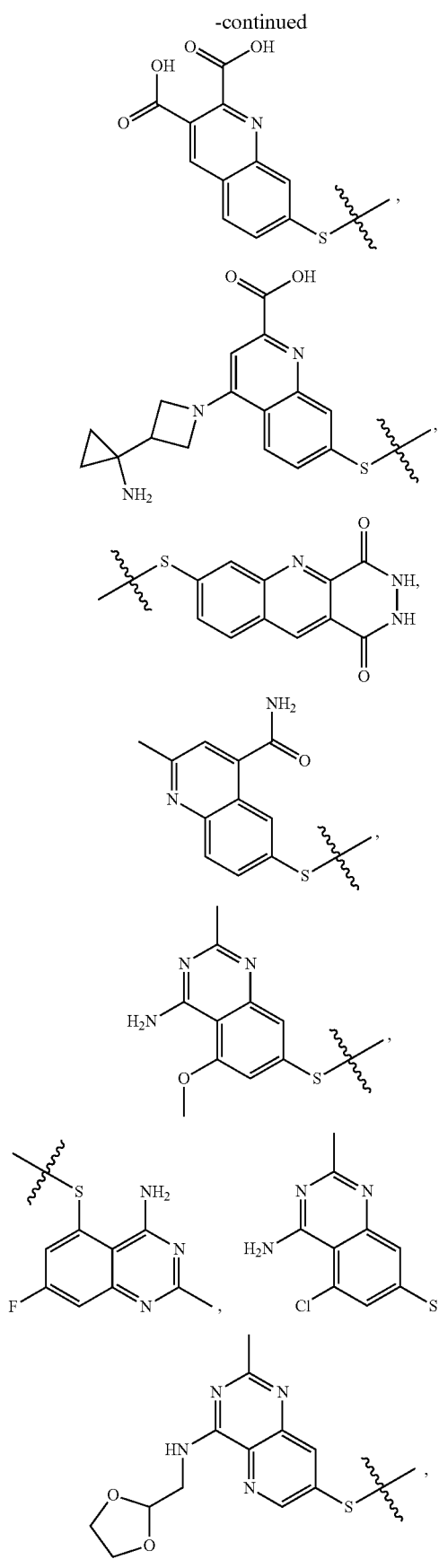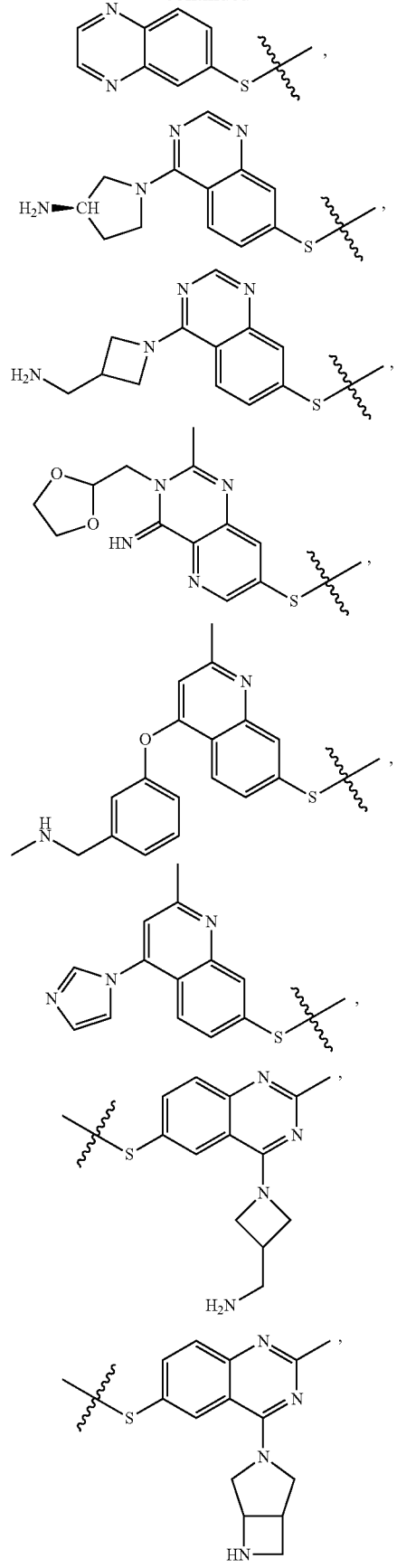

461
-continued
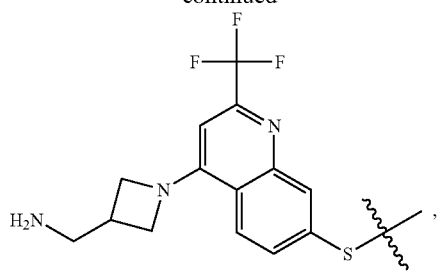
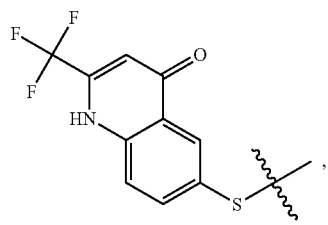
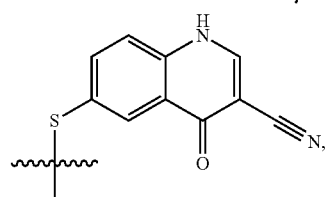
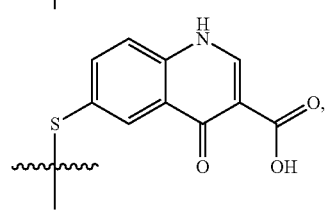
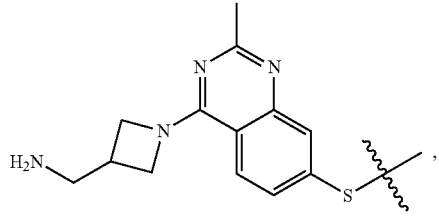
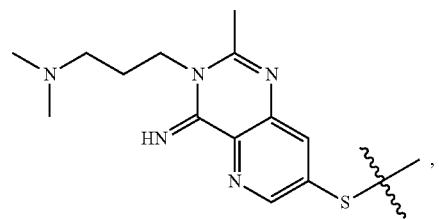
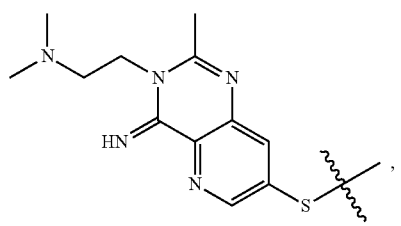
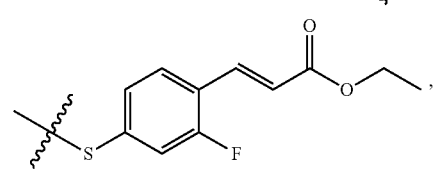
462
-continued
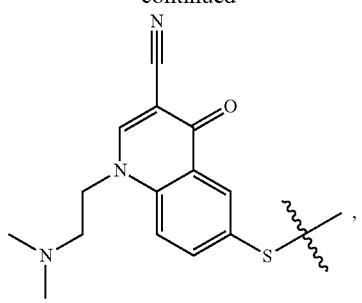
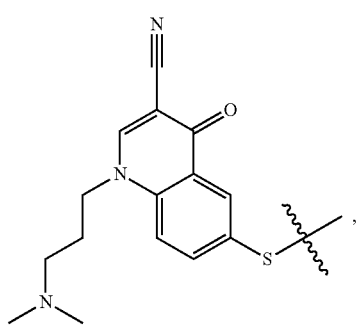
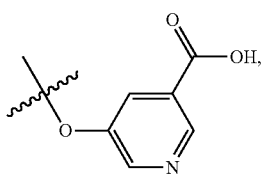
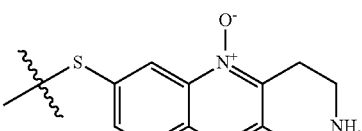
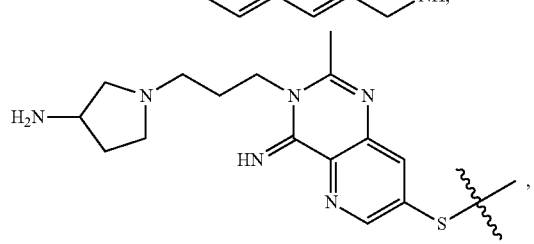
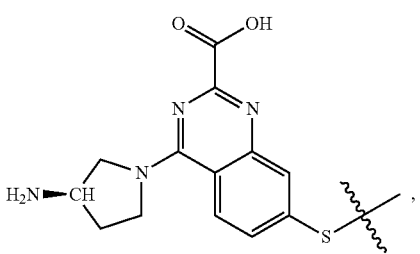
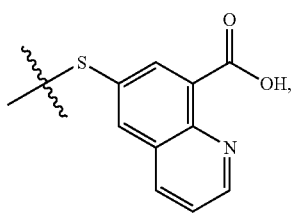

463
-continued
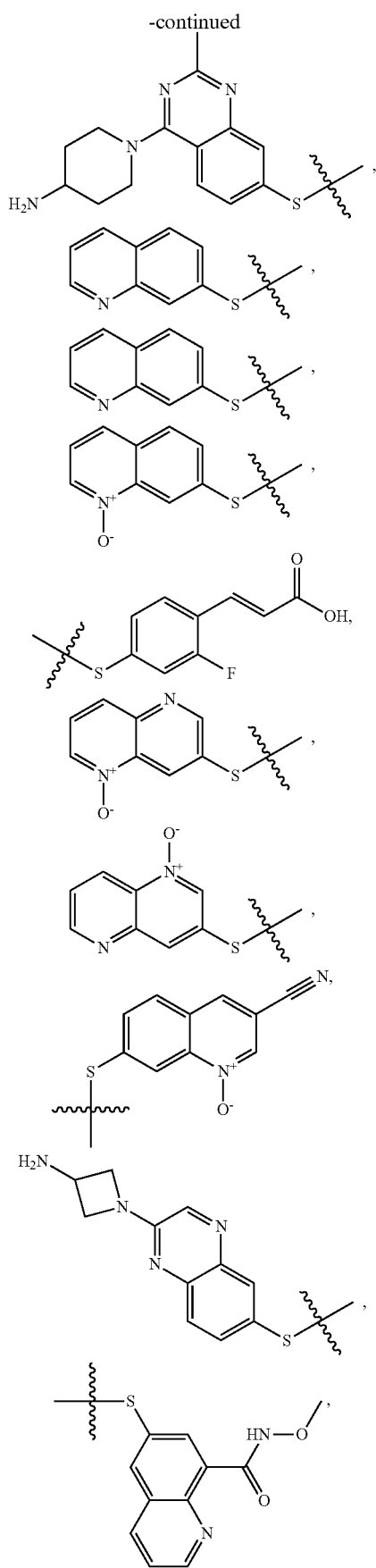
464
-continued
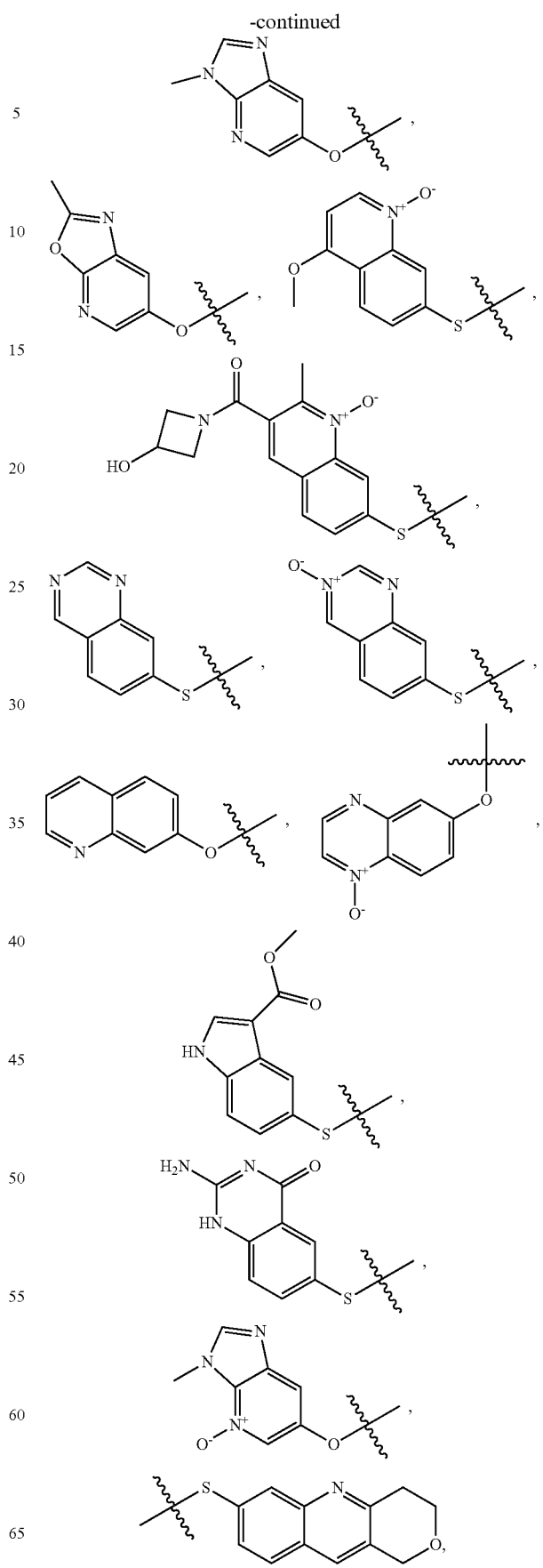

465
-continued
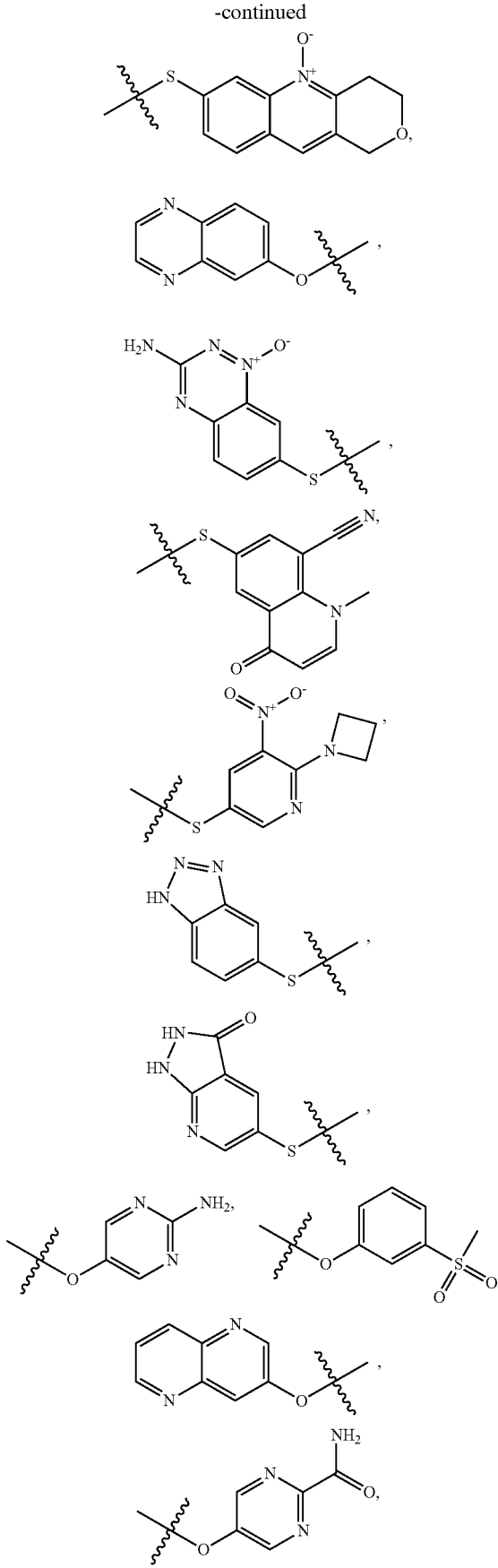
466
-continued
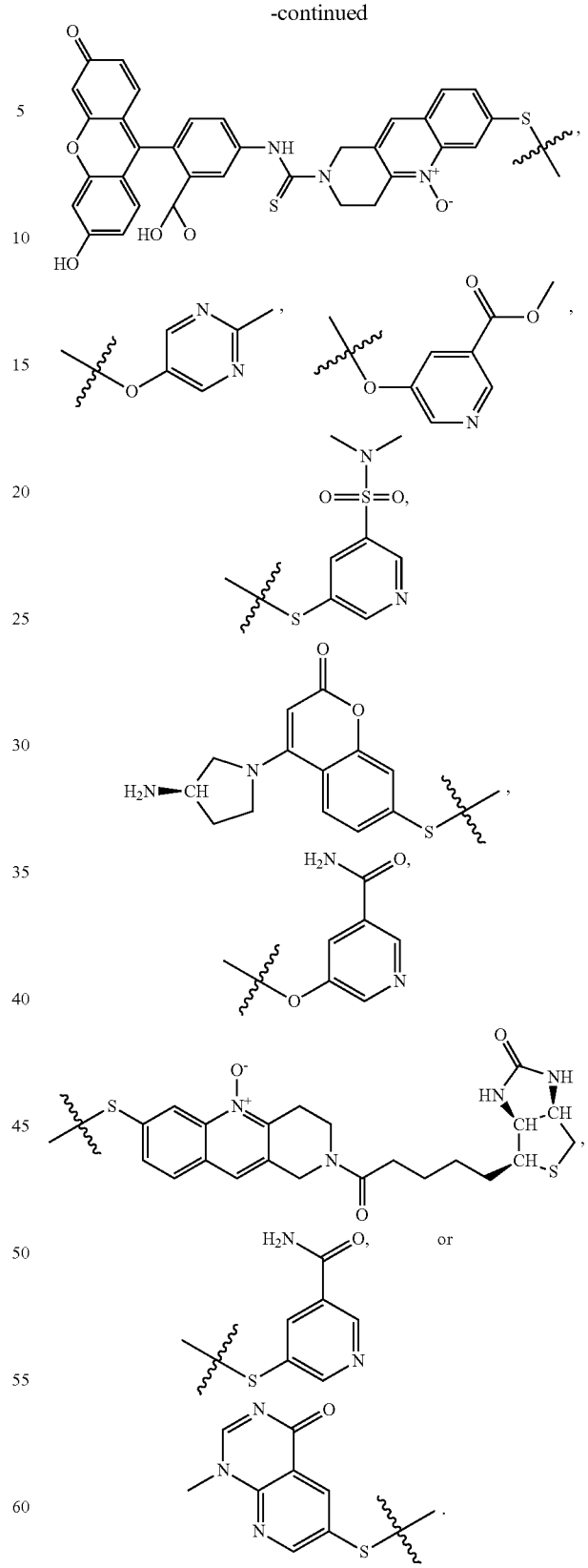
8. The compound of claim 1, or a pharmaceutically acceptable salt thereof, wherein $R^4$ is selected from the group consisting of 467
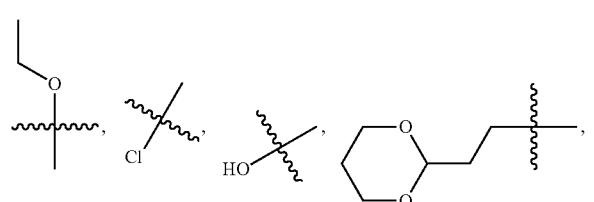
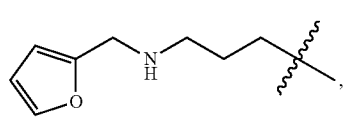
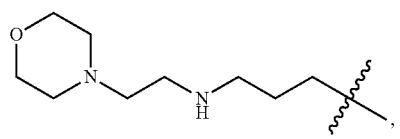
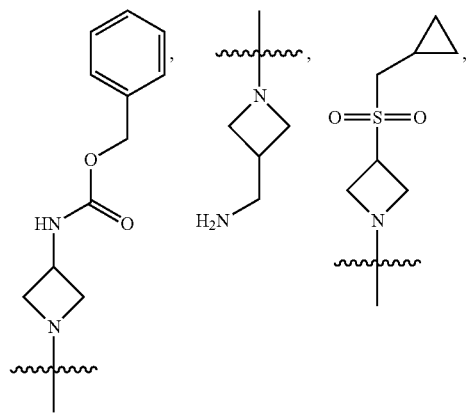
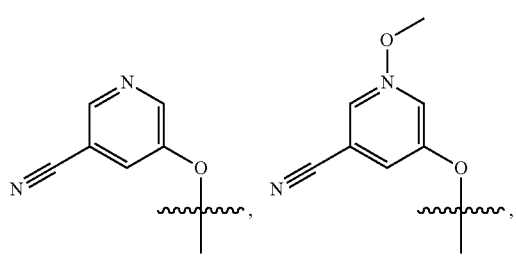
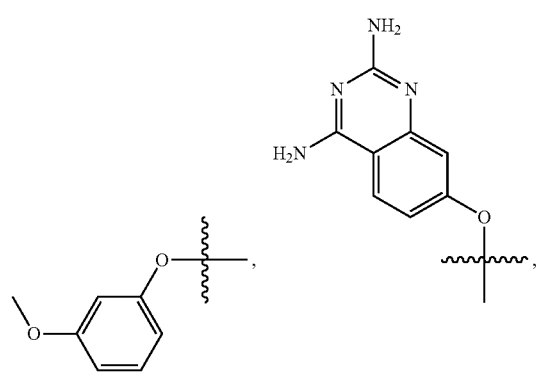
468
-continued
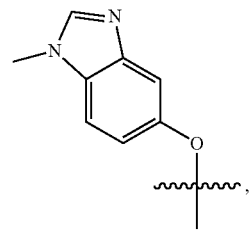
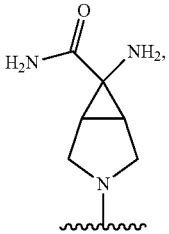
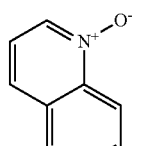
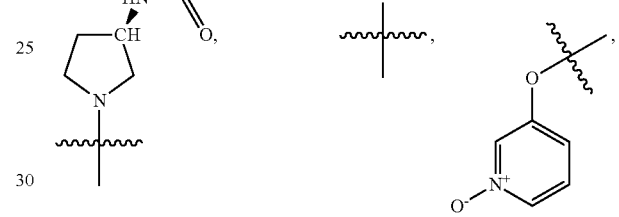
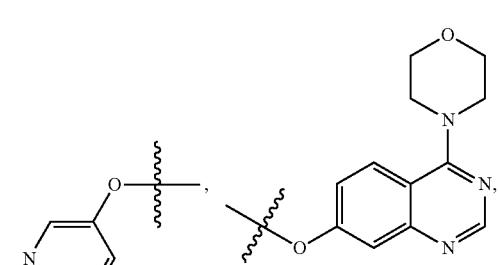

469
-continued
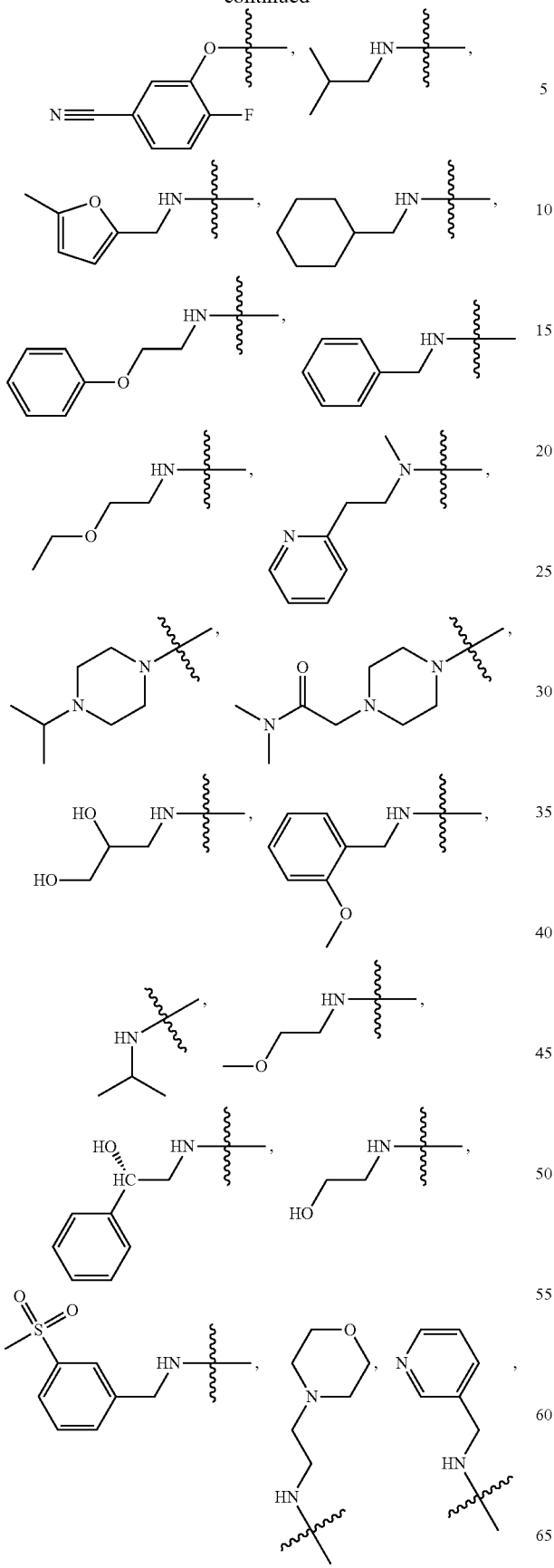
470
-continued
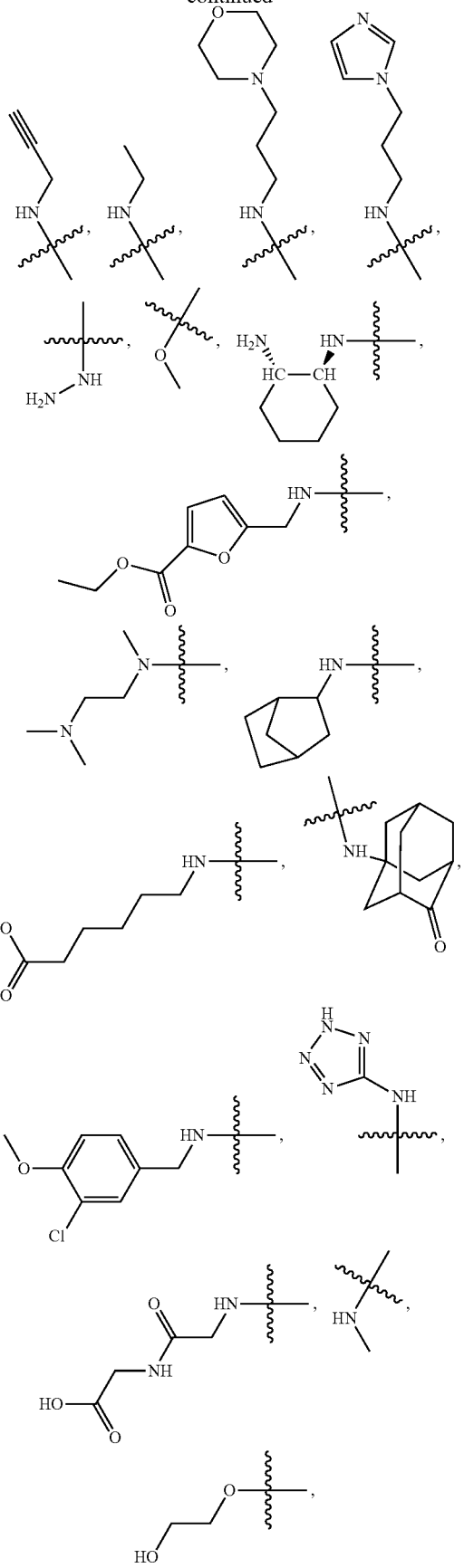

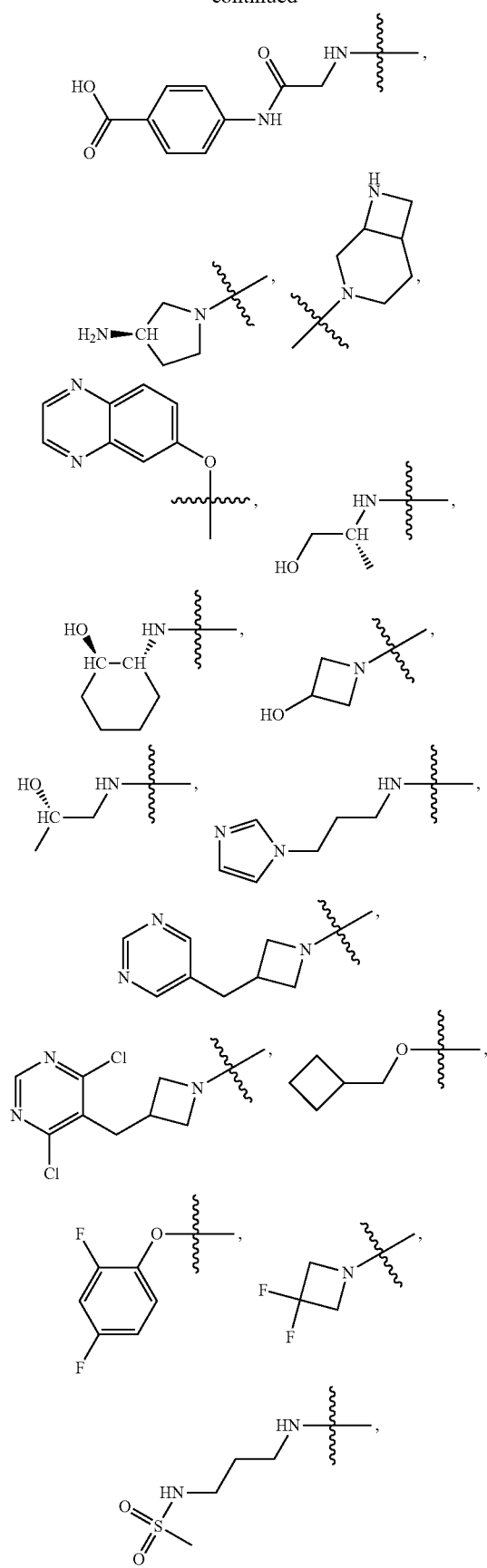
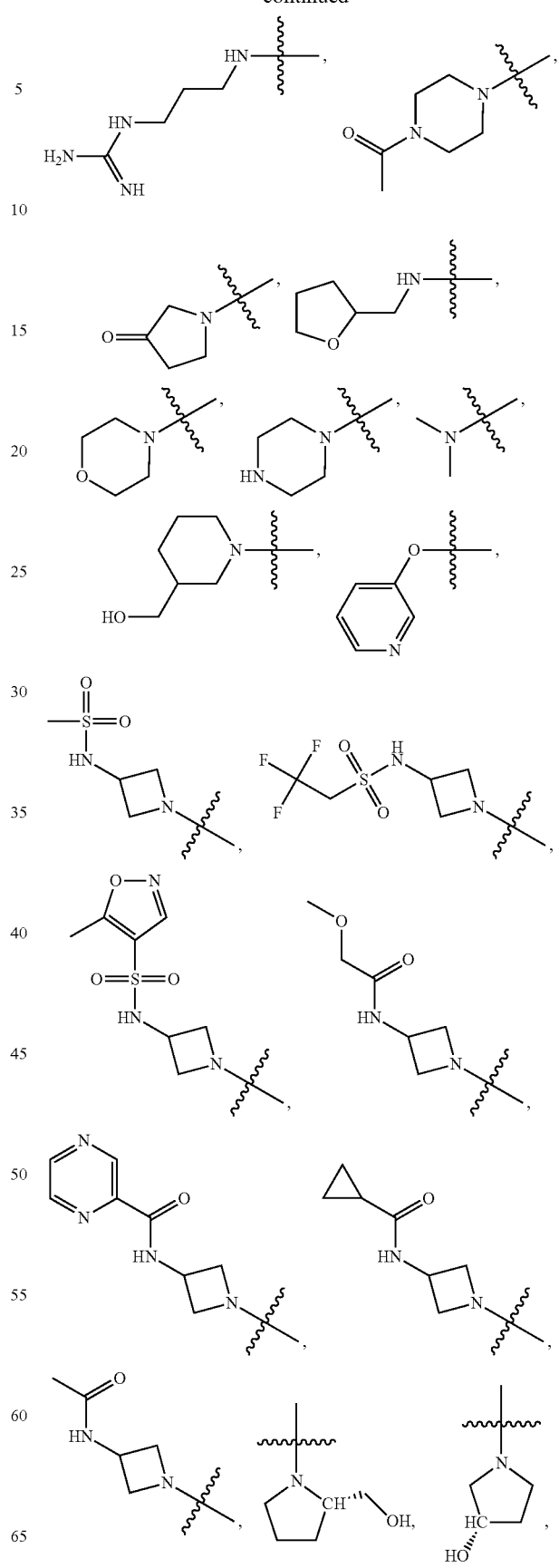

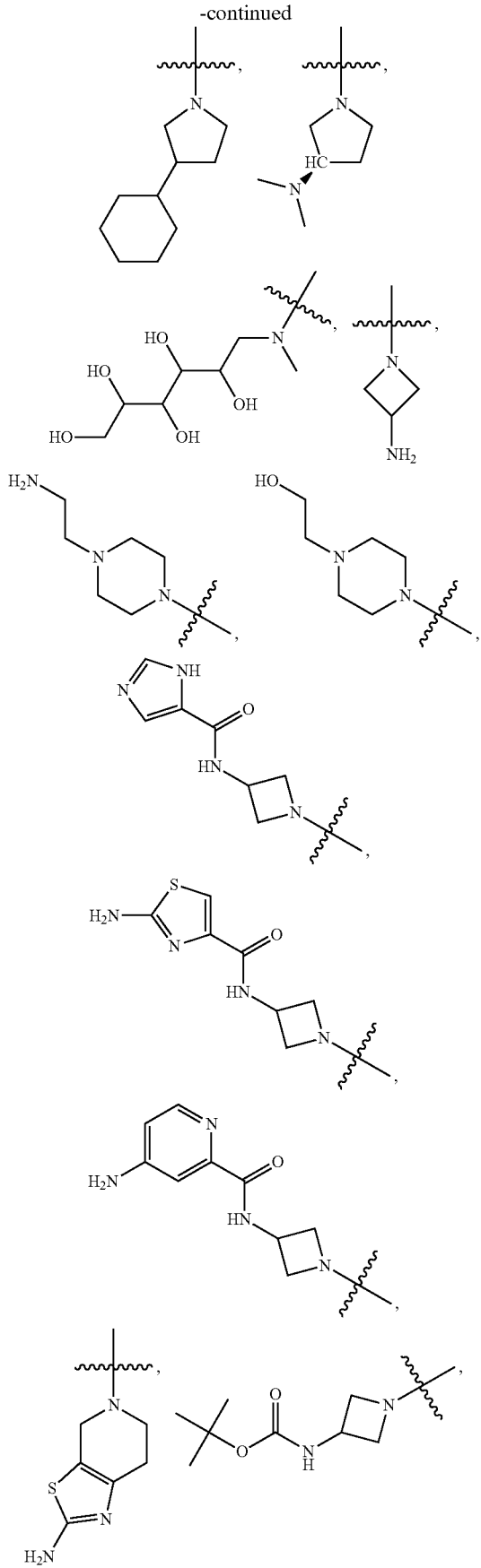
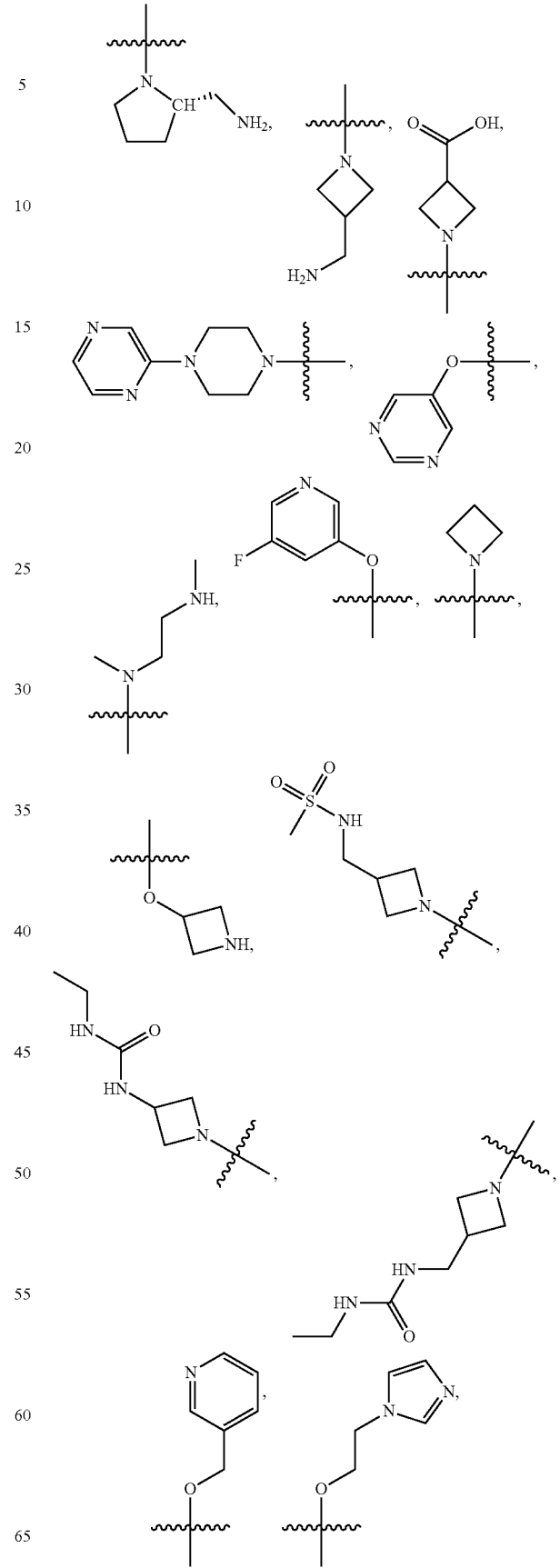

475
-continued
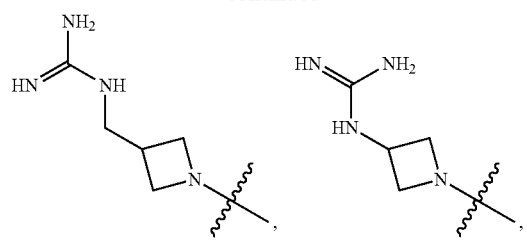
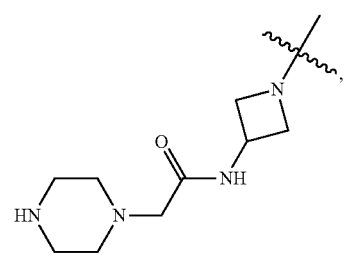
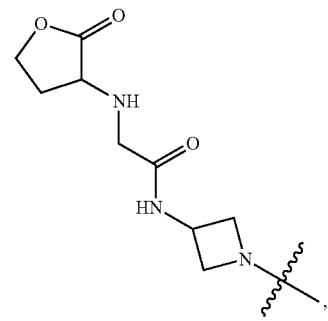
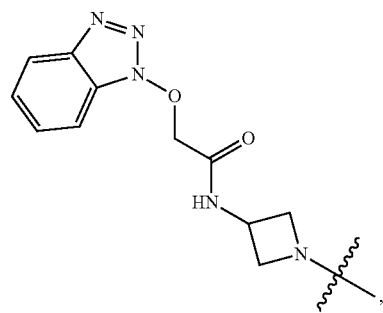
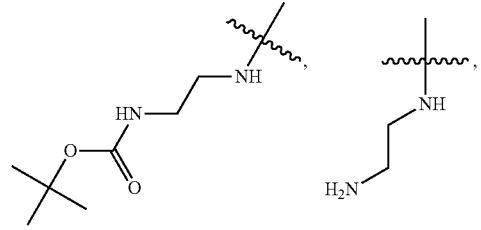
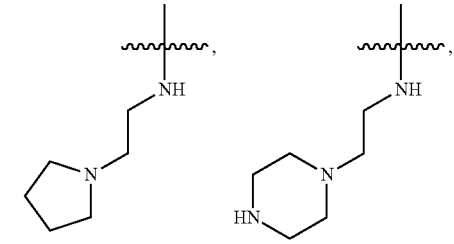
476
-continued
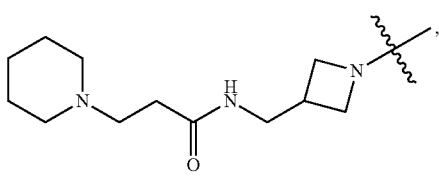
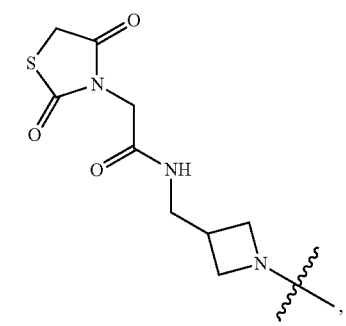
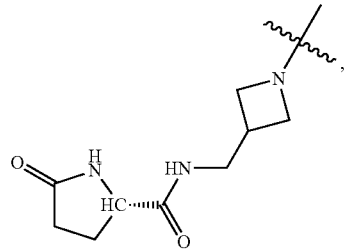
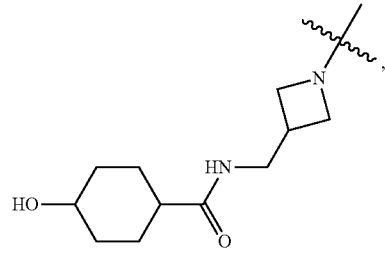

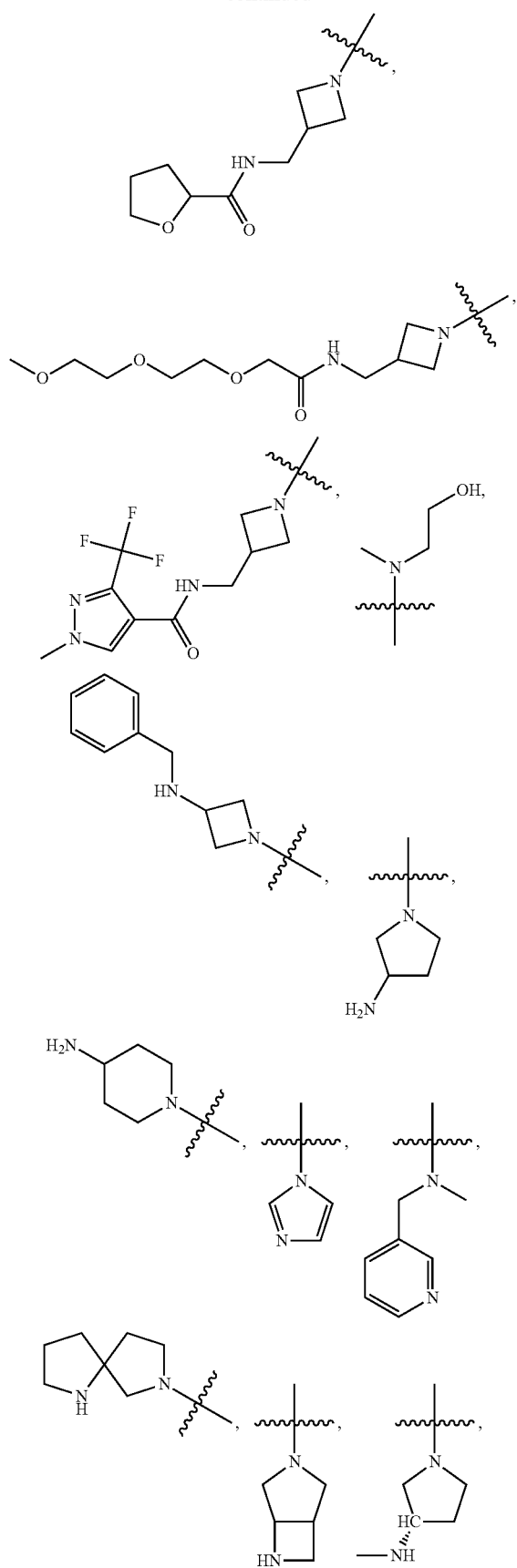
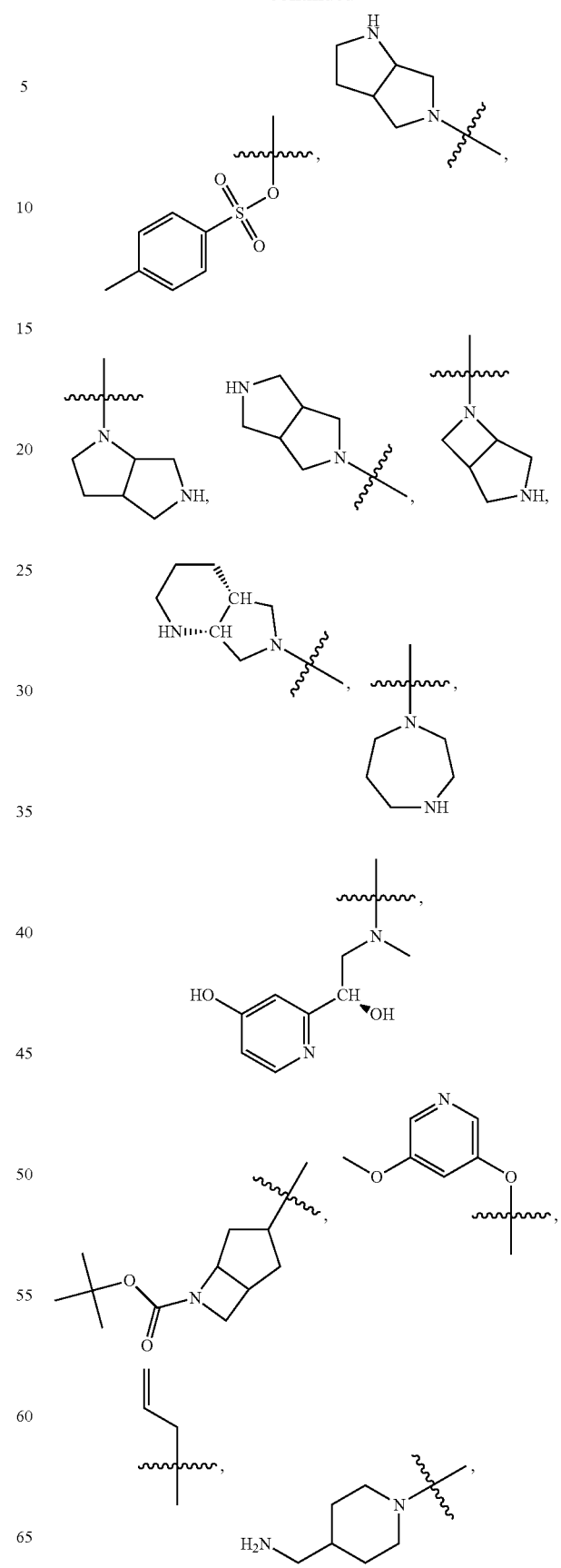

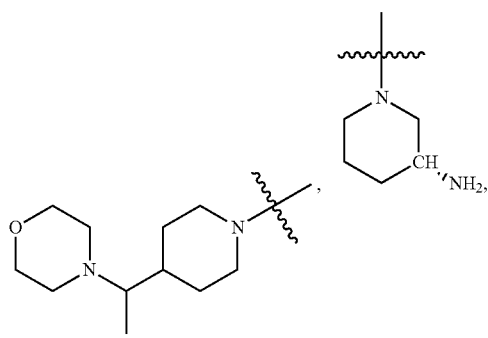
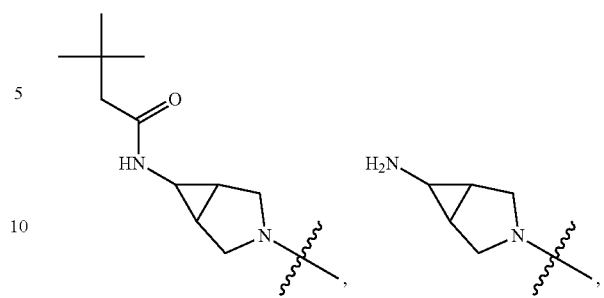
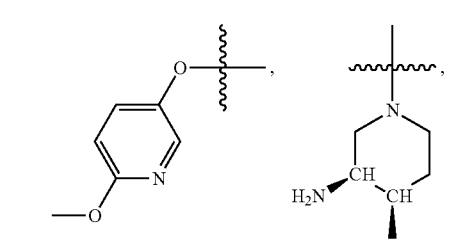
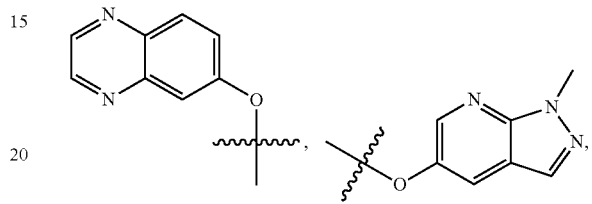
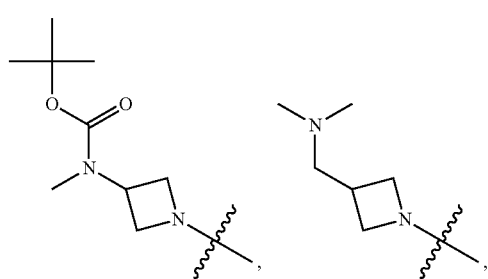
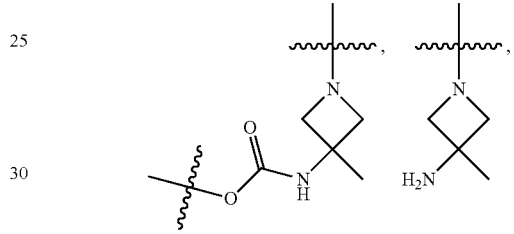
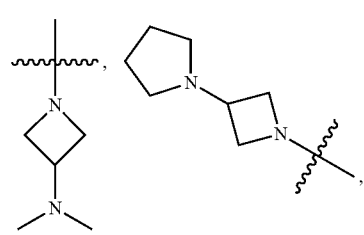
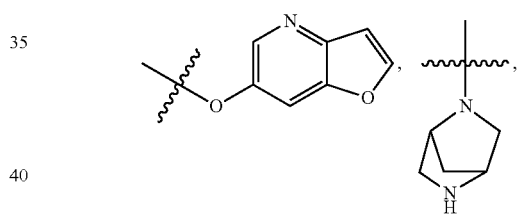
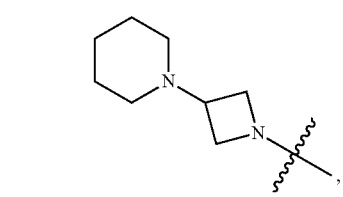
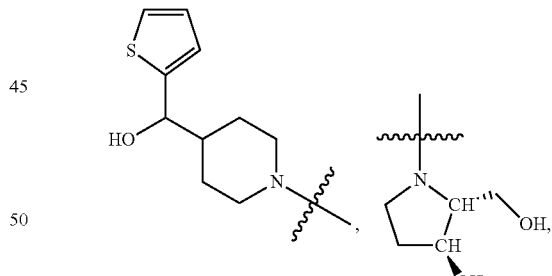
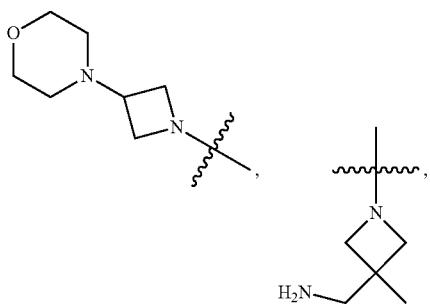
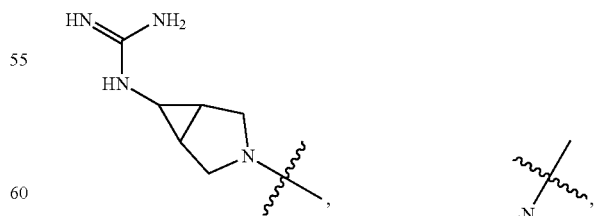

481
-continued
482
-continued
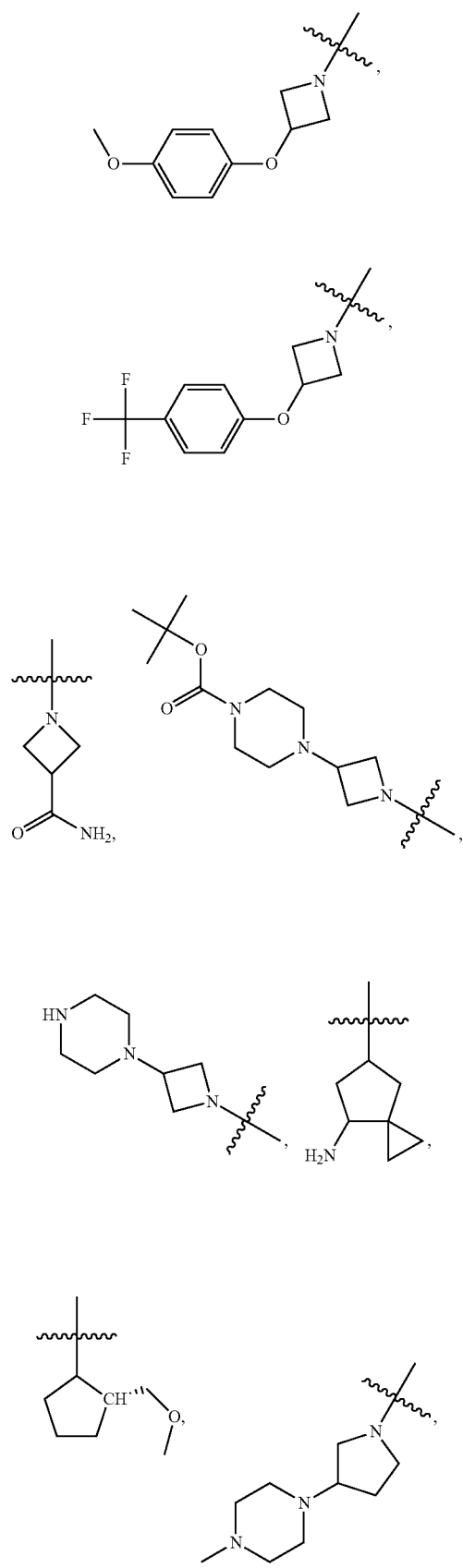
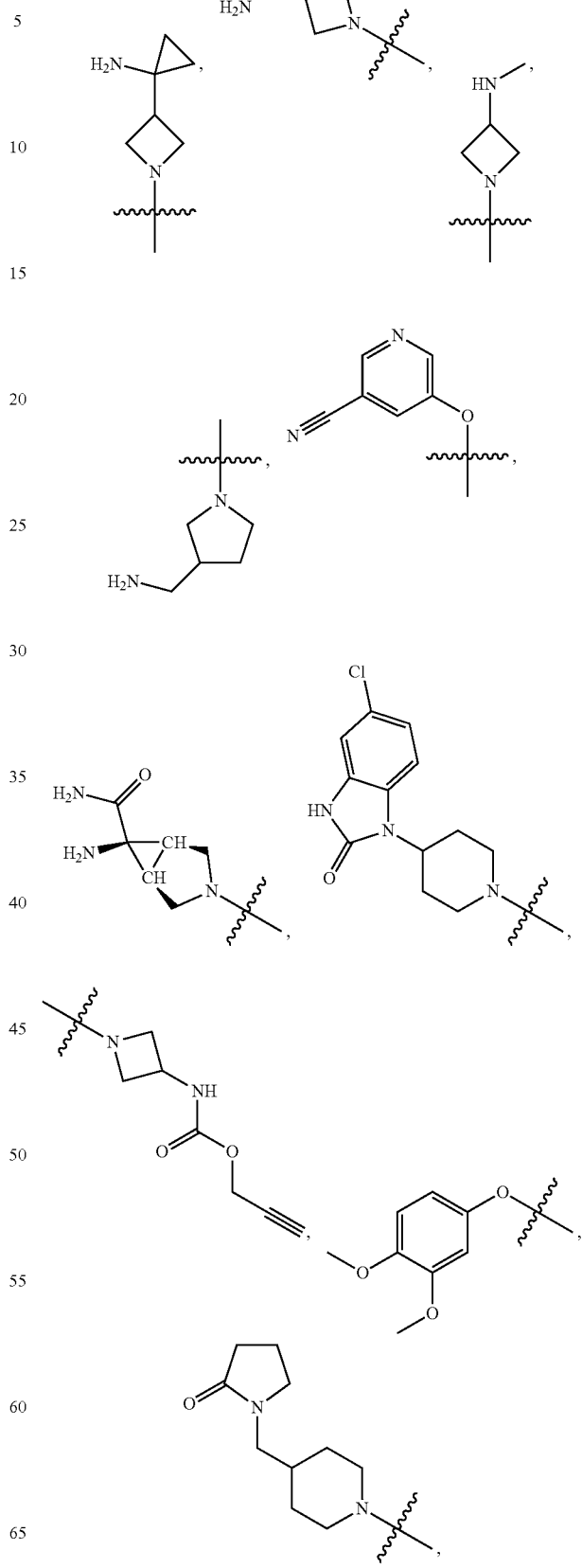

483
-continued
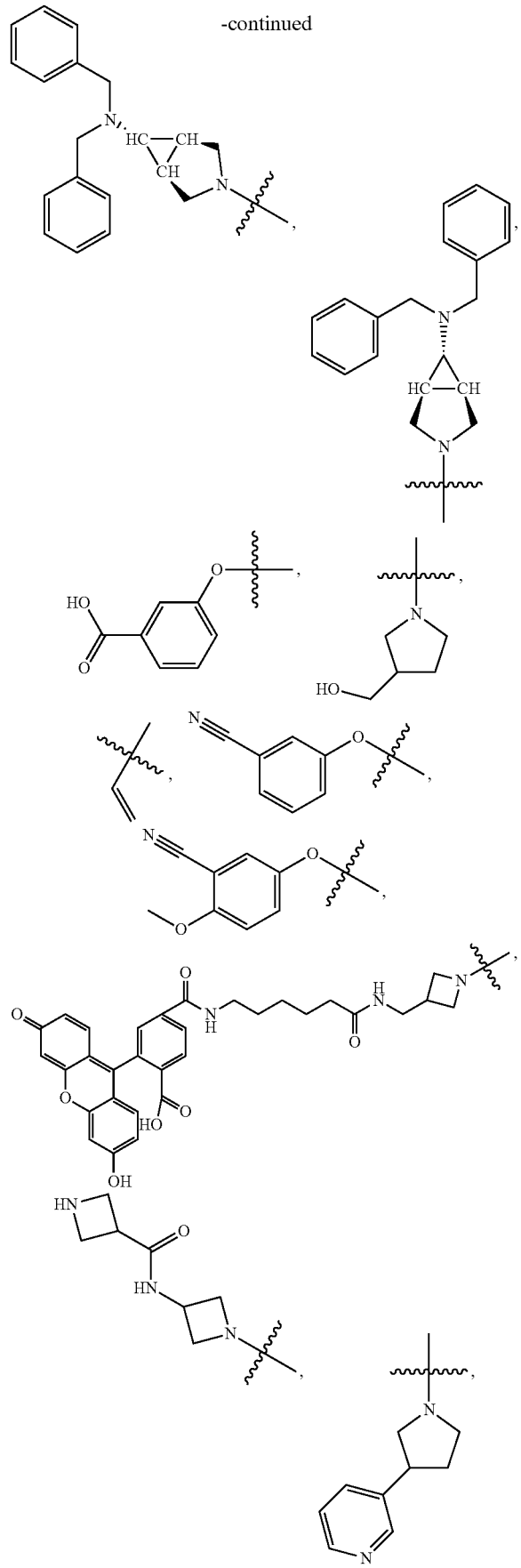
484
-continued
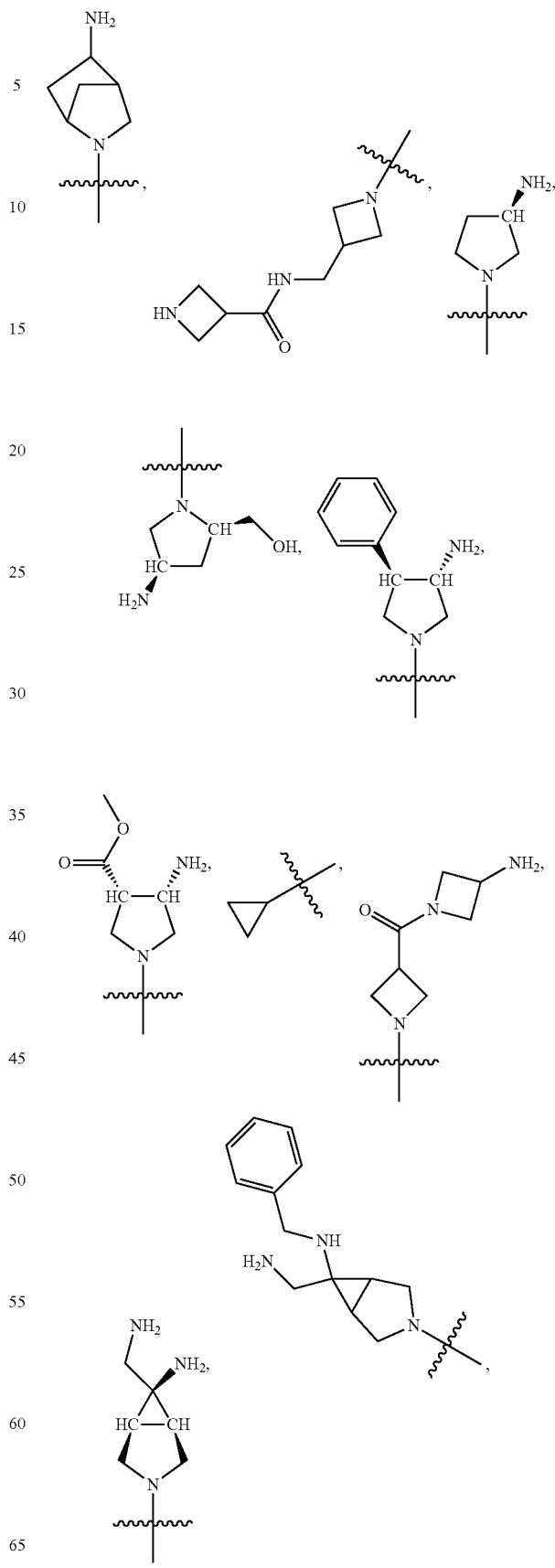

-continued
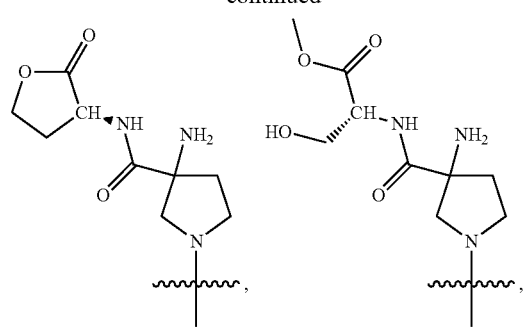
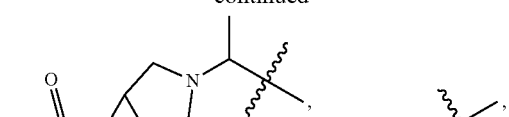
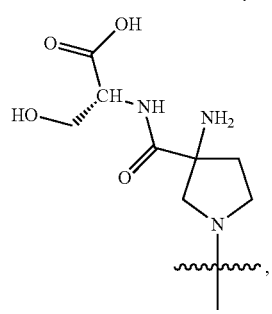
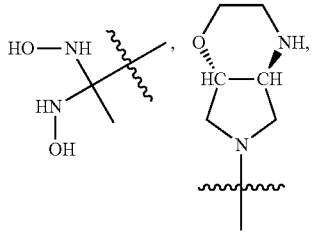
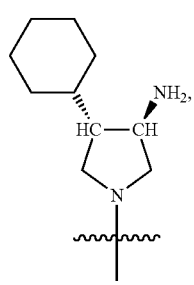
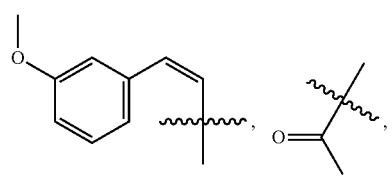
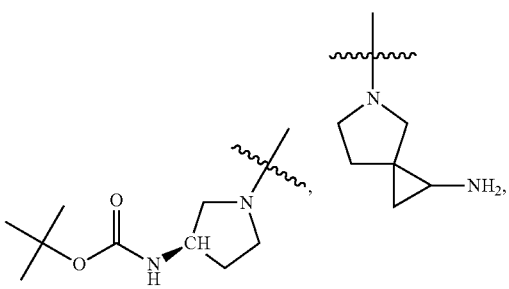
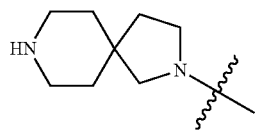
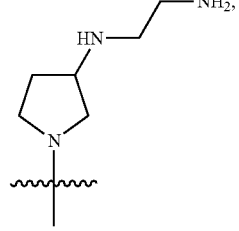
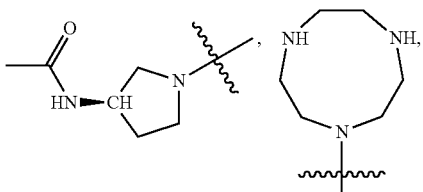
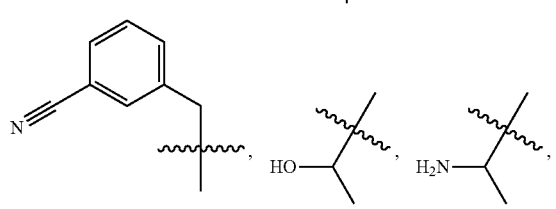
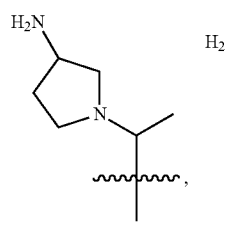
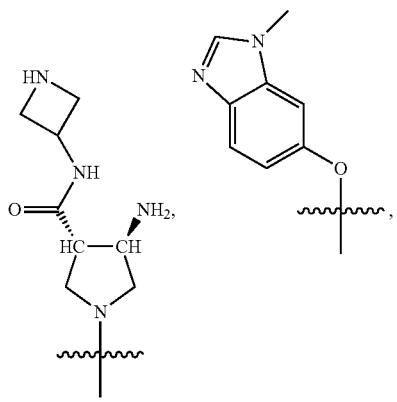

487
-continued
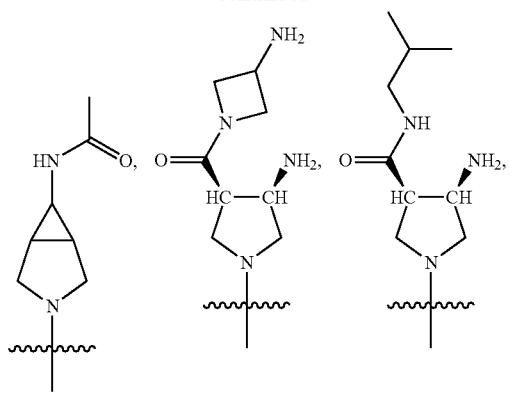
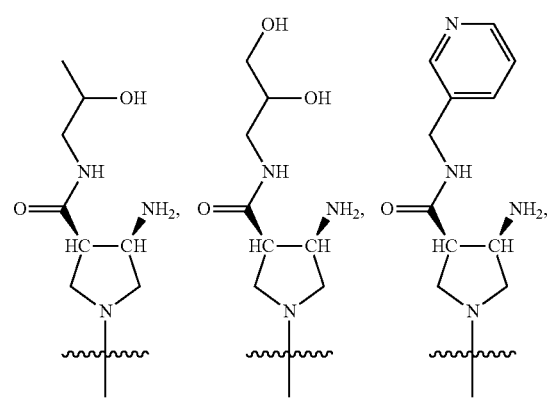
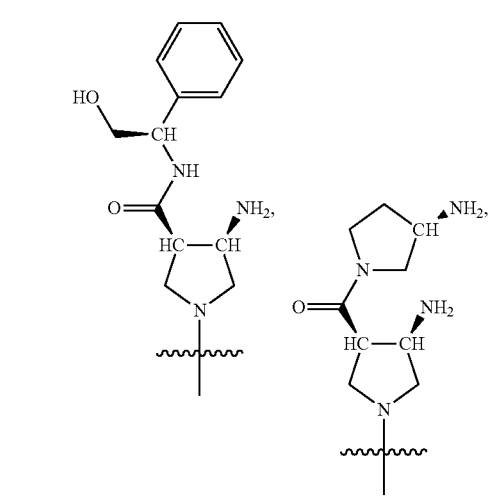
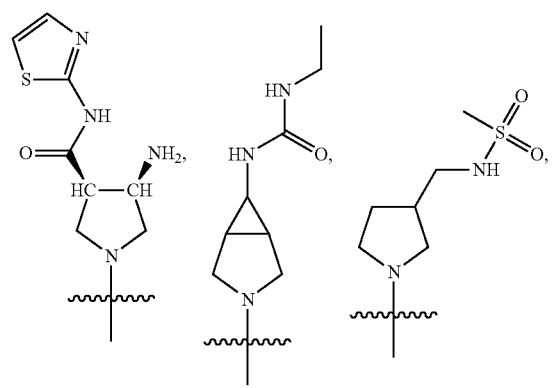
488
-continued
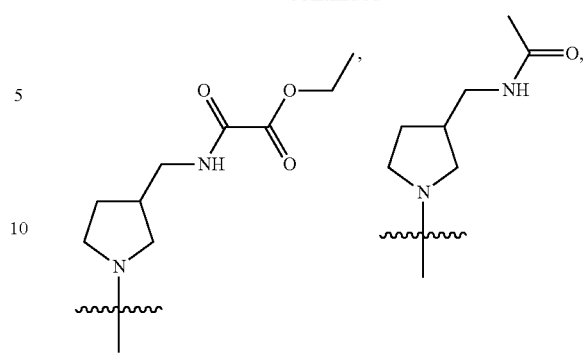
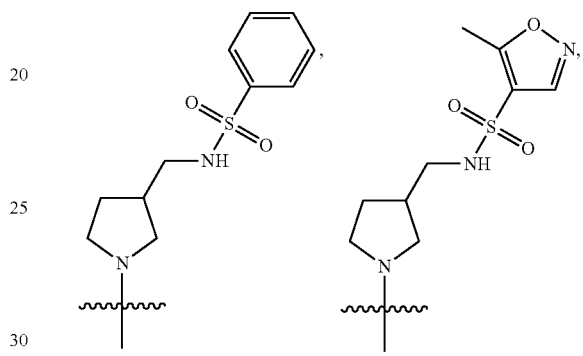
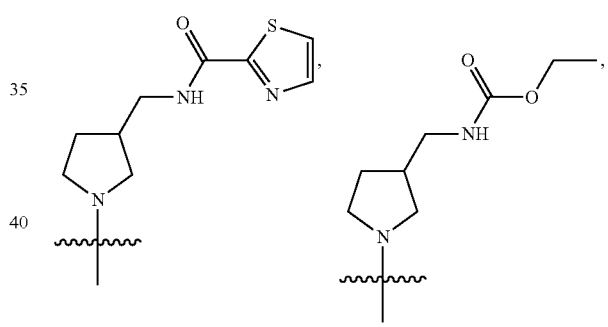
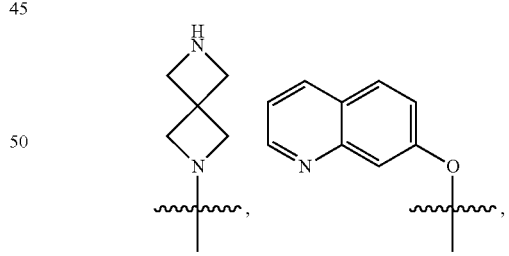
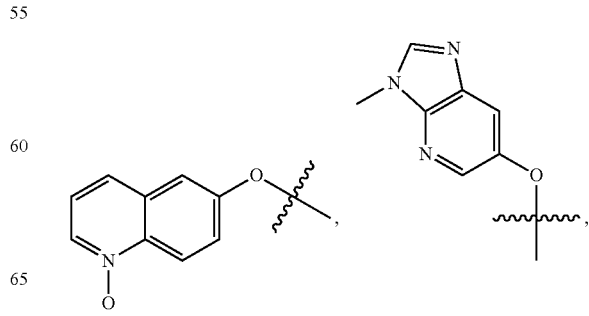

489
-continued
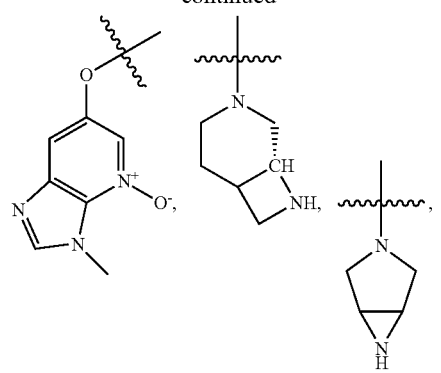
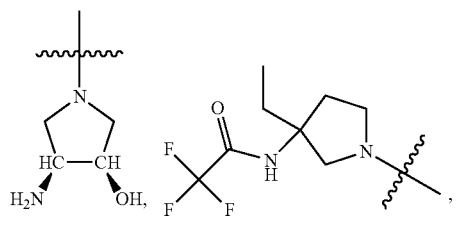
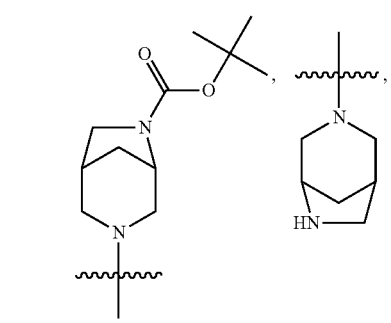
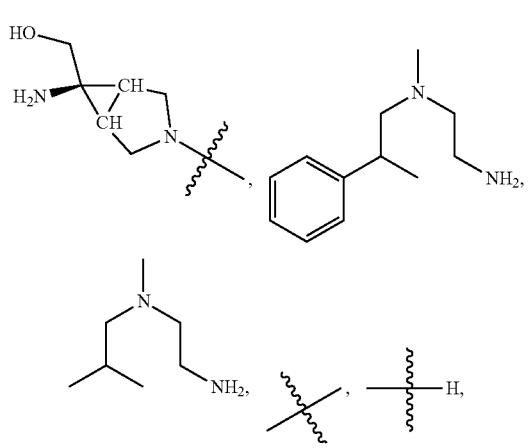
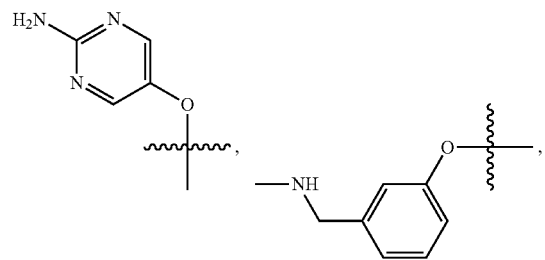
490
-continued
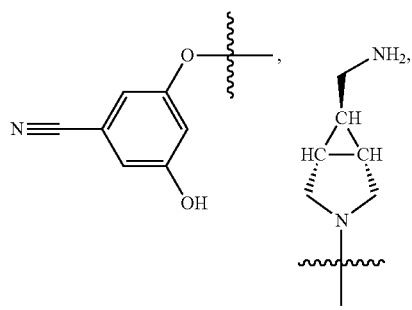
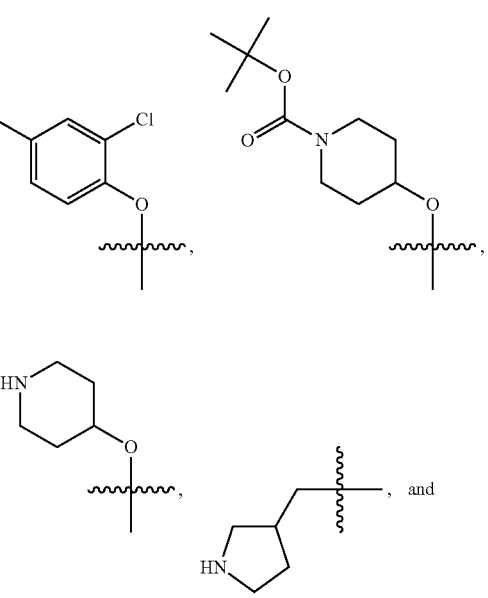
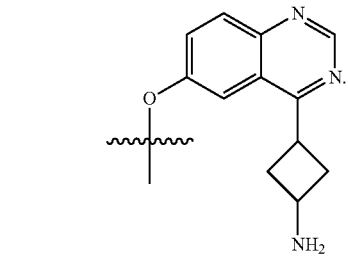
9. The compound of claim 1, or a pharmaceutically acceptable salt thereof, wherein $R^4$ is
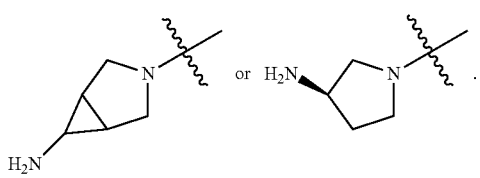 [SMILES: *N1CC2C(N)C2C1 ; *N1CC[C@@H](N)C1]

10. A compound which is
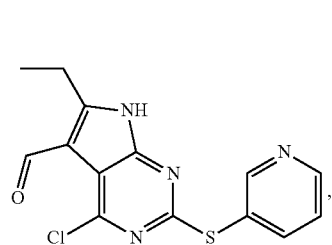 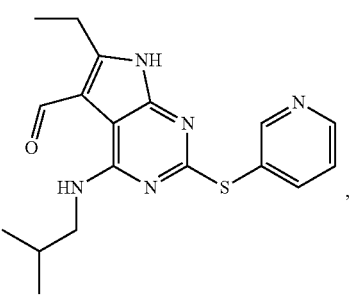 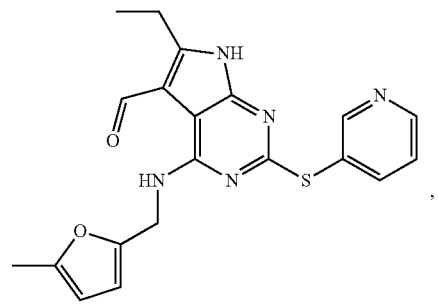
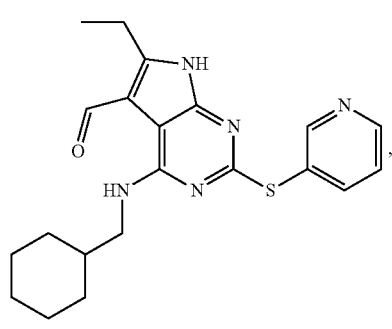 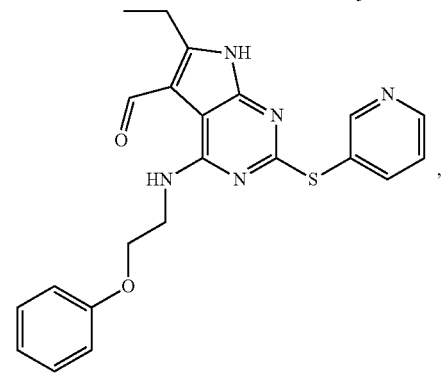
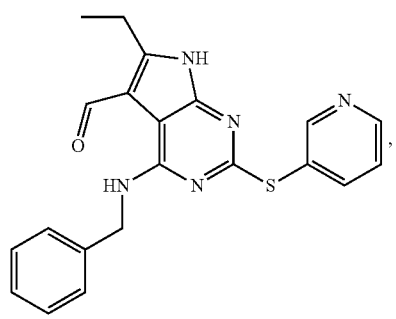 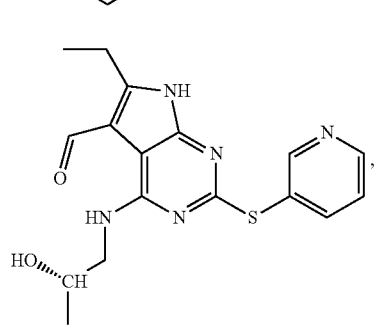 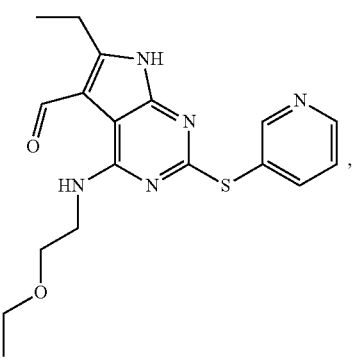
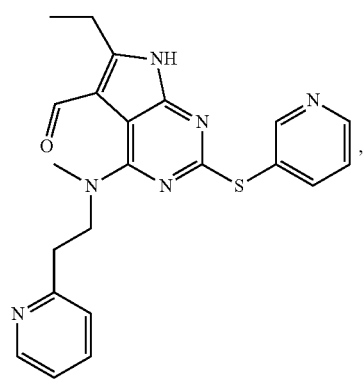 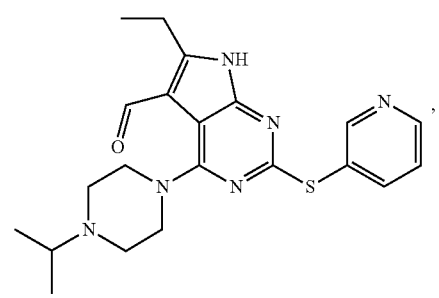
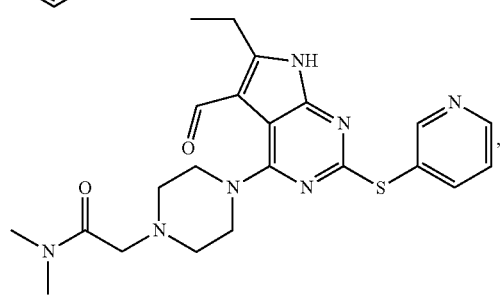 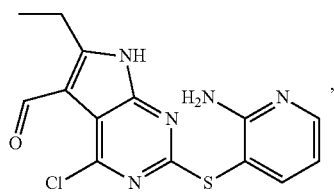

493
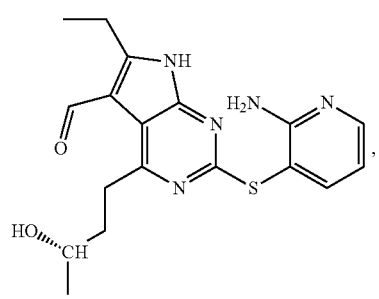,
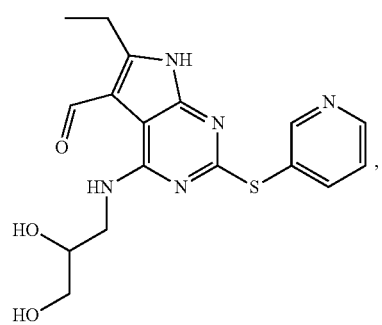,
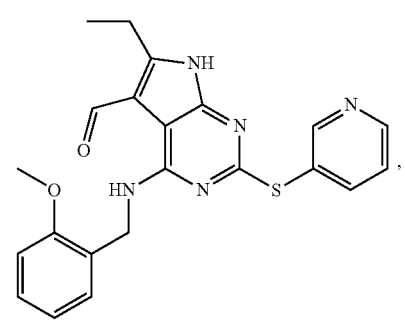,
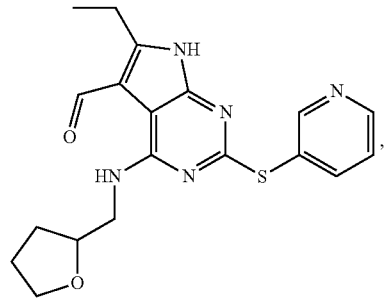,
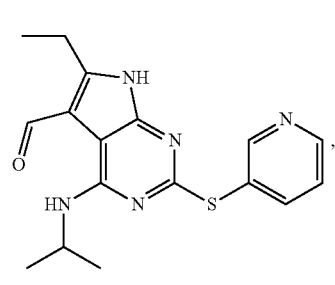,
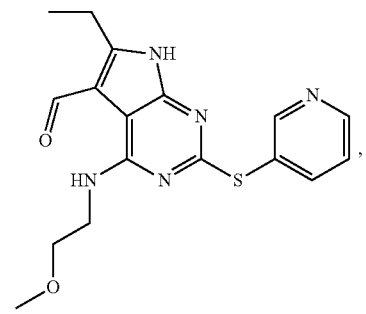,
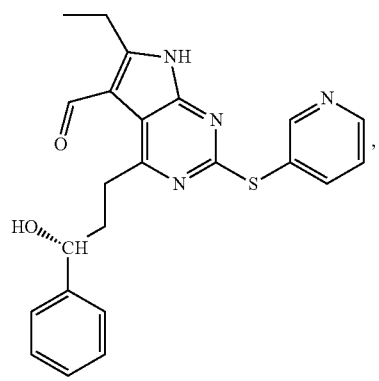,
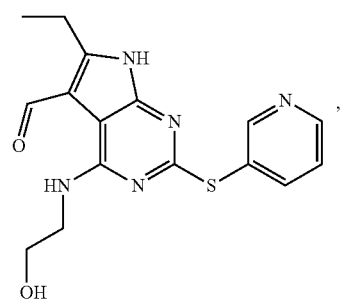,
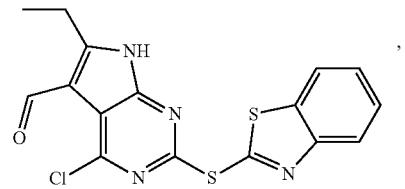,
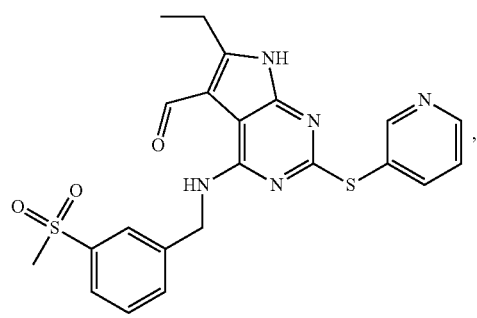,
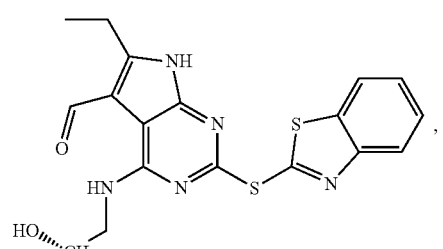,
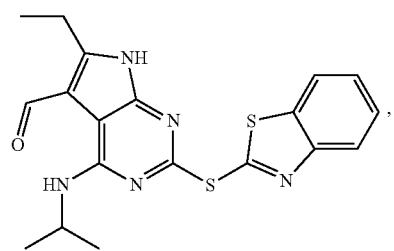,
494

495
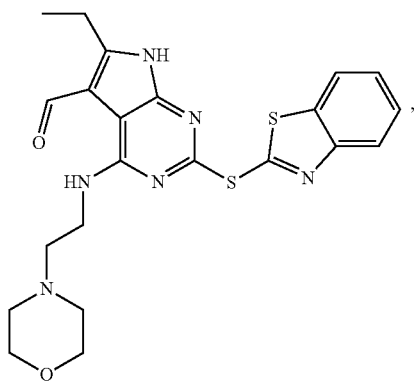
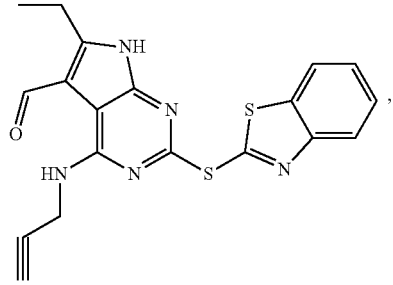
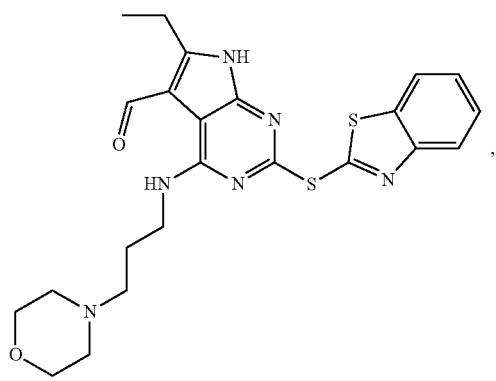
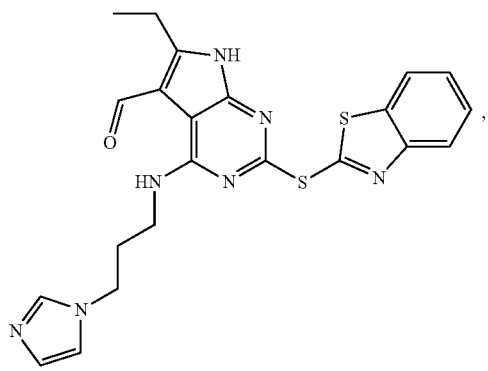
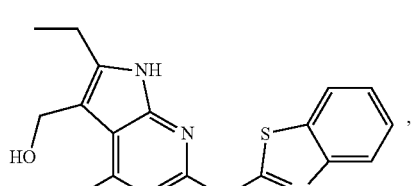
496
-continued
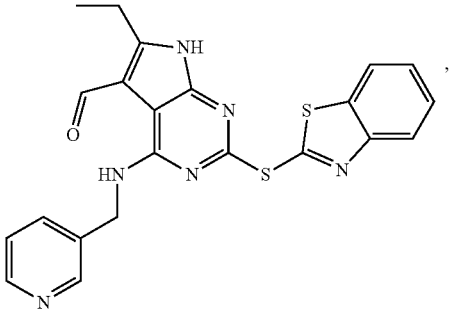
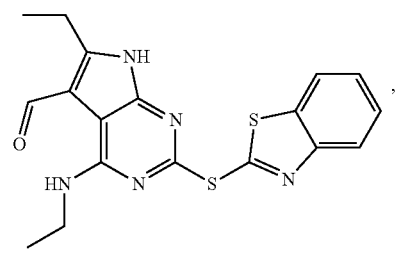
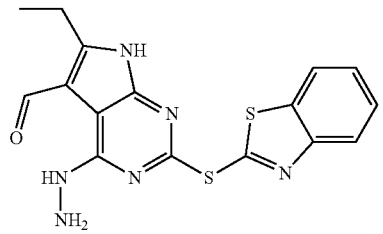
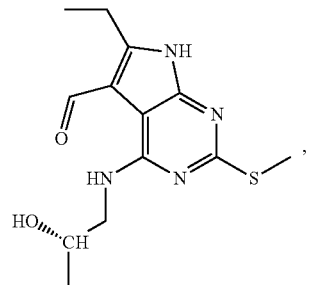
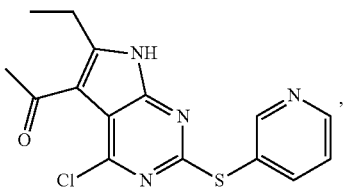

497
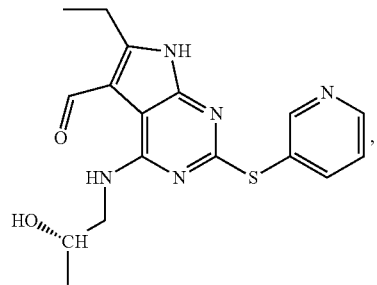
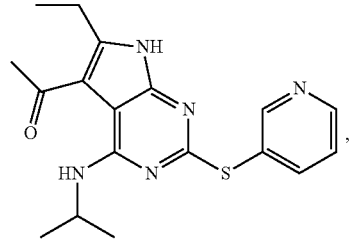
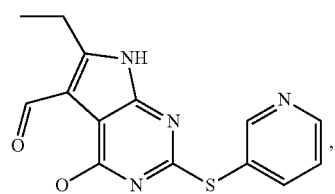
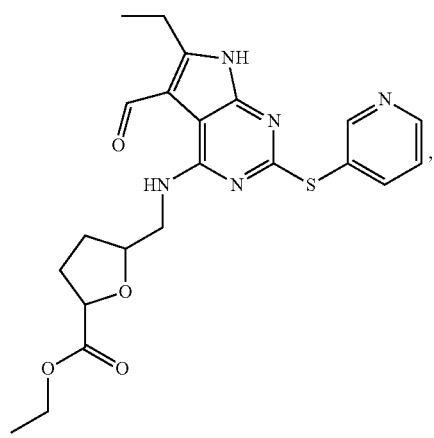
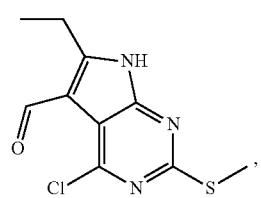
498
-continued
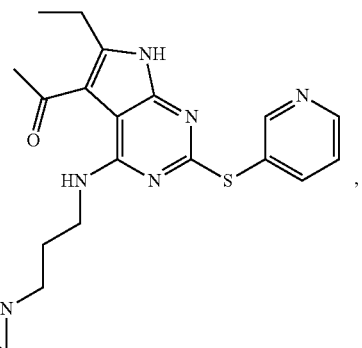
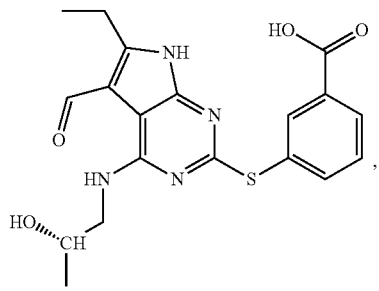
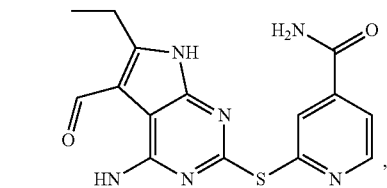
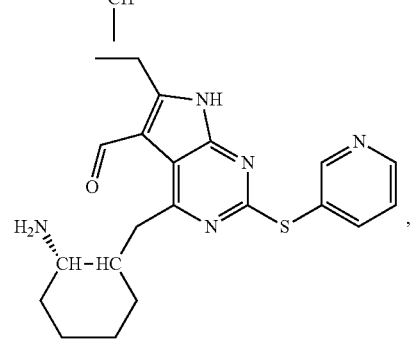
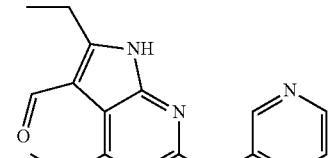
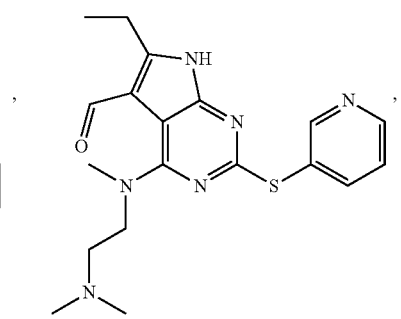
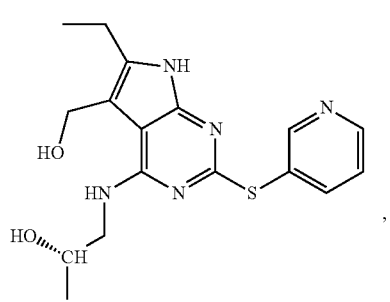
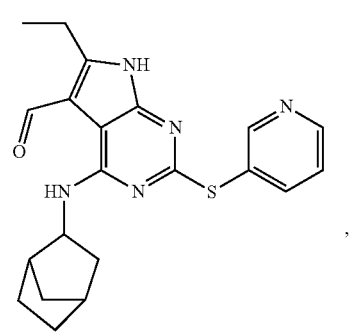

-continued
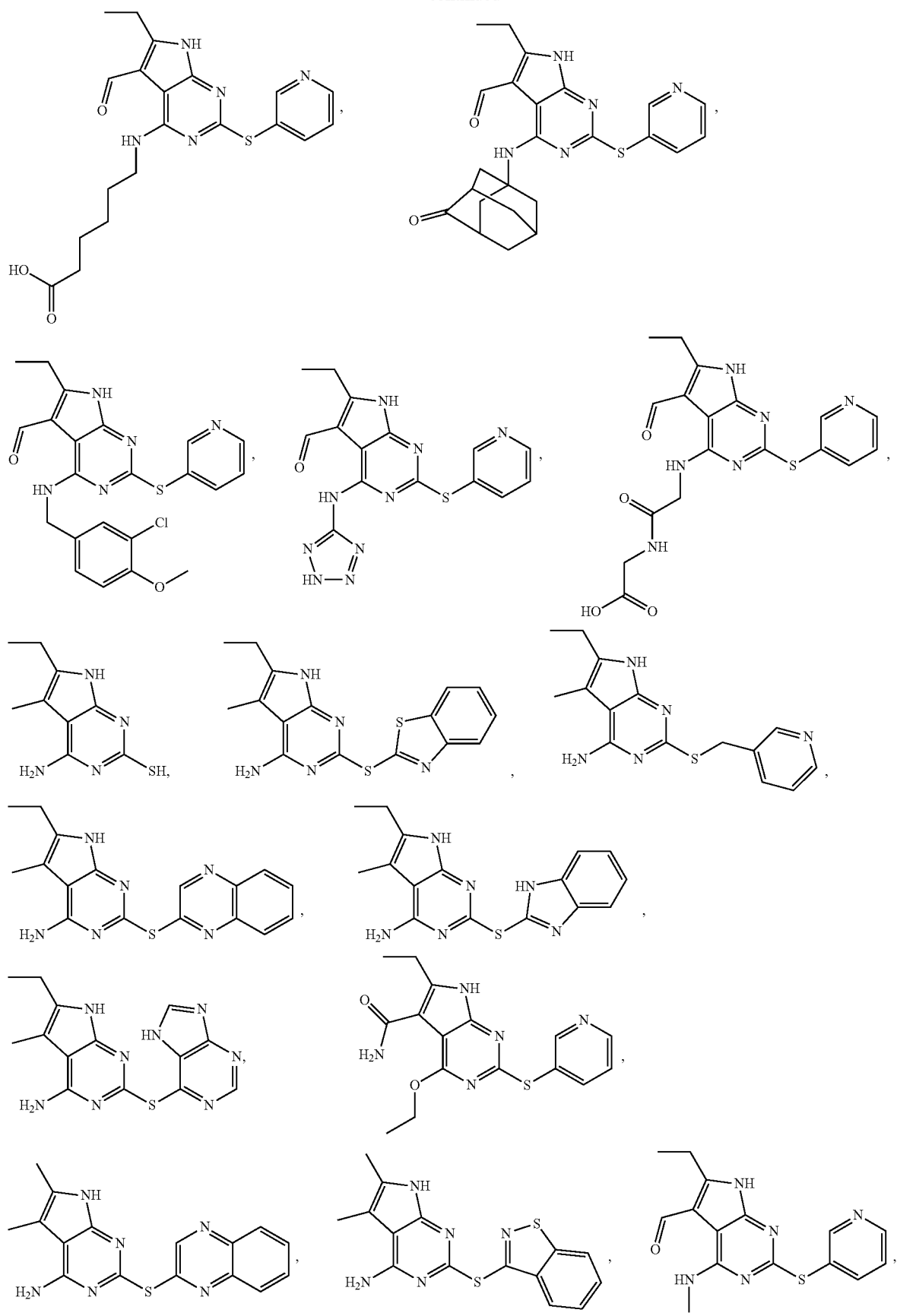

501
-continued
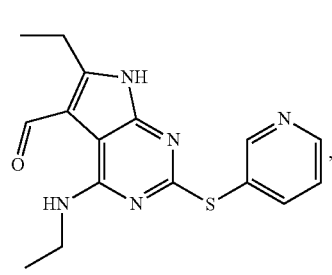, 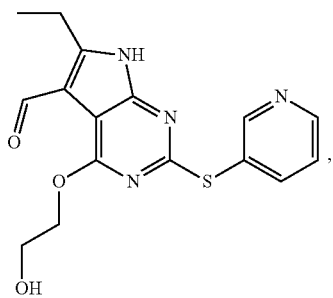, 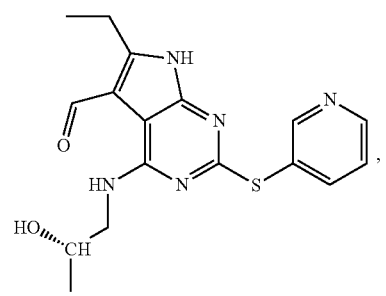,
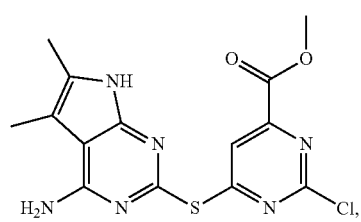, 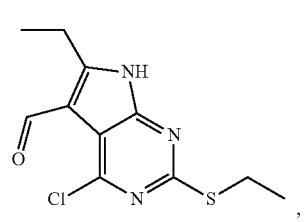, 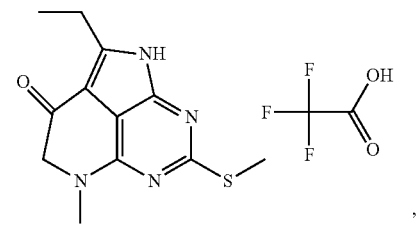,
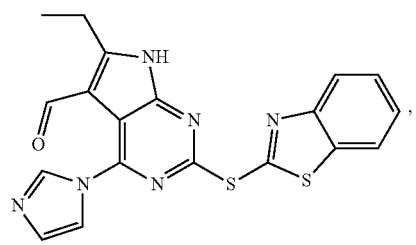, 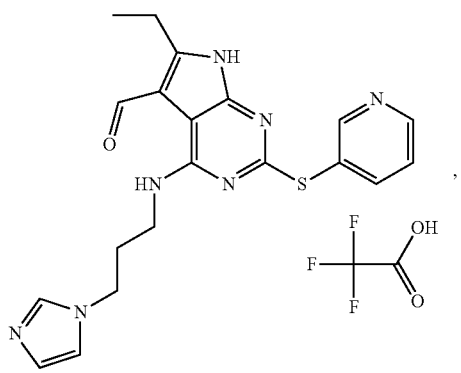,
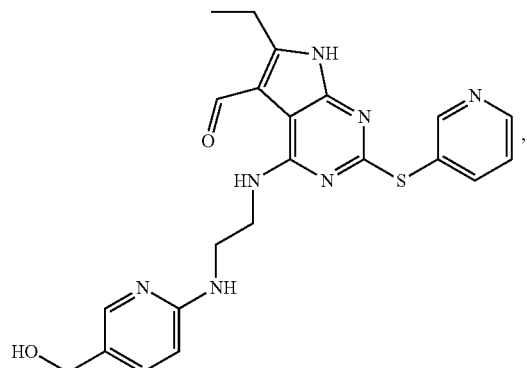, 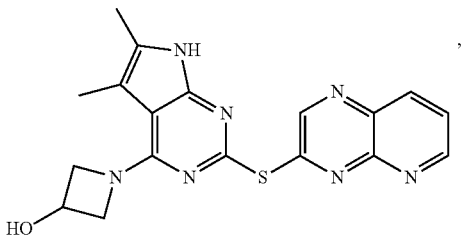,
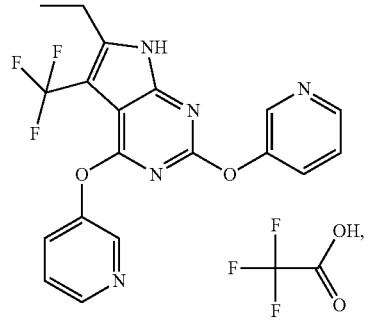, 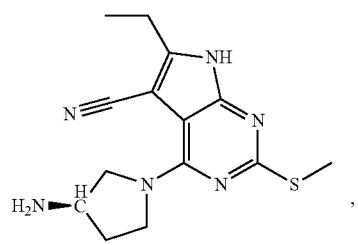,
502

503
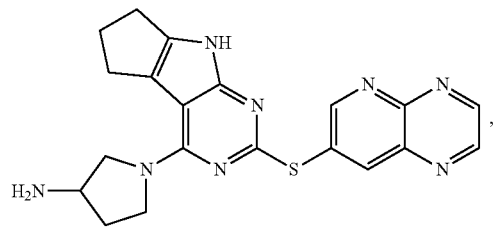
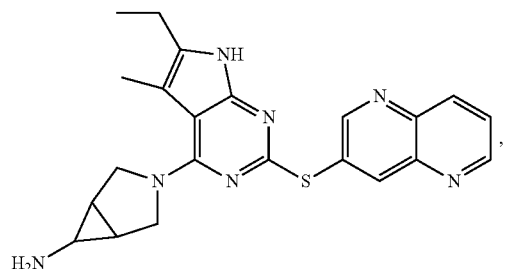
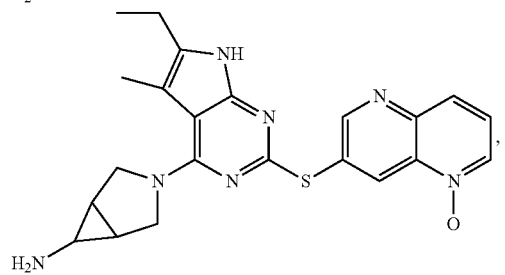
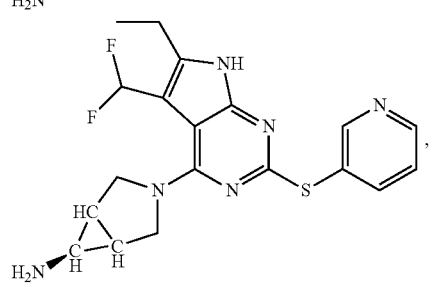
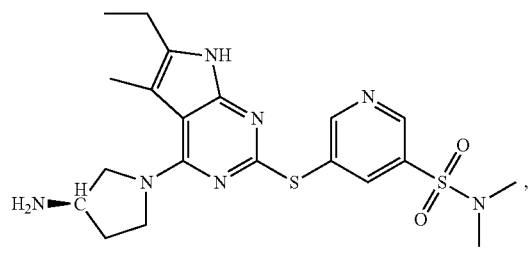
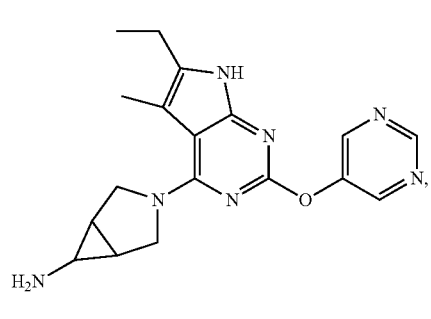
-continued
504
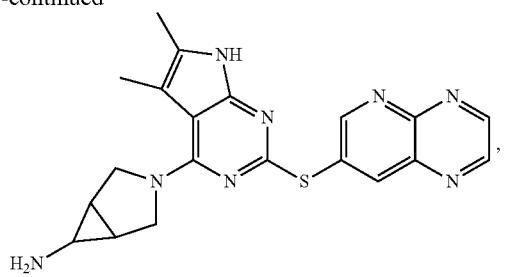
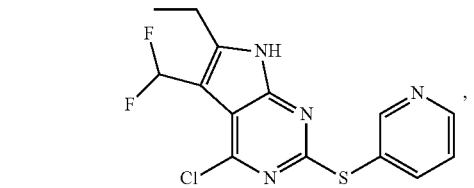
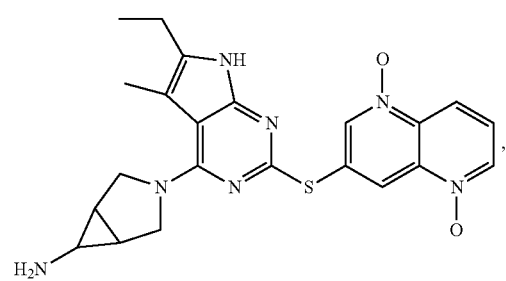
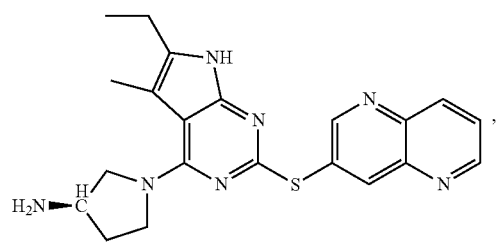
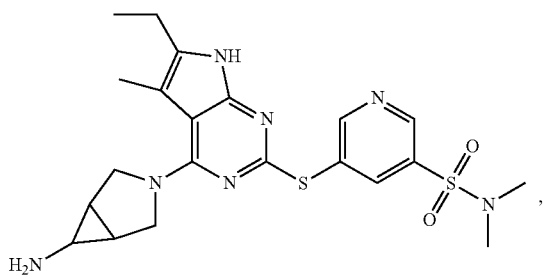
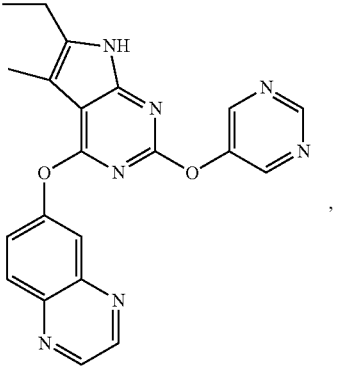

-continued
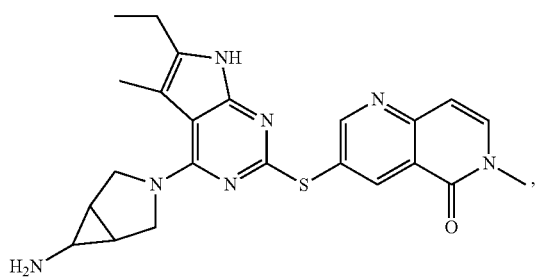
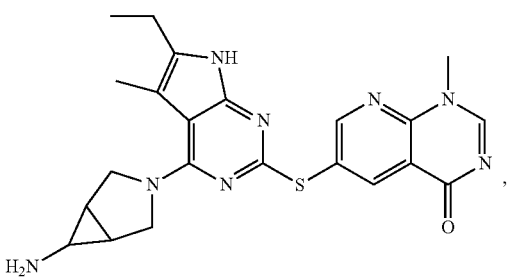
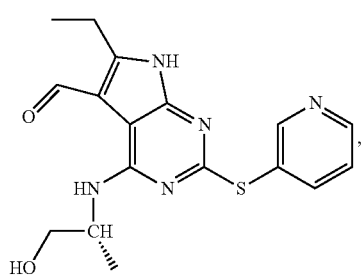
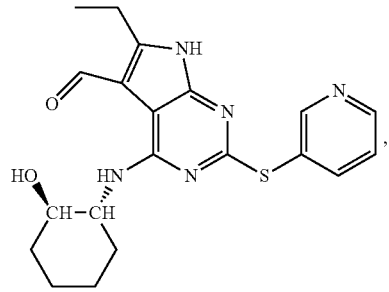
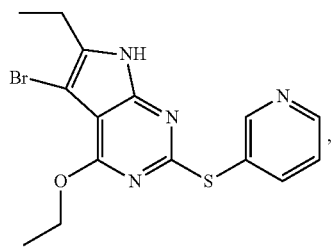
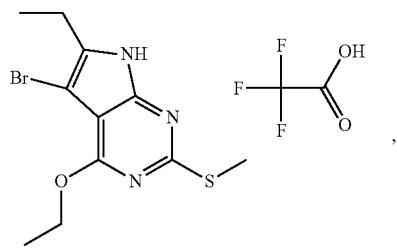
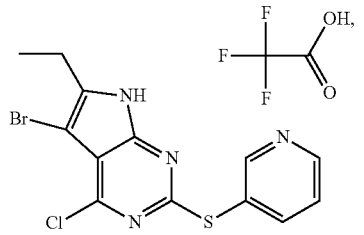
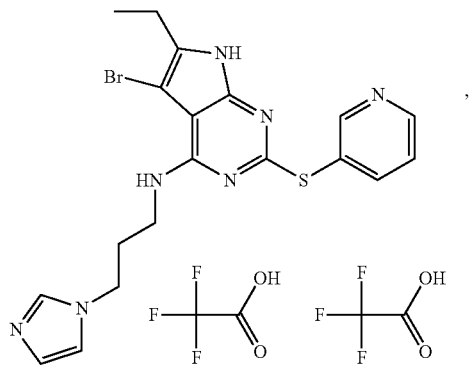
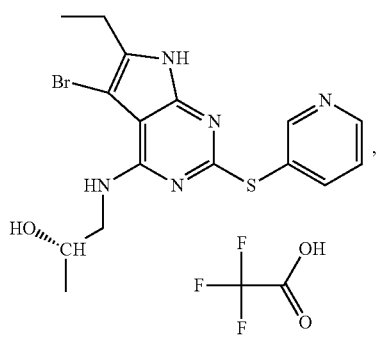
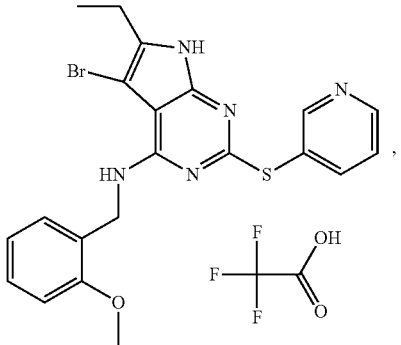

-continued
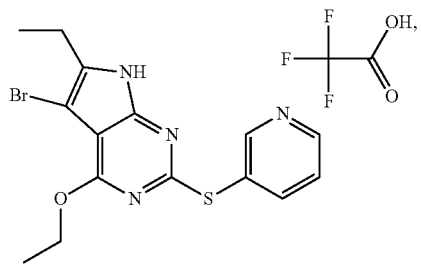
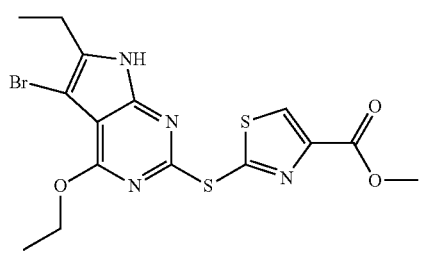
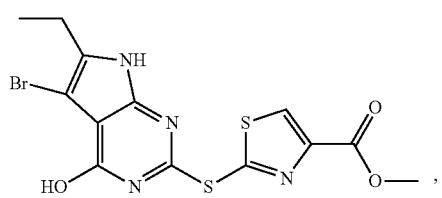
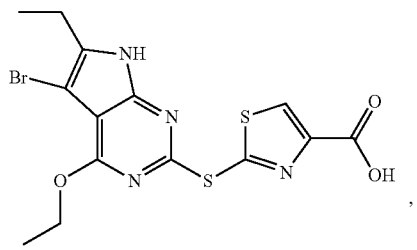
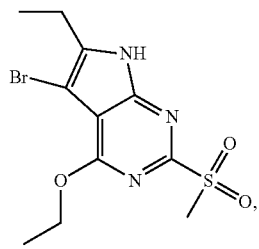
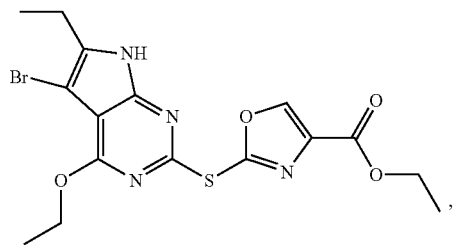
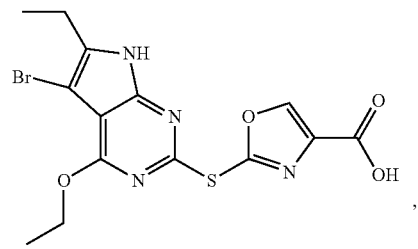
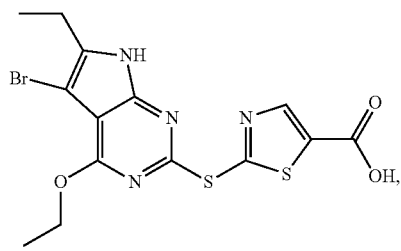
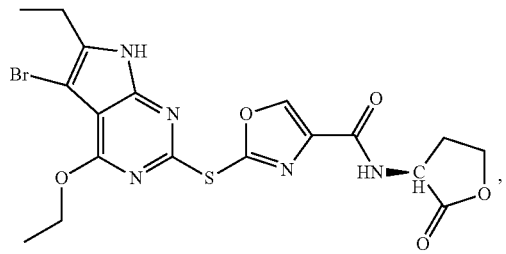
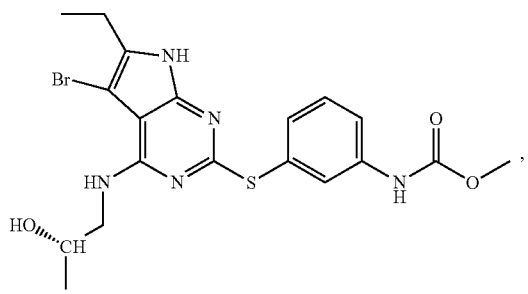
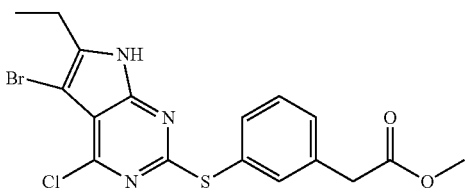
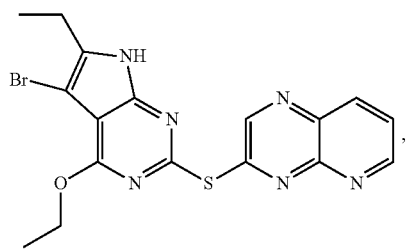
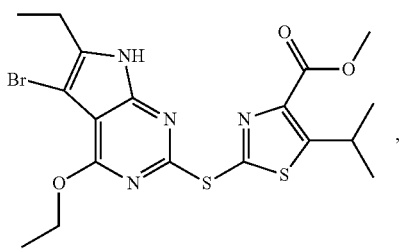

-continued
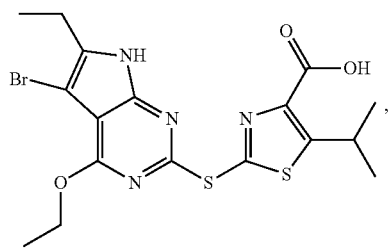
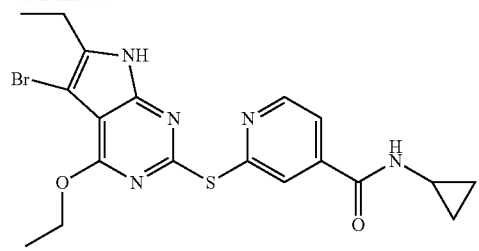
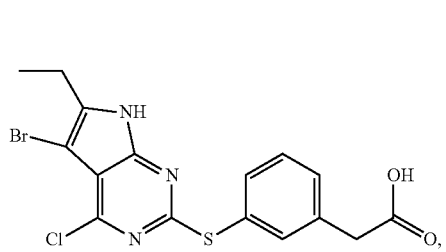
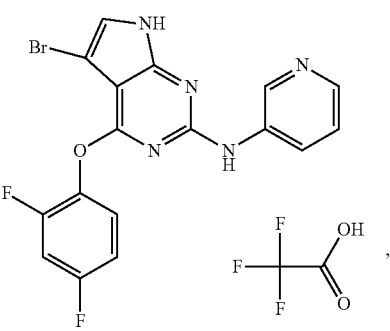
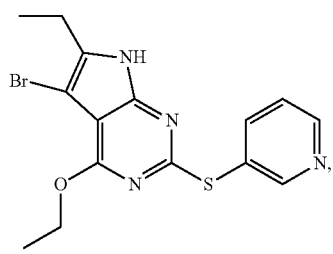
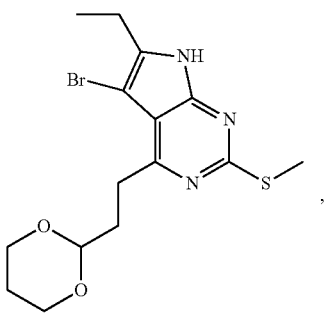
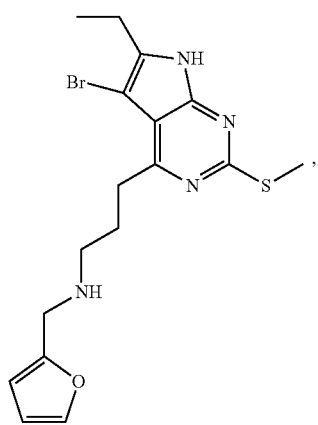
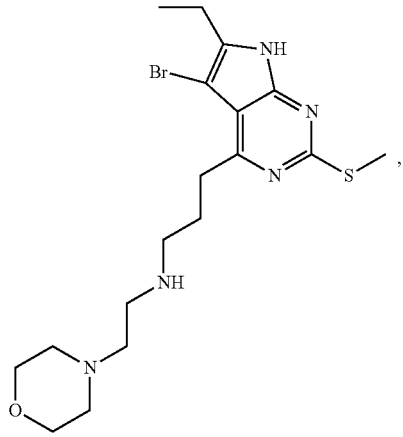
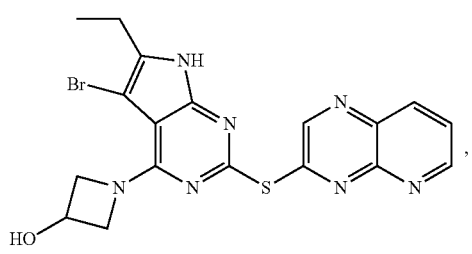
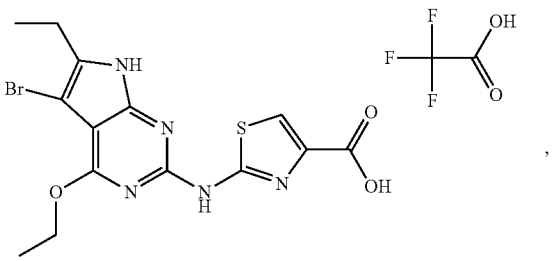

511
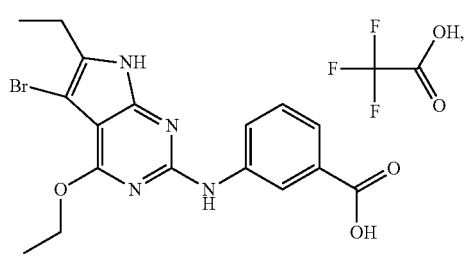
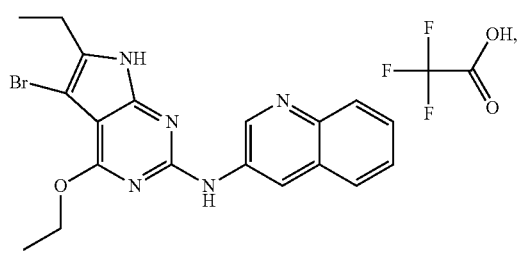
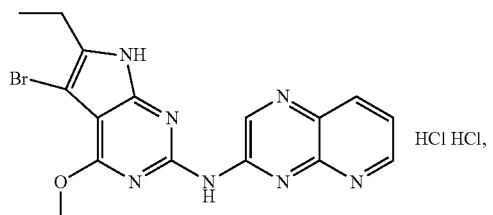
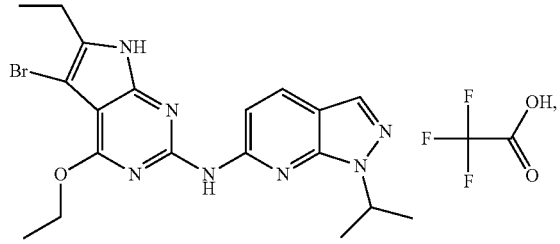
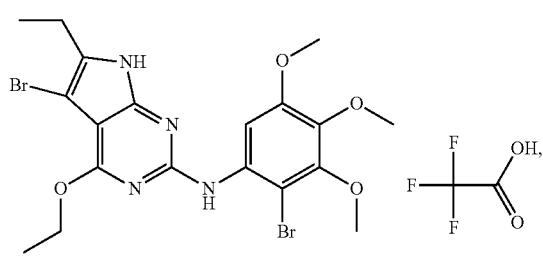
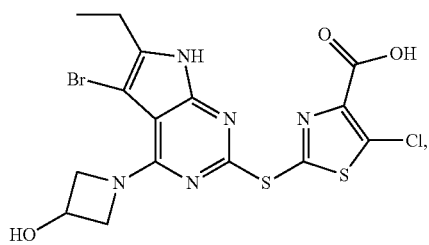
512
-continued
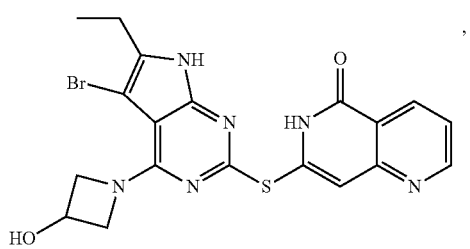
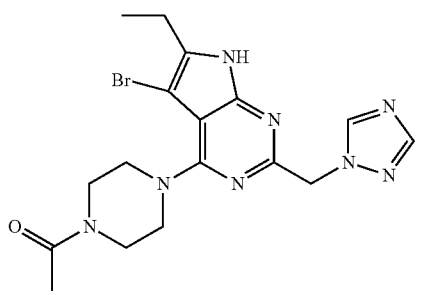
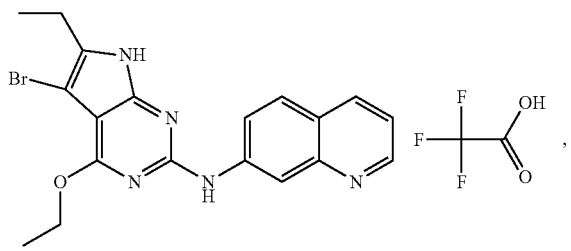
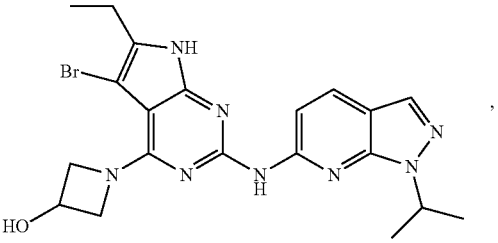
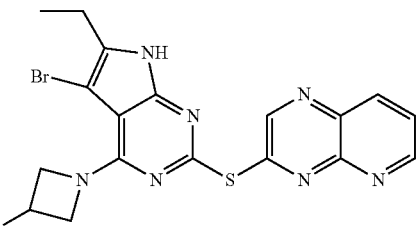
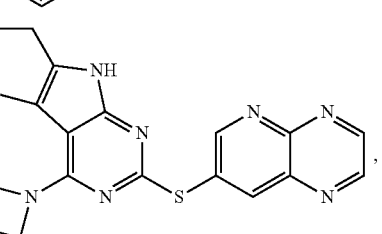

513
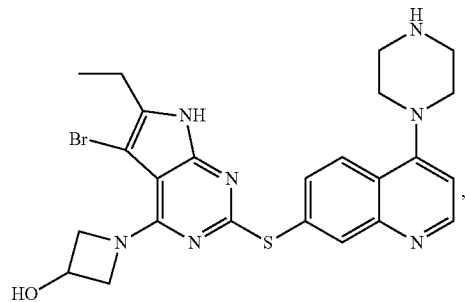
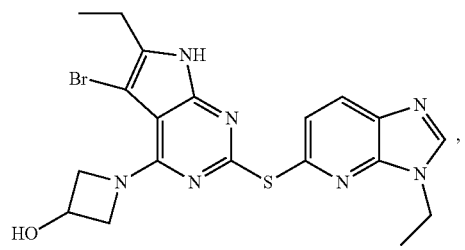
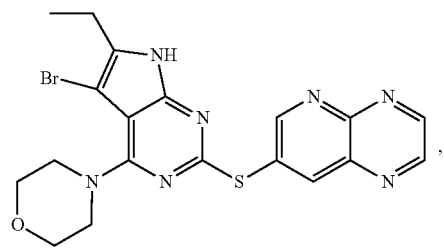
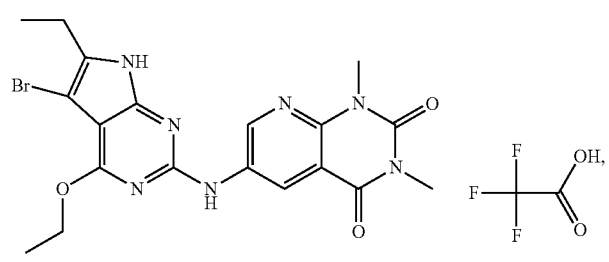
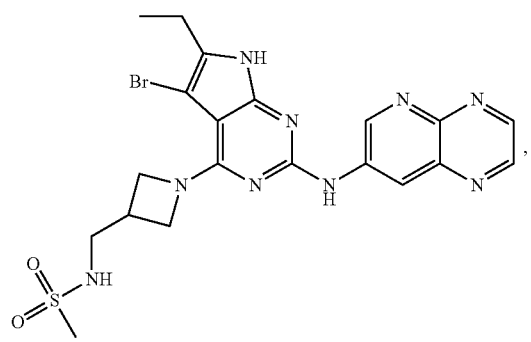
514
-continued
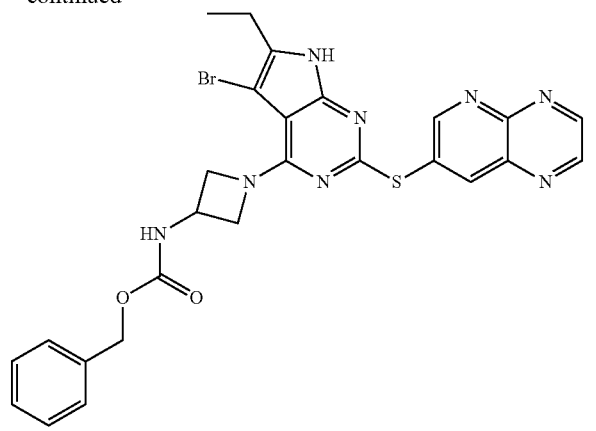
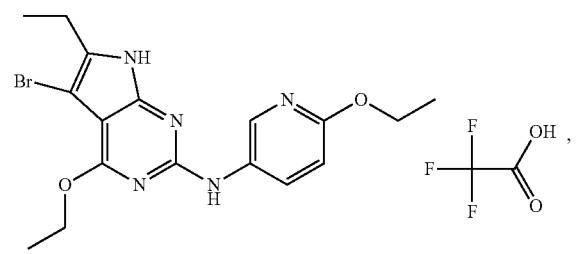
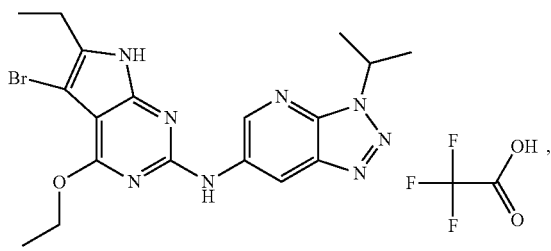
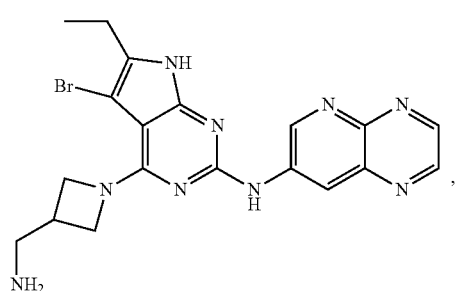
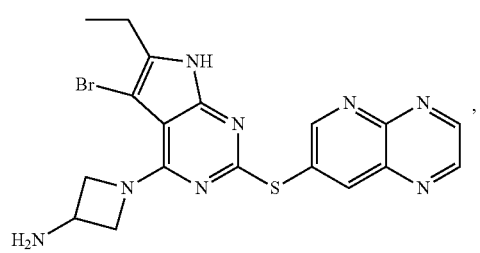

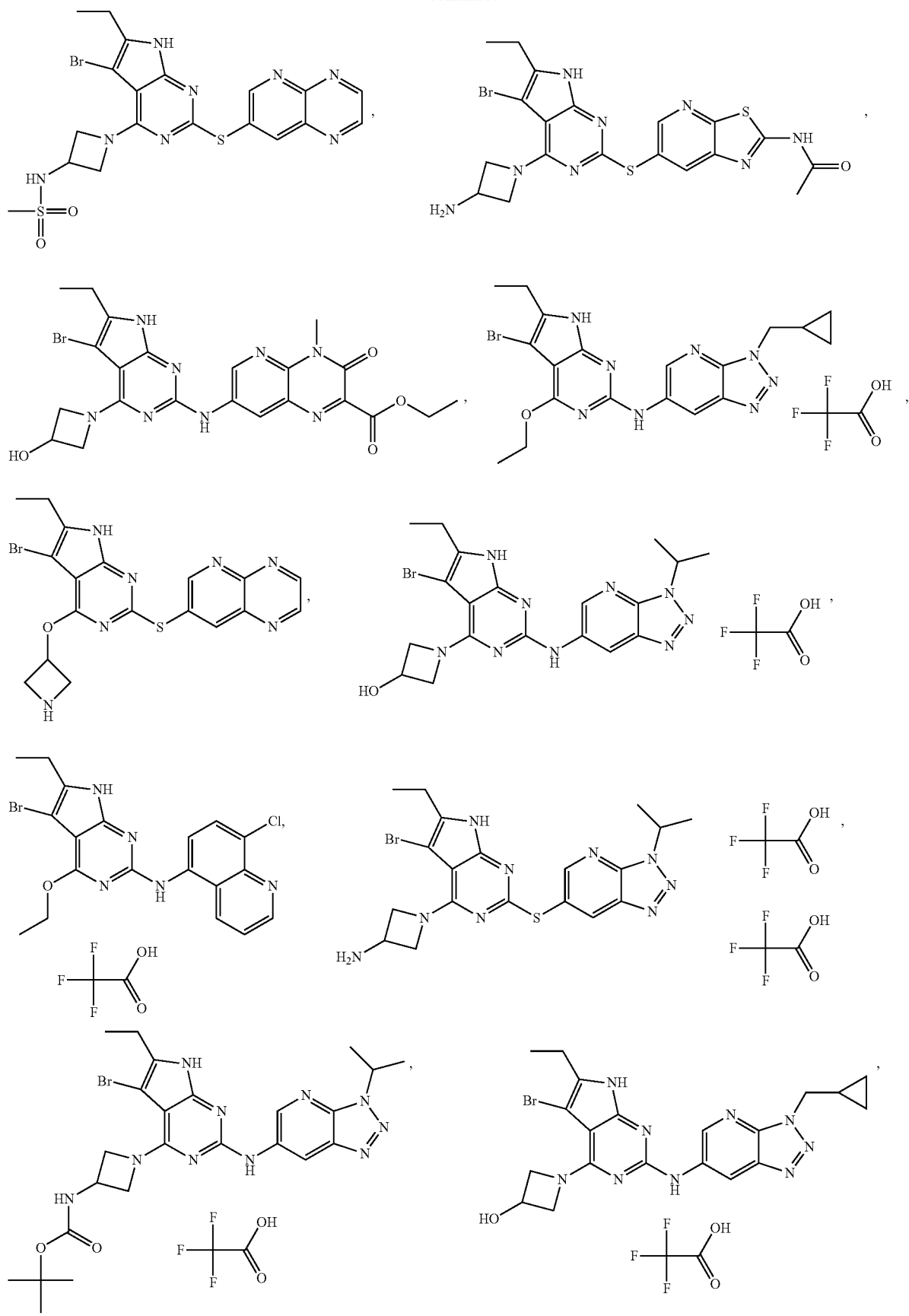

-continued
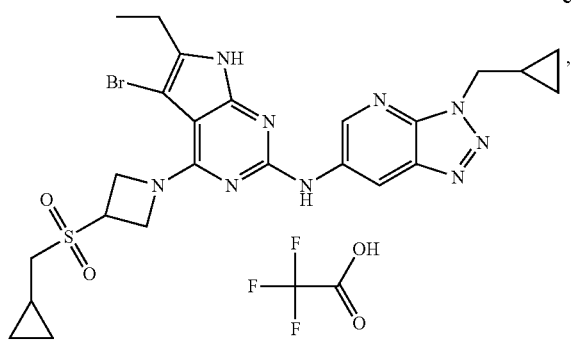
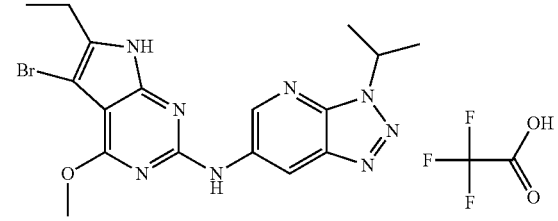
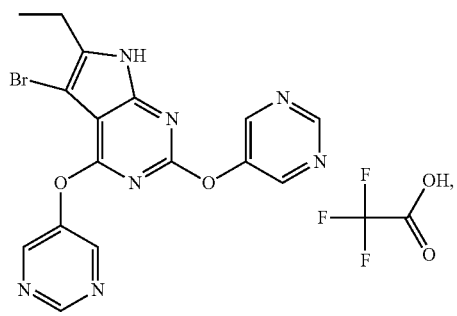
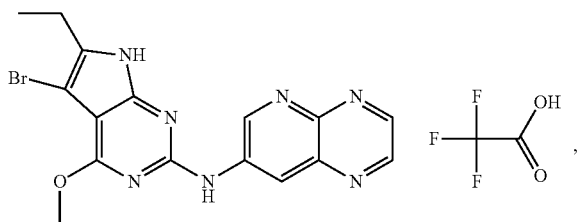
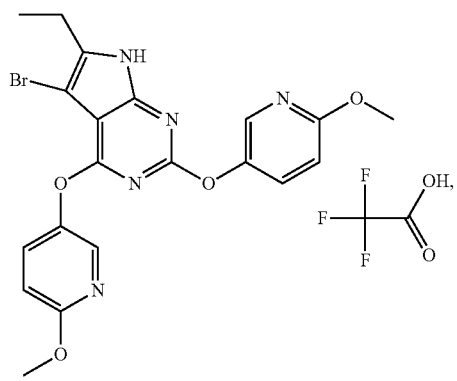
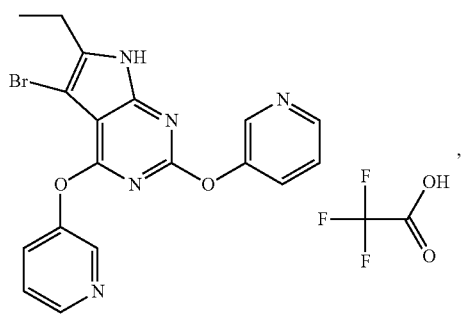
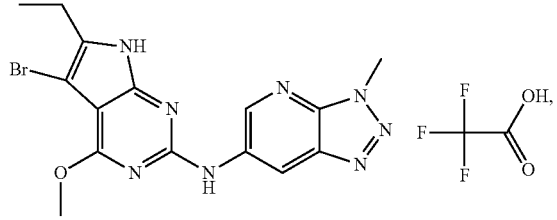
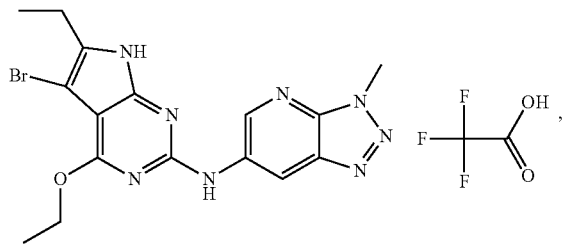
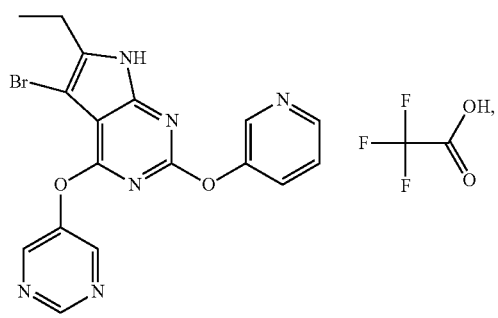
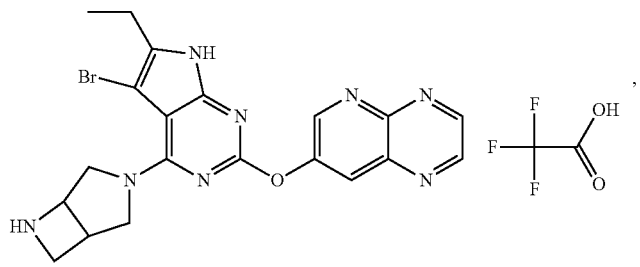

-continued
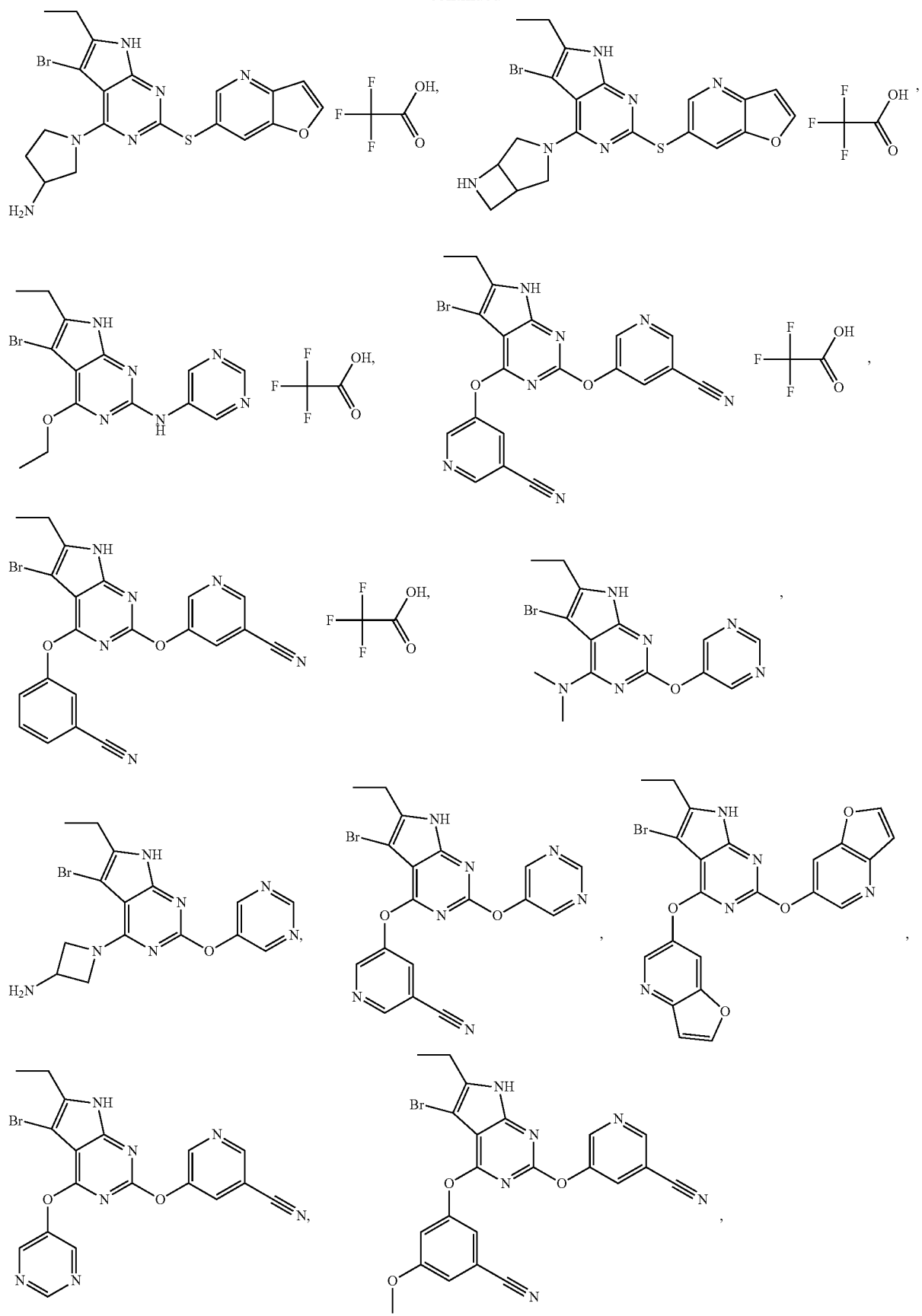

521
-continued
522
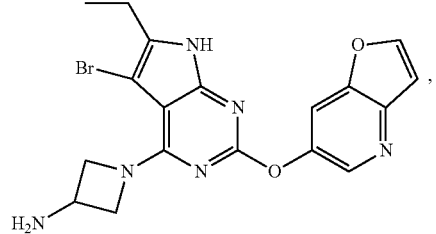 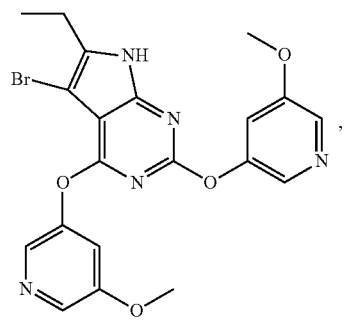 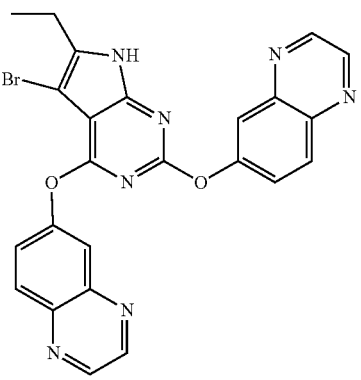
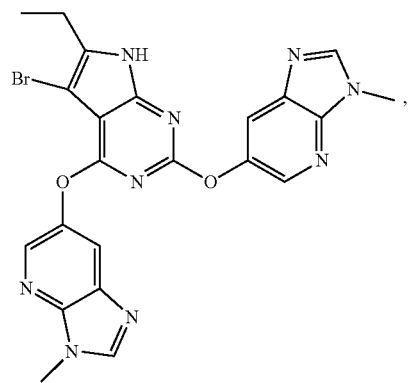 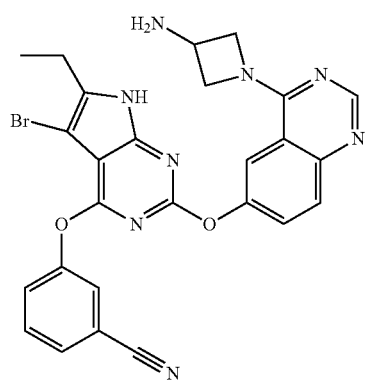 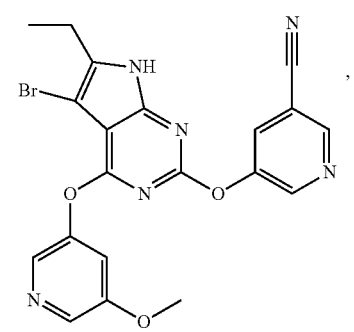
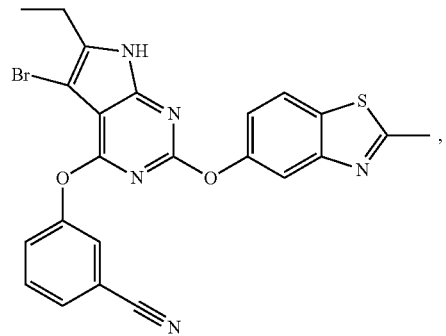 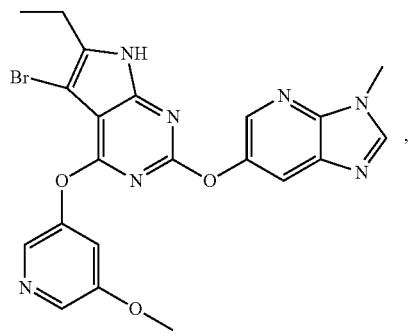
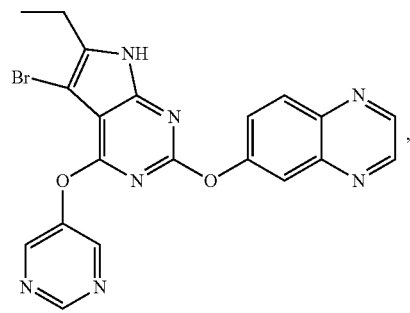 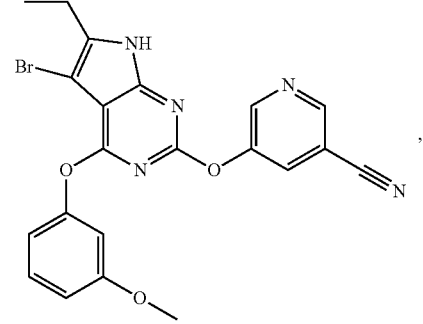

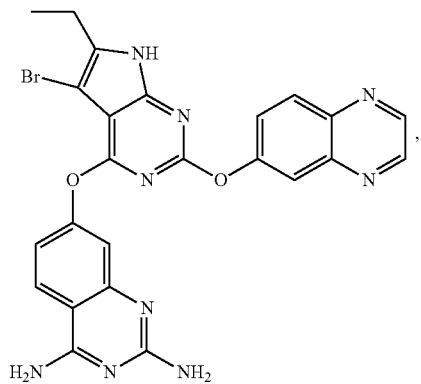
,
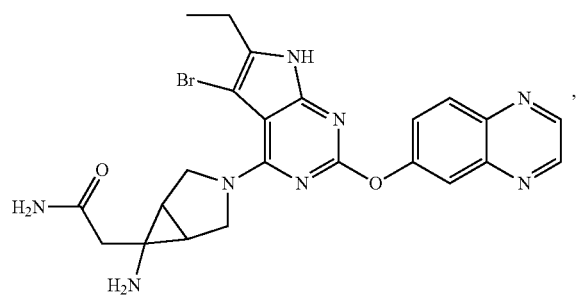
,
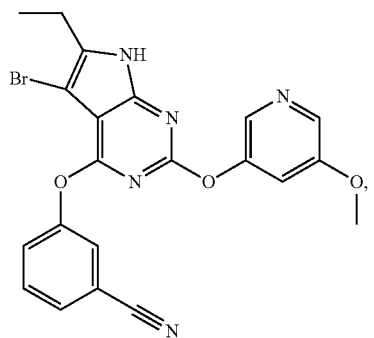
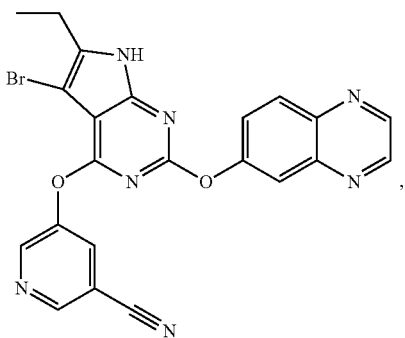
,
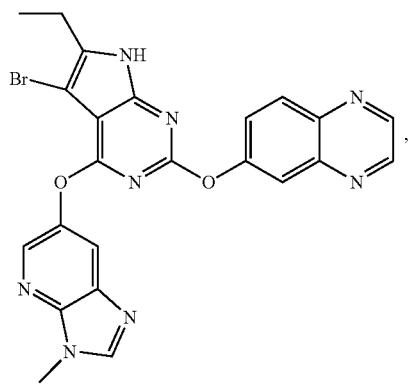
,
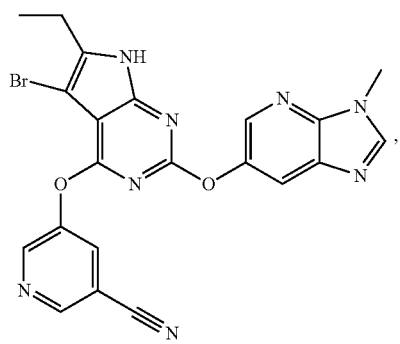
,
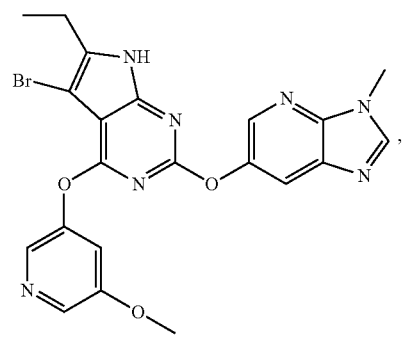
, -continued
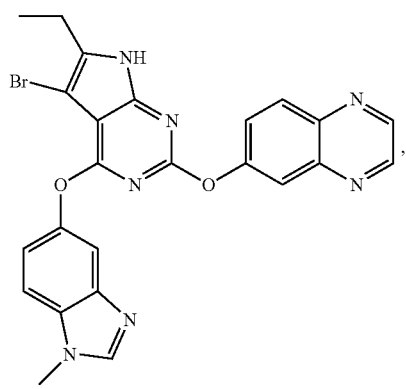
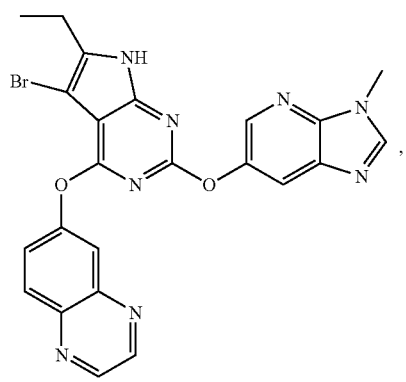
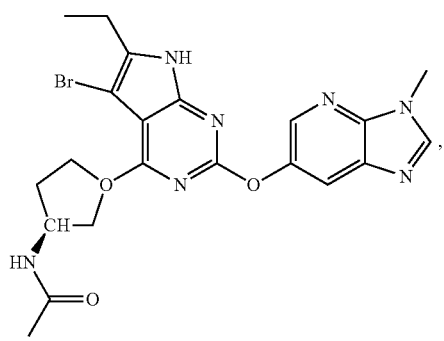
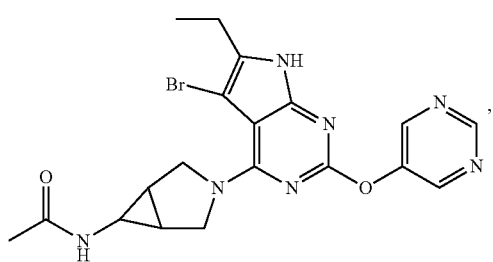
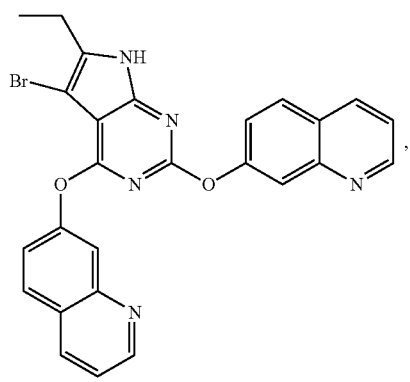
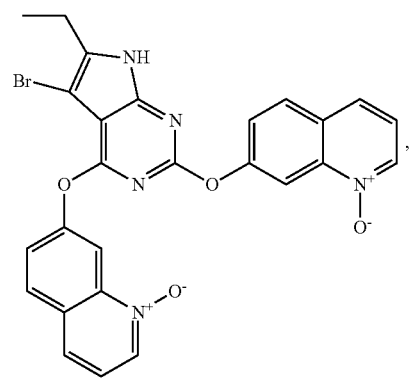
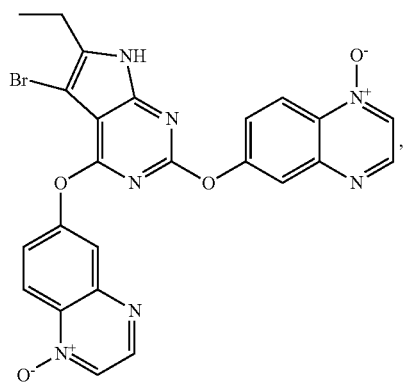

527
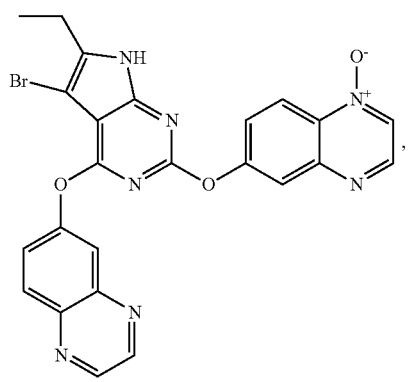
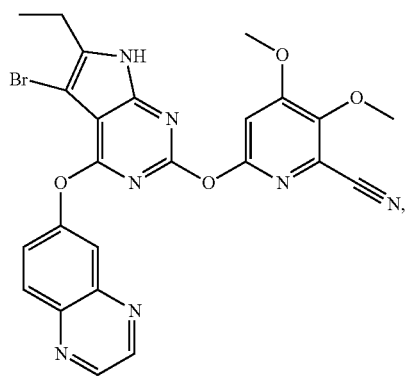
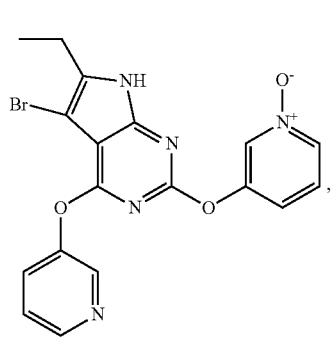
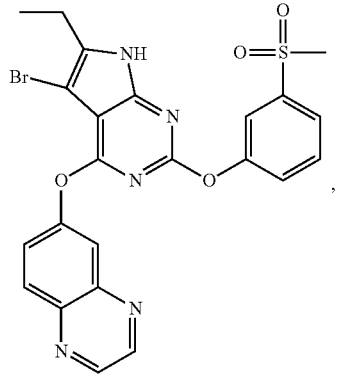
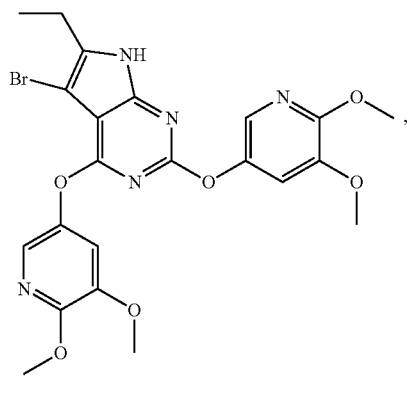
528
-continued
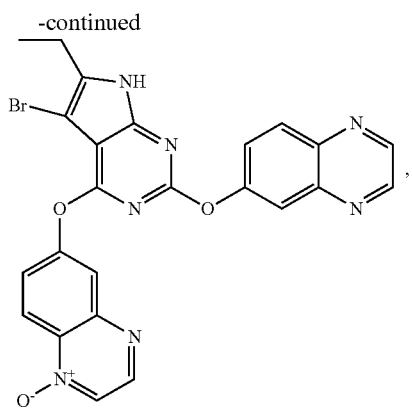
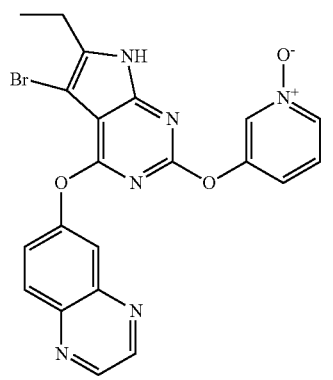
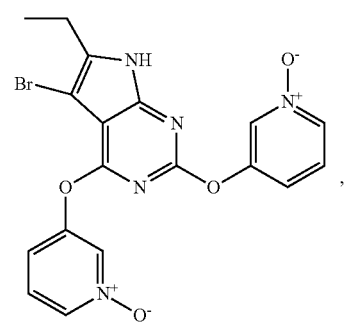
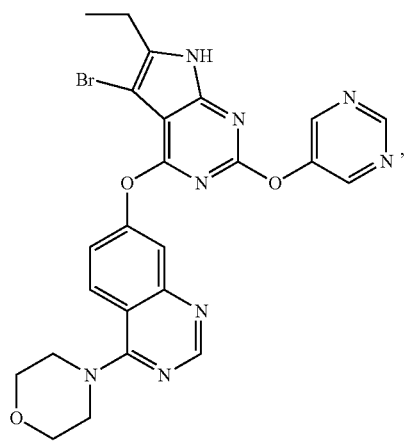

-continued
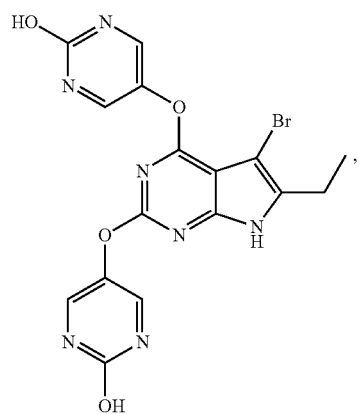
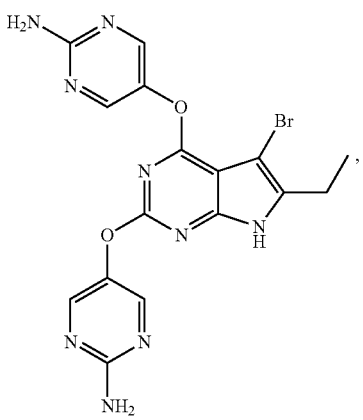
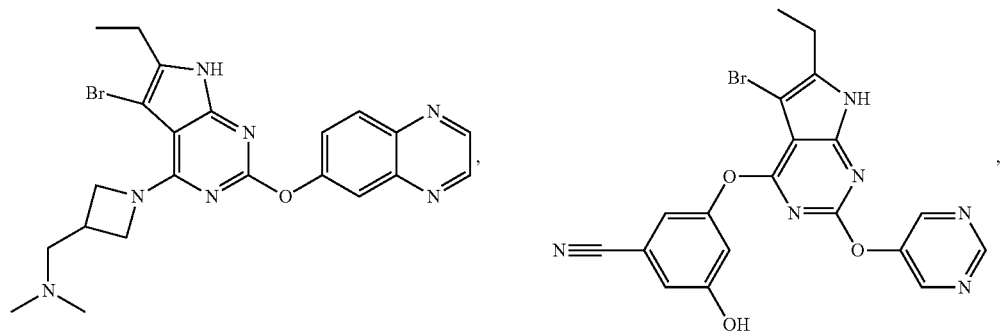
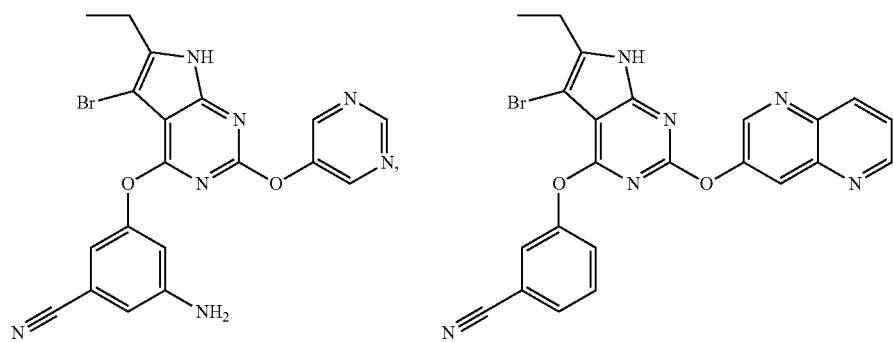
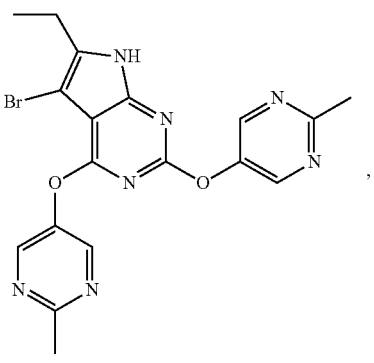
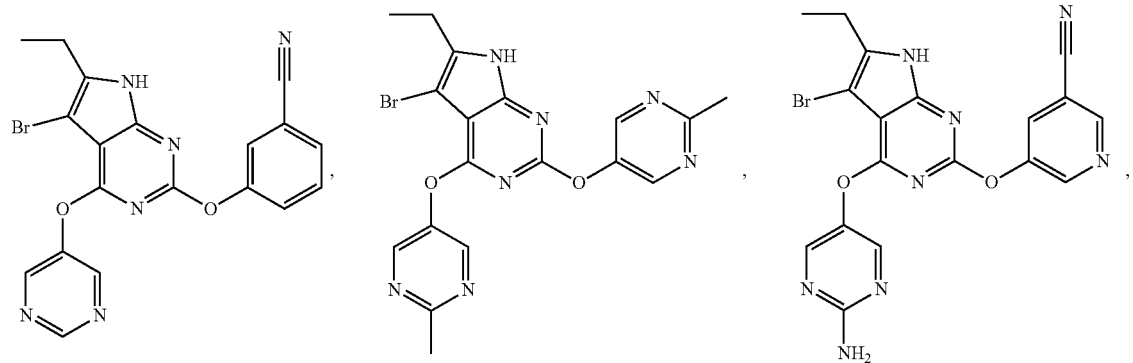
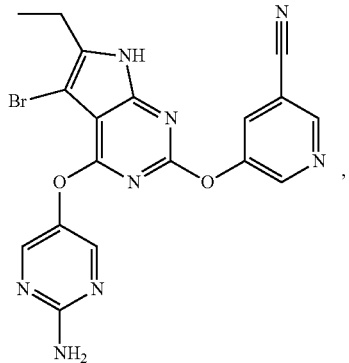

-continued
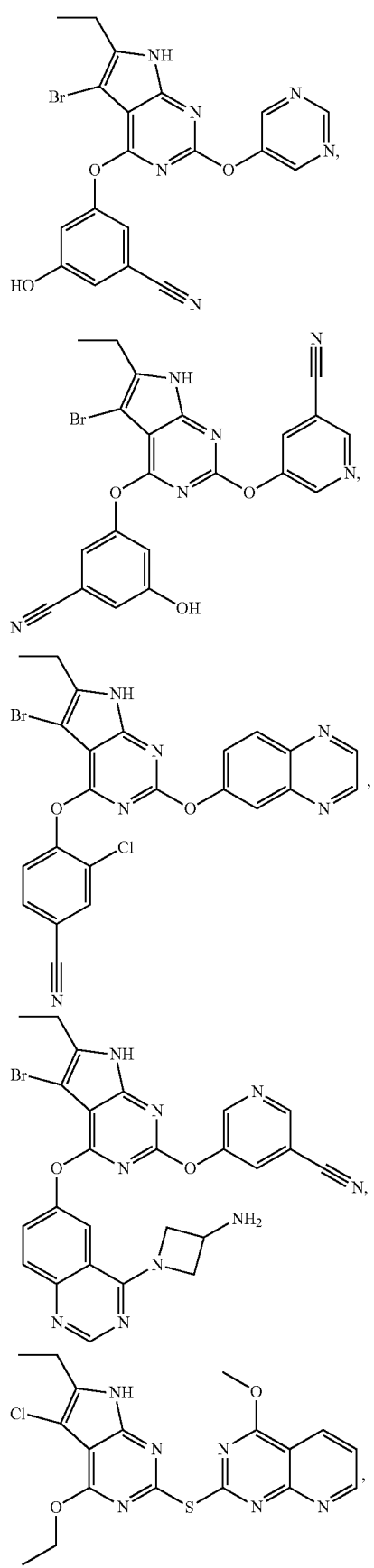
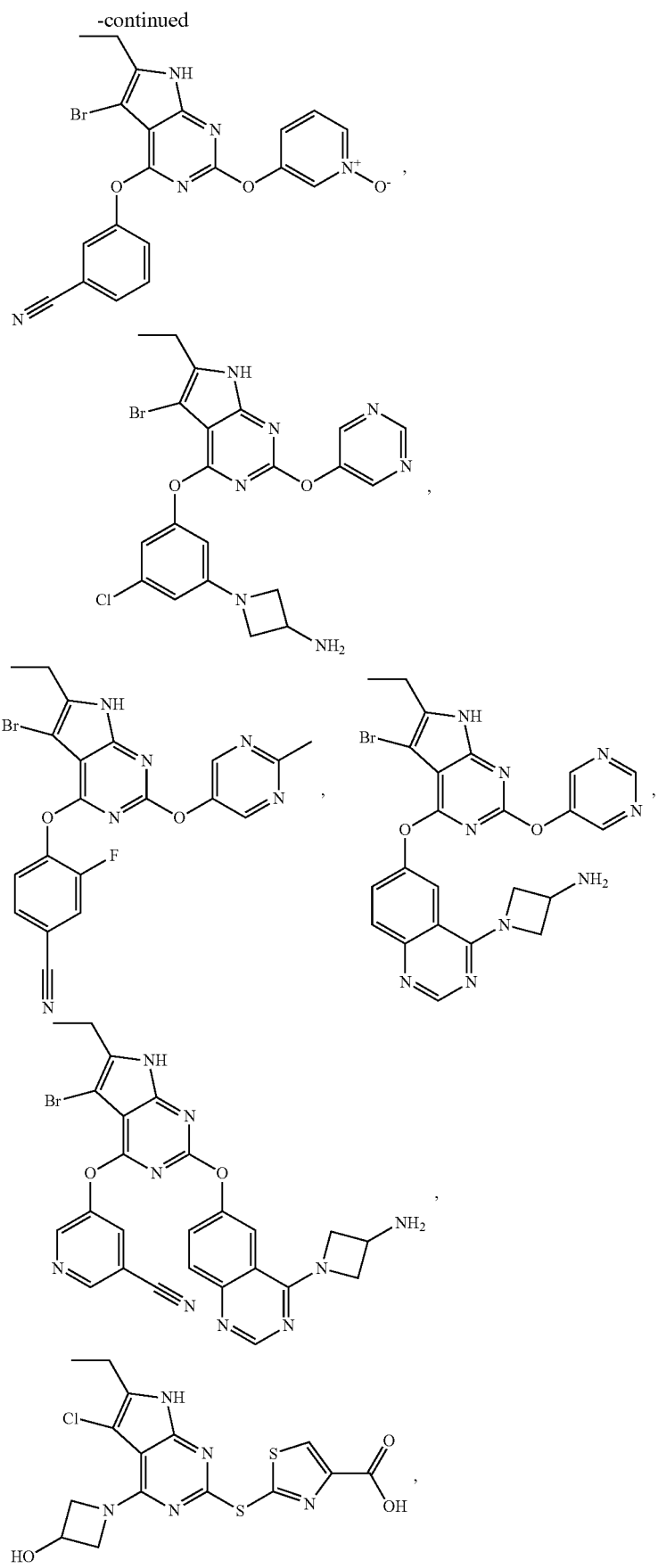

533
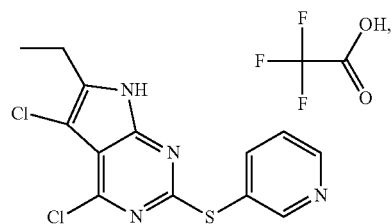
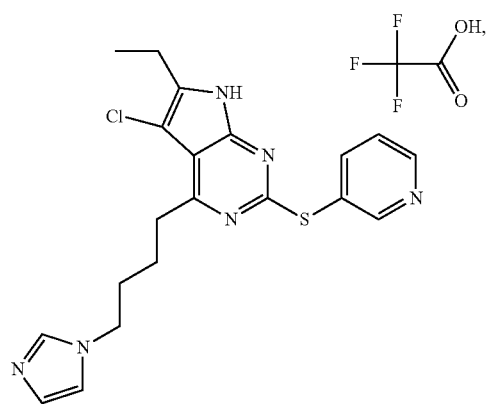
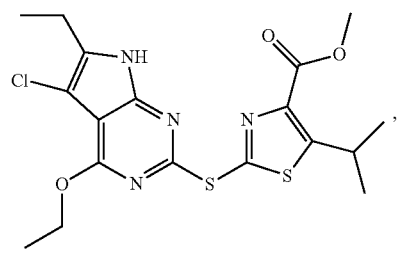
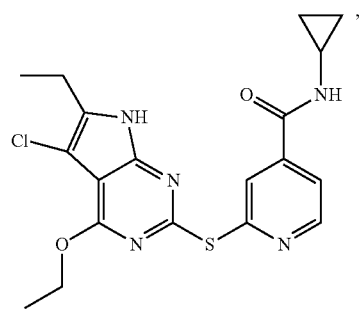
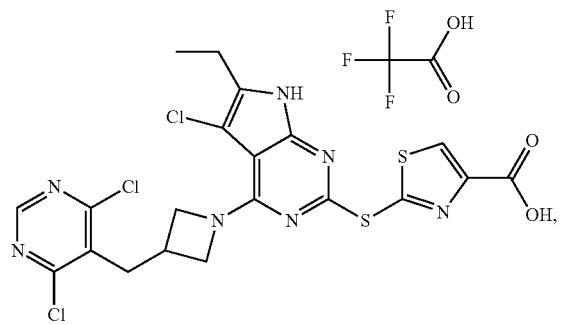
534
-continued
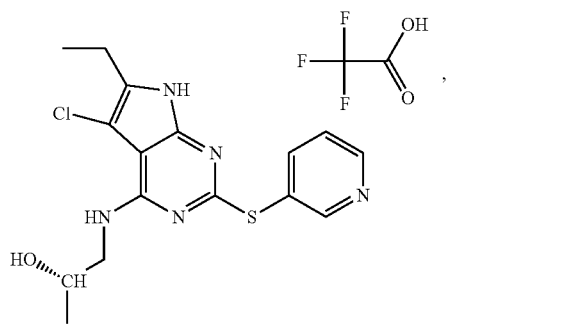
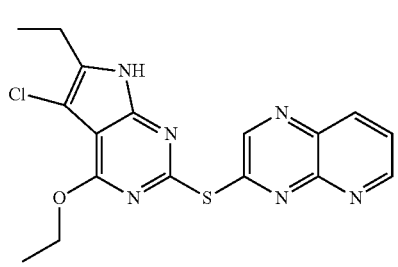
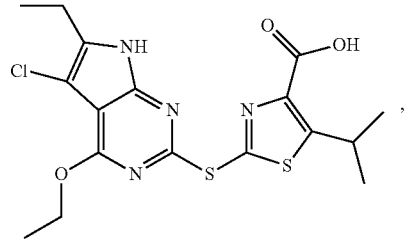
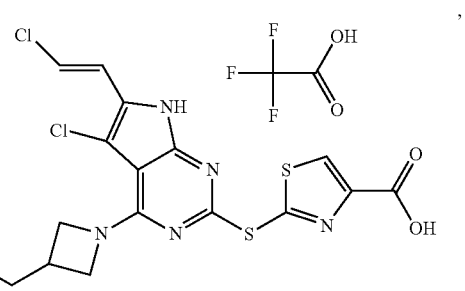
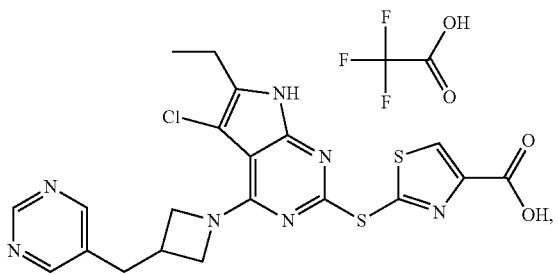

535
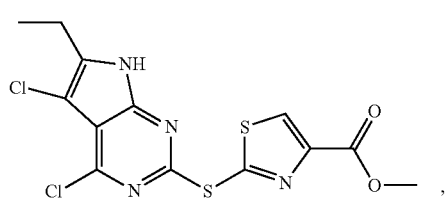
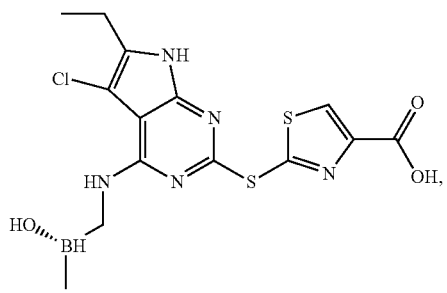
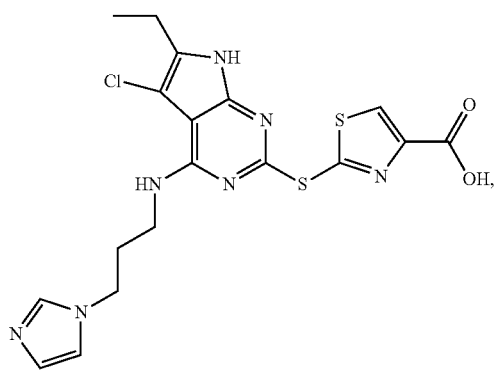
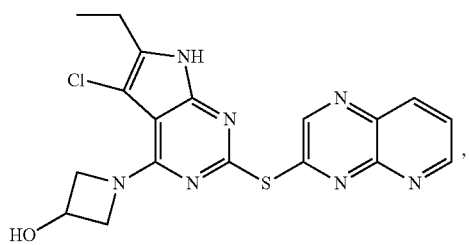
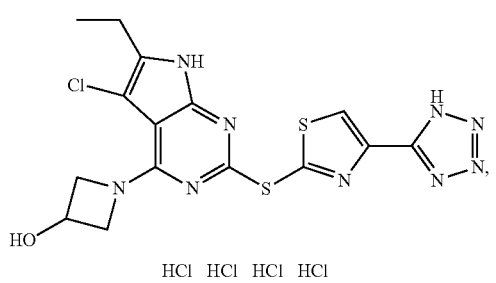
HCl HCl HCl HCl
536
-continued
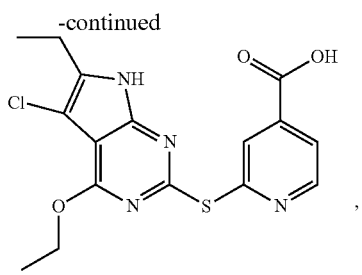
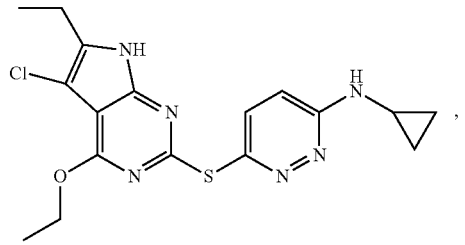
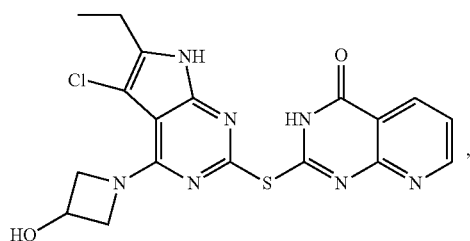
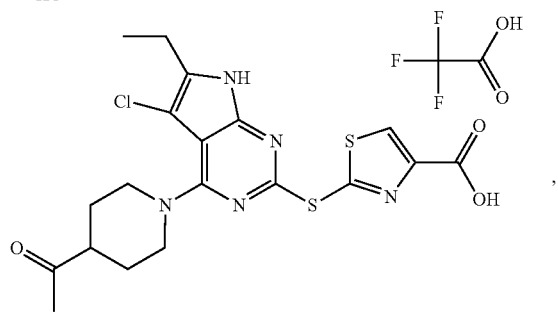

537
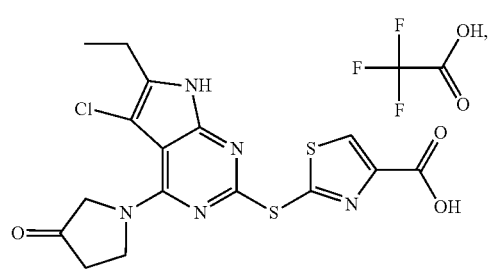
538
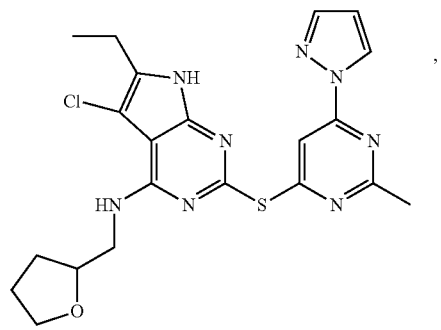
-continued
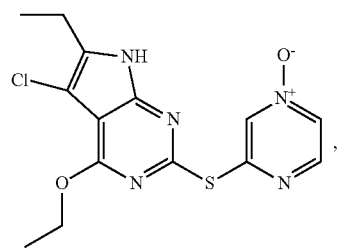
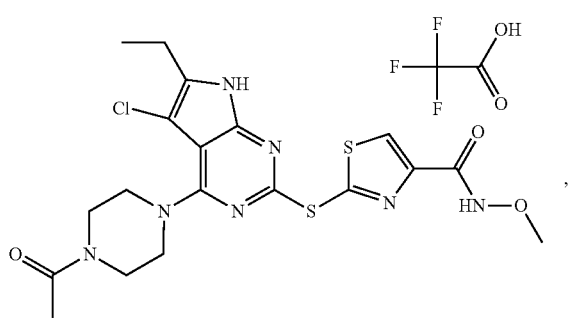
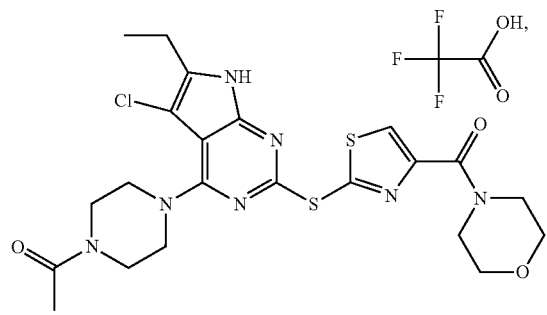
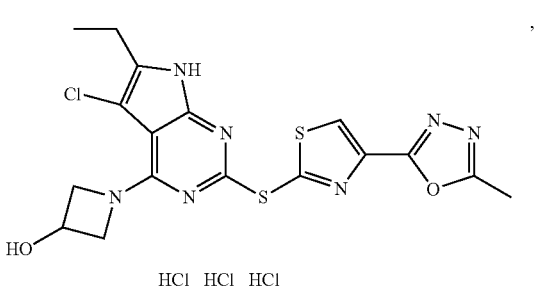
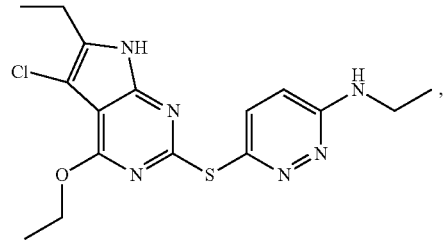
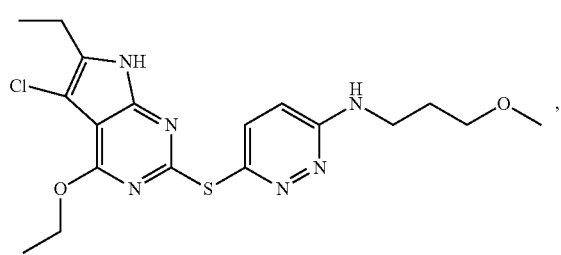
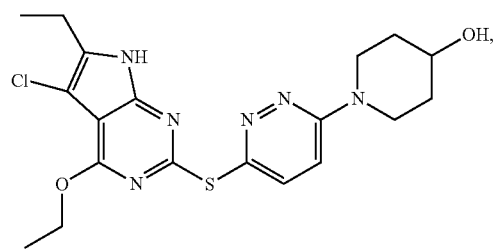
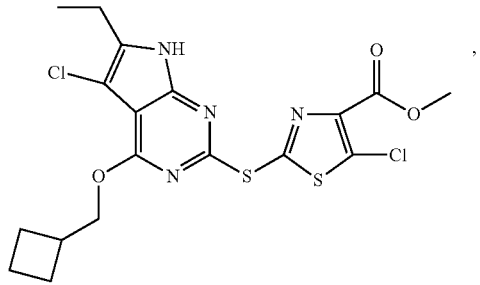

-continued
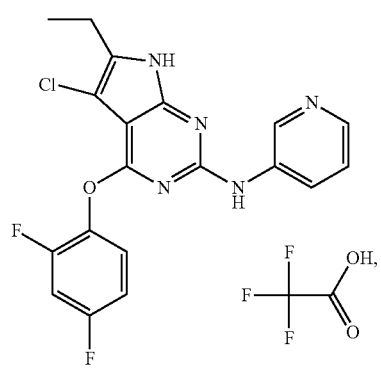 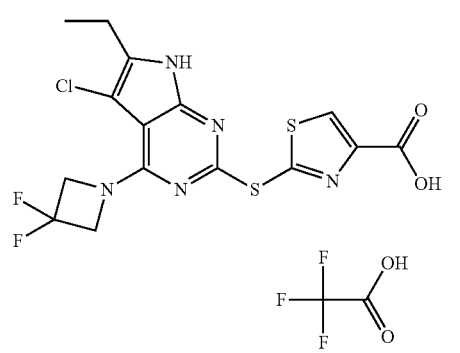
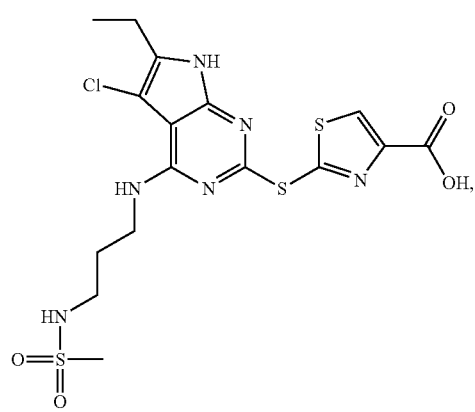 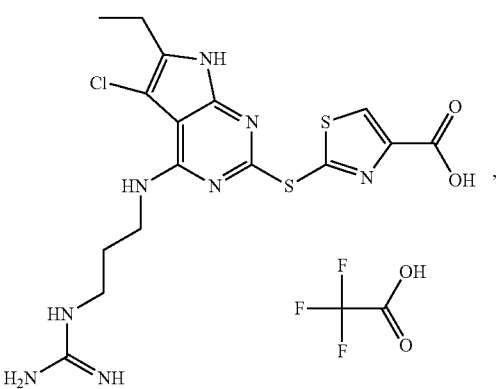
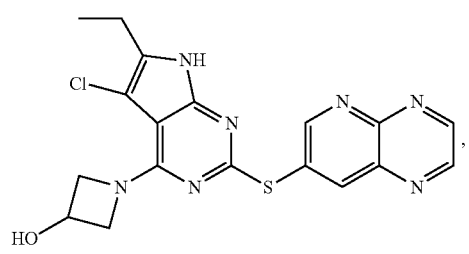 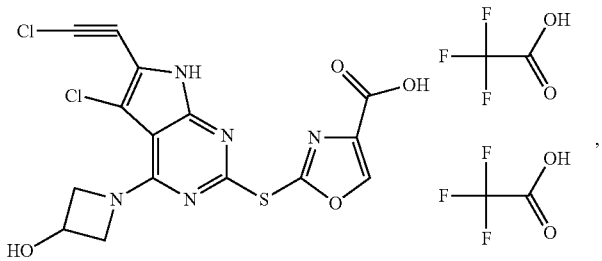
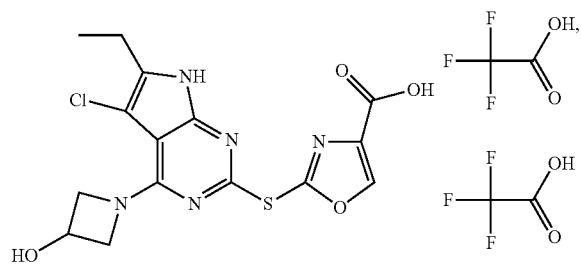 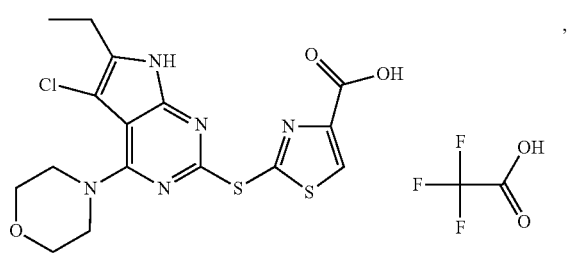
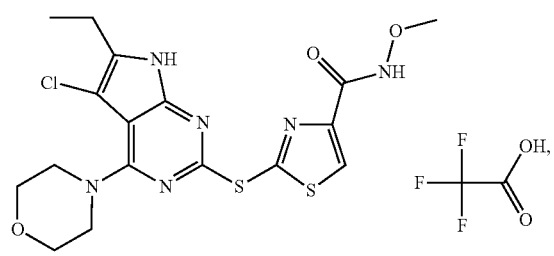 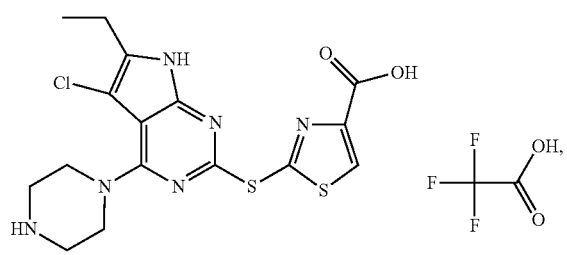

-continued
541
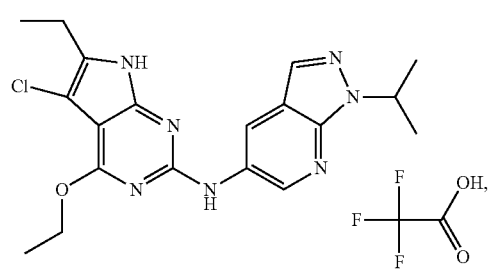
542
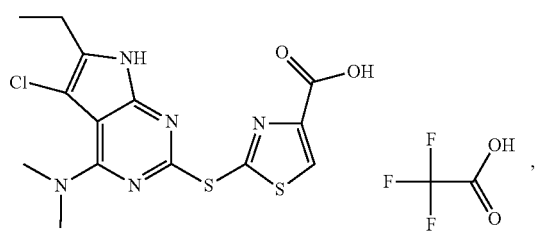
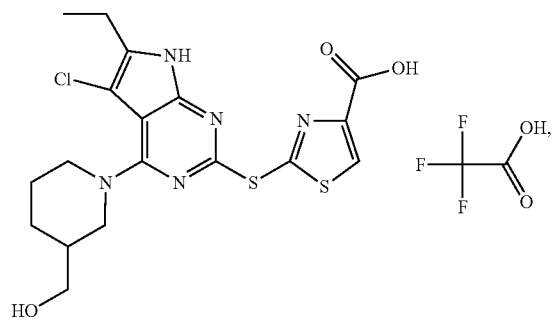
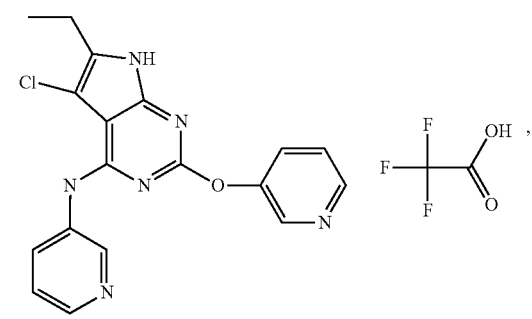
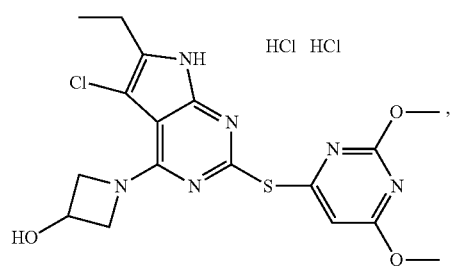
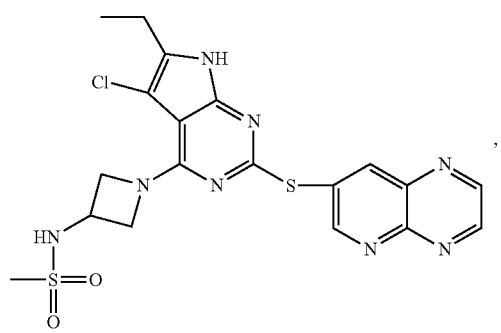
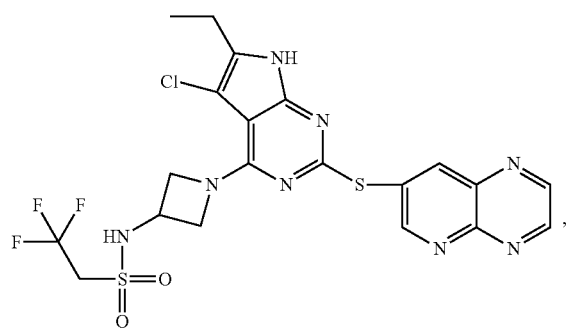
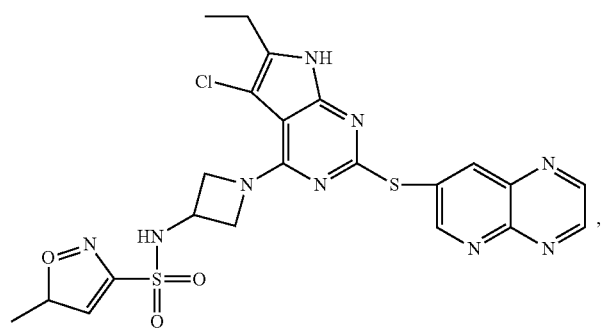
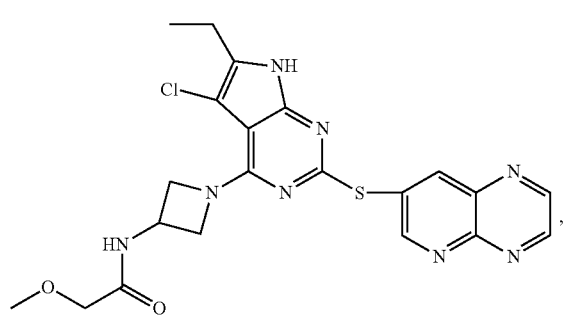
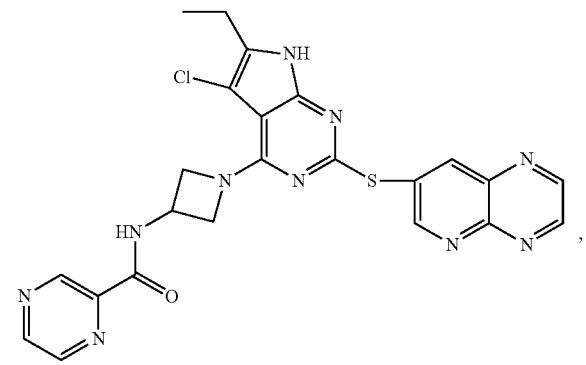

-continued
543
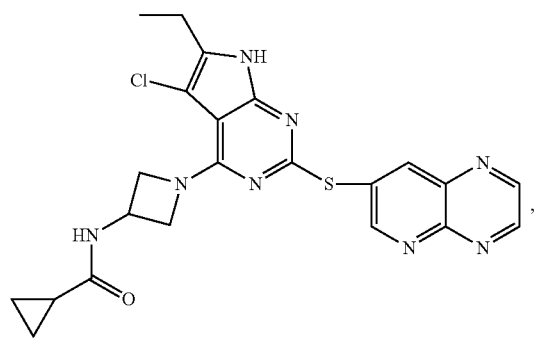
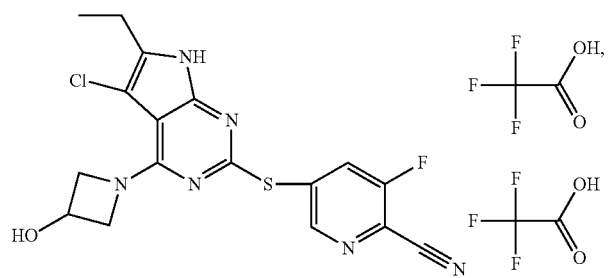
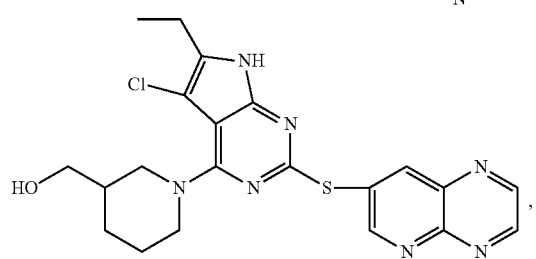
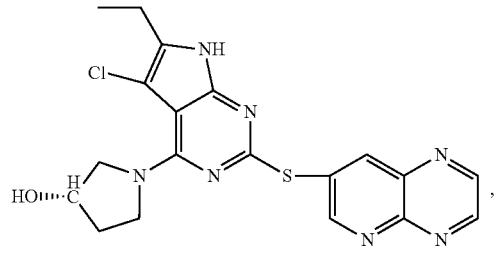
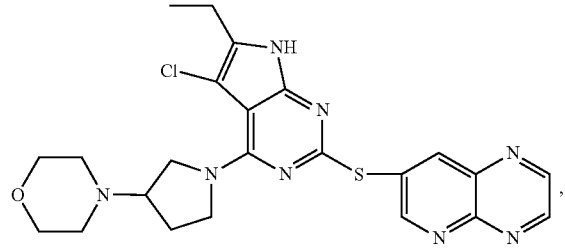
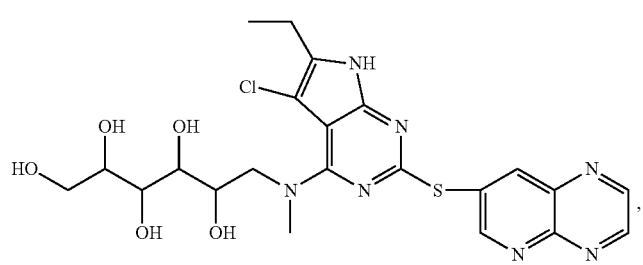
544
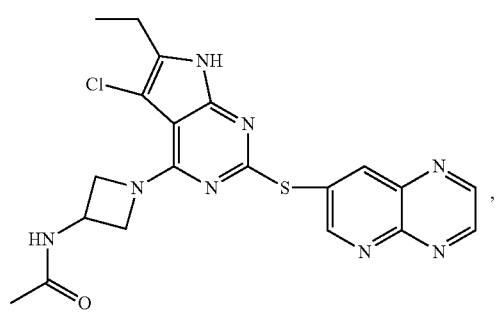
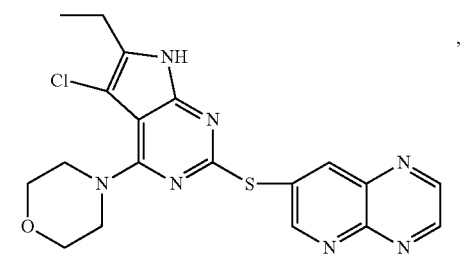
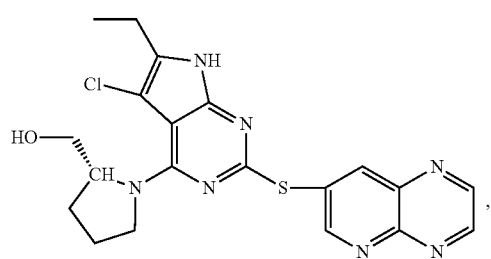
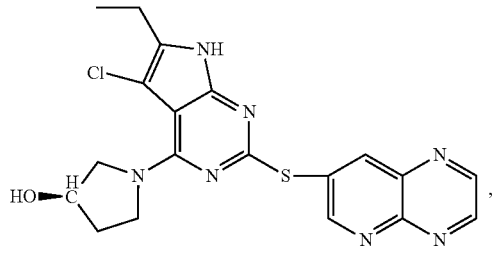
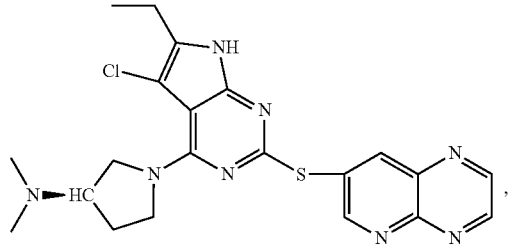
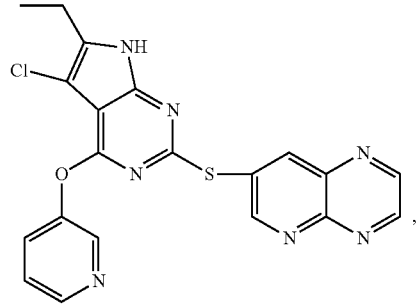

545
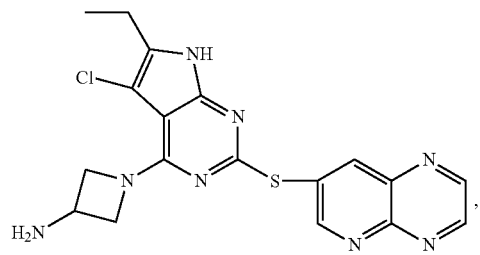
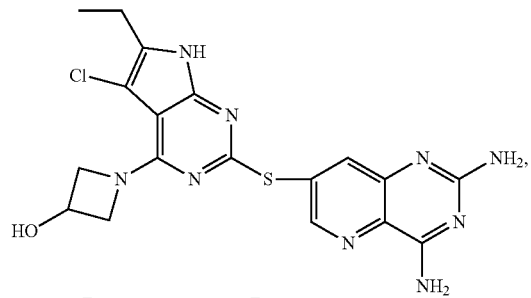
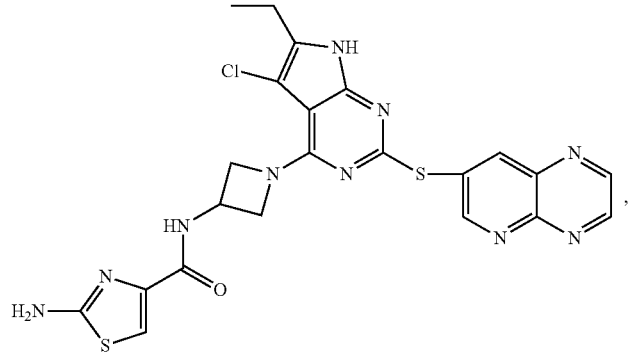
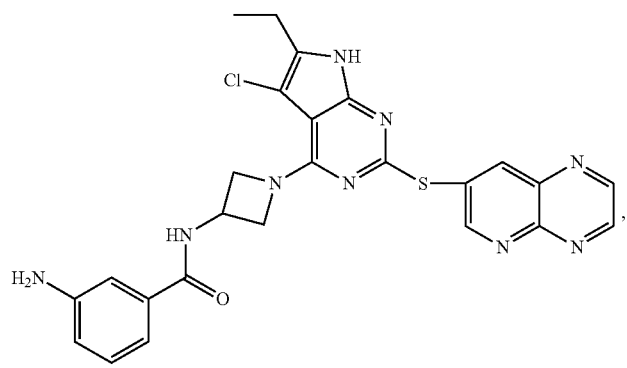
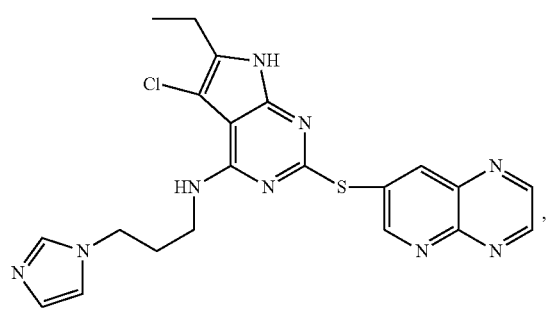
546
-continued
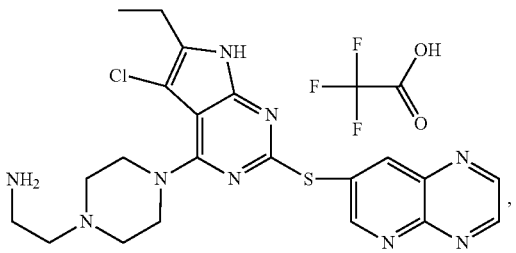
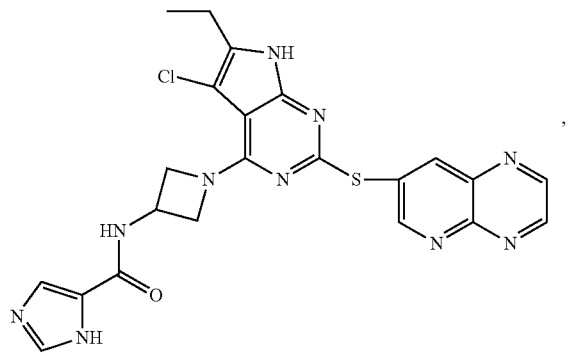
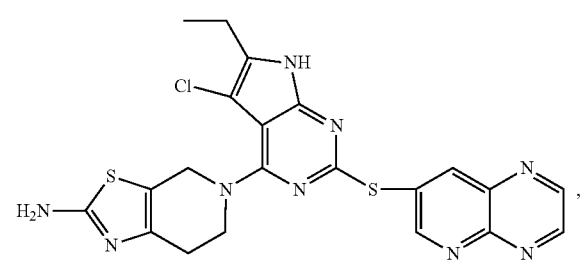

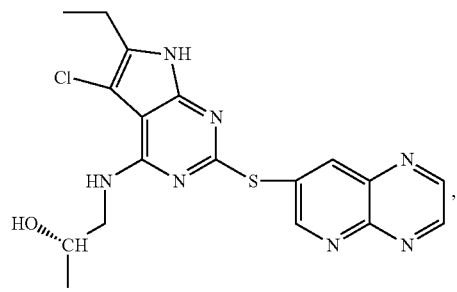
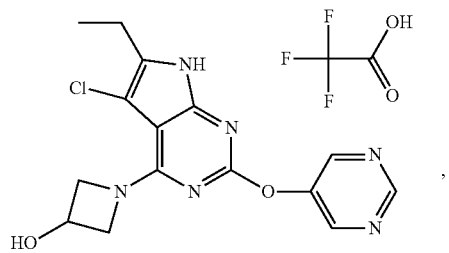
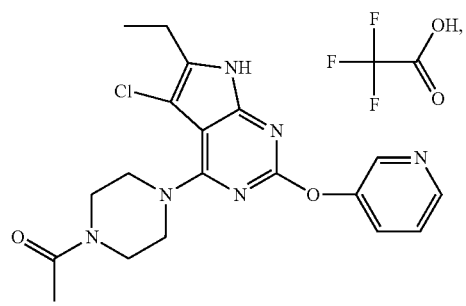
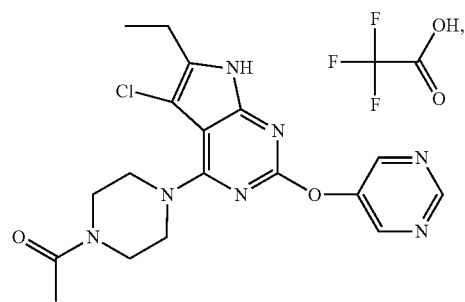
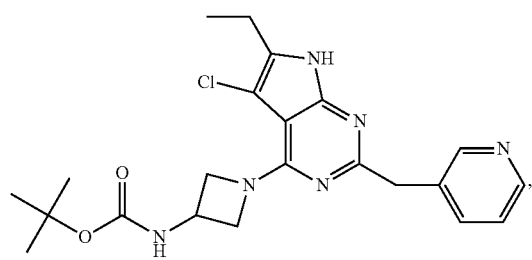
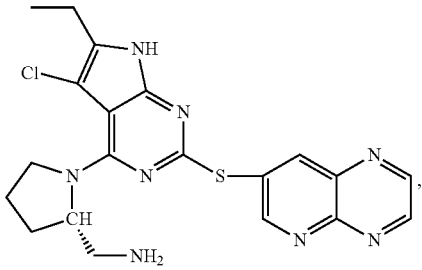
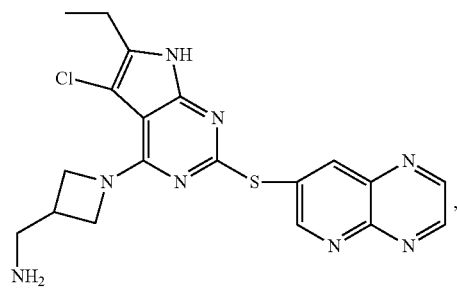
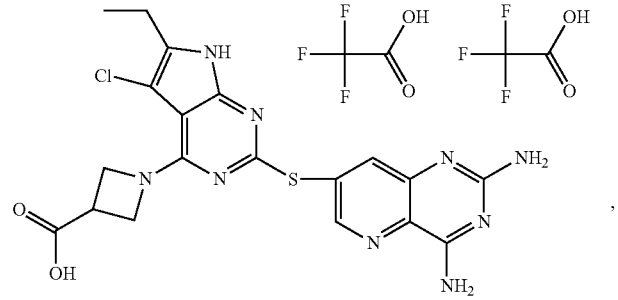
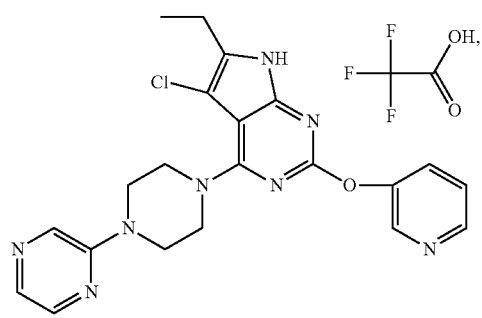
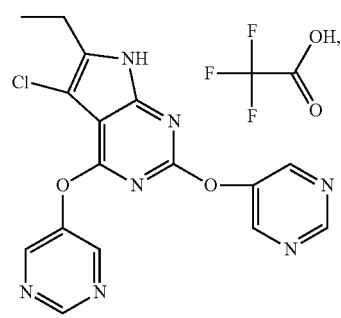

-continued
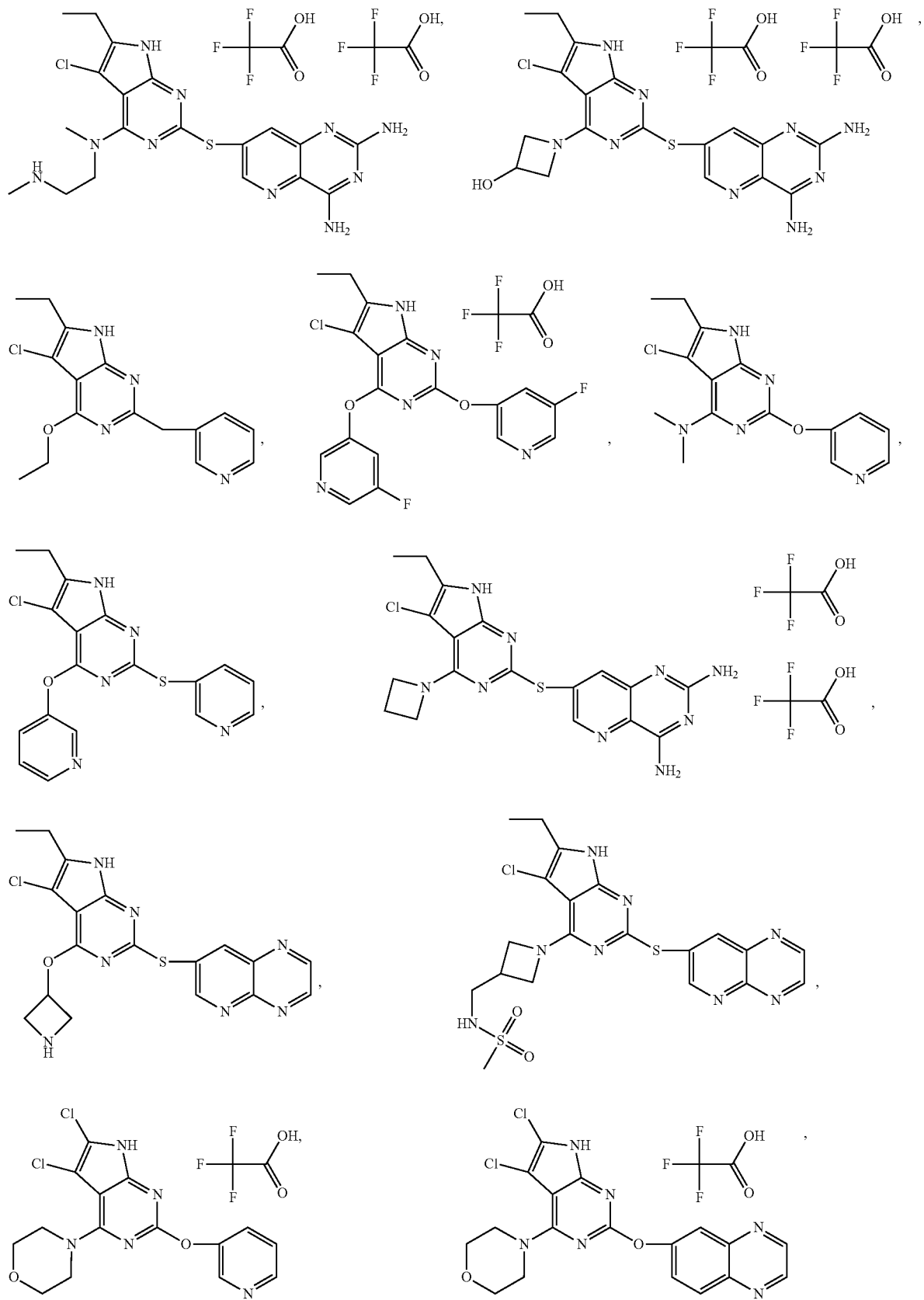

-continued
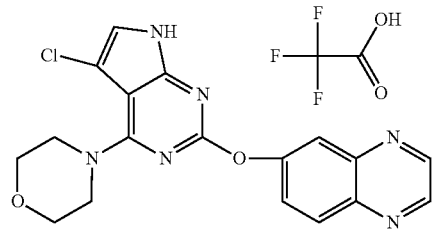
,
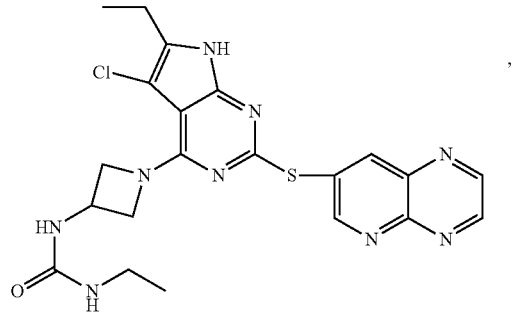
,
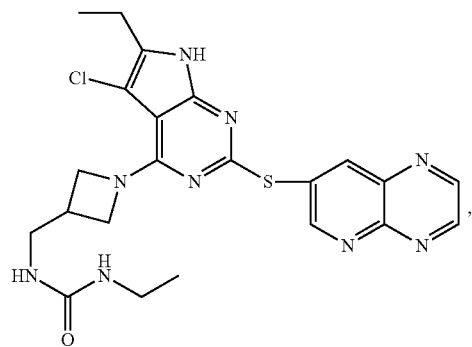
,
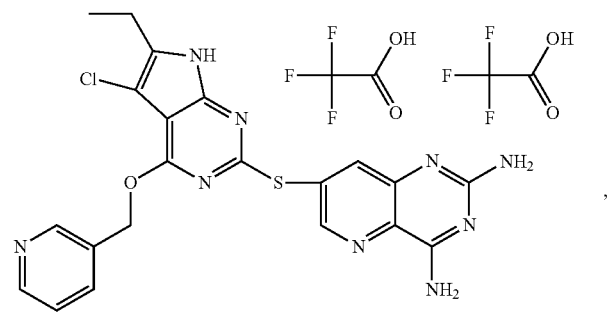
,
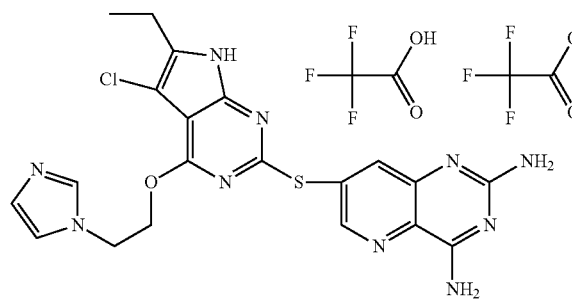
,
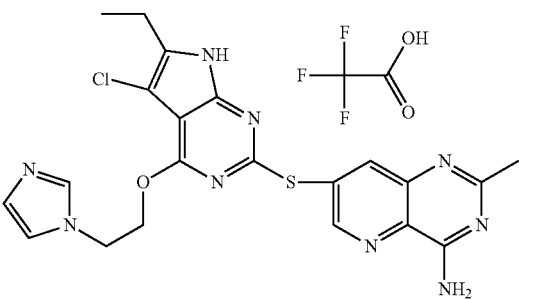
,
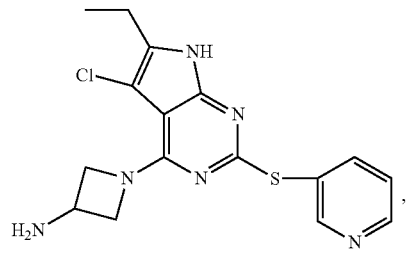
,
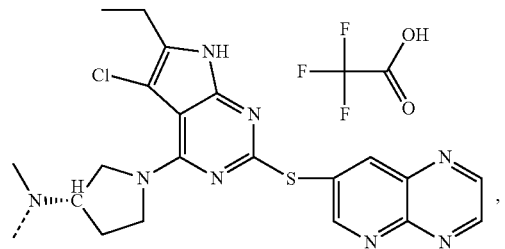
,
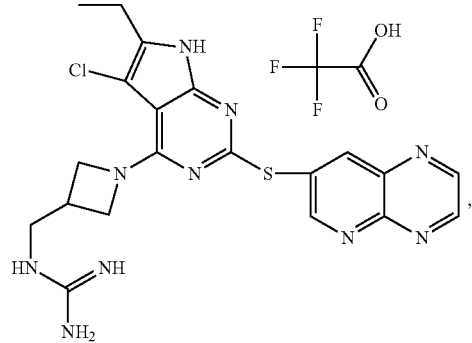
,
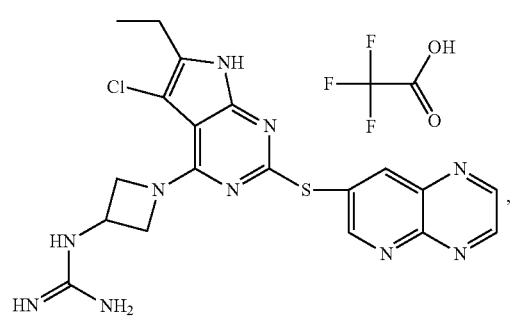
, -continued
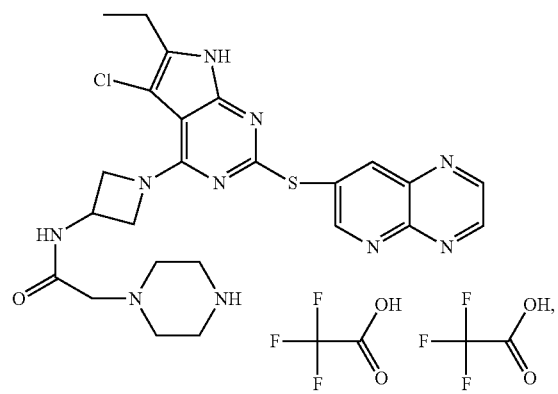
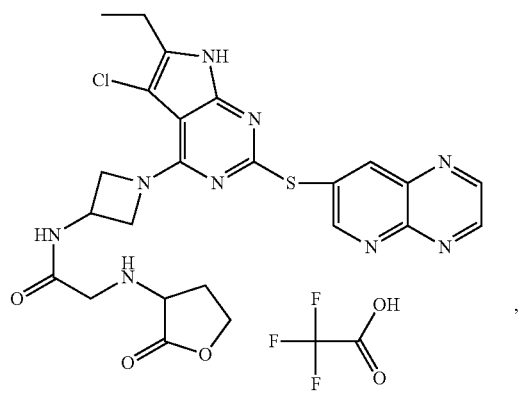
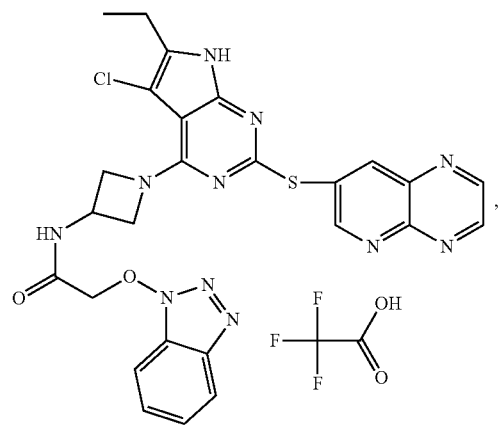
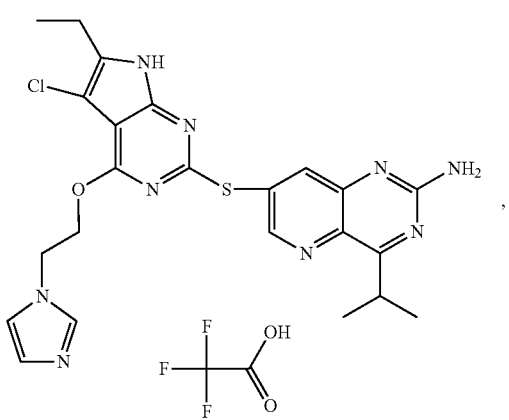
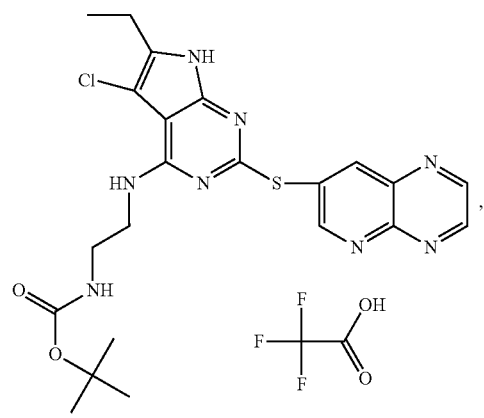
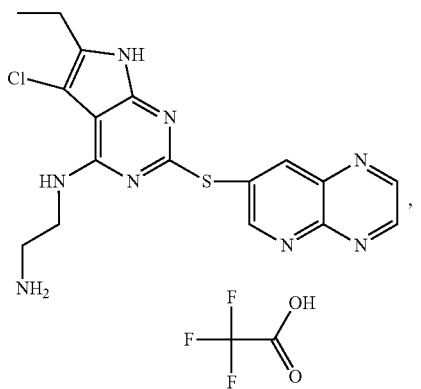
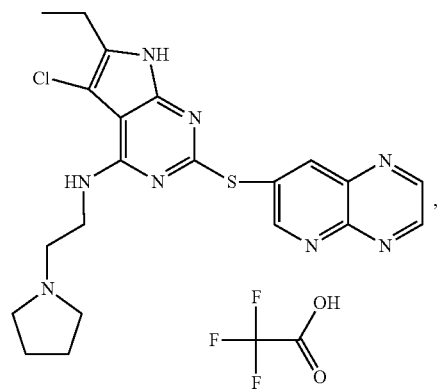
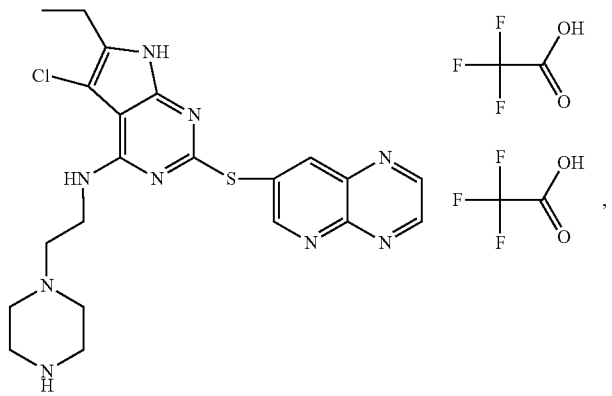

555
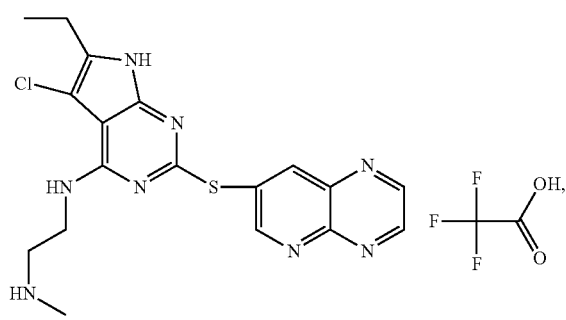
556
-continued
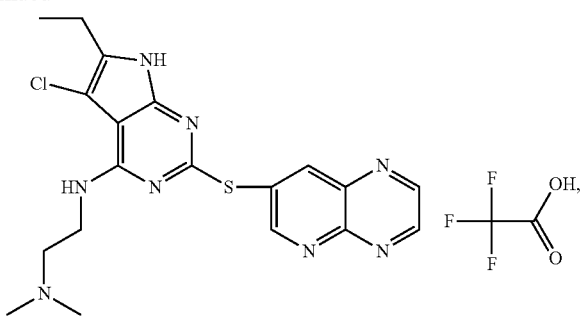
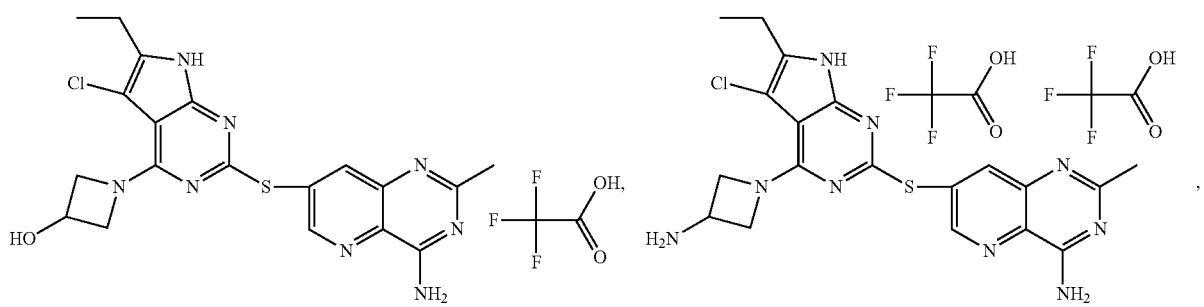
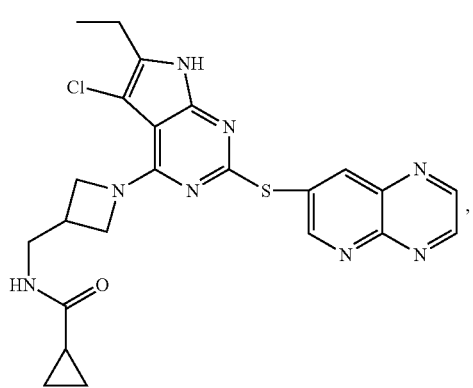
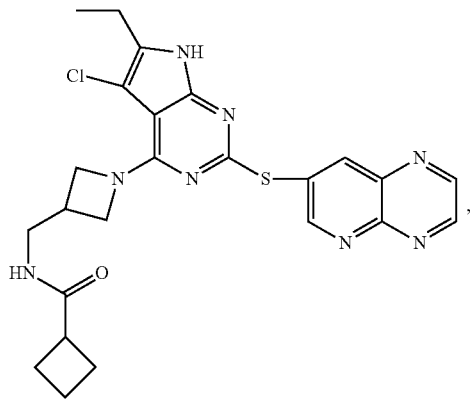
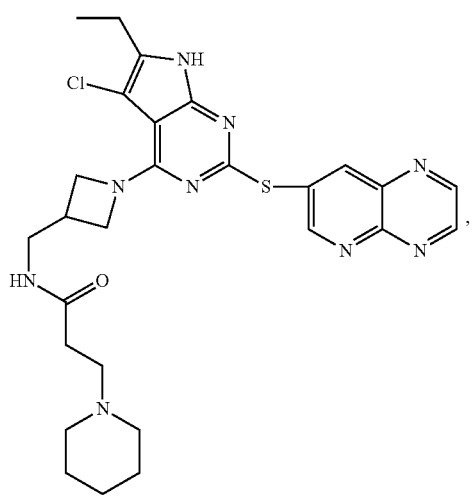
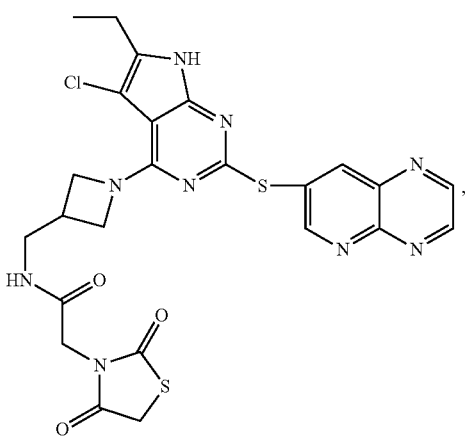

557
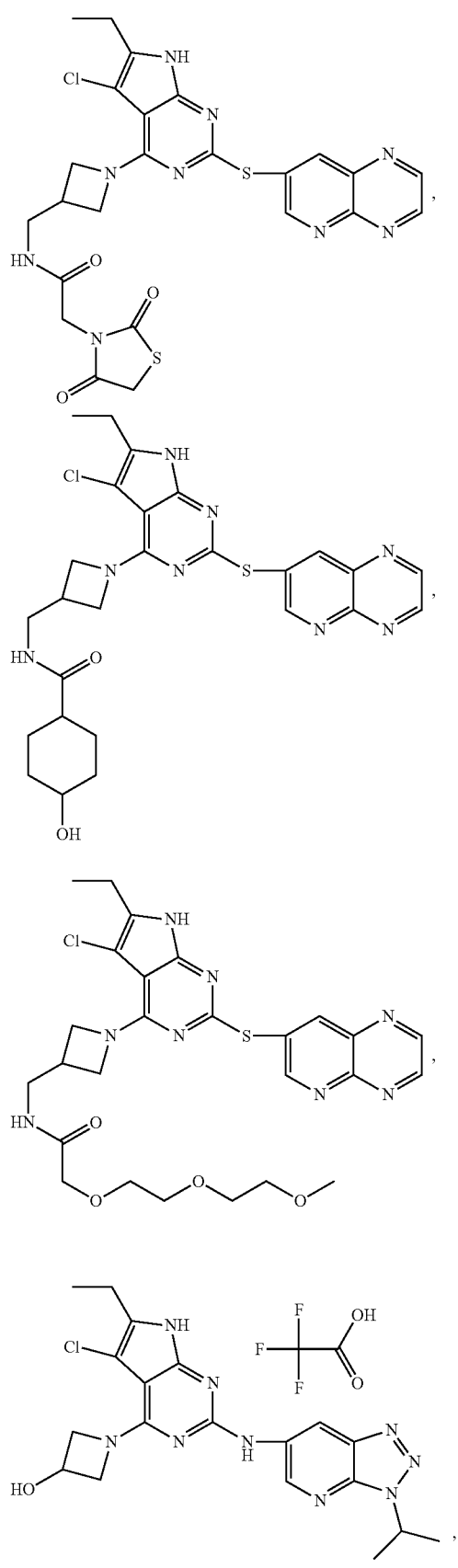
558
-continued
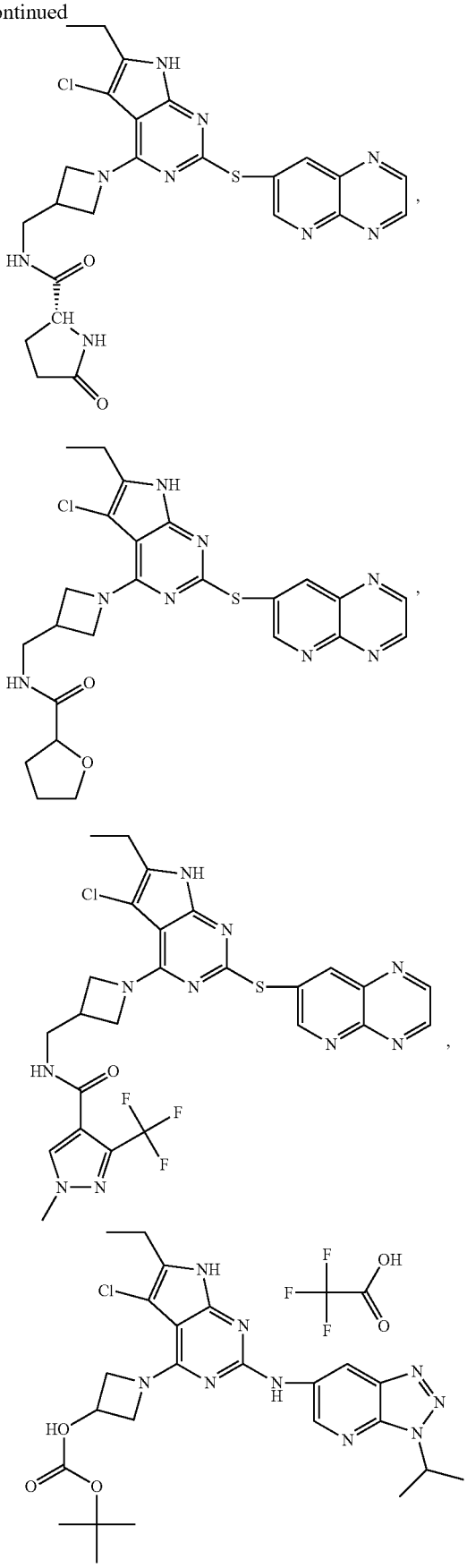

-continued
559
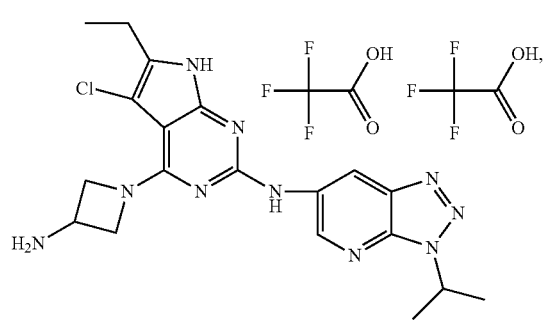
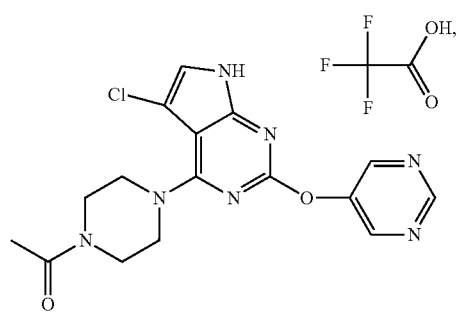
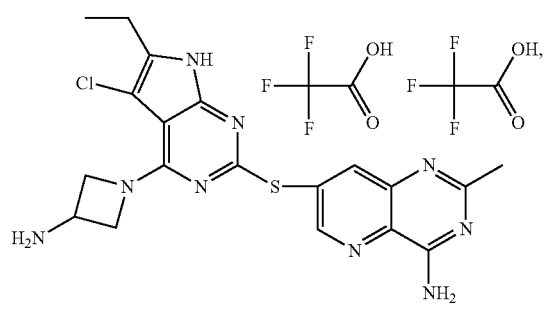
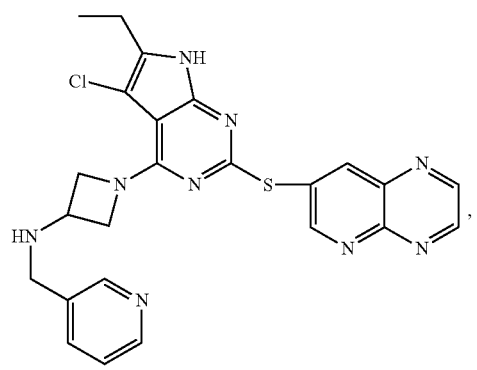
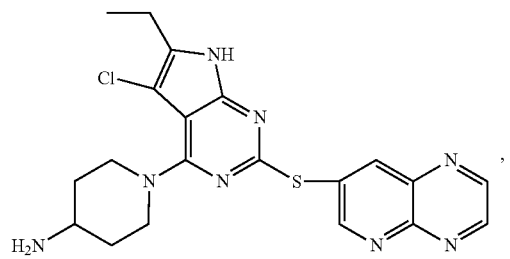
560
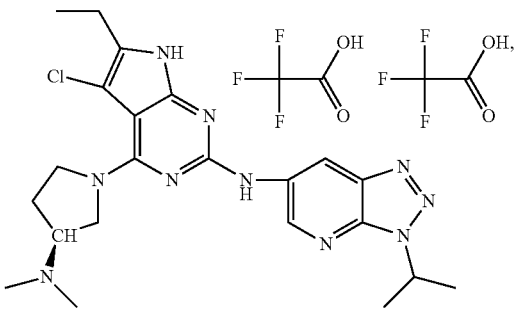
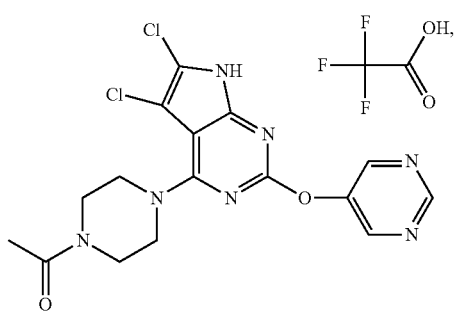
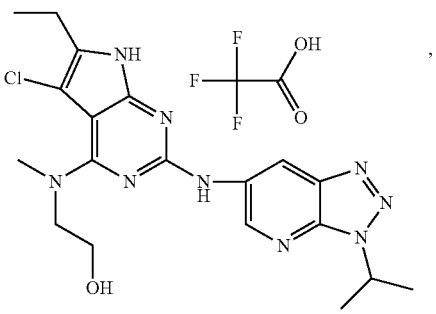
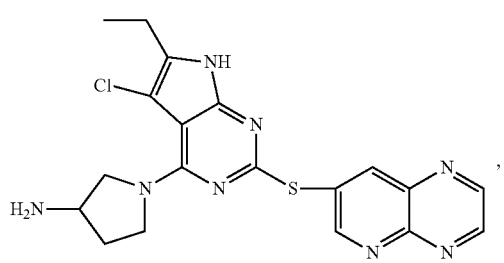
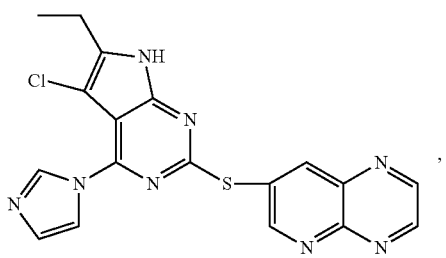

561
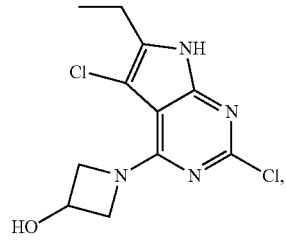
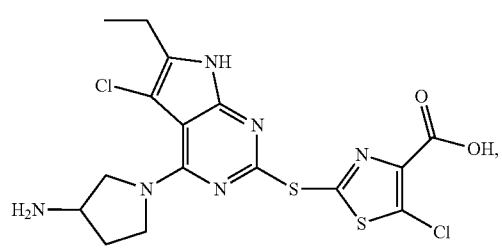
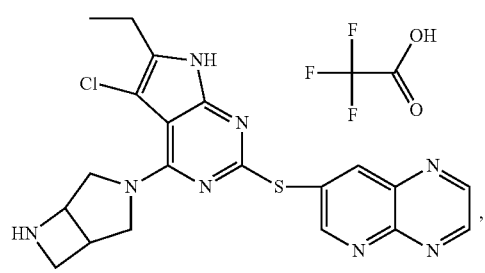
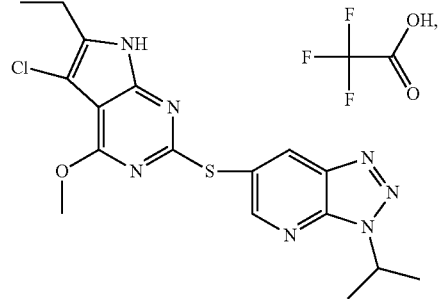
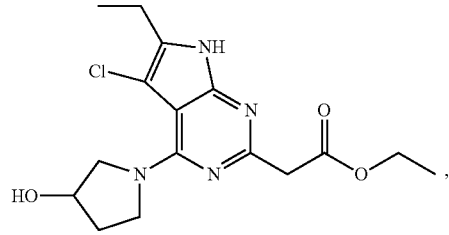
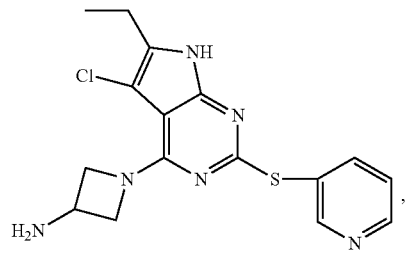
562
-continued
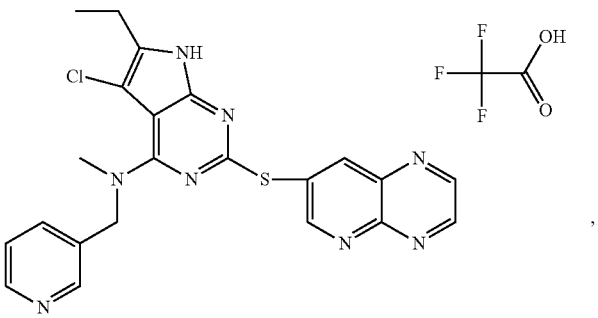
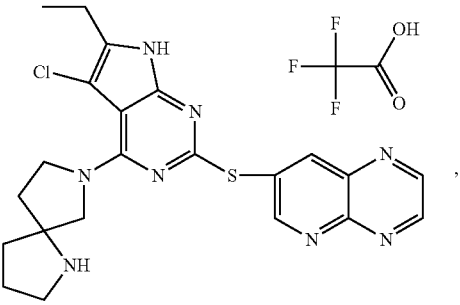
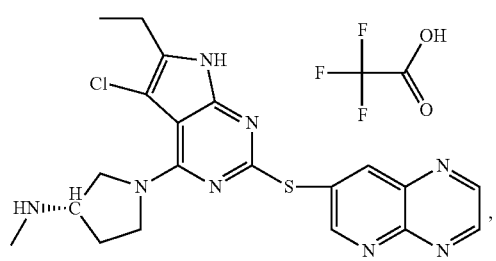
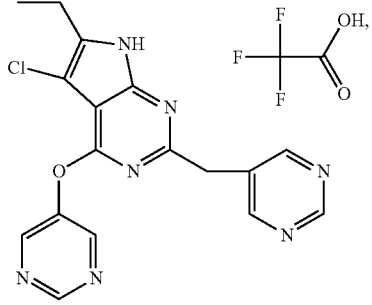
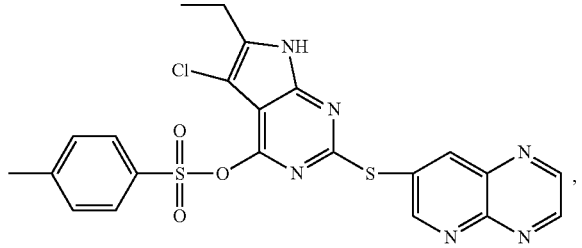
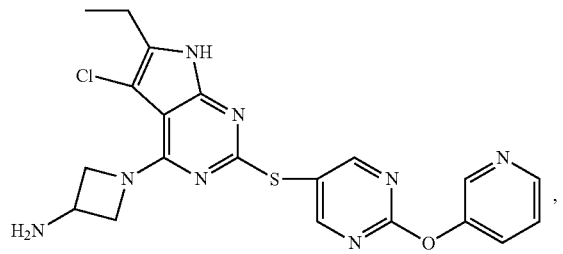

-continued
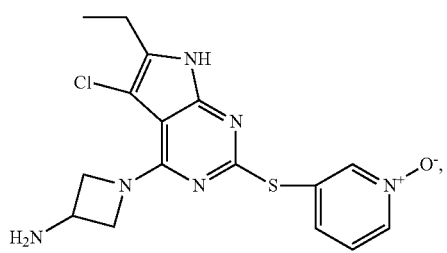
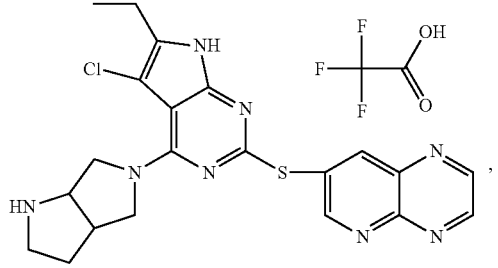
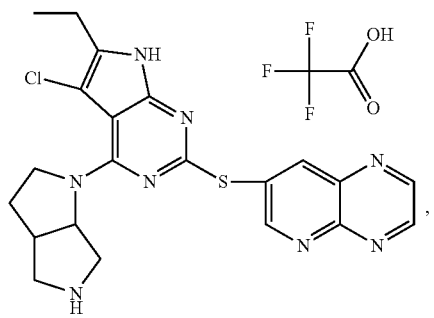
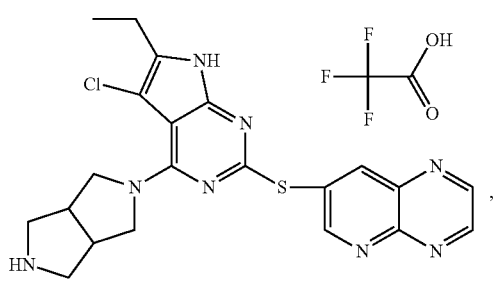
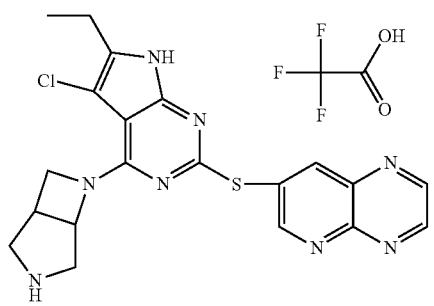
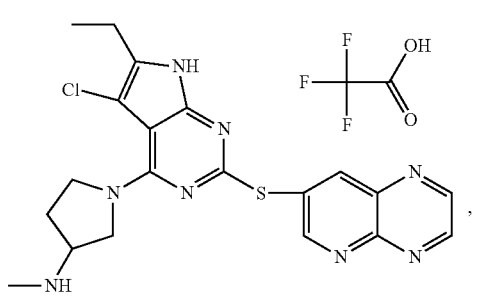
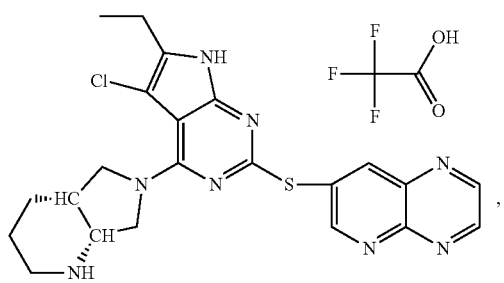
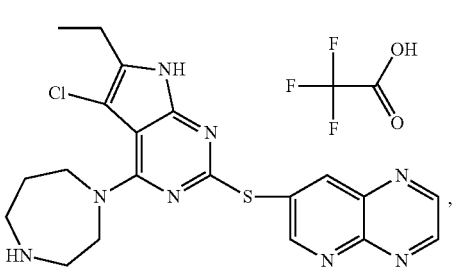
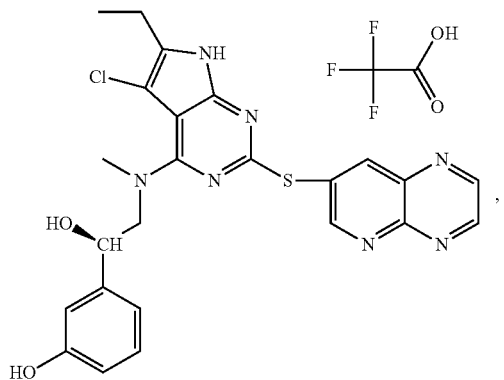
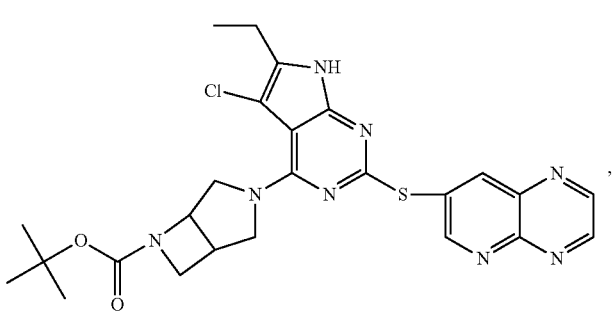

565
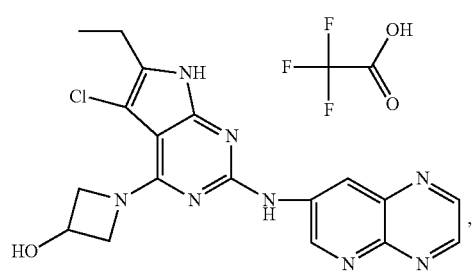
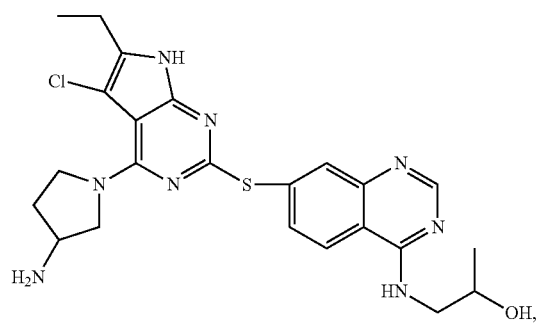
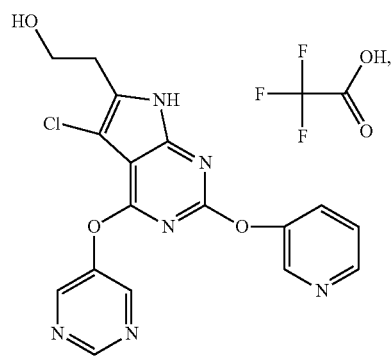
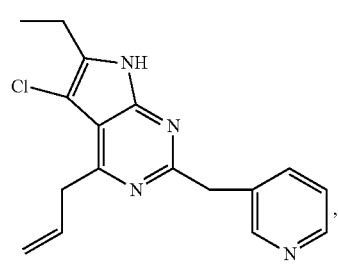
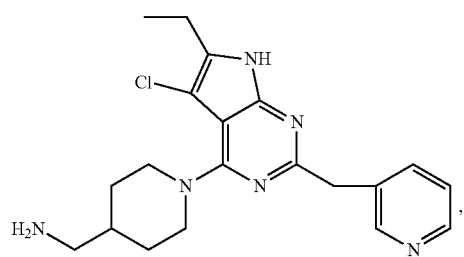
566
-continued
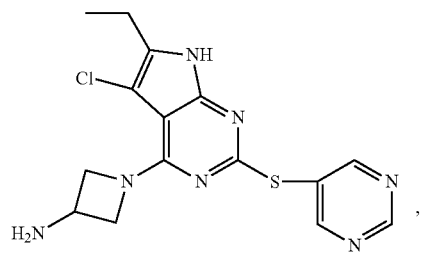
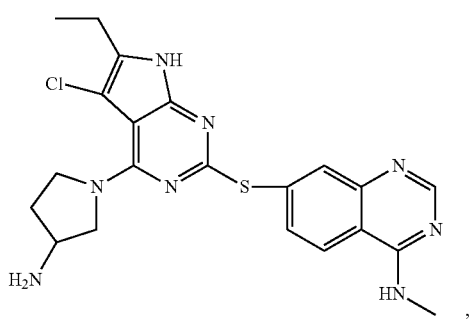
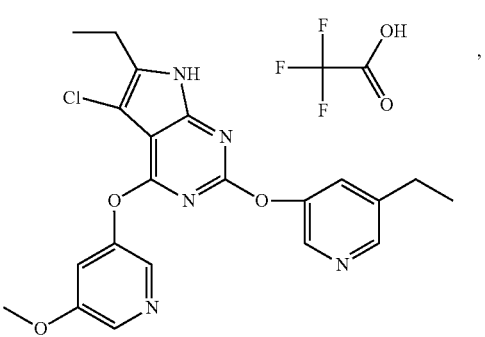
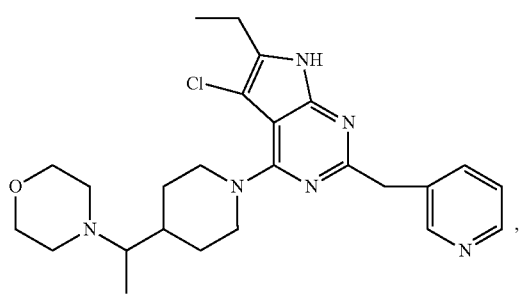
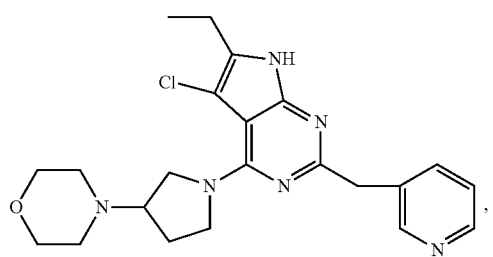

567
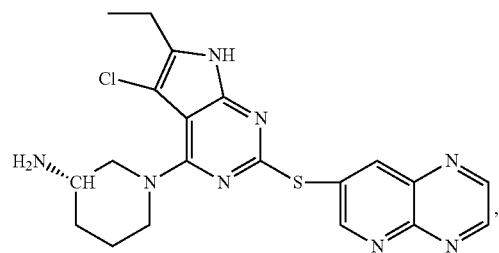
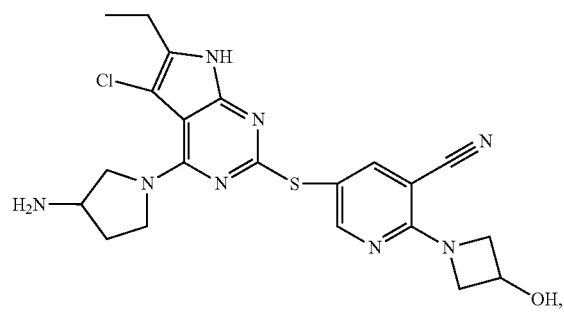
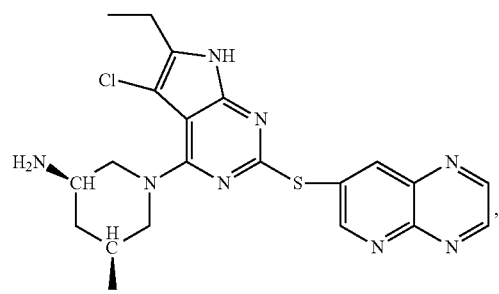
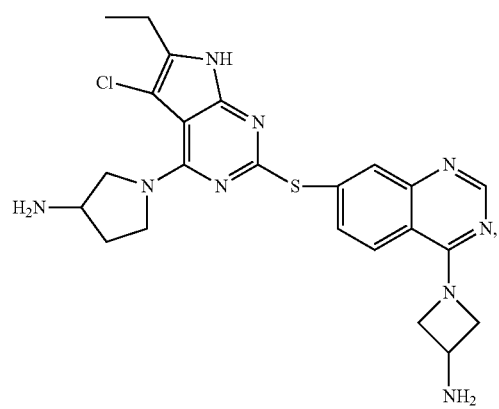
568
-continued
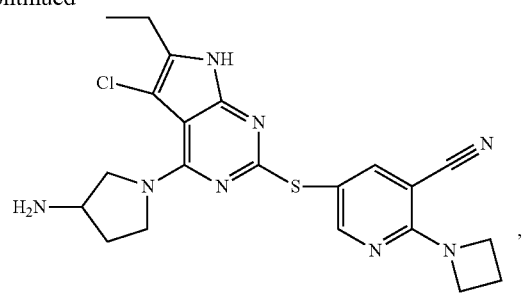
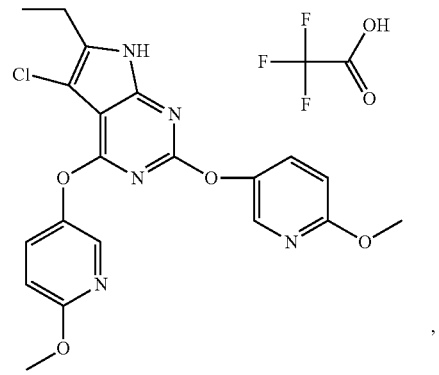
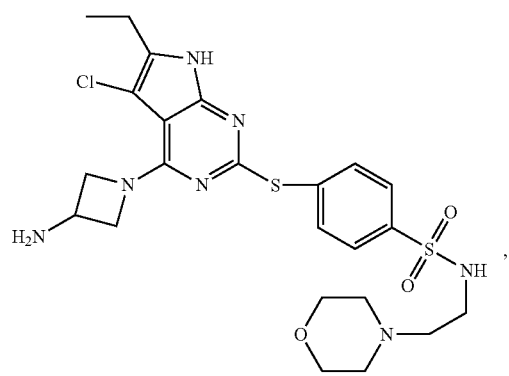
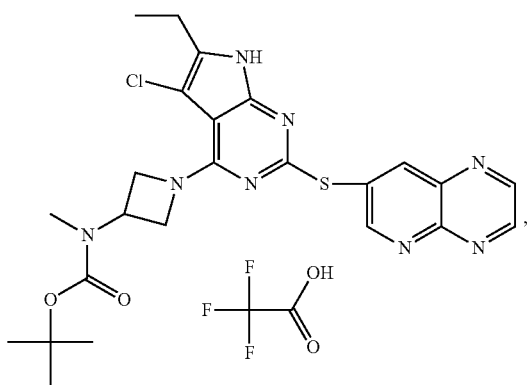

-continued
569
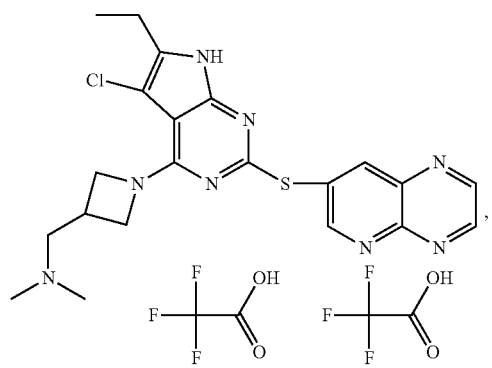
570
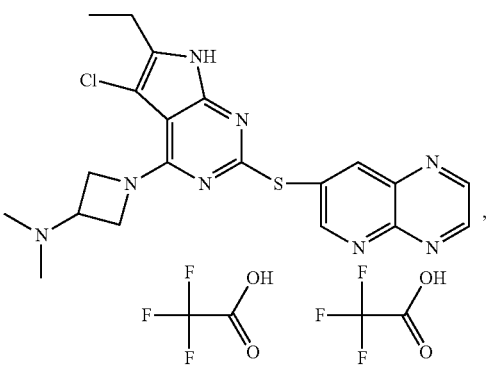
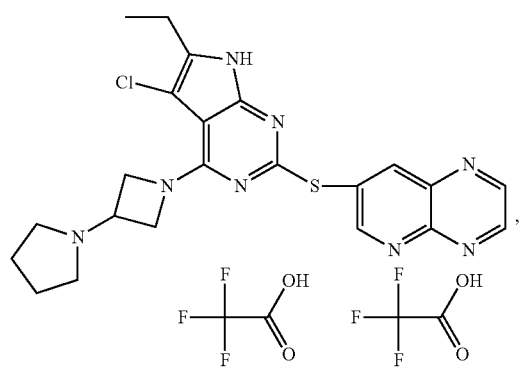
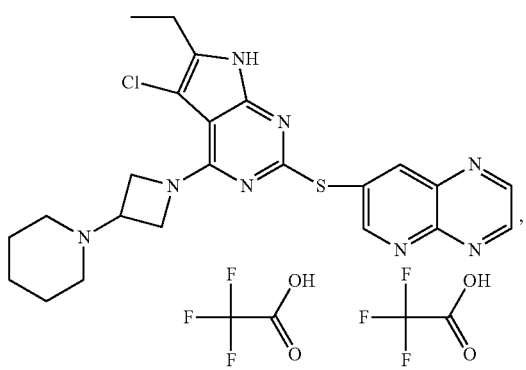
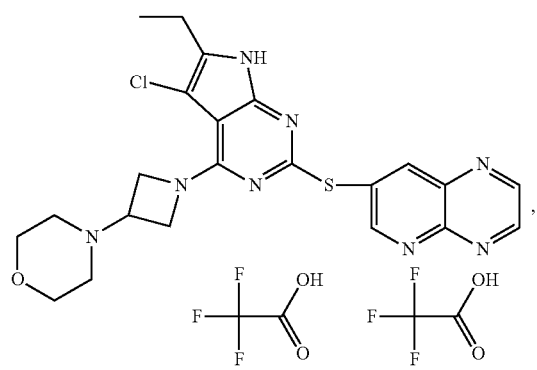
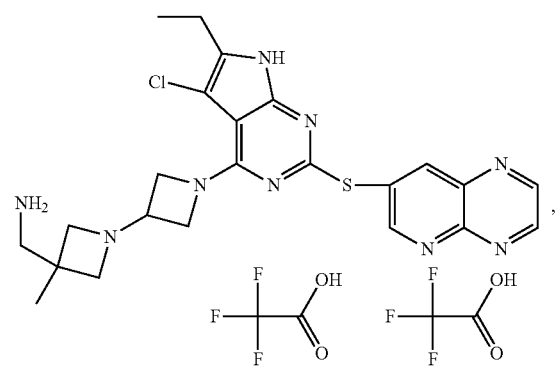
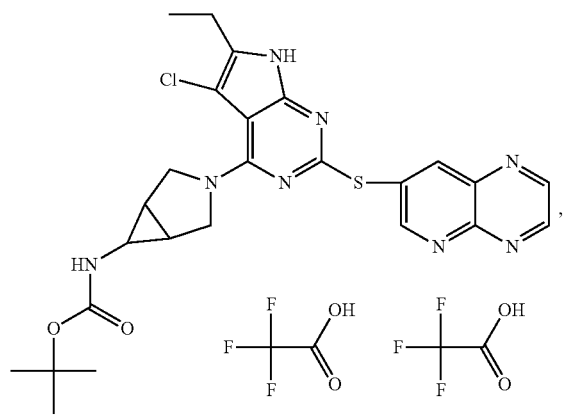
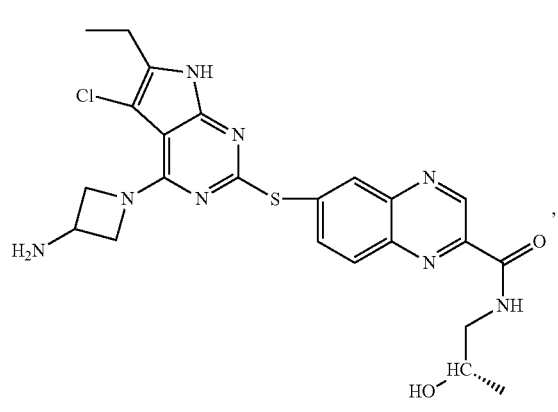

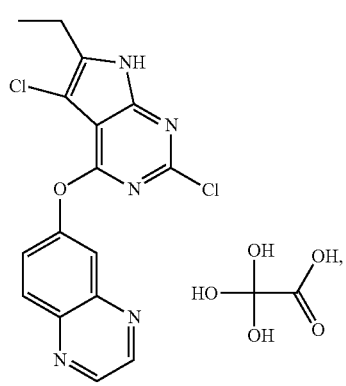
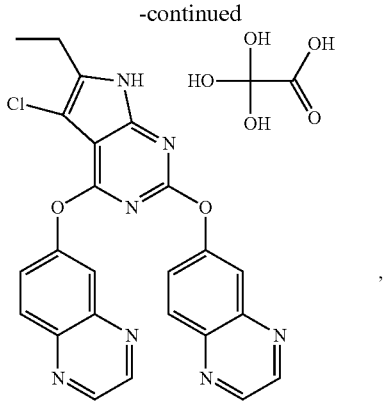
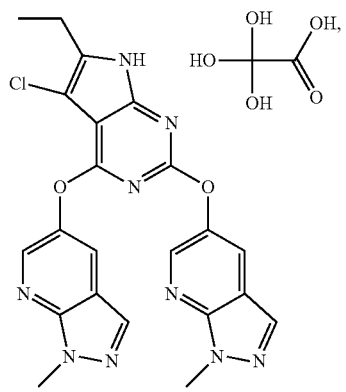
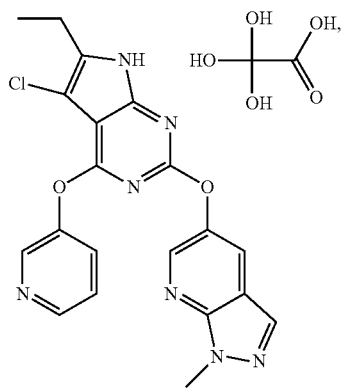
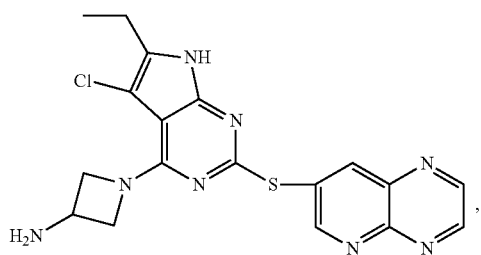
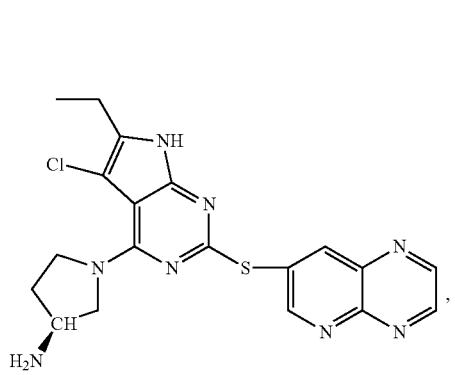
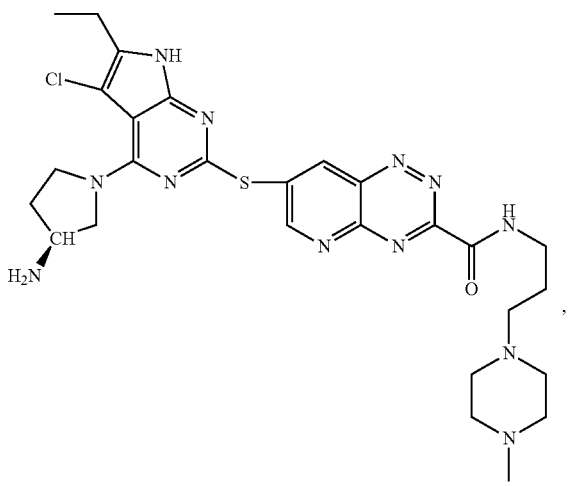

-continued
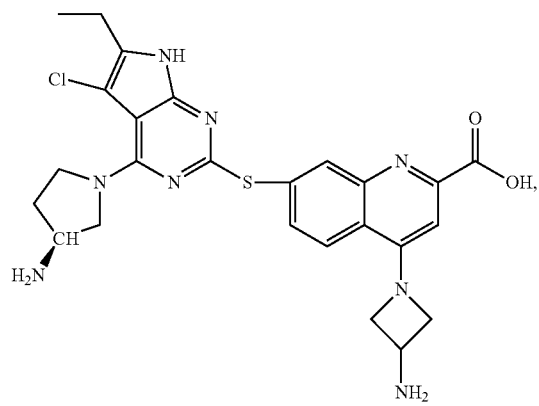
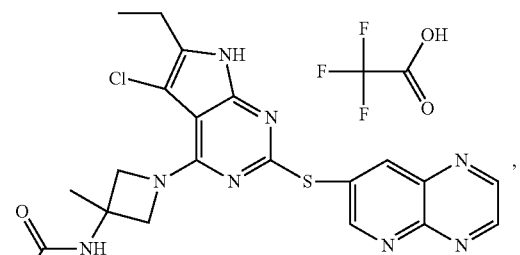
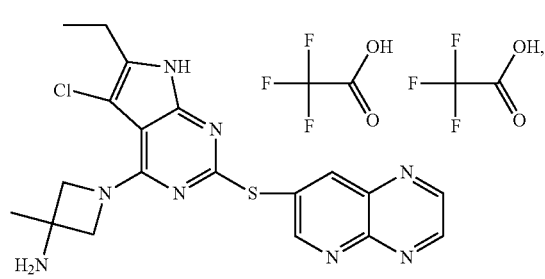
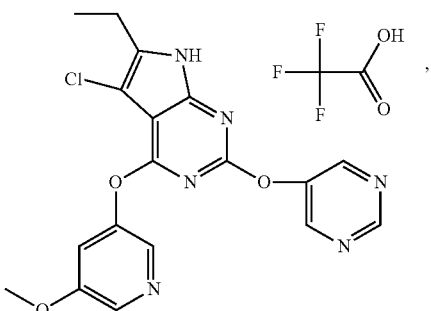
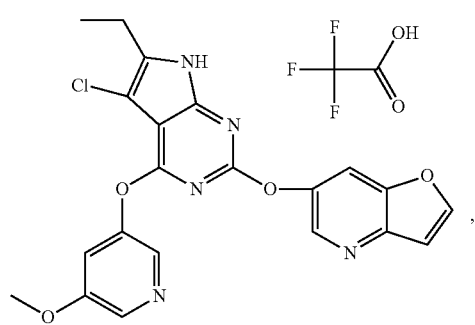
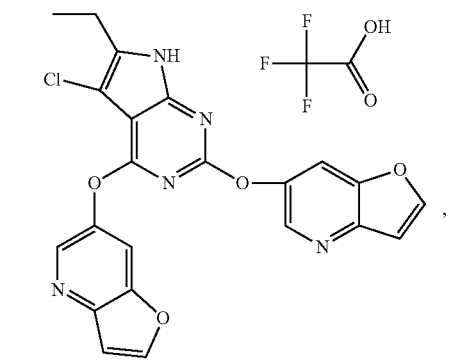
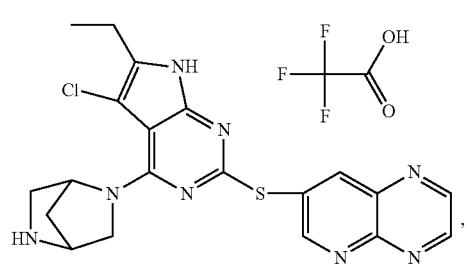
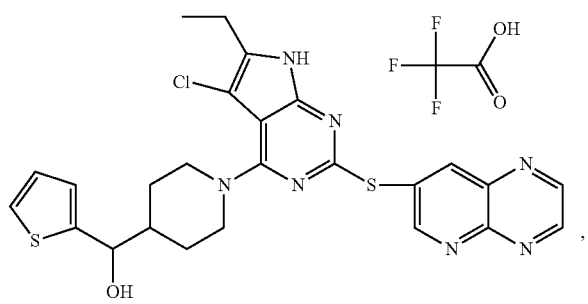
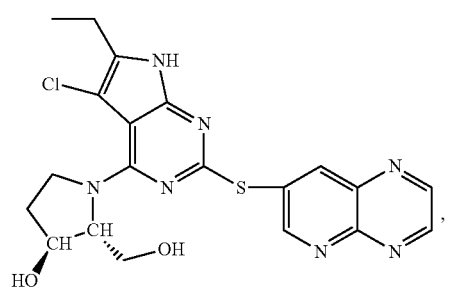
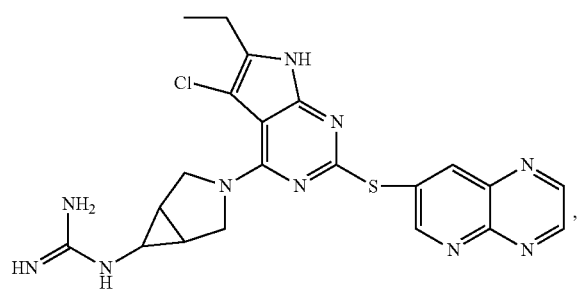

-continued
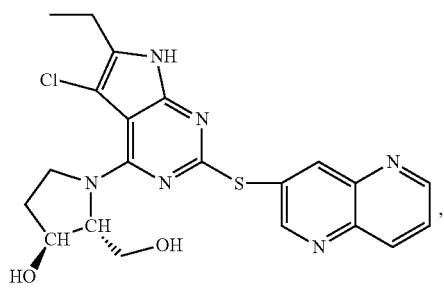
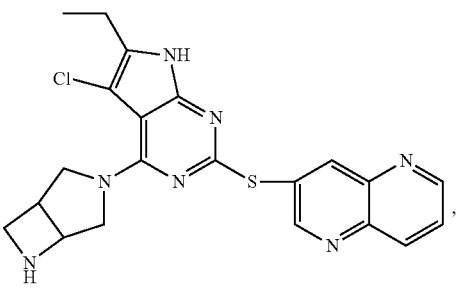
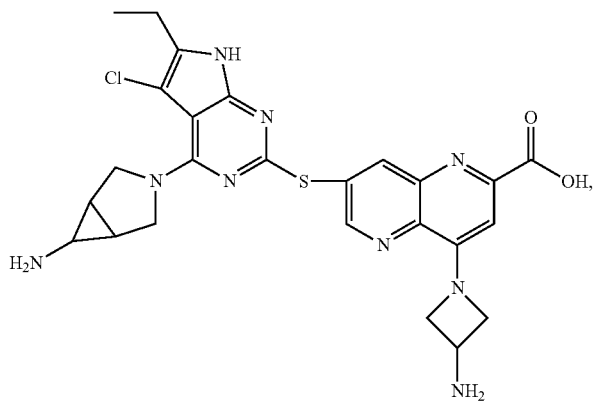
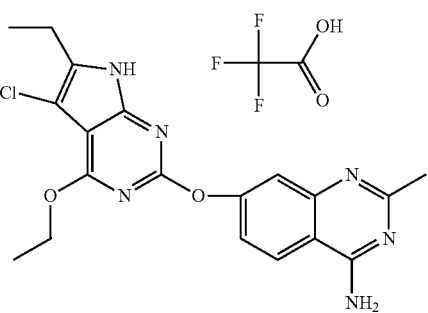
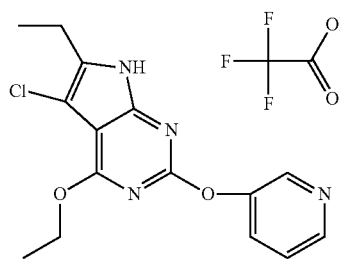
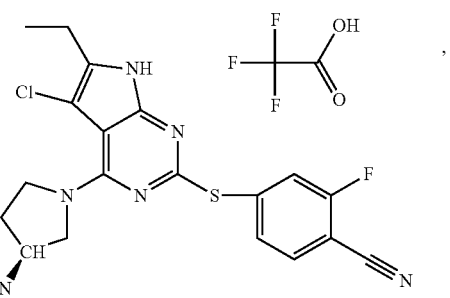
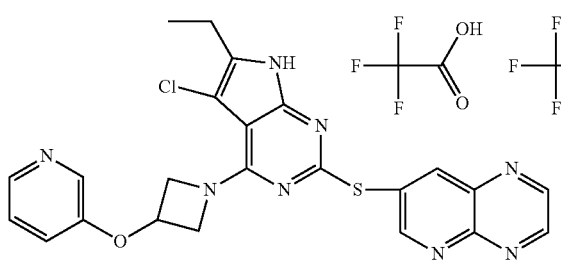
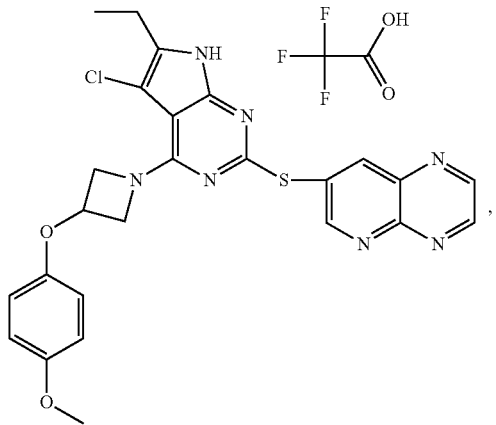

-continued
577
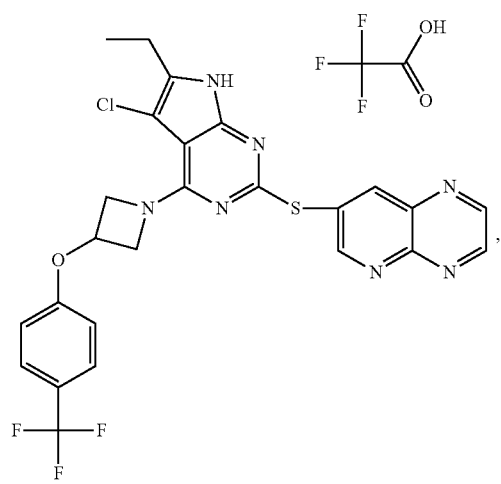
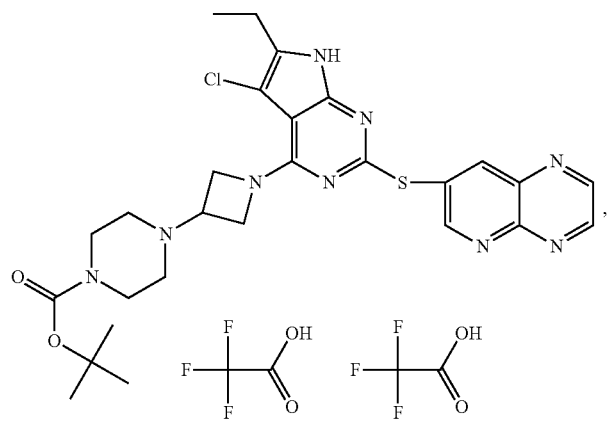
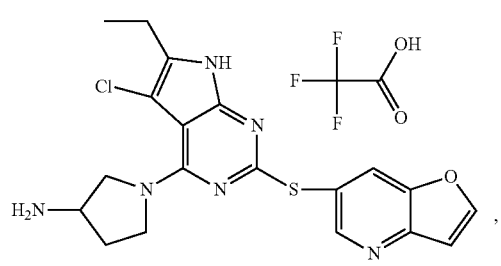
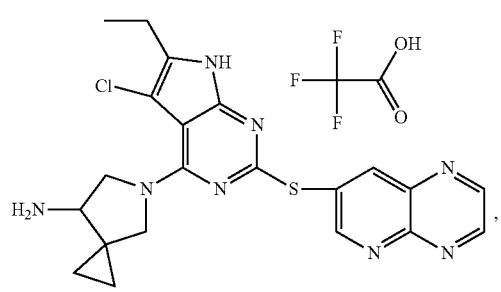
578
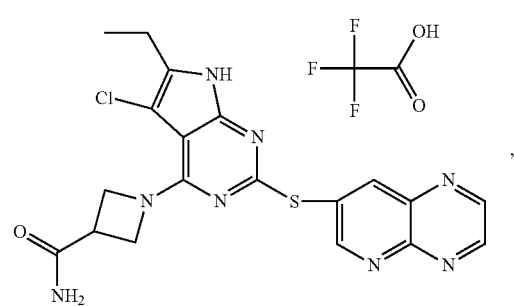
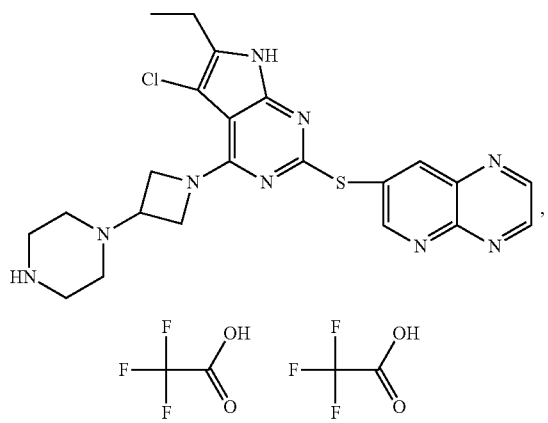
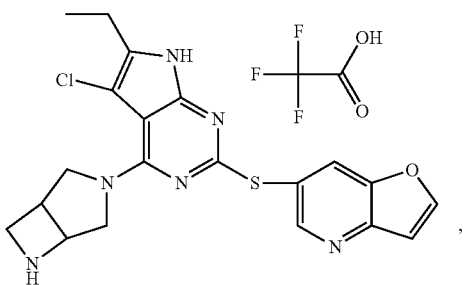
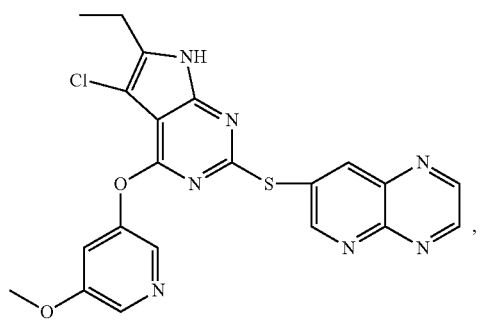

-continued
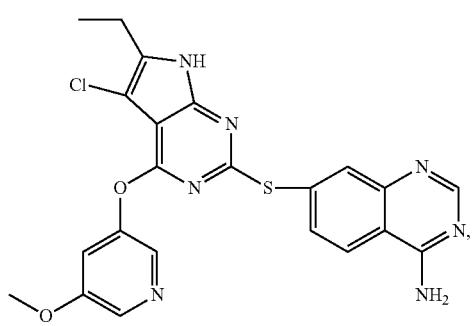
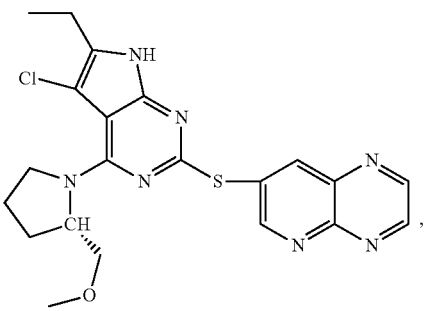
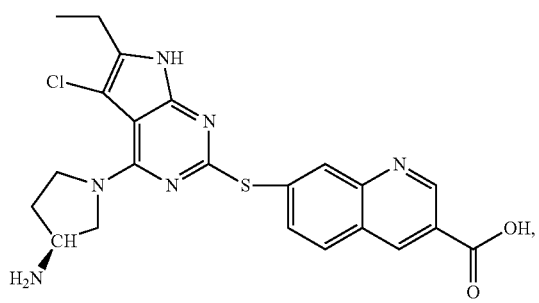
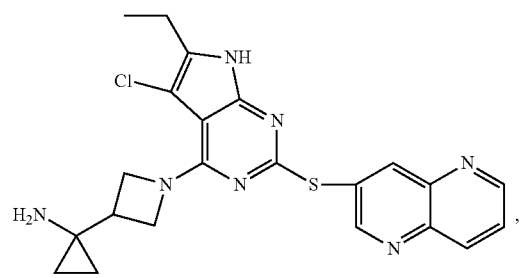
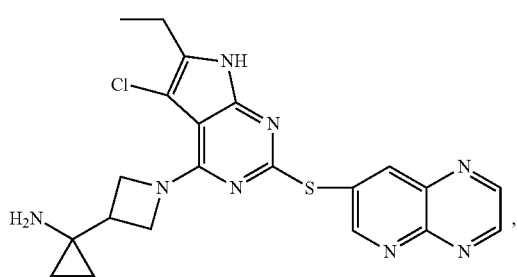
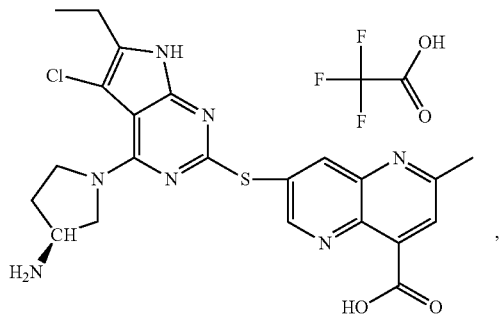
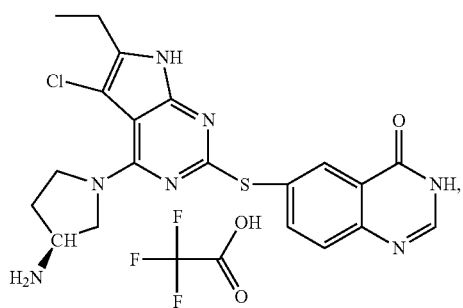
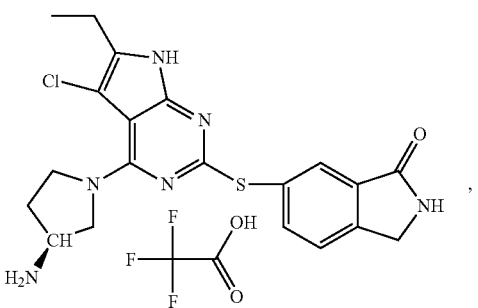
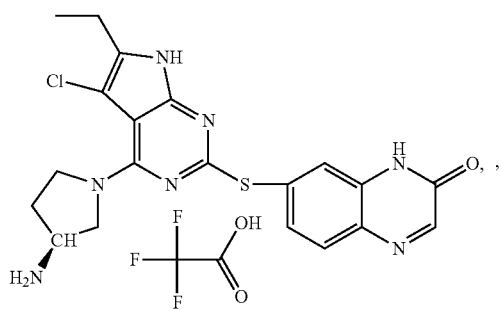
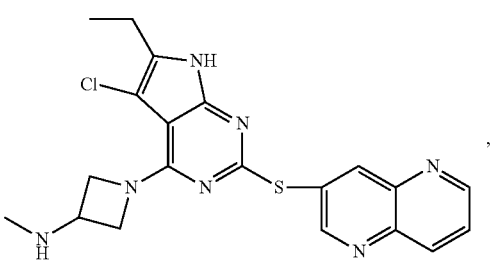

581
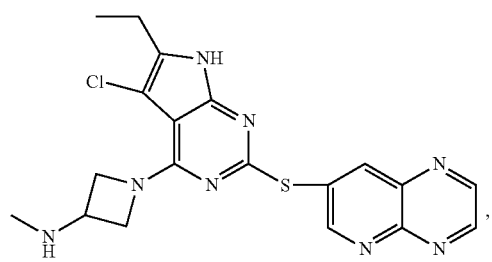
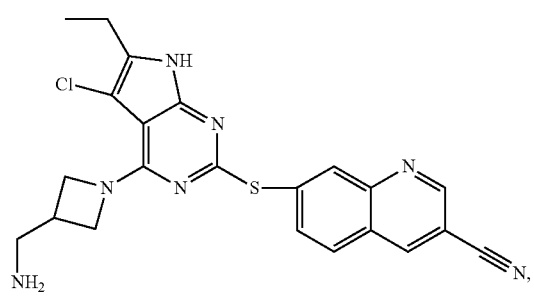
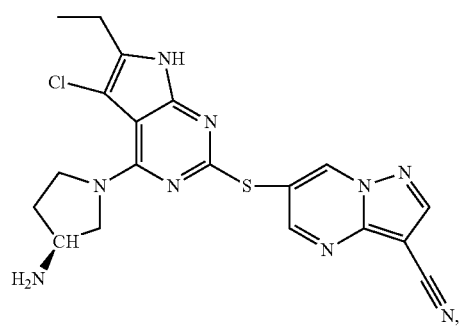
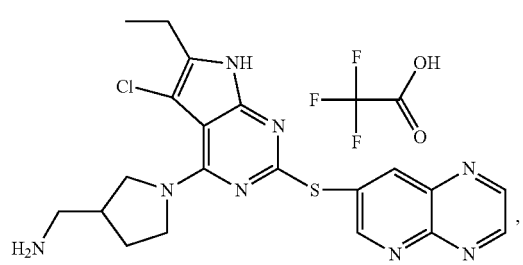
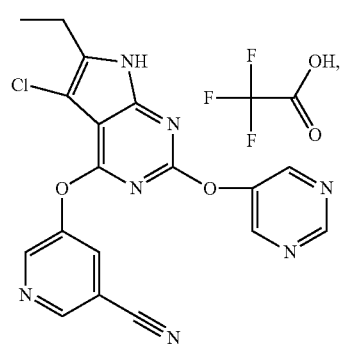
582
-continued
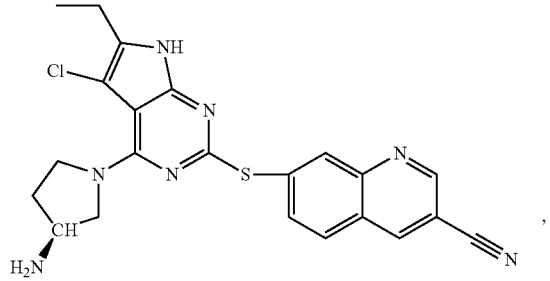
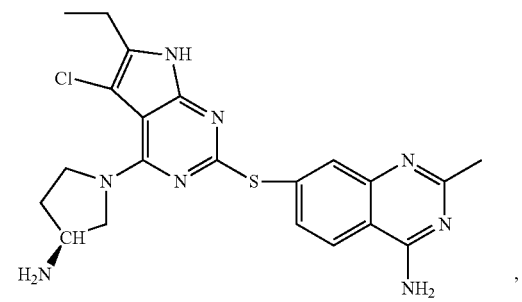
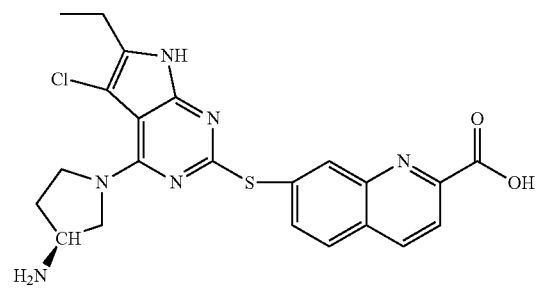
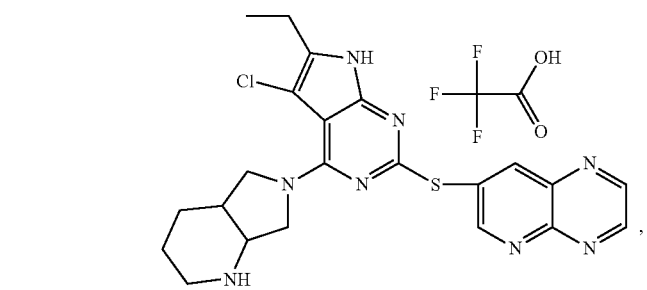
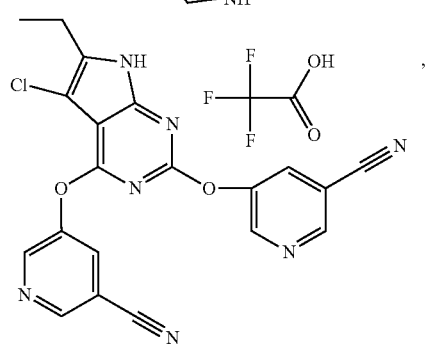

583
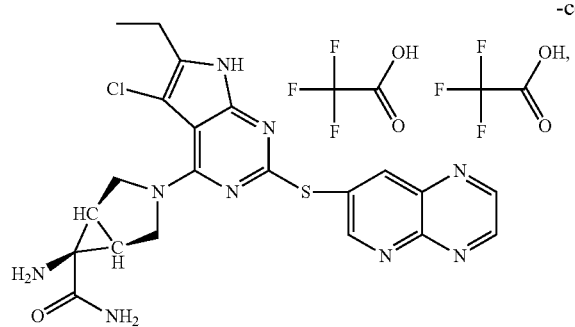
584
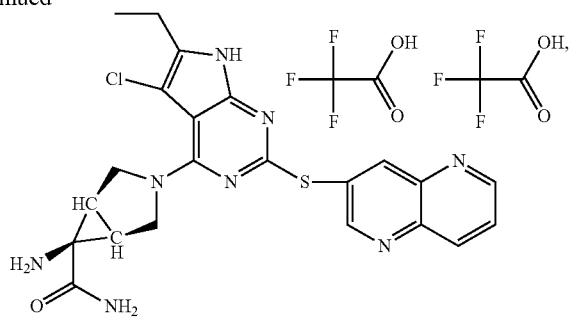
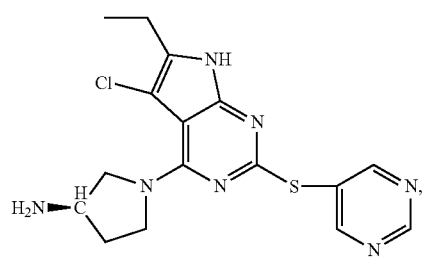
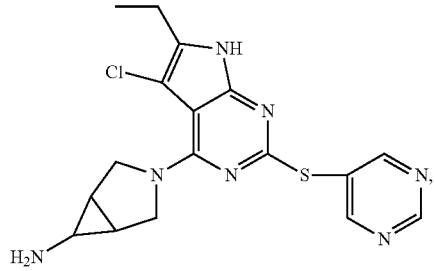
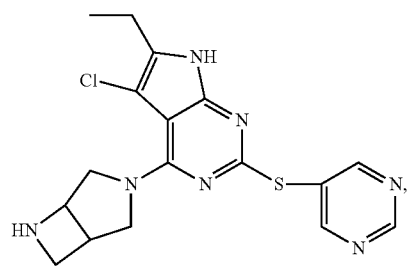
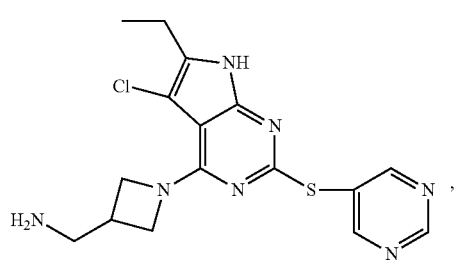
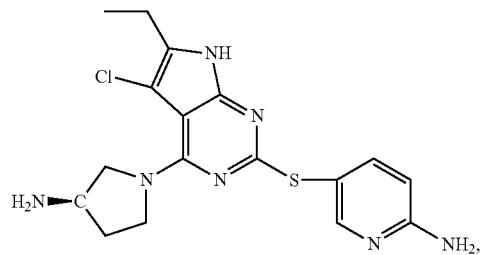
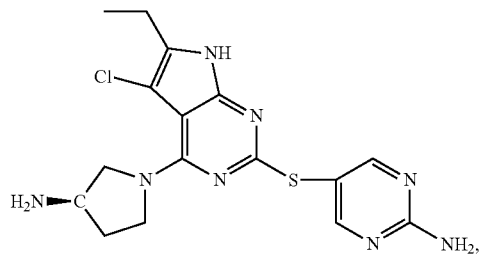
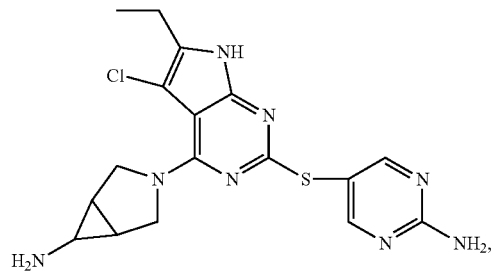
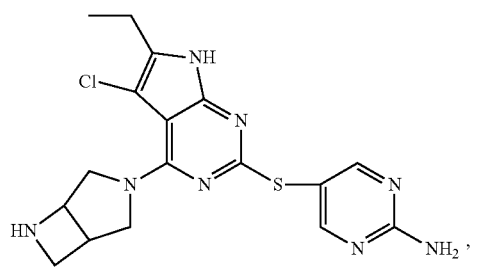

585
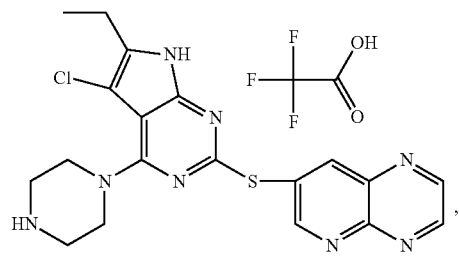
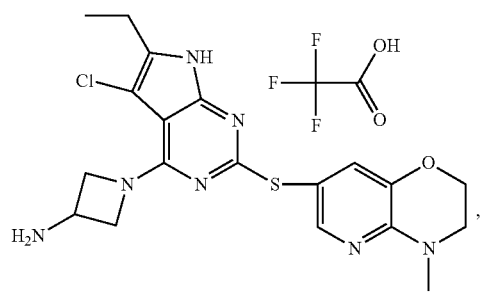
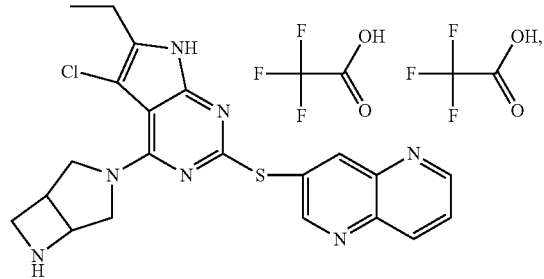
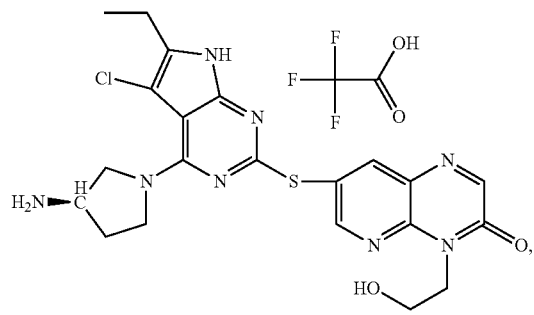
586
-continued
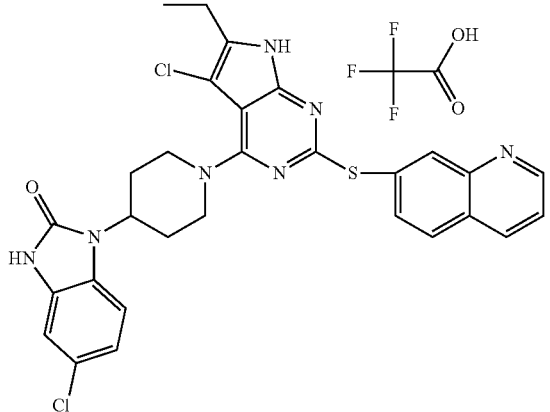
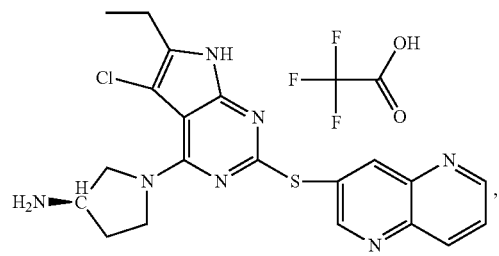
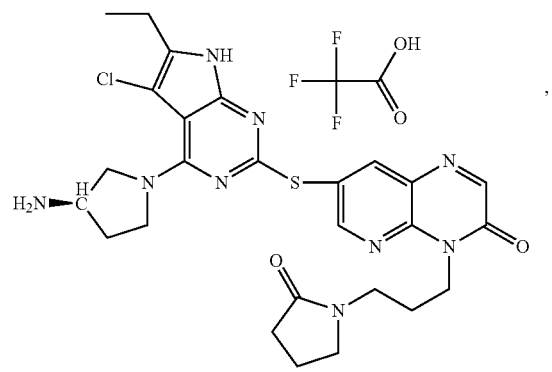
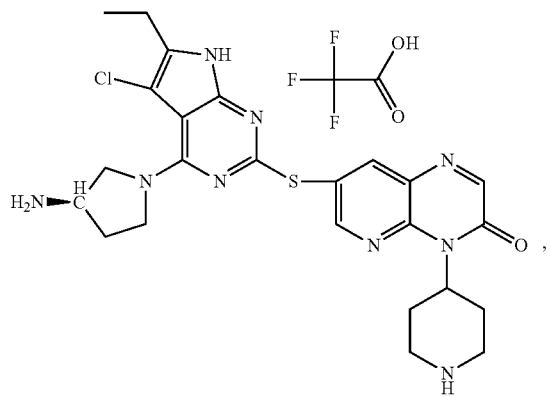

587
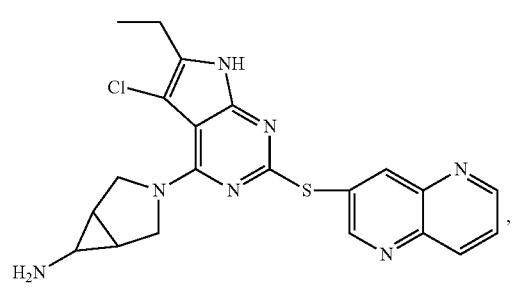
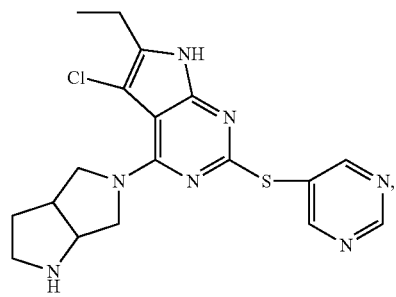
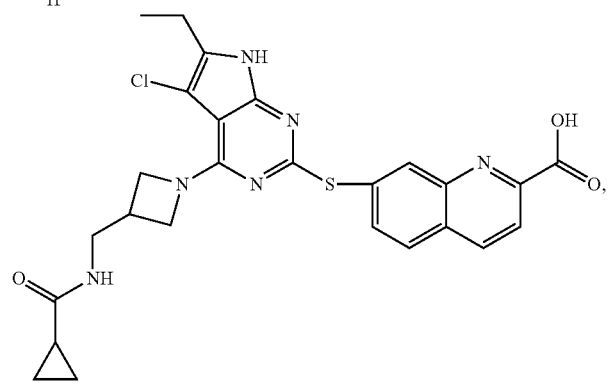
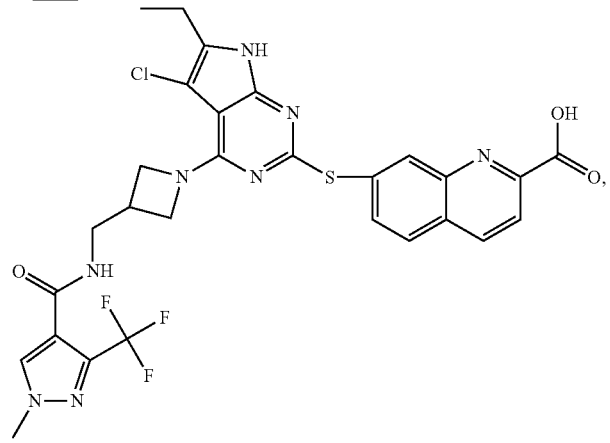
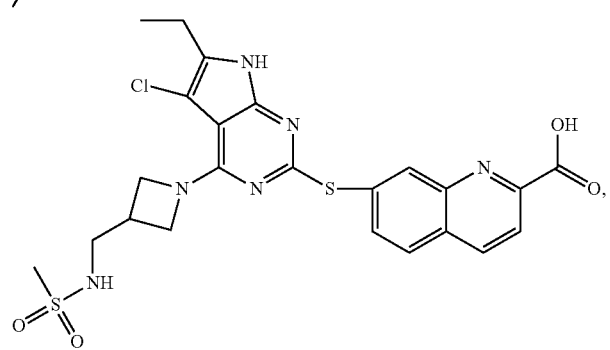
588
-continued
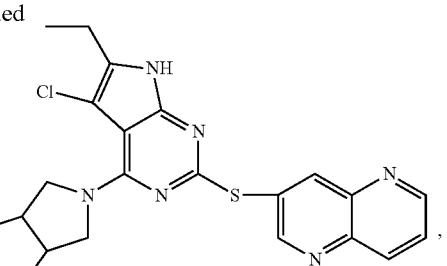
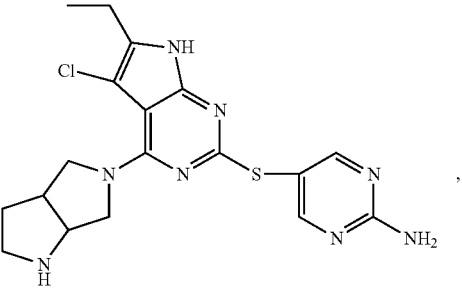

-continued
589
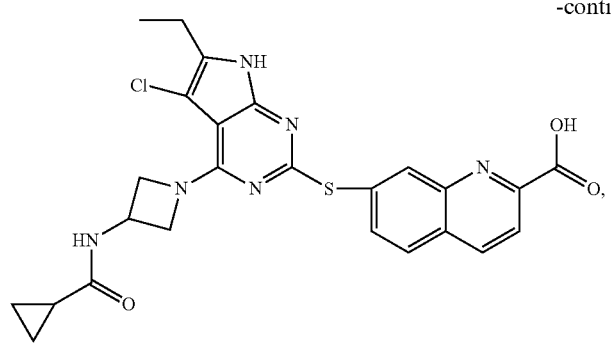
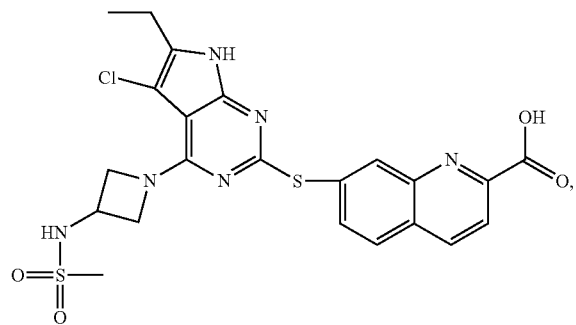
590
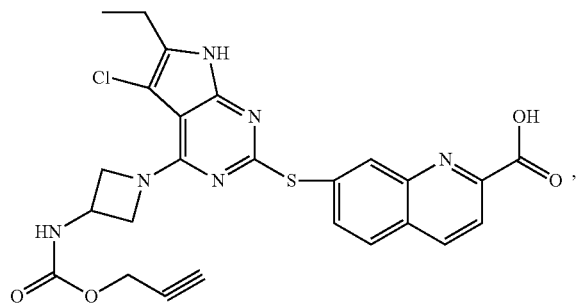
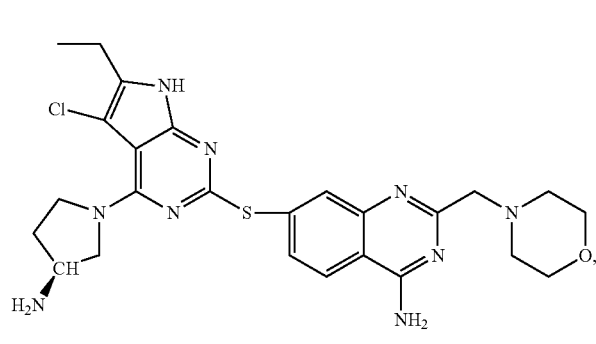
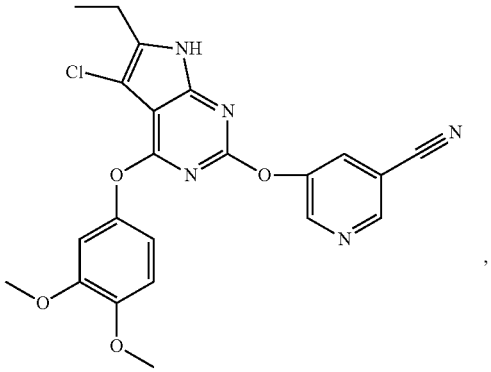
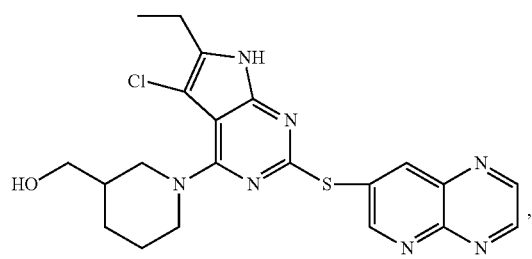
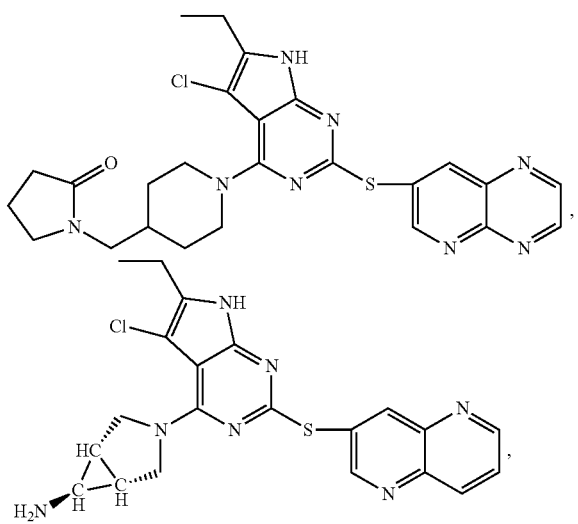
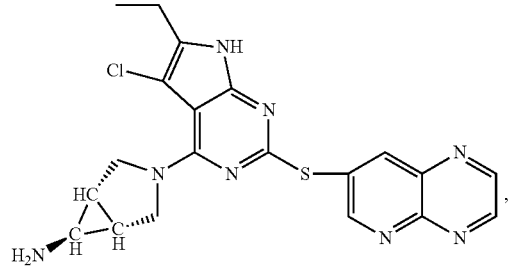

-continued
591
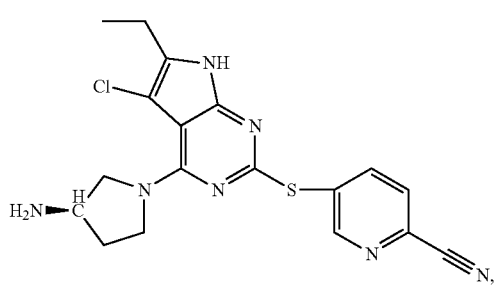
592
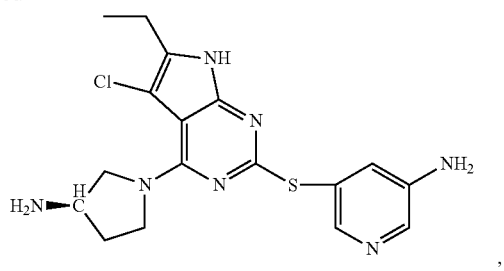
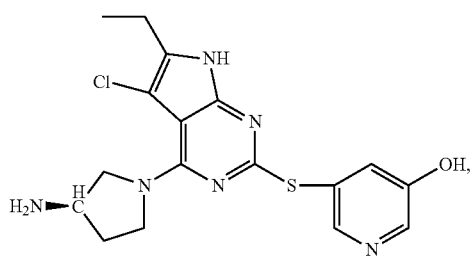
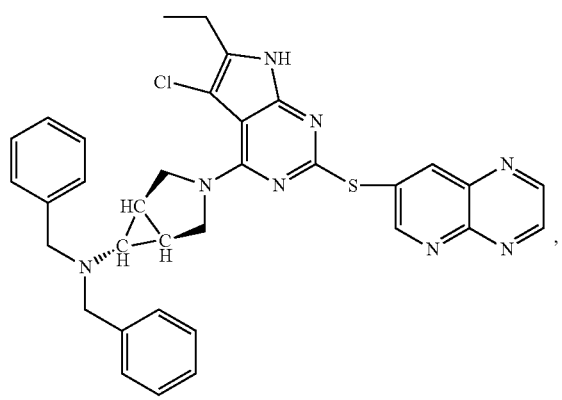
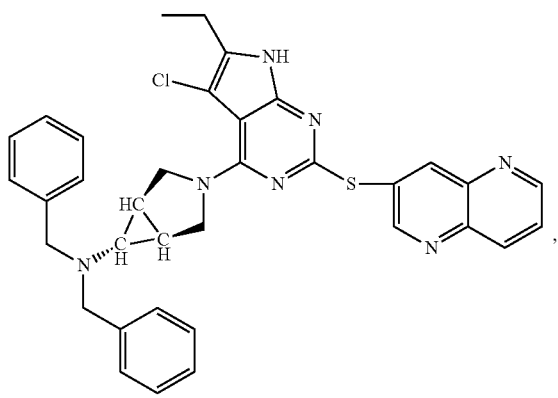
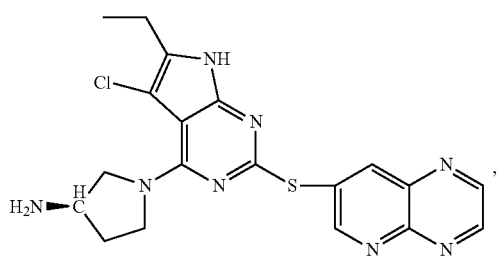
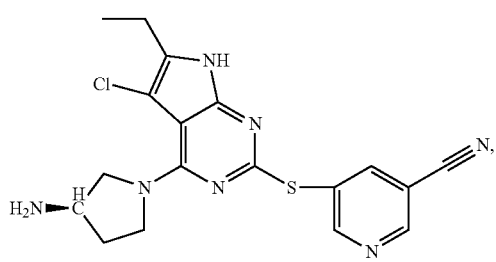
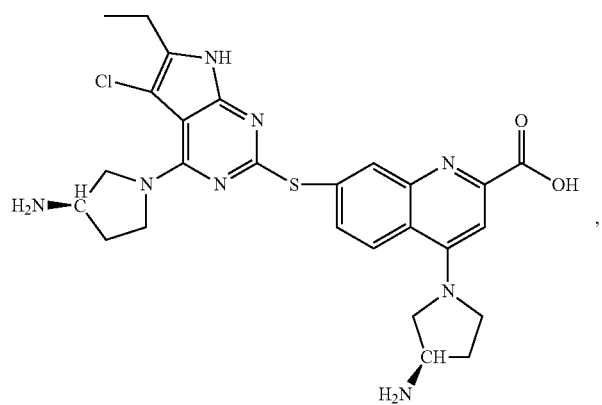

593
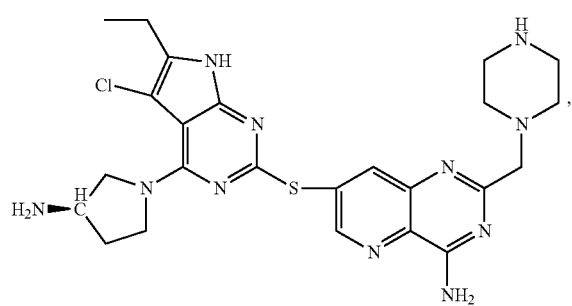
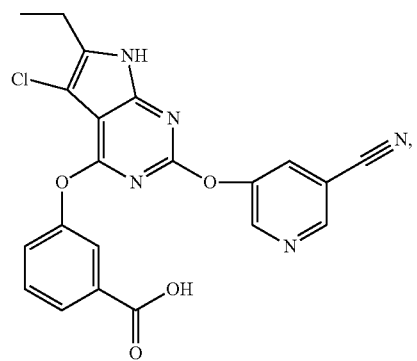
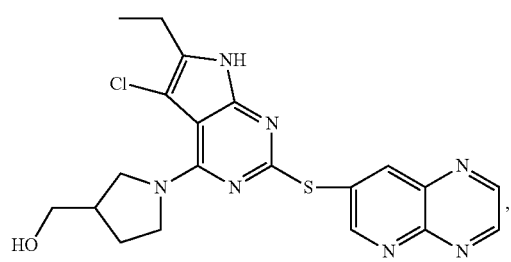
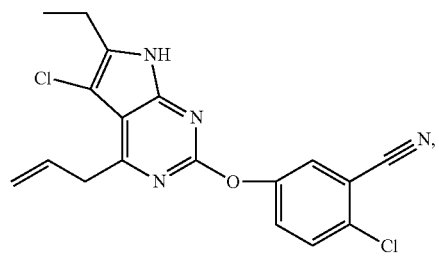
594
-continued
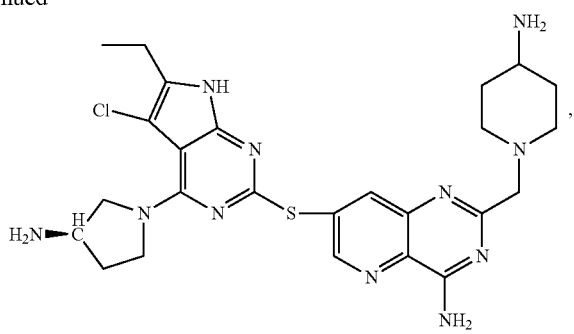
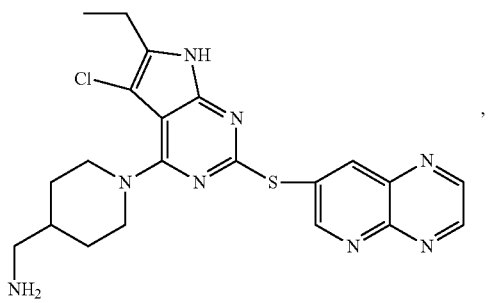
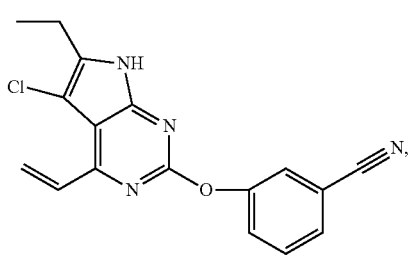
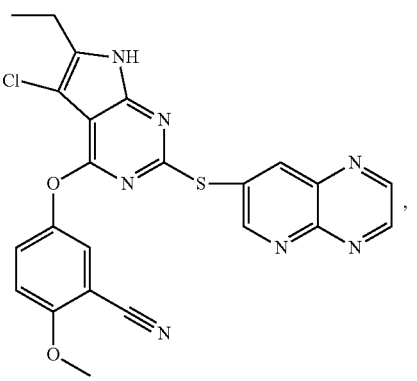

595
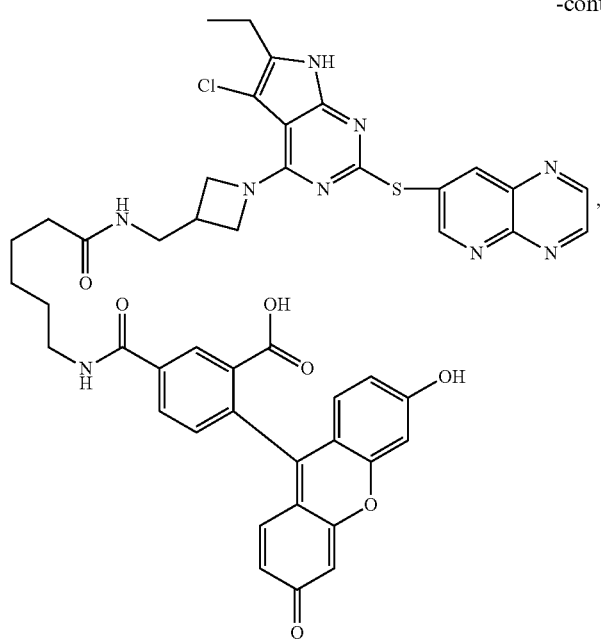
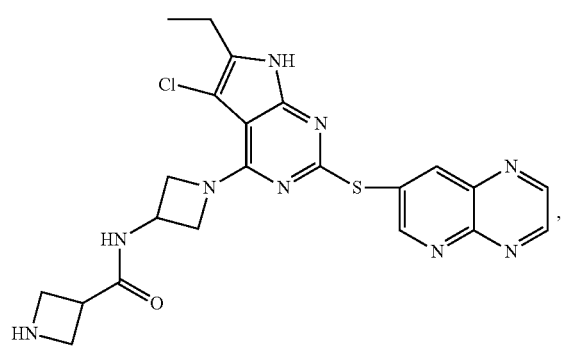
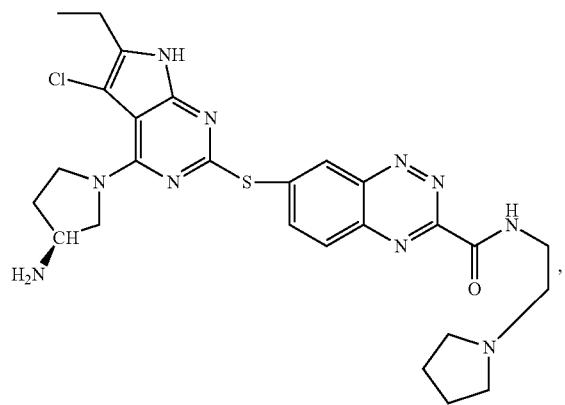
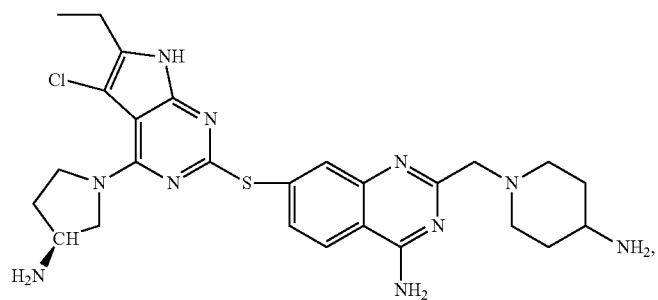
596
-continued
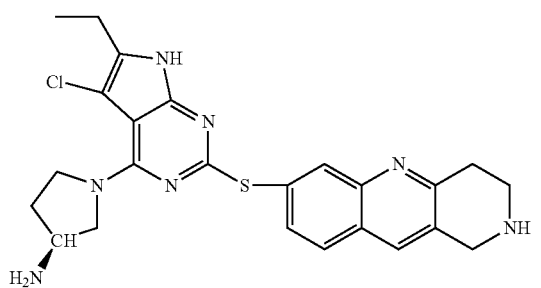
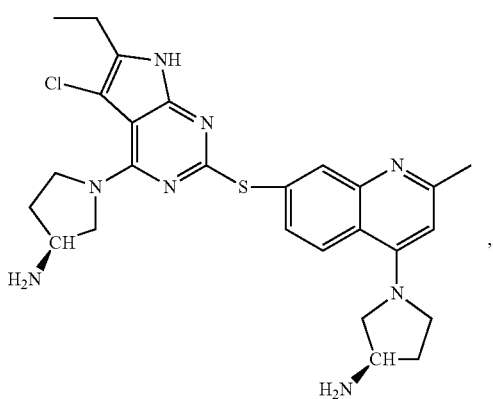
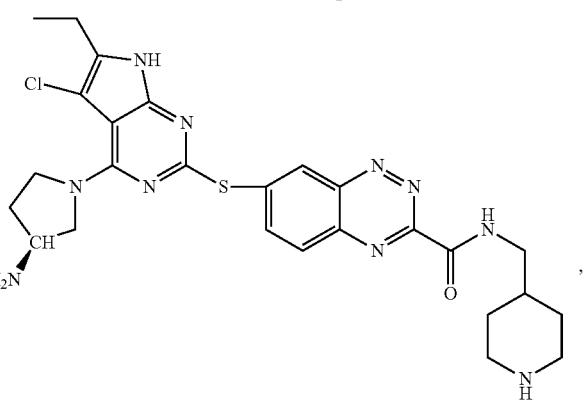
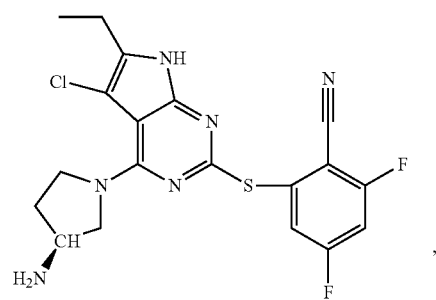

597
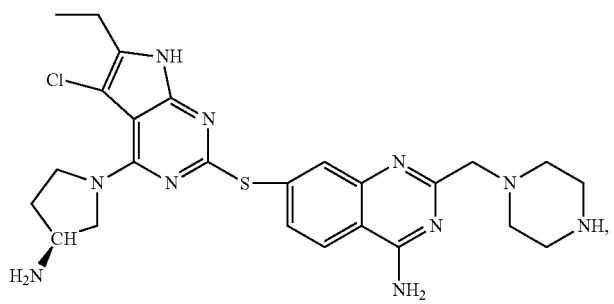
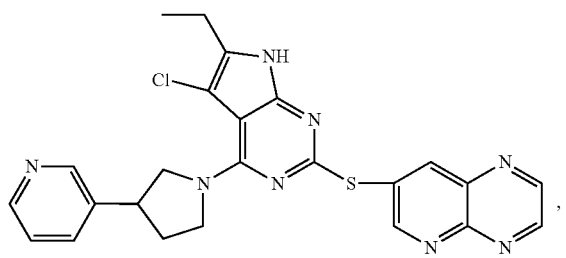
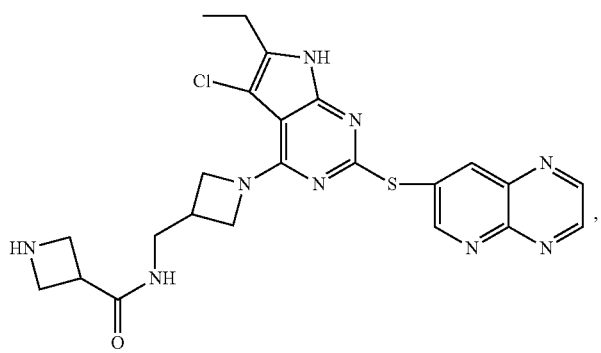
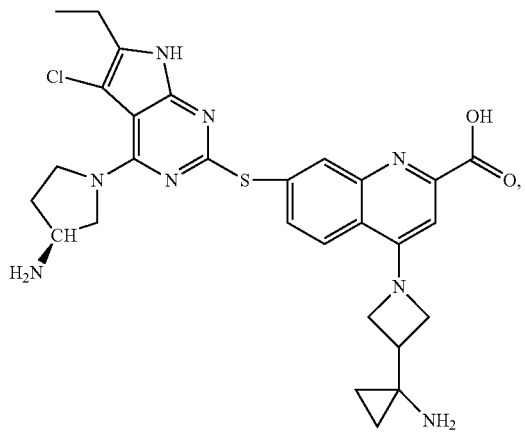
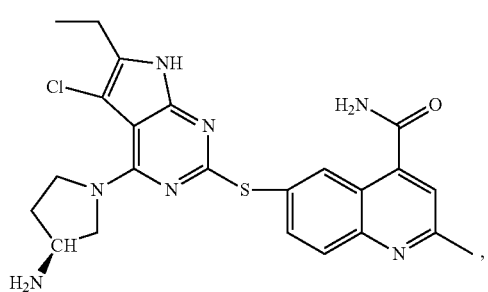
598
-continued
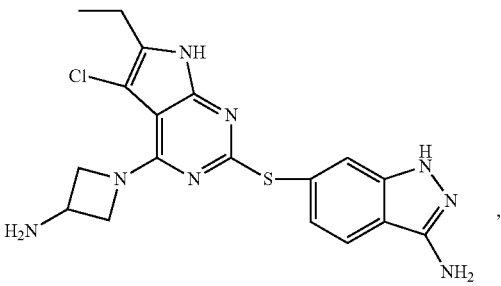
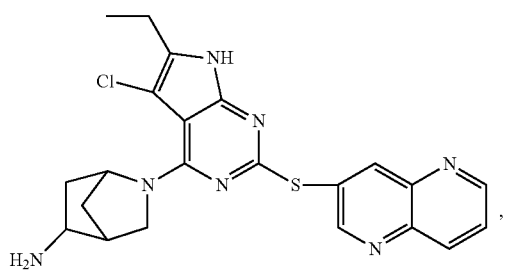
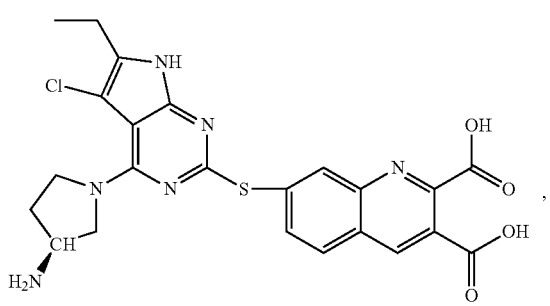
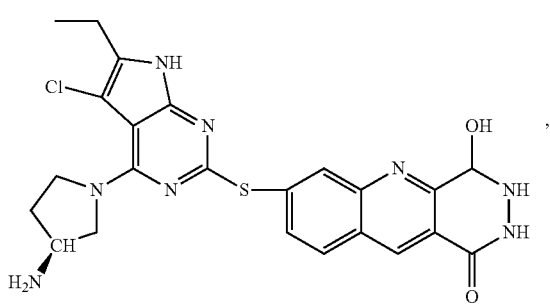
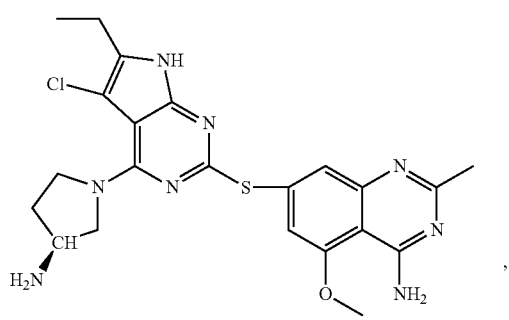

599
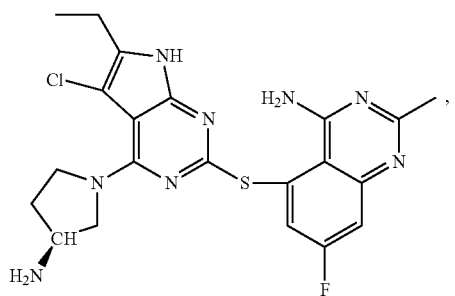
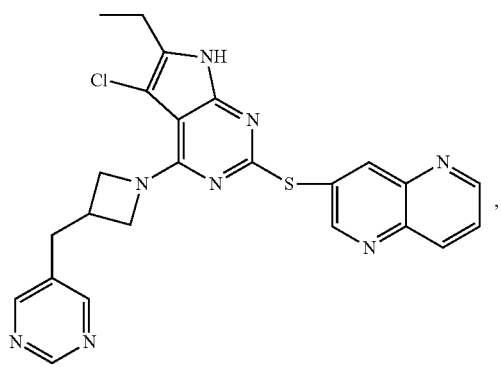
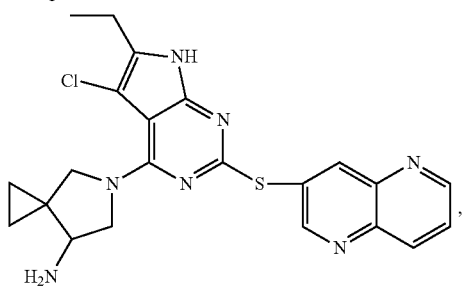
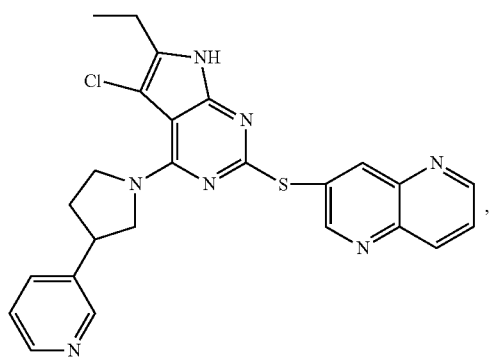
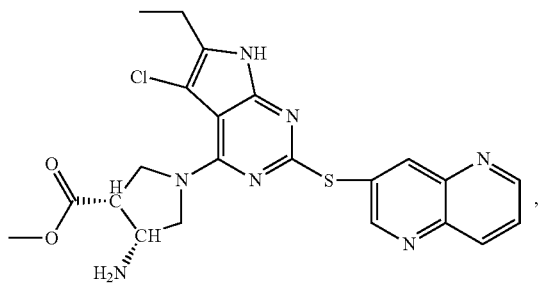
600
-continued
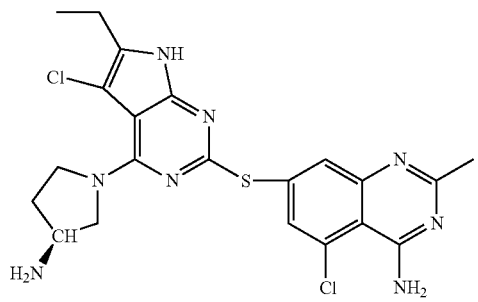
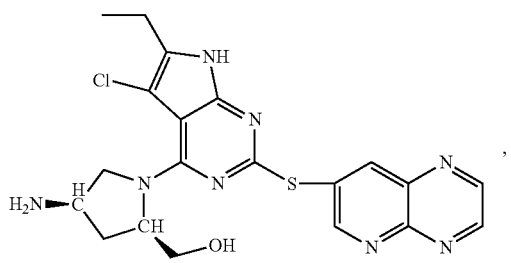
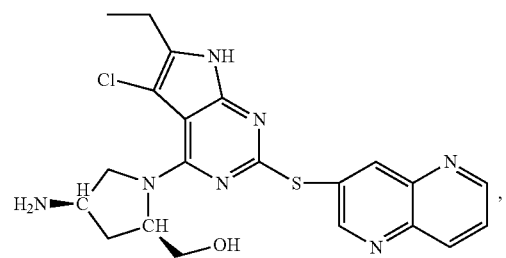
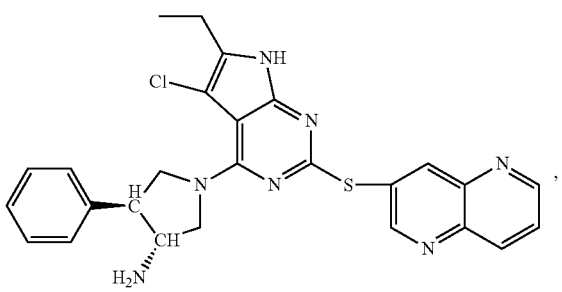
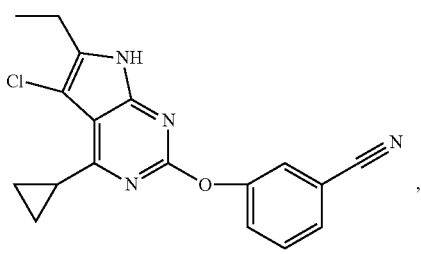

-continued
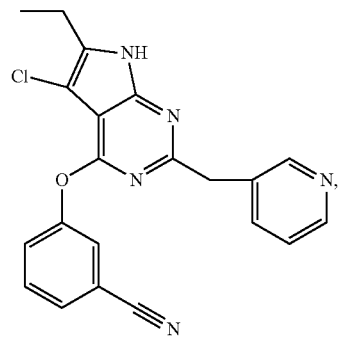
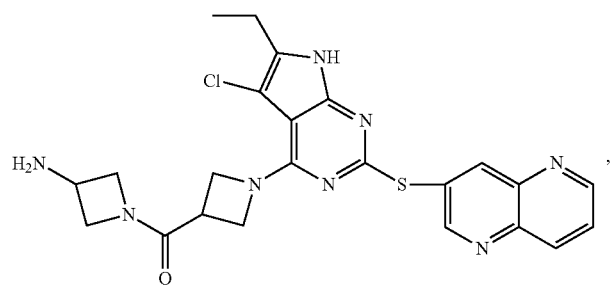
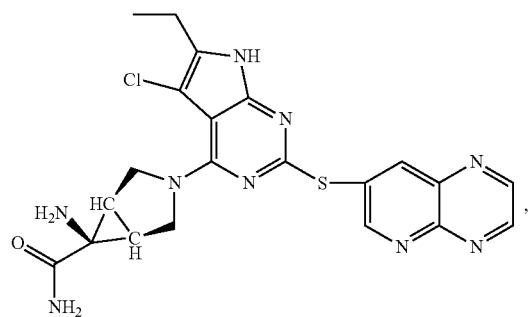
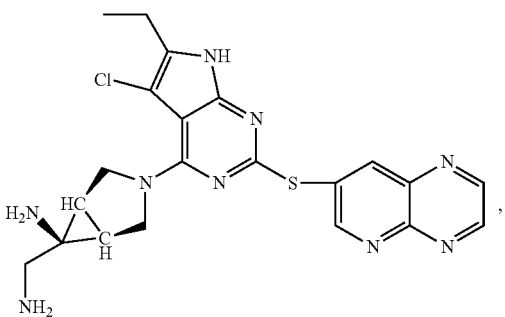
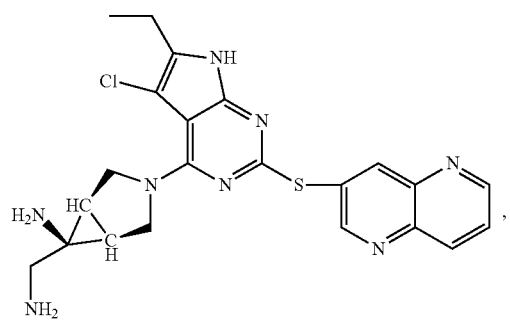
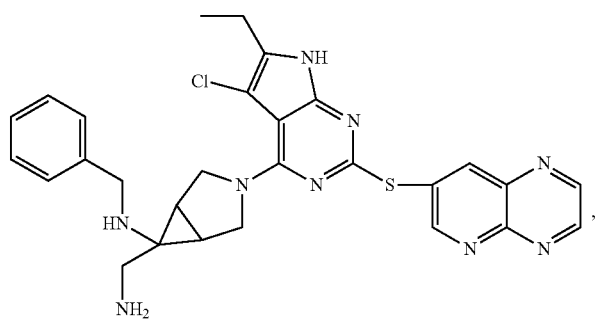
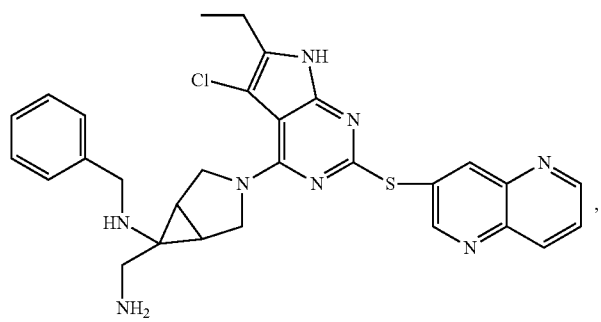
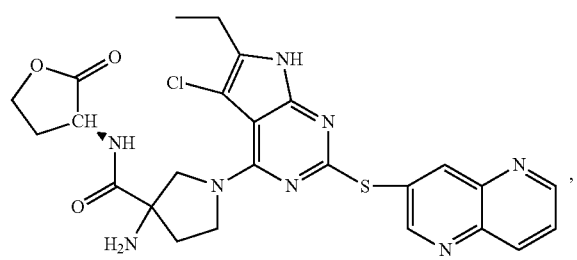
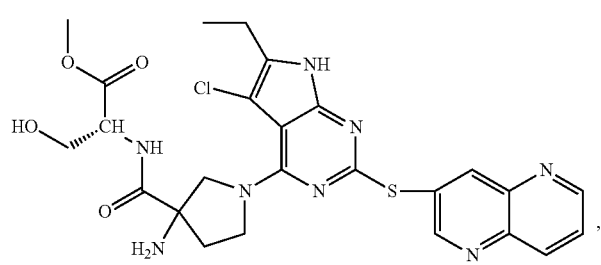
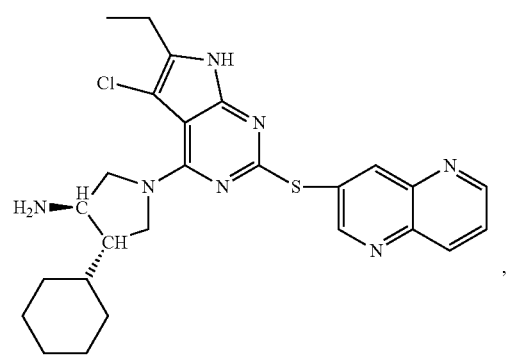

603
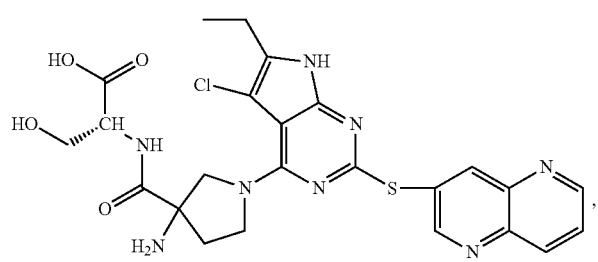
604
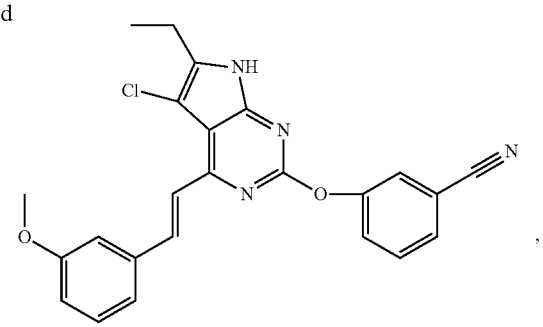
-continued
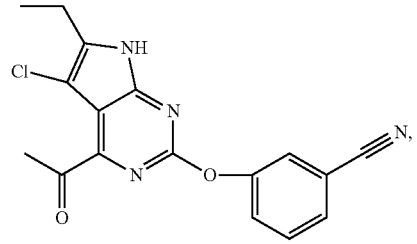
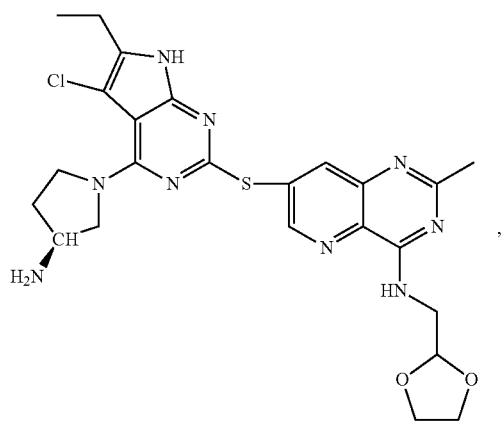
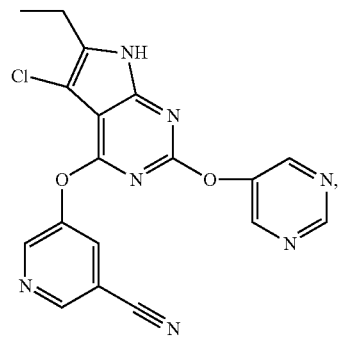
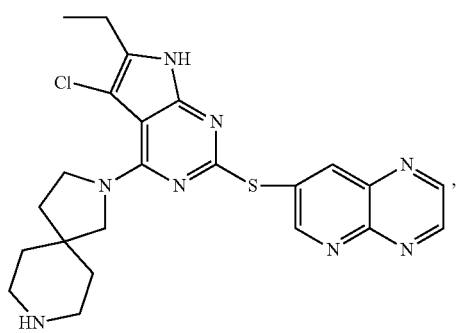
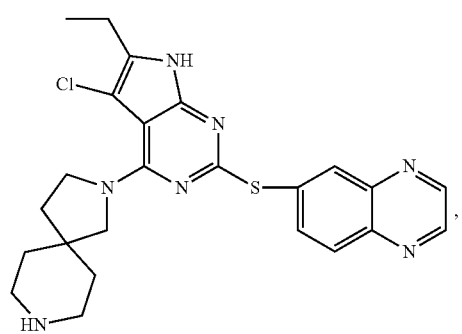
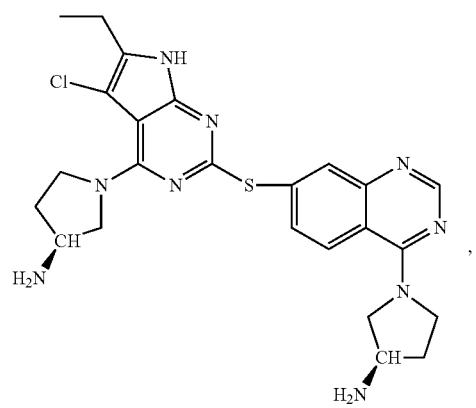

605
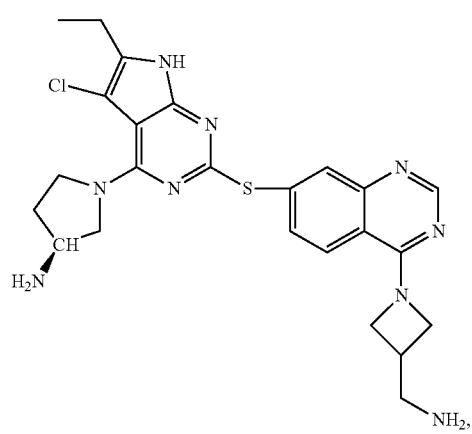
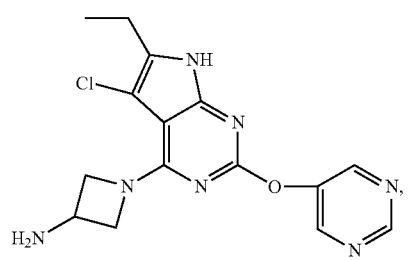
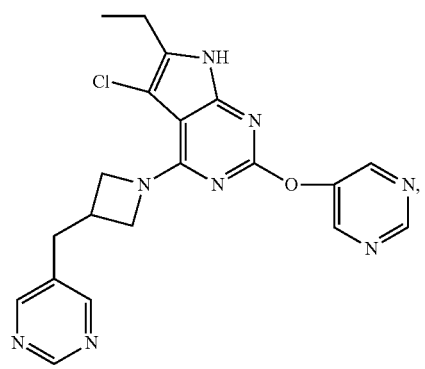
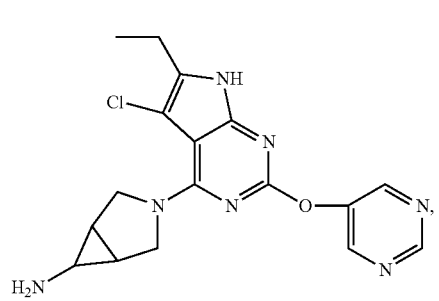
-continued
606
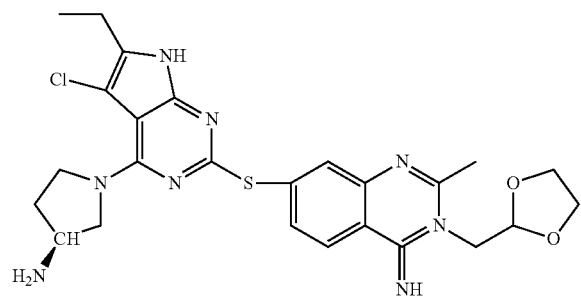
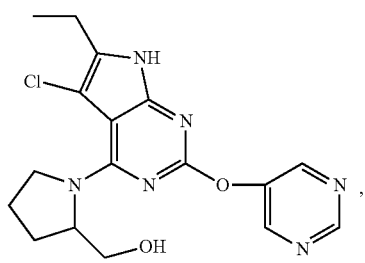
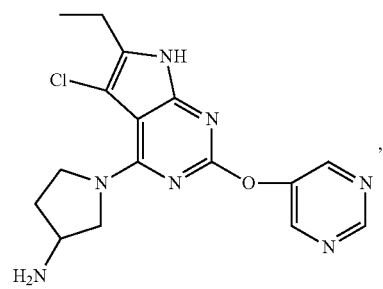
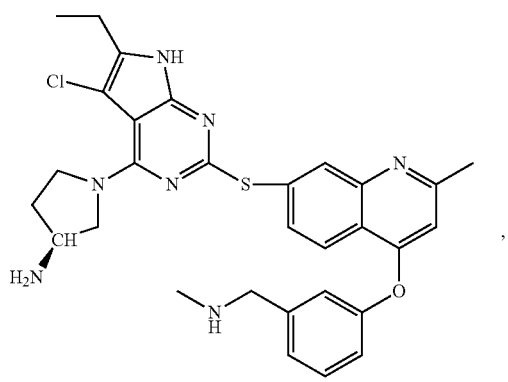

607  608
-continued
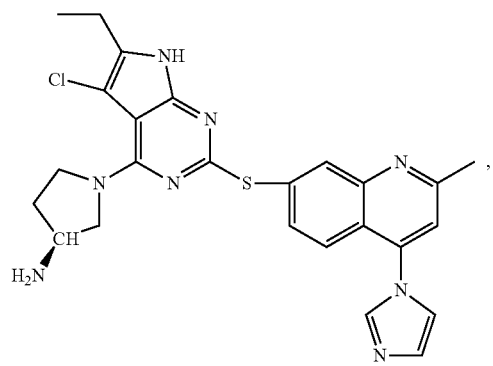
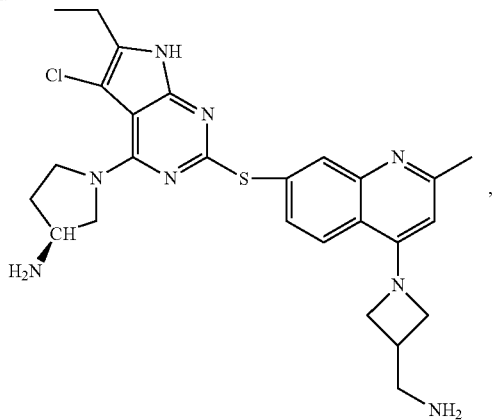
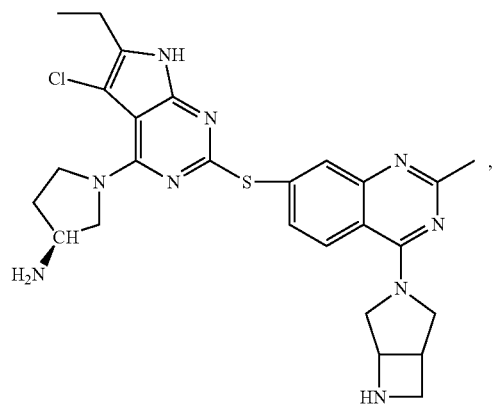
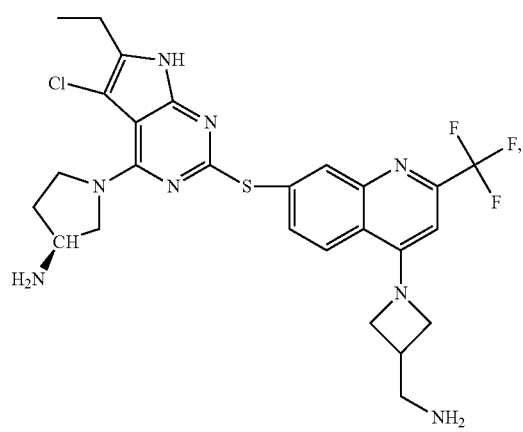
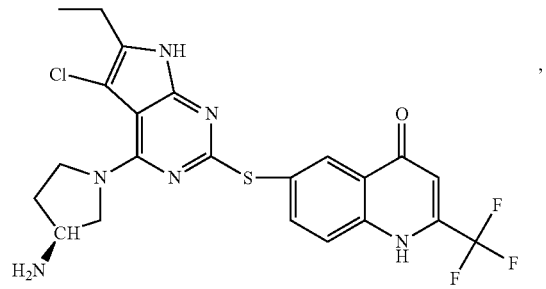
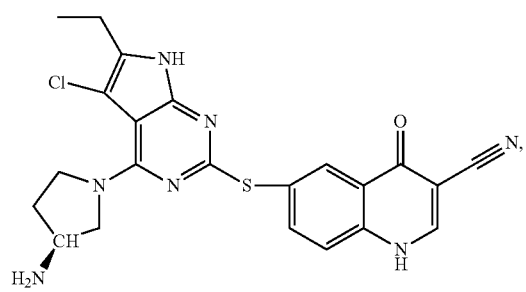
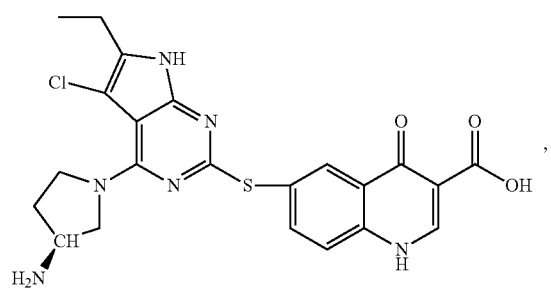

609
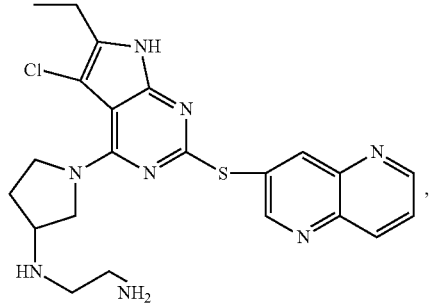
610
-continued
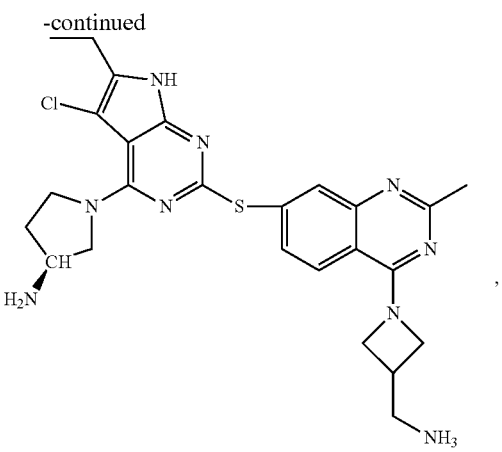
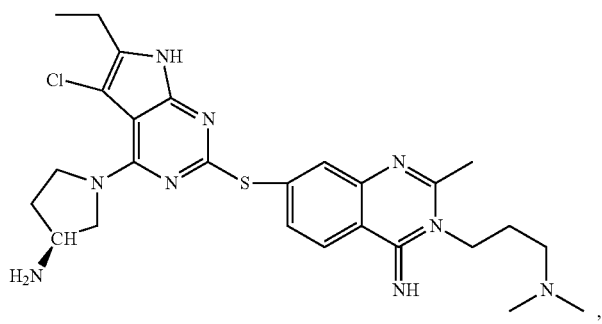
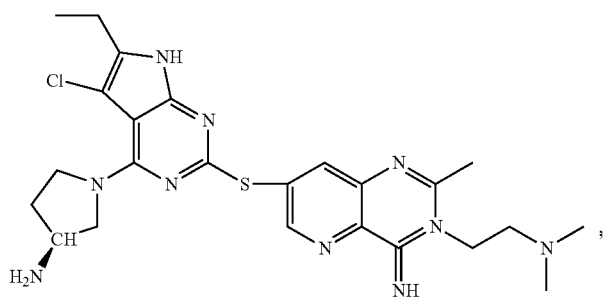
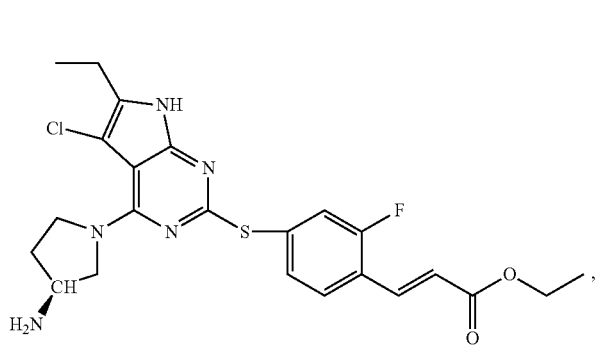
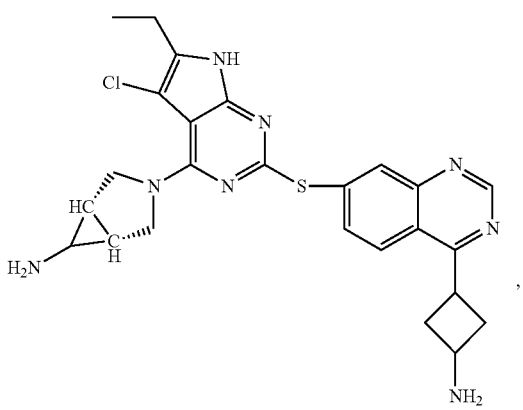

611
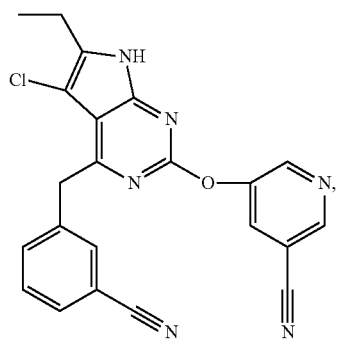
612
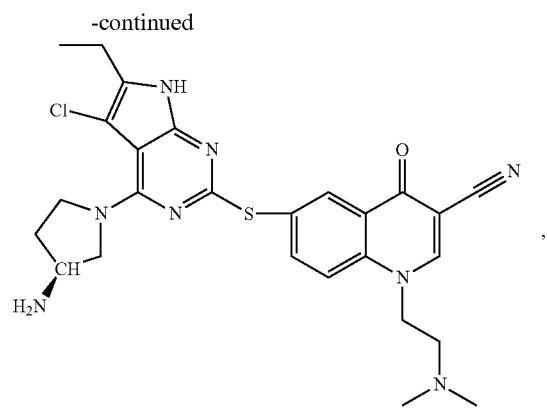
-continued
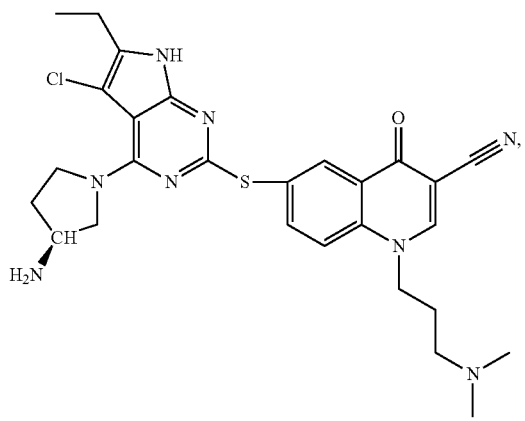
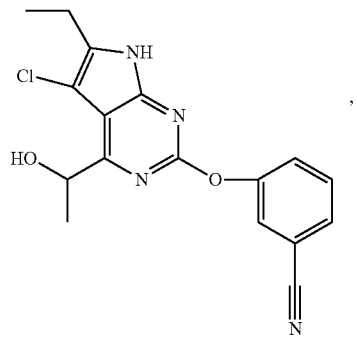
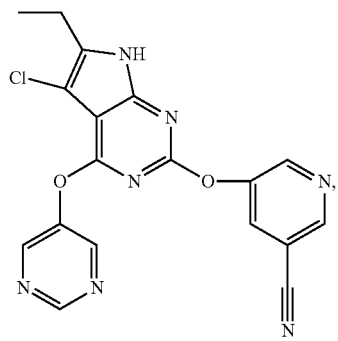
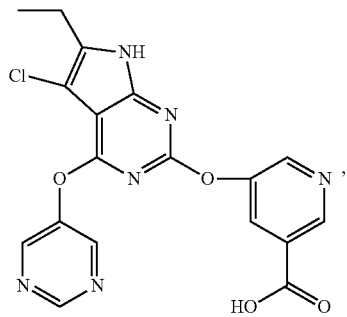
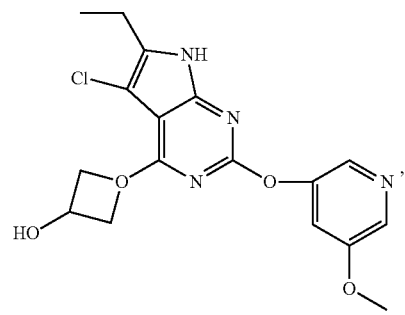
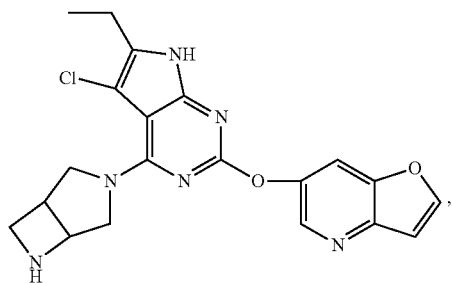
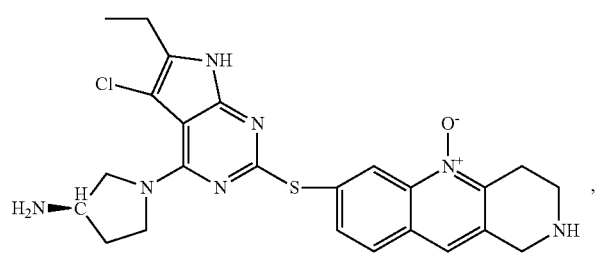

613
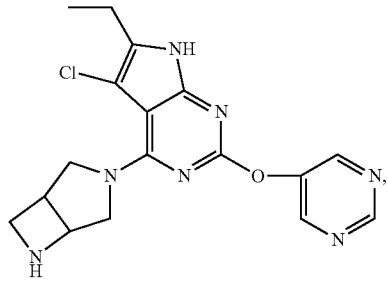
614
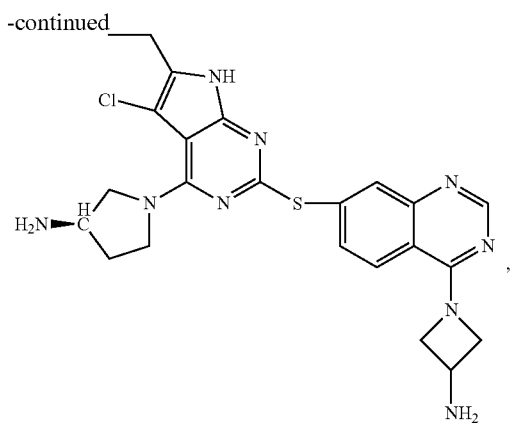
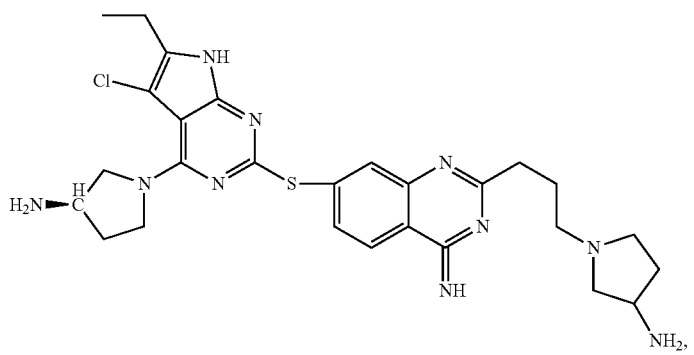
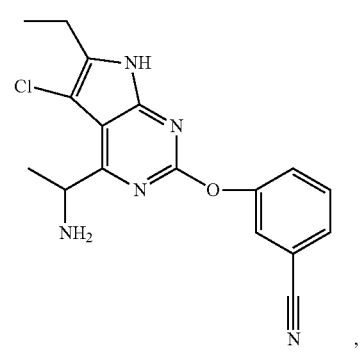
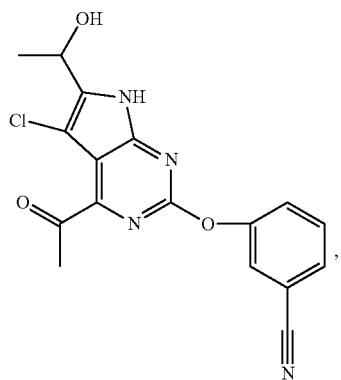
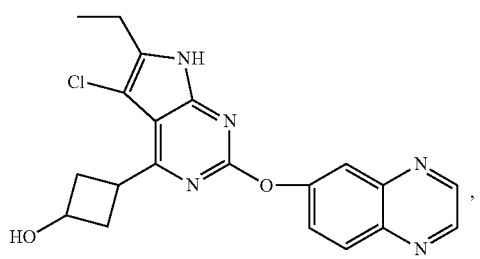
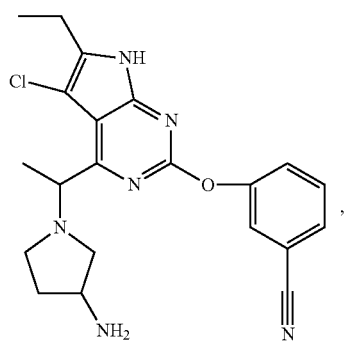

615
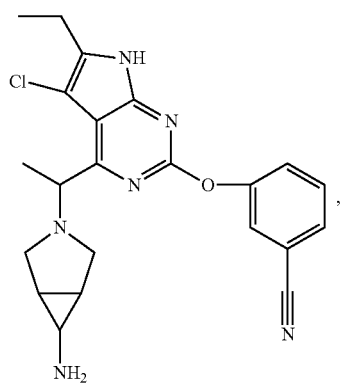
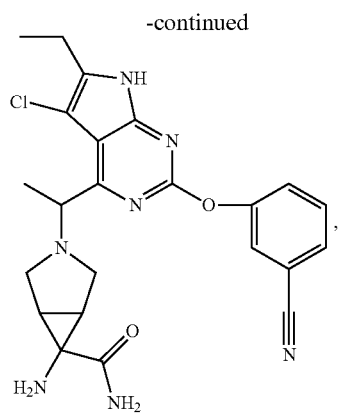
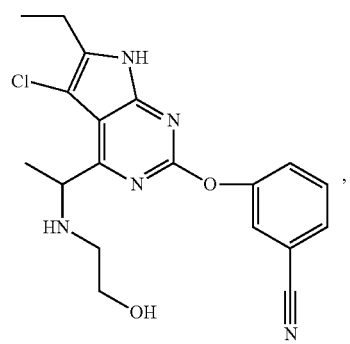
616
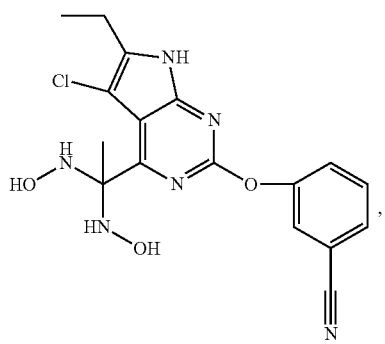
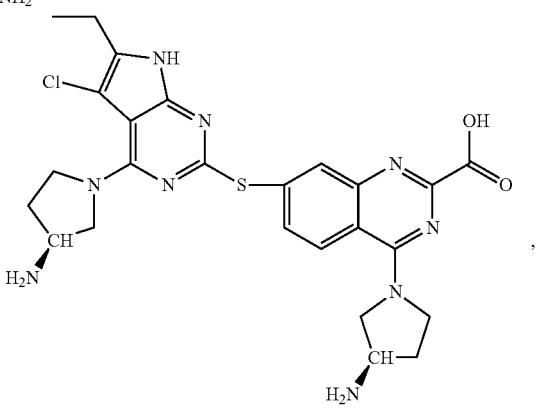
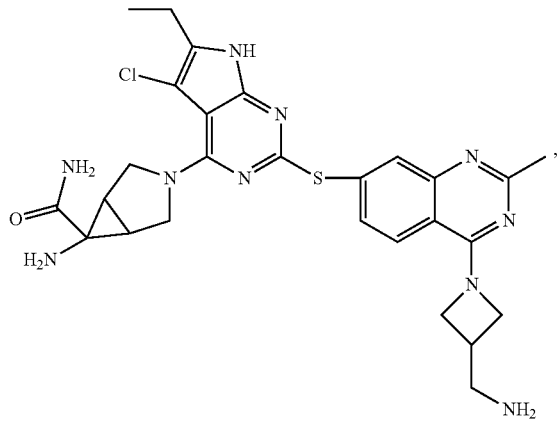
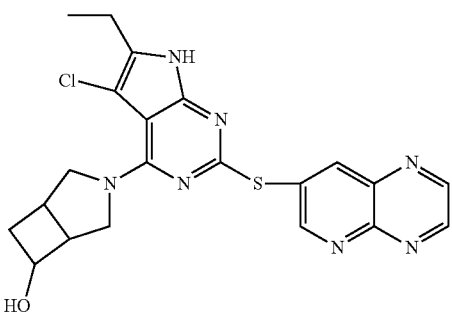
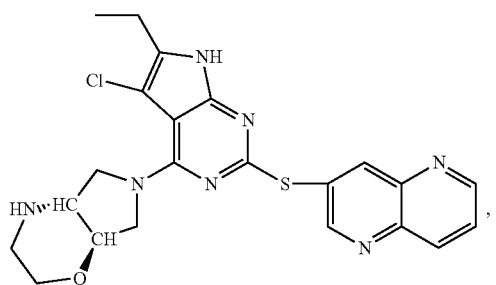
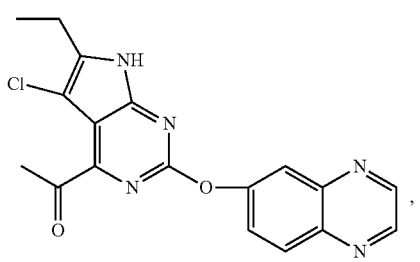
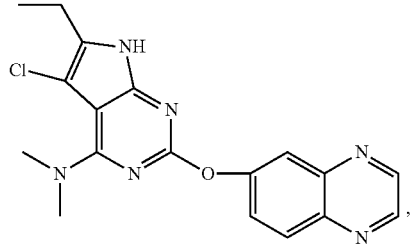
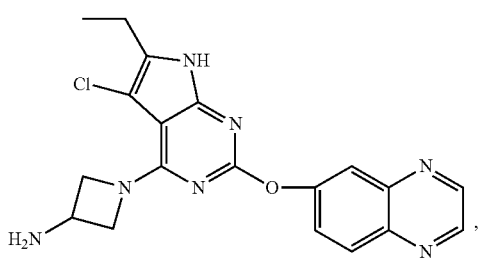

-continued
617
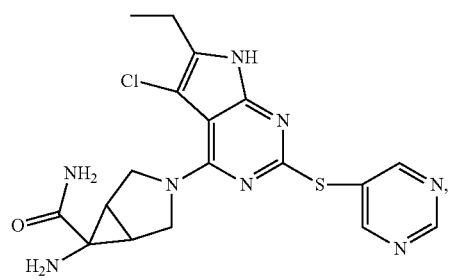
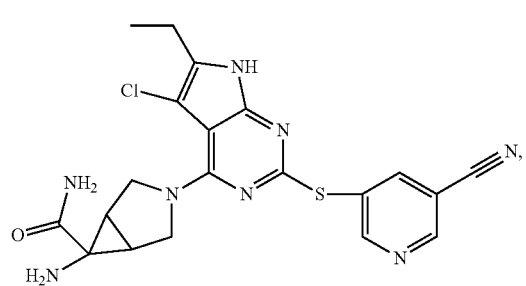
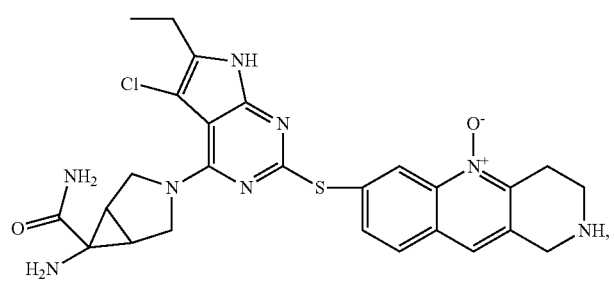
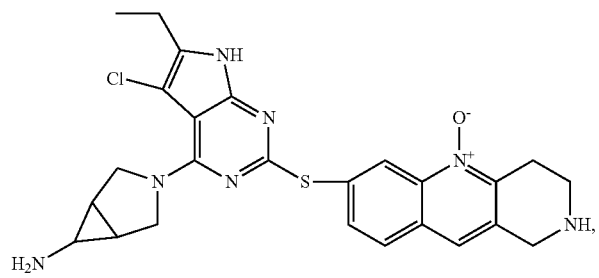
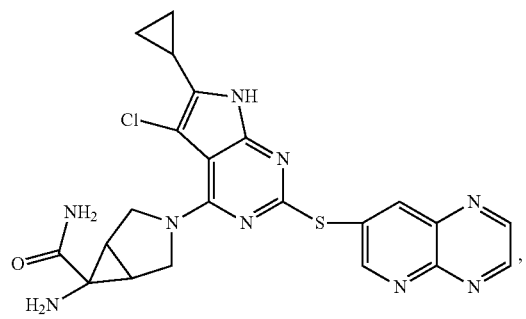
618
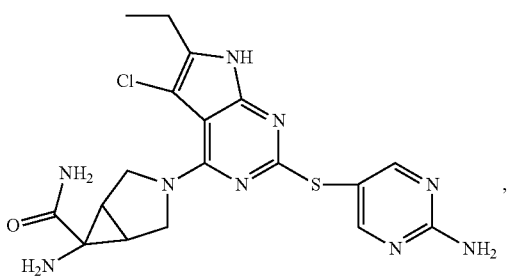
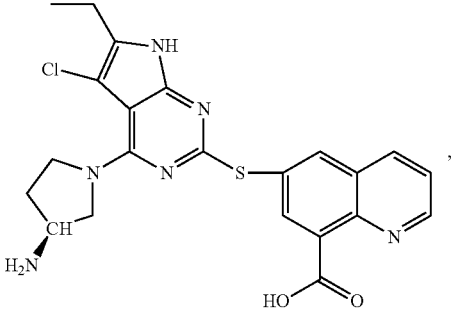
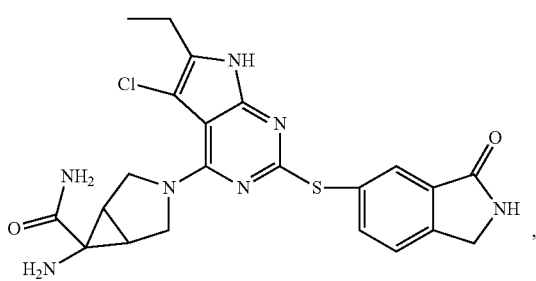
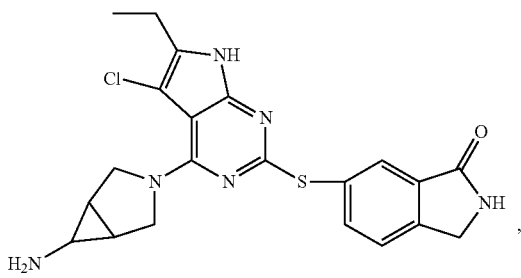
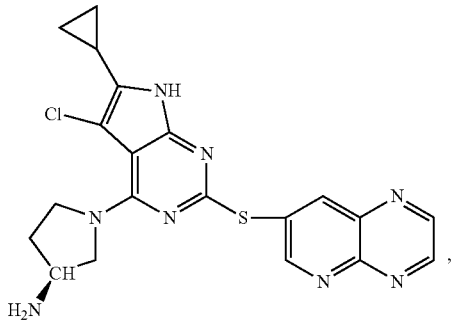

-continued
| 619 | 620 |
|---|---|
| 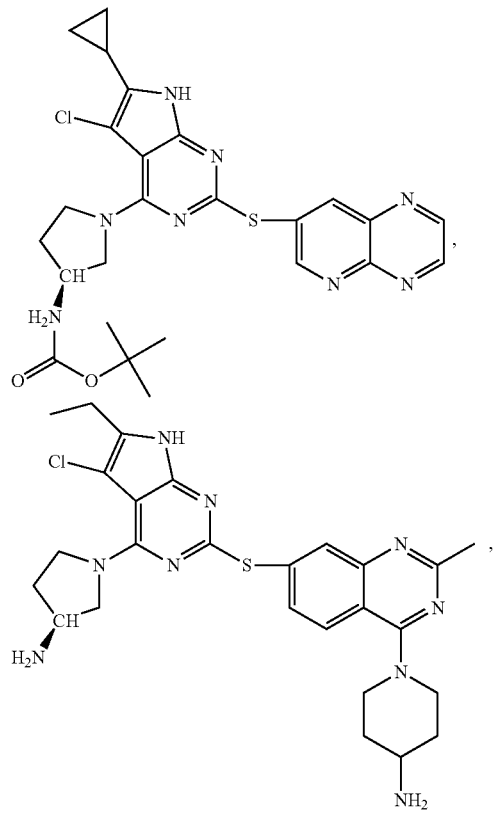 | 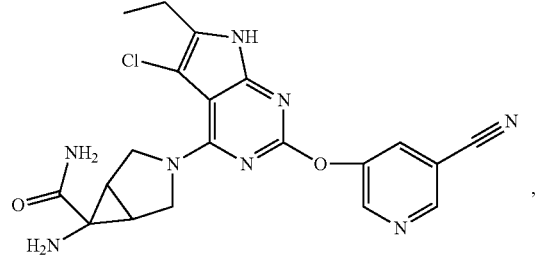 |
| 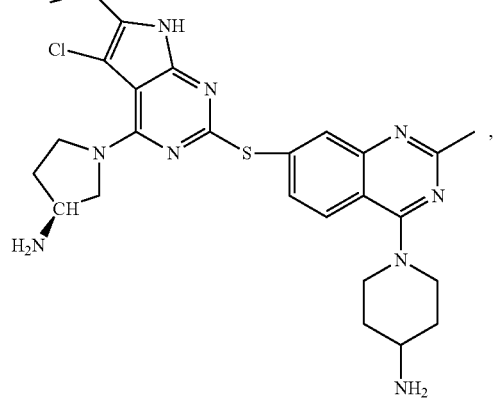 | 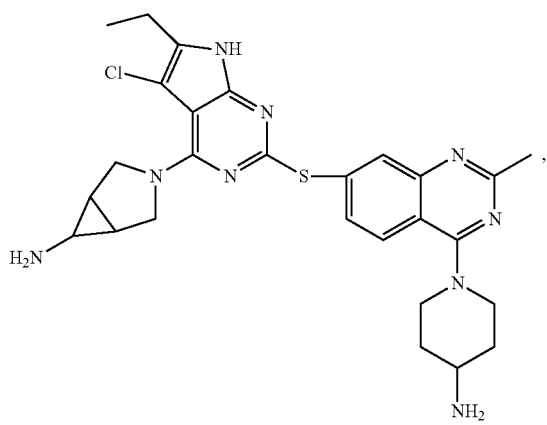 |
| 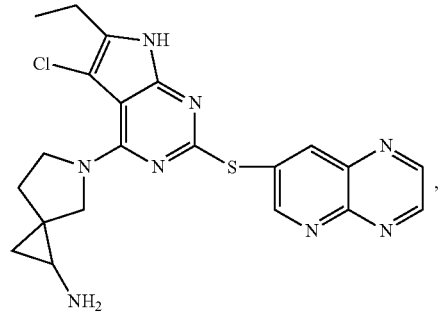 | 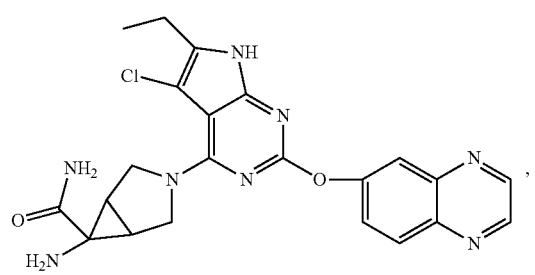 |
| 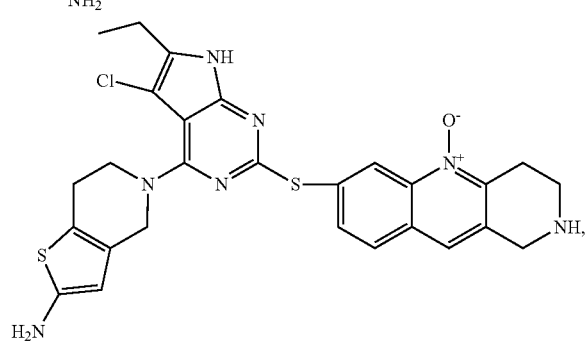 | 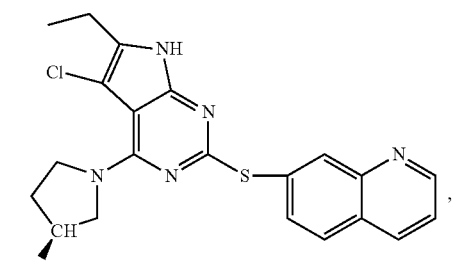 |
| 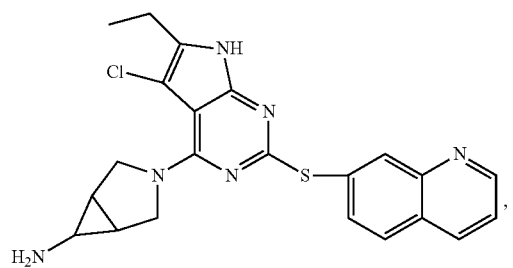 | 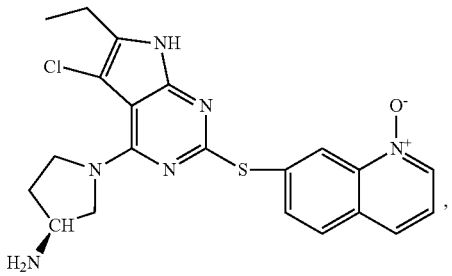 |

621
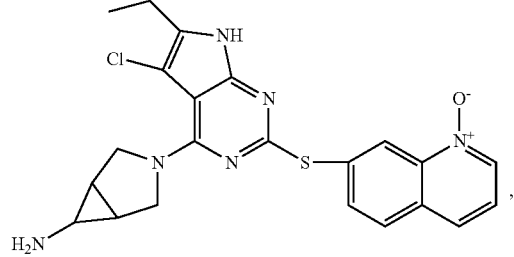
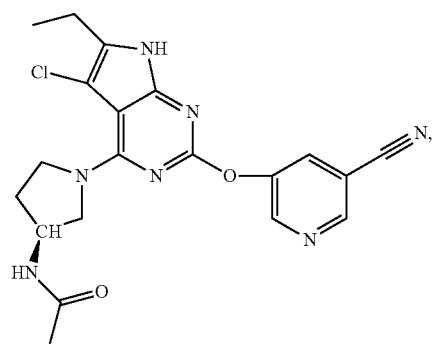
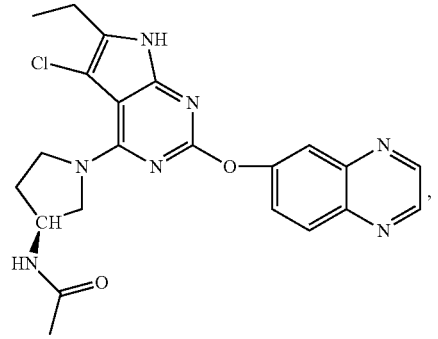
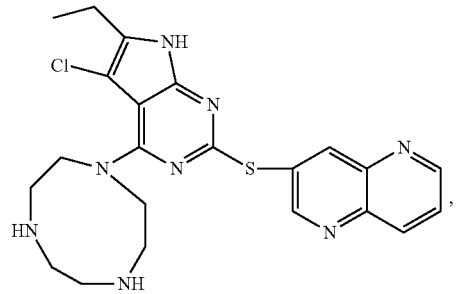
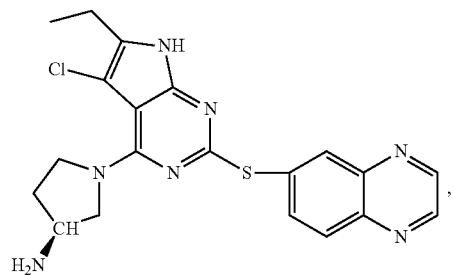
622
-continued
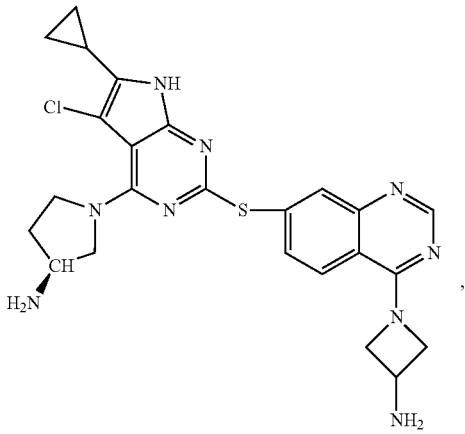
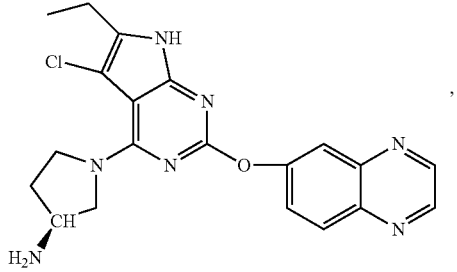
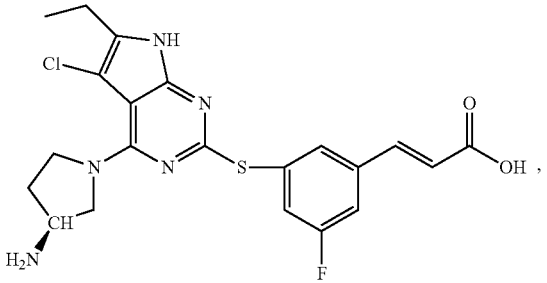
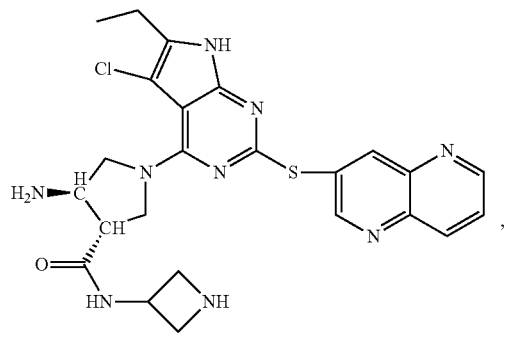
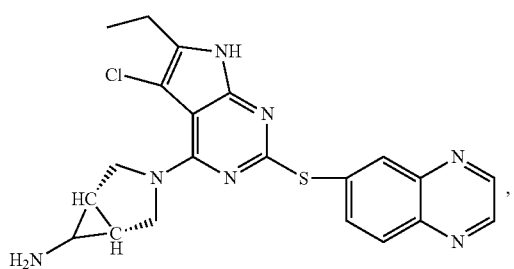

623
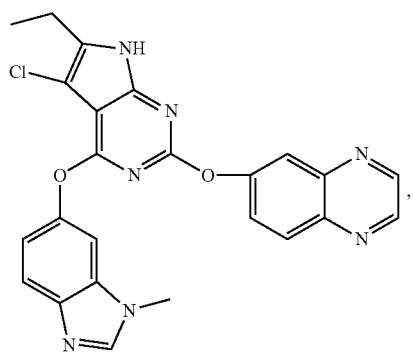
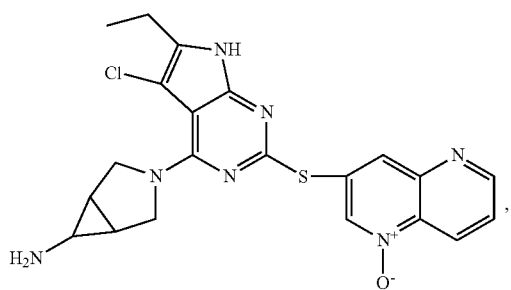
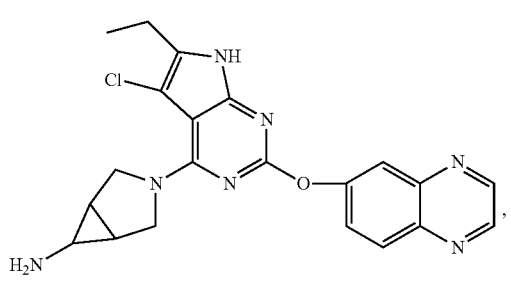
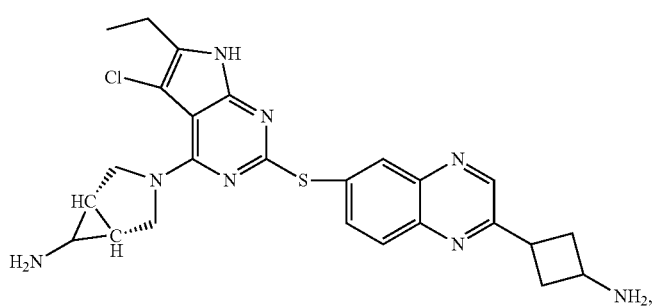
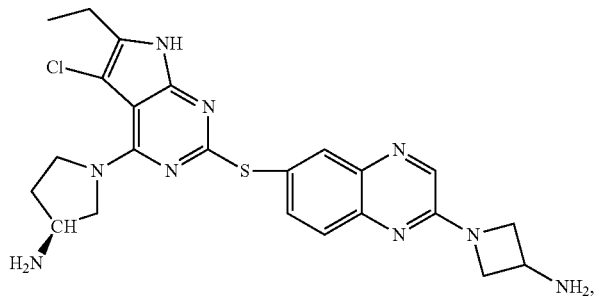
624
-continued
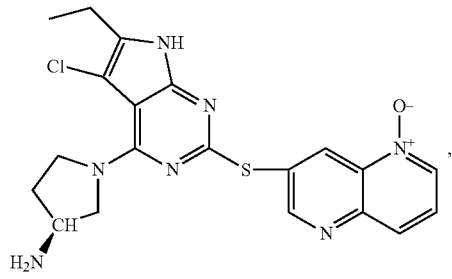
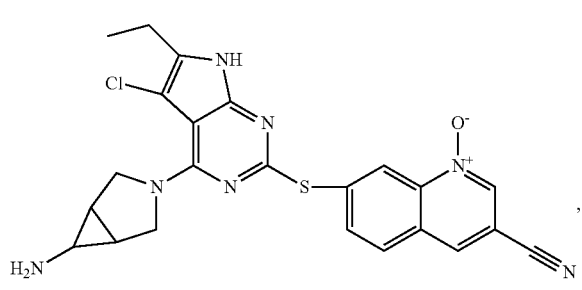
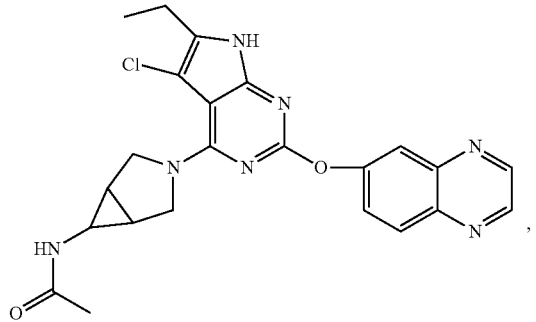
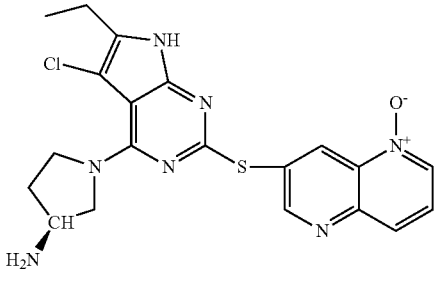
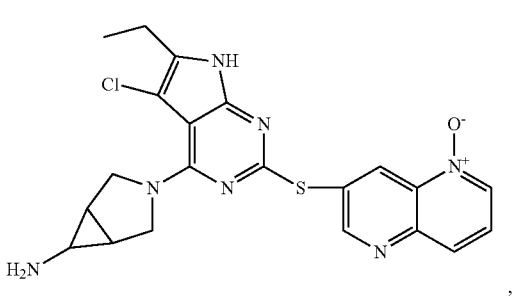

-continued
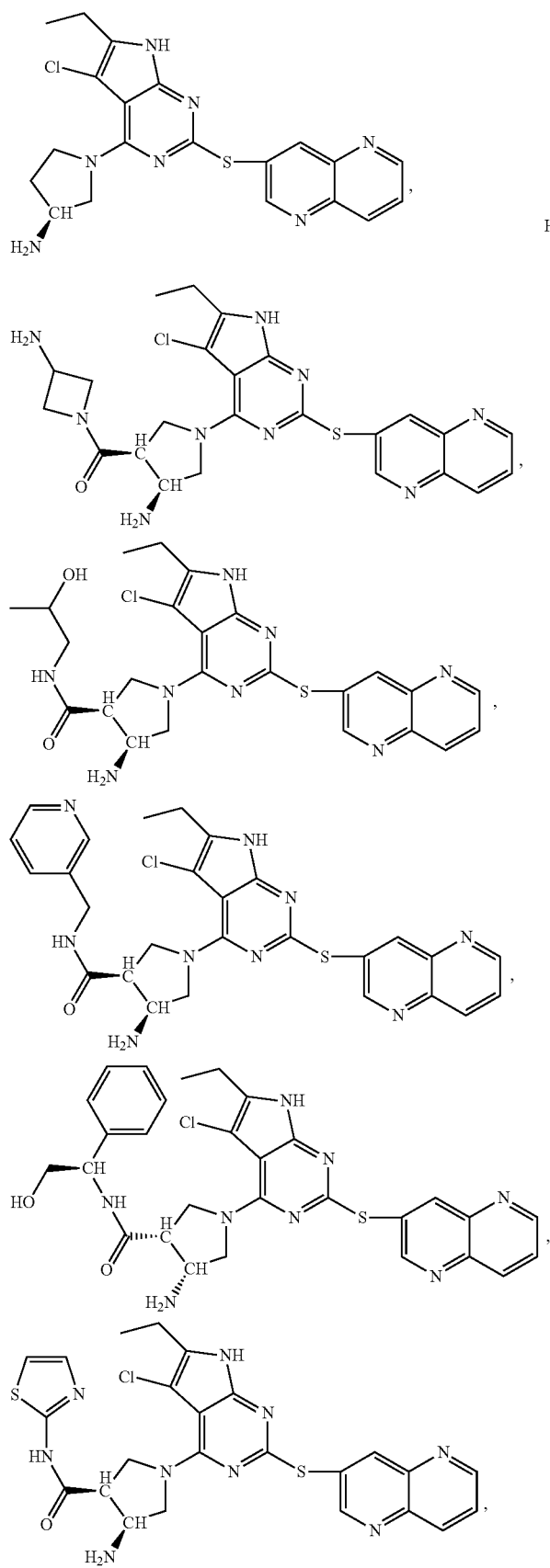
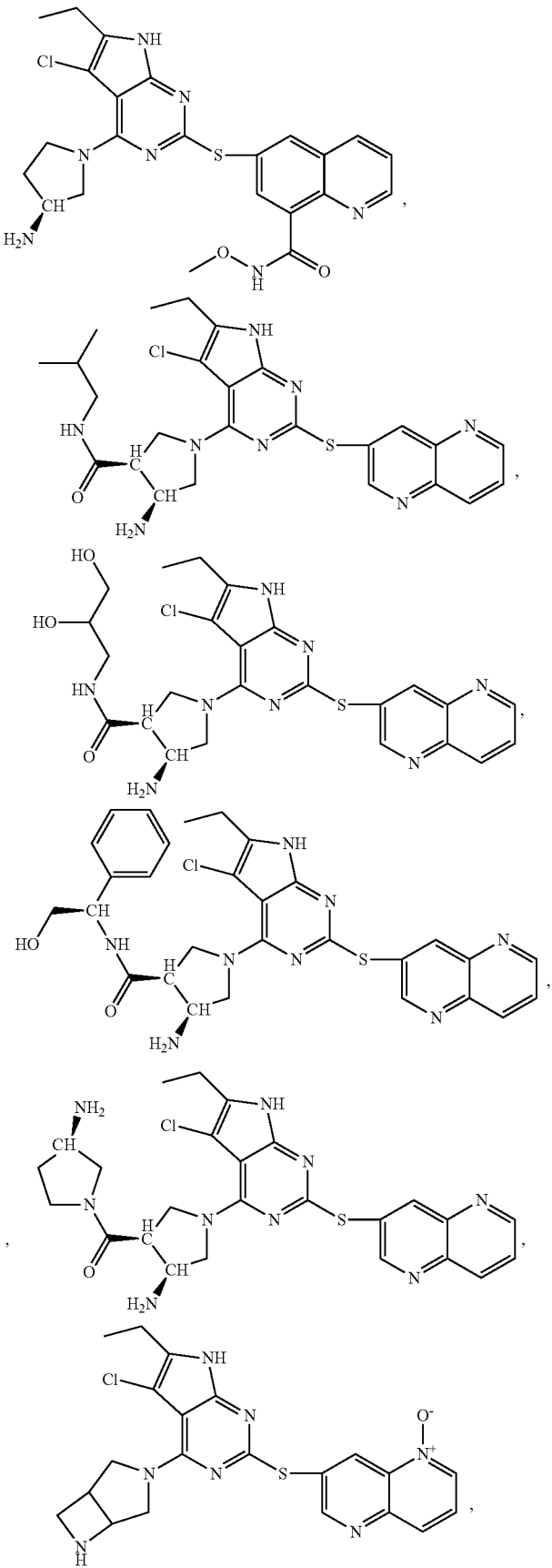

| 627 | 628 |
|---|---|
| 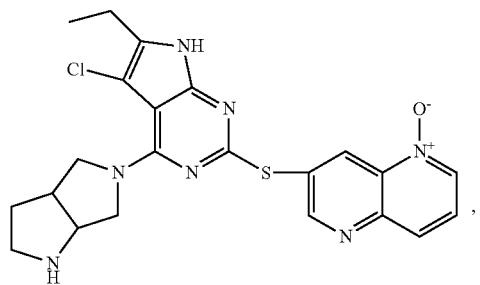 | 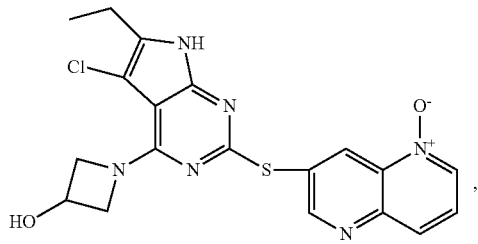 |
| 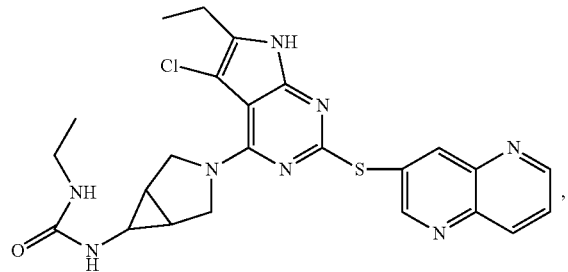 | 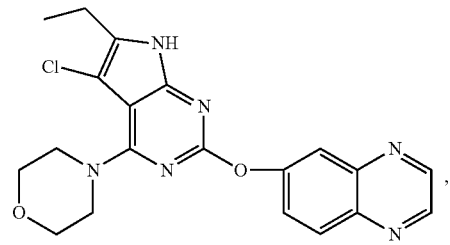 |
| 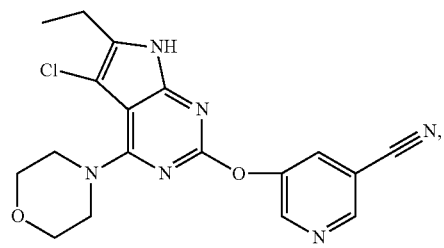 | 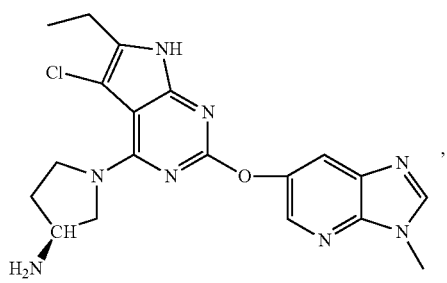 |
| 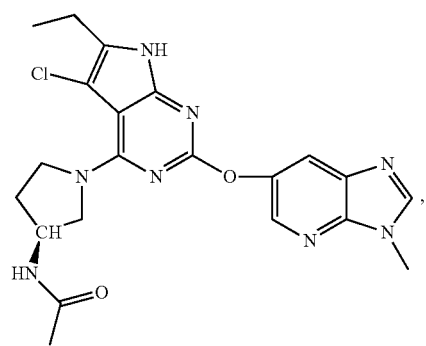 | 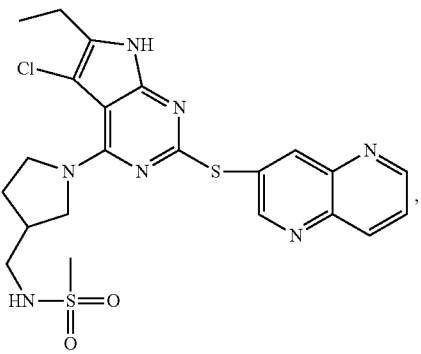 |
| 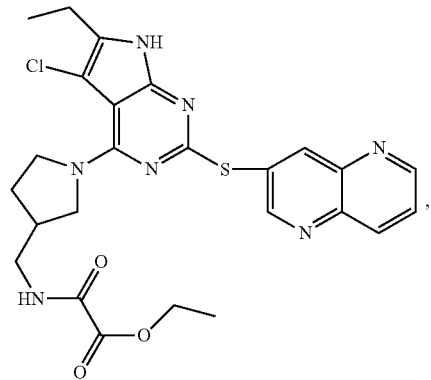 | 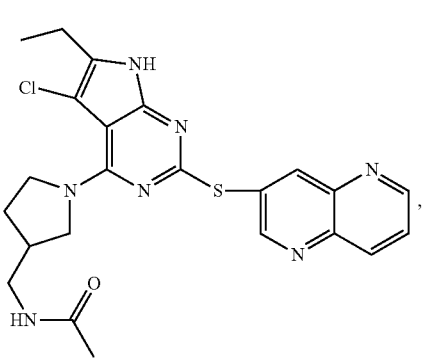 |

629
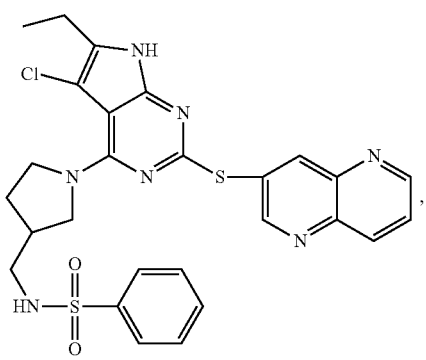
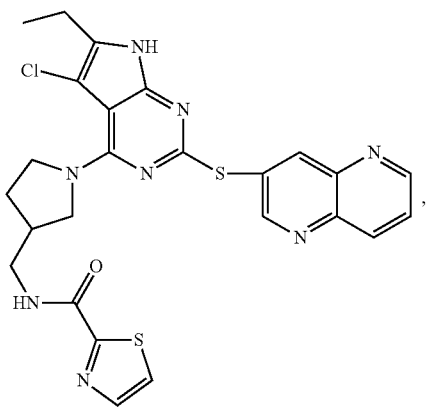
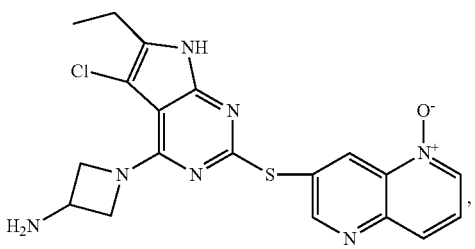
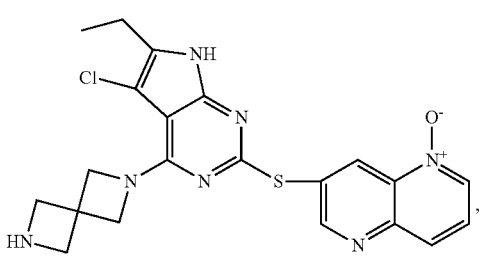
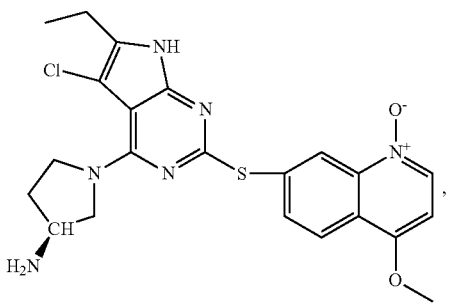
630
-continued
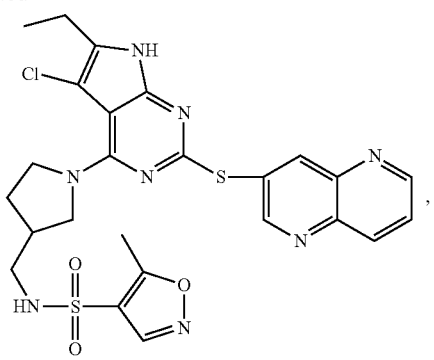
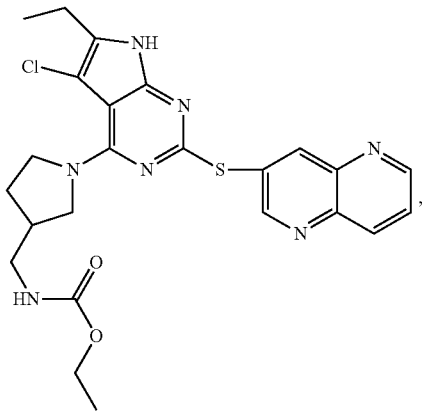
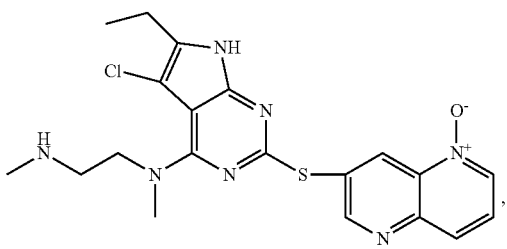
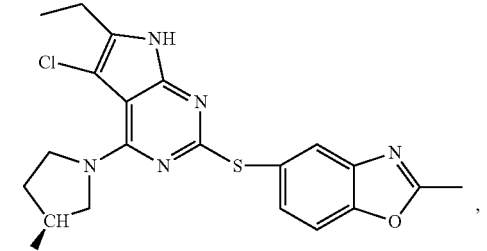
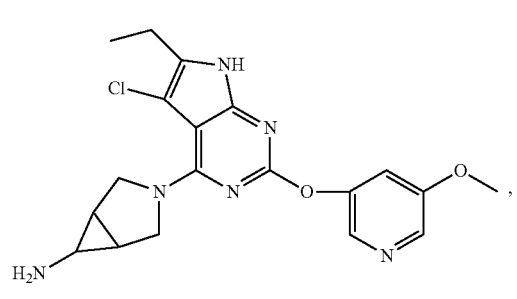

-continued
631
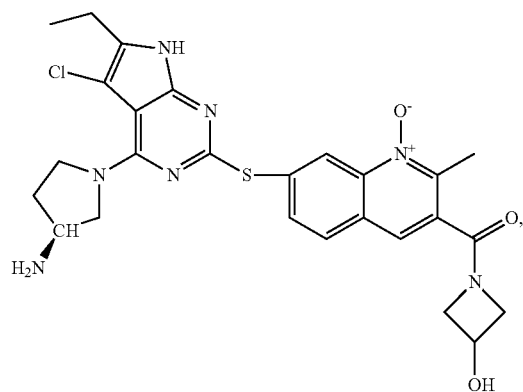
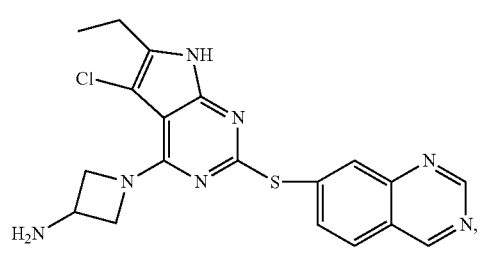
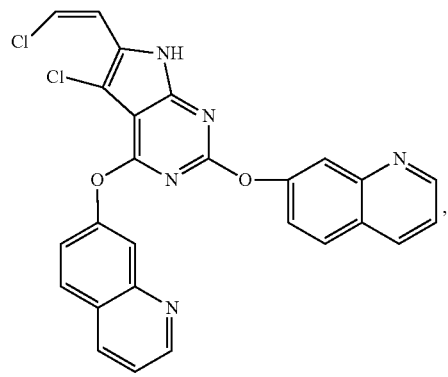
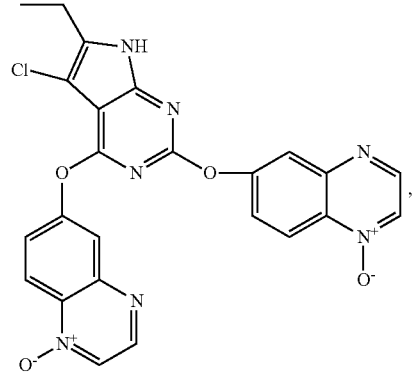
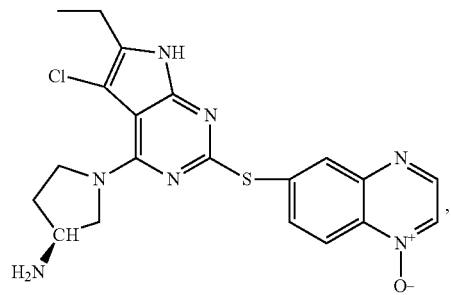
632
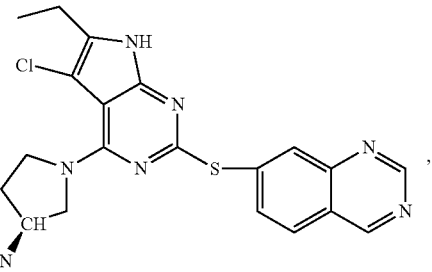
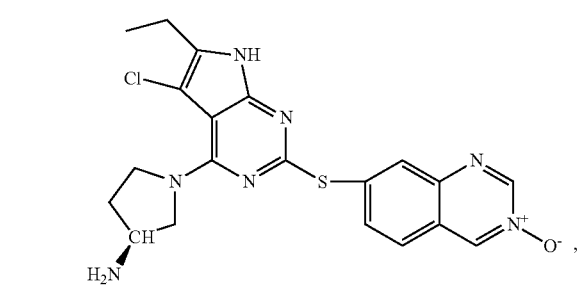
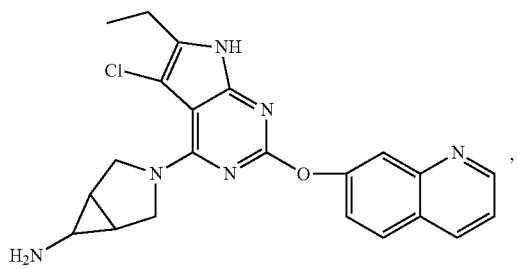
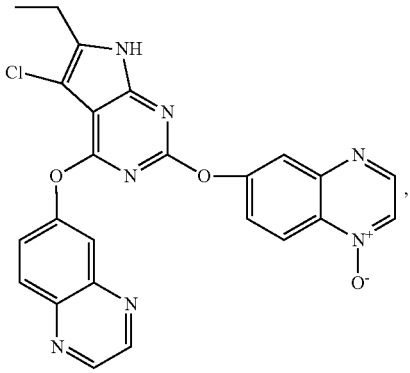
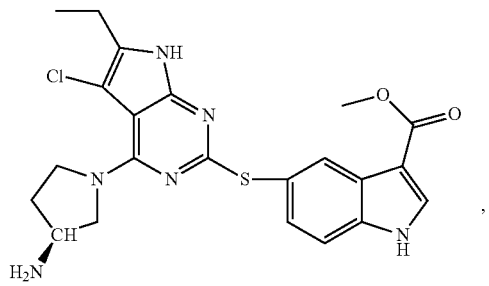

633
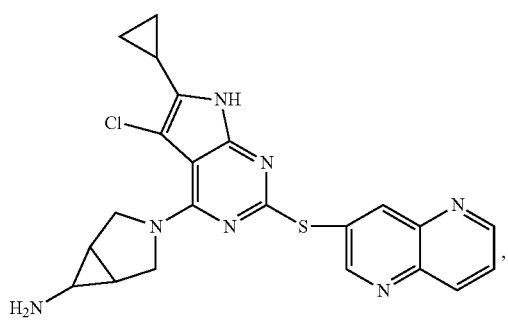
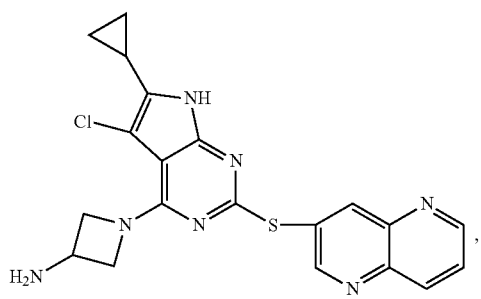
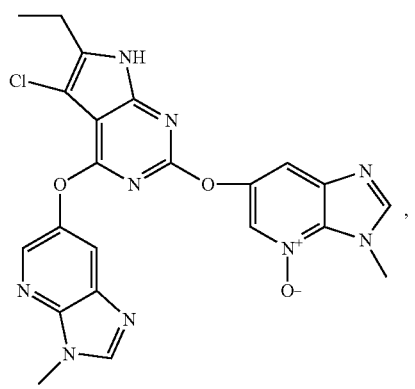
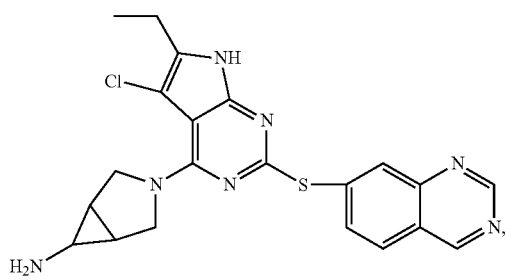
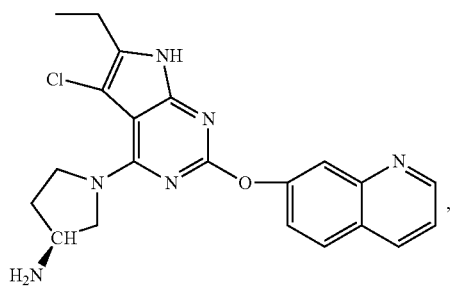
-continued
634
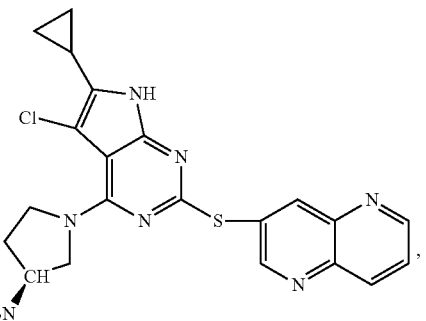
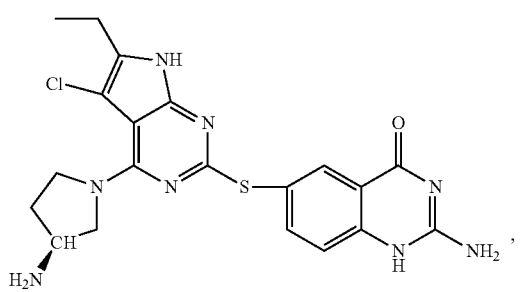
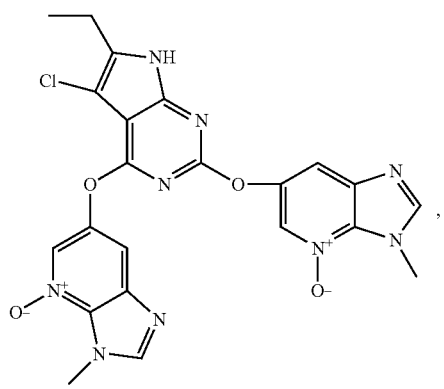
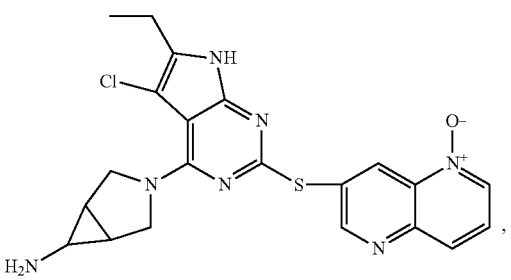
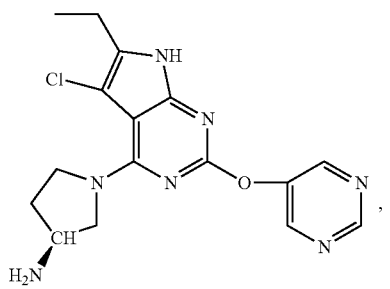

635
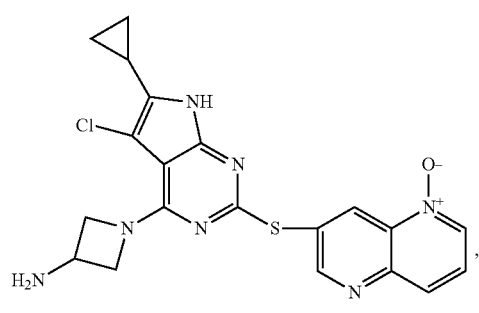
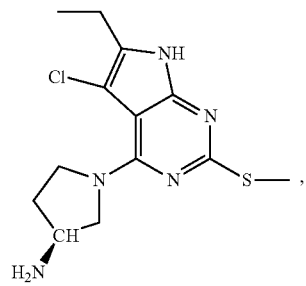
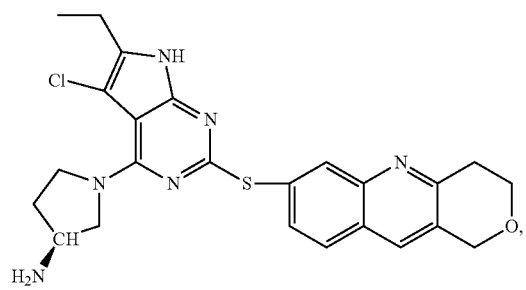
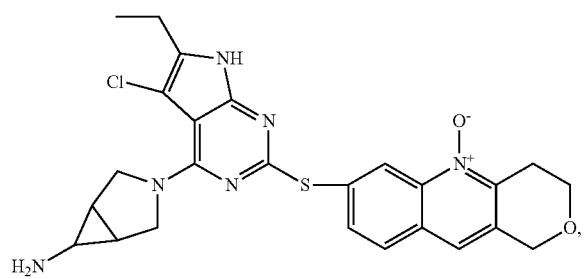
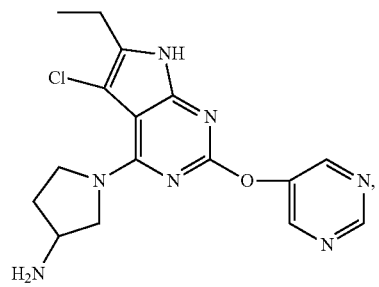
636
-continued
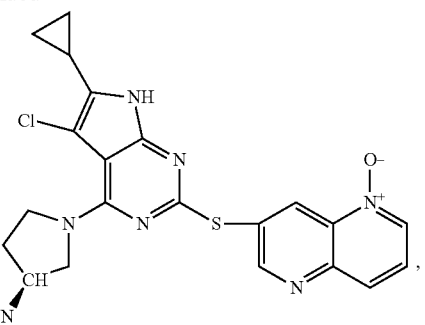
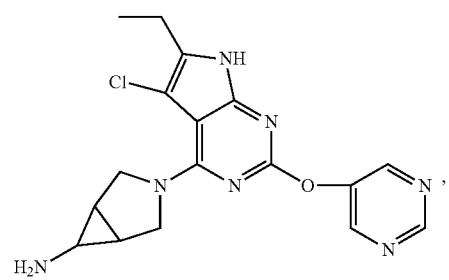
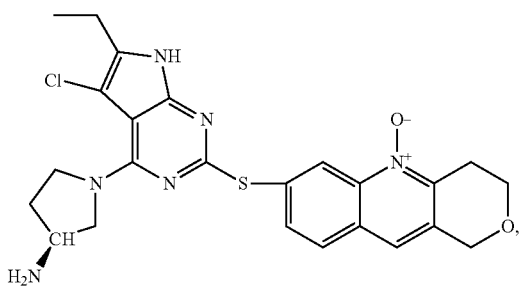
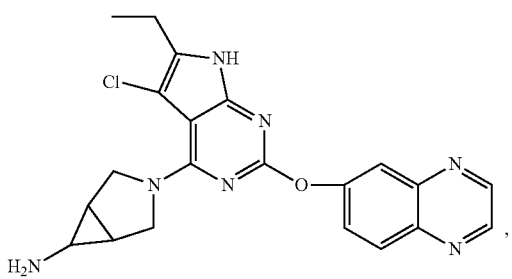
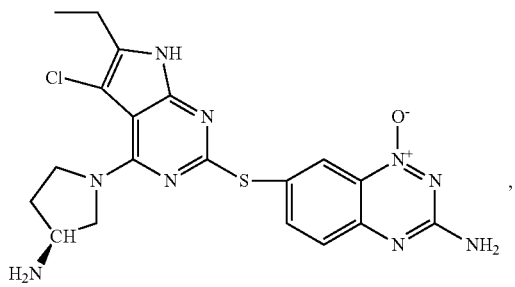

-continued
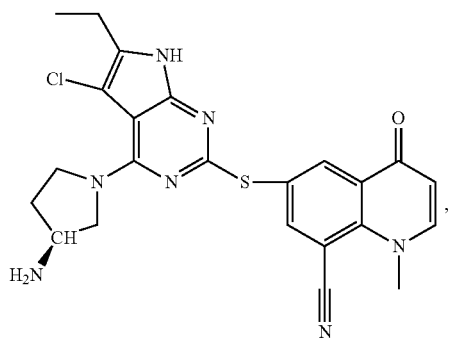
637
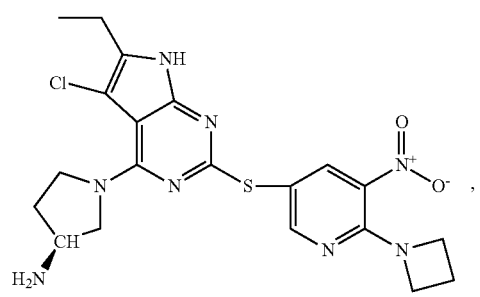
638
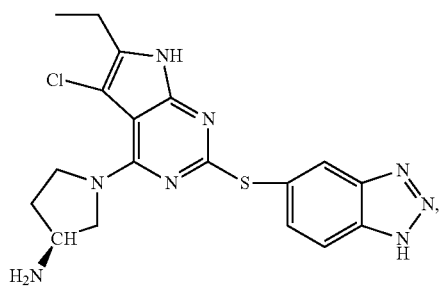
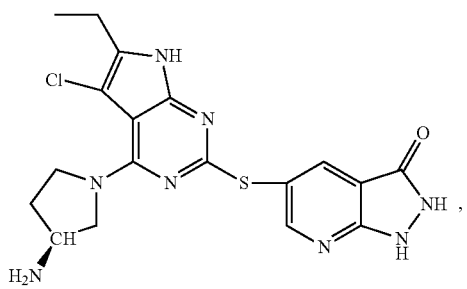
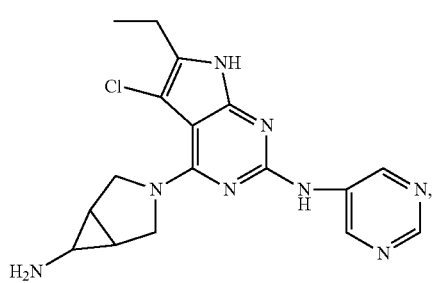
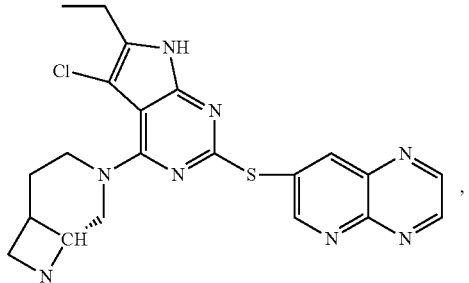
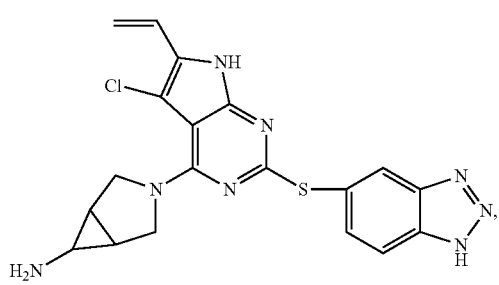
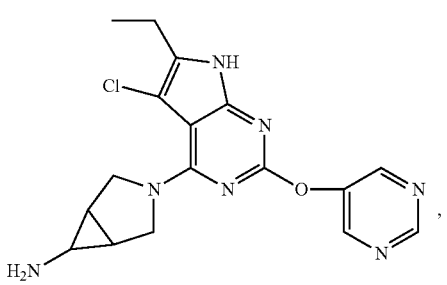
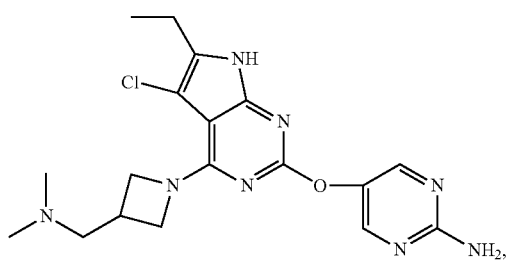
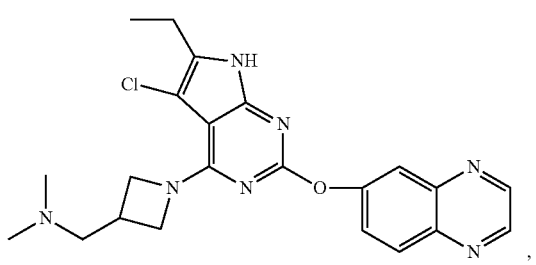

-continued
639
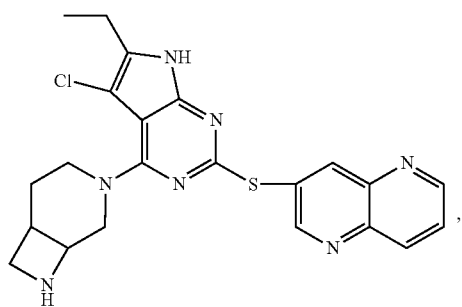,
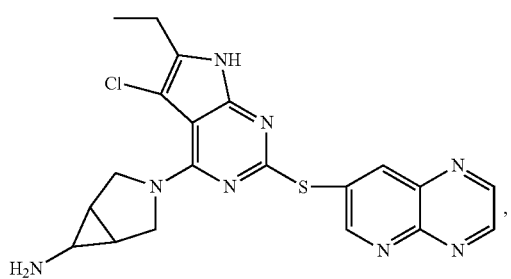,
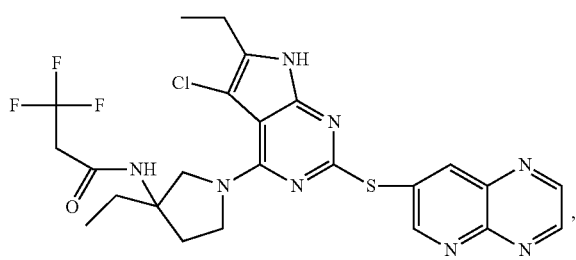,
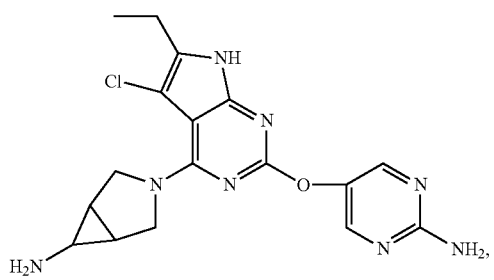,
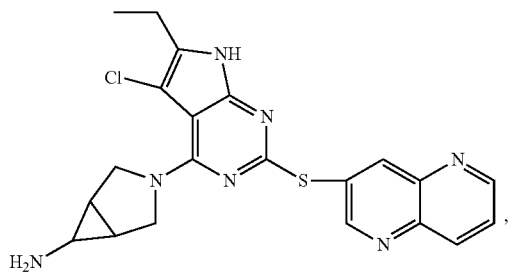,
640
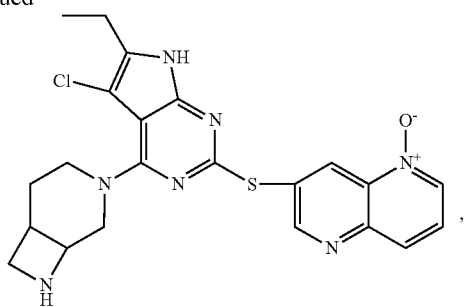,
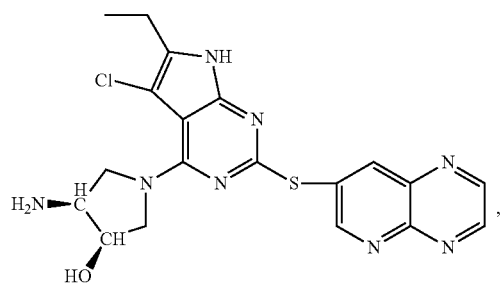,
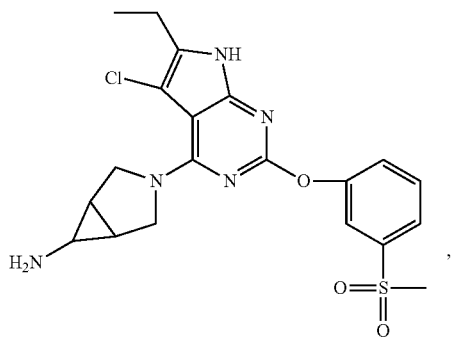,
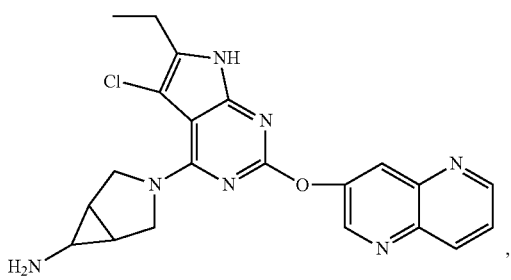,
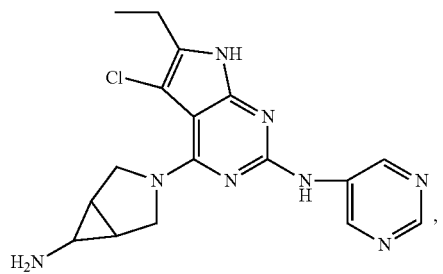, 641
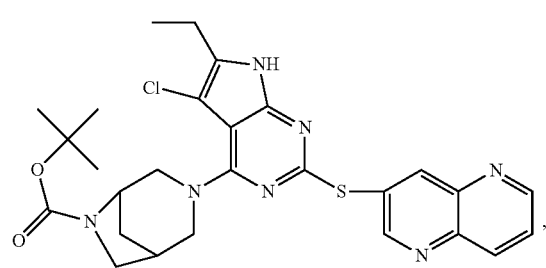
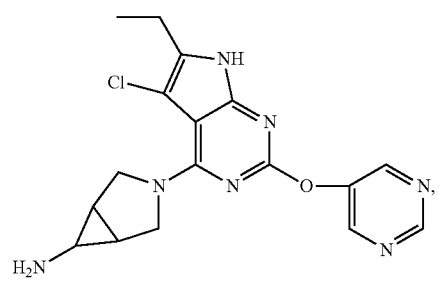
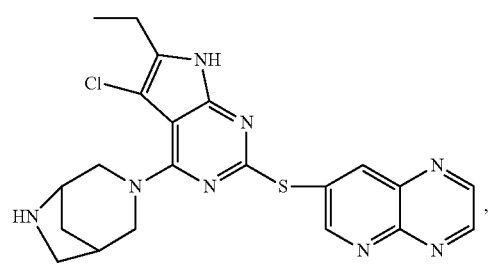
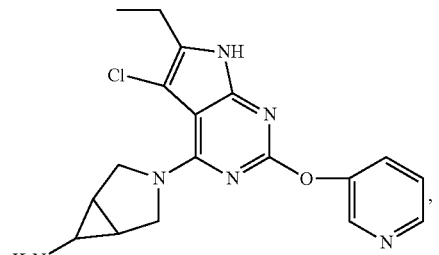
642
-continued
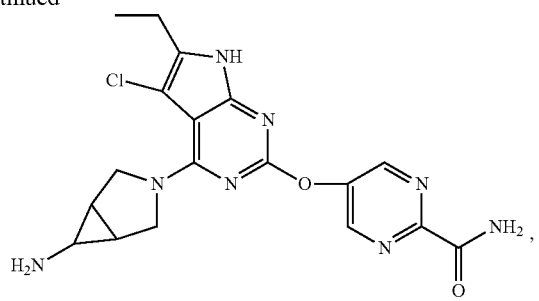
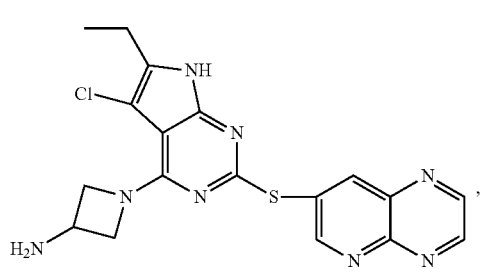
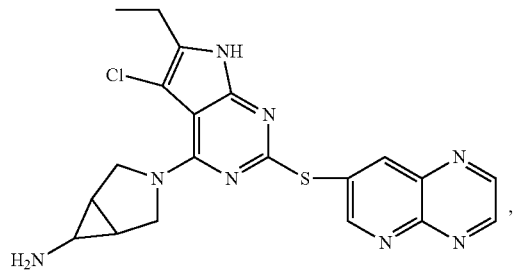
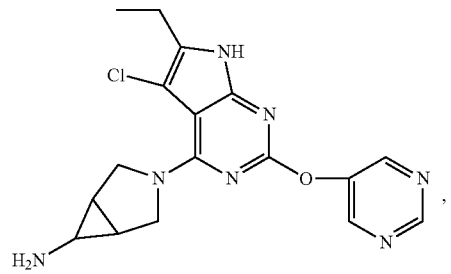
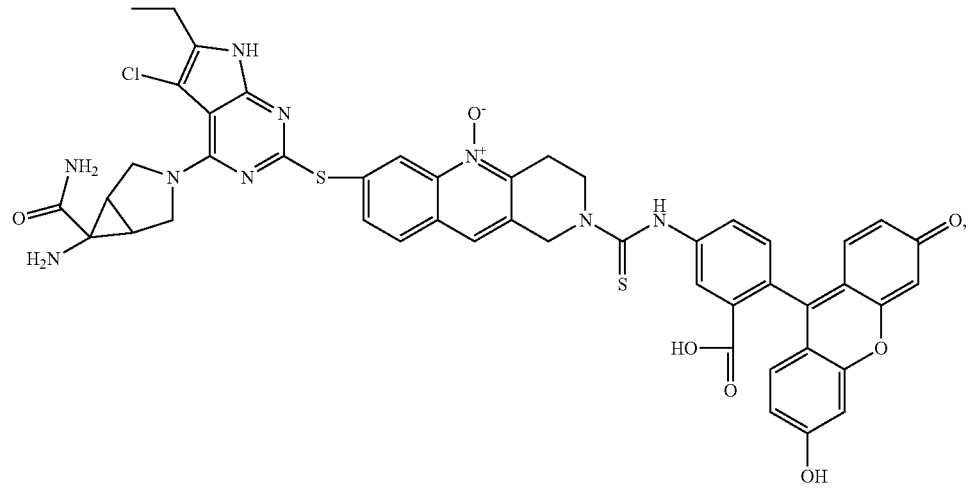

-continued
643
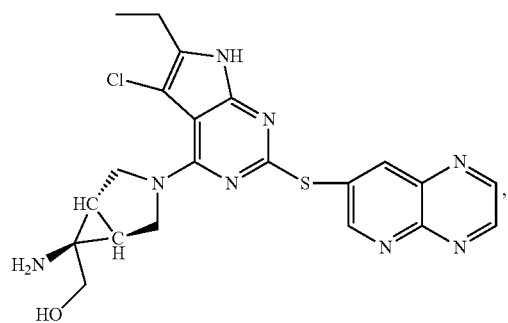
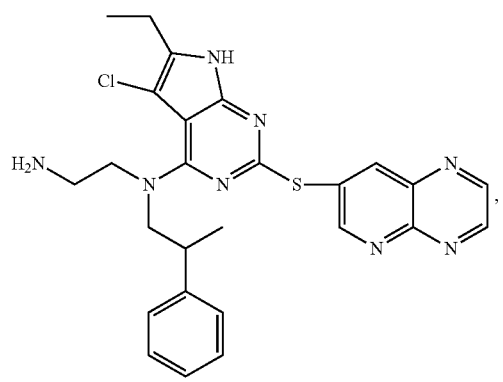
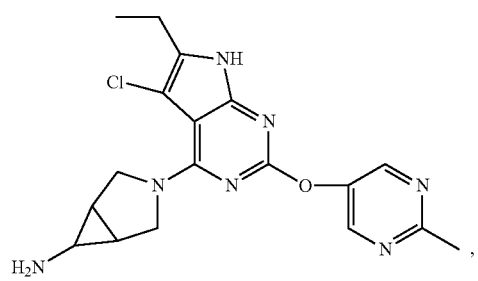
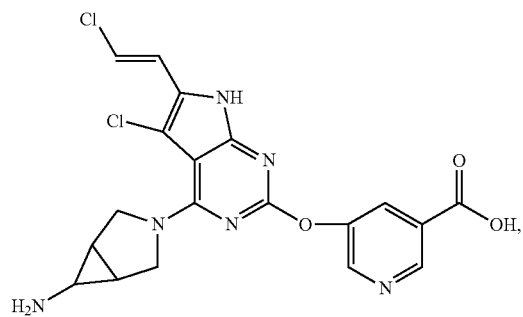
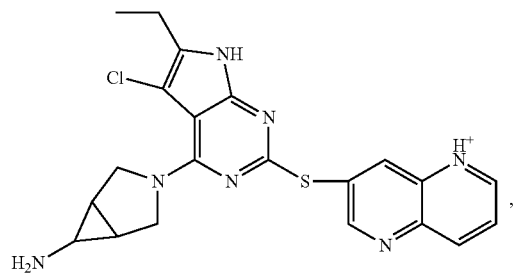
644
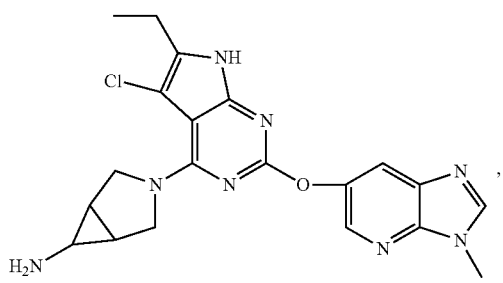
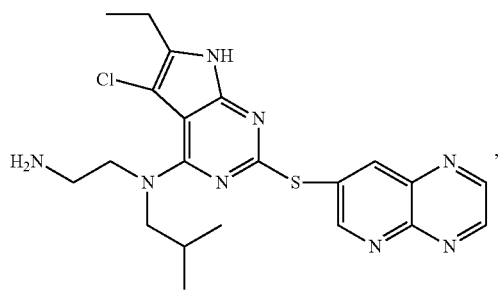
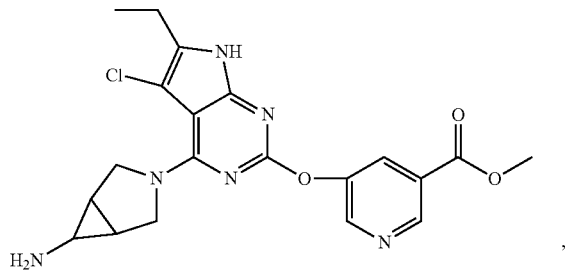
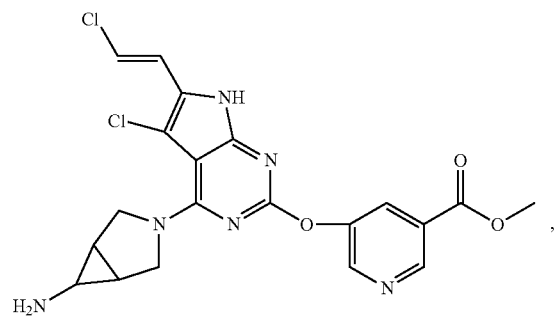
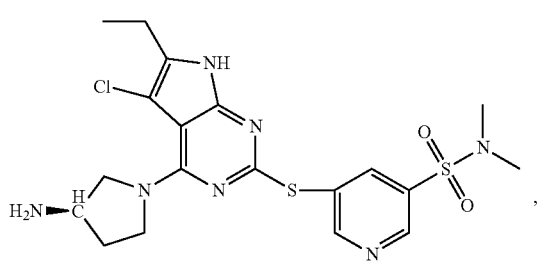

645
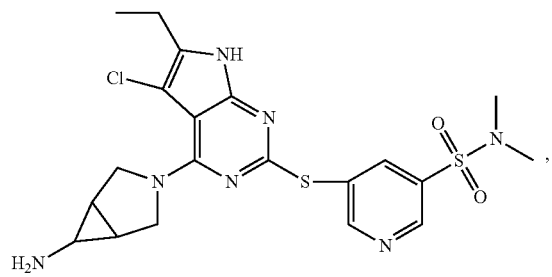
646
-continued
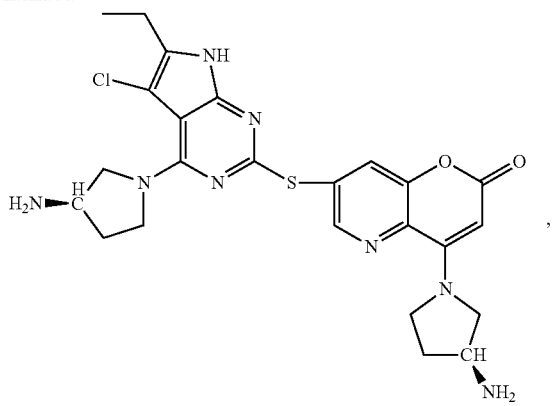
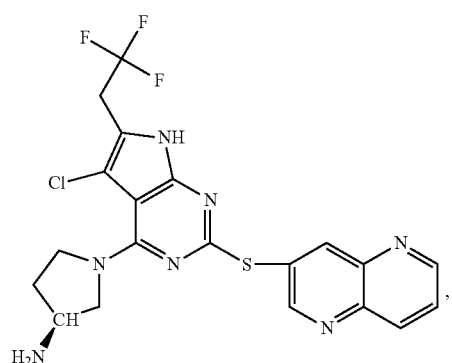
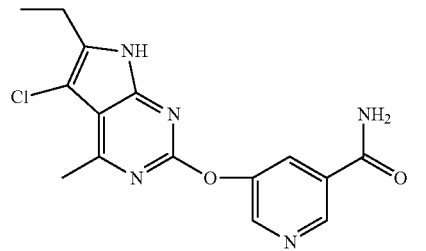
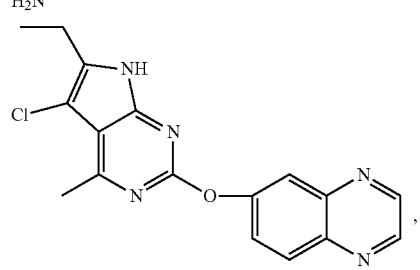
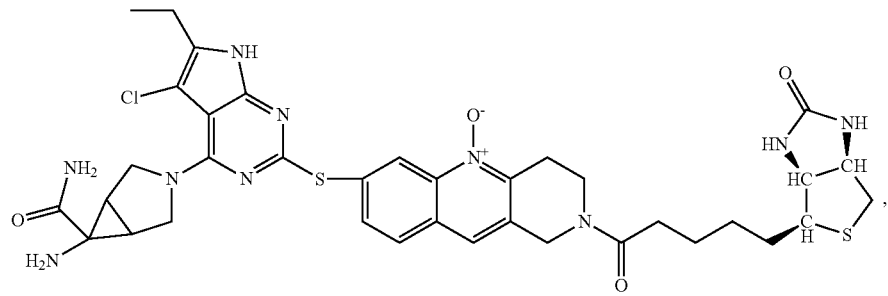
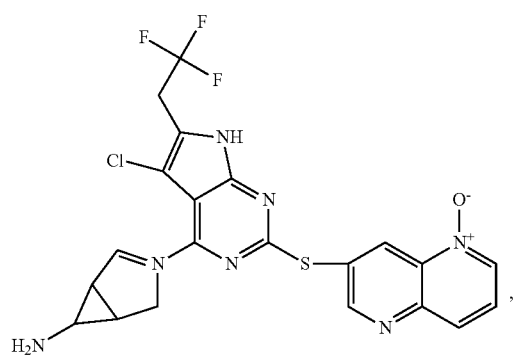
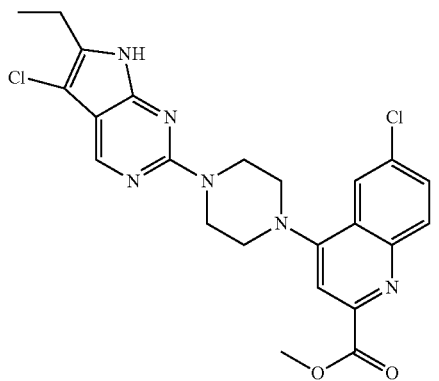

-continued
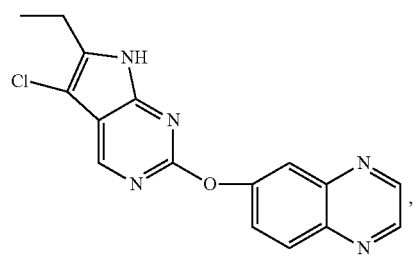
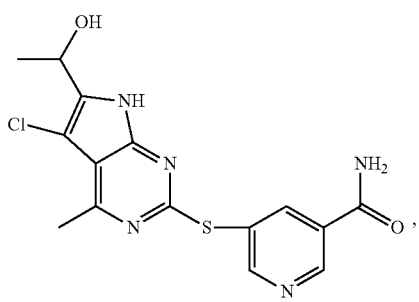
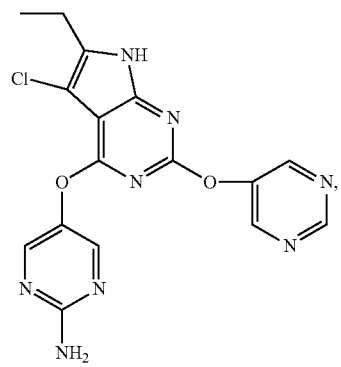
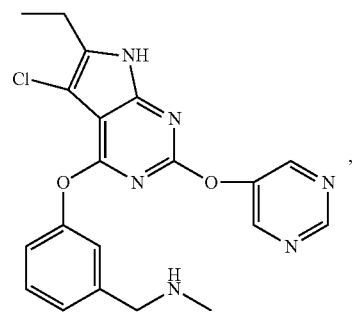
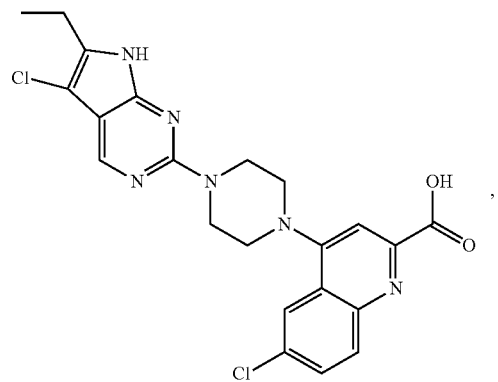
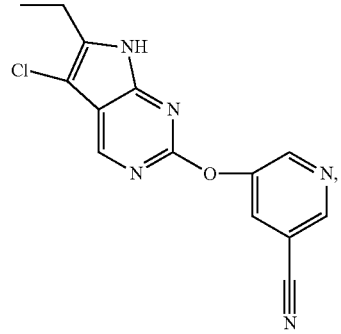
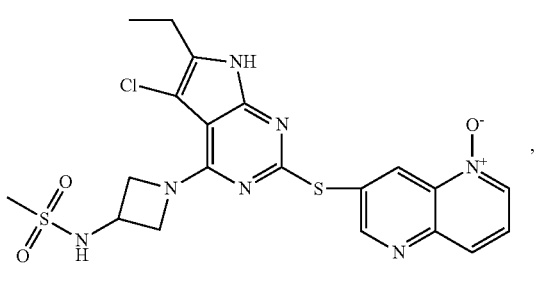
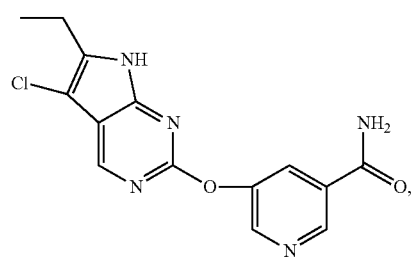
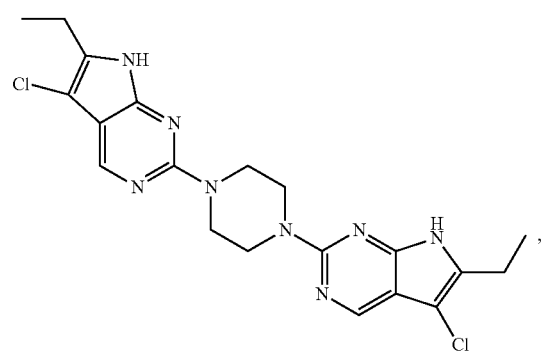
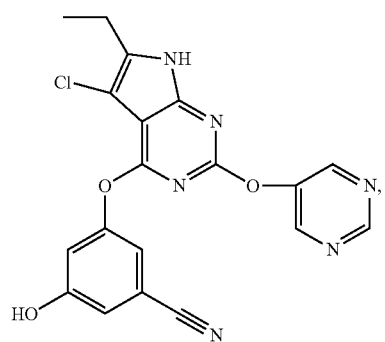
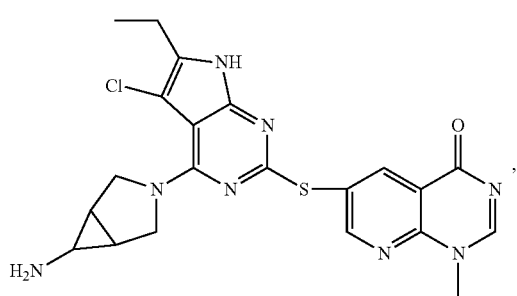

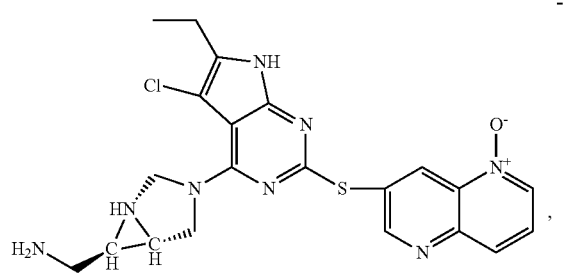

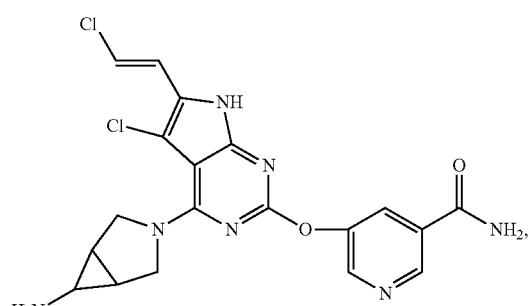

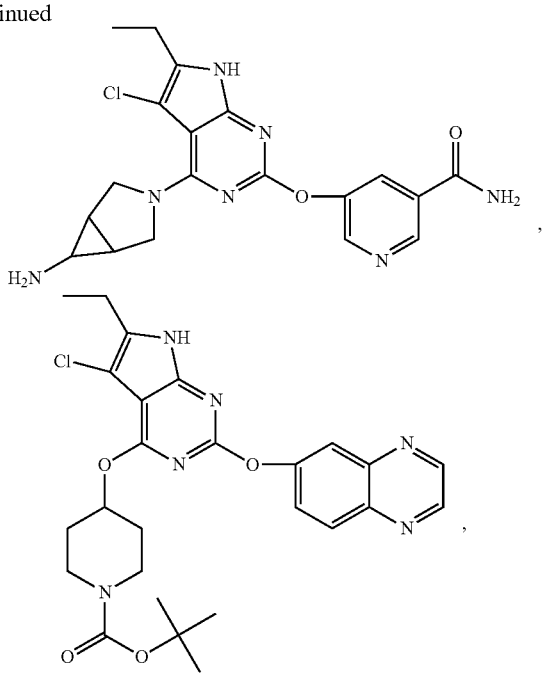

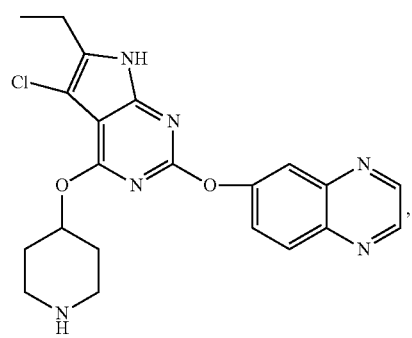

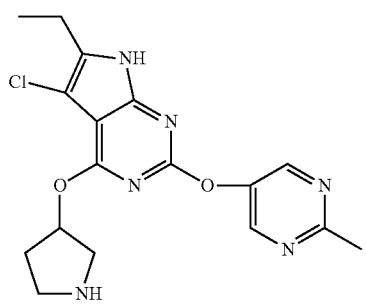

and

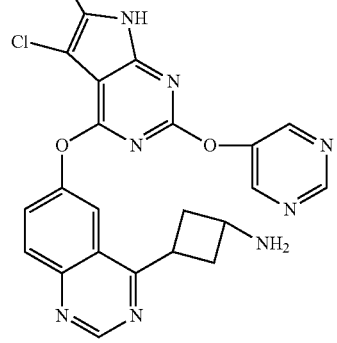

or a pharmaceutically acceptable salt thereof.

11. A pharmaceutical composition comprising the compound of claim 1 or a pharmaceutically acceptable salt thereof.

12. A pharmaceutical composition comprising the compound of claim 10, or a pharmaceutically acceptable salt thereof.

13. A method of making a compound of claim 1, or a pharmaceutically acceptable salt thereof, comprising deprotecting a protected form of a compound of Formula I wherein Z is C-halo.

14. The method of claim 13 comprising, before the deprotecting step, halogenating a protected form of the compound of Formula I wherein Z is CH to form a compound of Formula I, or a pharmaceutically acceptable salt thereof, wherein Z is C-halo.

15. A method of claim 13 comprising halogenating a compound of Formula I or a pharmaceutically acceptable salt thereof, wherein Z is CH to form a compound of Formula I, wherein Z is C-halo.

* * * * *